US007932270B2

(12) United States Patent
Lu et al.

(10) Patent No.: US 7,932,270 B2
(45) Date of Patent: Apr. 26, 2011

(54) CERTAIN CHEMICAL ENTITIES, COMPOSITIONS, AND METHODS

(75) Inventors: Pu-Ping Lu, Foster City, CA (US);
Xiangping Qian, Foster City, CA (US);
Jeffrey T. Finer, Foster City, CA (US);
Chihyuan (Grace) Chuang, San Mateo, CA (US); Bradley P. Morgan, Moraga, CA (US); David J. Morgans, Jr., Los Altos, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 783 days.

(21) Appl. No.: 11/888,625

(22) Filed: Jul. 31, 2007

(65) Prior Publication Data

US 2009/0012126 A1   Jan. 8, 2009

Related U.S. Application Data

(60) Provisional application No. 60/834,903, filed on Aug. 1, 2006, provisional application No. 60/835,183, filed on Aug. 1, 2006, provisional application No. 60/835,010, filed on Aug. 1, 2006.

(51) Int. Cl.
*C07D 401/14* (2006.01)
*A61K 31/44* (2006.01)

(52) U.S. Cl. ........ 514/333; 514/332; 514/336; 514/343; 546/256; 546/262; 546/268.1

(58) Field of Classification Search .................. None
See application file for complete search history.

(56) References Cited

U.S. PATENT DOCUMENTS

| 4,140,853 | A  | 2/1979  | Vorbrueggen |
| 6,878,714 | B2 | 4/2005  | Askew et al. |
| 2003/0229089 | A1 | 12/2003 | Yamada et al. |
| 2008/0132545 | A1 | 6/2008  | Lu et al. |
| 2008/0139575 | A1 | 6/2008  | Lu et al. |
| 2008/0146619 | A1 | 6/2008  | Lu et al. |

FOREIGN PATENT DOCUMENTS

| WO | WO 98/21199 A2 * | 5/1998 |
| WO | WO 2005/108391 A1 | 11/2005 |
| WO | WO 2008/016643 A2 | 2/2008 |

OTHER PUBLICATIONS

International Search Report mailed on Apr. 7, 2008, for PCT Application Publication No. WO 2008/016643 A2, published on Feb. 7, 2008.
U.S. Appl. No. 11/888,672—Non-final Office Action dated Jul. 26, 2010.
U.S. Appl. No. 11/888,647—Non-final Office Action dated Jul. 27, 2010.
U.S. Appl. No. 11/888,655—Non-final Office Action dated Jul. 27, 2010.

* cited by examiner

*Primary Examiner* — Zinna N Davis
(74) *Attorney, Agent, or Firm* — Foley and Lardner LLP

(57) ABSTRACT

Chemical entities that modulate smooth muscle myosin and/or non-muscle myosin, and chemical entities, pharmaceutical compositions and methods of treatment of diseases and conditions associated with smooth muscle myosin and/or non-muscle myosin are described.

66 Claims, No Drawings

CERTAIN CHEMICAL ENTITIES, COMPOSITIONS, AND METHODS

This application claims the benefit of U.S. Provisional Patent Application No. 60/834,903, filed Aug. 1, 2006, U.S. Provisional Patent Application No. 60/835,183, filed Aug. 1, 2006, and U.S. Provisional Patent Application No. 60/835,010, filed Aug. 1, 2006, each of which is incorporated herein by reference for all purposes.

Provided are certain substituted heterocycles, including chemical entities that modulate smooth muscle myosin and/or non-muscle myosin, and chemical entities, pharmaceutical compositions and methods of treatment of diseases and conditions associated with smooth muscle myosin and/or non-muscle myosin.

Myosin is present in all muscle and non-muscle cells. Of the ten distinct classes of myosin in human cells, myosin-II is thought to be the form responsible for contraction of skeletal, cardiac, and smooth muscle. Myosin-II is also the isoform present in non-muscle myosins, also known as cytoplasmic myosins. The non-muscle myosins are ubiquitously present in eukaryotic cells, where the smooth muscle myosins are generally present in smooth muscle cells.

Myosin-II is significantly different in amino acid composition and in overall structure from myosins in the other nine distinct classes. Myosin-II consists of two globular head domains, called Subfragment-1 or S1, linked together by a long alpha-helical coiled-coiled tail. Proteolysis of myosin generates either S1 or heavy meromyosin (HMM, a two-headed form with a truncated tail), depending on the proteolysis conditions. S1 contains the ATPase and actin-binding properties of the molecule. S1 has been shown to be sufficient to move actin filaments in vitro, and is therefore likely to be the motor domain of the molecule.

Although myosin-II isoforms from various tissues differ in a number of biological properties, they share the same basic molecular structure as a dimer of two heavy chains (approximately 200 kDa) which are noncovalently associated with two pairs of light chains (approximately 20 and 17 kDa). The two globular amino-terminal heads are tethered together by the carboxy-terminal alpha-helical coiled-coil that forms a tail. The tails are believed to be involved in the assembly of myosin molecules into filaments, whereas the heads are thought to have an actin-activated $Mg^{2+}$-ATPase activity. Each myosin head can be divided by three protease-sensitive regions into peptides of approximately 25, 50, and 20 kDa. The more amino-terminal 25 kDa-50 kDa junction is close to the ATP binding region, whereas the actin-binding domain is near the 50 kDa-20 kDa junction.

S1 consists of a globular actin binding and nucleotide binding region known as the catalytic domain. This domain is attached at its carboxy-terminus to an alpha-helix that has two light chains of about 20 kDa each wrapped around it. This light-chain binding domain of S1 is known as the lever arm. Upon transitioning from the pre-stroke to the post-stroke state, the lever arm is believed to swing through an angle of about 90 degrees about a fulcrum point in the catalytic domain near the nucleotide-binding site. The "power stroke" is driven by the hydrolysis of ATP.

The other end of the myosin molecule is an alpha-helical coiled-coiled tail involved in self assembly of myosin molecules into bipolar thick filaments. These thick filaments interdigitate between thinner actin filaments, and the two filament systems slide past one another during contraction of the muscle. This filament sliding mechanism is thought to involve conformational changes in the myosin heads causing them to walk along the thin actin filaments at the expense of ATP hydrolysis. While non-muscle myosins act in a similar manner, they are understood to slide at a slower velocity than the smooth muscle myosins.

The complete cDNA of the human smooth muscle myosin has been described. The sequence of human smooth muscle myosin is 52% identical to human cardiac myosin in the catalytic S1 region. See, for example, PCT publication No. WO 03/14323.

Provided is at least one chemical entity chosen from compounds of Formula I

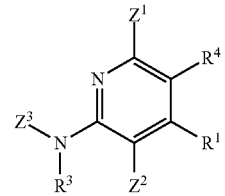

Formula I and pharmaceutically acceptable salts thereof, wherein $R^1$ and $R^4$ are independently chosen from hydrogen, cyano, halo, hydroxy, azido, nitro, sulfonyl, sulfinyl, sulfanyl, optionally substituted alkoxy, optionally substituted acylocy, optionally substituted aminocarbonyloxy, optionally substituted aryloxy, optionally substituted heteroaryloxy, optionally substituted heterocycloalkyloxy, optionally substituted alkoxycarbonyl, optionally substituted alkyl, optionally substituted alkenyl, optionally substituted alkynyl, optionally substituted aryloxy, optionally substituted aryl, optionally substituted heteroaryl, optionally substituted heterocycloalkyl, optionally substituted amino, optionally substituted acyl, optionally substituted aminocarbonyl, and optionally substituted carbaminodoyl;

$Z^1$ is chosen from optionally substituted aryl and optionally substituted heteroaryl;

$Z^2$ is chosen from hydrogen, optionally substituted amidino, carboxyl, optionally substituted alkoxy carbonyl, optionally substituted acyl, optionally substituted alkenyl, optionally substituted alkyl, optionally substituted heterocycloalkyl, optionally substituted heteroaryl, and optionally substituted aminocarbonyl;

$Z^3$ is chosen from hydrogen and optionally substituted alkyl; and $R^3$ is chosen from hydrogen and optionally substituted alkyl.

Also provided is a pharmaceutical composition comprising at least one chemical entity described herein, together with at least one pharmaceutically acceptable vehicle chosen from carriers, adjuvants, and excipients.

Also provided are methods of treatment of one or more diseases associated with smooth muscle myosin, or non-muscle myosin. The methods of treatment comprise administering a therapeutically effective amount of at least one chemical entity provided herein or a pharmaceutical composition comprising at least one chemical entity described herein, together with at least one pharmaceutically acceptable vehicle chosen from carriers, adjuvants, and excipients.

Other aspects and embodiments will be apparent to those skilled in the art from the following detailed description.

As used in the present specification, the following words and phrases are generally intended to have the meanings as set forth below, except to the extent that the context in which they are used indicates otherwise.

As used herein, when any variable occurs more than one time in a chemical formula, its definition on each occurrence is independent of its definition at every other occurrence.

The following abbreviations and terms have the indicated meanings throughout:
PIPES=1,4-piperazinediethanesulfonic acid
ATP=adenosine 5'-triphosphate
DTT=DL-dithiothreitol
BSA=bovine serum albumin
NADH=nicotinamide adenine dinucleotide
PEP=phosphoenolpyruvic acid
EGTA=ethylene glycol-bis(2-aminoethylether)-N,N,N',N'-tetraacetic acid
Ac=acetyl
APCI=atmospheric pressure chemical ionization
atm=atmosphere
Boc=tert-butoxycarbonyl
c-=cyclo
CBZ=carbobenzyloxy=benzyloxycarbonyl
CDI=carbonyldiimidazole
DCM=dichloromethane=methylene chloride=$CH_2Cl_2$
DIAD=diisopropyl azodicarboxylate
DIEA=DIPEA=N,N-diisopropylethylamine
DMAP=4-(dimethylamino)pyridine
DMF=N,N-dimethylformamide
DMSO=dimethyl sulfoxide
(DPPF)$PdCl_2$=[1,1'-bis(diphenylphosphino)ferrocene]dichloropalladium(II)
Et=ethyl
EtOAc=ethyl acetate
EtOH=ethanol
g=gram
GC=gas chromatography
h or hr=hour
HATU=O-(7-azabenzotriazol-1-yl)-N,N,N',N'-tetramethyluronium hexafluorophosphate
HBTU=O-(benzotriazol-1-yl)-N,N,N',N'-tetramethyluronium hexafluorophosphate
HOBT=1-hydroxybenzotriazole
HPLC=high pressure liquid chromatography
i-=iso
kg or Kg=kilogram
L or l=liter
LC/MS=LCMS=liquid chromatography-mass spectrometry
LDA=lithium diisopropylamide
LRMS=low resolution mass spectrometry
m/z=mass-to-charge ratio
Me=methyl
NMP=N-Methyl-2-pyrrolidone
NMR=nuclear magnetic resonance
MPLC=medium pressure liquid chromatography
min=minute
mL=milliliter
MW=microwave
n-=normal
Ph=phenyl
$(Ph_3P)_4Pd$=tetrakis(triphenylphosphine)palladium(0)
$(Ph_3P)_2PdCl_2$=dichlorobis(triphenylphosphine)palladium(II)
RP-HPLC=reverse phase-high pressure liquid chromatography
rt or RT=room temperature
s-=sec-=secondary
t-=tert-=tertiary
TBAF=tetrabutylammonium fluoride
TBS=TBDMS=tert-butyldimethylsilyl
TES=triethylsilyl or triethylsilane
TMS=trimethylsilyl or trimethylsilane
TFA=trifluoroacetic acid
THF=tetrahydrofuran
TLC=thin layer chromatography
UV=ultraviolet
vol=volume equivalent in mL/g or L/Kg or the limiting reagent unless otherwise specified A dash ("-") that is not between two letters or symbols is used to indicate a point of attachment for a substituent. For example, —$CONH_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

The term "ATPase," as used herein, refers to an enzyme that is capable of hydrolyzing ATP. ATPases include proteins comprising molecular motors such as myosins.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric combinations having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having one to four carbons.

"Alkenyl" refers to an unsaturated branched or straight-chain alkyl group having at least one carbon-carbon double bond derived by the removal of one hydrogen atom from a single carbon atom of a parent alkene. The group may be in either the cis or trans configuration about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. In certain embodiments, an alkenyl group has from 2 to 20 carbon atoms and in other embodiments, from 2 to 6 carbon atoms.

"Alkynyl" refers to an unsaturated branched or straight-chain alkyl group having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 3 to 6 carbon atoms.

"Cycloalkyl" indicates a non-aromatic carbocyclic ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged saturated ring groups such as norbornane.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. Alkoxy groups will usually have from 1 to 7 carbon atoms attached through the oxygen bridge. "Lower alkoxy" refers to alkoxy groups having one to four carbons.

The term "amidino" refers to the group —C(=NH)—NH$_2$. The term "substituted amidino" refers to the formula —C(=NR')—NR"R" in which each of the R" groups is independently chosen from hydrogen, optionally substituted alkyl, optionally substituted alkoxy, optionally substituted aminocarbonyl, optionally substituted aryl, optionally substituted heteroaryl, optionally substituted heterocyclyl, acyl, alkoxycarbonyl, sulfanyl, sulfinyl and sulfonyl and R' is chosen from hydrogen, cyano, optionally substituted alkyl, optionally substituted alkoxy, optionally substituted aminocarbonyl, optionally substituted aryl, optionally substituted heteroaryl, optionally substituted heterocyclyl, acyl, alkoxycarbonyl, sulfanyl, sulfinyl and sulfonyl, provided that at least one R' or R" group is not hydrogen.

"Mono- and di-alkylcarboxamide" encompasses a group of the formula —(C=O)NR$_a$R$_b$ where R$_a$ and R$_b$ are independently chosen from hydrogen and alkyl groups of the indicated number of carbon atoms, provided that R$_a$ and R$_b$ are not both hydrogen.

"Acyl" refers to the groups H—C(O)—; (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a C$_2$ acyl group is an acetyl group having the formula CH$_3$(C=O)—.

"Formyl" refers to the group —C(O)H.

"Carboxy" and/or "carboxyl" refer to the group —C(O)OH.

By "alkoxycarbonyl" is meant a group of the formula (alkoxy)(C=O)— attached through the carbonyl carbon wherein the alkoxy group has the indicated number of carbon atoms. Thus a C$_1$-C$_6$ alkoxycarbonyl group is an alkoxy group having from 1 to 6 carbon atoms attached through its oxygen to a carbonyl linker.

By "amino" is meant the group —NH$_2$.

"Mono- and di-(alkyl)amino" encompasses secondary and tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propylamino.

The term "aminocarbonyl" refers to the group —CONR$^b$R$^c$, where R$^b$ is chosen from H, optionally substituted C$_1$-C$_6$ alkyl, optionally substituted cycloalkyl, optionally substituted heterocycloalkyl, optionally substituted aryl, and optionally substituted heteroaryl; and R$^c$ is independently chosen from hydrogen and optionally substituted C$_1$-C$_4$ alkyl; or R$^b$ and R$^c$ taken together with the nitrogen to which they are bound, form an optionally substituted 5- to 7-membered nitrogen-containing heterocycloalkyl which optionally includes 1 or 2 additional heteroatoms selected from O, N, and S in the heterocycloalkyl ring;

where each substituted group is independently substituted with one or more substituents independently selected from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substitutent for cycloalkyl, heterocycloalkyl, or heteroaryl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ alkylphenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

"Aryl" encompasses:

6-membered carbocyclic aromatic rings, for example, benzene;

bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 6-membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

The term "aryloxy" refers to the group —O-aryl.

The term "aralkyl" refers to the group -alkyl-aryl.

"Carbamimidoyl" refers to the group —C(=NH)—NH$_2$.

"Substituted carbamimidoyl" refers to the group —C(=NR$^e$)—NR$^f$R$^g$ where R$^e$, is chosen from: hydrogen, cyano, optionally substituted alkyl, optionally substituted cycloalkyl, optionally substituted aryl, optionally substituted heteroaryl, and optionally substituted heterocycloalkyl; and R$^f$ and R$^g$ are independently chosen from: hydrogen optionally substituted alkyl, optionally substituted cycloalkyl, optionally substituted aryl, optionally substituted heteroaryl, and optionally substituted heterocycloalkyl, provided that at least one of R$^e$, R$^f$, and R$^g$ is not hydrogen and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted aryl, and optionally substituted heteroaryl;

$R^b$ is chosen from H, optionally substituted $C_1$-$C_6$ alkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl, heterocycloalkyl, or heteroaryl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)$(phenyl), —$N(C_1$-$C_4$ alkyl)$C(O)(C_1$-$C_4$ alkyl), —$N(C_1$-$C_4$ alkyl)$C(O)$(phenyl), —$C(O)C_1$-$C_4$ alkyl, —$C(O)C_1$-$C_4$ phenyl, —$C(O)C_1$-$C_4$ haloalkyl, —$OC(O)C_1$-$C_4$ alkyl, —$SO_2(C_1$-$C_4$ alkyl), —$SO_2$(phenyl), —$SO_2(C_1$-$C_4$ haloalkyl), —$SO_2NH_2$, —$SO_2NH(C_1$-$C_4$ alkyl), —$SO_2NH$(phenyl), —$NHSO_2(C_1$-$C_4$ alkyl), —$NHSO_2$(phenyl), and —$NHSO_2(C_1$-$C_4$ haloalkyl).

The term "halo" includes fluoro, chloro, bromo, and iodo, and the term "halogen" includes fluorine, chlorine, bromine, and iodine.

"Haloalkyl" indicates alkyl as defined above having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Heteroaryl" encompasses:
5- to 7-membered aromatic, monocyclic rings containing one or more, for example, from 1 to 4, or in certain embodiments, from 1 to 3, heteroatoms chosen from N, O, and S, with the remaining ring atoms being carbon;
bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring; and
tricyclic heterocycloalkyl rings containing one or more, for example, from 1 to 5, or in certain embodiments, from 1 to 4, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl or heterocycloalkyl ring. For such fused, bicyclic heteroaryl ring systems wherein only one of the rings contains one or more heteroatoms, the point of attachment may be at either ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridazinyl, triazolyl, quinolinyl, pyrazolyl, and 5,6,7,8-tetrahydroisoquinolinyl. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl, cycloalkyl, or heterocycloalkyl, as defined herein Substituted heteroaryl also includes ring systems substituted with one or more oxide (—$O^-$) substituents, such as pyridinyl N-oxides.

By "heterocycloalkyl" is meant a single, non-aromatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. The ring may be saturated or have one or more carbon-carbon double bonds. Suitable heterocycloalkyl groups include, for example (as numbered from the linkage position assigned priority 1), 2-pyrrolidinyl, 2,4-imidazolidinyl, 2,3-pyrazolidinyl, 2-piperidyl, 3-piperidyl, 4-piperidyl, and 2,5-piperizinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo (=O) or oxide (—$O^-$) substituents, such as piperidinyl N-oxide, morpholinyl-N-oxide, 1-oxo-1-thiomorpholinyl and 1,1-dioxo-1-thiomorpholinyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

As used herein, "modulation" refers to a change in activity as a direct or indirect response to the presence of a chemical entity as described herein, relative to the activity of in the absence of the chemical entity. The change may be an increase in activity or a decrease in activity, and may be due to the direct interaction of the compound with the a target or due to the interaction of the compound with one or more other factors that in turn affect the target's activity. For example, the presence of the chemical entity may, for example, increase or decrease the target activity by directly binding to the target, by causing (directly or indirectly) another factor to increase or decrease the target activity, or by (directly or indirectly) increasing or decreasing the amount of target present in the cell or organism.

The term "sulfanyl" includes the groups: —S-(optionally substituted ($C_1$-$C_6$)alkyl), —S-(optionally substituted aryl), —S-(optionally substituted heteroaryl), and —S-(optionally substituted heterocycloalkyl). Hence, sulfanyl includes the group $C_1$-$C_6$ alkylsulfanyl.

The term "sulfinyl" includes the groups: —S(O)-(optionally substituted ($C_1$-$C_6$)alkyl), —S(O)-optionally substituted aryl), —S(O)-optionally substituted heteroaryl), —S(O)-(optionally substituted heterocycloalkyl); and —S(O)-(optionally substituted amino).

The term "sulfonyl" includes the groups: —S($O_2$)-(optionally substituted ($C_1$-$C_6$)alkyl), —S($O_2$)-optionally substituted aryl), —S($O_2$)-optionally substituted heteroaryl), —S($O_2$)-(optionally substituted heterocycloalkyl), —S($O_2$)-(optionally substituted alkoxy), —S($O_2$)-optionally substituted aryloxy), —S($O_2$)-optionally substituted heteroaryloxy), —S($O_2$)-(optionally substituted heterocyclyloxy); and —S($O_2$)-(optionally substituted amino).

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl, cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from: —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted cycloalkyl, optionally substituted heterocycloalkyl, optionally substituted alkenyl, optionally substituted alkynyl, optionally substituted aryl, and optionally substituted heteroaryl;

$R^b$ is chosen from hydrogen, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl, heterocycloalkyl, or heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2NH$($C_1$-$C_4$ alkyl), —$SO_2NH$(phenyl), —$NHSO_2$($C_1$-$C_4$ alkyl), —$NHSO_2$(phenyl), and —$NHSO_2$($C_1$-$C_4$ haloalkyl).

The term "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl, refer respectively to alkyl, cycloalkyl, aryl, heteroaryl, and heterocycloalkyl wherein one or more (such as up to 5, for example, up to 3) hydrogen atoms are replaced by a substituent independently chosen from: —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl, heterocycloalkyl, or heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)C$_1$-C$_4$ alkylphenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

The term "substituted alkoxy" refers to alkoxy wherein the alkyl constituent is substituted (i.e., —O-(substituted alkyl)) wherein "substituted alkyl" refers to alkyl wherein one or more (such as up to 5, for example, up to 3) hydrogen atoms are replaced by a substituent independently chosen from: —R$^a$, —OR$^b$, optionally substituted amino (including —NR$^c$COR$^b$, —NR$^c$CO$_2$R$^a$, —NR$^c$CONR$^b$R$^c$, —NR$^b$C(NR$^c$)NR$^b$R$^c$, —NR$^b$C(NCN)NR$^b$R$^c$, and —NR$^c$SO$_2$R$^a$), halo, cyano, nitro, oxo (as a substitutent for cycloalkyl, heterocycloalkyl, and heteroaryl), optionally substituted acyl (such as —COR$^b$), optionally substituted alkoxycarbonyl (such as —CO$_2$R$^b$), aminocarbonyl (such as —CONR$^b$R$^c$), —OCOR$^b$, —OCO$_2$R$^a$, —OCONR$^b$R$^c$, —OP(O)(OR$^b$)OR$^c$, sulfanyl (such as SR$^b$), sulfinyl (such as —SOR$^a$), and sulfonyl (such as —SO$_2$R$^a$ and —SO$_2$NR$^b$R$^c$), where R$^a$ is chosen from optionally substituted C$_1$-C$_6$ alkyl, optionally substituted alkenyl, optionally substituted alkynyl, optionally substituted aryl, and optionally substituted heteroaryl;

R$^b$ is chosen from H, optionally substituted C$_1$-C$_6$ alkyl, optionally substituted cycloalkyl, optionally substituted heterocycloalkyl, optionally substituted aryl, and optionally substituted heteroaryl; and R$^c$ is independently chosen from hydrogen and optionally substituted C$_1$-C$_4$ alkyl; or R$^b$ and R$^c$, and the nitrogen to which they are attached, form an optionally substituted heterocycloalkyl group; and where each optionally substituted group is unsubstituted or independently substituted with one or more, such as one, two, or three, substituents independently selected from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substitutent for cycloalkyl, heterocycloalkyl, or heteroaryl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ alkylphenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl). In some embodiments, a substituted alkoxy group is "polyalkoxy" or —O-(optionally substituted alkylene)-(optionally substituted alkoxy), and includes groups such as —OCH$_2$CH$_2$OCH$_3$, and residues of glycol ethers such as polyethyleneglycol, and —O(CH$_2$CH$_2$O)$_x$CH$_3$, where x is an integer of 2-20, such as 2-10, and for example, 2-5. Another substituted alkoxy group is hydroxyalkoxy or —OCH$_2$(CH$_2$)$_y$OH, where y is an integer of 1-10, such as 1-4.

The term "substituted alkoxycarbonyl" refers to the group (substituted alkyl)-O—C(O)— wherein the group is attached to the parent structure through the carbonyl functionality and wherein substituted refers to alkyl wherein one or more (such as up to 5, for example, up to 3) hydrogen atoms are replaced by a substituent independently chosen from:

—R$^a$, —OR$^b$, optionally substituted amino (including —NR$^c$COR$^b$, —NR$^c$CO$_2$R$^a$, —NR$^c$CONR$^b$R$^c$, —NR$^b$C(NR$^c$)NR$^b$R$^c$, —NR$^b$C(NCN)NR$^b$R$^c$, and —NR$^c$SO$_2$R$^a$), halo, cyano, nitro, oxo (as a substitutent for cycloalkyl, heterocycloalkyl, and heteroaryl), optionally substituted acyl (such as —COR$^b$), optionally substituted alkoxycarbonyl (such as —CO$_2$R$^b$), aminocarbonyl (such as —CONR$^b$R$^c$), —OCOR$^b$, —OCO$_2$R$^a$, —OCONR$^b$R$^c$, —OP(O)(OR$^b$)OR$^c$, sulfanyl (such as SR$^b$), sulfinyl (such as —SOR$^a$), and sulfonyl (such as —SO$_2$R$^a$ and —SO$_2$NR$^b$R$^c$), where R$^a$ is chosen from optionally substituted C$_1$-C$_6$ alkyl, optionally substituted alkenyl, optionally substituted alkynyl, optionally substituted aryl, and optionally substituted heteroaryl;

R$^b$ is chosen from H, optionally substituted C$_1$-C$_6$ alkyl, optionally substituted cycloalkyl, optionally substituted heterocycloalkyl, optionally substituted aryl, and optionally substituted heteroaryl; and R$^c$ is independently chosen from hydrogen and optionally substituted C$_1$-C$_4$ alkyl; or R$^b$ and R$^c$, and the nitrogen to which they are attached, form an optionally substituted heterocycloalkyl group; and where each optionally substituted group is unsubstituted or independently substituted with one or more, such as one, two, or three, substituents independently selected from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substitutent for cycloalkyl, heterocycloalkyl, or heteroaryl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ alkylphenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

The term "substituted amino" refers to the group —NHR$^d$ or —NR$^d$R$^e$ wherein R$^d$ is chosen from: hydroxy, optionally substituted alkoxy, optionally substituted alkyl, optionally substituted cycloalkyl, optionally substituted acyl, optionally substituted carbamimidoyl, aminocarbonyl, optionally substituted aryl, optionally substituted heteroaryl, optionally substituted heterocycloalkyl, optionally substituted alkoxycarbonyl, sulfinyl and sulfonyl, and wherein R$^e$ is chosen from: optionally substituted alkyl, optionally substituted cycloalkyl, optionally substituted aryl, optionally substituted heteroaryl, and optionally substituted heterocycloalkyl, and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from:

—R$^a$, —OR$^b$, optionally substituted amino (including —NR$^c$COR$^b$, —NR$^c$CO$_2$R$^a$, —NR$^c$CONR$^b$R$^c$, —NR$^b$C(NR$^c$)NR$^b$R$^c$, —NR$^b$C(NCN)NR$^b$R$^c$, and —NR$^c$SO$_2$R$^a$), halo, cyano, nitro, oxo (as a substitutent for cycloalkyl, heterocycloalkyl, and heteroaryl), optionally substituted acyl (such as —COR$^b$), optionally substituted alkoxycarbonyl (such as —CO$_2$R$^b$), aminocarbonyl (such as —CONR$^b$R$^c$), —OCOR$^b$, —OCO$_2$R$^a$, —OCONR$^b$R$^c$, —OP(O)(OR$^b$)OR$^c$, sulfanyl (such as SR$^b$), sulfinyl (such as —SOR$^a$), and sulfonyl (such as —SO$_2$R$^a$ and —SO$_2$NR$^b$R$^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for cycloalkyl, heterocycloalkyl, or heteroaryl), —$CO_2$H, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl); and wherein optionally substituted acyl, optionally substituted alkoxycarbonyl, sulfinyl and sulfonyl are as defined herein.

The term "substituted amino" also refers to N-oxides of the groups —$NHR^d$, and $NR^dR^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

Compounds of Formula I include, but are not limited to, optical isomers of compounds of Formula I, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds of Formula I include Z- and E-forms (or cis- and trans-forms) of compounds with carbon-carbon double bonds. Where compounds of Formula I exists in various tautomeric forms, chemical entities of the present invention include all tautomeric forms of the compound.

Chemical entities of the present invention include, but are not limited to compounds of Formula I and all pharmaceutically acceptable forms thereof. Pharmaceutically acceptable forms of the chemical entities recited herein include pharmaceutically acceptable salts, solvates, crystal forms (including polymorphs and clathrates), chelates, non-covalent complexes, prodrugs, and mixtures thereof. In certain embodiments, the chemical entities described herein are in the form of pharmaceutically acceptable salts. Hence, the terms "chemical entity" and "chemical entities" also encompass pharmaceutically acceptable salts, solvates, chelates, non-covalent complexes, prodrugs, and mixtures.

"Pharmaceutically acceptable salts" include, but are not limited to salts with inorganic acids, such as hydrochloride, phosphate, diphosphate, hydrobromide, sulfate, sulfinate, nitrate, and like salts; as well as salts with an organic acid, such as malate, maleate, fumarate, tartrate, succinate, citrate, lactate, methanesulfonate, p-toluenesulfonate, 2-hydroxyethylsulfonate, benzoate, salicylate, stearate, and alkanoate such as acetate, HOOC—$(CH_2)_n$—COOH where n is 0-4, and like salts. Similarly, pharmaceutically acceptable cations include, but are not limited to sodium, potassium, calcium, aluminum, lithium, and ammonium.

In addition, if the compound of Formula I is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of chemical entities, for example ester or amide derivatives of the compounds of Formula I. The term "prodrugs" includes any chemical entities that become compounds of Formula I when administered to a patient, e.g., upon metabolic processing of the prodrug. Examples of prodrugs include, but are not limited to, acetate, formate, phosphate, and benzoate and like derivatives of functional groups (such as alcohol or amine groups) in the compounds of Formula I.

The term "solvate" refers to the chemical entity formed by the interaction of a solvent and a compound. Suitable solvates are pharmaceutically acceptable solvates, such as hydrates, including monohydrates and hemi-hydrates.

The term "chelate" refers to the chemical entity formed by the coordination of a compound to a metal ion at two (or more) points.

The term "non-covalent complex" refers to the chemical entity formed by the interaction of a compound and another molecule wherein a covalent bond is not formed between the compound and the molecule. For example, complexation can occur through van der Waals interactions, hydrogen bonding, and electrostatic interactions (also called ionic bonding).

The term "active agent" is used to indicate a chemical entity which has biological activity. In certain embodiments, an "active agent" is a compound having pharmaceutical utility. For example an active agent may be an anti-cancer therapeutic.

By "significant" is meant any detectable change that is statistically significant in a standard parametric test of statistical significance such as Student's T-test, where $p<0.05$.

The term "therapeutically effective amount" of a chemical entity described herein means an amount effective, when administered to a human or non-human patient, to provide a therapeutic benefit such as amelioration of symptoms, slowing of disease progression, or prevention of disease.

"Treatment" or "treating" means any treatment of a disease in a patient, including:
a) preventing the disease, that is, causing the clinical symptoms of the disease not to develop;
b) inhibiting the disease;
c) slowing or arresting the development of clinical symptoms; and/or
d) relieving the disease, that is, causing the regression of clinical symptoms.

"Patient" refers to an animal, such as a mammal, that has been or will be the object of treatment, observation or experiment. The methods described herein can be useful in both human therapy and veterinary applications. In some embodiments, the patient is a mammal; in some embodiments the patient is human; and in some embodiments the patient is chosen from cats and dogs.

Provided is at least one chemical entity chosen from compounds of Formula I

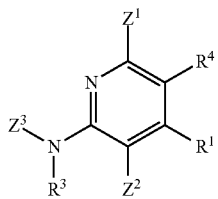

Formula I and pharmaceutically acceptable salts thereof, wherein $R^1$ and $R^4$ are independently chosen from hydrogen, cyano, halo, hydroxy, azido, nitro, sulfonyl, sulfinyl, sulfanyl, optionally substituted alkoxy, optionally substituted acylocy, optionally substituted aminocarbonyloxy, optionally substituted aryloxy, optionally substituted heteroaryloxy, optionally substituted heterocycloalkyloxy, optionally substituted alkoxycarbonyl, optionally substituted alkyl, optionally substituted alkenyl, optionally substituted alkynyl, optionally substituted aryloxy, optionally substituted aryl, optionally substituted heteroaryl, optionally substituted heterocycloalkyl, optionally substituted amino, optionally substituted acyl, optionally substituted aminocarbonyl, and optionally substituted carbaminodoyl;

$Z^1$ is chosen from optionally substituted aryl and optionally substituted heteroaryl;

$Z^2$ is chosen from hydrogen, optionally substituted amidino, carboxyl, optionally substituted alkoxy carbonyl, optionally substituted acyl, optionally substituted alkenyl, optionally substituted alkyl, optionally substituted heterocycloalkyl, optionally substituted heteroaryl, and optionally substituted aminocarbonyl;

$Z^3$ is chosen from hydrogen and optionally substituted alkyl; and $R^3$ is chosen from hydrogen and optionally substituted alkyl.

In certain embodiments of compounds of Formula I, $Z^1$ is optionally substituted aryl.

In certain embodiments of compounds of Formula I, $Z^1$ is optionally substituted heteroaryl.

In certain embodiments of compounds of Formula I, $Z^3$ is optionally substituted alkyl.

In certain embodiments of compounds of Formula I, $Z^3$ is chosen from optionally substituted aralkyl and optionally substituted heteroaralkyl.

Provided is at least one chemical entity chosen from compounds of Formula II

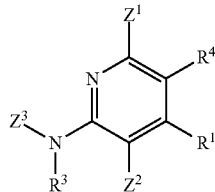

Formula II and pharmaceutically acceptable salts thereof wherein $R^1$ and $R^4$ are independently chosen from hydrogen, optionally substituted acyl, optionally substituted alkyl, cyano, halo, azido, optionally substituted amino, optionally substituted alkoxycarbonyl, optionally substituted aminocarbonyl, sulfonyl, sulfinyl, and sulfanyl;

$Z^1$ is optionally substituted aryl;

$Z^2$ is chosen from hydrogen, optionally substituted amidino, carboxyl, optionally substituted alkoxy carbonyl, optionally substituted acyl, optionally substituted alkenyl, optionally substituted alkyl, and optionally substituted aminocarbonyl;

$Z^3$ is chosen from optionally substituted aralkyl and optionally substituted heteroaralkyl; and $R^3$ is chosen from hydrogen and optionally substituted alkyl.

In certain embodiments of compounds of Formula II, $Z^2$ is chosen from carboxyl, optionally substituted alkoxycarbonyl, optionally substituted acyl, optionally substituted alkenyl, and optionally substituted alkyl. In certain embodiments, $Z^2$ is chosen from carboxyl, optionally substituted piperidinylcarbonyl, optionally substituted pyridinylcarbonyl, optionally substituted lower alkyl, optionally substituted lower alkenyl, and lower alkoxycarbonyl. In certain embodiments of compounds of Formula II, $Z^2$ is chosen from (2-(N-acetylaminomethyl)piperidin-1-yl)carbonyl; (2-aminomethylpiperidin-1-yl)carbonyl; 1-hydroxy-2-amino-ethyl; 2-((methylsulfonamido)methyl)piperidin-1-ylcarbonyl; 2-(methylaminocarbonyl)ethenyl; 2-(pyridin-3-ylmethyl)-2H-tetrazol-5-yl; aminomethyl; carboxyl; methoxycarbonyl; pyridin-2-ylcarbonyl; pyridin-3-ylcarbonyl; and pyridin-4-ylcarbonyl.

In certain embodiments of compounds of Formula II, $R^3$ is chosen from hydrogen and optionally substituted lower alkyl. In certain embodiments of compounds of Formula II, $R^3$ is chosen from hydrogen and lower alkyl. In certain embodiments of compounds of Formula II, $R^3$ is chosen from hydrogen and methyl. In certain embodiments of compounds of Formula II, $R^3$ is hydrogen.

In certain embodiments of compounds of Formula II, $R^4$ is chosen from hydrogen, cyano, halo, azido, optionally substituted aminocarbonyl, and optionally substituted alkyl. In certain embodiments of compounds of Formula II, $R^4$ is chosen from hydrogen, cyano, chloro, bromo, fluoro, azido, optionally substituted alkylaminocarbonyl, and optionally substituted methyl. In certain embodiments of compounds of Formula II, $R^4$ is chosen from hydrogen, cyano, chloro, bromo, azido, pyridin-3-ylmethylaminocarbonyl, aminomethyl, and hydroxymethyl. In certain embodiments of compounds of Formula II, $R^4$ is hydrogen.

In certain embodiments of compounds of Formula II, $Z^2$ is —C(O)—$NR^2R^5$ wherein $R^2$ is chosen from optionally substituted alkyl and optionally substituted cycloalkyl; and $R^5$ is chosen from hydrogen and optionally substituted alkyl.

In certain embodiments of compounds of Formula II, $R^2$ is chosen from optionally substituted methyl, optionally substituted ethyl, optionally substituted propyl, optionally substituted butyl, optionally substituted pentyl, optionally substituted hexyl, optionally substituted cyclopropyl, optionally substituted cyclopentyl, and optionally substituted cyclohexyl where each optionally substituted group is optionally substituted with one, two or three groups selected from optionally substituted aryl, optionally substituted heteroaryl, optionally substituted heterocycloalkyl, optionally substituted cycloalkyl, optionally substituted aminocarbonyl, optionally substituted amino, hydroxy, carboxyl, optionally substituted alkoxycarbonyl, and optionally substituted alkoxy.

In certain embodiments of compounds of Formula II, $R^2$ is chosen from methyl and ethyl, where the methyl and ethyl groups are optionally substituted with one or two groups selected from optionally substituted aryl, optionally substituted heteroaryl, optionally substituted heterocycloalkyl, optionally substituted cycloalkyl, optionally substituted aminocarbonyl, optionally substituted amino, hydroxy, carboxyl, optionally substituted alkoxycarbonyl, and optionally substituted alkoxy.

In certain embodiments of compounds of Formula II, $R^2$ is chosen from (1-(2-aminoethyl)-1H-pyrazol-3-yl)methyl; (1-(methylsulfonyl)piperidin-3-yl)methyl; (1-acetylpiperidin-3-yl)methyl; (1-acetylpyrrolidin-2-yl)methyl; (1H-imidazol-2-yl)methyl; (1H-pyrazol-3-yl)methyl; (1-methyl-1H-pyrazol-3-yl)methyl; (1-methyl-1H-pyrazol-5-yl)methyl; (2-(aminocarbonyl)ethylamino)carbonylmethyl; (2-(aminomethyl)pyridin-3-yl)methyl; (2-(carboxy)ethylamino)carbonylmethyl; (2-(dimethylamino)ethylamino)carbonylmethyl; (2-(hydroxy)ethylamino)carbonylmethyl; (2-(methylamino)ethylamino)carbonylmethyl; (2-(N-methyl-N-(t-butoxycarbonyl)-amino)ethylamino)carbonylmethyl; (2-oxopiperidin-3-yl)methyl; (3-(dimethylamino)propylamino)carbonylmethyl; (3-(hydroxy)ethylamino)carbonylmethyl; (3-(t-butoxycarbonylamino)propylamino)carbonylmethyl; (4-(aminomethyl)pyridin-2-yl)methyl; (5-(aminomethyl)pyridin-2-yl)methyl; (6-((1,3-dioxoisoindolin-2-yl)methyl)pyridin-2-yl)methyl; (6-(2-aminoethylamino)pyridin-2-yl)methyl; (6-(3-aminopropylamino)pyridin-2-yl)methyl; (6-(aminomethyl)pyridin-2-yl)methyl; (6-(hydroxymethyl)pyridin-2-yl)methyl; (6-bromopyridin-2-yl)methyl; (methylsulfonamido)carbonylmethyl; (pyridin-2-yl)ethylamino; 1-(2-(tert-butoxycarbonylamino)ethyl)-1H-pyrazol-3-ylmethyl; 1-(2-(tert-butoxycarbonylamino)ethyl)-1H-pyrazol-5-ylmethyl; 1-(aminocarbonyl)-2-(amino)-eth-1-yl; 1-(aminocarbonyl)-3-(amino)-propyl; 1-(aminocarbonyl)-4-(amino)-butyl; 1-(aminocarbonyl)-4-(benzyloxycarbonylamino)-pentyl; 1-(aminocarbonyl)-5-(amino)-pentyl; 1-(aminocarbonyl)eth-1-yl; 1-(carboxy)-2-(amino)-eth-1-yl; 1-(dimethylaminocarbonyl)-2-(amino)-eth-1-yl; 1-(hydroxy)-2-(aminocarbonylmethylamino)eth-1-yl; 1-(hydroxy)-2-(ethoxycarbonylmethylamino)eth-1-yl; 1-(hydroxy)-2-(pyridin-2-ylmethylamino)eth-1-yl; 1-(methoxycarbonyl)-2-(amino)-eth-1-yl; 1-(methoxycarbonyl)-2-(t-butoxycarbonylamino)-eth-1-yl; 1-(methoxycarbonyl)eth-1-yl; 1-(methylaminocarbonyl)-2-(amino)-eth-1-yl (2 occ); 1-(methylaminocarbonyl)eth-1-yl; 1-aminocarbonyl-2-hydroxy-eth-1-yl; 1-methoxycarbonyl-2-hydroxy-eth-1-yl; 2-(2-aminoethoxy)ethyl; 2-(2-aminoethyl)-pyridin-6-ylmethyl; 2-(2-aminoethylamino)ethyl; 2-(3-fluorophenyl)ethyl; 2-(3-methoxycarbonyl)ethyl; 2-(6-(aminomethyl)pyridin-2-yl)ethyl; 2-(acetylamino)ethyl; 2-(amino)ethyl; 2-(aminocarbonyl)-2-(acetylamino)-eth-1-yl; 2-(aminocarbonyl)-2-(amino)-eth-1-yl; 2-(aminocarbonyl)ethyl; 2-(aminomethyl)pyridin-5-ylmethyl; 2-(carboxy)-2-(amino)-eth-1-yl; 2-(dimethylamino)ethyl; 2-(dimethylaminocarbonyl)-2-(amino)-eth-1-yl; 2-(ethoxycarbonyl)ethyl; 2-(methoxycarbonyl)-2-(acetylamino)-eth-1-yl; 2-(methoxycarbonyl)-2-(amino)-eth-1-yl; 2-(methoxycarbonylamino)ethyl; 2-(methylamino)ethyl; 2-(methylaminocarbonyl)-2-(acetylamino)-eth-1-yl; 2-(methylaminocarbonyl)-2-(amino)-eth-1-yl; 2-(methylsulfonamido)ethyl; 2-(methyoxycarbonyl)-2-(amino)-eth-1-yl; 2-(N-(t-butoxycarbonyl)-N-(methyl)-amino)ethyl; 2-(piperazin-1-yl)ethyl; 2-(pyrazin-2-yl)ethyl; 2-(pyridin-2-yl)ethyl; 2-(pyridin-3-yl)ethyl; 2-(t-butoxycarbonylaminomethyl)pyridin-3-ylmethyl; 2-(t-butoxycarbonylaminomethyl)pyridin-6-ylmethyl; 2-(trifluoromethyl)-pyridin-6-ylmethyl; 2-aminopyridin-3-ylmethyl; 2-aminopyridin-5-ylmethyl; 2-chloropyridin-5-ylmethyl; 2-cyanopyridin-5-ylmethyl; 2-hydroxy-3-amino-prop-1-yl; 2-hydroxyethyl; 2-methoxyeth-1-yl; 2-methoxypyridin-3-ylmethyl; 2-methoxypyridin-5-ylmethyl; 2-methylpyridin-3-ylmethyl; 2-methylpyridin-5-ylmethyl; 2-methylpyridin-6-ylmethyl; 3-(2-aminoethyl)cyclohexyl)methyl; 3-(4-methylpiperazin-1-yl)propyl; 3-(amino)-3-(methylaminocarbonyl)prop-1-yl; 3-(aminocarbonyl)propyl; 3-(aminomethyl)benzyl; 3-(aminomethyl)pyridin-2-ylmethyl; 3-(methoxycarbonyl)propyl; 3-(methylaminocarbonyl)propyl; 3-(trifluoromethyl)-pyridin-2-ylmethyl; 3,4-difluorobenzyl; 3-aminomethylpyridin-4-ylmethyl; 3-aminopropyl; 3-carbamoylcyclopentyl; 3-carboxypropyl; 3-hydroxypropyl; 3-methoxypropyl; 4-(aminomethyl)-pyridin-2-ylmethyl; 4-(N,N-dimethylamino)pyridin-3-ylmethyl; 4-(t-butoxycarbonylamino)-morpholinomethyl; 4-aminobutyl; 4-aminomethylpyridin-3-ylmethyl; 4-cyanobenzyl; 4-fluorobenzyl; 4-methylaminopyridin-3-ylmethyl; 4-methylbenzyl; 4-morpholinopyridin-3-ylmethyl; 4-piperazinylpyridin-3-ylmethyl; 5-((bis(dimethylamino)methylamino)methyl)pyridin-3-ylmethyl; 5-(aminomethyl)pyridin-2-ylmethyl; 5-(aminomethyl)pyridin-3-ylmethyl; 5-(hydroxymethyl)pyridin-3-ylmethyl; 5-(t-butoxycarbonylaminomethyl)-pyridin-2-ylmethyl; 5-(trifluoromethyl)-pyridin-2-ylmethyl; 5-aminopentyl; 5-aminopyridin-2-ylmethyl; 6-((bis(dimethylamino)methyleneamino)methyl)pyridin-2-yl)methyl; 6-(4-acetylpiperazin-1-yl)pyridin-3-ylmethyl); 6-(aminomethyl)pyridin-2-yl)methyl; 6-aminohexyl; aminocarbonylmethyl; benzyl; cyclopropylmethyl; dimethylaminocarbonylmethyl; isopropyl; isoxazol-5-ylmethyl; methoxycarbonylmethyl; methyl; methylaminocarbonylmethyl; oxazol-2-ylmethyl; piperidin-4-ylmethyl; prop-2-en-1-yl; pyrazin-2-ylmethyl; pyridin-2-ylmethyl; pyridin-2-ylmethyl-N-oxide; pyridin-3-ylmethyl; pyridin-3-ylmethyl-N-oxide; pyridin-4-ylmethyl; thiophen-2-ylmethyl; and thiophen-3-ylmethyl.

In certain embodiments of compounds of Formula II, $Z^3$ is chosen from —$(CH_2)_r R^{20}$ wherein r is chosen from 1, 2, and 3 and $R^{20}$ is chosen from optionally substituted aryl and optionally substituted heteroaryl.

In certain embodiments of compounds of Formula II, $Z^3$ is chosen from 2-(3-methylphenyl)ethyl, 2-(1H-imidazol-4-yl)ethyl, 2-(1-methyl-1H-imidazol-4-yl)ethyl, 2-(2,3-difluorophenyl)ethyl, 2-(2,5-difluorophenyl)ethyl, 2-(2,6-difluorophenyl)ethyl, 2-(2-chlorophenyl)ethyl, 2-(2-cyanophenyl)ethyl, 2-(2-fluorophenyl)ethyl, 2-(2-hydroxyphenyl)ethyl, 2-(2-methoxyphenyl)ethyl, 2-(2-methylphenyl)ethyl, 2-(3-(trifluoromethyl)phenyl)ethyl, 2-(3,4-difluorophenyl)ethyl, 2-(3,5-difluorophenyl)ethyl, 2-(3,5-dimethyl-1H-pyrazol-1-yl)ethyl, 2-(3,5-dimethyl-1H-pyrazol-4-yl)ethyl, 2-(3-carbamoylphenyl)ethyl, 2-(3-carboxyphenyl)ethyl, 2-(3-cyanophenyl)ethyl, 2-(3-fluorophenyl)-2-(hydroxy)-ethyl, 2-(3-fluorophenyl)ethyl, 2-(3-fluoropyridin-2-yl)ethyl, 2-(3-methoxycarbonylphenyl)ethyl, 2-(3-methoxyphenyl)ethyl, 2-(3-methylphenyl)ethyl, 2-(4-aminophenyl)ethyl, 2-(4-chlorophenyl)ethyl, 2-(4-fluorophenyl)ethyl, 2-(4-hydroxyphenyl)ethyl, 2-(benzo[d][1,3]dioxol-5-yl)ethyl, 2-(furan-2-yl)ethyl, 2-(hydroxy)-2-(phenyl)ethyl, 2-(phenyl)ethyl, 2-(pyridin-2-yl)ethyl, 2-(pyridin-3-yl)ethyl, 2-(thiophen-2-yl)ethyl, 2-phenylprop-1-yl, 3-(1H-imidazol-1-yl)prop-1-yl, 3-phenylpropyl, benzyl, pyridin-2-ylmethyl, pyridin-3-ylmethyl, and thiophen-3-ylmethyl.

In certain embodiments of compounds of Formula II, $Z^3$ is 2-(pyridin-2-yl)ethyl.

In certain embodiments of compounds of Formula II, $Z^1$ is chosen from aryl optionally substituted by one or two groups selected from cyano, halo, hydroxy, formyl, optionally substituted alkyl, optionally substituted alkenyl, optionally substituted alkoxy, carboxyl, optionally substituted alkoxycarbonyl, optionally substituted acyl, optionally substituted aminocarbonyl, optionally substituted amino, optionally substituted heterocycloalkyl, optionally substituted heteroaryl, optionally substituted carbamimidoyl, and optionally substituted sulfonyl. In certain embodiments of compounds of Formula II, $Z^1$ is chosen from phenyl optionally substituted by one or two groups selected from cyano, halo, hydroxy, formyl, optionally substituted lower alkyl, lower alkenyl, lower alkoxy, carboxyl, optionally substituted lower alkoxycarbonyl, lower acyl, dialkylamino, acetylamino, carbamimidoyl optionally substituted with cyano, aralkyl, and heteroaralkyl, and aminocarbonyl. In certain embodiments of compounds of Formula II, $Z^1$ is chosen from phenyl, 2-aminocarbonylphenyl, 2-fluorophenyl, 2-chlorophenyl, 2-hydroxyphenyl, 2-methylphenyl, 2-methoxyphenyl, 2-cyanophenyl, 2-cyanomethylphenyl, 2-vinylphenyl, 2-formylphenyl, 3,4-difluorophenyl, 3-methylphenyl, 3-chlorophenyl, 3-fluorophenyl, 3-cyanophenyl, 3-dimethylaminophenyl, 3-methoxyphenyl, 3-methoxymethylphenyl, 3-hydroxyphenyl, 3-trifluoromethylphenyl, 4-aminocarbonylphenyl, 4-fluorophenyl, 4-chlorophenyl, 4-methylphenyl, 4-hydroxyphenyl, 4-cyanophenyl, 4-methoxyphenyl, 4-hydroxymethylphenyl, 4-trifluoromethylphenyl, 4-methoxycarbonylphenyl, 4-dimethylaminophenyl, 4-acetylphenyl, 4-carboxyphenyl, 4-ethylphenyl, 4-acetylaminophenyl, 3,4-dichlorophenyl, 3,4-difluorophenyl, 2,3-dimethylphenyl, 2,5-dimethylphenyl, 2,4-dimethylphenyl, 3,5-dimethylphenyl, 3,4-dimethylphenyl, 2-chloro-4-fluoro-phenyl, 2-cyano-4-fluoro-phenyl, 2-chloro-6-fluoro-phenyl, 2-chloro-4-methoxy-phenyl, 2-cyano-4-methoxy-phenyl, 2-cyano-6-fluorophenyl, 2-chloro-5-fluoro-phenyl, 2-cyano-5-fluoro-phenyl, 2-chloro-4-methylphenyl, 2-chloro-4-hydroxymethyl-phenyl, 2-(N-(pyridin-3-ylmethyl)carbamimidoyl)phenyl, and 2-cyano-4-methylphenyl.

In certain embodiments of compounds of Formula II, R' is chosen from hydrogen and optionally substituted lower alkyl. In certain embodiments of compounds of Formula II, $R^1$ is chosen from hydrogen and lower alkyl. In certain embodiments of compounds of Formula II, $R^1$ is chosen from hydrogen and methyl. In certain embodiments of compounds of Formula II, $R^1$ is hydrogen.

Provided is at least one chemical entity chosen from compounds of Formula III

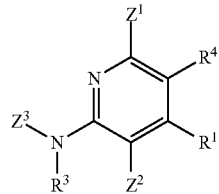

Formula III and pharmaceutically acceptable salts thereof wherein
$R^1$ and $R^4$ are independently chosen from hydrogen, optionally substituted acyl, optionally substituted alkyl, cyano, halo, azido, optionally substituted amino, optionally substituted alkoxycarbonyl, optionally substituted aminocarbonyl, sulfonyl, sulfinyl, and sulfanyl;
$Z^1$ is optionally substituted heteroaryl;
$Z^2$ is chosen from hydrogen, optionally substituted amidino, carboxyl, optionally substituted alkoxy carbonyl, optionally substituted acyl, optionally substituted alkenyl, optionally substituted alkyl, and optionally substituted aminocarbonyl;
$Z^3$ is chosen from optionally substituted aralkyl and optionally substituted heteroaralkyl; and
$R^3$ is chosen from hydrogen and optionally substituted alkyl.

In certain embodiments of compounds of Formula III, $Z^1$ is chosen from heteroaryl optionally substituted by one or two groups selected from cyano, halo, hydroxy, formyl, optionally substituted alkyl, optionally substituted alkenyl, optionally substituted alkoxy, carboxyl, optionally substituted alkoxycarbonyl, optionally substituted acyl, optionally substituted aminocarbonyl, optionally substituted heterocycloalkyl, optionally substituted heteroaryl, optionally substituted carbamimidoyl, and optionally substituted sulfonyl.

In certain embodiments of compounds of Formula III, $Z^1$ is chosen from 1H-pyrazol-3-yl; 1H-pyrazol-4-yl; 1H-tetrazol-5-yl; 1-methyl-1H-pyrazol-4-yl; 1-methyl-1H-pyrazol-5-yl; 2-(hydroxymethyl)thiophen-3-yl; 2,2'-bipyridine; 2,3'-bipyridine; 2,4'-bipyridine; 2-cyanothiophen-3-yl; 2-formylthiophen-3-yl; 3-(hydroxymethyl)thiophen-2-yl; 3-cyano-1-methyl-1H-pyrazol-4-yl; 3-formylthiophen-2-yl; 4-cyanothiophen-3-yl; 4-methylthiophen-2-yl; 4-methylthiophen-3-yl; 5-(1-hydroxyethyl)thiophen-2-yl; 5-(aminomethyl)thiophen-2-yl; 5-(hydroxymethyl)thiophen-2-yl; 5-(hydroxymethyl)thiophen-3-yl; 5-acetylthiophen-2-yl; 5-cyano-1H-pyrazol-4-yl; 5-cyano-1-methyl-1H-pyrazol-4-yl; 5-cyanothiophen-2-yl; 5-formylthiophen-2-yl; 5-formylthiophen-3-yl; 3-(aminomethyl)thiophen-2-yl; isoxazol-4-yl; thiazol-2-yl; thiophen-2-yl; and thiophen-3-yl.

In certain embodiments of compounds of Formula III, $Z^2$ is chosen from carboxyl, optionally substituted alkoxycarbonyl, optionally substituted acyl, optionally substituted alkenyl, and optionally substituted alkyl.

In certain embodiments of compounds of Formula III, $Z^2$ is chosen from carboxyl, optionally substituted piperidinylcarbonyl, optionally substituted pyridinylcarbonyl, optionally substituted lower alkyl, optionally substituted lower alkenyl, and lower alkoxycarbonyl.

In certain embodiments of compounds of Formula III, $Z^2$ is chosen from 2-(methylamino)-2-oxoethyl, 2-amino-2-oxoethyl, 3-amino-3-oxopropyl, (2-(N-acetylaminomethyl)piperidin-1-yl)carbonyl; (2-aminomethylpiperidin-1-yl)carbonyl; 1-hydroxy-2-amino-ethyl; 2-((methylsulfonamido)methyl)piperidin-1-ylcarbonyl; 2-(methylaminocarbonyl)ethenyl; 2-(pyridin-3-ylmethyl)-2H-tetrazol-5-yl; aminomethyl; carboxyl; methoxycarbonyl; pyridin-2-ylcarbonyl; pyridin-3-ylcarbonyl; and pyridin-4-ylcarbonyl.

In certain embodiments of compounds of Formula III, $R^3$ is chosen from hydrogen and optionally substituted lower alkyl. In certain embodiments of compounds of Formula III, $R^3$ is chosen from hydrogen and lower alkyl. In certain embodiments of compounds of Formula III, $R^3$ is chosen from hydrogen and methyl. In certain embodiments of compounds of Formula III, $R^3$ is hydrogen.

In certain embodiments of compounds of Formula III, $R^4$ is chosen from hydrogen, cyano, halo, azido, optionally substituted aminocarbonyl, and optionally substituted alkyl. In certain embodiments of compounds of Formula III, $R^4$ is chosen from hydrogen, cyano, chloro, bromo, fluoro, azido, optionally substituted alkylaminocarbonyl, and optionally substituted methyl. In certain embodiments of compounds of Formula III, $R^4$ is chosen from hydrogen, cyano, chloro, bromo, azido, pyridin-3-ylmethylaminocarbonyl, aminomethyl, and hydroxymethyl. In certain embodiments of compounds of Formula III, $R^4$ is hydrogen.

In certain embodiments of compounds of Formula III, $Z^2$ is —C(O)NR$^2$R$^5$ wherein $R^2$ is chosen from optionally substituted alkyl and optionally substituted cycloalkyl; and $R^5$ is chosen from hydrogen and optionally substituted alkyl.

In certain embodiments of compounds of Formula III, $R^2$ is chosen from optionally substituted methyl, optionally substituted ethyl, optionally substituted propyl, optionally substituted butyl, optionally substituted pentyl, optionally substituted hexyl, optionally substituted cyclopropyl, optionally substituted cyclopentyl, and optionally substituted cyclohexyl where each optionally substituted group is optionally substituted with one, two or three groups selected from optionally substituted aryl, optionally substituted heteroaryl, optionally substituted heterocycloalkyl, optionally substituted cycloalkyl, optionally substituted aminocarbonyl, optionally substituted amino, hydroxy, carboxyl, optionally substituted alkoxycarbonyl, and optionally substituted alkoxy.

In certain embodiments of compounds of Formula III, $R^2$ is chosen from methyl and ethyl, where the methyl and ethyl groups are optionally substituted with one or two groups selected from optionally substituted aryl, optionally substituted heteroaryl, optionally substituted heterocycloalkyl, optionally substituted cycloalkyl, optionally substituted aminocarbonyl, optionally substituted amino, hydroxy, carboxyl, optionally substituted alkoxycarbonyl, and optionally substituted alkoxy.

In certain embodiments of compounds of Formula III, $R^2$ is chosen from (1-(2-aminoethyl)-1H-pyrazol-3-yl)methyl; (1-(methylsulfonyl)piperidin-3-yl)methyl; (1-acetylpiperidin-3-yl)methyl; (1-acetylpyrrolidin-2-yl)methyl; (1H-imidazol-2-yl)methyl; (1H-pyrazol-3-yl)methyl; (1-methyl-1H-pyrazol-3-yl)methyl; (1-methyl-1H-pyrazol-5-yl)methyl; (2-(aminocarbonyl)ethylamino)carbonylmethyl; (2-(aminomethyl)pyridin-3-yl)methyl; (2-(carboxy)ethylamino)carbonylmethyl; (2-(dimethylamino)ethylamino)carbonylmethyl; (2-(hydroxy)ethylamino)carbonylmethyl; (2-(methylamino)ethylamino)carbonylmethyl; (2-(N-methyl-N-(t-butoxycarbonyl)-amino)ethylamino)carbonylmethyl; (2-oxopiperidin-3-yl)methyl; (3-(dimethylamino)propylamino)carbonylmethyl; (3-(hydroxy)ethylamino)carbonylmethyl; (3-(t-butoxycarbonylamino)propylamino)carbonylmethyl; (4-(aminomethyl)pyridin-2-yl)methyl; (5-(aminomethyl)pyridin-2-yl)methyl; (6-((1,3-dioxoisoindolin-2-yl)methyl)pyridin-2-yl)methyl; (6-(2-aminoethylamino)pyridin-2-yl)methyl; (6-(3-aminopropylamino)pyridin-2-yl)methyl; (6-(aminomethyl) pyridin-2-yl)methyl; (6-(hydroxymethyl)pyridin-2-yl)methyl; (6-bromopyridin-2-yl)methyl; (methylsulfonamido)carbonylmethyl; (pyridin-2-yl)ethylamino; 1-(2-(tert-butoxycarbonylamino)ethyl)-1H-pyrazol-3-ylmethyl; 1-(2-(tert-butoxycarbonylamino)ethyl)-1H-pyrazol-5-ylmethyl; 1-(aminocarbonyl)-2-(amino)-eth-1-yl; 1-(aminocarbonyl)-3-(amino)-propyl; 1-(aminocarbonyl)-4-(amino)-butyl; 1-(aminocarbonyl)-4-(benzyloxycarbonylamino)-pentyl; 1-(aminocarbonyl)-5-(amino)-pentyl; 1-(aminocarbonyl)eth-1-yl; 1-(carboxy)-2-(amino)-eth-1-yl; 1-(dimethylaminocarbonyl)-2-(amino)-eth-1-yl; 1-(hydroxy)-2-(aminocarbonylmethylamino)eth-1-yl; 1-(hydroxy)-2-(ethoxycarbonylmethylamino)eth-1-yl; 1-(hydroxy)-2-(pyridin-2-ylmethylamino)eth-1-yl; 1-(methoxycarbonyl)-2-(amino)-eth-1-yl; 1-(methoxycarbonyl)-2-(t-butoxycarbonylamino)-eth-1-yl; 1-(methoxycarbonyl)eth-1-yl; 1-(methylaminocarbonyl)-2-(amino)-eth-1-yl (2 occ); 1-(methylaminocarbonyl)eth-1-yl; 1-aminocarbonyl-2-hydroxy-eth-1-yl; 1-methoxycarbonyl-2-hydroxy-eth-1-yl; 2-(2-aminoethoxy)ethyl; 2-(2-aminoethyl)-pyridin-6-ylmethyl; 2-(2-aminoethylamino)ethyl; 2-(3-fluorophenyl)ethyl; 2-(3-methoxycarbonyl)ethyl; 2-(6-(aminomethyl)pyridin-2-yl)ethyl; 2-(acetylamino)ethyl; 2-(amino)ethyl; 2-(aminocarbonyl)-2-(acetylamino)-eth-1-yl; 2-(aminocarbonyl)-2-(amino)-eth-1-yl; 2-(aminocarbonyl)ethyl; 2-(aminomethyl)pyridin-5-ylmethyl; 2-(carboxy)-2-(amino)-eth-1-yl; 2-(dimethylamino)ethyl; 2-(dimethylaminocarbonyl)-2-(amino)-eth-1-yl; 2-(ethoxycarbonyl)ethyl; 2-(methoxycarbonyl)-2-(acetylamino)-eth-1-yl; 2-(methoxycarbonyl)-2-(amino)-eth-1-yl; 2-(methoxycarbonylamino)ethyl; 2-(methylamino)ethyl; 2-(methylaminocarbonyl)-2-(acetylamino)-eth-1-yl; 2-(methylaminocarbonyl)-2-(amino)-eth-1-yl; 2-(methylsulfonamido)ethyl; 2-(methyoxycarbonyl)-2-(amino)-eth-1-yl; 2-(N-(t-butoxycarbonyl)-N-(methyl)-amino)ethyl; 2-(piperazin-1-yl)ethyl; 2-(pyrazin-2-yl)ethyl; 2-(pyridin-2-yl)ethyl; 2-(pyridin-3-yl)ethyl; 2-(t-butoxycarbonylaminomethyl)pyridin-3-ylmethyl; 2-(t-butoxycarbonylaminomethyl)pyridin-6-ylmethyl; 2-(trifluoromethyl)-pyridin-6-ylmethyl; 2-aminopyridin-3-ylmethyl; 2-aminopyridin-5-ylmethyl; 2-chloropyridin-5-ylmethyl; 2-cyanopyridin-5-ylmethyl; 2-hydroxy-3-amino-prop-1-yl; 2-hydroxyethyl; 2-methoxyeth-1-yl; 2-methoxypyridin-3-ylmethyl; 2-methoxypyridin-5-ylmethyl; 2-methylpyridin-3-ylmethyl; 2-methylpyridin-5-ylmethyl; 2-methylpyridin-6-ylmethyl; 3-(2-aminoethyl)cyclohexyl)methyl; 3-(4-methylpiperazin-1-yl)propyl; 3-(amino)-3-(methylaminocarbonyl)prop-1-yl; 3-(aminocarbonyl)propyl; 3-(aminomethyl)benzyl; 3-(aminomethyl)pyridin-2-ylmethyl; 3-(methoxycarbonyl)propyl; 3-(methylaminocarbonyl)propyl; 3-(trifluoromethyl)-pyridin-2-ylmethyl; 3,4-difluorobenzyl; 3-aminomethylpyridin-4-ylmethyl; 3-aminopropyl; 3-carbamoylcyclopentyl; 3-carboxypropyl; 3-hydroxypropyl; 3-methoxypropyl; 4-(aminomethyl)-pyridin-2-ylmethyl; 4-(N,N-dimethylamino)pyridin-3-ylmethyl; 4-(t-butoxycarbonylamino)-morpholinomethyl; 4-aminobutyl; 4-aminomethylpyridin-3-ylmethyl; 4-cyanobenzyl; 4-fluorobenzyl; 4-methylaminopyridin-3-ylmethyl; 4-methylbenzyl; 4-morpholinopyridin-3-ylmethyl; 4-piperazinylpyridin-3-ylmethyl; 5-((bis(dimethylamino)methylamino)methyl)pyridin-3-ylmethyl; 5-(aminomethyl)pyridin-2-ylmethyl; 5-(aminomethyl)pyridin-3-ylmethyl; 5-(hydroxymethyl)pyridin-3-ylmethyl; 5-(t-butoxycarbonylaminomethyl)-pyridin-2-ylmethyl; 5-(trifluoromethyl)-pyridin-2-ylmethyl; 5-aminopentyl; 5-aminopyridin-2-ylmethyl; 6-((bis(dimethylamino)methyleneamino)methyl)pyridin-2-yl)methyl; 6-(4-acetylpiperazin-1-yl)pyridin-3-ylmethyl); 6-(aminomethyl)pyridin-2-yl)methyl;

6-aminohexyl; aminocarbonylmethyl; benzyl; cyclopropylmethyl; dimethylaminocarbonylmethyl; isopropyl; isoxazol-5-ylmethyl; methoxycarbonylmethyl; methyl; methylaminocarbonylmethyl; oxazol-2-ylmethyl; piperidin-4-ylmethyl; prop-2-en-1-yl; pyrazin-2-ylmethyl; pyridin-2-ylmethyl; pyridin-2-ylmethyl-N-oxide; pyridin-3-ylmethyl; pyridin-3-ylmethyl-N-oxide; pyridin-4-ylmethyl; thiophen-2-ylmethyl; and thiophen-3-ylmethyl.

In certain embodiments of compounds of Formula III, $Z^3$ is chosen from —$(CH_2)_rR^{20}$ wherein r is chosen from 1, 2, and 3 and $R^{20}$ is chosen from optionally substituted aryl and optionally substituted heteroaryl.

In certain embodiments of compounds of Formula III, $Z^3$ is chosen from 2-(3-methylphenyl)ethyl, 2-(1H-imidazol-4-yl)ethyl, 2-(1-methyl-1H-imidazol-4-yl)ethyl, 2-(2,3-difluorophenyl)ethyl, 2-(2,5-difluorophenyl)ethyl, 2-(2,6-difluorophenyl)ethyl, 2-(2-chlorophenyl)ethyl, 2-(2-cyanophenyl)ethyl, 2-(2-fluorophenyl)ethyl, 2-(2-hydroxyphenyl)ethyl, 2-(2-methoxyphenyl)ethyl, 2-(2-methylphenyl)ethyl, 2-(3-(trifluoromethyl)phenyl)ethyl, 2-(3,4-difluorophenyl)ethyl, 2-(3,5-difluorophenyl)ethyl, 2-(3,5-dimethyl-1H-pyrazol-1-yl)ethyl, 2-(3,5-dimethyl-1H-pyrazol-4-yl)ethyl, 2-(3-carbamoylphenyl)ethyl, 2-(3-carboxyphenyl)ethyl, 2-(3-cyanophenyl)ethyl, 2-(3-fluorophenyl)-2-(hydroxy)-ethyl, 2-(3-fluorophenyl)ethyl, 2-(3-fluoropyridin-2-yl)ethyl, 2-(3-methoxycarbonylphenyl)ethyl, 2-(3-methoxyphenyl)ethyl, 2-(3-methylphenyl)ethyl, 2-(4-aminophenyl)ethyl, 2-(4-chlorophenyl)ethyl, 2-(4-fluorophenyl)ethyl, 2-(4-hydroxyphenyl)ethyl, 2-(benzo[d][1,3]dioxol-5-yl)ethyl, 2-(furan-2-yl)ethyl, 2-(hydroxy)-2-(phenyl)ethyl, 2-(phenyl)ethyl, 2-(pyridin-2-yl)ethyl, 2-(pyridin-3-yl)ethyl, 2-(thiophen-2-yl)ethyl, 2-phenylprop-1-yl, 3-(1H-imidazol-1-yl)prop-1-yl, 3-phenylpropyl, benzyl, pyridin-2-ylmethyl, pyridin-3-ylmethyl, and thiophen-3-ylmethyl.

In certain embodiments of compounds of Formula III, $Z^3$ is chosen from 3-fluorophenethyl, 3,5-difluorophenethyl, and 2-(pyridin-2-yl)ethyl. In certain embodiments of compounds of Formula III, $Z^3$ is 2-(pyridin-2-yl)ethyl.

In certain embodiments of compounds of Formula III, $R^1$ is chosen from hydrogen and optionally substituted lower alkyl. In certain embodiments of compounds of Formula III, $R^1$ is chosen from hydrogen and lower alkyl. In certain embodiments of compounds of Formula III, $R^1$ is chosen from hydrogen and methyl. In certain embodiments of compounds of Formula III, $R^1$ is hydrogen.

Provided is at least one chemical entity chosen from compounds of Formula IV

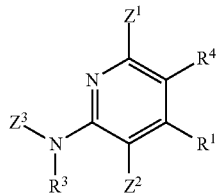

Formula IV and pharmaceutically acceptable salts thereof wherein
$R^1$ and $R^4$ are independently chosen from hydrogen, optionally substituted acyl, optionally substituted alkyl, cyano, halo, azido, optionally substituted amino, optionally substituted alkoxycarbonyl, optionally substituted aminocarbonyl, sulfonyl, sulfinyl, and sulfanyl;
$Z^1$ is chosen from optionally substituted aryl and optionally substituted heteroaryl;
$Z^2$ is chosen from hydrogen, carboxyl, optionally substituted alkoxy carbonyl, optionally substituted acyl, optionally substituted alkenyl, optionally substituted alkyl, optionally substituted amidino, and optionally substituted aminocarbonyl;
$Z^3$ is optionally substituted alkyl; and
$R^3$ is chosen from hydrogen and optionally substituted alkyl.

In certain embodiments of compounds of Formula IV, $Z^1$ is chosen from aryl optionally substituted by one or two groups selected from cyano, halo, hydroxy, formyl, optionally substituted alkyl, optionally substituted alkenyl, optionally substituted alkoxy, carboxyl, optionally substituted alkoxycarbonyl, optionally substituted acyl, optionally substituted aminocarbonyl, optionally substituted amino optionally substituted heterocycloalkyl, optionally substituted heteroaryl, optionally substituted carbamimidoyl, and optionally substituted sulfonyl, and heteroaryl optionally substituted by one or two groups selected from cyano, halo, hydroxy, formyl, optionally substituted alkyl, optionally substituted alkenyl, optionally substituted alkoxy, carboxyl, optionally substituted alkoxycarbonyl, optionally substituted acyl, optionally substituted aminocarbonyl, optionally substituted heterocycloalkyl, optionally substituted heteroaryl, optionally substituted carbamimidoyl, and optionally substituted sulfonyl.

In certain embodiments of compounds of Formula IV, $Z^1$ is chosen from aryl optionally substituted by one or two groups selected from cyano, halo, hydroxy, formyl, optionally substituted lower alkyl, optionally substituted lower alkenyl, optionally substituted lower alkoxy, carboxyl, optionally substituted lower alkoxycarbonyl, optionally substituted lower acyl, optionally substituted aminocarbonyl, optionally substituted heterocycloalkyl, optionally substituted heteroaryl, and amino optionally substituted with alkyl, and heteroaryl optionally substituted by one or two groups selected from optionally substituted by one or two groups selected from cyano, halo, hydroxy, formyl, optionally substituted lower alkyl, optionally substituted lower alkenyl, optionally substituted lower alkoxy, carboxyl, optionally substituted lower alkoxycarbonyl, optionally substituted lower acyl, optionally substituted aminocarbonyl, optionally substituted heterocycloalkyl, optionally substituted heteroaryl, and amino optionally substituted with alkyl.

In certain embodiments of compounds of Formula IV, $Z^1$ is chosen from phenyl, 1H-pyrazol-3-yl; 1H-pyrazol-4-yl; 1H-tetrazol-5-yl; 1-methyl-1H-pyrazol-4-yl; 1-methyl-1H-pyrazol-5-yl; 2-aminomethylthiophen-5-yl; 2-cyanothiophen-3-yl; 2-formylthiophen-3-yl; 2-formylthiophen-4-yl; 2H-pyrrol-1(5H)-yl; 2-hydroxymethylthiophen-3-yl; 2-hydroxymethylthiophen-4-yl; 2-hydroxymethylthiophen-5-yl; 3-aminomethylthiophen-2-yl; 3-cyano-1-methyl-1H-pyrazol-4-yl; 3-cyanothiophen-4-yl; 3-formylthiophen-2-yl; 3-hydroxymethylthiophen-2-yl; 4-methylthiophen-2-yl; 4-methylthiophen-3-yl; 5-(1-hydroxyeth-1-yl)-thiophen-2-yl; 5-acetylthiophen-5-yl; 5-cyano-1H-pyrazol-4-yl; 5-cyano-1-methyl-1H-pyrazol-4-yl; 5-cyanothiophen-2-yl; 5-formylthiophen-2-yl; 5-hydroxymethylthiophen-2-yl; isoxazol-4-yl; pyridin-2-yl; pyridin-3-yl; pyridin-4-yl; thiazol-2-yl; thiophen-2-yl; and thiophen-3-yl. In certain embodiments of compounds of Formula IV, $Z^1$ is phenyl.

In certain embodiments of compounds of Formula IV, $Z^2$ is chosen from carboxyl, optionally substituted alkoxycarbonyl, optionally substituted acyl, optionally substituted alkenyl, and optionally substituted alkyl.

In certain embodiments of compounds of Formula IV, $Z^2$ is chosen from carboxyl, optionally substituted pyridinylmethylcarbonyl, optionally substituted piperidinylcarbonyl, optionally substituted pyridinylcarbonyl, optionally substituted lower alkyl, optionally substituted lower alkenyl, and lower alkoxycarbonyl.

In certain embodiments of compounds of Formula IV, $Z^2$ is chosen from pyridin-3-ylmethylcarbonyl, (2-(N-acetylaminomethyl)piperidin-1-yl)carbonyl; (2-aminomethylpiperidin-1-yl)carbonyl; 1-hydroxy-2-amino-ethyl; 2-((methylsulfonamido)methyl)piperidin-1-ylcarbonyl; 2-(methylaminocarbonyl)ethenyl; 2-(pyridin-3-ylmethyl)-2H-tetrazol-5-ylmethyl; aminomethyl; carboxyl; methoxycarbonyl; pyridin-2-ylcarbonyl; pyridin-3-ylcarbonyl; and pyridin-4-ylcarbonyl.

In certain embodiments of compounds of Formula IV, $Z^2$ is —C(O)NR$^2$R$^5$ wherein R$^2$ is chosen from optionally substituted alkyl and optionally substituted cycloalkyl; and R$^5$ is chosen from hydrogen and optionally substituted alkyl.

In certain embodiments of compounds of Formula IV, R$^2$ is chosen from optionally substituted methyl, optionally substituted ethyl, optionally substituted propyl, optionally substituted butyl, optionally substituted pentyl, optionally substituted hexyl, optionally substituted cyclopropyl, optionally substituted cyclopentyl, and optionally substituted cyclohexyl where each optionally substituted group is optionally substituted with one, two or three groups selected from optionally substituted aryl, optionally substituted heteroaryl, optionally substituted heterocycloalkyl, optionally substituted cycloalkyl, optionally substituted aminocarbonyl, optionally substituted amino, hydroxy, carboxyl, optionally substituted alkoxycarbonyl, and optionally substituted alkoxy.

In certain embodiments of compounds of Formula IV, R$^2$ is chosen from methyl and ethyl, where the methyl and ethyl groups are optionally substituted with one or two groups selected from optionally substituted aryl, optionally substituted heteroaryl, optionally substituted heterocycloalkyl, optionally substituted cycloalkyl, optionally substituted aminocarbonyl, optionally substituted amino, hydroxy, carboxyl, optionally substituted alkoxycarbonyl, and optionally substituted alkoxy.

In certain embodiments of compounds of Formula IV, R$^2$ is chosen from (1-(2-aminoethyl)-1H-pyrazol-3-yl)methyl; (1-(methylsulfonyl)piperidin-3-yl)methyl; (1-acetylpiperidin-3-yl)methyl; (1-acetylpyrrolidin-2-yl)methyl; (1H-imidazol-2-yl)methyl; (1H-pyrazol-3-yl)methyl; (1-methyl-1H-pyrazol-3-yl)methyl; (1-methyl-1H-pyrazol-5-yl)methyl; (2-(aminocarbonyl)ethylamino)carbonylmethyl; (2-(aminomethyl)pyridin-3-yl)methyl; (2-(carboxy)ethylamino)carbonylmethyl; (2-(dimethylamino)ethylamino)carbonylmethyl; (2-(hydroxy)ethylamino)carbonylmethyl; (2-(methylamino)ethylamino)carbonylmethyl; (2-(N-methyl-N-(t-butoxycarbonyl)-amino)ethylamino)carbonylmethyl; (2-oxopiperidin-3-yl)methyl; (3-(dimethylamino)propylamino)carbonylmethyl; (3-(hydroxy)ethylamino)carbonylmethyl; (3-(t-butoxycarbonylamino)propylamino)carbonylmethyl; (4-(aminomethyl)pyridin-2-yl)methyl; (5-(aminomethyl)pyridin-2-yl)methyl; (6-((1,3-dioxoisoindolin-2-yl)methyl)pyridin-2-yl)methyl; (6-(2-aminoethylamino)pyridin-2-yl)methyl; (6-(3-aminopropylamino)pyridin-2-yl)methyl; (6-(aminomethyl)pyridin-2-yl)methyl; (6-(hydroxymethyl)pyridin-2-yl)methyl; (6-bromopyridin-2-yl)methyl; (methylsulfonamido)carbonylmethyl; (pyridin-2-yl)ethylamino; 1-(2-(tert-butoxycarbonylamino)ethyl)-1H-pyrazol-3-ylmethyl; 1-(2-(tert-butoxycarbonylamino)ethyl)-1H-pyrazol-5-ylmethyl; 1-(aminocarbonyl)-2-(amino)-eth-1-yl; 1-(aminocarbonyl)-3-(amino)-propyl; 1-(aminocarbonyl)-4-(amino)-butyl; 1-(aminocarbonyl)-4-(benzyloxycarbonylamino)-pentyl; 1-(aminocarbonyl)-5-(amino)-pentyl; 1-(aminocarbonyl)eth-1-yl; 1-(carboxy)-2-(amino)-eth-1-yl; 1-(dimethylaminocarbonyl)-2-(amino)-eth-1-yl; 1-(hydroxy)-2-(aminocarbonylmethylamino)eth-1-yl; 1-(hydroxy)-2-(ethoxycarbonylmethylamino)eth-1-yl; 1-(hydroxy)-2-(pyridin-2-ylmethylamino)eth-1-yl; 1-(methoxycarbonyl)-2-(amino)-eth-1-yl; 1-(methoxycarbonyl)-2-(t-butoxycarbonylamino)-eth-1-yl; 1-(methoxycarbonyl)eth-1-yl; 1-(methylaminocarbonyl)-2-(amino)-eth-1-yl (2 occ); 1-(methylaminocarbonyl)eth-1-yl; 1-aminocarbonyl-2-hydroxy-eth-1-yl; 1-methoxycarbonyl-2-hydroxy-eth-1-yl; 2-(2-aminoethoxy)ethyl; 2-(2-aminoethyl)-pyridin-6-ylmethyl; 2-(2-aminoethylamino)ethyl; 2-(3-fluorophenyl)ethyl; 2-(3-methoxycarbonyl)ethyl; 2-(6-(aminomethyl)pyridin-2-yl)ethyl; 2-(acetylamino)ethyl; 2-(amino)ethyl; 2-(aminocarbonyl)-2-(acetylamino)-eth-1-yl; 2-(aminocarbonyl)-2-(amino)-eth-1-yl; 2-(aminocarbonyl)ethyl; 2-(aminomethyl)pyridin-5-ylmethyl; 2-(carboxy)-2-(amino)-eth-1-yl; 2-(dimethylamino)ethyl; 2-(dimethylaminocarbonyl)-2-(amino)-eth-1-yl; 2-(ethoxycarbonyl)ethyl; 2-(methoxycarbonyl)-2-(acetylamino)-eth-1-yl; 2-(methoxycarbonyl)-2-(amino)-eth-1-yl; 2-(methoxycarbonylamino)ethyl; 2-(methylamino)ethyl; 2-(methylaminocarbonyl)-2-(acetylamino)-eth-1-yl; 2-(methylaminocarbonyl)-2-(amino)-eth-1-yl; 2-(methylsulfonamido)ethyl; 2-(methyoxycarbonyl)-2-(amino)-eth-1-yl; 2-(N-(t-butoxycarbonyl)-N-(methyl)-amino)ethyl; 2-(piperazin-1-yl)ethyl; 2-(pyrazin-2-yl)ethyl; 2-(pyridin-2-yl)ethyl; 2-(pyridin-3-yl)ethyl; 2-(t-butoxycarbonylaminomethyl)pyridin-3-ylmethyl; 2-(t-butoxycarbonylaminomethyl)pyridin-6-ylmethyl; 2-(trifluoromethyl)-pyridin-6-ylmethyl; 2-aminopyridin-3-ylmethyl; 2-aminopyridin-5-ylmethyl; 2-chloropyridin-5-ylmethyl; 2-cyanopyridin-5-ylmethyl; 2-hydroxy-3-amino-prop-1-yl; 2-hydroxyethyl; 2-methoxyeth-1-yl; 2-methoxypyridin-3-ylmethyl; 2-methoxypyridin-5-ylmethyl; 2-methylpyridin-3-ylmethyl; 2-methylpyridin-5-ylmethyl; 2-methylpyridin-6-ylmethyl; 3-(2-aminoethyl)cyclohexyl)methyl; 3-(4-methylpiperazin-1-yl)propyl; 3-(amino)-3-(methylaminocarbonyl)prop-1-yl; 3-(aminocarbonyl)propyl; 3-(aminomethyl)benzyl; 3-(aminomethyl)pyridin-2-ylmethyl; 3-(methoxycarbonyl)propyl; 3-(methylaminocarbonyl)propyl; 3-(trifluoromethyl)-pyridin-2-ylmethyl; 3,4-difluorobenzyl; 3-aminomethylpyridin-4-ylmethyl; 3-aminopropyl; 3-carbamoylcyclopentyl; 3-carboxypropyl; 3-hydroxypropyl; 3-methoxypropyl; 4-(aminomethyl)-pyridin-2-ylmethyl; 4-(N,N-dimethylamino)pyridin-3-ylmethyl; 4-(t-butoxycarbonylamino)-morpholinomethyl; 4-aminobutyl; 4-aminomethylpyridin-3-ylmethyl; 4-cyanobenzyl; 4-fluorobenzyl; 4-methylaminopyridin-3-ylmethyl; 4-methylbenzyl; 4-morpholinopyridin-3-ylmethyl; 4-piperazinylpyridin-3-ylmethyl; 5-((bis(dimethylamino)methylamino)methyl)pyridin-3-ylmethyl; 5-(aminomethyl)pyridin-2-ylmethyl; 5-(aminomethyl)pyridin-3-ylmethyl; 5-(hydroxymethyl)pyridin-3-ylmethyl; 5-(t-butoxycarbonylaminomethyl)-pyridin-2-ylmethyl; 5-(trifluoromethyl)-pyridin-2-ylmethyl; 5-aminopentyl; 5-aminopyridin-2-ylmethyl; 6-((bis(dimethylamino)methyleneamino)methyl)pyridin-2-yl)methyl; 6-(4-acetylpiperazin-1-yl)pyridin-3-ylmethyl); 6-(aminomethyl)pyridin-2-yl)methyl; 6-aminohexyl; aminocarbonylmethyl; benzyl; cyclopropylmethyl; dimethylaminocarbonylmethyl; isopropyl; isoxazol-5-ylmethyl; methoxycarbonylmethyl; methyl; methylaminocarbonylmethyl; oxazol-2-ylmethyl; piperidin-4-ylmethyl; prop-2-en-1-yl; pyrazin-2-ylmethyl; pyridin-2-ylmethyl; pyridin-2-ylmethyl-N-oxide; pyridin-3-ylmethyl; pyridin-3-ylmethyl-N-oxide; pyridin-4-ylmethyl; thiophen-2-ylmethyl; and thiophen-3-ylmethyl.

In certain embodiments of compounds of Formula IV, $R^2$ is pyridin-3-ylmethyl.

In certain embodiments of compounds of Formula IV, $R^5$ is chosen from hydrogen and lower alkyl. In certain embodiments of compounds of Formula IV, $R^5$ is chosen from hydrogen and methyl. In certain embodiments of compounds of Formula IV, $R^5$ is hydrogen.

In certain embodiments of compounds of Formula IV, $Z^3$ is chosen from optionally substituted cycloalkylalkyl, optionally substituted heterocycloalkylalkyl. In certain embodiments of compounds of Formula IV, $Z^3$ is chosen from —$(CH_2)_r R^{20}$ wherein r is chosen from 1, 2, and 3 and $R^{20}$ is chosen from optionally substituted heterocycloalkyl and optionally substituted cycloalkyl.

In certain embodiments of compounds of Formula IV, $Z^3$ is chosen from (tetrahydrofuran-2-yl)methyl, 1-hydroxycyclohexylmethyl, 2-(1,3-dioxolan-2-yl)ethyl, 2-(1-methylpiperidin-4-yl)ethyl, 2-(2-oxoimidazolidin-1-yl)ethyl, 2-(2-oxopiperidin-1-yl)ethyl, 2-(2-oxopyrrolidin-1-yl)ethyl, 2-cyclohex-1-enylethyl, 2-cyclohexylethyl, and 2-morpholinoethyl.

In certain embodiments of compounds of Formula IV, $R^1$ is chosen from hydrogen and optionally substituted lower alkyl. In certain embodiments of compounds of Formula IV, $R^1$ is chosen from hydrogen and lower alkyl. In certain embodiments of compounds of Formula IV, $R^1$ is chosen from hydrogen and methyl. In certain embodiments of compounds of Formula IV, $R^1$ is hydrogen.

In certain embodiments of compounds of Formula IV, $R^3$ is chosen from hydrogen and optionally substituted lower alkyl. In certain embodiments of compounds of Formula IV, $R^3$ is chosen from hydrogen and lower alkyl. In certain embodiments of compounds of Formula IV, $R^3$ is chosen from hydrogen and methyl. In certain embodiments of compounds of Formula IV, $R^3$ is hydrogen.

In certain embodiments of compounds of Formula IV, $R^4$ is chosen from hydrogen, cyano, halo, azido, optionally substituted aminocarbonyl, and optionally substituted alkyl. In certain embodiments of compounds of Formula IV, $R^4$ is chosen from hydrogen, cyano, chloro, bromo, fluoro, azido, optionally substituted alkylaminocarbonyl, and optionally substituted methyl. In certain embodiments of compounds of Formula IV, $R^4$ is chosen from hydrogen, cyano, chloro, bromo, azido, pyridin-3-ylmethylaminocarbonyl, aminomethyl, and hydroxymethyl. In certain embodiments of compounds of Formula IV, $R^4$ is hydrogen.

In certain embodiments, the compound of Formula I is chosen from

| COMPOUND | CHEMICAL NAME |
|---|---|
| 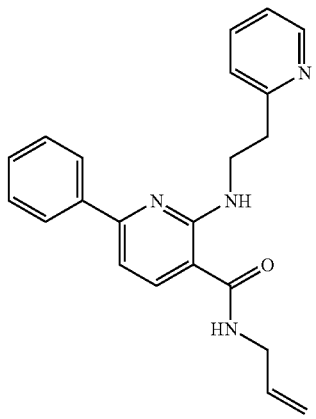 | {6-phenyl-2-[(2-(2-pyridyl)ethyl)amino](3-pyridyl)}-N-prop-2-enylcarboxamide |
| 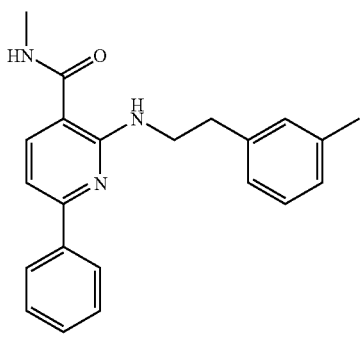 | N-methyl(2-{[2-(3-methylphenyl)ethyl]amino}-6-phenyl(3-pyridyl))carboxamide |

-continued

| COMPOUND | CHEMICAL NAME |
|---|---|
| | N-methyl{6-phenyl-2-[(2-phenylethyl)amino](3-pyridyl)}carboxamide |
| | {6-phenyl-2-[(2-phenylethyl)amino](3-pyridyl)}-N-prop-2-enylcarboxamide |
| | (2-{[2-(3-methylphenyl)ethyl]amino}-6-phenyl(3-pyridyl))-N-prop-2-enylcarboxamide |
| | N-methyl{6-phenyl-2-[(2-(2-pyridyl)ethyl)amino](3-pyridyl)}carboxamide |

-continued

| COMPOUND | CHEMICAL NAME |
|---|---|
| | N-benzyl{6-phenyl-2-[(2-(2-pyridyl)ethyl)amino](3-pyridyl)}carboxamide |
| | {6-phenyl-2-[(2-phenylethyl)amino](3-pyridyl)}-N-(3-pyridylmethyl)carboxamide |
| | N-(methylethyl){6-phenyl-2-[(2-(2-pyridyl)ethyl)amino](3-pyridyl)}carboxamide |
| | {6-phenyl-2-[(2-(2-pyridyl)ethyl)amino](3-pyridyl)}-N-(2-pyridylmethyl)carboxamide |

| COMPOUND | CHEMICAL NAME |
|---|---|
| 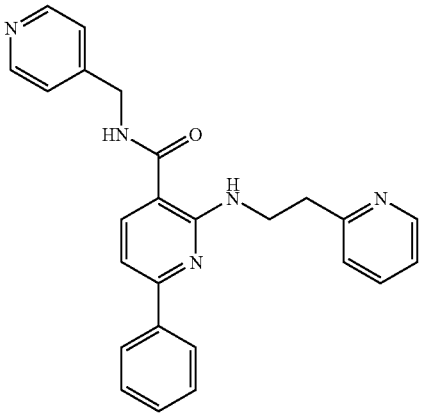 | {6-phenyl-2-[(2-(2-pyridyl)ethyl)amino](3-pyridyl)}-N-(4-pyridylmethyl)carboxamide |
| 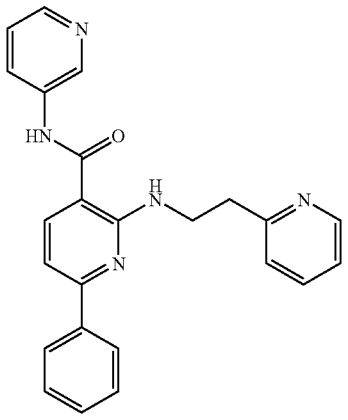 | {6-phenyl-2-[(2-(2-pyridyl)ethyl)amino](3-pyridyl)}-N-(3-pyridyl)carboxamide |
| 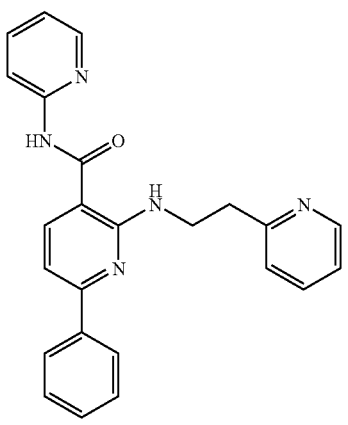 | {6-phenyl-2-[(2-(2-pyridyl)ethyl)amino](3-pyridyl)}-N-(2-pyridyl)carboxamide |

-continued
| COMPOUND | CHEMICAL NAME |
|---|---|
| 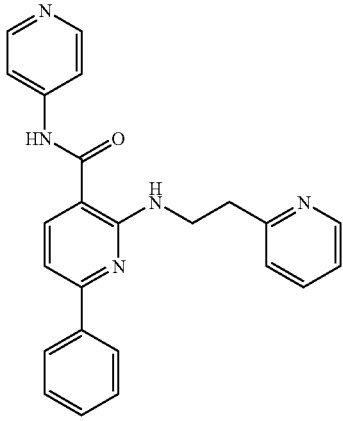 | {6-phenyl-2-[(2-(2-pyridyl)ethyl)amino](3-pyridyl)}-N-(4-pyridyl)carboxamide |
| 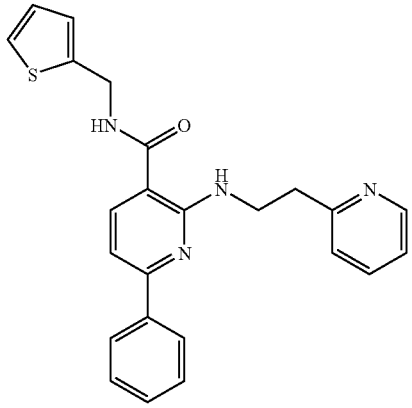 | {6-phenyl-2-[(2-(2-pyridyl)ethyl)amino](3-pyridyl)}-N-(2-thienylmethyl)carboxamide |
| 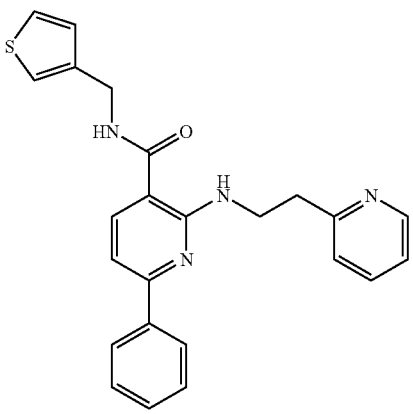 | {6-phenyl-2-[(2-(2-pyridyl)ethyl)amino](3-pyridyl)}-N-(3-thienylmethyl)carboxamide |

| COMPOUND | CHEMICAL NAME |
|---|---|
| | N-(oxolan-2-ylmethyl){6-phenyl-2-[(2-(2-pyridyl)ethyl)amino](3-pyridyl)}carboxamide |
| | N-[((2S)oxolan-2-yl)methyl]{6-phenyl-2-[(2-(2-pyridyl)ethyl)amino](3-pyridyl)}carboxamide |
| | tert-butyl 2-[({6-phenyl-2-[(2-(2-pyridyl)ethyl)amino]-3-pyridyl}carbonylamino)methyl]morpholine-4-carboxylate |

-continued
| COMPOUND | CHEMICAL NAME |
|---|---|
| 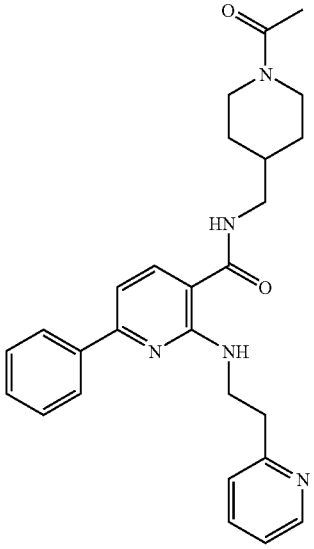 | N-[(1-acetyl(4-piperidyl))methyl]{6-phenyl-2-[(2-(2-pyridyl)ethyl)amino](3-pyridyl)}carboxamide |
| 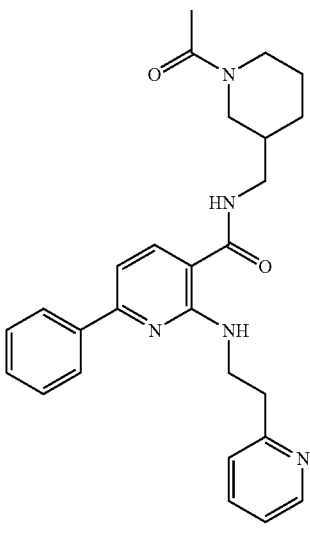 | N-[(1-acetyl(3-piperidyl))methyl]{6-phenyl-2-[(2-(2-pyridyl)ethyl)amino](3-pyridyl)}carboxamide |
| 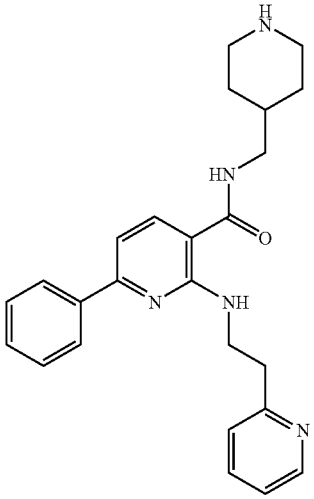 | {6-phenyl-2-[(2-(2-pyridyl)ethyl)amino](3-pyridyl)}-N-(4-piperidylmethyl)carboxamide |

| COMPOUND | CHEMICAL NAME |
|---|---|
| | {2-[(2-cyclohex-1-enylethyl)amino]-6-phenyl(3-pyridyl)}-N-(3-pyridylmethyl)carboxamide |
| | {6-phenyl-2-[(3-phenylpropyl)amino](3-pyridyl)}-N-(3-pyridylmethyl)carboxamide |
| | {6-phenyl-2-[benzylamino](3-pyridyl)}-N-(3-pyridylmethyl)carboxamide |

| COMPOUND | CHEMICAL NAME |
|---|---|
|  | N-(1,3-oxazol-2-ylmethyl){6-phenyl-2-[(2-(2-pyridyl)ethyl)amino](3-pyridyl)}carboxamide |
|  | N-(imidazol-2-ylmethyl){6-phenyl-2-[(2-(2-pyridyl)ethyl)amino](3-pyridyl)}carboxamide |
|  | N-[((2S)-1-acetylpyrrolidin-2-yl)methyl]{6-phenyl-2-[(2-(2-pyridyl)ethyl)amino](3-pyridyl)}carboxamide |

| COMPOUND | CHEMICAL NAME |
|---|---|
| | N-[((3R)-1-acetylpyrrolidin-3-yl)methyl]{6-phenyl-2-[(2-(2-pyridyl)ethyl)amino](3-pyridyl)}carboxamide |
| | N-[((3S)-1-acetylpyrrolidin-3-yl)methyl]{6-phenyl-2-[(2-(2-pyridyl)ethyl)amino](3-pyridyl)}carboxamide |
| | methyl 2-({6-phenyl-2-[(2-phenylethyl)amino]-3-pyridyl}carbonylamino)acetate |

| COMPOUND | CHEMICAL NAME |
|---|---|
| | [6-phenyl-2-(propylamino)(3-pyridyl)]-N-(3-pyridylmethyl)carboxamide |
| | {2-[3-methylbutyl)amino]-6-phenyl(3-pyridyl)}-N-(3-pyridylmethyl)carboxamide |
| | {2-[(2-cyclohexylethyl)amino]-6-phenyl(3-pyridyl)}-N-(3-pyridylmethyl)carboxamide |

-continued

| COMPOUND | CHEMICAL NAME |
|---|---|
|  | N-{[1-(methylsulfonyl)(3-piperidyl)]methyl}{6-phenyl-2-[(2-(2-pyridyl)ethyl)amino](3-pyridyl)}carboxamide |
|  | 2-(aminomethyl)piperidyl 6-phenyl-2-[(2-(2-pyridyl)ethyl)amino](3-pyridyl) ketone |
|  | N-{[1-({6-phenyl-2-[(2-(2-pyridyl)ethyl)amino]-3-pyridyl}carbonyl)-2-piperidyl]methyl}acetamide |
|  | 2-{[(methylsulfonyl)amino]methyl}piperidyl 6-phenyl-2-[(2-(2-pyridyl)ethyl)amino](3-pyridyl) ketone |

| COMPOUND | CHEMICAL NAME |
|---|---|
| | N-[(1-methylpyrazol-5-yl)methyl]{6-phenyl-2-[(2-(2-pyridyl)ethyl)amino](3-pyridyl)}carboxamide |
| | N-[(1-methylpyrazol-3-yl)methyl]{6-phenyl-2-[(2-(2-pyridyl)ethyl)amino](3-pyridyl)}carboxamide |
| | {6-phenyl-2-[(2-(2-pyridyl)ethyl)amino](3-pyridyl)}-N-(pyrazol-3-ylmethyl)carboxamide |

| COMPOUND | CHEMICAL NAME |
|---|---|
| | N-(isoxazol-5-ylmethyl){6-phenyl-2-[(2-(2-pyridyl)ethyl)amino](3-pyridyl)}carboxamide |
| | N-[((3S)pyrrolidin-3-yl)methyl]{6-phenyl-2-[(2-(2-pyridyl)ethyl)amino](3-pyridyl)}carboxamide |
| | N-[((3R)pyrrolidin-3-yl)methyl]}6-phenyl-2[(2-(2-pyridyl)ethyl)amino](3-pyridyl)}carboxamide |

| COMPOUND | CHEMICAL NAME |
|---|---|
| | {6-phenyl-2-[(2-phenylethyl)amino](3-pyridyl)}-N-(2-(2-pyridyl)ethyl)carboxamide |
| | {6-phenyl-2-[(2-phenylethyl)amino](3-pyridyl)}-N-(2-(3-pyridyl)ethyl)carboxamide |
| | N-methyl-2-({6-phenyl-2-[(2-phenylethyl)amino](3-pyridyl)}carbonylamino)acetamide |

| COMPOUND | CHEMICAL NAME |
|---|---|
| | N,N-dimethyl-2-({6-phenyl-2-[(2-phenylethyl)amino](3-pyridyl)}carbonylamino)acetamide |
| | N-(carbamoylmethyl){6-phenyl-2-[(2-phenylethyl)amino](3-pyridyl)}carboxamide |
| | (2-{[2-(2-oxopiperidyl)ethyl]amino}-6-phenyl(3-pyridyl))-N-(3-pyridylmethyl)carboxamide |

| COMPOUND | CHEMICAL NAME |
|---|---|
| 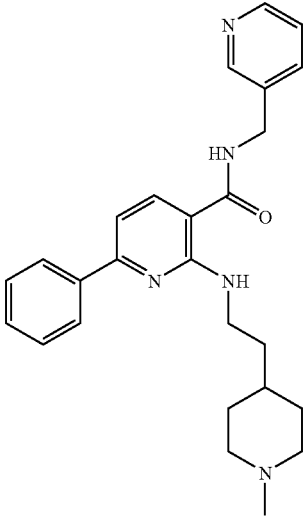 | (2-{[2-(1-methyl(4-piperidyl))ethyl]amino}-6-phenyl(3-pyridyl))-N-(3-pyridylmethyl)carboxamide |
| 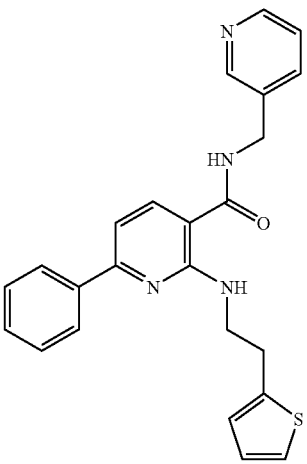 | {6-phenyl-2-[(2-(2-thienyl)ethyl)amino](3-pyridyl)}-N-(3-pyridylmethyl)carboxamide |
| 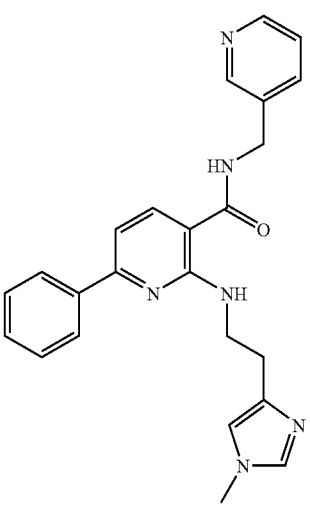 | (2-{[2-(1-methylimidazol-4-yl)ethyl]amino}-6-phenyl(3-pyridyl))-N-(3-pyridylmethyl)carboxamide |

-continued
| COMPOUND | CHEMICAL NAME |
|---|---|
| 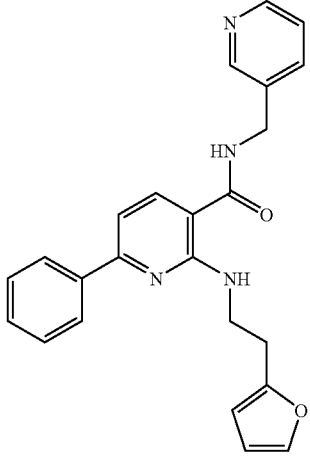 | {2-[(2-(2-furyl)ethyl)amino]-6-phenyl(3-pyridyl)}-N-(3-pyridylmethyl)carboxamide |
| 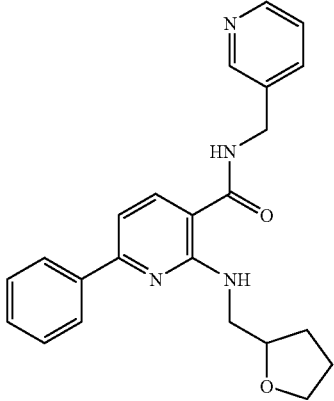 | {2-[(oxolan-2-ylmethyl)amino]-6-phenyl(3-pyridyl)}-N-(3-pyridylmethyl)carboxamide |
| 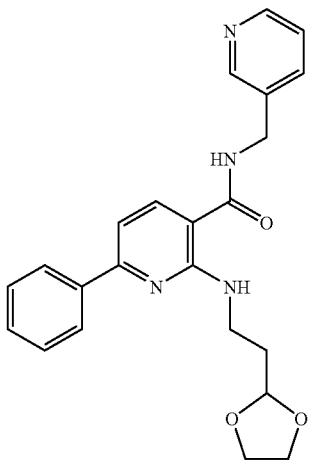 | {2-[(2-(1,3-dioxolan-2-yl)ethyl)amino]-6-phenyl(3-pyridyl)}-N-(3-pyridylmethyl)carboxamide |

| COMPOUND | CHEMICAL NAME |
|---|---|
| 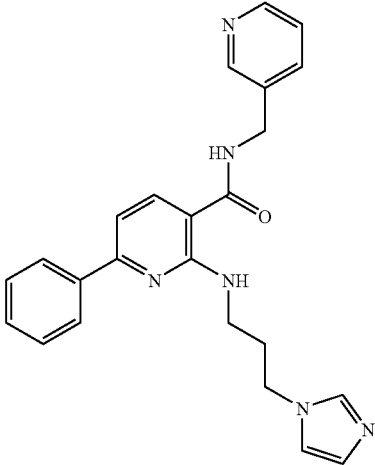 | {2-[(3-imidazolylpropyl)amino]-6-phenyl(3-pyridyl)}-N-(3-pyridylmethyl)carboxamide |
| 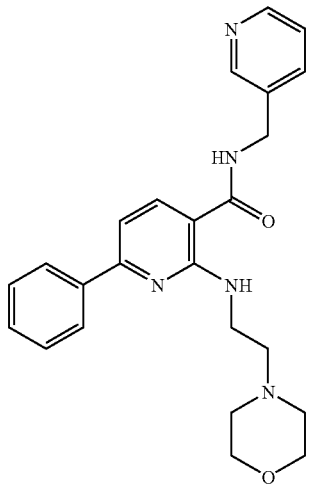 | {2-[(2-morpholin-4-ylethyl)amino]-6-phenyl(3-pyridyl)}-N-(3-pyridylmethyl)carboxamide |
| 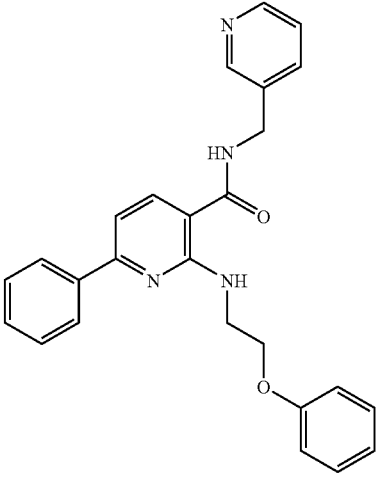 | {6-phenyl-2-[(2-phenyoxyethyl)amino](3-pyridyl)}-N-(3-pyridylmethyl)carboxamide |

| COMPOUND | CHEMICAL NAME |
|---|---|
| | {2-[(2-(2H-benzo[3,4-d]1,3-dioxolen-5-yl)ethyl)amino]-6-phenyl(3-pyridyl)}-N-(3-pyridylmethyl)carboxamide |
| | (2-{[2-(2-oxoimidazolidinyl)ethyl]amino}-6-phenyl(3-pyridyl))-N-(3-pyridylmethyl)carboxamide |
| | (2-{[2-(2-oxopyrrolidinyl)ethyl]amino}-6-phenyl(3-pyridyl))-N-(3-pyridylmethyl)carboxamide |

| COMPOUND | CHEMICAL NAME |
|---|---|
|  | {2-[(2-imidazol-4-ylethyl)amino]-6-phenyl(3-pyridyl)}-N-(3-pyridylmethyl)carboxamide |
|  | (2-{[hydroxycyclohexyl)methyl]amino}-6-phenyl(3-pyridyl))-N-(3-pyridylmethyl)carboxamide |
|  | (2-{[2-(3,5-dimethylpyrazol-4-yl)ethyl]amino}-6-phenyl(3-pyridyl))-N-(3-pyridylmethyl)carboxamide |

-continued

| COMPOUND | CHEMICAL NAME |
| --- | --- |
| | (2-{[2-(3,5-dimethylpyrazolyl)ethyl]amino}-6-phenyl(3-pyridyl))-N-(3-pyridylmethyl)carboxamide |
| | (2-{[2-(2-chlorophenyl)ethyl]amino}-6-(2-cyanophenyl)(3-pyridyl))-N-(3-pyridylmethy)carboxamide |
| | (6-(2-cyanophenyl)-2-{[2-(2-methylphenyl)ethyl]amino}(3-pyridyl))-N-(3-pyridylmethyl)carboxamide |

| COMPOUND | CHEMICAL NAME |
|---|---|
|  | (6-(2-cyanophenyl)-2-{[2-(2-fluorophenyl)ethyl]amino}(3-pyridyl))-N-(3-pyridylmethyl)carboxamide |
|  | (6-(2-cyanophenyl)-2-{[2-(2-cyanophenyl)ethyl]amino}(3-pyridyl))-N-(3-pyridylmethyl)carboxamide |
|  | {6-(2-cyanophenyl)-2-[(2-(2-thienyl)ethyl)amino](3-pyridyl)-N-(3-pyridylmethyl)carboxamide |

-continued

| COMPOUND | CHEMICAL NAME |
|---|---|
| | {6-(2-cyanophenyl)-2-[(2-(2-furyl)ethyl)amino](3-pyridyl)}-N-(3-pyridylmethyl)carboxamide |
| | (2-{[2-(3-fluoro(2-pyridyl))ethyl]amino}-6-phenyl(3-pyridyl))-N-(3-pyridylmethyl)carboxamide |
| | (2-{[2-(3-methylphenyl)ethyl]amino}-6-phenyl(3-pyridyl))-N-(3-pyridylmethyl)carboxamide |
| | (6-(2-cyanophenyl)-2-{[2-(2-hydroxyphenyl)ethyl]amino}(3-pyridyl))-N-(3-pyridylmethyl)carboxamide |

| COMPOUND | CHEMICAL NAME |
|---|---|
| | N-{[2-(aminomethyl)(3-pyridyl)]methyl}{6-pyrazol-4-yl-2[(2-(2-pyridyl)ethyl)amino](3-pyridyl)}carboxamide |
| | N-{(1R)-2-[(5-fluoro-2-{[2-(3-fluorophenyl)-2-hydroxyethyl]amino}-6-pyrazol-4-yl(3-pyridyl))carbonylamino]-isopropyl}-2-[(tert-butoxy)carbonylamino]acetamide |
| | {5-fluoro-6-pyrazol-4-yl-2-[(2-pyrazolylethyl)amino](3-pyridyl)}-N-(3-pyridylmethyl)carboxamide |
| | N-[(1R)-2-({5-fluoro-6-pyrazol-4-yl-2-[(2-pyrazolylethyl)amino](3-pyridyl)}carbonylamino)-isopropyl]-2-aminoacetamide |

| COMPOUND | CHEMICAL NAME |
|---|---|
| | (6-(2-cyanophenyl)-2-{[2-(3-fluorophenyl)ethyl]amino}(3-pyridyl))-N-{[6-(trifluoromethyl)(2-pyridyl)]methyl}carboxamide |
| | (6-(2-cyanophenyl)-2-{[2-(3-fluorophenyl)ethyl]amino}(3-pyridyl))-N-{[5-(trifluoromethyl)(2-pyridyl)]methyl}carboxamide |
| | (6-(2-cyanophenyl)-2-{[2-(3-fluorophenyl)ethyl]amino}(3-pyridyl))-N-{[3-(trifluoromethyl)(2-pyridyl)]methyl}carboxamide |
| | N-[(6-chloro(3-pyridyl))methyl](6-(2-cyanophenyl)-2-{[2-(3-fluorophenyl)ethyl]amino}(3-pyridyl))carboxamide |

| COMPOUND | CHEMICAL NAME |
|---|---|
|  | (6-(2-cyano(3-thienyl))-2-{[2-(3-fluorophenyl)ethyl]amino}(3-pyridyl))-N-(3-pyridylmethyl)carboxamide |
|  | (2E)-3-(2-{[2-(3-fluorophenyl)ethyl]amino}-6-phenyl(3-pyridyl))-N-methylprop-2-enamide |
|  | (6-(2-cyanophenyl)-2-{[2-(3-fluorophenyl)ethyl]amino}(3-pyridyl))-N-{[6-(methylamino)(3-pyridyl)]methyl}carboxamide |
|  | N-{[6-(dimethylamino)(3-pyridyl)]methyl}(6-(2-cyanophenyl)-2-{[-(3-fluorophenyl)ethyl]amino}(3-pyridyl))carboxamide |

| COMPOUND | CHEMICAL NAME |
|---|---|
| | (2-{[2-(3-fluorophenyl)ethyl]amino}-4-(hydroxymethyl)-6-phenyl(3-pyridyl))-N-(3-pyridylmethyl)carboxamide |
| | N-[(5-amino(2-pyridyl))methyl](6-(2-cyanophenyl)-2-{[2-(3-fluorophenyl)ethyl]amino}(3-pyridyl))carboxamide |
| | (2-{[2-(3-fluorophenyl)ethyl]amino}-5-(hydroxymethyl)-6-phenyl(3-pyridyl))-N-(3-pyridylmethyl)carboxamide |
| | (2-{[2-(3-fluorophenyl)ethyl]amino}-6-phenyl-5-[N-(3-pyridylmethyl)carbamoyl](3-pyridyl))-N-(3-pyridylmethyl)carboxamide |

| COMPOUND | CHEMICAL NAME |
|---|---|
| | (5-(2-diazo-2-azavinyl)-2-{[2-(3-fluorophenyl)ethyl]amino}-6-phenyl(3-pyridyl))-N-(3-pyridylmethyl)carboxamide |
| | (5-(aminomethyl)-2-{[2-(3-fluorophenyl)ethyl]amino}-6-phenyl(3-pyridyl))-N-(3-pyridylmethyl)carboxamide |
| | (2-{[2-(3-fluorophenyl)ethyl]amino}-6-(1-methylpyrazol-3-yl)(3-pyridyl))-N-(3-pyridylmethyl)carboxamide |

| COMPOUND | CHEMICAL NAME |
|---|---|
| | N-({6-[3,3-bus(dimethylamino)-2-azaprop-2-enyl](2-pyridyl)}methyl)(6-(2-cyanophenyl)-2-{[2-(3-fluorophenyl)ethyl]amino}(3-pyridyl))carboxamide |
| | tert-butyl 2-(6-{[(6-(2-cyanophenyl)-2-{[2-(3-fluorophenyl)ethyl]amino}-3-pyridyl)carbonylamino]methyl}-2-pyridyl)acetate |
| | N-{[4-(aminomethyl)(3-pyridyl)]methyl}(6-(2-cyanophenyl)-2-{[2-(3-fluorophenyl)ethyl]amino}(3-pyridyl))carboxamide |

| COMPOUND | CHEMICAL NAME |
|---|---|
| | N-{[3-(aminomethyl)(4-pyridyl)]methyl}(6-(2-cyanophenyl)-2-{[2-(3-fluorophenyl)ethyl]amino}(3-pyridyl))carboxamide |
| | (5-bromo-2-{[2-(3-fluorophenyl)ethyl]amino}-6-pyrazol-4-yl(3-pyridyl))-N-(3-pyridylmethyl)carboxamide |
| | (5-bromo-2-{[2-(3-fluorophenyl)ethyl]amino}-6-(1-methylpyrazol-4-yl)(3-pyridyl))-N-(3-pyridylmethyl)carboxamide |
| | (6-(5-cyanopyrazol-4-yl)-2-{[2-(3-fluorophenyl)ethyl]amino}(3-pyridyl))-N-(3-pyridylmethyl)carboxamide |

| COMPOUND | CHEMICAL NAME |
|---|---|
| | (5-cyano-2-{[2-(3-fluorophenyl)ethyl]amino}-6-(1-methylpyrazol-4-yl)(3-pyridyl))-N-(3-pyridylmethyl)carboxamide |
| | (2-{[2-(3-fluorophenyl)ethyl]amino}-6-pyrazol-3-yl(3-pyridyl))-N-(3-pyridylmethyl)carboxamide |
| | (6-(3-cyano-1-methylpyrazol-4-yl)-2-{[2-(3-fluorophenyl)ethyl]amino}(3-pyridyl))-N-(3-pyridylmethyl)carboxamide |
| | (6-(5-cyano-1-methylpyrazol-4-yl)-2-{[2-(3-fluorophenyl)ethyl]amino}(3-pyridyl))-N-(3-pyridylmethyl)carboxamide |

| COMPOUND | CHEMICAL NAME |
|---|---|
| | 2-[(2-{[2-(3-fluorophenyl)ethyl]amino}-6-pyrazol-4-yl(3-pyridyl))carbonylamino]-N-methylacetamide |
| | 2-[(2-{[2-(3-fluorophenyl)ethyl]amino}-6-(1-methylpyrazol-4-yl)(3-pyridyl))carbonylamino]-N-methylacetamide |
| | (5-chloro-2-{[2-(3-fluorophenyl)ethyl]amino}-6-(1-methylpyrazol-4-yl)(3-pyridyl))-N-(3-pyridylmethyl)carboxamide |
| | N-{[6-(aminomethyl)(2-pyridyl)]methyl}(5-bromo-2-{[2-(3-fluorophenyl)ethyl]amino}-6-phenyl(3-pyridyl))carboxamide |

-continued

| COMPOUND | CHEMICAL NAME |
|---|---|
| | N-[(1-{2-[(tert-butoxy)carbonylamino]ethyl}pyrazol-3-yl)methyl](6-(2-cyanophenyl)-2-{[2-(3-fluorophenyl)ethyl]amino}(3-pyridyl))carboxamide |
| | N-[(1-{2-[(tert-butoxy)carbonylamino]ethyl}pyrazol-5-yl)methyl](6-(2-cyanophenyl)-2-{[2-(3-fluorophenyl)ethyl]amino}(3-pyridyl))carboxamide |
| | N-{[1-(2-aminoethyl)pyrazol-3-yl]methyl}(6-(2-cyanophenyl)-2-{[2-(3-fluorophenyl)ethyl]amino}(3-pyridyl))carboxamide |
| | N-{[1-(2-aminoethyl)pyrazol-5-yl]methyl}(6-(2-cyanophenyl)-2-{[2-(3-fluorophenyl)ethyl]amino}(3-pyridyl))carboxamide |

| COMPOUND | CHEMICAL NAME |
|---|---|
|  | N-{[6-(aminomethyl)(2-pyridyl)]methyl}(2-{[2-(3-fluorophenyl)ethyl]amino}-6-(1-methylpyrazol-4-yl)(3-pyridyl))carboxamide |
|  | N-{[6-(aminomethyl)(2-pyridyl)]methyl}(2-{[2-(3-fluorophenyl)ethyl]amino}-6-pyrazol-4-yl(3-pyridyl))carboxamide |
|  | N-{[6-(aminomethyl)(2-pyridyl)]methyl}(5-bromo-2-{[2-(3-fluorophenyl)ethyl]amino}-6-(1-methylpyrazol-4-yl)(3-pyridyl))carboxamide |

| COMPOUND | CHEMICAL NAME |
|---|---|
| | N-[((2R)-5-oxopyrrolidin-2-yl)methyl](6-(2-cyanophenyl)-2-{[2-(3-fluorophenyl)ethyl]amino}(3-pyridyl))carboxamide |
| | N-[((2S)-5-oxopyrrolidin-2-yl)methyl](6-(2-cyanophenyl)-2-{[2-(3-fluorophenyl)ethyl]amino}(3-pyridyl))carboxamide |
| | N-{3-[(5S)-5-(2-diazo-2-azavinyl)-2-oxopyrrolidinyl]propyl}(6-(2-cyanophenyl)-2-{[2-(3-fluorophenyl)ethyl]amino}(3-pyridyl))carboxamide |
| | N-[((2S)-1-{3-[(tert-butoxy)carbonylamino]propyl}-5-oxopyrrolidin-2-yl)methyl](6-(2-cyanophenyl)-2-{[2-(3-fluorophenyl)ethyl]amino}(3-pyridyl))carboxamide |

| COMPOUND | CHEMICAL NAME |
|---|---|
| 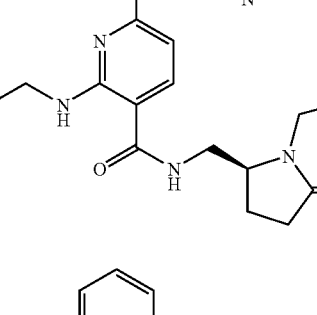 | N-{[(2S)-1-(2-aminoethyl)-5-oxopyrrolidin-2-yl]methyl}(6-(2-cyanophenyl)-2-{[2-(3-fluorophenyl)ethyl]amino}(3-pyridyl))carboxamide |
| 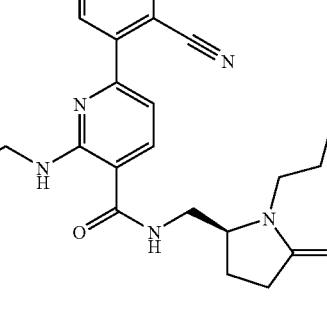 | N-{[(2S)-1-(3-aminopropyl)-5-oxopyrrolidin-2-yl]methyl}(6-(2-cyanophenyl)-2-{[2-(3-fluorophenyl)ethyl}(3-pyridyl))carboxamide |
| 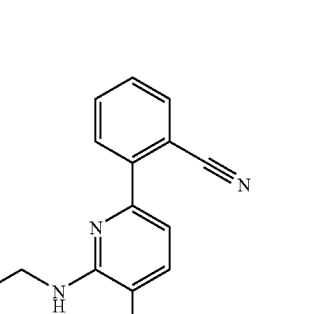 | N-{3-[(5S)-5-(aminomethyl)-2-oxopyrrolidinyl]propyl}(6-(2-cyanophenyl)-2-{[2-(3-fluorophenyl)ethyl]amino}(3-pyridyl))carboxamide |
| 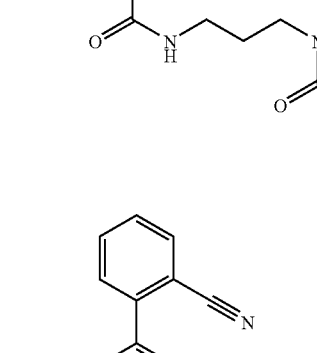 | N-{[(2R)-1-(2-aminoethyl)-5-oxopyrrolidin-2-yl]methyl}(6-(2-cyanophenyl)-2-{[2-(3-fluorophenyl)ethyl]amino}(3-pyridyl))carboxamide |

| COMPOUND | CHEMICAL NAME |
|---|---|
| | N-{3-[(5R)-5-(2-diazo-2-azavinyl)-2-oxopyrrolidinyl]propyl}(6-(2-cyanophenyl)-2-{[2-(3-fluorophenyl)ethyl]amino}(3-pyridyl))carboxamide |
| | N-{3-[(5R)-5-(aminomethyl)-2-oxopyrrolidinyl]propyl}(6-(2-cyanophenyl)-2-{[2-(3-fluorophenyl)ethyl]amino}(3-pyridyl))carboxamide |
| | N-{2-[(5R)-5-(aminomethyl)-2-oxopyrrolidinyl]ethyl}(6-(2-cyanophenyl)-2-{[2-(3-fluorophenyl)ethyl]amino}(3-pyridyl))carboxamide |

| COMPOUND | CHEMICAL NAME |
|---|---|
| 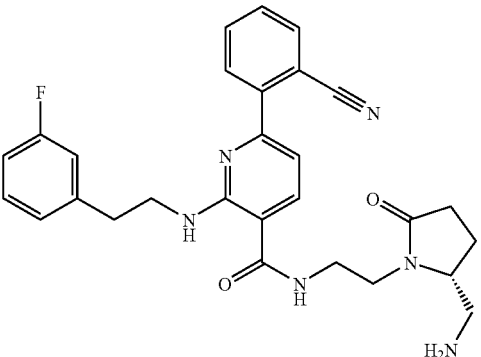<br>Compound 412 | N-{2-[(5R)-5-(aminomethyl)-2-oxopyrrolidinyl]ethyl}(6-(2-cyanophenyl)-2-{[2-(3-fluorophenyl)ethyl]amino}(3-pyridyl))carboxamide |
| 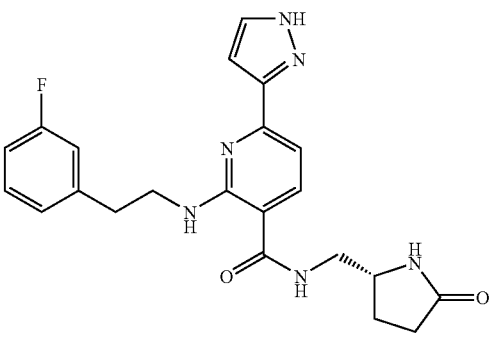<br>Compound 413 | N-[((2R)-5-oxopyrrolidin-2-yl)methyl](2-{[2-(3-fluorophenyl)ethyl]amino}-6-pyrazol-3-yl(3-pyridyl))carboxamide |
| 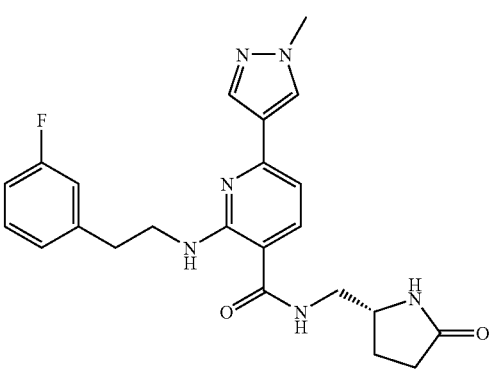<br>Compound 414 | N-[((2R)-5-oxopyrrolidin-2-yl)methyl](2-{[2-(3-fluorophenyl)ethyl]amino}-6-(1-methylpyrazol-4-yl)(3-pyridyl))carboxamide |
| 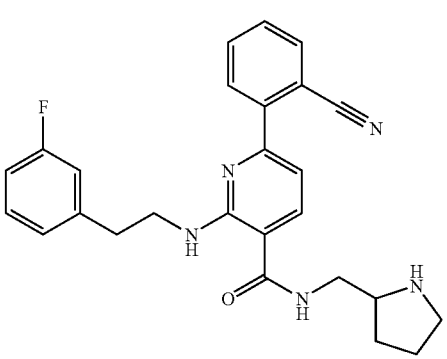<br>Compound 419 | (6-(2-cyanophenyl)-2-{[2-(3-fluorophenyl)ethyl[amino}(3-pyridyl))-N-(pyrrolidin-2-ylmethyl)carboxamide |

-continued

| COMPOUND | CHEMICAL NAME |
|---|---|
| 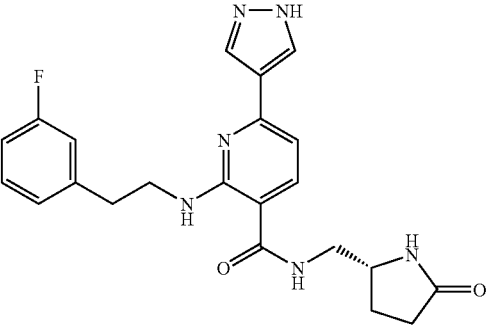<br>Compound 420 | N-[((2R)-5-oxopyrrolidin-2-yl)methyl](2-{[2-(3-fluorophenyl)ethyl]amino}-6-pyrazol-4-yl(3-pyridyl))carboxamide |
| 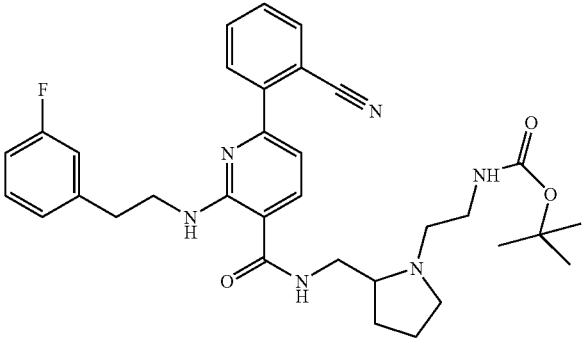<br>Compound 422 | N-[(1-{2-[(tert-butoxy)carbonylamino]ethyl}pyrrolidin-2-yl)methyl](6-(2-cyanophenyl)-2-{[2-(3-fluorophenyl)ethyl]amino}(3-pyridyl))carboxamide |
| 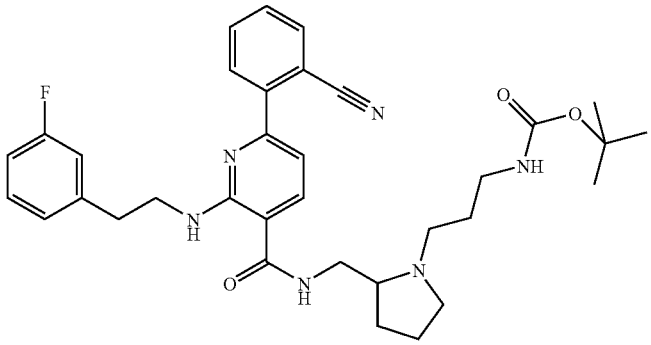<br>Compound 423 | N-[(1{3-[(tert-butoxy)carbonylamino]propyl}pyrrolidin-2-yl)methyl](6-(2-cyanophenyl)-2-{[2-(3-fluorophenyl)ethyl]amino}(3-pyridyl))carboxamide |
| 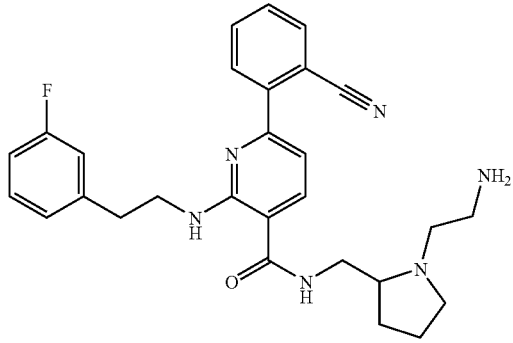<br>Compound 424 | N-{[1-(2-aminoethyl)pyrrolidin-2-yl]methyl}(6-(2-cyanophenyl)-2-{[2-(3-fluorophenyl)ethyl]amino}(3-pyridyl))carboxamide |

| COMPOUND | CHEMICAL NAME |
|---|---|
| 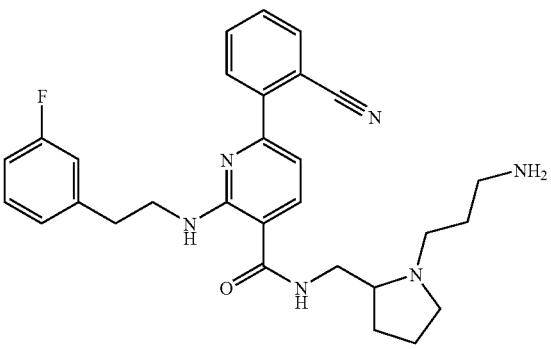<br>Compound 425 | N-{[1-(4-aminobutyl)pyrrolidin-2-yl]methyl}(6-(2-cyanophenyl)-2-{[2-(3-fluorophenyl)ethyl]amino}(3-pyridyl))carboxamide |
| 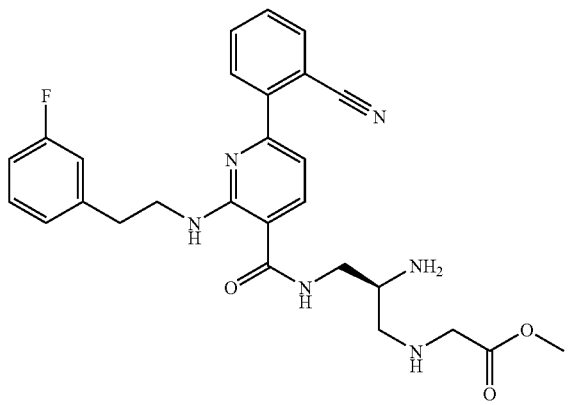<br>Compound 428 | methyl 2-({(2S)-2-amino-3-[(6-(2-cyanophenyl)-2-{[2-(3-fluorophenyl)ethyl]amino}(3-pyridyl))carbonylamino]propyl}amino)acetate |
| 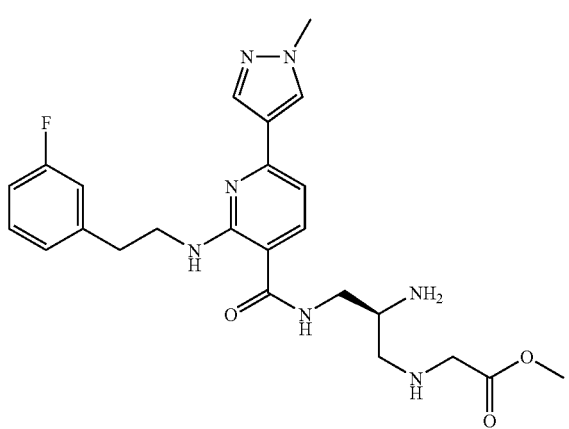<br>Compound 429 | methyl 2-({(2S)-2-amino-3-[(2-{[2-(3-fluorophenyl)ethyl]amino}-6-(1-methylpyrazol-4-yl)(3-pyridyl))carbonylamino]propyl}amino)acetate |

| COMPOUND | CHEMICAL NAME |
|---|---|
| <br>Compound 433 | N-[((2S)-6-oxopiperazin-2-yl)methyl](2-{[2-(3-fluorophenyl)ethyl]amino}-6-pyrazol-4-yl(3-pyridyl))carboxamide |
| 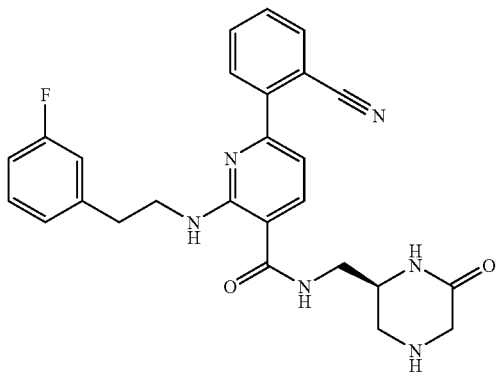<br>Compound 434 | N-[((2S)-6-oxopiperazin-2-yl)methyl](6-(2-cyanophenyl)-2-{[2-(3-fluorophenyl)ethyl]amino}(3-pyridyl))carboxamide |
| 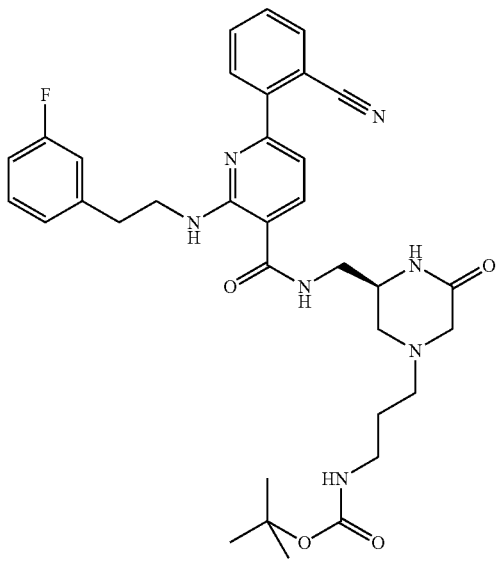<br>Compound 435 | N-[((2R)-4-{3-[(tert-butoxy)carbonylamino]propyl}-6-oxopiperazin-2-yl)methyl](6-(2-cyanophenyl)-2-{[2-(3-fluorophenyl)ethyl]amino}(3-pyridyl))carboxamide |

| COMPOUND | CHEMICAL NAME |
|---|---|
| 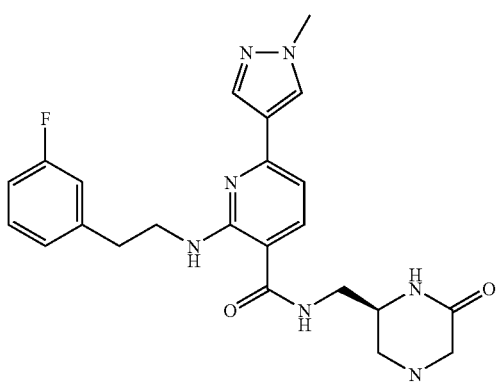<br>Compound 436 | N-[((2S)-6-oxopiperazin-2-yl)methyl](2-{[2-(3-fluorophenyl)ethyl]amino}-6-(1-methylpyrazol-4-yl)(3-pyridyl))carboxamide |
| 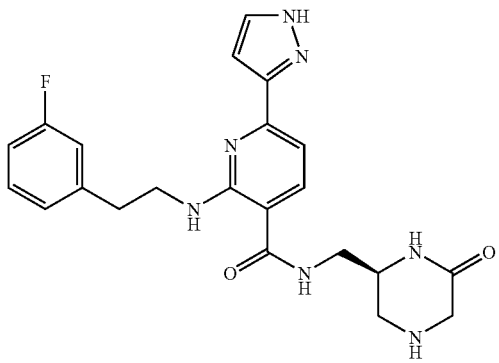<br>Compound 437 | N-[((2S)-6-oxopiperazin-2-yl)methyl](2-{[2-(3-fluorophenyl)ethyl]amino}-6-pyrazol-3-yl(3-pyridyl))carboxamide |
| 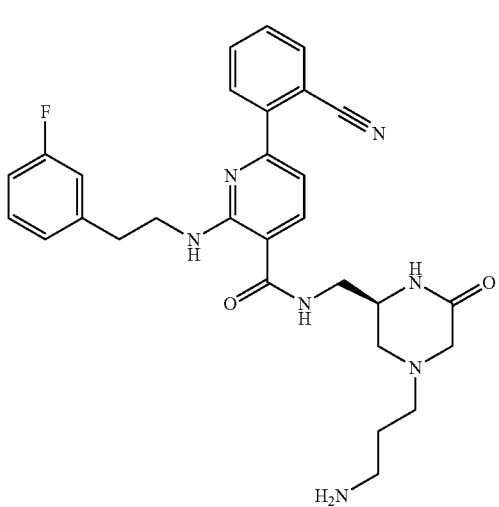<br>Compound 438 | N-{[(2R)-4-(3-aminopropyl)-6-oxopiperazin-2-yl]methyl}(6-(2-cyanophenyl)-2-{[2-(3-fluorophenyl)ethyl]amino}(3-pyridyl))carboxamide |

-continued

| COMPOUND | CHEMICAL NAME |
|---|---|
| 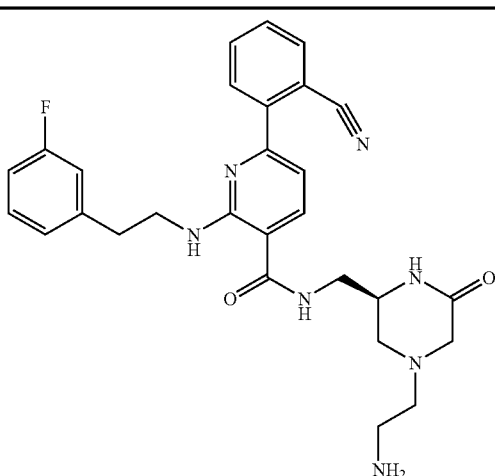<br>Compound 0 | N-{[(2R)-4-(2-aminoethyl)-6-oxopiperazin-2-yl]methyl}(6-(2-cyanophenyl)-2-{[2-(3-fluorophenyl)ethyl]amino}(3-pyridyl))carboxamide |
| 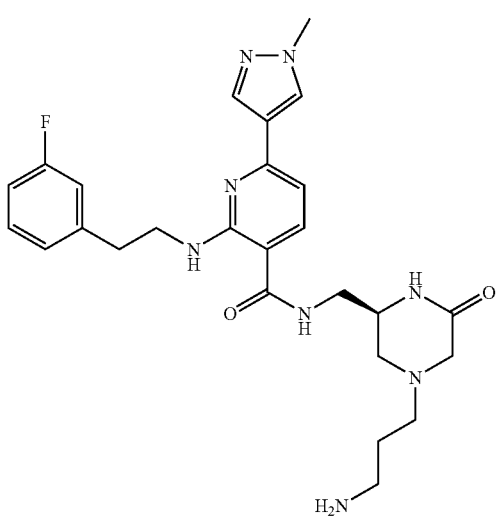<br>Compound 440 | N-[((2R)-6-oxopiperazin-2-yl)methyl](6-(2-cyanophenyl)-2-{[2-(3-fluorophenyl)ethyl]amino}(3-pyridyl))carboxamide |
| 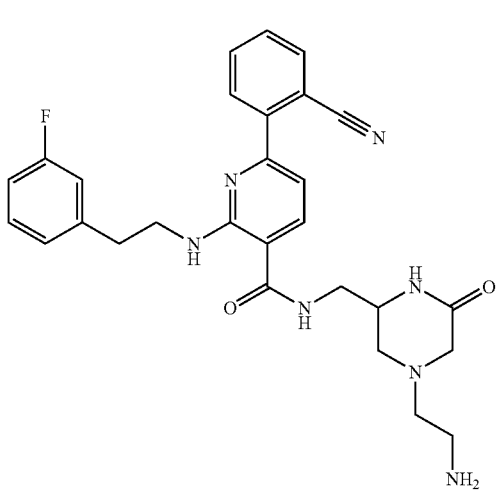<br>Compound 451 | N-{[(2S)-4-(2-aminoethyl)-6-oxopiperazin-2-yl]methyl}(6-(2-cyanophenyl)-2-{[2-(3-fluorophenyl)ethyl]amino}(3-pyridyl))carboxamide |

-continued

| COMPOUND | CHEMICAL NAME |
|---|---|
| 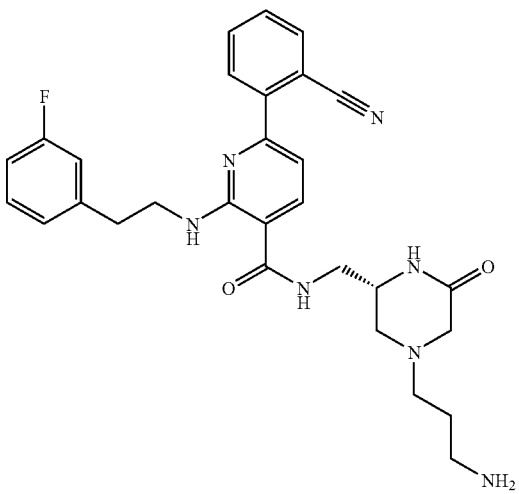  Compound 452 | N-{[(2S)-4-(3-aminopropyl)-6-oxopiperazin-2-yl]methyl}(6-(2-cyanophenyl)-2-{[2-(3-fluorophenyl)ethyl]amino}(3-pyridyl))carboxamide |
| 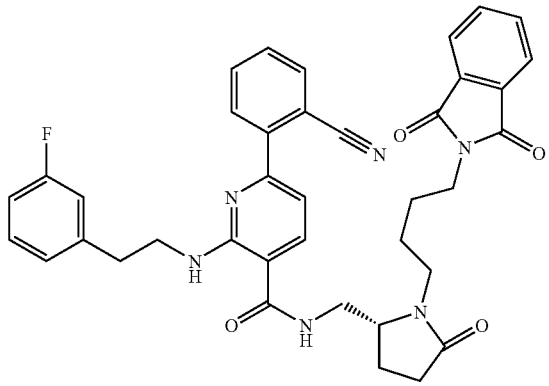  Compound 453 | N-({(2R)-1-[4-(1,3-dioxobenzo[c]azolin-2-yl)butyl]-5-oxopyrrolidin-2-yl}methyl)(6-(2-cyanophenyl)-2-{[2-(3-fluorophenyl)ethyl]amino}(3-pyridyl))carboxamide |
| 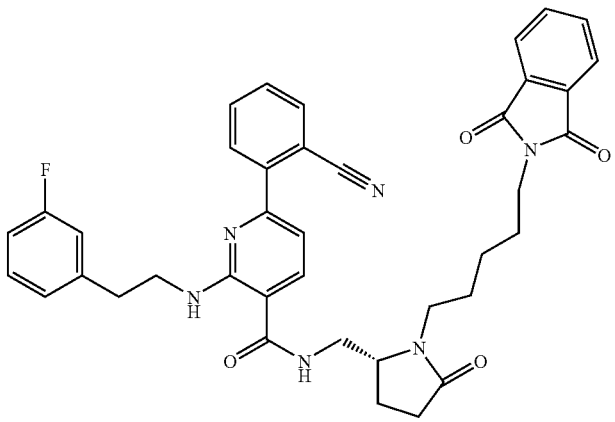  Compound 454 | N-({(2R)-1-[5-(1,3-dioxobenzo[c]azolin-2-yl)pentyl]-5-oxopyrrolidin-2-yl}methyl)(6-(2-cyanophenyl)-2-{[2-(3-fluorophenyl)ethyl]amino}(3-pyridyl))carboxamide |

| COMPOUND | CHEMICAL NAME |
|---|---|
| Compound 455 | tert-butyl (2R)-2-{[(6-(2-cyanophenyl)-2-{[2-(3-fluorophenyl)ethyl]amino}(3-pyridyl))carbonylamino]methyl}pyrrolidinecarboxylate |
| Compound 1 | N-{[(2R)-1-(4-aminobutyl)-5-oxopyrrolidin-2-yl]methyl}(6-(2-cyanophenyl)-2-{[2-(3-fluorophenyl)ethyl]amino}(3-pyridyl))carboxamide |
| Compound 2 | N-{[(2R)-1-(5-aminopentyl)-5-oxopyrrolidin-2-yl]methyl}(6-(2-cyanophenyl)-2-{[2-(3-fluorophenyl)ethyl]amino}(3-pyridyl))carboxamide |
| Compound 3 | N-[((2R)pyrrolidin-2-yl)methyl](6-(2-cyanophenyl)-2-{[2-(3-fluorophenyl)ethyl]amino}(3-pyridyl))carboxamide |

| COMPOUND | CHEMICAL NAME |
|---|---|
| 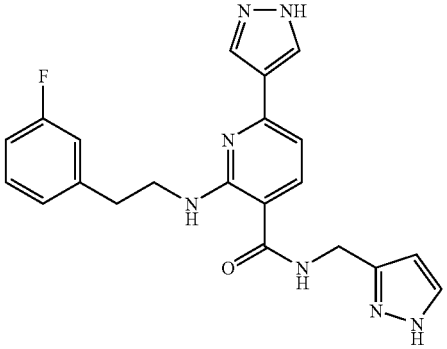
Compound 459 | (2-{[2-(3-fluorophenyl)ethyl]amino}-6-pyrazol-4-yl(3-pyridyl))-N-(pyrazol-3-ylmethyl)carboxamide |
| 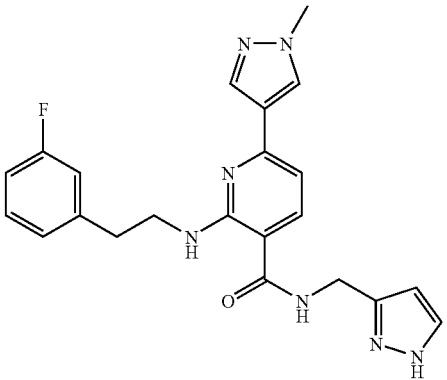
Compound 460 | (2-{[2-(3-fluorophenyl)ethyl]amino}-6-(1-methylpyrazol-4-yl)(3-pyridyl))-N-(pyrazol-3-ylmethyl)carboxamide |
| 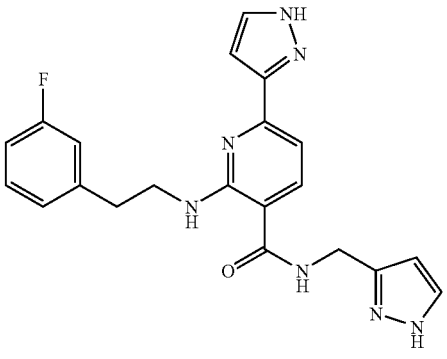
Compound 461 | (2-{[2-(3-fluorophenyl)ethyl]amino}-6-pyrazol-3-yl(3-pyridyl))-N-(pyrazol-3-ylmethyl)carboxamide |

-continued

| COMPOUND | CHEMICAL NAME |
|---|---|
| 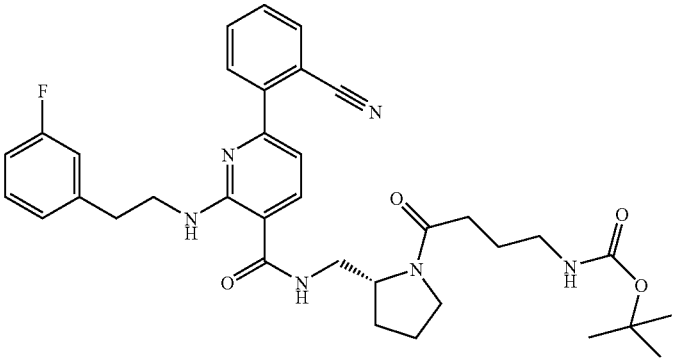  Compound 462 | N-[((2R)-1-{4-[(tert-butoxy)carbonylamino]butanoyl}pyrrolidin-2-yl)methyl](6-(2-cyanophenyl)-2-{[2-(3-fluorophenyl)ethyl]amino}(3-pyridyl))carboxamide |
| 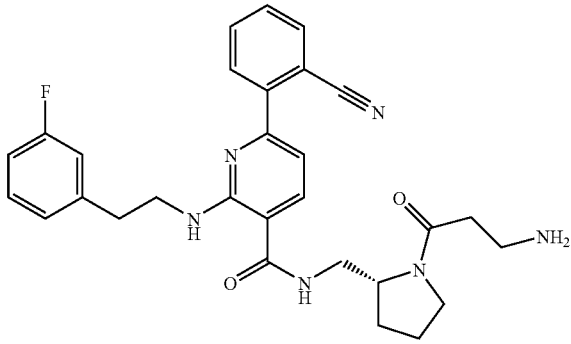  Compound 464 | N-{[(2R)-1-(3-aminopropanoyl)pyrrolidin-2-yl]methyl}(6-(2-cyanophenyl)-2-{[2-(3-fluorophenyl)ethyl]amino}(3-pyridyl))carboxamide |
| 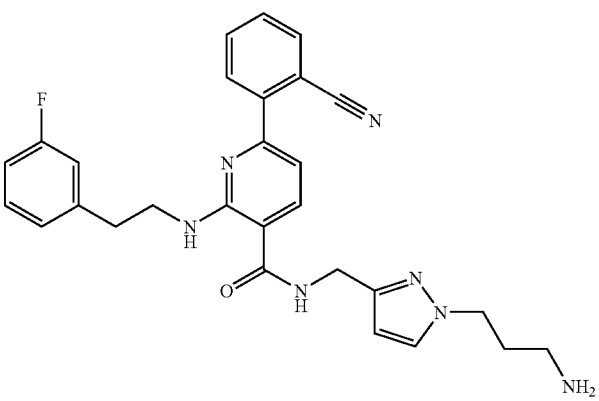  Compound 466 | N-{[1-(3-aminopropyl)pyrazol-3-yl]methyl}(6-(2-cyanophenyl)-2-{[2-(3-fluorophenyl)ethyl]amino}(3-pyridyl))carboxamide |

| COMPOUND | CHEMICAL NAME |
|---|---|
| 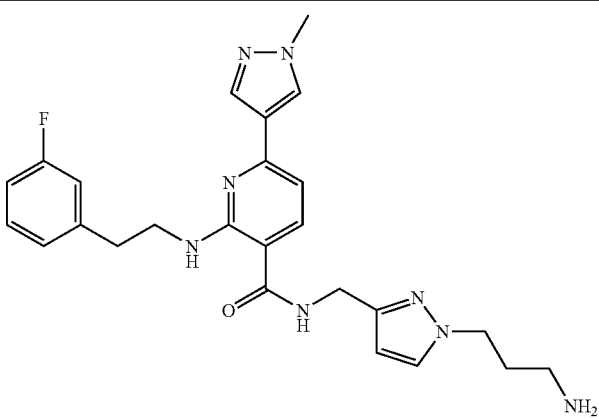<br>Compound 467 | N-{[1-(3-aminopropyl)pyrazol-3-yl]methyl}(2-{[2-(3-fluorophenyl)ethyl]amino}-6-(1-methylpyrazol-4-yl)(3-pyridyl))carboxamide |
| 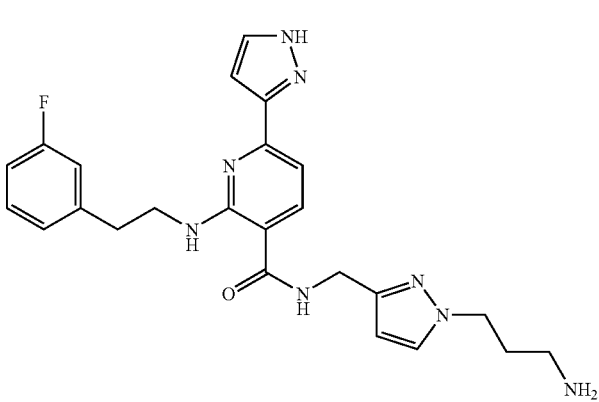<br>Compound 468 | N-{[1-(3-aminopropyl)pyrazol-3-yl]methyl}(2-{[2-(3-fluorophenyl)ethyl]amino}-6-pyrazol-3-yl(3-pyridyl))carboxamide |
| 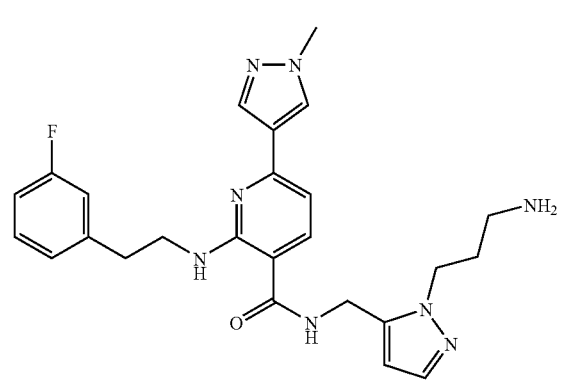<br>Compound 469 | N-{[1-(3-aminopropyl)pyrazol-5-yl]methyl}(2-{[2-(3-fluorophenyl)ethyl]amino}-6-(1-methylpyrazol-4-yl)(3-pyridyl))carboxamide |

-continued

| COMPOUND | CHEMICAL NAME |
|---|---|
| 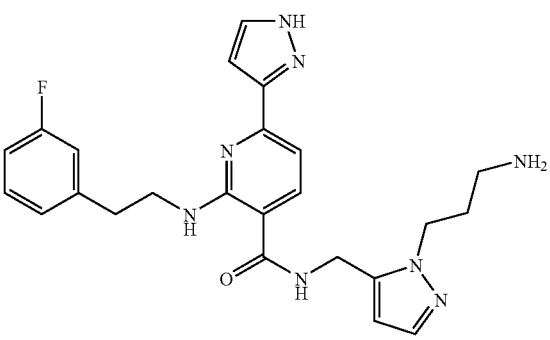<br>Compound 470 | N-{[1-(3-aminopropyl)pyrazol-5-yl]methyl}(2-{[2-(3-fluorophenyl)ethyl]amino}-6-pyrazol-3-yl(3-pyridyl))carboxamide |
| 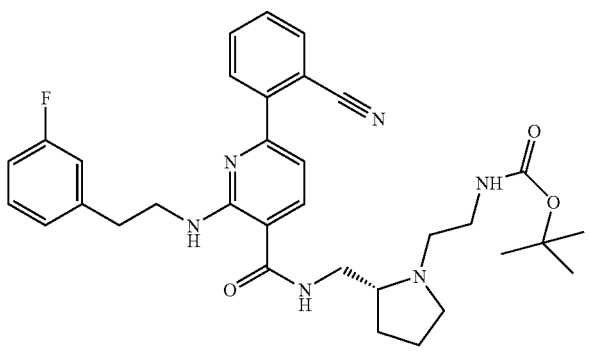<br>Compound 471 | N-[((2R)-1-{2-[(tert-butoxy)carbonylamino]ethyl}pyrrolidin-2-yl)methyl](6-(2-cyanophenyl)-2-{[2-(3-fluorophenyl)ethyl]amino}(3-pyridyl))carboxamide |
| 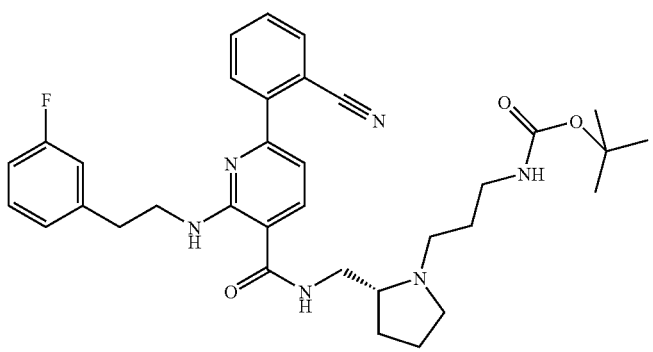<br>Compound 472 | N-[((2R)-1-{3-[(tert-butoxy)carbonylamino]propyl}pyrrolidin-2-yl)methyl](6-(2-cyanophenyl)-2-{[2-(3-fluorophenyl)ethyl]amino}(3-pyridyl))carboxamide |
| 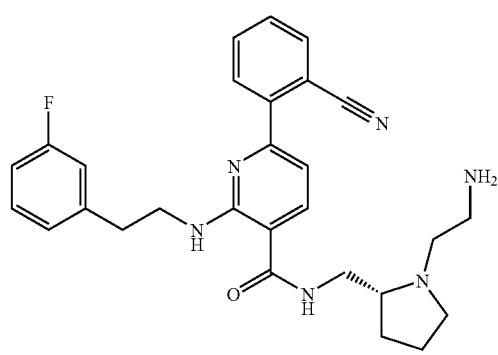<br>Compound 473 | N-{[(2R)-1-(2-aminoethyl)pyrrolidin-2-yl]methyl}(6-(2-cyanophenyl)-2-{[2-(3-fluorophenyl)ethyl]amino}(3-pyridyl))carboxamide |

-continued

| COMPOUND | CHEMICAL NAME |
|---|---|
| Compound 474 | N-{[(2R)-1-(3-aminopropyl)pyrrolidin-2-yl]methyl}(6-(2-cyanophenyl)-2-{[2-(3-fluorophenyl)ethyl]amino}(3-pyridyl))carboxamide |
| Compound 475 | N-[(1-{2-[(tert-butoxy)carbonylamino]ethyl}pyrazol-3-yl)methyl](2-{[2-(3-fluorophenyl)ethyl]amino}-6-pyrazol-3-yl(3-pyridyl))carboxamide |
| Compound 480 | N-{[1-(2-aminoethyl)pyrazol-3-yl]methyl}(2-{[2-(3-fluorophenyl)ethyl]amino}-6-pyrazol-4-yl(3-pyridyl))carboxamide |
| Compound 481 | N-{[1-(2-aminoethyl)pyrazol-3-yl]methyl}(2-{[2-(3-fluorophenyl)ethyl]amino}-6-pyrazol-3-yl(3-pyridyl))carboxamide |

| COMPOUND | CHEMICAL NAME |
|---|---|
| 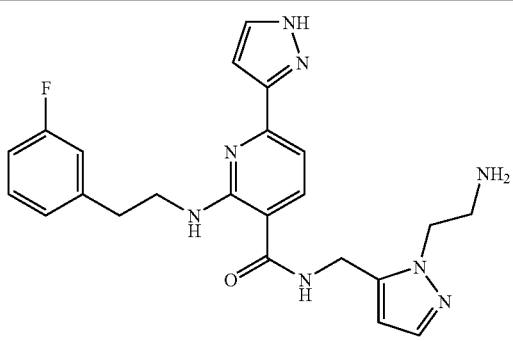<br>Compound 482 | N-{[1-(2-aminoethyl)pyrazol-5-yl]methyl}(2-{[2-(3-fluorophenyl)ethyl]amino}-6-pyrazol-3-yl(3-pyridyl))carboxamide |
| 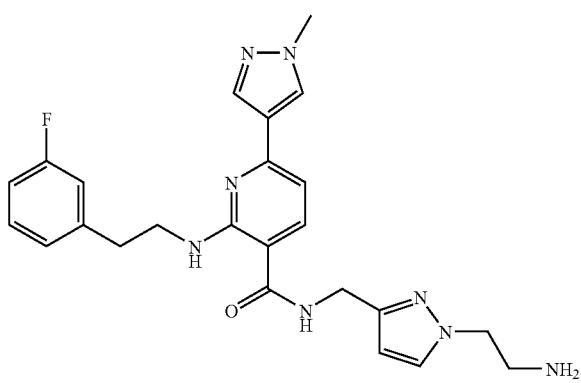<br>Compound 483 | N-{[1-(2-aminoethyl)pyrazol-3-yl]methyl}(2-{[2-(3-fluorophenyl)ethyl]amino}-6-(1-methylpyrazol-4-yl)(3-pyridyl))carboxamide |
| 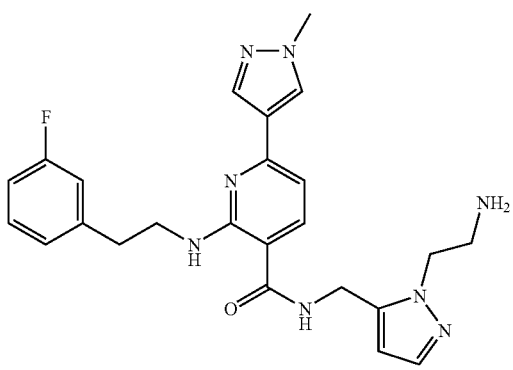<br>Compound 484 | N-{[1-(2-aminoethyl)pyrazol-5-yl]methyl}(2-{[2-(3-fluorophenyl)ethyl]amino}-6-(1-methylpyrazol-4-yl)(3-pyridyl))carboxamide |

| COMPOUND | CHEMICAL NAME |
|---|---|
| 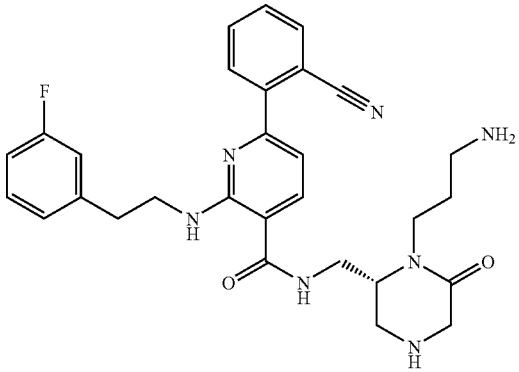
Compound 485 | N-{[(2R)-1-(3-aminopropyl)-6-oxopiperazin-2-yl]methyl}(6-(2-cyanophenyl)-2-{[2-(3-fluorophenyl)ethyl]amino}(3-pyridyl))carboxamide |
| 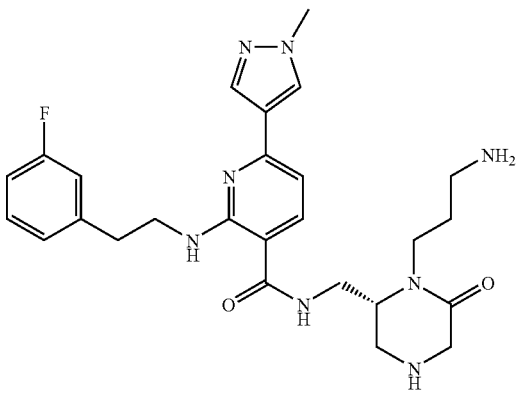
Compound 486 | N-{[(2R)-1-(3-aminopropyl)-6-oxopiperazin-2-yl]methyl}(2-{[2-(3-fluorophenyl)ethyl]amino}-6-(1-methylpyrazol-4-yl)(3-pyridyl))carboxamide |
| 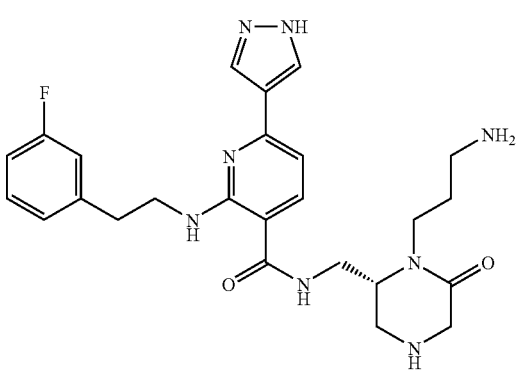
Compound 487 | N-{[(2R)-1-(3-aminopropyl)-6-oxopiperazin-2-yl]methyl}(2-{[2-(3-fluorophenyl)ethyl]amino}-6-pyrazol-4-yl(3-pyridyl))carboxamide |

| COMPOUND | CHEMICAL NAME |
|---|---|
| 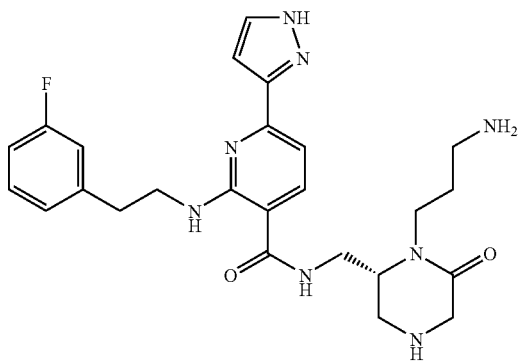<br>Compound 488 | N-{[(2R)-1-(3-aminopropyl)-6-oxopiperazin-2-yl]methyl}(2-{[2-(3-fluorophenyl)ethyl]amino}-6-pyrazol-3-yl(3-pyridyl))carboxamide |
| 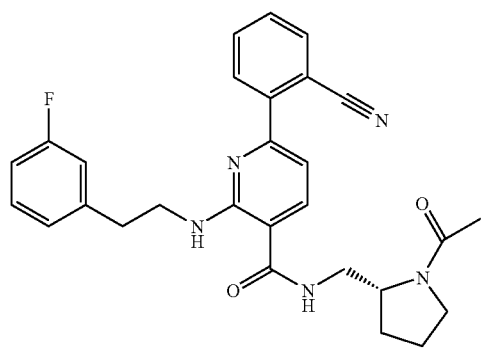<br>Compound 489 | N-[((2R)-1-acetylpyrrolidin-2-yl)methyl](6-(2-cyanophenyl)-2-{[2-(3-fluorophenyl)ethyl]amino}(3-pyridyl))carboxamide |
| 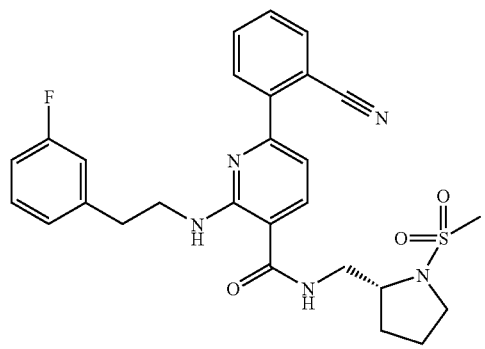<br>Compound 490 | N-{[(2R)-1-(methylsulfonyl)pyrrolidin-2-yl]methyl}(6-(2-cyanophenyl)-2-{[2-(3-fluorophenyl)ethyl]amino}(3-pyridyl))carboxamide |
| 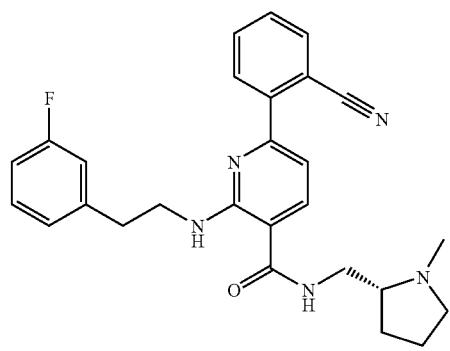<br>Compound 491 | N-[((2R)-1-methylpyrrolidin-2-yl)methyl](6-(2-cyanophenyl)-2-{[2-(3-fluorophenyl)ethyl]amino}(3-pyridyl))carboxamide |

| COMPOUND | CHEMICAL NAME |
|---|---|
| 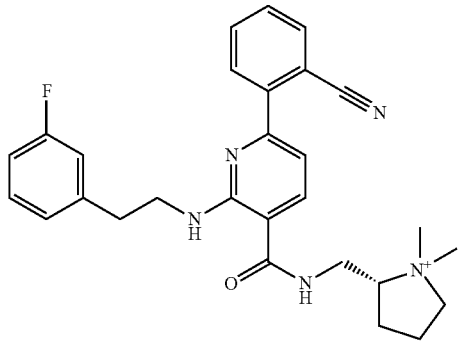<br>Compound 492 | N-[((2R)-1,1-dimethylpyrrolidin-2-yl)methyl](6-(2-cyanophenyl)-2-{[2-(3-fluorophenyl)ethyl]amino}(3-pyridyl))carbxamide |
| 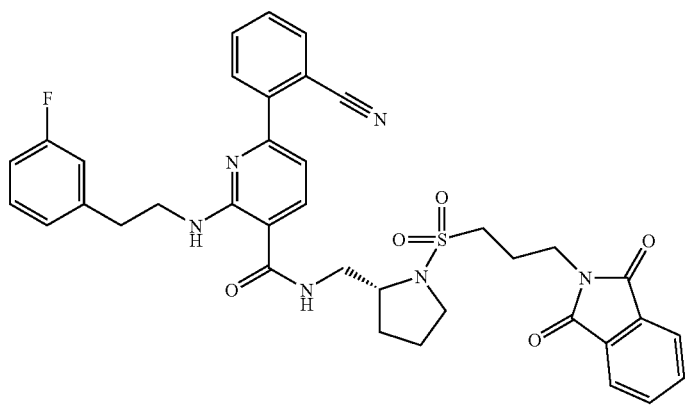<br>Compound 494 | N-[((2R)-1-{[3-(1,3-dioxobenzo[c]azolin-2-yl)propyl]sulfonyl}pyrrolidin-2-yl)methyl](6-(2-cyanophenyl)-2-{[2-(3-fluorophenyl)ethyl]amino}(3-pyridyl))carboxamide |
| 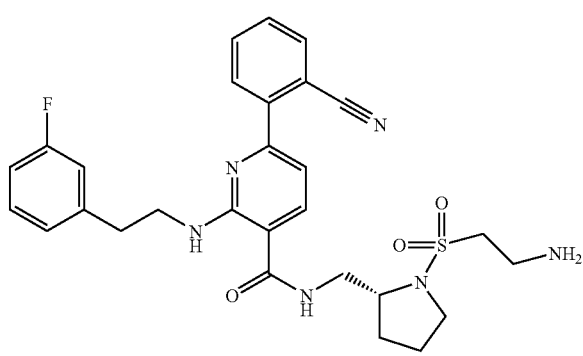<br>Compound 495 | N-({(2R)-1-[(2-aminoethyl)sulfonyl]pyrrolidin-2-yl}methyl)(6-(2-cyanophenyl)-2-{[2-(3-fluorophenyl)ethyl]amino}(3-pyridyl))carboxamide |

| COMPOUND | CHEMICAL NAME |
|---|---|
| 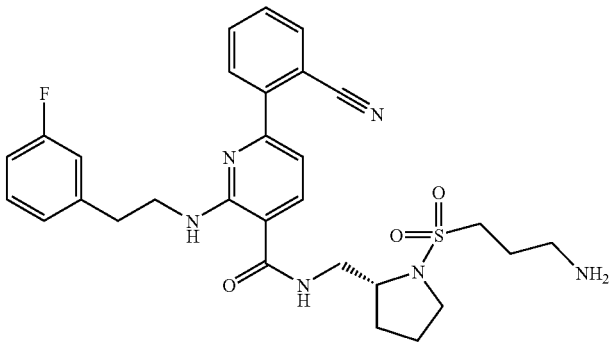
Compound 496 | N-({(2R)-1-[(3-aminopropyl)sulfonyl]pyrrolidin-2-yl}methyl)(6-(2-cyanophenyl)-2-{[2-(3-fluorophenyl)ethyl]amino}(3-pyridyl))carboxamide |
| 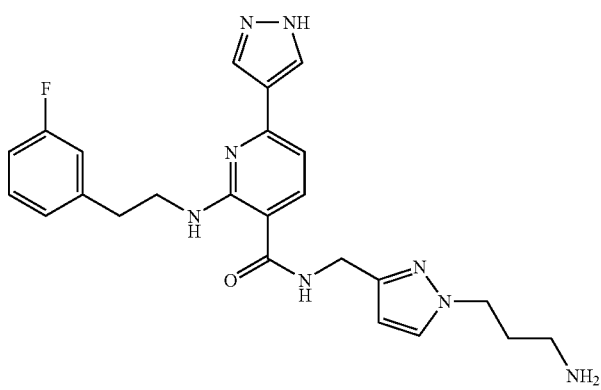
Compound 497 | N-{[1-(3-aminopropyl)pyrazol-3-yl]methyl}(2-{[2-(3-fluorophenyl)ethyl]amino}-6-pyrazol-4-yl(3-pyridyl))carboxamide |
| 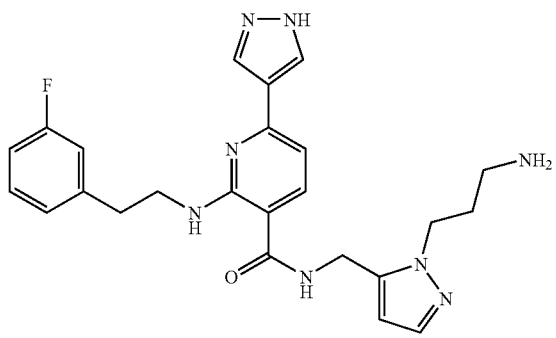
Compound 498 | N-{[1-(3-aminopropyl)pyrazol-5-yl]methyl}(2-{[2-(3-fluorophenyl)ethyl]amino}-6-pyrazol-4-yl(3-pyridyl))carboxamide |

-continued

| COMPOUND | CHEMICAL NAME |
|---|---|
| 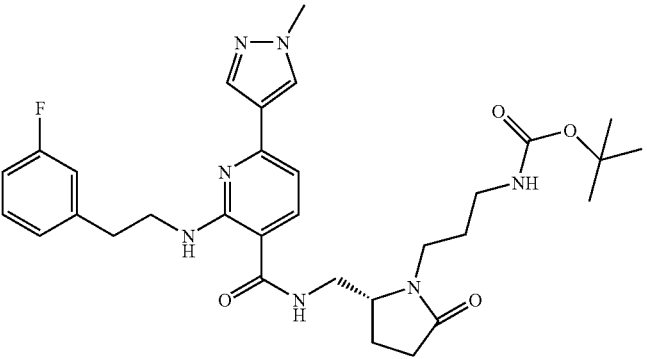<br>Compound 520 | N-[((2R)-1-{3-[(tert-butoxy)carbonylamino]propyl}-5-oxopyrrolidin-2-yl)methyl](2-{[2-(3-fluorophenyl)ethyl]amino}-6-(1-methylpyrazol-4-yl)(3-pyridyl))carboxamide |
| 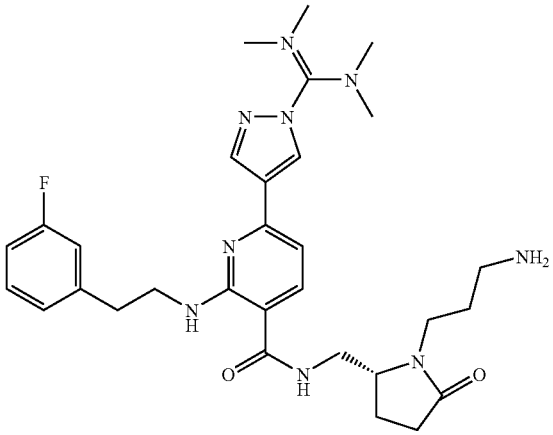<br>Compound 522 | N-{[1-(3-aminopropyl)-5-oxopyrrolidin-2-yl]methyl}(6-{1-[(dimethylamino)(dimethylylidene)methyl]pyrazol-4-yl}-2-{[2-(3-fluorophenyl)ethyl]amino}(3-pyridyl))carboxamide |
| 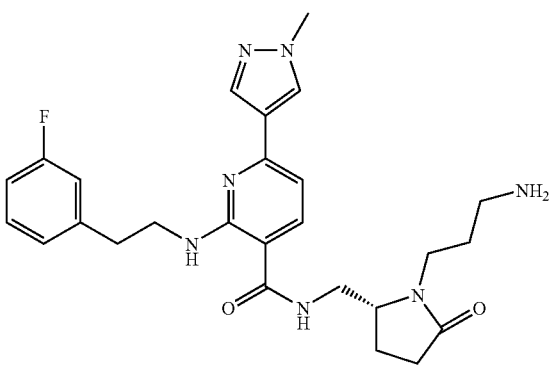<br>Compound 523 | N-{[(2R)-1-(3-aminopropyl)-5-oxopyrrolidin-2-yl]methyl}(2-{[2-(3-fluorophenyl)ethyl]amino}-6-(1-methylpyrazol-4-yl)(3-pyridyl))carboxamide |

-continued

| COMPOUND | CHEMICAL NAME |
|---|---|
| 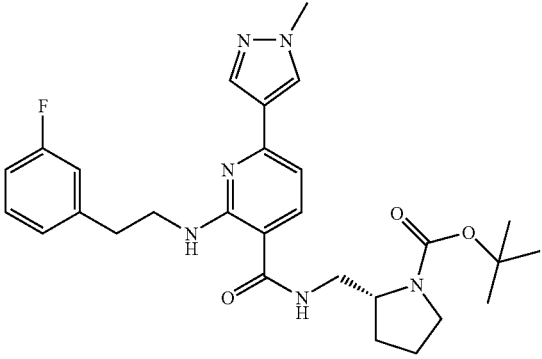<br>Compound 525 | tert-butyl (2R)-2-{[(2-{[2-(3-fluorophenyl)ethyl]amino}-6-(1-methylpyrazol-4-yl)(3-pyridyl))carbonylamino]methyl}pyrrolidinecarboxylate |
| 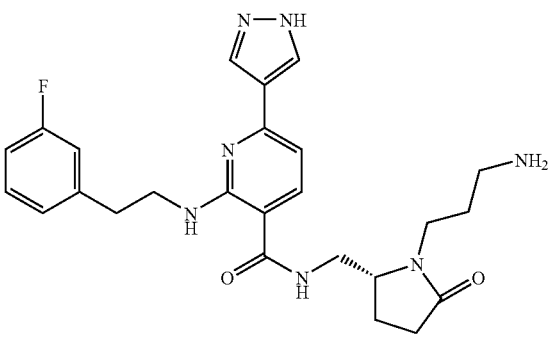<br>Compound 526 | N-{[(2R)-1-(3-aminopropyl)-5-oxopyrrolidin-2-yl]methyl}(2-{[2-(3-fluorophenyl)ethyl]amino}-6-pyrazol-4-yl(3-pyridyl))carboxamide |
| 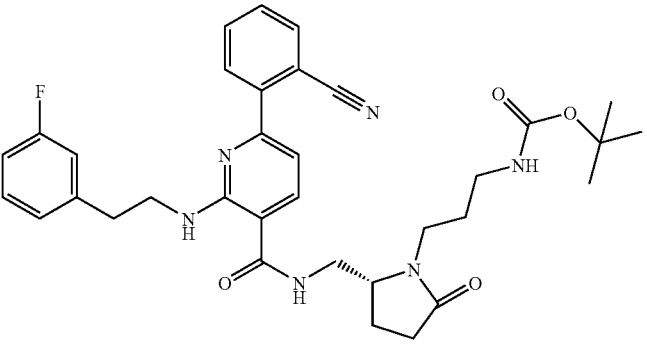<br>Compound 528 | N-[((2R)-1-{3-[(tert-butoxy)carbonylamino]propyl}-5-oxopyrrolidin-2-yl)methyl](6-(2-cyanophenyl)-2-{[2-(3-fluorophenyl)ethyl]amino}(3-pyridyl))carboxamide |
| 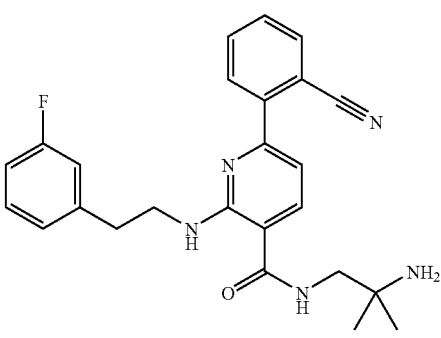<br>Compound 530 | N-(2-amino-2-methylpropyl)(6-(2-cyanophenyl)-2-{[2-(3-fluorophenyl)ethyl]amino}(3-pyridyl))carboxamide |

-continued

| COMPOUND | CHEMICAL NAME |
|---|---|
| Compound 531 | N-[((2R)pyrrolidin-2-yl)methyl](2-{[2-(3-fluorophenyl)ethyl]amino}-6-pyrazol-4-yl(3-pyridyl))carboxamide |
| Compound 534 | N-[((2R)pyrrolidin-2-yl)methyl](2-{[2-(3-fluorophenyl)ethyl]amino}-6-(1-methylpyrazol-4-yl)(3-pyridyl))carboxamide |
| Compound 537 | (6-(2-cyanophenyl)-2-{[2-(3-fluorophenyl)ethyl]amino}(3-pyridyl))-N-{2-methyl-2-[(methylsulfonyl)amino]propyl}carboxamide |
| Compound 538 | N-[((2R)-1-{2-(tert-butoxy)carbonylamino]acetyl}pyrrolidin-2-yl)methyl](2-(3-fluorophenyl)ethyl]amino}-6-(1-methylpyrazol-4-yl)(3-pyridyl))carboxamide |

| COMPOUND | CHEMICAL NAME |
|---|---|
| 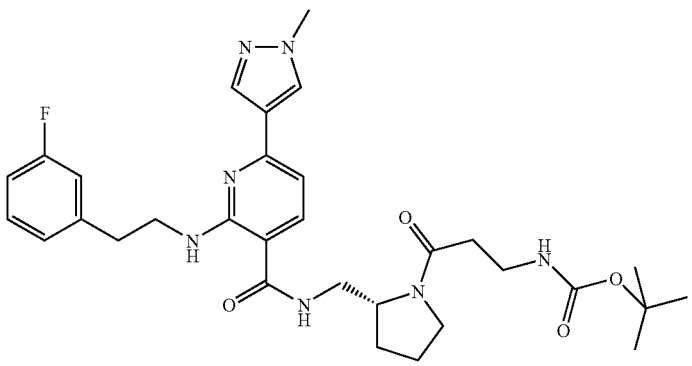<br>Compound 539 | N-[((2R)-1-{3-[(tert-butoxy)carbonylamino]propanoyl}pyrrolidin-2-yl)methyl](2-{[2-(3-fluorophenyl)ethyl]amino}-6-(1-methylpyrazol-4-yl)(3-pyridyl))carboxamide |
| 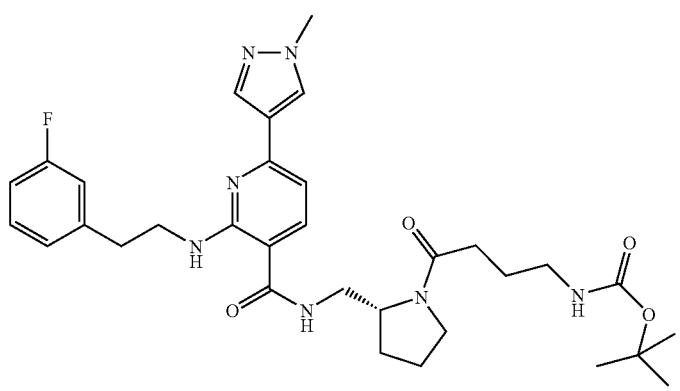<br>Compound 540 | N-[((2R)-1-{4-[(tert-butoxy)carbonylamino]butanoyl}pyrrolidin-2-yl)methyl](2-{[2-(3-fluorophenyl)ethyl]amino}-6-(1-methylpyrazol-4-yl)(3-pyridyl))carboxamide |
| 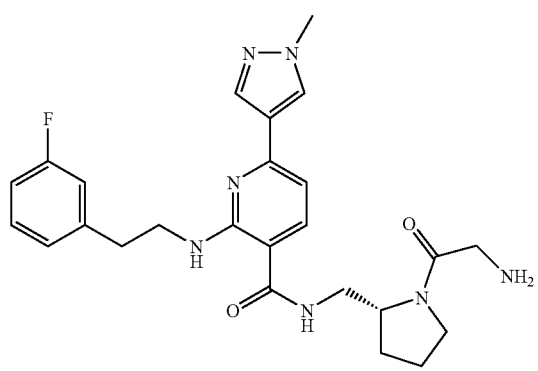<br>Compound 541 | N-{[(2R)-1-(2-aminoacetyl)pyrrolidin-2-yl]methyl}(2-{[2-(3-fluorophenyl)ethyl]amino}-6-(1-methylpyrazol-4-yl)(3-pyridyl))carboxamide |

-continued

| COMPOUND | CHEMICAL NAME |
|---|---|
| Compound 542 | N-{[(2R)-1-(3-aminopropanoyl)pyrrolidin-2-yl]methyl}(2-{[2-(3-fluorophenyl)ethyl]amino}-6-(1-methylpyrazol-4-yl)(3-pyridyl))carboxamide |
| Compound 543 | N-{[(2R)-1-(4-aminobutanoyl)pyrrolidin-2-yl]methyl}(2-{[2-(3-fluorophenyl)ethyl]amino}-6-(1-methylpyrazol-4-yl)(3-pyridyl))carboxamide |
| Compound 544 | N-((2S)-2-aminopropyl)(6-(2-cyanophenyl)-2-{[2-(3-fluorophenyl)ethyl]amino}(3-pyridyl))carboxamide |
| Compound 545 | 2-[(tert-butoxy)carbonylamino]-N-{2-[(6-(2-cyanophenyl)-2-{[2-(3-fluorophenyl)ethyl]amino}(3-pyridyl))carbonylamino]-tert-butyl}acetamide |

| COMPOUND | CHEMICAL NAME |
|---|---|
| Compound 546 | 4-[(tert-butoxy)carbonylamino]-N-{2-[(6-(2-cyanophenyl)-2-{[2-(3-fluorophenyl)ethyl]amino}(3-pyridyl))carbonylamino]-tert-butyl}butanamide |
| Compound 547 | N-{(1S)-2-[(6-(2-cyanophenyl)-2-{[2-(3-fluorophenyl)ethyl]amino}(3-pyridyl))carbonylamino]-isopropyl}-4-[(tert-butoxy)carbonylamino]butanamide |
| Compound 548 | N-[((2R)-1-{5-(tert-butoxy)carbonylamino]pentanoyl}pyrrolidin-2-yl)methyl](6-(2-cyanophenyl)-2-{[2-(3-fluorophenyl)ethyl]amino}(3-pyridyl))carboxamide |
| Compound 549 | 2-amino-N-{2-[(6-(2-cyanophenyl)-2-{[2-(3-fluorophenyl)ethyl]amino}(3-pyridyl))carbonylamino]-tert-butyl}acetamide |

| COMPOUND | CHEMICAL NAME |
|---|---|
| 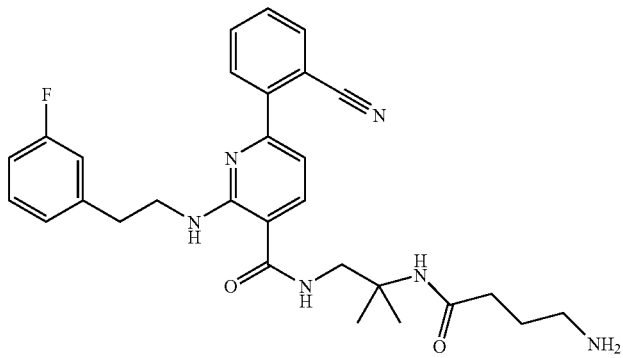
Compound 550 | 4-amino-N-{2-[(6-(2-cyanophenyl)-2-{[2-(3-fluorophenyl)ethyl]amino}(3-pyridyl))carbonylamino]-tert-butyl}butanamide |
| 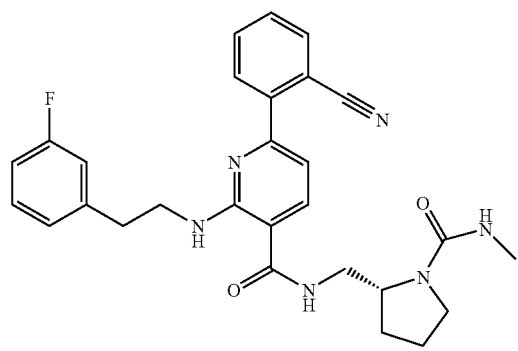
Compound 551 | N-{[(2R)-1-(N-methylcarbamoyl)pyrrolidin-2-yl]methyl}(6-(2-cyanophenyl)-2-{[2-(3-fluorophenyl)ethyl]amino}(3-pyridyl))carboxamide |
| 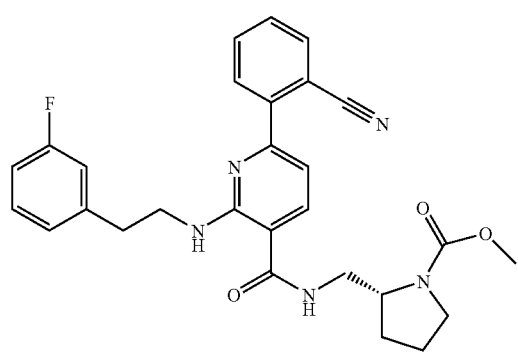
Compound 552 | methyl (2R)-2-{[6-(2-cyanophenyl)-2-{[2-(3-fluorophenyl)ethyl]amino}(3-pyridyl))carbonylamino]methyl}pyrrolidinecarboxylate |

-continued

| COMPOUND | CHEMICAL NAME |
|---|---|
| Compound 555 | N-{(1S)-2-[(6-(2-cyanophenyl)-2-{[2-(3-fluorophenyl)ethyl]amino}(3-pyridyl))carbonylamino]-isopropyl}-2-aminoacetamide |
| Compound 556 | N-{(1S)-2-[(6-(2-cyanophenyl)-2-{[2-(3-fluorophenyl)ethyl]amino}(3-pyridyl))carbonylamino]-isopropyl}-3-aminopropanamide |
| Compound 557 | N-{[(2R)-1-(5-aminopentanoyl)pyrrolidin-2-yl]methyl}(6-(2-cyanophenyl)-2-{[2-(3-fluorophenyl)ethyl]amino}(3-pyridyl))carboxamide |
| Compound 558 | N-{(2S)-2-[(methylsulfonyl)amino]propyl}(6-(2-cyanophenyl)-2-{[2-(3-fluorophenyl)ethyl]amino}(3-pyridyl))carboxamide |

| COMPOUND | CHEMICAL NAME |
|---|---|
| 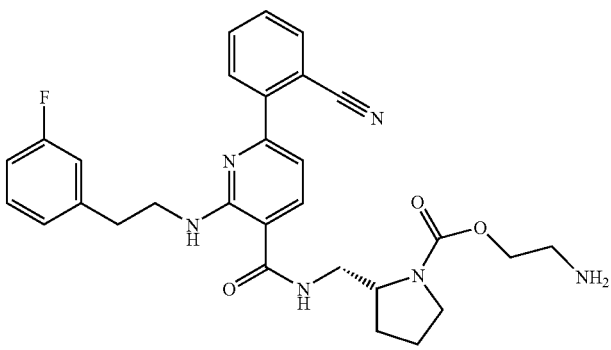<br>Compound 602 | 2-aminoethyl (2R)-2-{[(6-(2-cyanophenyl)-2-{[2-(3-fluorophenyl)ethyl]amino}(3-pyridyl))carbonylamino]methyl}pyrrolidinecarboxylate |
| 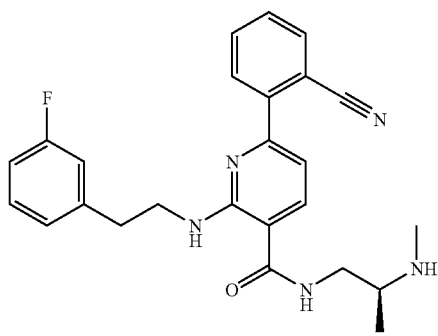<br>Compound 603 | N-[(2S)-2-(methylamino)propyl](6-(2-cyanophenyl)-2-{[2-(3-fluorophenyl)ethyl]amino}(3-pyridyl))carboxamide |
| 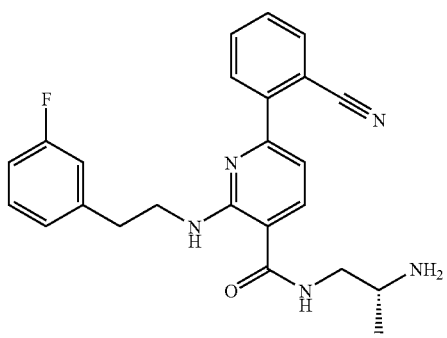<br>Compound 604 | N-((2R)-2-aminopropyl)(6-(2-cyanophenyl)-2-{[2-(3-fluorophenyl)ethyl]amino}(3-pyridyl))carboxamide |
| 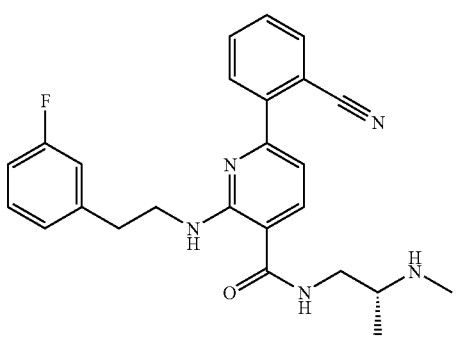<br>Compound 605 | N-[(2R)-2-(methylamino)propyl](6-(2-cyanophenyl)-2-{[2-(3-fluorophenyl)ethyl[amino}(3-pyridyl))carboxamide |

-continued

| COMPOUND | CHEMICAL NAME |
|---|---|
| 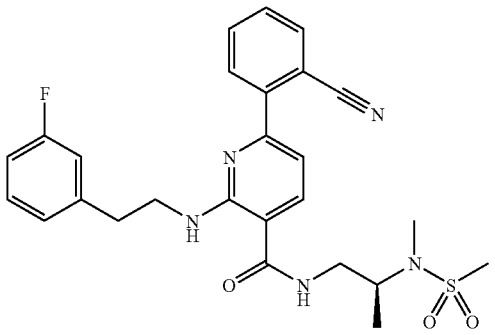<br>Compound 606 | N-{(2S)-2-[methyl(methylsulfonyl)amino]propyl}(6-(2-cyanophenyl)-2-{[2-(3-fluorophenyl)ethyl]amino}(3-pyridyl))carboxamide |
| 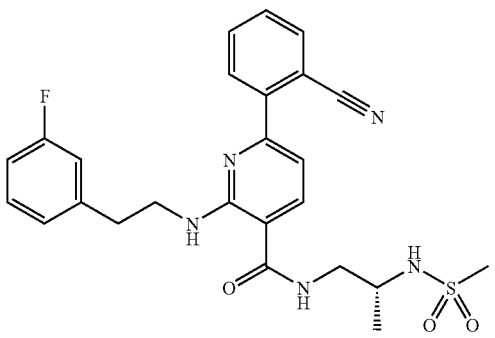<br>Compound 607 | N-{(2R)-2-[(methylsulfonyl)amino]propyl}(6-(2-cyanophenyl)-2-{[2-(3-fluorophenyl)ethyl]amino}(3-pyridyl))carboxamide |
| 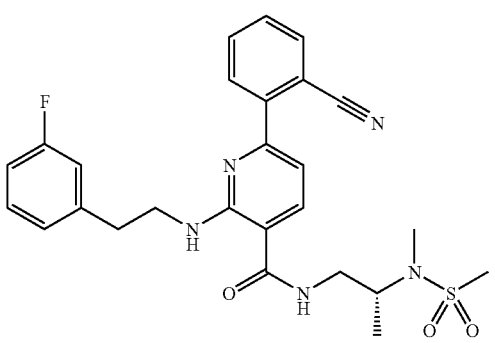<br>Compound 608 | N-{(2R)-2-[methyl(methylsulfonyl)amino]propyl}(6-(2-cyanophenyl)-2-{[2-(3-fluorophenyl)ethyl]amino}(3-pyridyl))carboxamide |
| 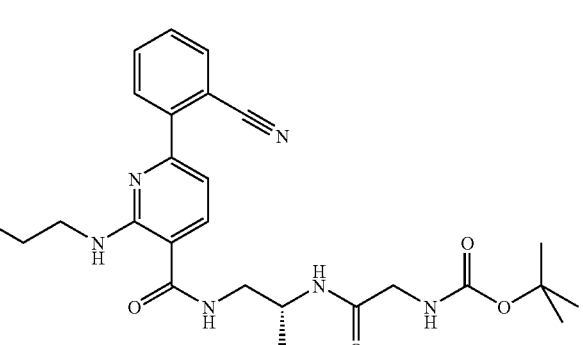<br>Compound 609 | N-{(1R)-2-[(6-(2-cyanophenyl)-2-{[2-(3-fluorophenyl)ethyl]amino}(3-pyridyl))carbonylamino]-isopropyl}-2-[(tert-butoxy)carbonylamino]acetamide |

| COMPOUND | CHEMICAL NAME |
|---|---|
| 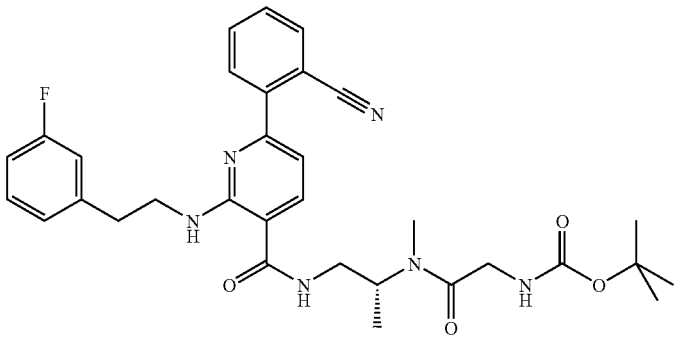
Compound 610 | N-{(1R)-2-[(6-(2-cyanophenyl)-2-{[2-(3-fluorophenyl)ethyl]amino}(3-pyridyl))carbonylamino]-isopropyl}-2-[(tert-butoxy)carbonylamino]-N-methylacetamide |
| 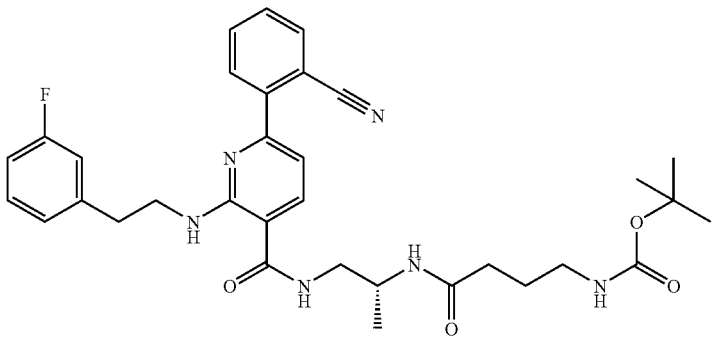
Compound 611 | N-{(1R)-2-[(6-(2-cyanophenyl)-2-{[2-(3-fluorophenyl)ethyl]amino}(3-pyridyl))carbonylamino]-isopropyl}-4-[(tert-butoxy)carbonylamino]butanamide |
| 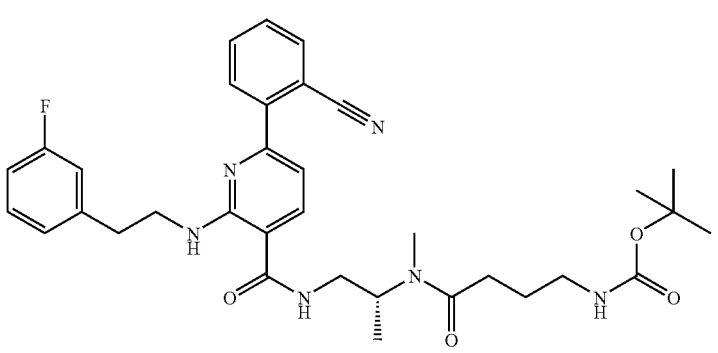
Compound 612 | N-{(1R)-2-[(6-(2-cyanophenyl)-2-{[2-(3-fluorophenyl)ethyl]amino}(3-pyridyl))carbonylamino]-isopropyl}-4-[(tert-butoxy)carbonylamino]-N-methylbutanamide |
| 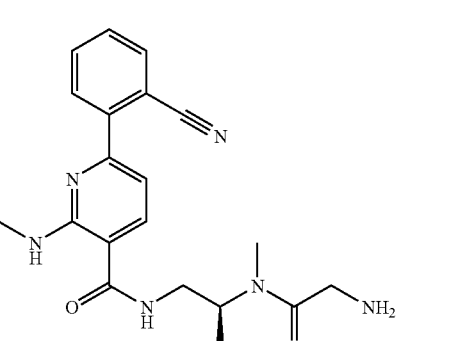
Compound 613 | N-{(1S)-2-[(6-(2-cyanophenyl)-2-{[2-(3-fluorophenyl)ethyl]amino}(3-pyridyl))carbonylamino]-isopropyl}-2-amino-N-methylacetamide |

| COMPOUND | CHEMICAL NAME |
|---|---|
| Compound 614 | N-{(1S)-2-[(6-(2-cyanophenyl)-2-{[2-(3-fluorophenyl)ethyl]amino}(3-pyridyl))carbonylamino]-isopropyl}-4-amino-N-methylbutanamide |
| Compound 615 | N-{(1R)-2-[(6-(2-cyanophenyl)-2-{[2-(3-fluorophenyl)ethyl]amino}(3-pyridyl))carbonylamino]-isopropyl}-2-aminoacetamide |
| Compound 616 | N-{(1R)-2-[(6-(2-cyanophenyl)-2-{[2-(3-fluorophenyl)ethyl]amino}(3-pyridyl))carbonylamino]-isopropyl}-4-aminobutanamide |
| Compound 617 | N-{(1R)-2-[(6-(2-cyanophenyl)-2-{[2-(3-fluorophenyl)ethyl]amino}(3-pyridyl))carbonylamino]-isopropyl}-4-amino-N-methylbutanamide |

| COMPOUND | CHEMICAL NAME |
|---|---|
| 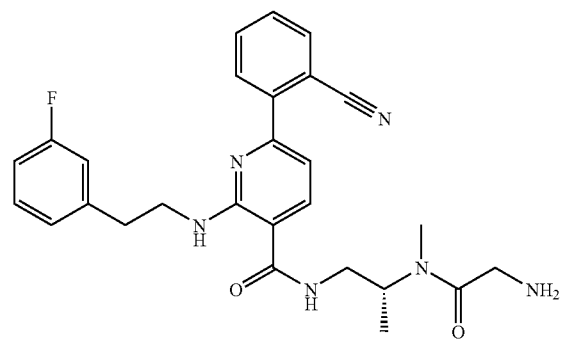

Compound 618 | N-{(1R)-2-[(6-(2-cyanophenyl)-2-{[2-(3-fluorophenyl)ethyl]amino}(3-pyridyl))carbonylamino]-isopropyl}-2-amino-N-methylacetamide |
| 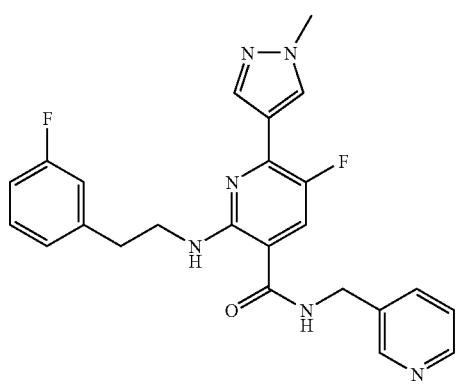

Compound 619 | (5-fluoro-2-{[2-(3-fluorophenyl)ethyl]amino}-6-(1-methylpyrazol-4-yl)(3-pyridyl))-N-(3-pyridylmethyl)carboxamide |
| 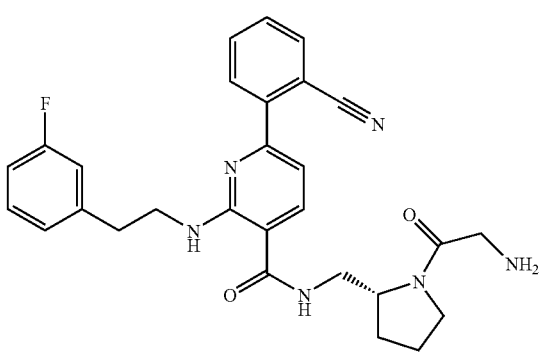

Compound 463 | N-{[(2R)-1-(2-aminoacetyl)pyrrolidin-2-yl]methyl}(6-(2-cyanophenyl)-2-{[2-(3-fluorophenyl)ethyl]amino}(3-pyridyl))carboxamide |
| 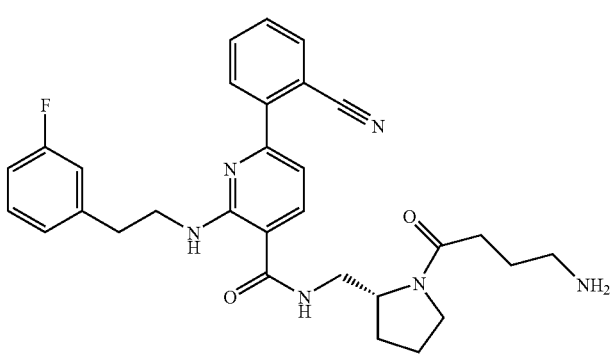

Compound 465 | N-{[(2R)-1-(4-aminobutanoyl)pyrrolidin-2-yl]methyl}(6-(2-cyanophenyl)-2-{[2-(3-fluorophenyl)ethyl]amino}(3-pyridyl))carboxamide |

-continued

| COMPOUND | CHEMICAL NAME |
|---|---|
| Compound 410 | N-{[(2R)-1-(3-aminopropyl)-5-oxopyrrolidin-2-yl]methyl}(6-(2-cyanophenyl)-2-{[2-(3-fluorophenyl)ethyl]amino}(3-pyridyl))carboxamide |
| Compound 311 | (2-{[2-(3-fluorophenyl)ethyl]amino}-6-pyrazol-4-yl(3-pyridyl))-N-(3-pyridylmethyl)carboxamide |
| Compound 36 | {6-(3-methylphenyl)-2-[(2-(2-pyridyl)ethyl)amino](3-pyridyl)}-N-(3-pyridylmethyl)carboxamide |
| Compound 35 | {6-(3-fluorophenyl)-2-[(2-(2-pyridyl)ethyl)amino](3-pyridyl)}-N-(3-pyridylmethyl)carboxamide |

| COMPOUND | CHEMICAL NAME |
|---|---|
| 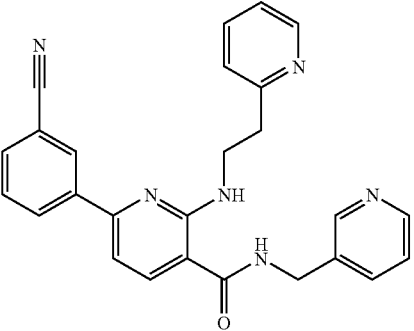<br>Compound 32 | {6-(3-cyanophenyl)-2-[(2-(2-pyridyl)ethyl)amino](3-pyridyl)}-N-(3-pyridylmethyl)carboxamide |
| 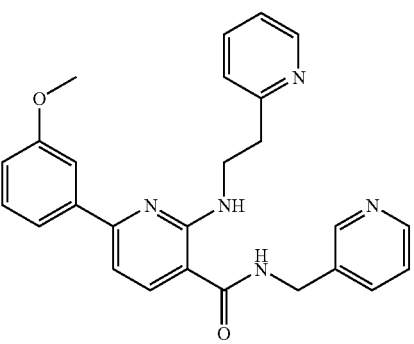<br>Compound 31 | {6-(3-methoxyphenyl)-2-[(2-(2-pyridyl)ethyl)amino](3-pyridyl)}-N-(3-pyridylmethyl)carboxamide |
| 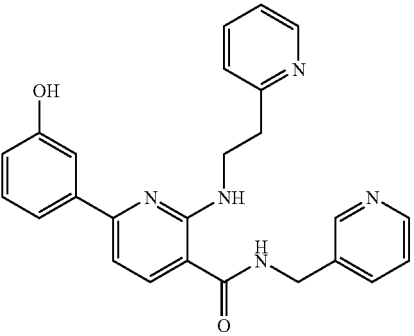<br>Compound 29 | {6-(3-hydroxyphenyl)-2-[(2-(2-pyridyl)ethyl)amino](3-pyridyl)}-N-(3-pyridylmethyl)carboxamide |
| 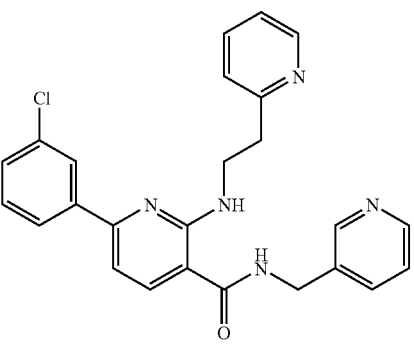<br>Compound 7 | {6-(3-chlorophenyl)-2-[(2-(2-pyridyl)ethyl)amino](3-pyridyl)}-N-(3-pyridylmethyl)carboxamide |

-continued

| COMPOUND | CHEMICAL NAME |
|---|---|
| Compound 10 | {2-[(2-(2-pyridyl)ethyl)amino]-6-[3-(trifluoromethyl)phenyl](3-pyridyl)}-N-(3-pyridylmethyl)carboxamide |
| Compound 11 | {6-[3-(dimethylamino)phenyl]-2-[(2-(2-pyridyl)ethyl)amino](3-pyridyl)}-N-(3-pyridylmethyl)carboxamide |
| Compound 12 | {6-(2-fluorophenyl)-2-[(2-(2-pyridyl)ethyl)amino](3-pyridyl)}-N-(3-pyridylmethyl)carboxamide |
| Compound 67 | {6-(2-chlorophenyl)-2-[(2-(2-pyridyl)ethyl)amino](3-pyridyl)}-N-(3-pyridylmethyl)carboxamide |

| COMPOUND | CHEMICAL NAME |
|---|---|
| Compound 14 | {6-(2-methylphenyl)-2-[(2-(2-pyridyl)ethyl)amino](3-pyridyl)}-N-(3-pyridylmethyl)carboxamide |
| Compound 15 | {6-(2-methoxyphenyl)-2-[(2-(2-pyridyl)ethyl)amino](3-pyridyl)}-N-(3 pyridylmethyl)carboxamide |
| Compound 16 | {6-(2-cyanophenyl)-2-[(2-(2-pyridyl)ethyl)amino](3-pyridyl)}-N-(3-pyridylmethyl)carboxamide |
| Compound 17 | {2-[(2-(2-pyridyl)ethyl)amino]-6-(2-thienyl)(3-pyridyl)}-N-(3-pyridylmethyl)carboxamide |

-continued

| COMPOUND | CHEMICAL NAME |
|---|---|
| 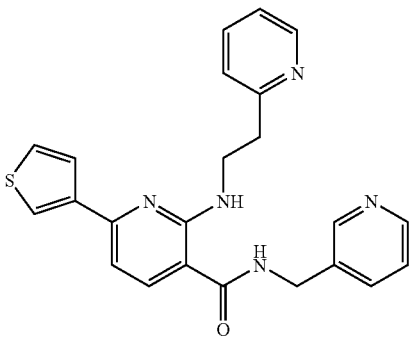<br>Compound 58 | {2-[(2-(2-pyridyl)ethyl)amino]-6-(3-thienyl)(3-pyridyl)}-N-(3-pyridylmethyl)carboxamide |
| 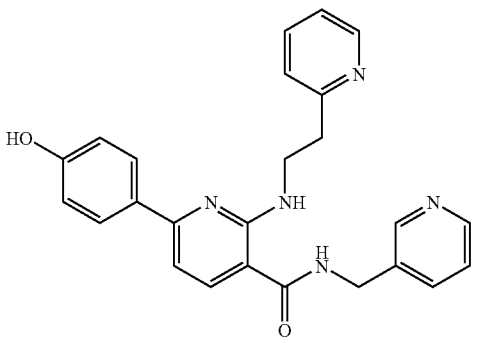<br>Compound 172 | {6-(4-hydroxyphenyl)-2-[(2-(2-pyridyl)ethyl)amino](3-pyridyl)}-N-(3-pyridylmethyl)carboxamide |
| 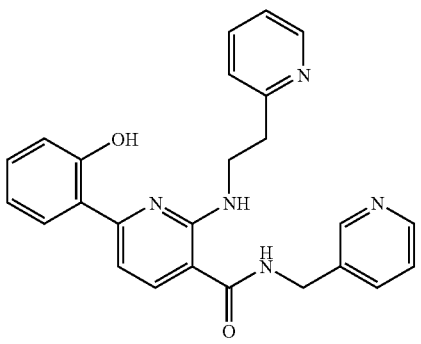<br>Compound 171 | {6-(2-hydroxyphenyl)-2-[(2-(2-pyridyl)ethyl)amino](3-pyridyl)}-N-(3-pyridylmethyl)carboxamide |
| 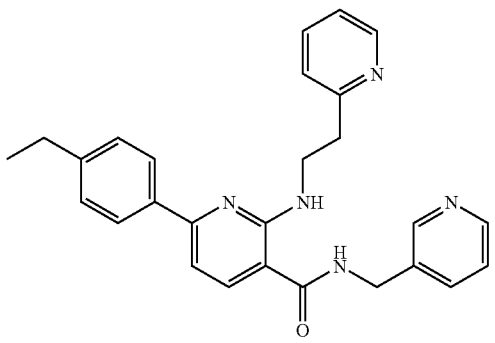<br>Compound 26 | {6-(4-ethylphenyl)-2-[(2-(2-pyridyl)ethyl)amino](3-pyridyl)}-N-(3-pyridylmethyl)carboxamide |

| COMPOUND | CHEMICAL NAME |
|---|---|
| 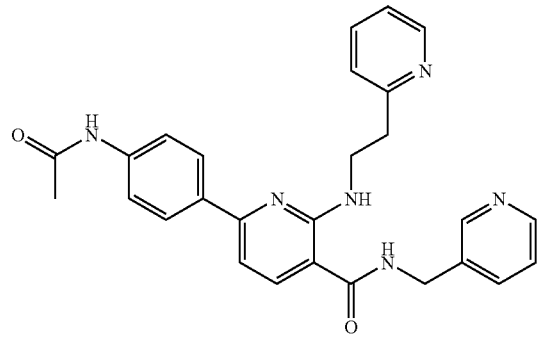<br>Compound 861 | N-(4-{6-[(2-(2-pyridyl)ethyl)amino]-5-[N-(3-pyridylmethyl)carbamoyl]-2-pyridyl}phenyl)acetamide |
| 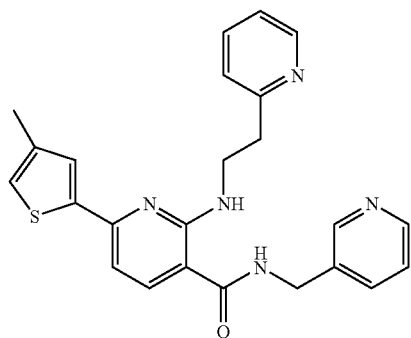<br>Compound 28 | {6-(4-methyl(2-thienyl))-2-[(2-(2-pyridyl)ethyl)amino](3-pyridyl)}-N-(3-pyridylmethyl)carboxamide |
| 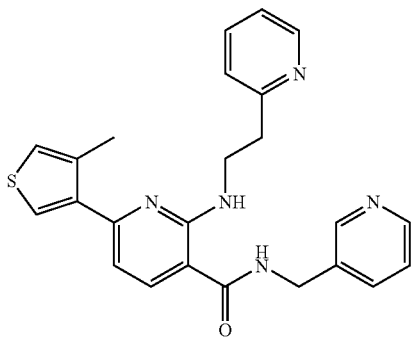<br>Compound 55 | {6-(4-methyl(3-thienyl))-2-[(2-(2-pyridyl)ethyl)amino](3-pyridyl)}-N-(3-pyridylmethyl)carboxamide |
| 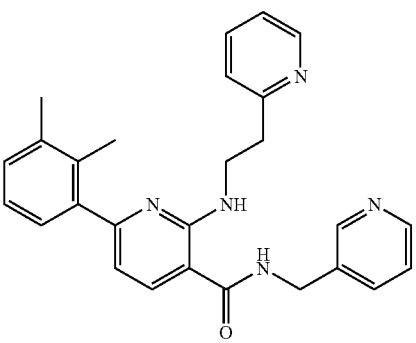<br>Compound 400 | {6-(2,3-dimethylphenyl)-2-[(2-(2-pyridyl)ethyl)amino](3-pyridyl)}-N-(3-pyridylmethyl)carboxamide |

| COMPOUND | CHEMICAL NAME |
|---|---|
| 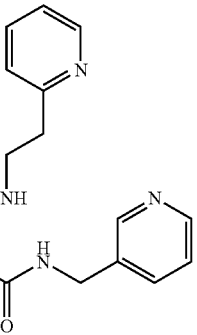\nCompound 53 | {6-(2,5-dimethylphenyl)-2-[(2-(2-pyridyl)ethyl)amino](3-pyridyl)}-N-(3-pyridylmethyl)carboxamide |
| 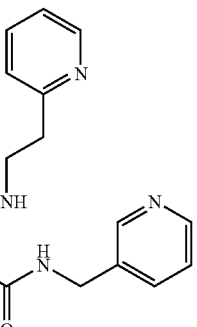\nCompound 52 | {6-(2,4-dimethylphenyl)-2-[(2-(2-pyridyl)ethyl)amino](3-pyridyl)}-N-(3-pyridylmethyl)carboxamide |
| 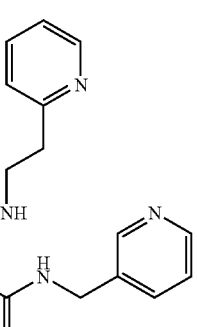\nCompound 33 | {6-(3,5-dimethylphenyl)-2-[(2-(2-pyridyl)ethyl)amino](3-pyridyl)}-N-(3-pyridylmethyl)carboxamide |
| 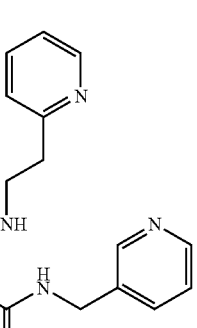\nCompound 34 | {6-(3,4-dimethylphenyl)-2-[(2-(2-pyridyl)ethyl)amino](3-pyridyl)}-N-(3-pyridylmethyl)carboxamide |

| COMPOUND | CHEMICAL NAME |
|---|---|
| 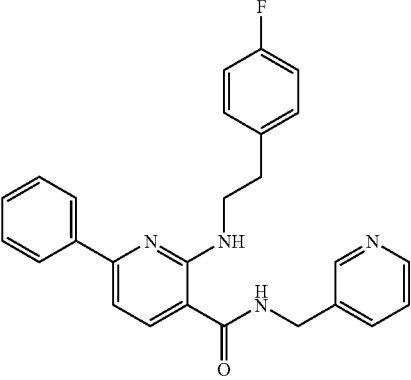<br>Compound 158 | (2-{[2-(4-fluorophenyl)ethyl]amino}-6-phenyl(3-pyridyl))-N-(3-pyridylmethyl)carboxamide |
| 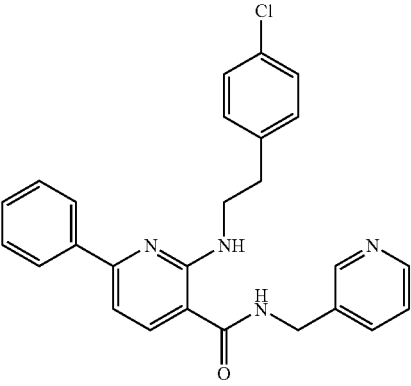<br>Compound 41 | (2-{[2-(4-chlorophenyl)ethyl]amino}-6-phenyl(3-pyridyl))-N-(3-pyridylmethyl)carboxamide |
| 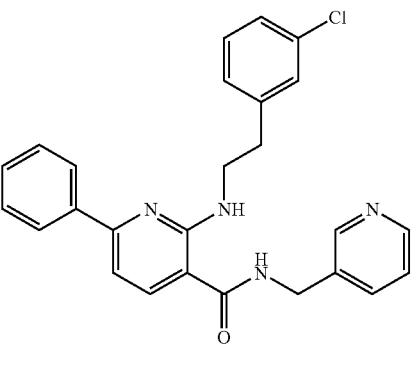<br>Compound 375 | (2-{[2-(3-chlorophenyl)ethyl]amino}-6-phenyl(3-pyridyl))-N-(3-pyridylmethyl)carboxamide |

| COMPOUND | CHEMICAL NAME |
|---|---|
| Compound 56 | (2-{[2-(3-methoxyphenyl)ethyl]amino}-6-phenyl(3-pyridyl))-N-(3-pyridylmethyl)carboxamide |
| Compound 57 | (2-{[2-(3-fluorophenyl)ethyl]amino}-6-phenyl(3-pyridyl))-N-(3-pyridylmethyl)carboxamide |
| Compound 70 | (2-{[2-(2-chlorophenyl)ethyl]amino}-6-phenyl(3-pyridyl))-N-(3-pyridylmethyl)carboxamide |
| Compound 71 | (2-{[2-(2-methoxyphenyl)ethyl]amino}-6-phenyl(3-pyridyl))-N-(3-pyridylmethyl)carboxamide |

-continued

| COMPOUND | CHEMICAL NAME |
|---|---|
| 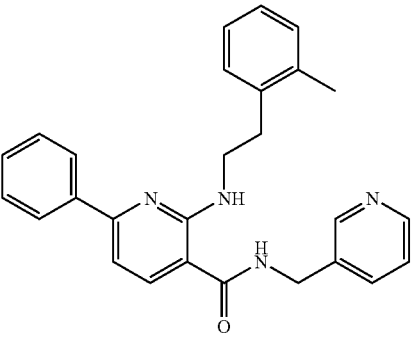<br>Compound 72 | (2-{[2-(2-methylphenyl)ethyl]amino}-6-phenyl(3-pyridyl))-N-(3-pyridylmethyl)carboxamide |
| 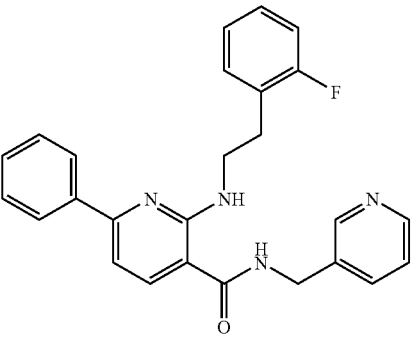<br>Compound 73 | (2-{[2-(2-fluorophenyl)ethyl]amino}-6-phenyl(3-pyridyl))-N-(3-pyridylmethyl)carboxamide |
| 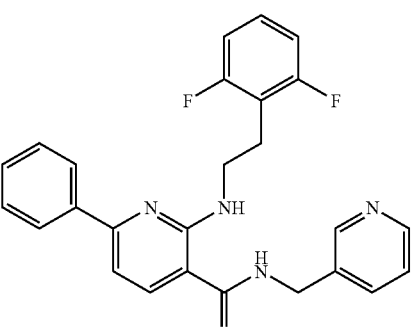<br>Compound 74 | (2-{[2-(2,6-difluorophenyl)ethyl]amino}-6-phenyl(3-pyridyl))-N-(3-pyridylmethyl)carboxamide |
| 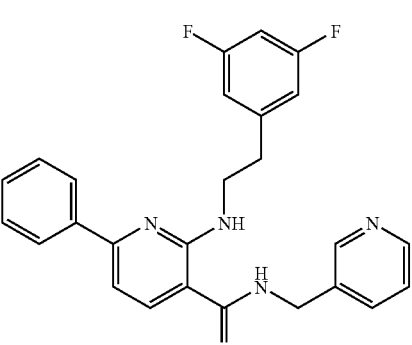<br>Compound 75 | (2-{[2-(3,5-difluorophenyl)ethyl]amino}-6-phenyl(3-pyridyl))-N-(3-pyridylmethyl)carboxamide |

| COMPOUND | CHEMICAL NAME |
|---|---|
| 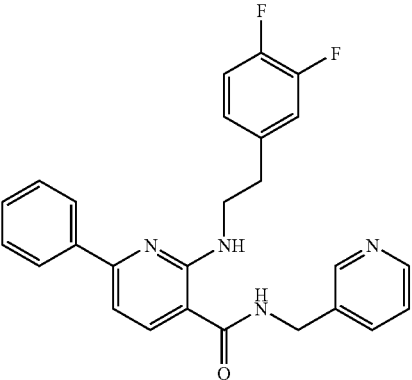<br>Compound 84 | (2-{[2-(3,4-difluorophenyl)ethyl]amino}-6-phenyl(3-pyridyl))-N-(3-pyridylmethyl)carboxamide |
| 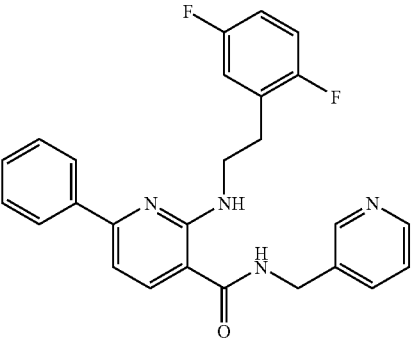<br>Compound 85 | (2-{[2-(2,5-difluorophenyl)ethyl]amino}-6-phenyl(3-pyridyl))-N-(3-pyridylmethyl)carboxamide |
| 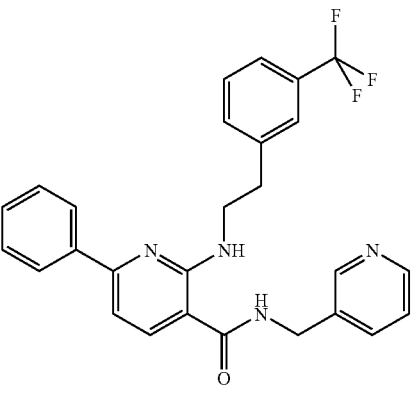<br>Compound 86 | {6-phenyl-2-({2-[3-(trifluoromethyl)phenyl]ethyl}amino)(3-pyridyl)]-N-(3-pyridylmethyl)carboxamide |

| COMPOUND | CHEMICAL NAME |
|---|---|
| 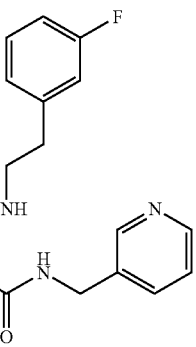
Compound 87 | (2-{[2-(3-fluorophenyl)ethyl]amino}-6-(4-methyl(2-thienyl))(3-pyridyl))-N-(3-pyridylmethyl)carboxamide |
| 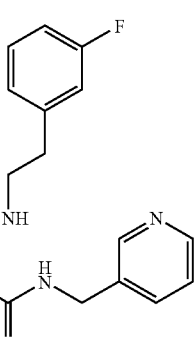
Compound 88 | (2-{[2-(3-fluorophenyl)ethyl]amino}-6-(3-thienyl)(3-pyridyl))-N-(3-pyridylmethyl)carboxamide |
| 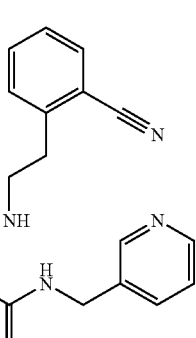
Compound 89 | (2-{[2-(2-cyanophenyl)ethyl]amino}-6-phenyl(3-pyridyl))-N-(3-pyridylmethyl)carboxamide |
| 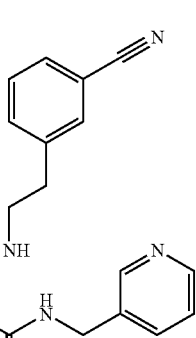
Compound 90 | (2-{[2-(3-cyanophenyl)ethyl]amino}-6-phenyl(3-pyridyl))-N-(3-pyridylmethyl)carboxamide |

| COMPOUND | CHEMICAL NAME |
|---|---|
| 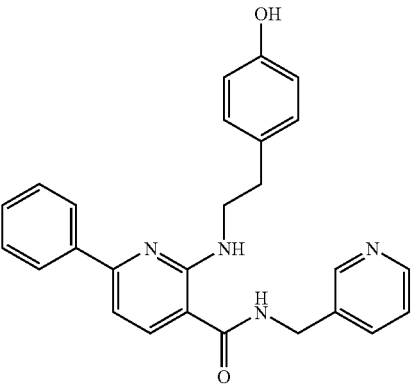
Compound 91 | (2-{[2-(4-hydroxyphenyl)ethyl]amino}-6-phenyl(3-pyridyl))-N-(3-pyridylmethyl)carboxamide |
| 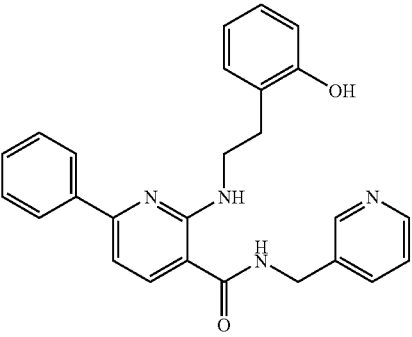
Compound 92 | (2-{[2-(2-hydroxyphenyl)ethyl]amino}-6-phenyl(3-pyridyl))-N-(3-pyridylmethyl)carboxamide |
| 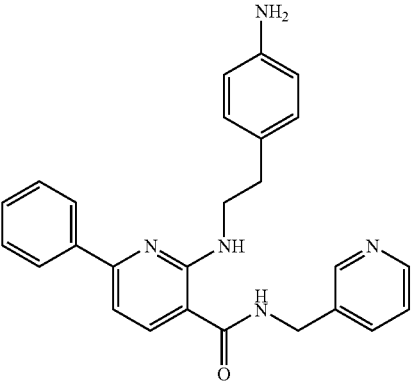
Compound 95 | (2-{[2-(4-aminophenyl)ethyl]amino}-6-phenyl(3-pyridyl))-N-(3-pyridylmethyl)carboxamide |

-continued

| COMPOUND | CHEMICAL NAME |
|---|---|
| Compound 96 | 3-[2-({6-phenyl-3-[N-(3-pyridylmethyl)carbamoyl]-2-pyridyl}amino)ethyl]benzamide |
| Compound 97 | (2-{[2-(3,5-difluorophenyl)ethyl]amino}-6-(3-thienyl)(3-pyridyl))-N-(3-pyridylmethyl)carboxamide |
| Compound 98 | (2-{[2-(3,5-difluorophenyl)ethyl]amino}-6-(4-methyl(2-thienyl))(3-pyridyl))-N-(3-pyridylmethyl)carboxamide |
| Compound 99 | (2-{[2-(3,5-difluorophenyl)ethyl]amino}-6-(2-cyanophenyl)(3-pyridyl))-N-(3-pyridylmethyl)carboxamide |

-continued

| COMPOUND | CHEMICAL NAME |
|---|---|
| 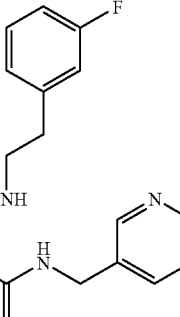<br>Compound 105 | (2-{[2-(3-fluorophenyl)ethyl]amino}-6-(2-thienyl)(3-pyridyl))-N-(3-pyridylmethyl)carboxamide |
| 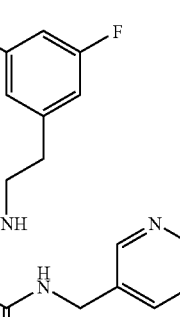<br>Compound 106 | (2-{[2-(3,5-difluorophenyl)ethyl]amino}-6-(2-thienyl)(3-pyridyl))-N-(3-pyridylmethyl)carboxamide |
| 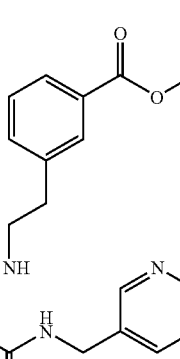<br>Compound 107 | methyl 3-[2-({6-phenyl-3-[N-(3-pyridylmethyl)carbamoyl]-2-pyridyl}amino)ethyl]benzoate |
| 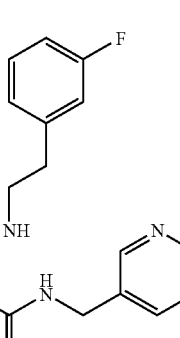<br>Compound 108 | 2-(6-{[2-(3-fluorophenyl)ethyl]amino}-5-[N-(3-pyridylmethyl)carbamoyl]-2-pyridyl)benzamide |

-continued
| COMPOUND | CHEMICAL NAME |
|---|---|
| 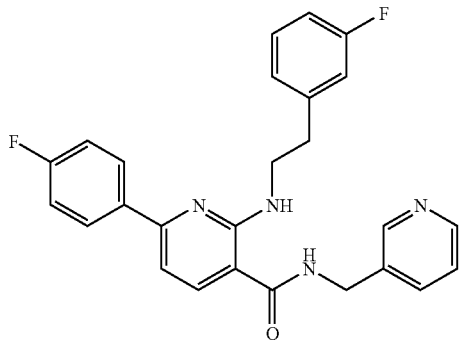<br>Compound 109 | (6-(4-fluorophenyl)-2-{[2-(3-fluorophenyl)ethyl]amino}(3-pyridyl))-N-(3-pyridylmethyl)carboxamide |
| 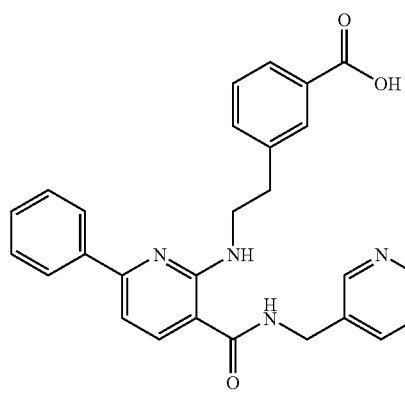<br>Compound 123 | 3-[2-({6-phenyl-3-[N-(3-pyridylmethyl)carbamoyl]-2-pyridyl}amino)ethyl]benzoic acid |
| 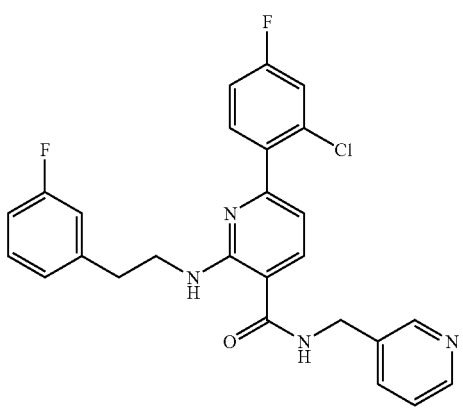<br>Compound 156 | (6-(2-chloro-4-fluorophenyl)-2-{[2-(3-fluorophenyl)ethyl]amino}(3-pyridyl))-N-(3-pyridylmethyl)carboxamide |

| COMPOUND | CHEMICAL NAME |
|---|---|
| 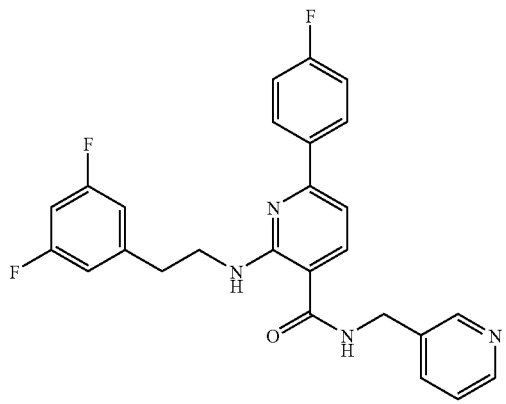
Compound 157 | (2-{[2-(3,5-difluorophenyl)ethyl]amino}-6-(4-fluorophenyl)(3-pyridyl))-N-(3-pyridylmethyl)carboxamide |
| 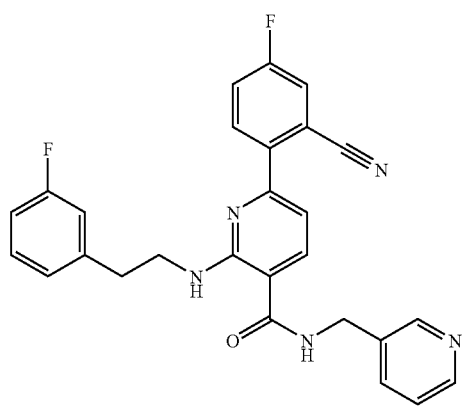
Compound 179 | (6-(2-cyano-4-fluorophenyl)-2-{[2-(3-fluorophenyl)ethyl]amino}(3-pyridyl))-N-(3-pyridylmethyl)carboxamide |
| 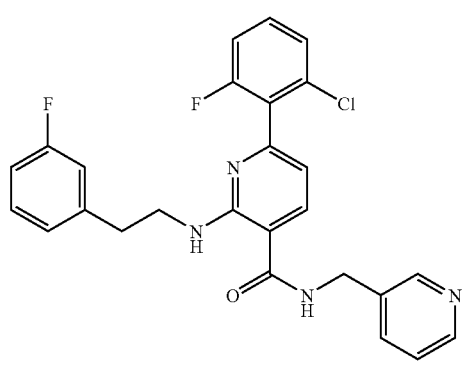
Compound 180 | (6-(2-chloro-6-fluorophenyl)-2-{[2-(3-fluorophenyl)ethyl]amino}(3-pyridyl))-N-(3-pyridylmethyl)carboxamide |

| COMPOUND | CHEMICAL NAME |
| --- | --- |
| Compound 204 | (6-(2-chloro-5-methoxyphenyl)-2-{[2-(3-fluorophenyl)ethyl]amino}(3-pyridyl))-N-(3-pyridylmethyl)carboxamide |
| Compound 228 | (6-(2-cyano-5-methoxyphenyl)-2-{[2-(3-fluorophenyl)ethyl]amino}(3-pyridyl))-N-(3-pyridylmethyl)carboxamide |
| Compound 206 | (6-(2-cyano-6-fluorophenyl)-2-{[2-(3-fluorophenyl)ethyl]amino}(3-pyridyl))-N-(3-pyridylmethyl)carboxamide |

-continued

| COMPOUND | CHEMICAL NAME |
|---|---|
| Compound 207 | (6-(2-fluorophenyl)-2-{[2-(3-fluorophenyl)ethyl]amino}(3-pyridyl))-N-(3-pyridylmethyl)carboxamide |
| Compound 229 | (2-{[2-(2,3-difluorophenyl)ethyl]amino}-6-(2-cyanophenyl)(3-pyridyl))-N-(3-pyridylmethyl)carboxamide |
| Compound 230 | (6-(2-chloro-5-fluorophenyl)-2-{[2-(3-fluorophenyl)ethyl]amino}(3-pyridyl))-N-(3-pyridylmethyl)carboxamide |
| Compound 253 | (6-(2-cyano-5-fluorophenyl)-2-{[2-(3-fluorophenyl)ethyl]amino}(3-pyridyl))-N-(3-pyridylmethyl)carboxamide |

-continued

| COMPOUND | CHEMICAL NAME |
|---|---|
| Compound 254 | (6-(3-fluorophenyl)-2-{[2-(3-fluorophenyl)ethyl]amino}(3-pyridyl))-N-(3-pyridylmethyl)carboxamide |
| Compound 261 | (6-[2-(cyanomethyl)phenyl]-2-{[2-(3-fluorophenyl)ethyl]amino}(3-pyridyl))-N-(3-pyridylmethyl)carboxamide |
| Compound 263 | (2-{[2-(3-fluorophenyl)ethyl]amino}-6-[3-(hydroxymethyl)(2-thienyl)](3-pyridyl))-N-(3-pyridylmethyl)carboxamide |
| Compound 264 | (2-{[2-(3-fluorophenyl)ethyl]amino}-6-(5-formyl(3-thienyl))(3-pyridyl))-N-(3-pyridylmethyl)carboxamide |

| COMPOUND | CHEMICAL NAME |
|---|---|
| 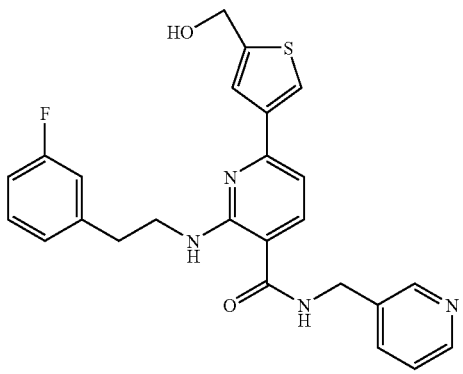
Compound 265 | (2-{[2-(3-fluorophenyl)ethyl]amino}-6-[5-(hydroxymethyl)(3-thienyl)](3-pyridyl))-N-(3-pyridylmethyl)carboxamide |
| 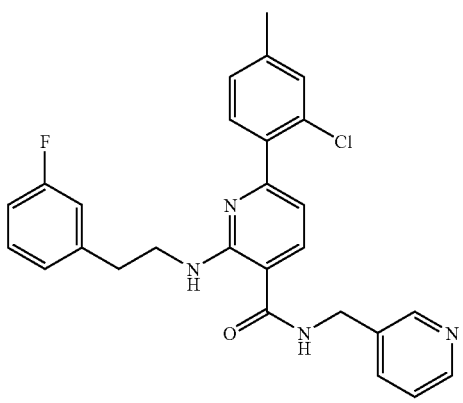
Compound 276 | (6-(2-chloro-4-methylphenyl)-2-{[2-(3-fluorophenyl)ethyl]amino}(3-pyridyl))-N-(3-pyridylmethyl)carboxamide |
| 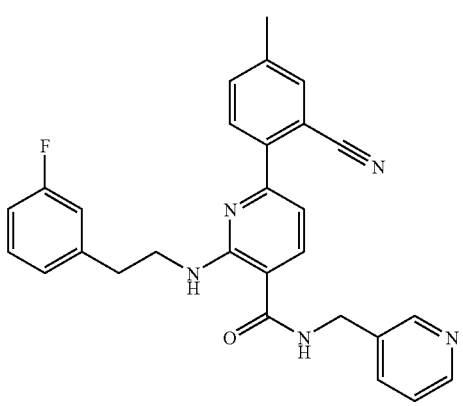
Compound 280 | (6-(2-cyano-4-methylphenyl)-2-{[2-(3-fluorophenyl)ethyl]amino}(3-pyridyl))-N-(3-pyridylmethyl)carboxamide |

| COMPOUND | CHEMICAL NAME |
|---|---|
| Compound 281 | (2-{[2-(3-fluorophenyl)ethyl]amino}-6-[3-(hydroxymethyl)phenyl](3-pyridyl))-N-(3-pyridylmethyl)carboxamide |
| Compound 282 | (2-{[2-(3-fluorophenyl)ethyl]amino}-6-[3-(methoxymethyl)phenyl](3-pyridyl))-N-(3-pyridylmethyl)carboxamide |
| Compound 285 | (6-(1H-1,2,3,4-tetraazol-5-yl)-2-{[2-(3-fluorophenyl)ethyl]amino}(3-pyridyl))-N-(3-pyridylmethyl)carboxamide |
| Compound 289 | (6-[2-chloro-5-(hydroxymethyl)phenyl]-2-{[2-(3-fluorophenyl)ethyl]amino}(3-pyridyl))-N-(3-pyridylmethyl)carboxamide |

-continued

| COMPOUND | CHEMICAL NAME |
|---|---|
| Compound 290 | (2R)-2-amino-4-[(6-(2-cyanophenyl)-2-{[2-(3-fluorophenyl)ethyl]amino}(3-pyridyl))carbonylamino]-N-methylbutanamide |
| Compound 294 | (2S)-2-amino-4-[(6-(2-cyanophenyl)-2-{[2-(3-fluorophenyl)ethyl]amino}(3-pyridyl))carbonylamino]-N-methylbutanamide |
| Compound 295 | N-(3-amino-2-hydroxypropyl)(6-(2-cyanophenyl)-2-{[2-(3-fluorophenyl)ethyl]amino}(3-pyridyl))carboxamide |
| boc | N-[(2-{[(tert-butoxy)carbonylamino]methyl}(3-pyridyl))methyl](6-(2-cyanophenyl)-2-{[2-(3-fluorophenyl)ethyl]amino}(3-pyridyl))carboxamide |

| COMPOUND | CHEMICAL NAME |
|---|---|
| 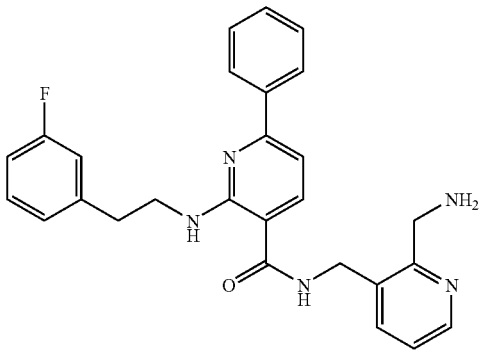<br>Compound 399 | N-{[2-(aminomethyl)(3-pyridyl)]methyl}(2-{[2-(3-fluorophenyl)ethyl]amino}-6-phenyl(3-pyridyl))carboxamide |
| 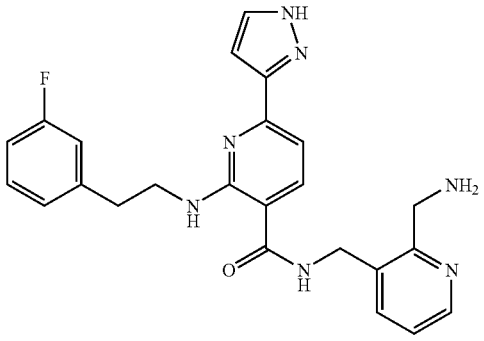<br>Compound 426 | N-{[2-(aminomethyl)(3-pyridyl)]methyl}(2-{[2-(3-fluorophenyl)ethyl]amino}-6-pyrazol-3-yl(3-pyridyl))carboxamide |
| 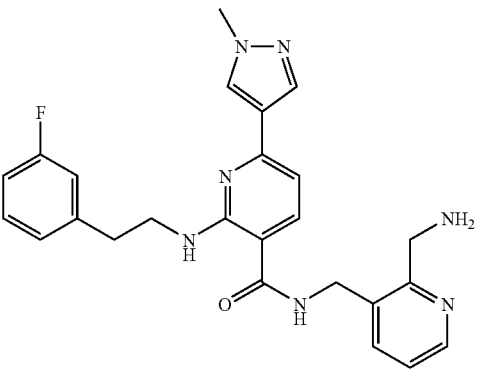<br>Compound 427 | N-{[2-(aminomethyl)(3-pyridyl)]methyl}(2-{[2-(3-fluorophenyl)ethyl]amino}-6-(1-methylpyrazol-3-yl)(3-pyridyl))carboxamide |

| COMPOUND | CHEMICAL NAME |
|---|---|
| 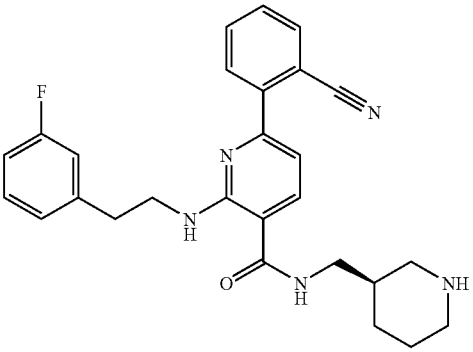
Compound 503 | N-[((3R)(3-piperidyl))methyl](6-(2-cyanophenyl)-2-{[2-(3-fluorophenyl)ethyl]amino}(3-pyridyl))carboxamide |
| 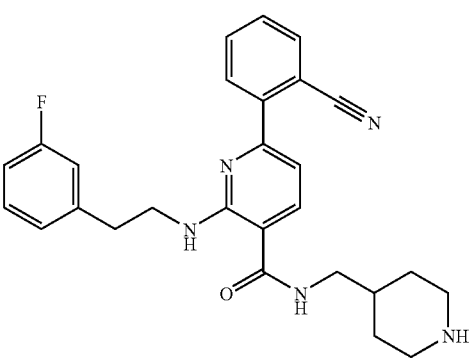
Compound 504 | (6-(2-cyanophenyl)-2-{[2-(3-fluorophenyl)ethyl]amino}(3-pyridyl))-N-(4-piperidylmethyl)carboxamide |
| 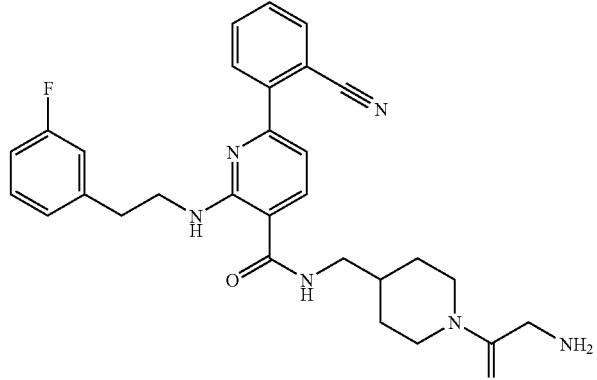
Compound 505 | N-{[1-(2-aminoacetyl)(4-piperidyl)]methyl}(6-(2-cyanophenyl)-2-{[2-(3-fluorophenyl)ethyl]amino}(3-pyridyl))carboxamide |

-continued

| COMPOUND | CHEMICAL NAME |
| --- | --- |
| 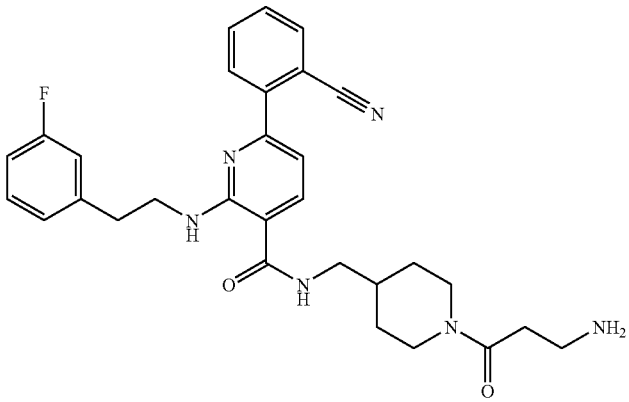<br>Compound 506 | N-{[1-(3-aminopropanoyl)(4-piperidyl)]methyl}(6-(2-cyanophenyl)-2-{[2-(3-fluorophenyl)ethyl]amino}(3-pyridyl))carboxamide |
| 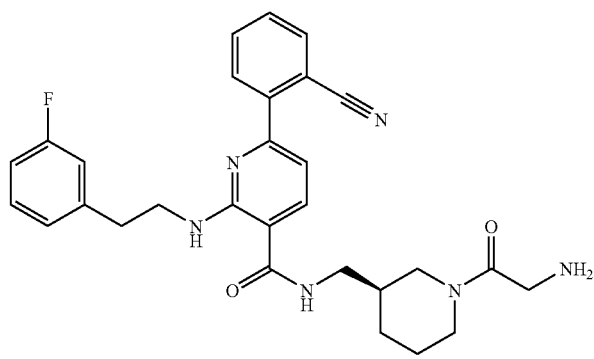<br>Compound 507 | N-{[(3S)-1-(2-aminoacetyl)(3-piperidyl)]methyl}(6-(2-cyanophenyl)-2-{[2-(3-fluorophenyl)ethyl]amino}(3-pyridyl))carboxamide |
| 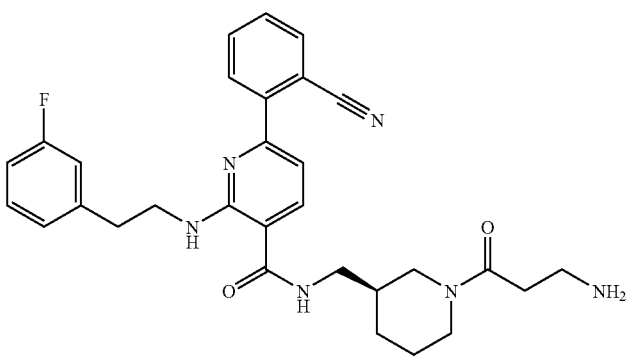<br>Compound 508 | N-{[(3S)-1-(3-aminopropanoyl)(3-piperidyl)]methyl}(6-(2-cyanophenyl)-2-{[2-(3-fluorophenyl)ethyl]amino}(3-pyridyl))carboxamide |

-continued
| COMPOUND | CHEMICAL NAME |
|---|---|
| 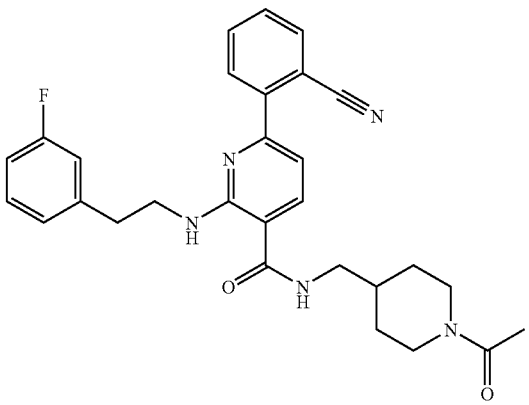<br>Compound 509 | N-[(1-acetyl(4-piperidyl))methyl](6-(2-cyanophenyl)-2-{[2-(3-fluorophenyl)ethyl]amino}(3-pyridyl))carboxamide |
| 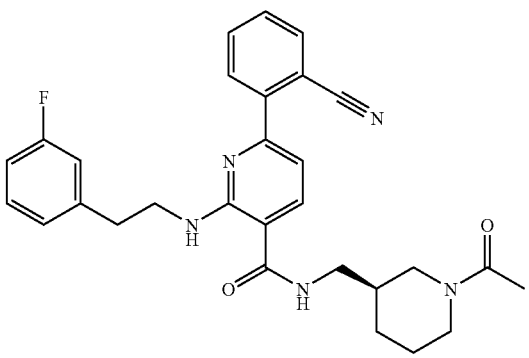<br>Compound 510 | N-[((3S)-1-acetyl(3-piperidyl))methyl](6-(2-cyanophenyl)-2-{[2-(3-fluorophenyl)ethyl]amino}(3-pyridyl))carboxamide |
| 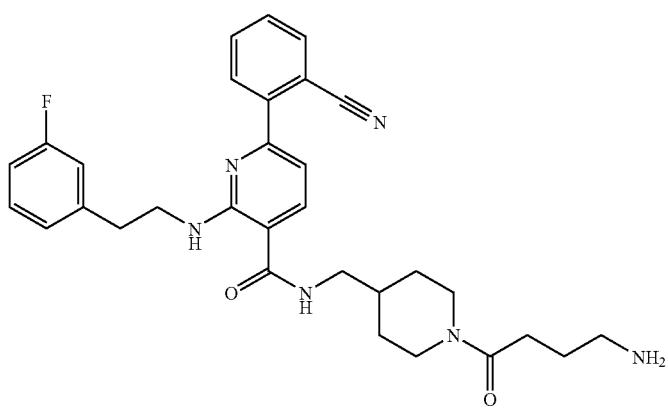<br>Compound 553 | N-{[1-(4-aminobutanoyl)(4-piperidyl)]methyl}(6-(2-cyanophenyl)-2-{[2-(3-fluorophenyl)ethyl]amino}(3-pyridyl))carboxamide |

| COMPOUND | CHEMICAL NAME |
|---|---|
| 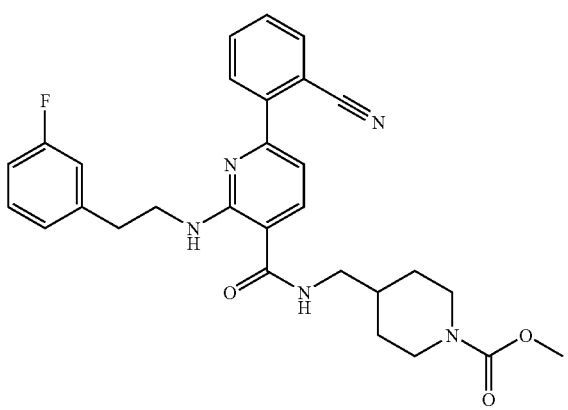<br>Compound 554 | methyl 4-{[(6-(2-cyanophenyl)-2-{[2-(3-fluorophenyl)ethyl]amino}-3-pyridyl)carbonylamino]methyl}piperidinecarboxylate |
| 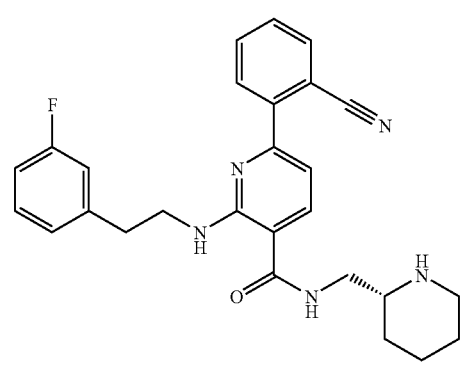<br>Compound 559 | N-[((2R)(2-piperidyl))methyl](6-(2-cyanophenyl)-2-{[2-(3-fluorophenyl)ethyl]amino}(3-pyridyl))carboxamide |
| 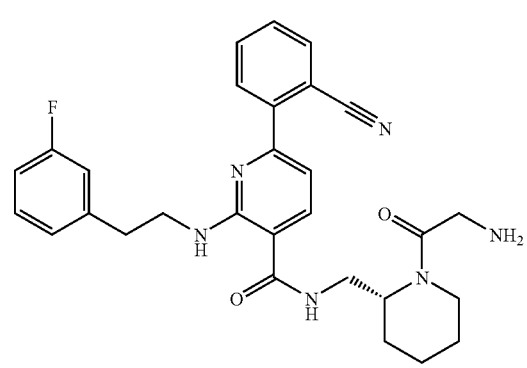<br>Compound 560 | N-{[(2R)-1-(2-aminoacetyl)(2-piperidyl)]methyl}(6-(2-cyanophenyl)-2-{[2-(3-fluorophenyl)ethyl]amino}(3-pyridyl))carboxamide |

-continued

| COMPOUND | CHEMICAL NAME |
|---|---|
| 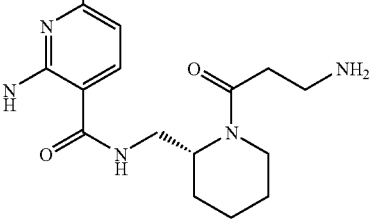<br>Compound 561 | N-{[(2R)-1-(3-aminopropanoyl)(2-piperidyl)]methyl}(6-(2-cyanophenyl)-2-{[2-(3-fluorophenyl)ethyl]amino}(3-pyridyl))carboxamide |
| 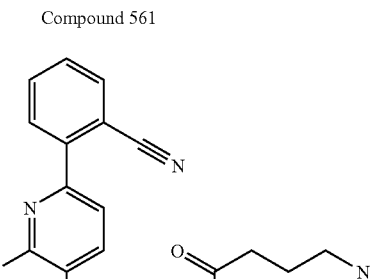<br>Compound 562 | N-{[(2R)-1-(4-aminobutanoyl)(2-piperidyl)]methyl}(6-(2-cyanophenyl)-2-{[2-(3-fluorophenyl)ethyl]amino}(3-pyridyl))carboxamide |
| 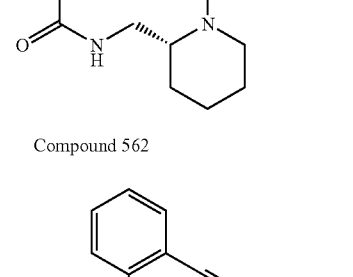<br>Compound 563 | N-[((2R)-1-acetyl(2-piperidyl))methyl](6-(2-cyanophenyl)-2-{[2-(3-fluorophenyl)ethyl]amino}(3-pyridyl))carboxamide |
| 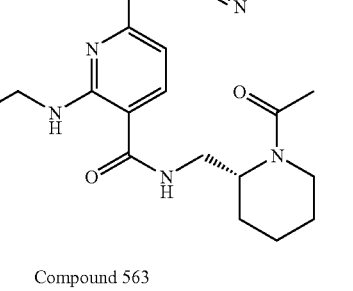<br>Compound 564 | methyl (2R)-2-{[(6-(2-cyanophenyl)-2-{[2-(3-fluorophenyl)ethyl]amino}(3-pyridyl))carbonylamino]methyl}piperidinecarboxylate |

| COMPOUND | CHEMICAL NAME |
|---|---|
| 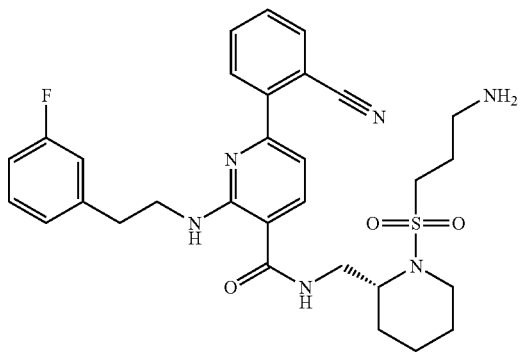<br>Compound 597 | N-({(2R)-1-[(3-aminopropyl)sulfonyl](2-piperidyl)}methyl)(6-(2-cyanophenyl)-{[2-(3-fluorophenyl)ethyl]amino}(3-pyridyl))carboxamide |
| 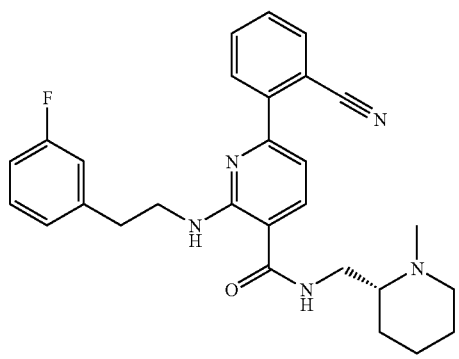<br>Compound 598 | N-[((2R)-1-methyl(2-piperidyl))methyl](6-(2-cyanophenyl)-2-{[2-(3-fluorophenyl)ethyl]amino}(3-pyridyl))carboxamide |
| 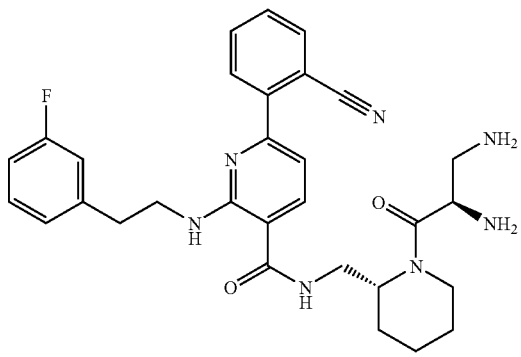<br>Compound 599 | N-{[(2R)-1-((2R)-2,3-diaminopropanoyl)(2-piperidyl)]methyl}(6-(2-cyanophenyl)-2-{[2-(3-fluorophenyl)ethyl]amino}(3-pyridyl))carboxamide |

| COMPOUND | CHEMICAL NAME |
|---|---|
| 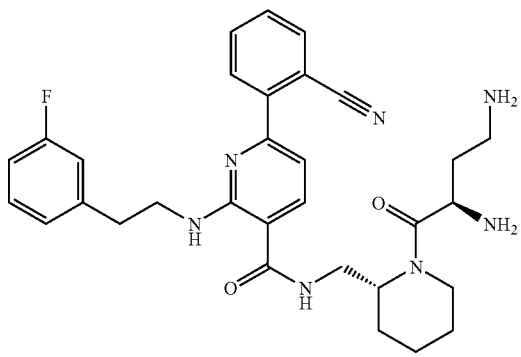<br>Compound 600 | N-{[(2R)-1-((2R)-2,4-diaminobutanoyl)(2-piperidyl)]methyl}(6-(2-cyanophenyl)-2-{[2-(3-fluorophenyl)ethyl]amino}(3-pyridyl))carboxamide |
| 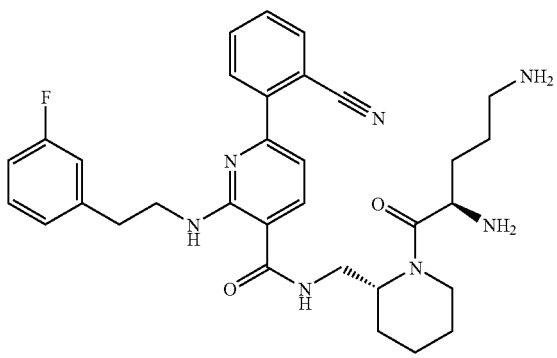<br>Compound 601 | N-{[(2R)-1-((2R)-2,5-diaminopentanoyl)(2-piperidyl)]methyl}(6-(2-cyanophenyl)-2-{[2-(3-fluorophenyl)ethyl]amino}(3-pyridyl))carboxamide |
| 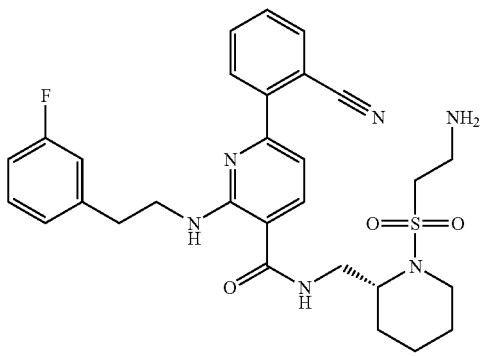<br>Compound 626 | N-({(2R)-1-[(2-aminoethyl)sulfonyl](2-piperidyl)}methyl)(6-(2-cyanophenyl)-2-{[2-(3-fluorophenyl)ethyl]amino}(3-pyridyl))carboxamide |

| COMPOUND | CHEMICAL NAME |
|---|---|
| 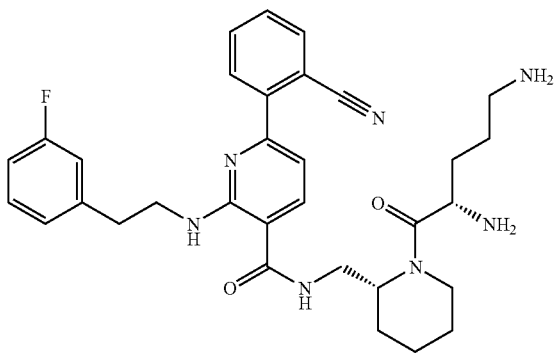<br>Compound 627 | N-{[(2R)-1-((2S)-2,5-diaminopentanoyl)(2-piperidyl)]methyl}(6-(2-cyanophenyl)-2-{[2-(3-fluorophenyl)ethyl]amino}(3-pyridyl))carboxamide |
| 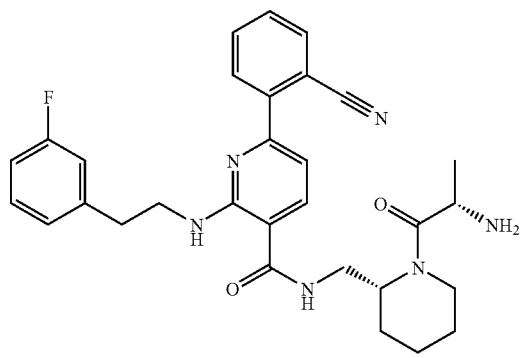<br>Compound 628 | N-{[(2R)-1-((2S)-2-aminopropanoyl)(2-piperidyl)]methyl}(6-(2-cyanophenyl)-2-{[2-(3-fluorophenyl)ethyl]amino}(3-pyridyl))carboxamide |
| 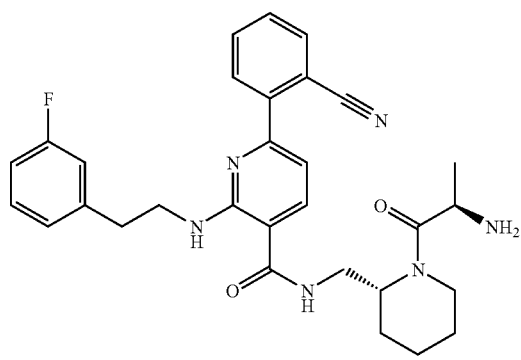<br>Compound 629 | N-{[(2R)-1-((2R)-2-aminopropanoyl)(2-piperidyl)]methyl}(6-(2-cyanophenyl)-2-{[2-(3-fluorophenyl)ethyl](3-pyridyl))carboxamide |

-continued

| COMPOUND | CHEMICAL NAME |
|---|---|
| Compound 630 | 2-chloroethyl (2R)-2-{[(6-(2-cyanophenyl)-2-{[2-(3-fluorophenyl)ethyl]amino}(3-pyridyl))carbonylamino]methyl}piperidinecarboxylate |
| Compound 631 | 2-aminoethyl (2R)-2-{[(6-(2-cyanophenyl)-2-{[2-(3-fluorophenyl)ethyl]amino}(3-pyridyl))carbonylamino]methyl}piperidinecarboxylate |
| Compound 637 | N-{[(2R)-1-(4-aminobutanoyl)pyrrolidin-2-yl]methyl}(2-{[2-(3,5-difluorophenyl)ethyl]amino}-6-(2-cyanophenyl)(3-pyridyl))carboxamide |
| Compound 638 | N-{[(2R)-1-(4-aminobutanoyl)pyrrolidin-2-yl]methyl}{6-(2-cyanophenyl)-2-[(2-cyclohex-1-enylethyl)amino](3-pyridyl)}carboxamide |

-continued

| COMPOUND | CHEMICAL NAME |
|---|---|
| 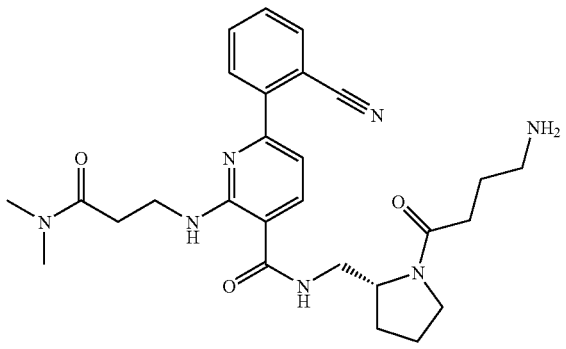<br>Compound 639 | 3-{[3-(N-{[(2R)-1-(4-aminobutanoyl)pyrrolidin-2-yl]methyl}carbamoyl)-6-(2-cyanophenyl)(2-pyridyl)]amino}-N,N-dimethylpropanamide |
| 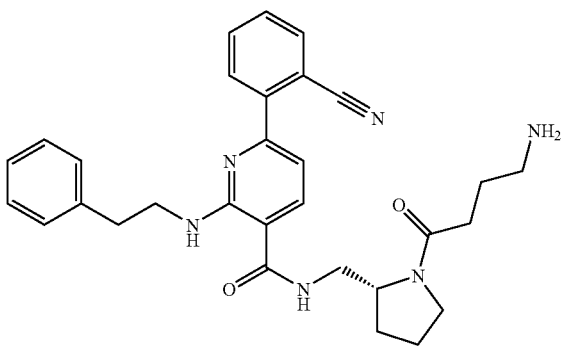<br>Compound 673 | N-{[(2R)-1-(4-aminobutanoyl)pyrrolidin-2-yl]methyl}{6-(2-cyanophenyl)-2-[(2-phenylethyl)amino](3-pyridyl)}carboxamide |
| 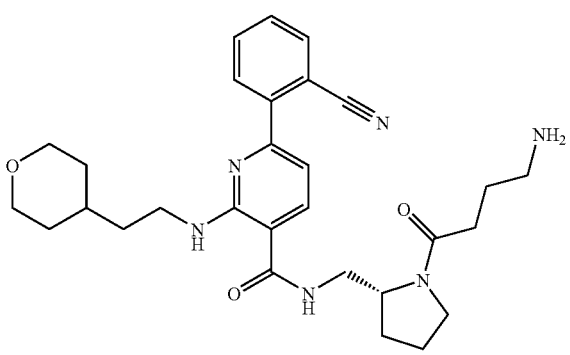<br>Compound 674 | N-{[(2R)-1-(4-aminobutanoyl)pyrrolidin-2-yl]methyl}{6-(2-cyanophenyl)-2-[(2-(2H-3,4,5,6-tetrahydropyran-4-yl)ethyl)amino](3-pyridyl)}carboxamide |

-continued

| COMPOUND | CHEMICAL NAME |
|---|---|
| 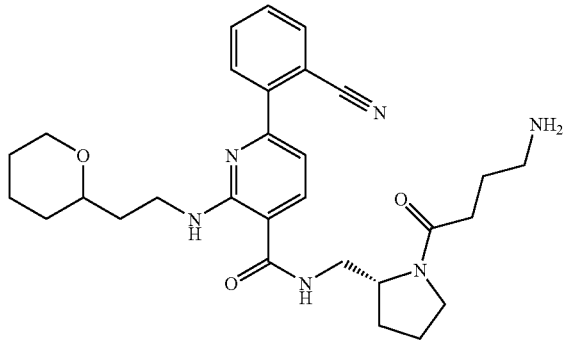<br>Compound 681 | N-{[(2R)-1-(4-aminobutanoyl)pyrrolidin-2-yl]methyl}{6-(2-cyanophenyl)-2-[(2-(2H-3,4,5,6-tetrahydropyran-2-yl)ethyl)amino](3-pyridyl)}carboxamide |
| 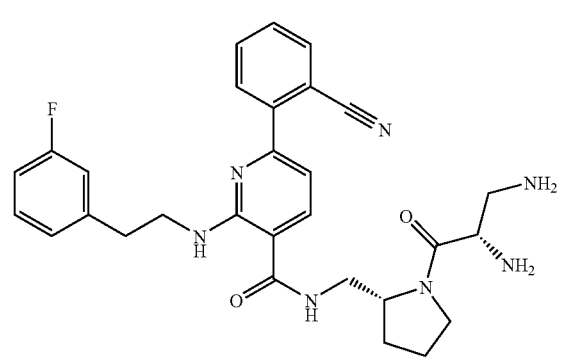<br>Compound 689 | N-{[(2R)-1-((2S)-2,3-diaminopropanoyl)pyrrolidin-2-yl]methyl}(6-(2-cyanophenyl)-2-{[2-(3-fluorophenyl)ethyl]amino}(3-pyridyl))carboxamide |
| 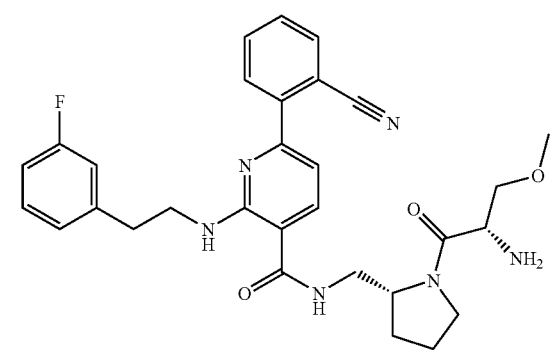<br>Compound 690 | N-{[(2R)-1-((2S)-2-amino-3-methoxypropanoyl)pyrrolidin-2-yl]methyl}(6-(2-cyanophenyl)-2-{[2-(3-fluorophenyl)ethyl]amino}(3-pyridyl))carboxamide |
| 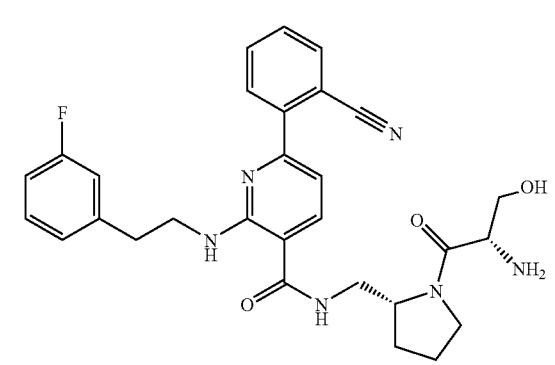<br>Compound 691 | N-{[(2R)-1-((2S)-2-amino-3-hydroxypropanoyl)pyrrolidin-2-yl]methyl}(6(2-cyanophenyl)-2-{[2-(3-fluorophenyl)ethyl]amino}(3-pyridyl))carboxamide |

-continued

| COMPOUND | CHEMICAL NAME |
|---|---|
| 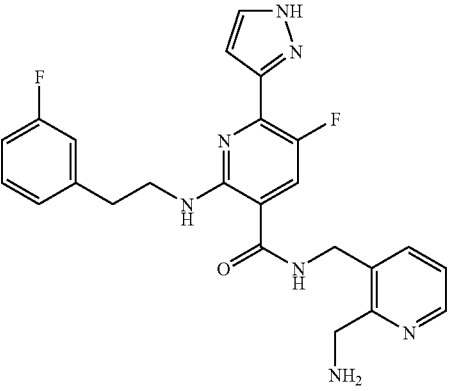<br>Compound 772 | N-{[2-(aminomethyl)(3-pyridyl)]methyl}(5-fluoro-2-{[2-(3-fluorophenyl)ethyl]amino}-6-pyrazol-3-yl(3-pyridyl))carboxamide |
| 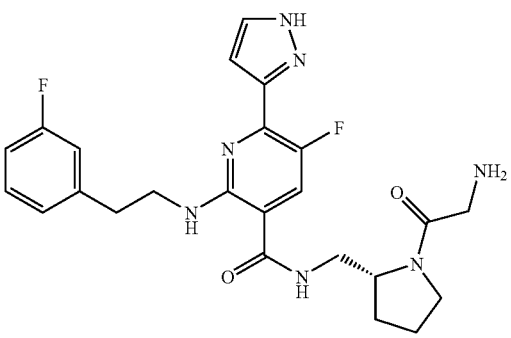<br>Compound 773 | N-{[(2R)-1-(2-aminoacetyl)pyrrolidin-2-yl]methyl}(5-fluoro-2-{[2-(3-fluorophenyl)ethyl]amino}-6-pyrazol-3-yl(3-pyridyl))carboxamide |
| 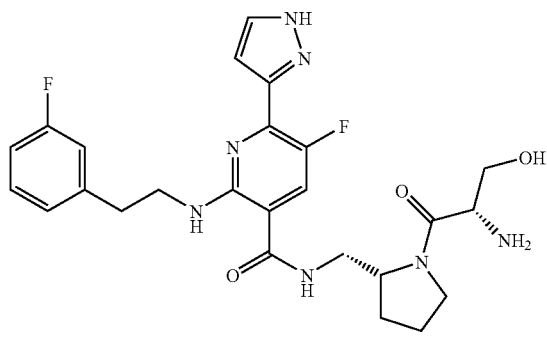<br>Compound 774 | N-{[(2R)-1-((2S)-2-amino-3-hydroxypropanoyl)pyrrolidin-2-yl]methyl}(5-fluoro-2-{[2-(3-fluorophenyl)ethyl]amino}-6-pyrazol-3-yl(3-pyridyl))carboxamide |
| 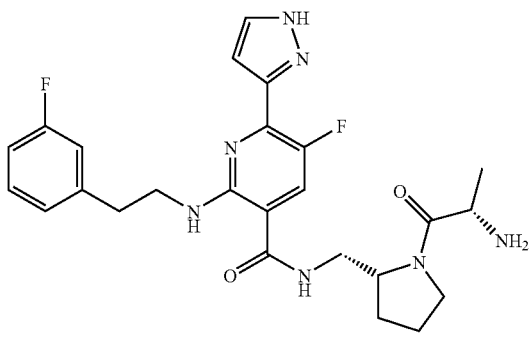<br>Compound 775 | N-{[(2R)-1-((2S)-2-aminopropanoyl)pyrrolidin-2-yl]methyl}(5-fluoro-2-{[2-(3-fluorophenyl)ethyl]amino}-6-pyrazol-3-yl(3-pyridyl))carboxamide |

| COMPOUND | CHEMICAL NAME |
|---|---|
| 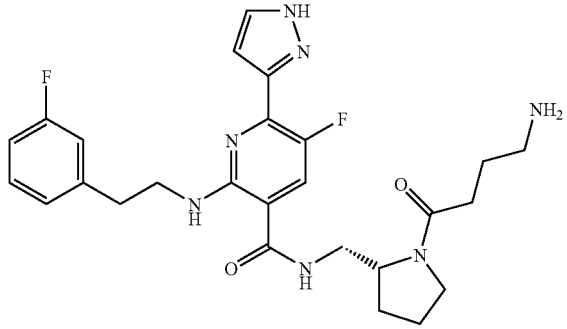
Compound 776 | N-{[(2R)-1-(4-aminobutanoyl)pyrrolidin-2-yl]methyl}(5-fluoro-2-{[2-(3-fluorophenyl)ethyl]amino}-6-pyrazol-3-yl(3-pyridyl))carboxamide |
| 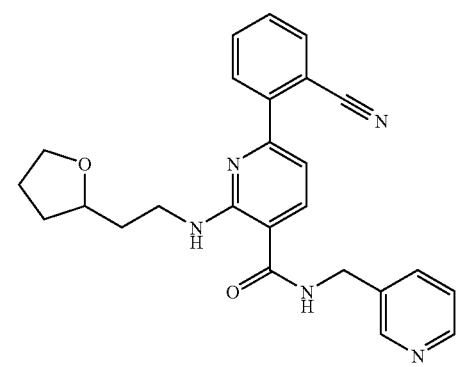
Compound 777 | {6-(2-cyanophenyl)-2-[(2-oxolan-2-ylethyl)amino](3-pyridyl)}-N-(3-pyridylmethyl)carboxamide |
| 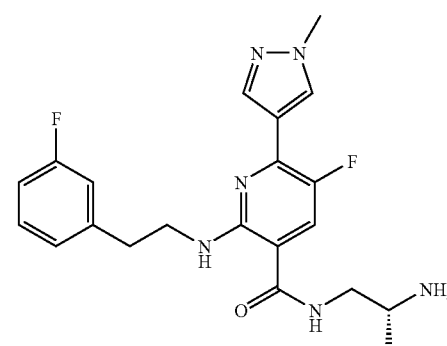
Compound 778 | N-((2R)-2-aminopropyl)(5-fluoro-2-{[2-(3-fluorophenyl)ethyl]amino}-6-(1-methylpyrazol-4-yl)(3-pyridyl))carboxamide |
| 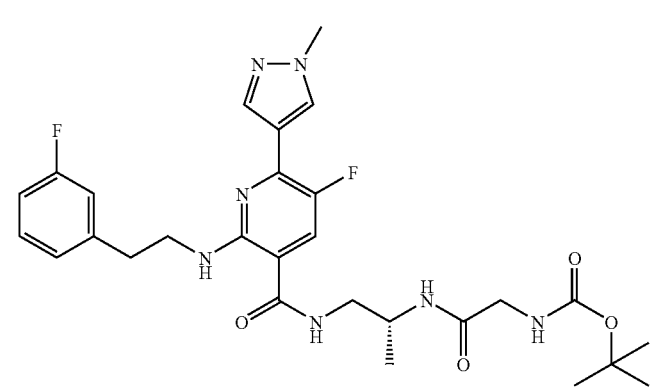
Compound 779 | N-{(1R)-2-[(5-fluoro-2-{[2-(3-fluorophenyl)ethyl]amino}-6-(1-methylpyrazol-4-yl)(3-pyridyl))carbonylamino]-isopropyl}-2-[(tert-butoxy)carbonylamino]acetamide |

-continued

| COMPOUND | CHEMICAL NAME |
|---|---|
| 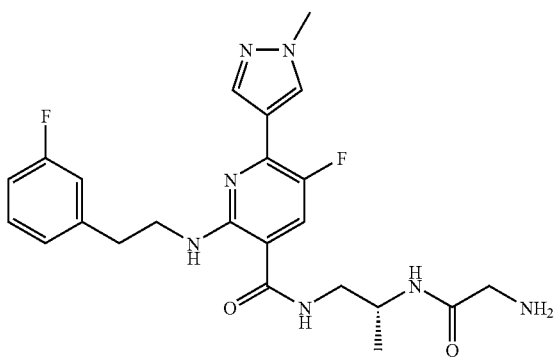<br>Compound 780 | N-{(1R)-2-[(5-fluoro-2-{[2-(3-fluorophenyl)ethyl]amino}-6-(1-methylpyrazol-4-yl)(3-pyridyl))carbonylamino]-isopropyl}-2-aminoacetamide |
| 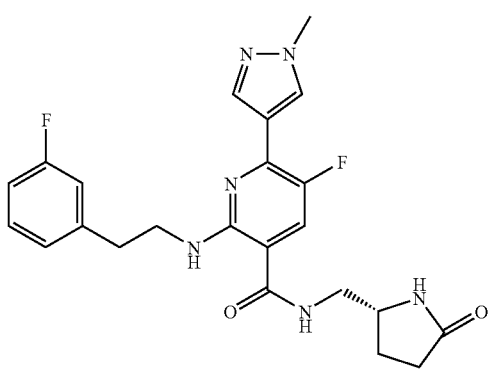<br>Compound 787 | N-[((2R)-5-oxopyrrolidin-2-yl)methyl](5-fluoro-2-{[2-(3-fluorophenyl)ethyl]amino}-6-(1-methylpyrazol-4-yl)(3-pyridyl))carboxamide |
| 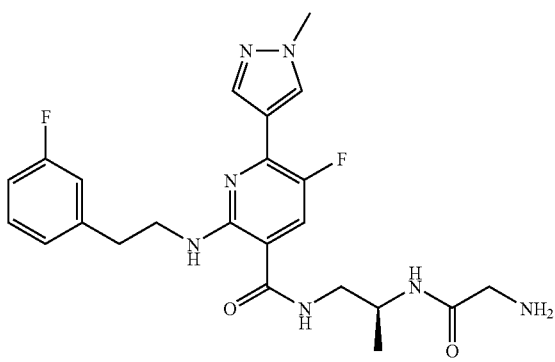<br>Compound 808 | N-{(1S)-2-[(5-fluoro-2-{[2-(3-fluorophenyl)ethyl]amino}-6-(1-methylpyrazol-4-yl)(3-pyridyl))carbonylamino]-isopropyl}-2-aminoacetamide |

| COMPOUND | CHEMICAL NAME |
|---|---|
| Compound 812 | N-{(1R)-2-[(5-fluoro-2-{[2-(3-fluorophenyl)ethyl]amino}-6-(1-methylpyrazol-4-yl)(3-pyridyl))carbonylamino]-isopropyl}-2-hydroxyacetamide |
| Compound 813 | N-{(1R)-2-[(5-fluoro-2-{[2-(3-fluorophenyl)ethyl]amino}-6-(1-methylpyrazol-4-yl)(3-pyridyl))carbonylamino]-isopropyl}-4-[(tert-butoxy)carbonyl-amino]butanamide |
| Compound 814 | N-{(1R)-2-[(5-fluoro-2-{[2-(3-fluorophenyl)ethyl]amino}-6-(1-methylpyrazol-4-yl)(3-pyridyl))carbonylamino]-isopropyl}-4-aminobutanamide |
| Compound 830 | N-{(2R)-2-[(2-methoxyethyl)amino]propyl}(5-fluoro-2-{[2-(3-fluorophenyl)ethyl]amino}-6-(1-methylpyrazol-4-yl)(3-pyridyl))carboxamide |

-continued

| COMPOUND | CHEMICAL NAME |
|---|---|
| 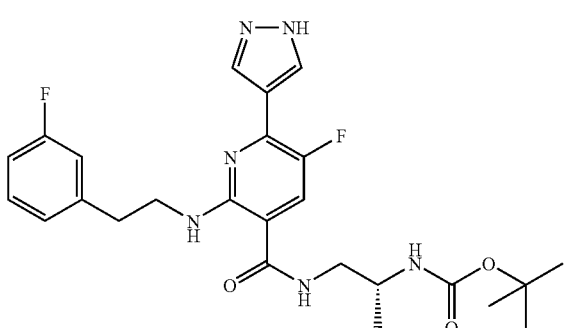<br>Compound 831 | N-{(2R)-2-[tert-butoxy)carbonylamino]propyl}(5-fluoro-2-{[2-(3-fluorophenyl)ethyl]amino}-6-pyrazol-4-yl(3-pyridyl))carboxamide |
| 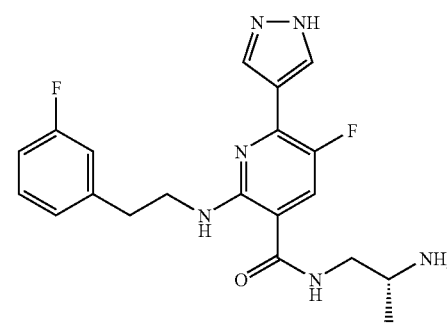<br>Compound 832 | N-((2R)-2-aminopropyl)(5-fluoro-2-{[2-(3-fluorophenyl)ethyl]amino}-6-pyrazol-4-yl(3-pyridyl))carboxamide |
| 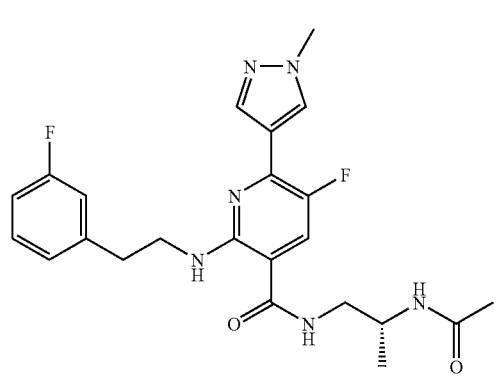<br>Compound 833 | N-{(1R)-2-[(5-fluoro-2-{[2-(3-fluorophenyl)ethyl]amino}-6-(1-methylpyrazol-4-yl)(3-pyridyl))carbonylamino]-isopropyl}acetamide |
| 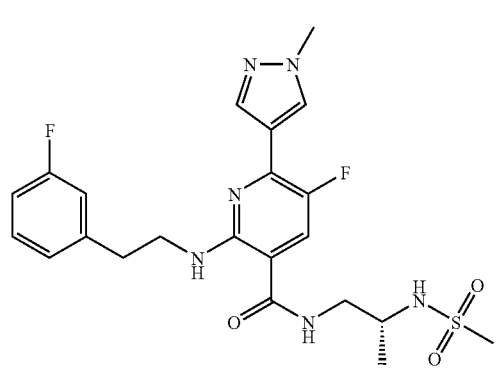<br>Compound 834 | N-{(2R)-2-[(methylsulfonyl)amino]propyl}(5-fluoro-2-{[2-(3-fluorophenyl)ethyl]amino}-6-(1-methylpyrazol-4-yl)(3-pyridyl))carboxamide |

| COMPOUND | CHEMICAL NAME |
|---|---|
| Compound 835 | N-{(1R)-2-[(5-fluoro-2-{[2-(3-fluorophenyl)ethyl]amino}-6-pyrazol-4-yl(3-pyridyl))carbonylamino]-isopropyl}-2-aminoacetamide |
| Compound 836 | (5-fluoro-2-{[2-(3-fluorophenyl)ethyl]amino}-6-pyrazol-4-yl(3-pyridyl))-N-(2-pyridylmethyl)carboxamide |
| Compound 837 | N-{(2R)-2-[(2-hydroxyethyl)amino]propyl}(5-fluoro-2-{[2-(3-fluorophenyl)ethyl]amino}-6-(1-methylpyrazol-4-yl)(3-pyridyl))carboxamide |
| Compound 847 | N-{(2R)-2-[(carbamoylmethyl)amino]propyl}(5-fluoro-2-{[2-(3-fluorophenyl)ethyl]amino}-6-(1-methylpyrazol-4-yl)(3-pyridyl))carboxamide |

-continued

| COMPOUND | CHEMICAL NAME |
|---|---|
| Compound 848 | N-{(1R)-2-[(5-fluoro-2-{[2-(3-fluorophenyl)ethyl]amino}-6-(1-methylpyrazol-4-yl)(3-pyridyl))carbonylamino]-isopropyl}-2-(dimethylamino)acetamide |
| Compound 849 | N-{(1R)-2-[(5-fluoro-2-{[2-(3-fluorophenyl)ethyl]amino}-6-(1-methylpyrazol-4-yl)(3-pyridyl))carbonylamino]-isopropyl}(2S)-2-[(tert-butoxy)carbonylamino]-3-hydroxypropanamide |
| Compound 850 | N-{(1R)-2-[(5-fluoro-2-{[2-(3-fluorophenyl)ethyl]amino}-6-(1-methylpyrazol-4-yl)(3-pyridyl))carbonylamino]-isopropyl}(2S)-2-amino-3-hydroxypropanamide |
| Compound 851 | N-{(1R)-2-[(5-fluoro-2-{[2-(3-fluorophenyl)ethyl]amino}-6-(1-methylpyrazol-4-yl)(3-pyridyl))carbonylamino]-isopropyl}-2-amino-2-methylpropanamide |

| COMPOUND | CHEMICAL NAME |
|---|---|
| 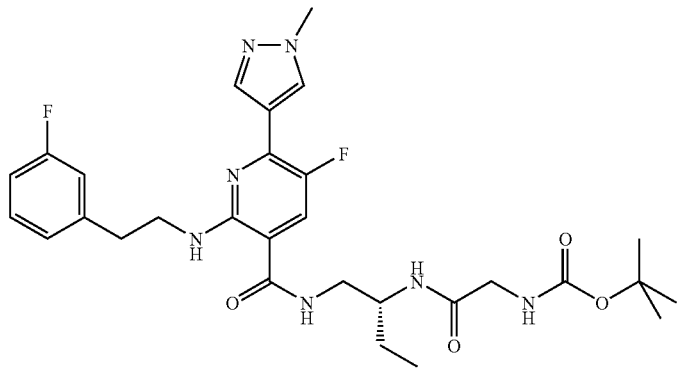

Compound 871 | N-((1R)-1-{[(5-fluoro-2-{[2-(3-fluorophenyl)ethyl]amino}-6-(1-methylpyrazol-4-yl)(3-pyridyl))carbonylamino]methyl}propyl)-2-[(tert-butoxy)carbonylamino]acetamide |
| 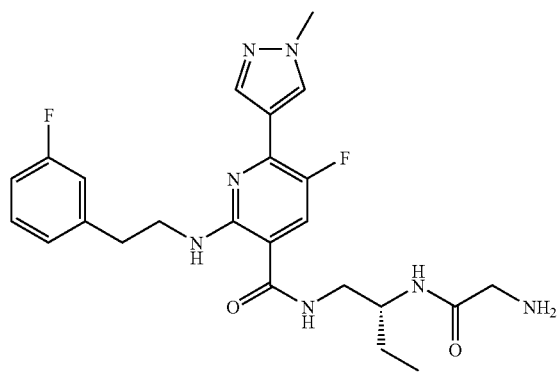

Compound 872 | N-((1R)-1-{[(5-fluoro-2-{[2-(3-fluorophenyl)ethyl]amino}-6-(1-methylpyrazol-4-yl)(3-pyridyl))carbonylamino]methyl}propyl)-2-aminoacetamide |
| 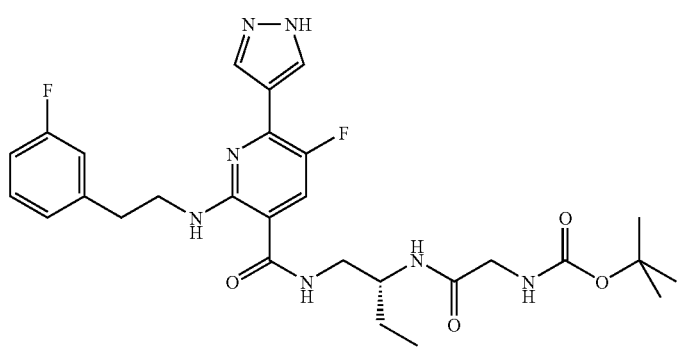

Compound 873 | N-((1R)-1-{[(5-fluoro-2-{[2-(3-fluorophenyl)ethyl]amino}-6-pyrazol-4-yl(3-pyridyl))carbonylamino]methyl}propyl)-2-[(tert-butoxy)carbonylamino]acetamide |

-continued

| COMPOUND | CHEMICAL NAME |
|---|---|
| Compound 874 | N-((1R)-1-{[(5-fluoro-2-{[2-(3-fluorophenyl)ethyl]amino}-6-pyrazol-4-yl(3-pyridyl))carbonylamino]methyl}propyl)-2-aminoacetamide |
| Compound 877 | N-{(1R)-2-[(5-fluoro-2-{[2-(3-fluorophenyl)ethyl]amino}-6-(1-methylpyrazol-4-yl)(3-pyridyl))carbonylamino]-isopropyl}(2S)-2-aminopropanamide |
| Compound 878 | N-((2R)-3-hydroxy-2-methylbutyl)(5-fluoro-2-{[2-(3-fluorophenyl)ethyl]amino}-6-(1-methylpyrazol-4-yl)(3-pyridyl))carboxamide |
| Compound 348 | N-{[2-(aminomethyl)(3-pyridyl)]methyl}(6-(2-cyanophenyl)-2-{[2-(3-fluorophenyl)ethyl]amino}(3-pyridyl))carboxamide |

| COMPOUND | CHEMICAL NAME |
|---|---|
| 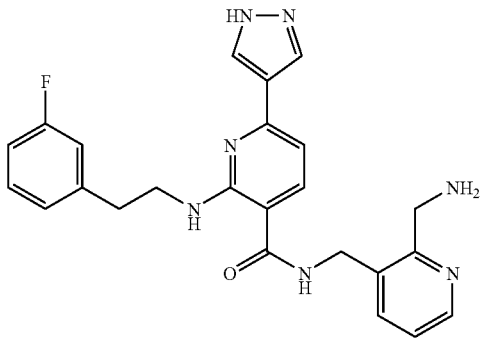<br>Compound 398 | N-{[2-(aminomethyl)(3-pyridyl)]methyl}(2-{[2-(3-fluorophenyl)ethyl[amino}-6-pyrazol-4-yl(3-pyridyl))carboxamide |
| 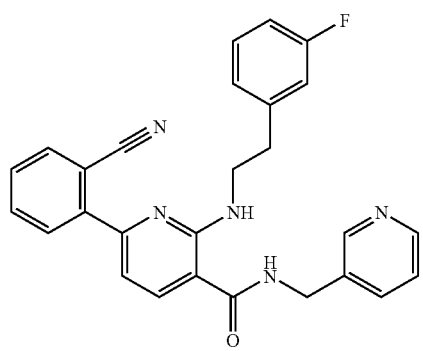<br>Compound 125 | (6-(2-cyanophenyl)-2-{[2-(3-fluorophenyl)ethyl]amino}(3-pyridyl))-N-(3-pyridylmethyl)carboxamide |
| 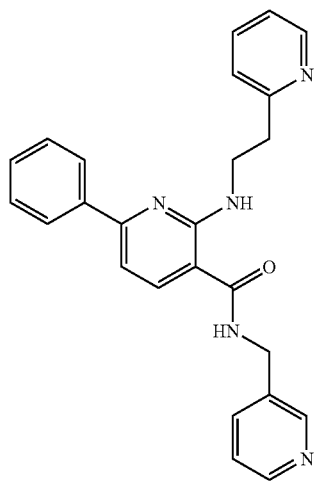<br>Compound 30 | {6-phenyl-2-[(2-(2-pyridyl)ethyl)amino](3-pyridyl)}-N-(3-pyridylmethyl)carboxamide |

-continued
| COMPOUND | CHEMICAL NAME |
|---|---|
| 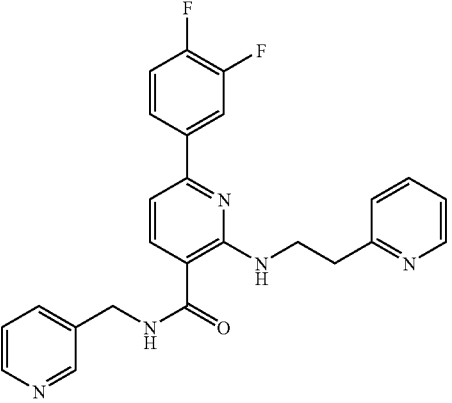<br>Compound 39 | {6-(3,4-difluorophenyl)-2-[(2-(2-pyridyl)ethyl)amino](3-pyridyl)}-N-(3-pyridylmethyl)carboxamide |
| 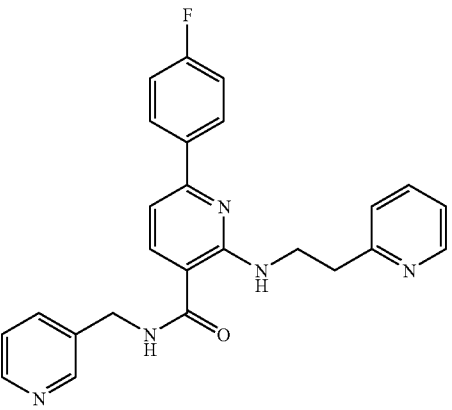<br>Compound 27 | {6-(4-fluorophenyl)-2-[(2-(2-pyridyl)ethyl)amino](3-pyridyl)}-N-(3-pyridylmethyl)carboxamide |
| 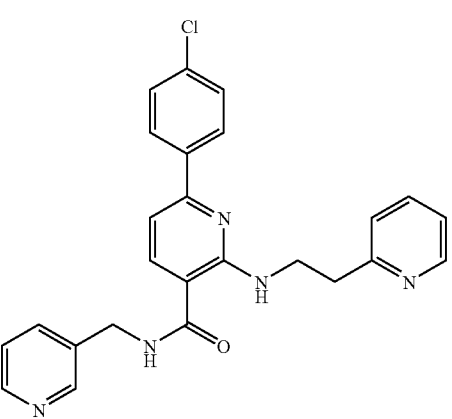<br>Compound 24 | {6-(4-chlorophenyl)-2-[(2-(2-pyridyl)ethyl)amino](3-pyridyl)}-N-(3-pyridylmethyl)carboxamide |

| COMPOUND | CHEMICAL NAME |
|---|---|
| 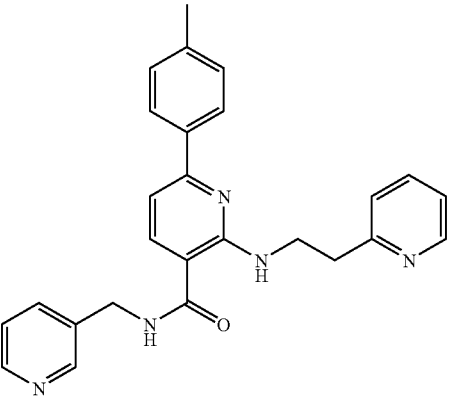<br>Compound 23 | {6-(4-methylphenyl)-2-[(2-(2-pyridyl)ethyl)amino](3-pyridyl)}-N-(3-pyridylmethyl)carboxamide |
| 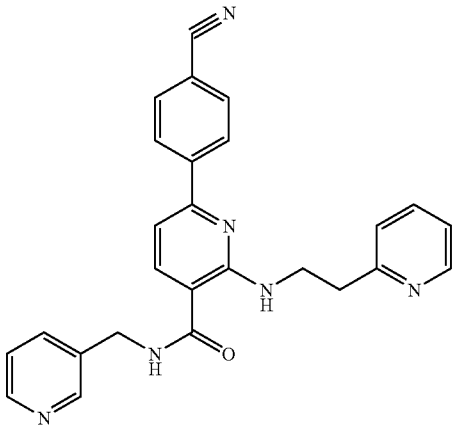<br>Compound 205 | {6-(4-cyanophenyl)-2-[(2-(2-pyridyl)ethyl)amino](3-pyridyl)}-N-(3-pyridylmethyl)carboxamide |
| 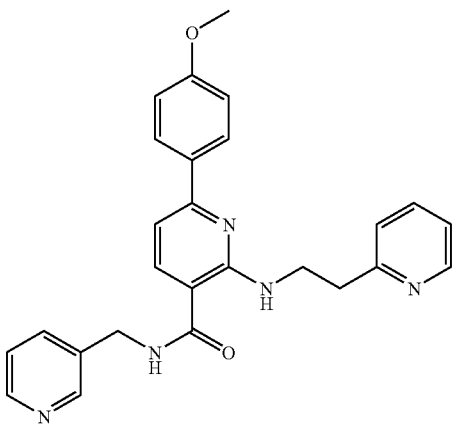<br>Compound 19 | {6-(4-methoxyphenyl)-2-[(2-(2-pyridyl)ethyl)amino](3-pyridyl)}-N-(3-pyridylmethyl)carboxamide |

| COMPOUND | CHEMICAL NAME |
|---|---|
| 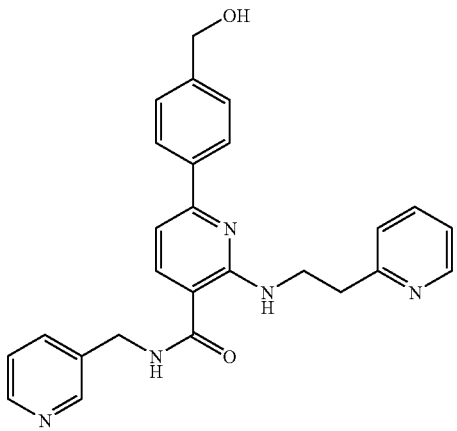
Compound 18 | {6-[4-hydroxymethyl)phenyl]-2-[(2-(2-pyridyl)ethyl)amino](3-pyridyl)}-N-(3-pyridylmethyl)carboxamide |
| 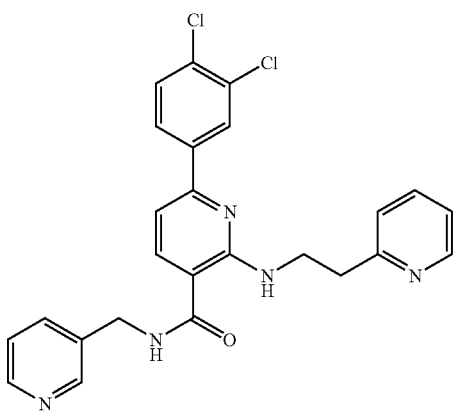
Compound 13 | {6-(3,4-dichlorophenyl)-2-[(2-(2-pyridyl)ethyl)amino](3-pyridyl)}-N-(3-pyridylmethyl)carboxamide |
| 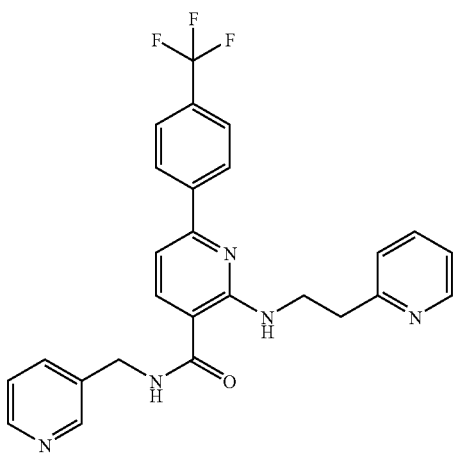
Compound 4 | {2-[(2-(2-pyridyl)ethyl)amino]-6-[4-(trifluoromethyl)phenyl](3-pyridyl)}-N-(3-pyridylmethyl)carboxamide |

-continued

| COMPOUND | CHEMICAL NAME |
|---|---|
| Compound 3 | methyl 4-{6-[(2-(2-pyridyl)ethyl)amino]-5-[N-(3-pyridylmethyl)carbamoyl]-2-pyridyl}benzoate |
| Compound 43 | {6-[4-(dimethylamino)phenyl]-2-[(2-(2-pyridyl)ethyl)amino](3-pyridyl)}-N-(3-pyridylmethyl)carboxamide |
| Compound 2 | {6-(4-acetylphenyl)-2-[(2-(2-pyridyl)ethyl)amino](3-pyridyl)}-N-(3-pyridylmethyl)carboxamide |

-continued
| COMPOUND | CHEMICAL NAME |
|---|---|
| 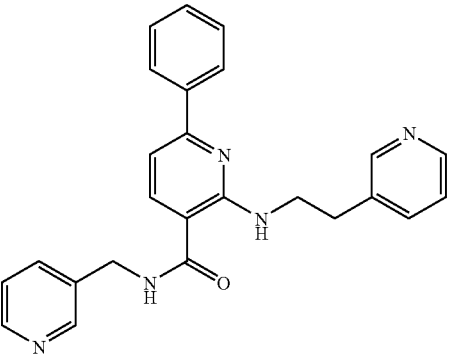<br>Compound 40 | {6-phenyl-2-[(2-(3-pyridyl)ethyl)amino](3-pyridyl)}-N-(3-pyridylmethyl)carboxamide |
| 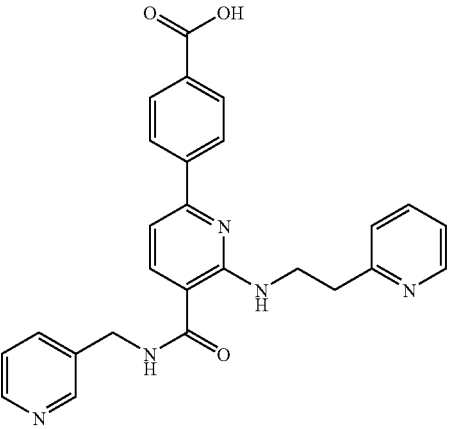<br>Compound 6 | 4-{6[(2-(2-pyridyl)ethyl)amino]-5-[N-(3-pyridylmethyl)carbamoyl]-2-pyridyl}benzoic acid |
| 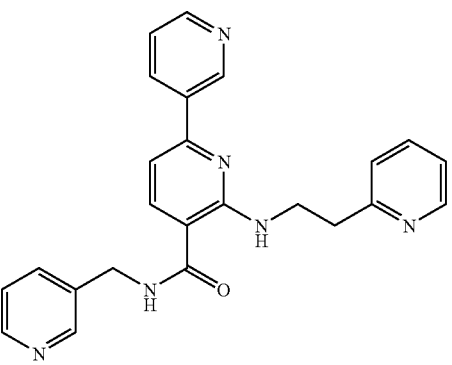<br>Compound 44 | N-(3-pyridylmethyl){6-(3-pyridyl)-2-[(2-(2-pyridyl)ethyl)amino](3-pyridyl)}carboxamide |

-continued
| COMPOUND | CHEMICAL NAME |
|---|---|
| 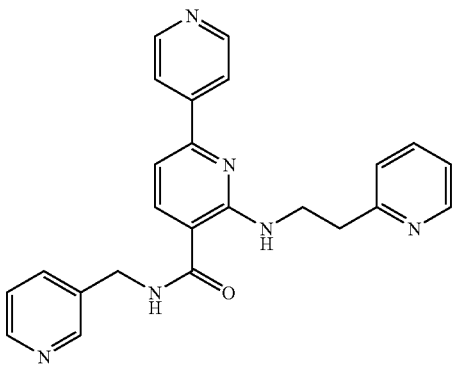<br>Compound 8 | N-(3-pyridylmethyl){6-(4-pyridyl)-2-[(2-(2-pyridyl)ethyl)amino](3-pyridyl)}carboxamide |
| 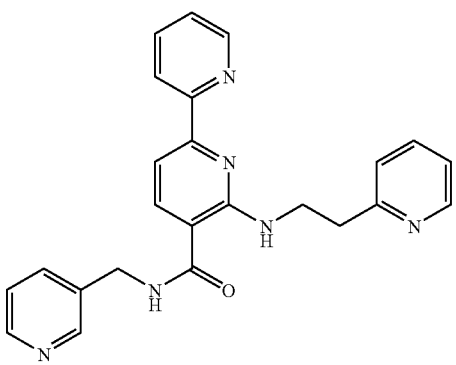<br>Compound 9 | N-(3-pyridylmethyl){6-(2-pyridyl)-2-[(2-(2-pyridyl)ethyl)amino](3-pyridyl)}carboxamide |
| 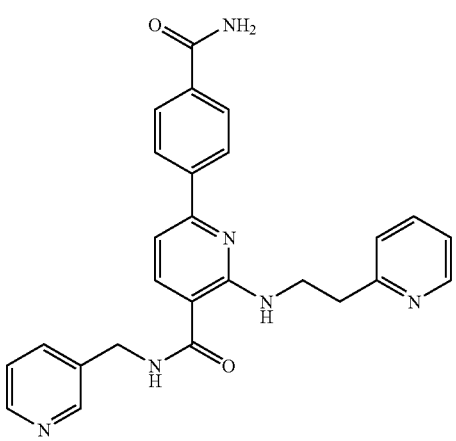<br>Compound 49 | 4-{6-[(2-(2-pyridyl)ethyl)amino]-5-[N-(3-pyridylmethyl)carbamoyl]-2-pyridyl}benzamide |

-continued
| COMPOUND | CHEMICAL NAME |
|---|---|
| 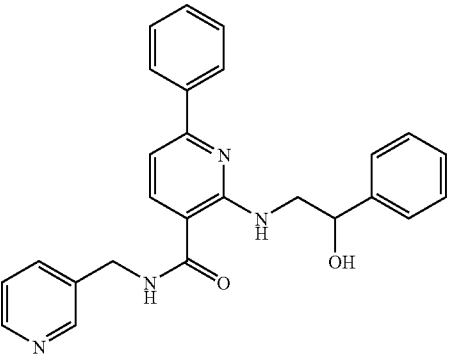<br>Compound 93 | {2-[(2-hydroxy-2-phenylethyl)amino]-6-phenyl(3-pyridyl)}-N-(3-pyridylmethyl)carboxamide |
| 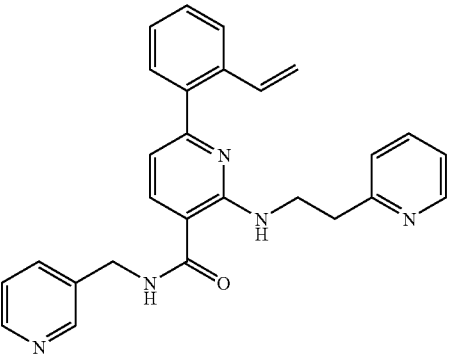<br>Compound 100 | {2-[(2-(2-pyridyl)ethyl)amino]-6-(2-vinylphenyl)(3-pyridyl)}-N-(3-pyridylmethyl)carboxamide |
| 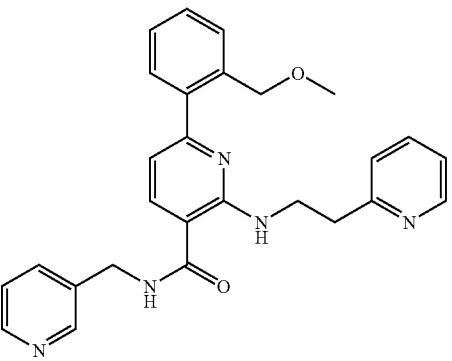<br>Compound 101 | {6-[2-(methoxymethyl)phenyl]-2-[(2-(2-pyridyl)ethyl)amino](3-pyridyl)}-N-(3-pyridylmethyl)carboxamide |

| COMPOUND | CHEMICAL NAME |
|---|---|
| Compound 102 | {6-(2-formylphenyl)-2-[(2-(2-pyridyl)ethyl)amino](3-pyridyl)}-N-(3-pyridylmethyl)carboxamide |
| Compound 110 | (2-{[2-(3-fluorophenyl)-2-hydroxyethyl]amino}-6-phenyl(3-pyridyl))-N-(3-pyridylmethyl)carboxamide |
| Compound 111 | (6-(2-cyanophenyl)-2-{[2-(3-fluorophenyl)-2-hydroxyethyl]amino}(3-pyridyl))-N-(3-pyridylmethyl)carboxamide |
| Compound 121 | {2-[(2-(2-pyridyl)ethyl)amino]-6-(1,3-thiazol-2-yl)(3-pyridyl)}-N-(3-pyridylmethyl)carboxamide |

| COMPOUND | CHEMICAL NAME |
|---|---|
| 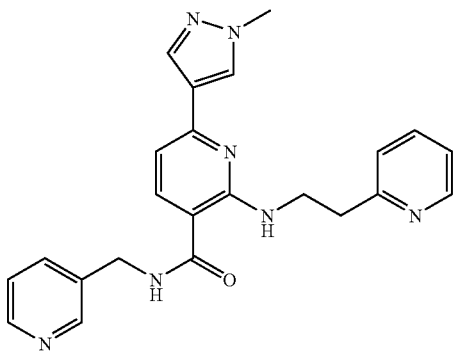<br>Compound 122 | {6-(1-methylpyrazol-4-yl)-2-[(2-(2-pyridyl)ethyl)amino](3-pyridyl)}-N-(3-pyridylmethyl)carboxamide |
| 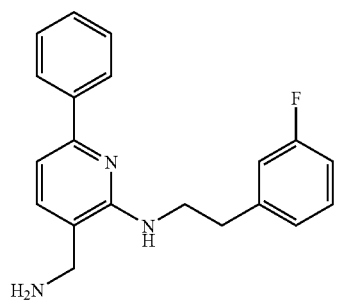<br>Compound 763 | [3-(aminomethyl)-6-phenyl(2-pyridyl)][2-(3 fluorophenyl)ethyl]amine |
| 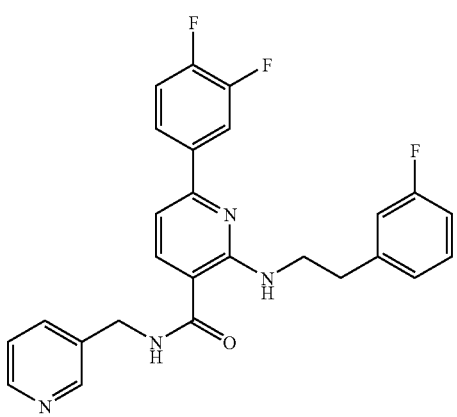<br>Compound 275 | (6-(3,4-difluorophenyl)-2-{[2-(3-fluorophenyl)ethyl]amino}(3-pyridyl))-N-(3-pyridylmethyl)carboxamide |

| COMPOUND | CHEMICAL NAME |
|---|---|
| 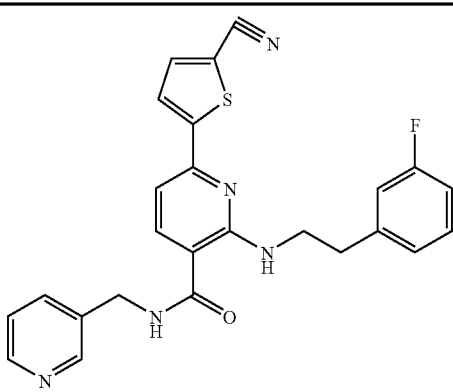<br>Compound 274 | (6-(5-cyano(2-thienyl))-2-{[2-(3-fluorophenyl)ethyl]amino}(3-pyridyl))-N-(3-pyridylmethyl)carboxamide |
| 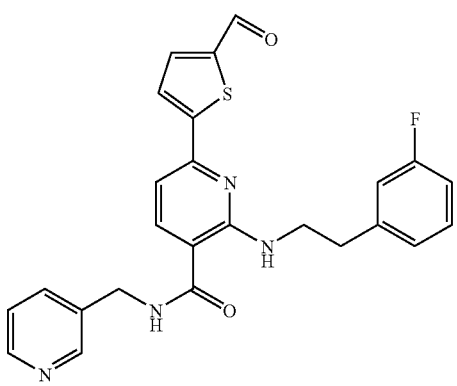<br>Compound 273 | (2-{[2-(3-fluorophenyl)ethyl]amino}-6-(5-formyl(2-thienyl))(3-pyridyl))-N-(3-pyridylmethyl)carboxamide |
| 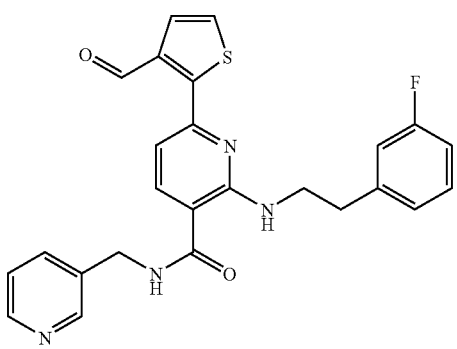<br>Compound 243 | (2-{[2-(3-fluorophenyl)ethyl]amino}-6-(3-formyl(2-thienyl))(3-pyridyl))-N-(3-pyridylmethyl)carboxamide |

| COMPOUND | CHEMICAL NAME |
|---|---|
| 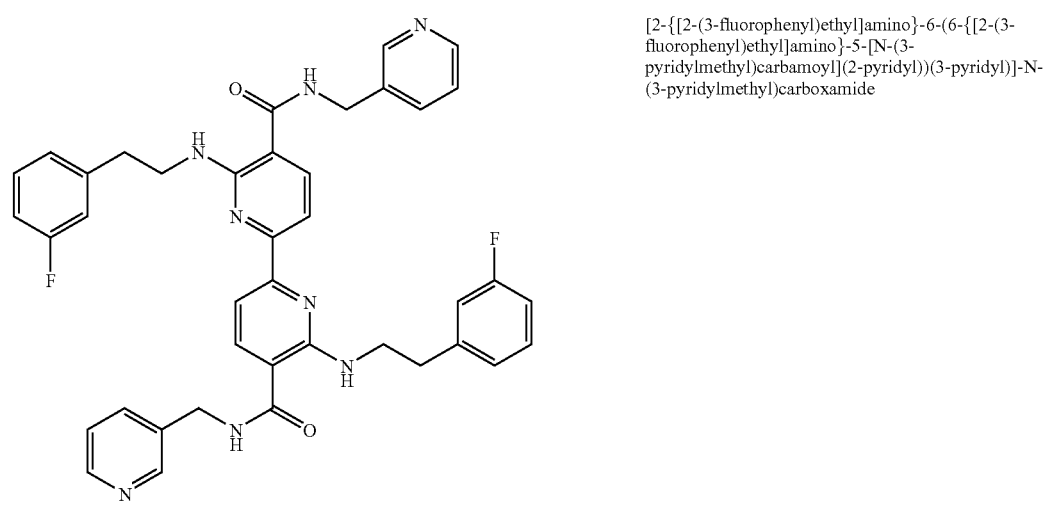<br>Compound 191 | (2-{[2-(3-fluorophenyl)ethyl]amino}-6-(2-formyl(3-thienyl))(3-pyridyl))-N-(3-pyridylmethyl)carboxamide |
| Compound 211 | [2-{[2-(3-fluorophenyl)ethyl]amino}-6-(6-{[2-(3-fluorophenyl)ethyl]amino}-5-[N-(3-pyridylmethyl)carbamoyl](2-pyridyl))(3-pyridyl)]-N-(3-pyridylmethyl)carboxamide |
| 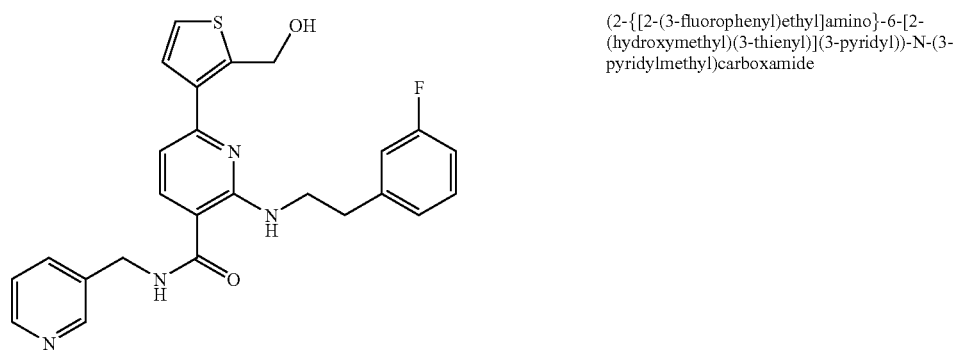<br>Compound 213 | (2-{[2-(3-fluorophenyl)ethyl]amino}-6-[2-(hydroxymethyl)(3-thienyl)](3-pyridyl))-N-(3-pyridylmethyl)carboxamide |

-continued
| COMPOUND | CHEMICAL NAME |
|---|---|
| 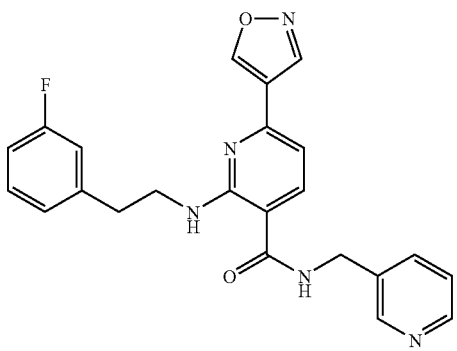<br>Compound 214 | (2-{[2-(3-fluorophenyl)ethyl]amino}-6-isoxazol-4-yl(3-pyridyl))-N-(3-pyridylmethyl)carboxamide |
| 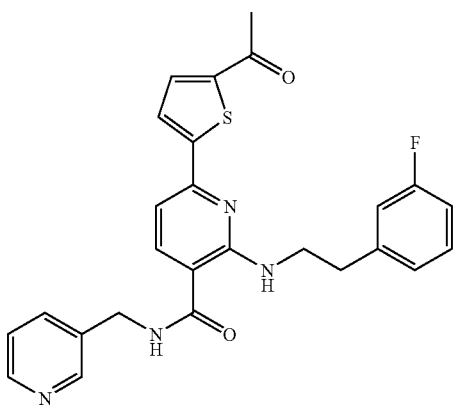<br>Compound 215 | (6-(5-acetyl(2-thienyl))-2-{[2-(3-fluorophenyl)ethyl]amino}(3-pyridyl))-N-(3-pyridylmethyl)carboxamide |
| 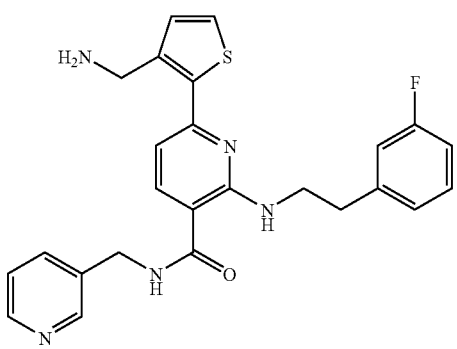<br>Compound 226 | (6-[3-(aminomethyl)(2-thienyl)]-2-{[2-(3-fluorophenyl)ethyl]amino}(3-pyridyl))-N-(3-pyridylmethyl)carboxamide |

| COMPOUND | CHEMICAL NAME |
|---|---|
| 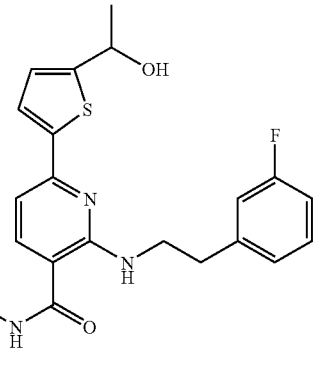<br>Compound 227 | (2-{[2-(3-fluorophenyl)ethyl]amino}-6-[5-(hydroxyethyl)(2-thienyl)](3-pyridyl))-N-(3-pyridylmethyl)carboxamide |
| 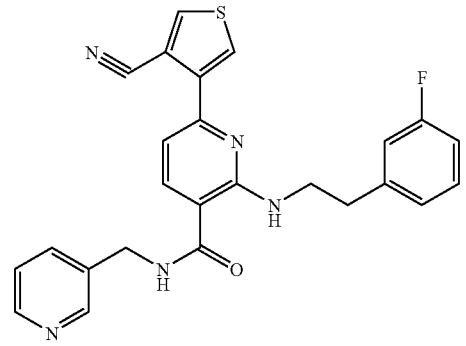<br>Compound 240 | (6-(4-cyano(3-thienyl))-2-{[2-(3-fluorophenyl)ethyl]amino}(3-pyridyl))-N-(3-pyridylmethyl)carboxamide |
| 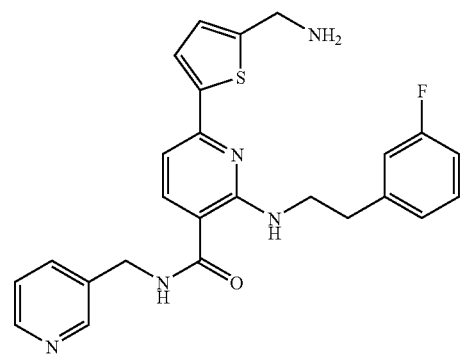<br>Compound 241 | (6-[5-(aminomethyl)(2-thienyl)]-2-{[2-(3-fluorophenyl)ethyl]amino}(3-pyridyl))-N-(3-pyridylmethyl)carboxamide |

-continued
| COMPOUND | CHEMICAL NAME |
|---|---|
| 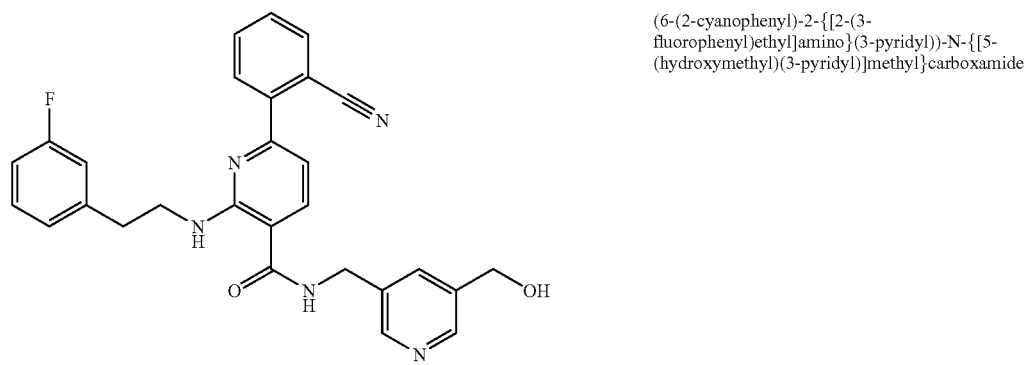  Compound 306 | N-{[5-(aminomethyl)(3-pyridyl)]methyl}(6-(2-cyanophenyl)-2-{[2-(3-fluorophenyl)ethyl]amino}(3-pyridyl))carboxamide |
| 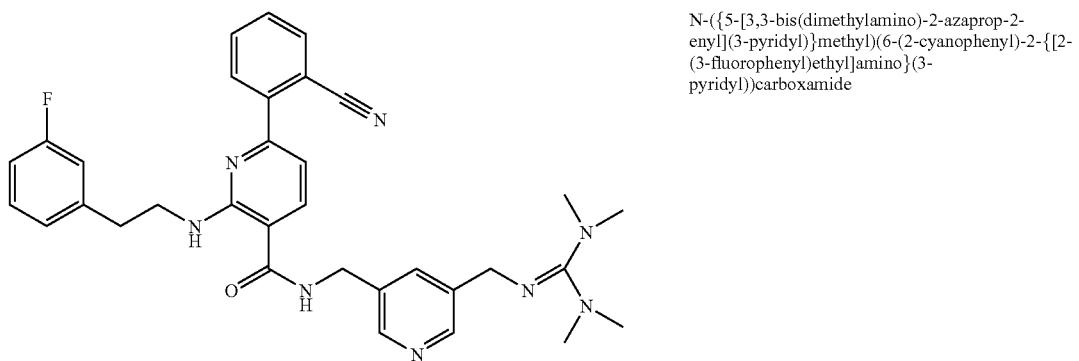  Compound 307 | (6-(2-cyanophenyl)-2-{[2-(3-fluorophenyl)ethyl]amino}(3-pyridyl))-N-{[5-(hydroxymethyl)(3-pyridyl)]methyl}carboxamide |
| Compound 314 | N-({5-[3,3-bis(dimethylamino)-2-azaprop-2-enyl](3-pyridyl)}methyl)(6-(2-cyanophenyl)-2-{[2-(3-fluorophenyl)ethyl]amino}(3-pyridyl))carboxamide |

| COMPOUND | CHEMICAL NAME |
|---|---|
| 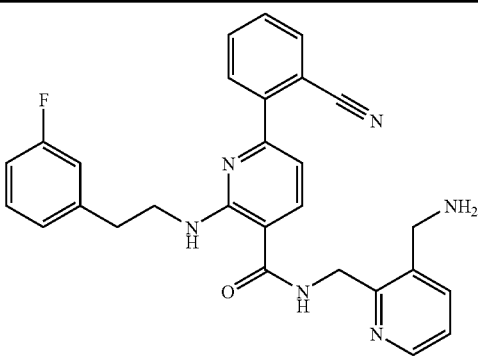<br>Compound 315 | N-{[3-(aminomethyl)(2-pyridyl)]methyl}(6-(2-cyanophenyl)-2-{[2-(3-fluorophenyl)ethyl]amino}(3-pyridyl))carboxamide |
| 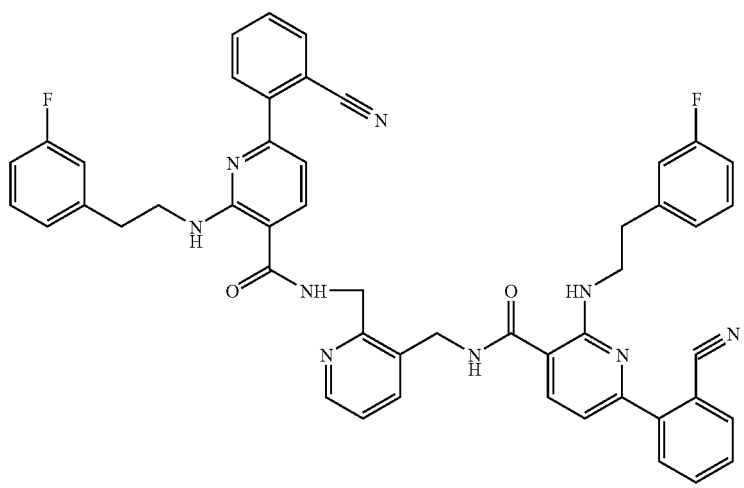<br>Compound 316 | (6-(2-cyanophenyl)-2-{[2-(3-fluorophenyl)ethyl]amino}(3-pyridyl))-N-[(3-{[(6-(2-cyanophenyl)-2-{[2-(3-fluorophenyl)ethyl]amino}(3-pyridyl))carbonylamino]methyl}(2-pyridyl))methyl]carboxamide |
| 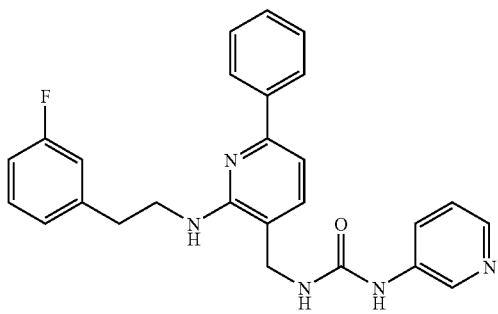<br>Compound 331 | N-[(2-{[2-(3-fluorophenyl)ethyl]amino}-6-phenyl(3-pyridyl))methyl](3-pyridylamino)carboxamide |

| COMPOUND | CHEMICAL NAME |
|---|---|
| 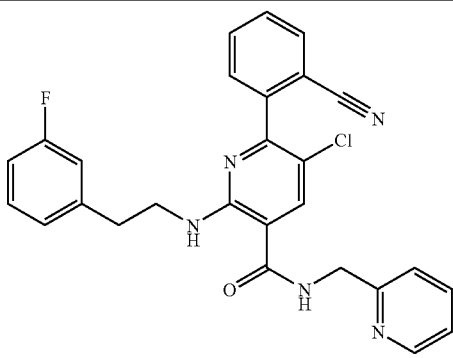<br>Compound 359 | (5-chloro-6-(2-cyanophenyl)-2-{[2-(3-fluorophenyl)ethyl]amino}(3-pyridyl))-N-(3-pyridylmethyl)carboxamide |
| 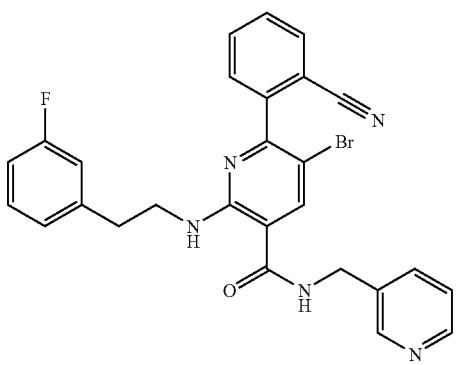<br>Compound 368 | (5-bromo-6-(2-cyanophenyl)-2-{[2-(3-fluorophenyl)ethyl]amino}(3-pyridyl))-N-(3-pyridylmethyl)carboxamide |
| 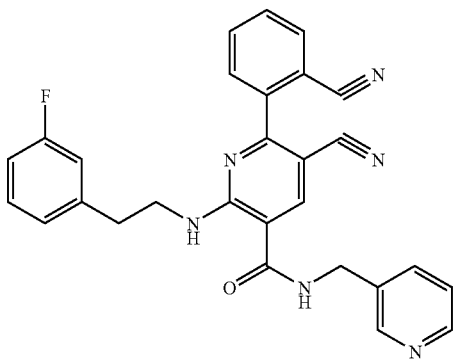<br>Compound 369 | (5-cyano-6-(2-cyanophenyl)-2-{[2-(3-fluorophenyl)ethyl]amino}(3-pyridyl))-N-(3-pyridylmethyl)carboxamide |
| 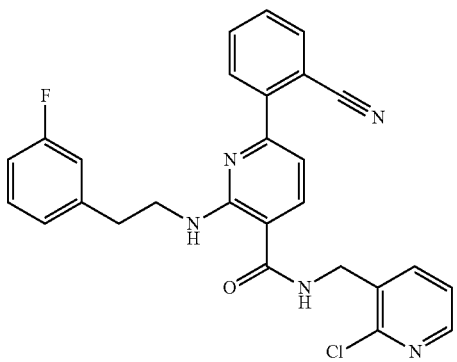<br>Compound 370 | N-[(2-chloro(3-pyridyl))methyl](6-(2-cyanophenyl)-2-{[2-(3-fluorophenyl)ethyl]amino}(3-pyridyl))carboxamide |

-continued
| COMPOUND | CHEMICAL NAME |
|---|---|
| 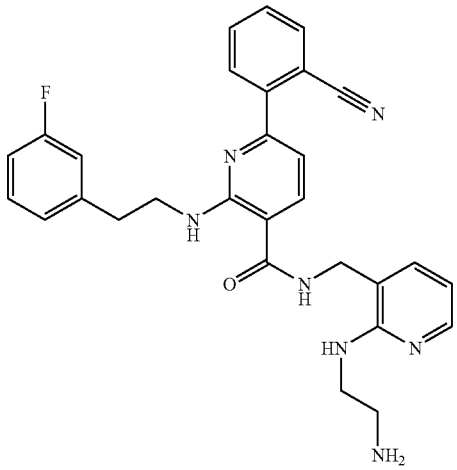<br>Compound 371 | N-({2-[(2-aminoethyl)amino](3-pyridyl)}methyl)(6-(2-cyanophenyl)-2-{[2-(3-fluorophenyl)ethyl]amino}(3-pyridyl))carboxamide |
| 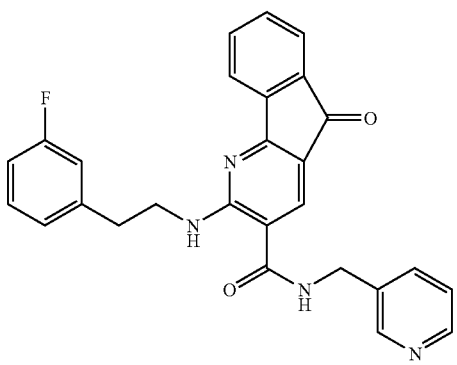<br>Compound 404 | (2-{[2-(3-fluorophenyl)ethyl]amino}-5-oxoindeno[3,2-b]pyridin-3-yl)-N-(3-pyridylmethyl)carboxamide |
| 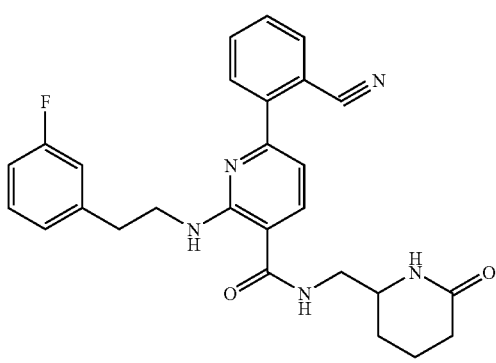<br>Compound 408 | (6-(2-cyanophenyl)-2-{[2-(3-fluorophenyl)ethyl]amino}(3-pyridyl))-N-[(6-oxo(2-piperidyl))methyl]carboxamide |

| COMPOUND | CHEMICAL NAME |
|---|---|
| 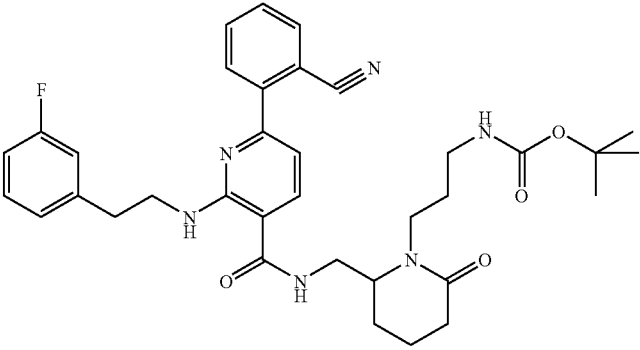<br>Compound 430 | N-[(1-{3-[(tert-butoxy)carbonylamino]propyl}-6-oxo(2-piperidyl))methyl](6-(2-cyanophenyl)-2-{[2-(3-fluorophenyl)ethyl]amino}(3-pyridyl))carboxamide |
| 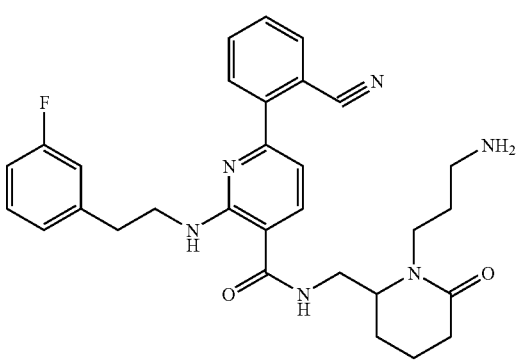<br>Compound 431 | N-{[1-(3-aminopropyl)-6-oxo(2-piperidyl)]methyl}(6-(2-cyanophenyl)-2-{[2-(3-fluorophenyl)ethyl]amino}(3-pyridyl))carboxamide |
| 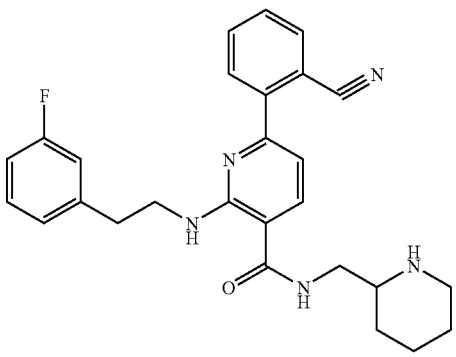<br>Compound 432 | N-[((2S)(2-piperidyl))methyl](6-(2-cyanophenyl)-2-{[2-(3-fluorophenyl)ethyl]amino}(3-pyridyl))carboxamide |
| 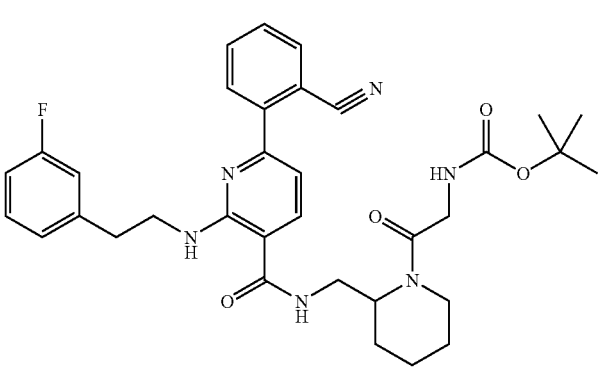<br>Compound 445 | N-[((2S)-1-{2-[(tert-butoxy)carbonylamino]acetyl}(2-piperidyl))methyl](6-(2-cyanophenyl)-2-{[2-(3-fluorophenyl)ethyl]amino}(3-pyridyl))carboxamide |

-continued

| COMPOUND | CHEMICAL NAME |
|---|---|
| 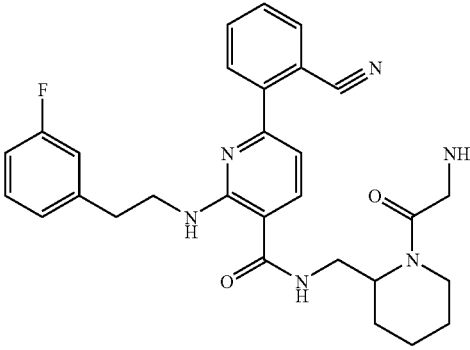<br>Compound 446 | N-{[(2S)-1-(2-aminoacetyl)(2-piperidyl)]methyl}(6-(2-cyanophenyl)-2-{[2-(3-fluorophenyl)ethyl]amino}(3-pyridyl))carboxamide |
| 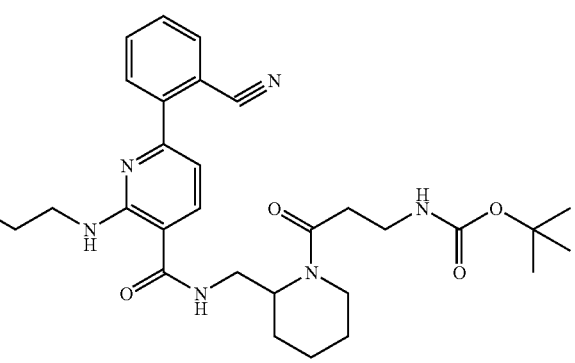<br>Compound 448 | N-[((2S)-1-{3-[(tert-butoxy)carbonylamino]propanoyl}(2-piperidyl))methyl](6-(2-cyanophenyl)-2-{[2-(3-fluorophenyl)ethyl]amino}(3-pyridyl))carboxamide |
| 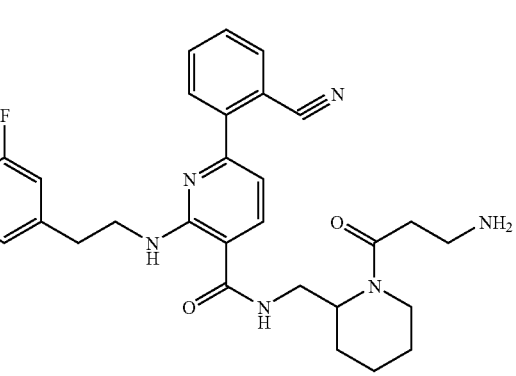<br>Compound 450 | N-{[(2S)-1-(3-aminopropanoyl)(2-piperidyl)]methyl}(6-(2-cyanophenyl)-2-{[2-(3-fluorophenyl)ethyl]amino}(3-pyridyl))carboxamide |
| 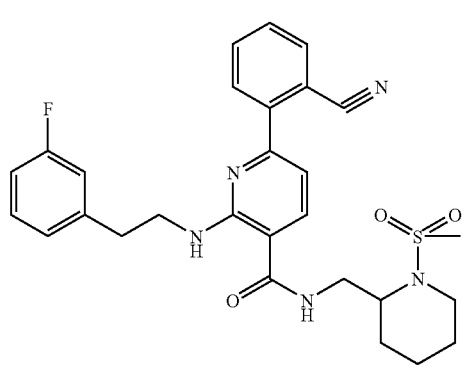<br>Compound 479 | N-{[(2S)-1-(methylsulfonyl)(2-piperidyl)]methyl}(6-(2-cyanophenyl)-2-{[2-(3-fluorophenyl)ethyl]amino}(3-pyridyl))carboxamide |

| COMPOUND | CHEMICAL NAME |
|---|---|
| Compound 511 | N-[((2R)-6-oxo(2-piperidyl))methyl](6-(2-cyanophenyl)-2-{[2-(3-fluorophenyl)ethyl]amino}(3-pyridyl))carboxamide |
| Compound 512 | N-[((2R)-1-{3-[(tert-butoxy)carbonylamino]propyl}-6-oxo(2-piperidyl))methyl](6-(2-cyanophenyl)-2-{[2-(3-fluorophenyl)ethyl]amino}(3-pyridyl))carboxamide |
| Compound 513 | N-{[(2R)-1-(3-aminopropyl)-6-oxo(2-piperidyl)]methyl}(6-(2-cyanophenyl)-2-{[2-(3-fluorophenyl)ethyl]amino}(3-pyridyl))carboxamide |
| Compound 516 | N-[((3S)(3-piperidyl))methyl](6-(2-cyanophenyl)-2-{[2-(3-fluorophenyl)ethyl]amino}(3-pyridyl))carboxamide |

-continued

| COMPOUND | CHEMICAL NAME |
|---|---|
| 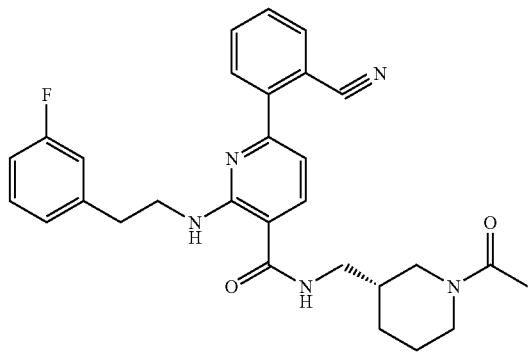  Compound 518 | N-[((3R)-1-acetyl(3-piperidyl))methyl](6-(2-cyanophenyl)-2-{[2-(3-fluorophenyl)ethyl]amino}(3-pyridyl))carboxamide |
| 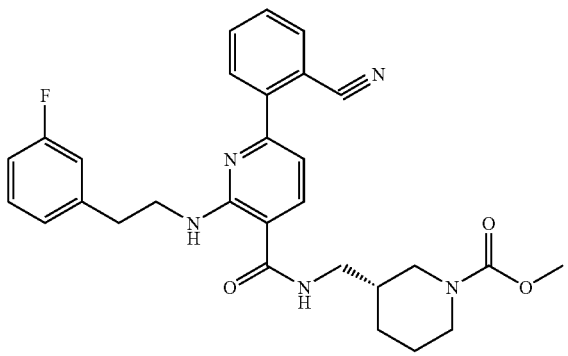  Compound 519 | methyl (3R)-3-{[(6-(2-cyanophenyl)-2-{[2-(3-fluorophenyl)ethyl]amino}(3-pyridyl))carbonylamino]methyl}piperidinecarboxylate |
| 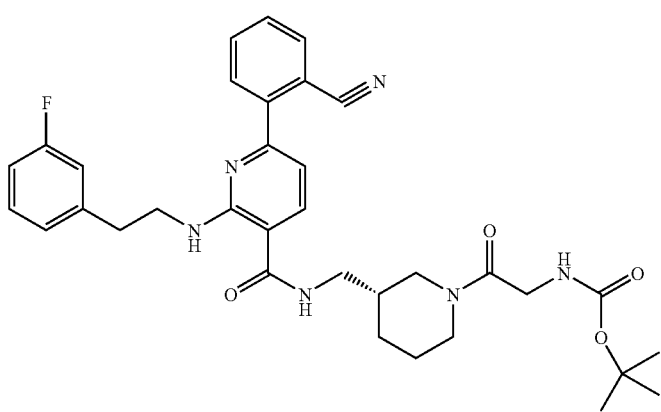  Compound 521 | N-[((3R)-1-{2-[(tert-butoxy)carbonylamino]acetyl}(3-piperidyl))methyl](6-(2-cyanophenyl)-2-{[2-(3-fluorophenyl)ethyl]amino}(3-pyridyl))carboxamide |

| COMPOUND | CHEMICAL NAME |
|---|---|
| 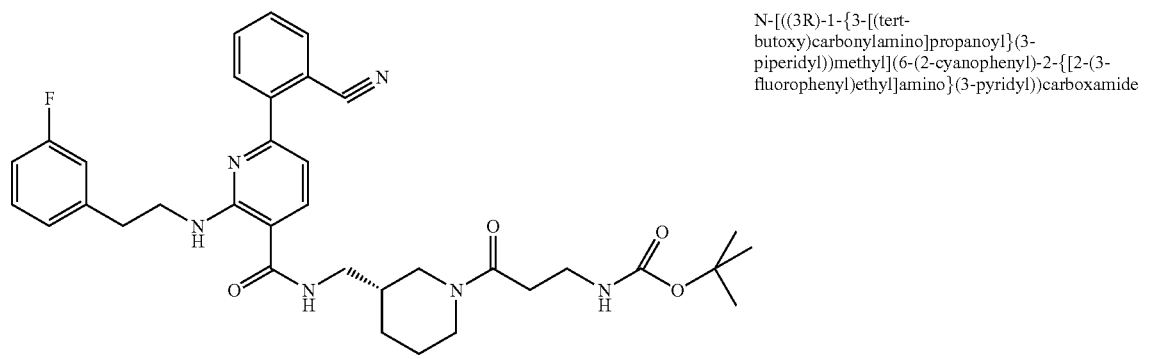

Compound 524 | N-[((3R)-1-{3-[(tert-butoxy)carbonylamino]propanoyl}(3-piperidyl))methyl](6-(2-cyanophenyl)-2-{[2-(3-fluorophenyl)ethyl]amino}(3-pyridyl))carboxamide |
| 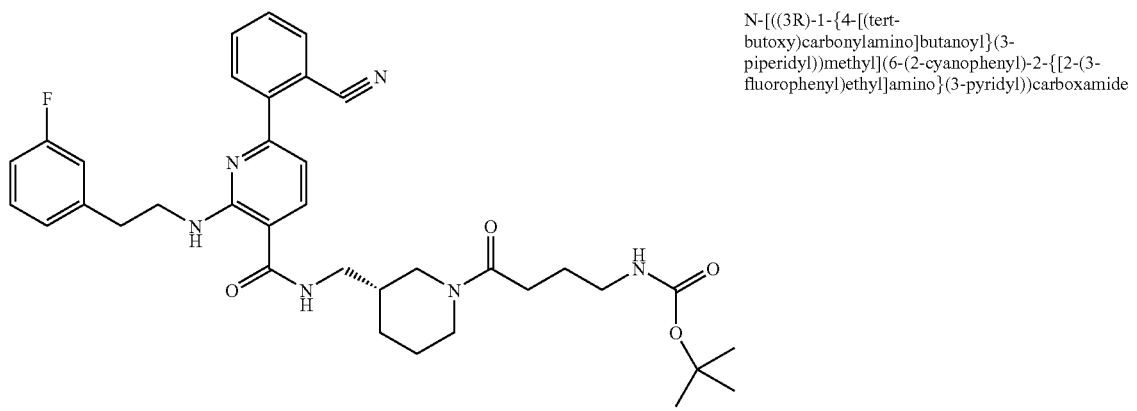

Compound 527 | N-[((3R)-1-{4-[(tert-butoxy)carbonylamino]butanoyl}(3-piperidyl))methyl](6-(2-cyanophenyl)-2-{[2-(3-fluorophenyl)ethyl]amino}(3-pyridyl))carboxamide |
| 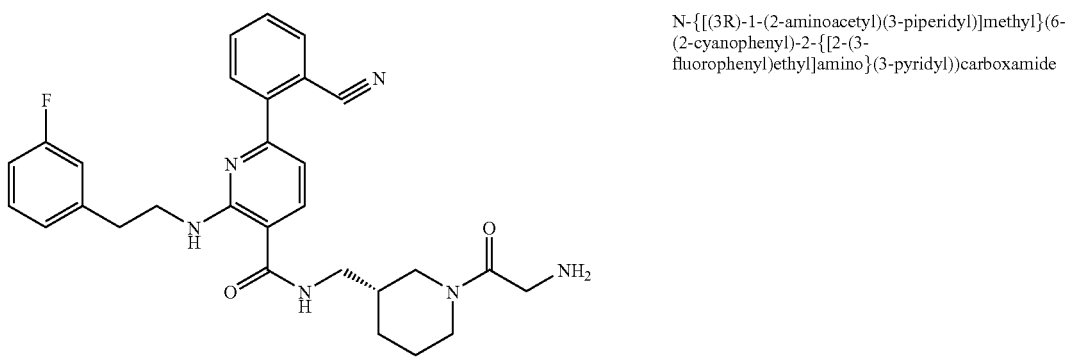

Compound 529 | N-{[(3R)-1-(2-aminoacetyl)(3-piperidyl)]methyl}(6-(2-cyanophenyl)-2-{[2-(3-fluorophenyl)ethyl]amino}(3-pyridyl))carboxamide |

| COMPOUND | CHEMICAL NAME |
|---|---|
| 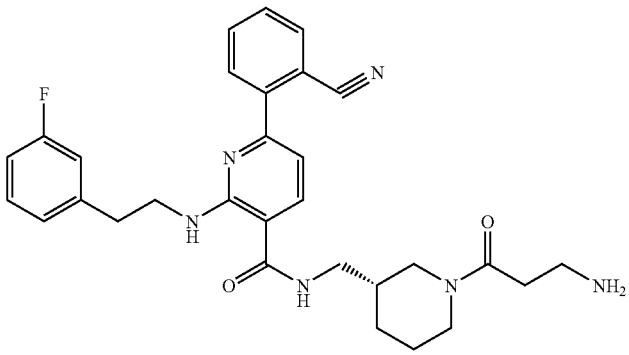<br>Compound 532 | N-{[(3R)-1-(3-aminopropanoyl)(3-piperidyl)]methyl}(6-(2-cyanophenyl)-2-{[2-(3-fluorophenyl)ethyl]amino}(3-pyridyl))carboxamide |
| 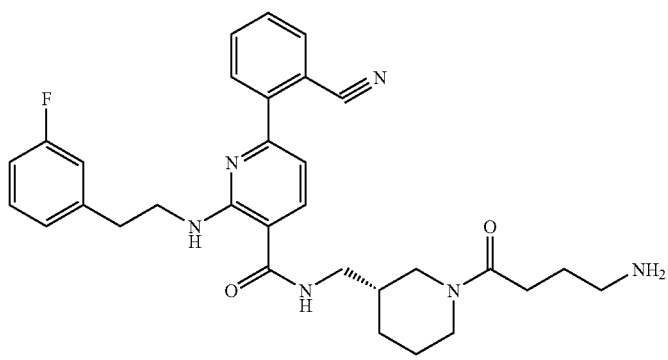<br>Compound 533 | N-{[(3R)-1-(4-aminobutanoyl)(3-piperidyl)]methyl}(6-(2-cyanophenyl)-2-{[2-(3-fluorophenyl)ethyl]amino}(3-pyridyl))carboxamide |
| 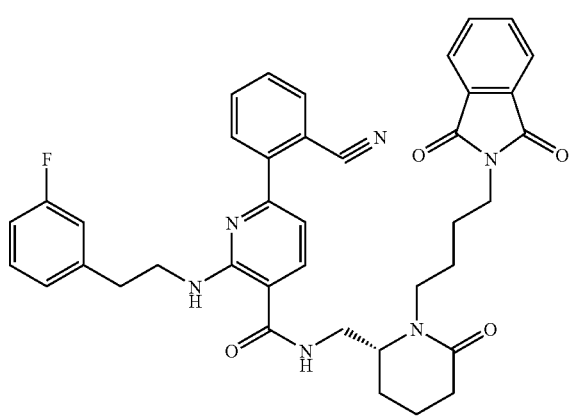<br>Compound 535 | N-({(2R)-1-[4-(1,3-dioxobenzo[c]azolin-2-yl)butyl]-6-oxo(2-piperidyl)}methyl)(6-(2-cyanophenyl)-2-{[2-(3-fluorophenyl)ethyl]amino}(3-pyridyl))carboxamide |

-continued

| COMPOUND | CHEMICAL NAME |
|---|---|
| 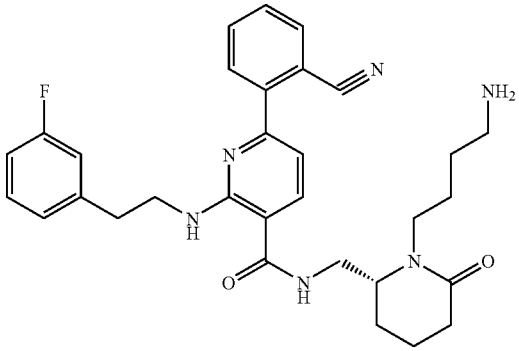<br>Compound 536 | N-{[(2R)-1-(4-aminobutyl)-6-oxo(2-piperidyl)]methyl}(6-(2-cyanophenyl)-2-{[2-(3-fluorophenyl)ethyl]amino}(3-pyridyl))carboxamide |
| 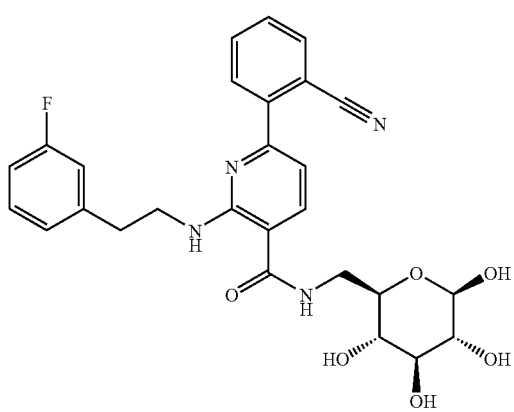<br>Compound 596 | N-[((3S,4S,2R,5R)-3,4,5,6-tetrahydroxy(2H-3,4,5,6-tetrahydropyran-2-yl))methyl](6-(2-cyanophenyl)-2-{[2-(3-fluorophenyl)ethyl]amino}(3-pyridyl))carboxamide |
| 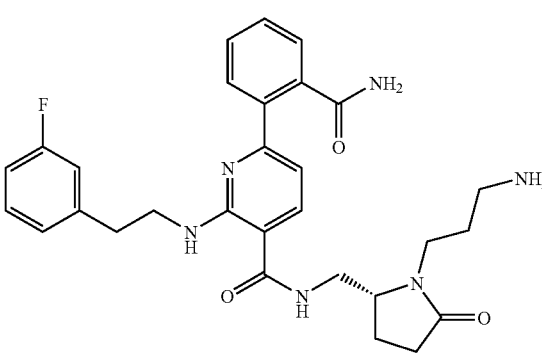<br>Compound 667 | 2-[5-(N-{[(2R)-1-(3-aminopropyl)-5-oxopyrrolidin-2-yl]methyl}carbamoyl)-6-{[2-(3-fluorophenylethyl]amino}-2-pyridyl]benzamide |

-continued

| COMPOUND | CHEMICAL NAME |
|---|---|
| Compound 668 | N-[2-((2R)-2-{[(6-(2-cyanophenyl)-2-{[2-(3-fluorophenyl)ethyl]amino}(3-pyridyl))carbonylamino]methyl}pyrrolidinyl)(1S)-1-methyl-2-oxoethyl](tert-butoxy)carboxamide |
| Compound 669 | N-{[(2R)-1-((2S)-2-aminopropanoyl)pyrrolidin-2-yl]methyl}(6-(2-cyanophenyl)-2-{[2-(3-fluorophenyl)ethyl]amino}(3-pyridyl))carboxamide |
| Compound 670 | N-[(1R)-2-((2R)-2-{[(6-(2-cyanophenyl)-2-{[2-(3-fluorophenyl)ethyl]amino}(3-pyridyl))carbonylamino]methyl}pyrrolidinyl)-1-methyl-2-oxoethyl](tert-butoxy)carboxamide |
| Compound 671 | N-{[(2R)-1-((2R)-2-aminopropanoyl)pyrrolidin-2-yl]methyl}(6-(2-cyanophenyl)-2-{[2-(3-fluorophenyl)ethyl]amino}(3-pyridyl))carboxamide |

-continued

| COMPOUND | CHEMICAL NAME |
|---|---|
| Compound 672 | N-{[(2R)-1-((2S)-2,5-diaminopentanoyl)pyrrolidin-2-yl]methyl}(6-(2-cyanophenyl)-2-{[2-(3-fluorophenyl)ethyl]amino}(3-pyridyl))carboxamide |
| Compound 696 | N-[(2-chloro(3-pyridyl))methyl](2-{[2-(3-fluorophenyl)ethyl]amino}-6-(1-methylpyrazol-4-yl)(3-pyridyl))carboxamide |
| Compound 699 | N-({2-[(3-aminopropyl)amino](3-pyridyl)}methyl)(2-{[2-(3-fluorophenyl)ethyl]amino}-6-(1-methylpyrazol-4-yl(3-pyridyl))carboxamide |
| Compound 711 | N-({2-[(2-aminoethyl)amino](3-pyridyl)}methyl)(2-{[2-(3-fluorophenyl)ethyl]amino}-6-pyrazol-4-yl(3-pyridyl))carboxamide |

| COMPOUND | CHEMICAL NAME |
|---|---|
| 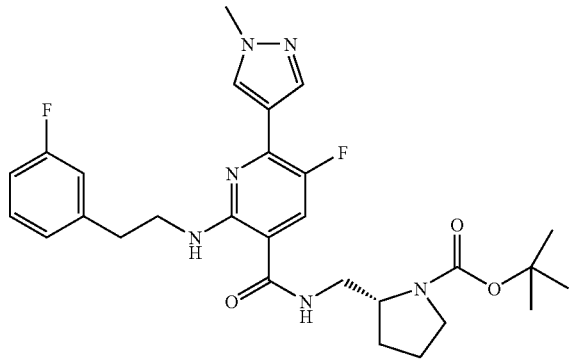<br>Compound 712 | tert-butyl (2R)-2-{[(5-fluoro-2-{[2-(3-fluorophenyl)ethyl]amino}-6-(1-methylpyrazol-4-yl)(3-pyridyl))carbonylamino]methyl}pyrrolidinecarboxylate |
| 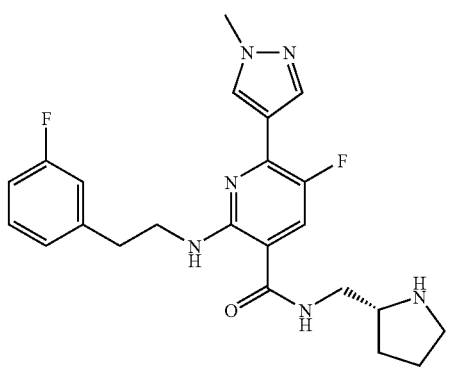<br>Compound 713 | N-[((2R)pyrrolidin-2-yl)methyl](5-fluoro-2-{[2-(3-fluorophenyl)ethyl]amino}-6-(1-methylpyrazol-4-yl)(3-pyridyl))carboxamide |
| 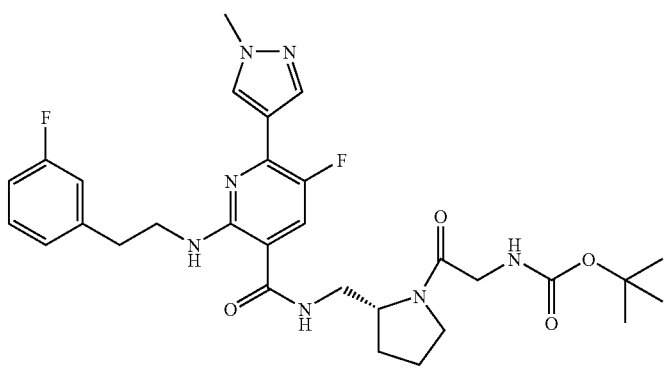<br>Compound 714 | N-[((2R)-1-{2-[(tert-butoxy)carbonylamino]acetyl}pyrrolidin-2-yl)methyl](5-fluoro-2-{[2-(3-fluorophenyl)ethyl]amino}-6-pyrazol-4-yl(3-pyridyl))carboxamide |

-continued

| COMPOUND | CHEMICAL NAME |
|---|---|
| 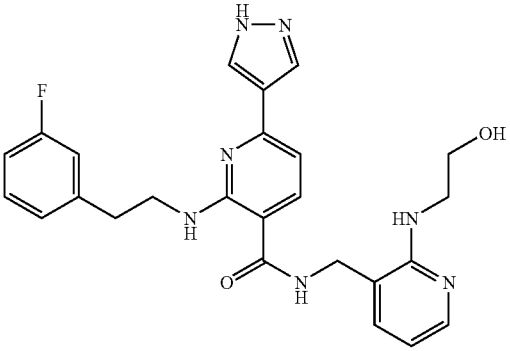 Compound 717 | (2-{[2-(3-fluorophenyl)ethyl]amino}-6-pyrazol-4-yl(3-pyridyl))-N-({2-[(2-hydroxyethyl)amino](3-pyridyl)}methyl)carboxamide |
| 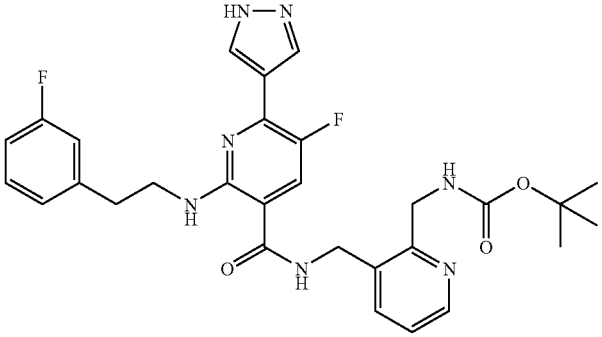 Compound 745 | N-[(2-{[(tert-butoxy)carbonylamino]methyl}(3-pyridyl))methyl](5-fluoro-2-{[2-(3-fluorophenyl)ethyl]amino}-6-pyrazol-4-yl(3-pyridyl))carboxamide |
| 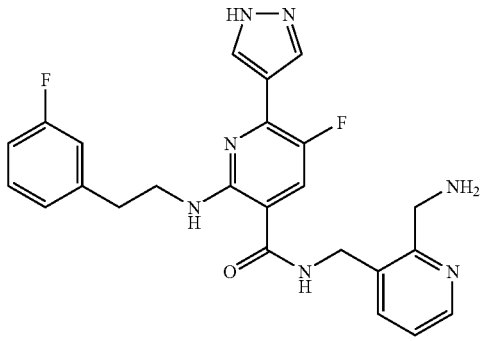 Compound 746 | N-{[2-(aminomethyl)(3-pyridyl)]methyl}(5-fluoro-2-{[2-(3-fluorophenyl)ethyl]amino}-6-pyrazol-4-yl(3-pyridyl))carboxamide |
| 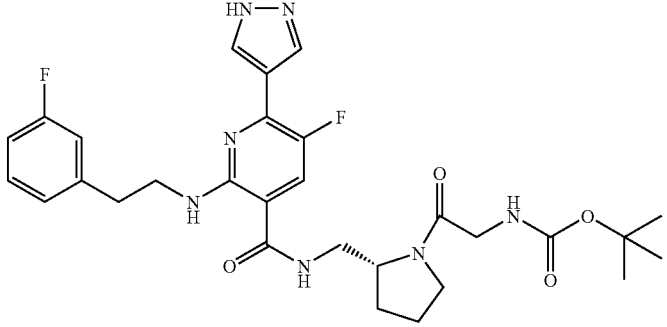 Compound 747 | N-[((2R)-1-{2-[(tert-butoxy)carbonylamino]acetyl}pyrrolidin-2-yl)methyl](5-fluoro-2-{[2-(3-fluorophenyl)ethyl]amino}-6-pyrazol-4-yl(3-pyridyl))carboxamide |

| COMPOUND | CHEMICAL NAME |
|---|---|
| 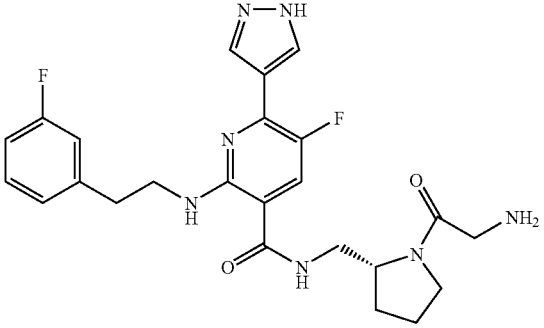
Compound 748 | N-{[(2R)-1-(2-aminoacetyl)pyrrolidin-2-yl]methyl}(5-fluoro-2-{[2-(3-fluorophenyl)ethyl]amino}-6-pyrazol-4-yl(3-pyridyl))carboxamide |
| 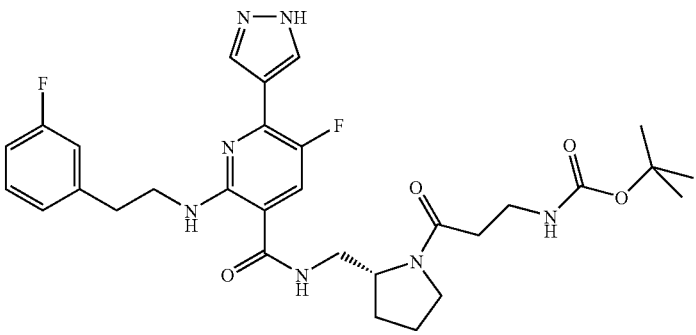
Compound 749 | N-[((2R)-1-{3-[(tert-butoxy)carbonylamino]propanoyl}pyrrolidin-2-yl)methyl](5-fluoro-2-{[2-(3-fluorophenyl)ethyl]amino}-6-pyrazol-4-yl(3-pyridyl))carboxamide |
| 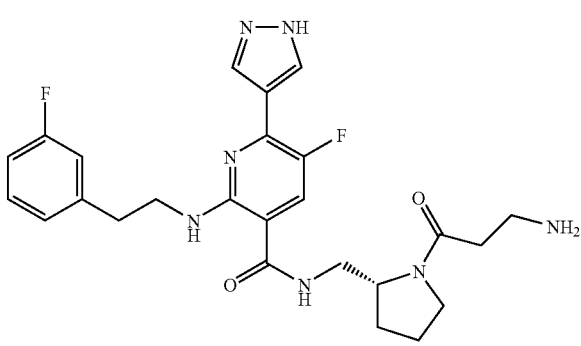
Compound 750 | N-{[(2R)-1-(3-aminopropanoyl)pyrrolidin-2-yl]methyl}(5-fluoro-2-{[2-(3-fluorophenyl)ethyl]amino}-6-pyrazol-4-yl(3-pyridyl))carboxamide |
| 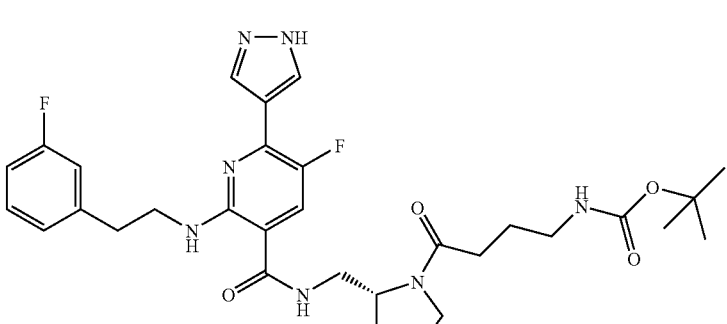
Compound 751 | N-[((2R)-1-{4-[(tert-butoxy)carbonylamino]butanoyl}pyrrolidin-2-yl)methyl](5-fluoro-2-{[2-(3-fluorophenyl)ethyl]amino}-6-pyrazol-4-yl(3-pyridyl))carboxamide |

-continued

| COMPOUND | CHEMICAL NAME |
|---|---|
| 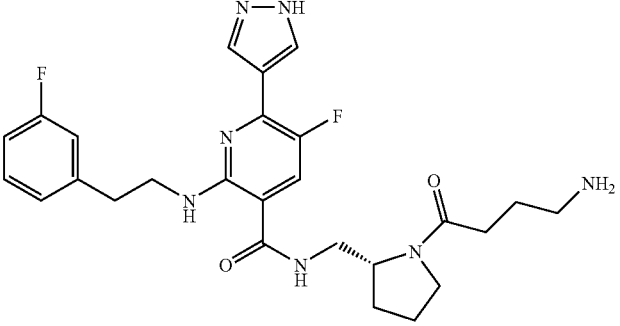<br>Compound 752 | N-{[(2R)-1-(4-aminobutanoyl)pyrrolidin-2-yl]methyl}(5-fluoro-2-{[2-(3-fluorophenyl)ethyl]amino}-6-pyrazol-4-yl(3-pyridyl))carboxamide |
| 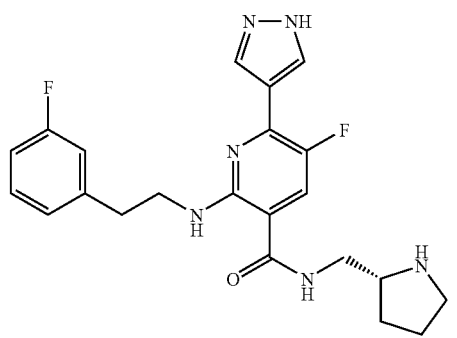<br>Compound 753 | N-[((2R)pyrrolidin-2-yl)methyl](5-fluoro-2-{[2-(3-fluorophenyl)ethyl]amino}-6-pyrazol-4-yl(3-pyridyl))carboxamide |
| 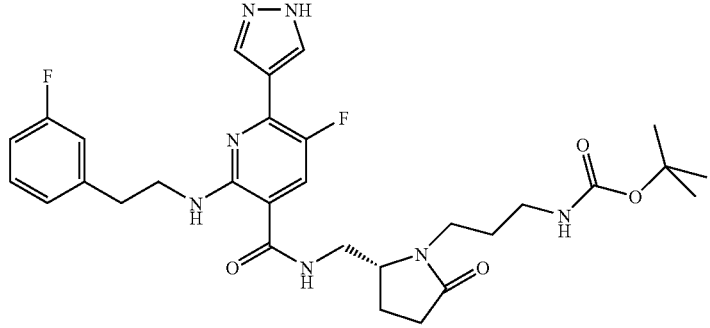<br>Compound 757 | N-[((2R)-1-{3-[(tert-butoxy)carbonylamino]propyl}-5-oxopyrrolidin-2-yl)methyl](5-fluoro-2-{[2-(3-fluorophenyl)ethyl]amino}-6-pyrazol-4-yl(3-pyridyl))carboxamide |
| 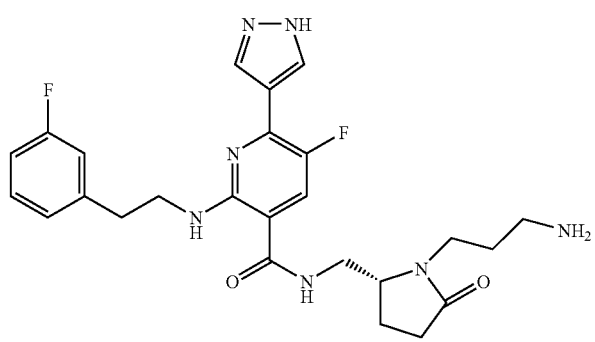<br>Compound 758 | N-{[(2R)-1-(3-aminopropyl)-5-oxopyrrolidin-2-yl]methyl}(5-fluoro-2-{[2-(3-fluorophenyl)ethyl]amino}-6-pyrazol-4-yl(3-pyridyl))carboxamide |

| COMPOUND | CHEMICAL NAME |
|---|---|
| 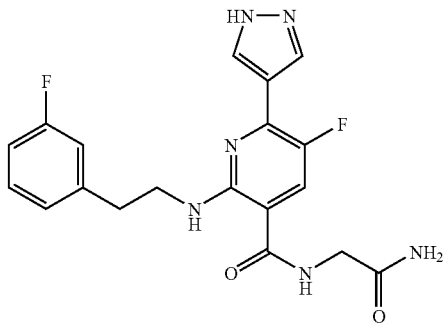<br>Compound 759 | N-(carbamoylmethyl)(5-fluoro-2-{[2-(3-fluorophenyl)ethyl]amino}-6-pyrazol-4-yl(3-pyridyl))carboxamide |
| 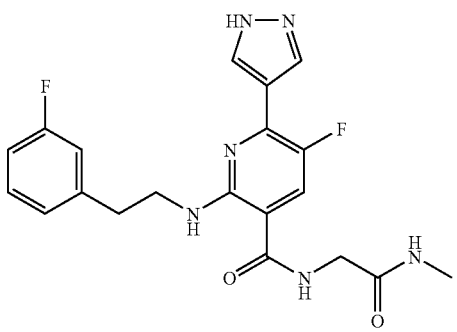<br>Compound 760 | 2-[(5-fluoro-2-{[2-(3-fluorophenyl)ethyl]amino}-6-pyrazol-4-yl(3-pyridyl))carbonylamino]-N-methylacetamide |
| 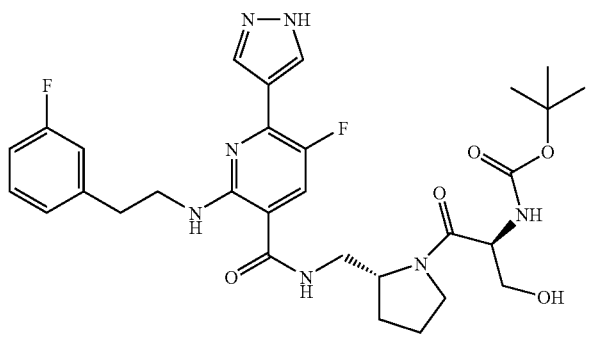<br>Compound 761 | N-[((2R)-1-{(2S)-2-[(tert-butoxy)carbonylamino]-3-hydroxypropanoyl}pyrrolidin-2-yl)methyl](5-fluoro-2-{[2-(3-fluorophenyl)ethyl]amino}-6-pyrazol-4-yl(3-pyridyl))carboxamide |
| 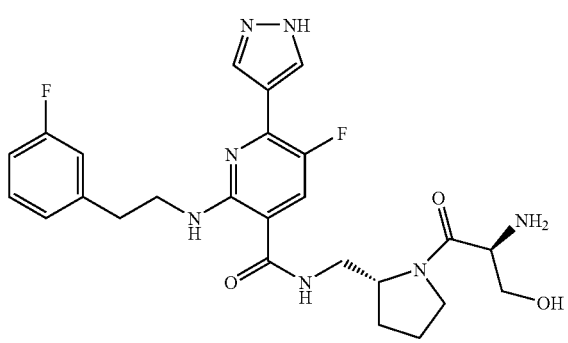<br>Compound 762 | N-{[(2R)-1-((2S)-2-amino-3-hydroxypropanoyl)pyrrolidin-2-yl]methyl}(5-fluoro-2-{[2-(3-fluorophenyl)ethyl]amino}-6-pyrazol-4-yl(3-pyridyl))carboxamide |

-continued

| COMPOUND | CHEMICAL NAME |
|---|---|
| 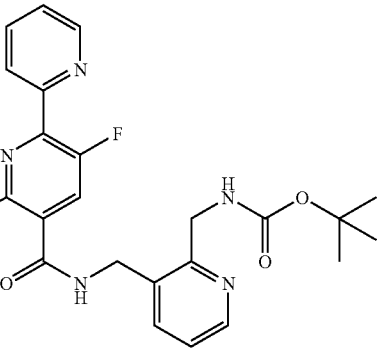<br>Compound 806 | N-[(2-{[(tert-butoxy)carbonylamino]methyl}(3-pyridyl))methyl](5-fluoro-2-{[2-(3-fluorophenyl)ethyl]amino}-6-(2-pyridyl)(3-pyridyl))carboxamide |
| 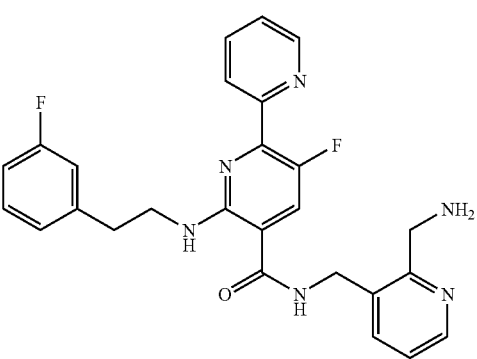<br>Compound 807 | N-{[2-aminomethyl)(3-pyridyl)]methyl}(5-fluoro-2-{[2-(3-fluorophenyl)ethyl]amino}-6-(2-pyridyl)(3-pyridyl))carboxamide |
| 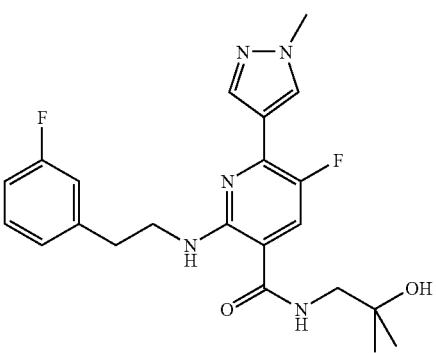<br>Compound 869 | (5-fluoro-2-{[2-(3-fluorophenyl)ethyl]amino}-6-(1-methylpyrazol-4-yl)(3-pyridyl))-N-(2-hydroxy-2-methylpropyl)carboxamide |
| 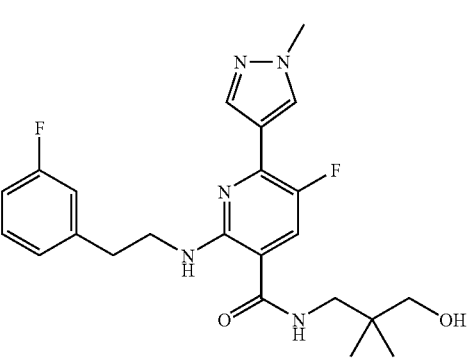<br>Compound 870 | (5-fluoro-2-{[2-(3-fluorophenyl)ethyl]amino}-6-(1-methylpyrazol-4-yl)(3-pyridyl))-N-(3-hydroxy-2,2-dimethylpropyl)carboxamide |

-continued

| COMPOUND | CHEMICAL NAME |
|---|---|
| Compound 879 | N-((2R)-2-methyl-3-oxobutyl)(5-fluoro-2-{[2-(3-fluorophenyl)ethyl]amino}-6-(1-methylpyrazol-4-yl)(3-pyridyl))carboxamide |
| Compound 880 | N-((2R)-3-hydroxy-2,3-dimethylbutyl)(5-fluoro-2-{[2-(3-fluorophenyl)ethyl]amino}-6-(1-methylpyrazol-4-yl)(3-pyridyl))carboxamide |
| boc | 2-((2R)-2-{[(5-fluoro-2-{[2-(3-fluorophenyl)ethyl]amino}-6-(2-methylpyrazol-4-yl)(3-pyridyl))carbonylamino]methyl}azetidinyl)-2-oxoethyl 2-[(tert-butoxy)carbonylamino]acetate |
| Compound 908 | 2-((2R)-2-{[(5-fluoro-2-{[2-(3-fluorophenyl)ethyl]amino}-6-(1-methylpyrzol-4-yl)(3-pyridyl))carbonylamino]methyl}azetidinyl)-2-oxoethyl 2-aminoacetate |

-continued

| COMPOUND | CHEMICAL NAME |
|---|---|
| 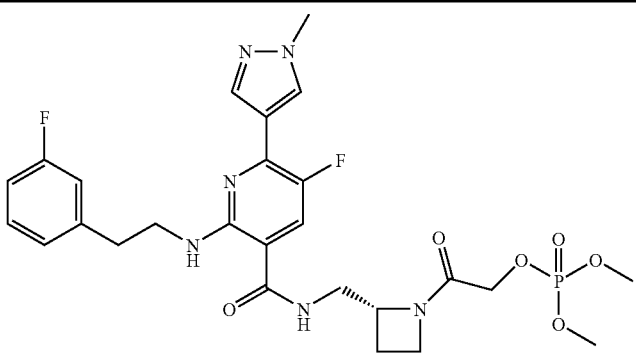<br>Compound 909 | 2-((2R)-2-{[(5-fluoro-2-{[2-(3-fluorophenyl)ethyl]amino}-6-(1-methylpyrazol-4-yl)(3-pyridyl))carbonylamino]methyl}azetidinyl)-2-oxoethyl dimethyl phosphate |
| 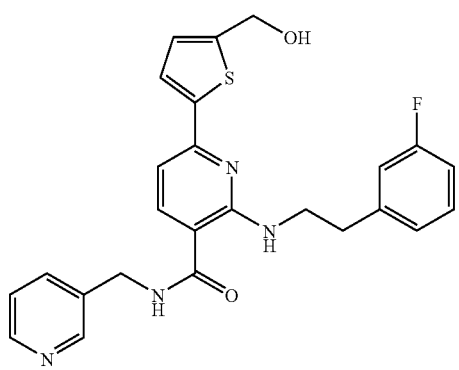<br>Compound 212 | (2-{[2-(3-fluorophenyl)ethyl]amino}-6-[5-(hydroxymethyl)(2-thienyl)](3-pyridyl))-N-(3-pyridylmethyl)carboxamide |
| 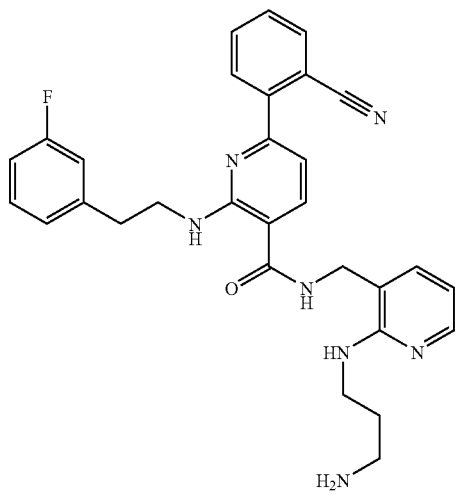<br>Compound 385 | N-({2-[(3-aminopropyl)amino](3-pyridyl)}methyl)(6-(2-cyanophenyl)-2-{[2-(3-fluorophenyl)ethyl]amino}(3-pyridyl))carboxamide |

-continued
| COMPOUND | CHEMICAL NAME |
|---|---|
| 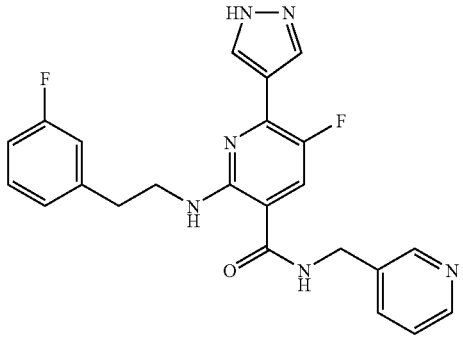<br>Compound 695 | (5-fluoro-2-{[2-(3-fluorophenyl)ethyl]amino-6-pyrazol-4-yl(3-pyridyl))-N-(3-pyridylmethyl)carboxamide |
| 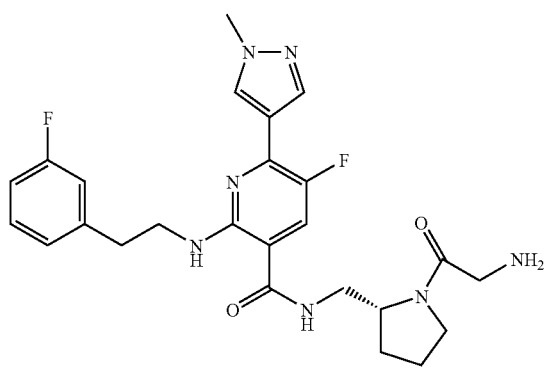<br>Compound 715 | N-{[(2R)-1-(2-aminoacetyl)pyrrolidin-2-yl]methyl}(5-fluoro-2-{[2-(3-fluorophenyl)ethyl]amino}-6-(1-methylpyrazol-4-yl)(3-pyridyl))carboxamide |
| 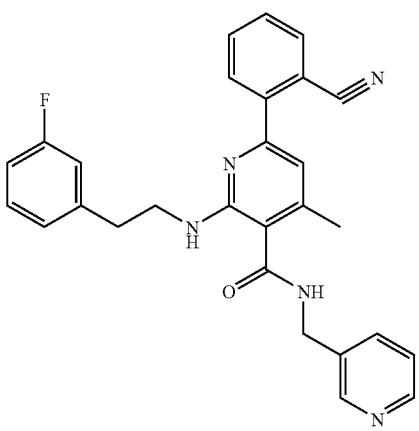<br>Compound 181 | (6-(2-cyanophenyl)-2-{[2-(3-fluorophenyl)ethyl]amino}-4-methyl(3-pyridyl))-N-(3-pyridylmethyl)carboxamide |

-continued

| COMPOUND | CHEMICAL NAME |
|---|---|
| Compound 210 | (6-(2-cyanophenyl)-2-{[2-(3-fluorophenyl)ethyl]amino}(3-pyridyl))-N-[(6-morpholin-4-yl(3-pyridyl))methyl]carboxamide |
| Compound 217 | (6-(2-cyanophenyl)-2-{[2-(3-fluorophenyl)ethyl]amino}(3-pyridyl))-N-[(6-pyrrolidinyl(3-pyridyl))methyl]carboxamide |
| Compound 218 | (6-(2-cyanophenyl)-2-{[2-(3-fluorophenyl)ethyl]amino}(3-pyridyl))-N-[(6-piperazinyl(3-pyridyl))methyl]carboxamide |

-continued

| COMPOUND | CHEMICAL NAME |
|---|---|
| Compound 231 | N-{[6-(4-acetylpiperazinyl)(3-pyridyl)]methyl}(6-(2-cyanophenyl)-2-{[2-(3-fluorophenyl)ethyl]amino}(3-pyridyl))carboxamide |
| Compound 242 | N-[(6-bromo(2-pyridyl)methyl](6-(2-cyanophenyl)-2-{[2-(3-fluorophenyl)ethyl]amino}(3-pyridyl))carboxamide |
| Compound 266 | 2-[(2-{[2-(3-fluorophenyl)ethyl]amino}-6-[5-(hydroxymethyl)(2-thienyl)](3-pyridyl))carbonylamino]-N-methylacetamide |

| COMPOUND | CHEMICAL NAME |
|---|---|
| 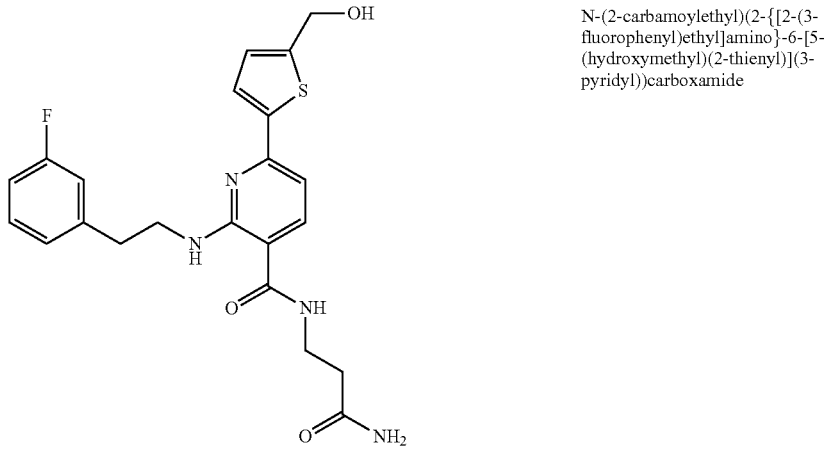<br>Compound 267 | N-(2-carbamoylethyl)(2-{[2-(3-fluorophenyl)ethyl]amino}-6-[5-(hydroxymethyl)(2-thienyl)](3-pyridyl))carboxamide |
| 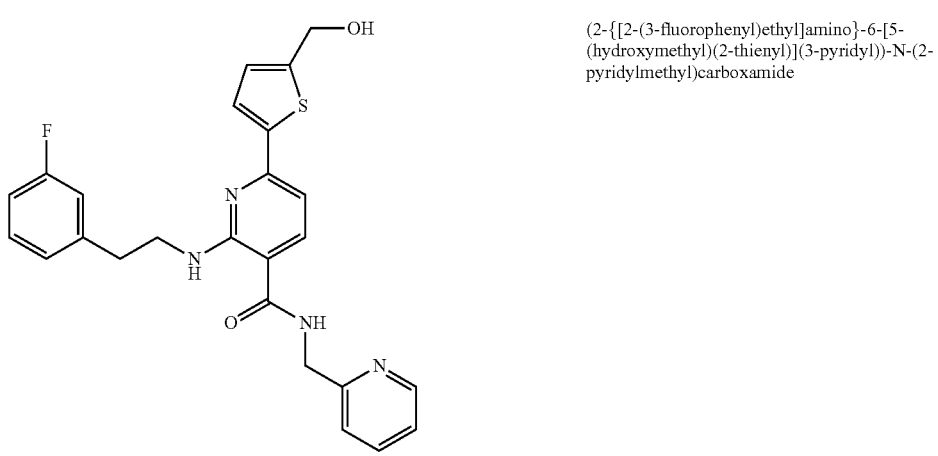<br>Compound 268 | (2-{[2-(3-fluorophenyl)ethyl]amino}-6-[5-(hydroxymethyl)(2-thienyl)](3-pyridyl))-N-(2-pyridylmethyl)carboxamide |
| 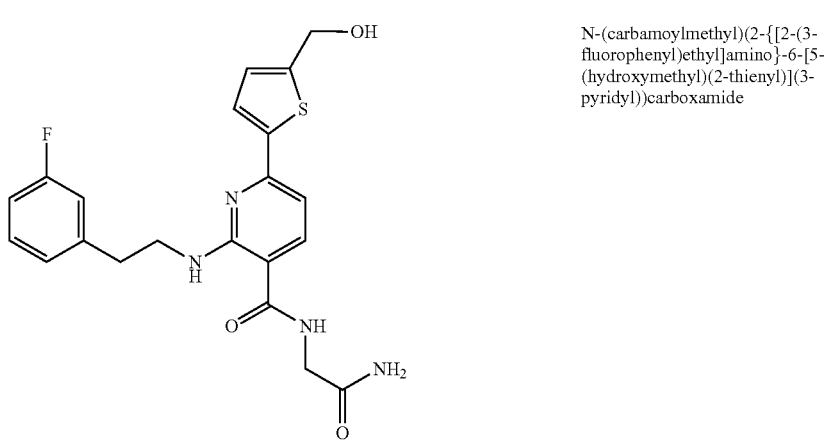<br>Compound 269 | N-(carbamoylmethyl)(2-{[2-(3-fluorophenyl)ethyl]amino}-6-[5-(hydroxymethyl)(2-thienyl)](3-pyridyl))carboxamide |

-continued
| COMPOUND | CHEMICAL NAME |
|---|---|
| 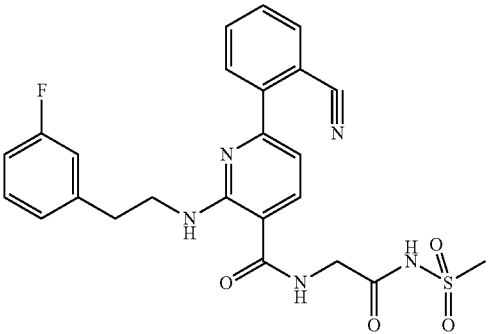<br>Compound 308 | 2-[(6-(2-cyanophenyl)-2-{[2-(3-fluorophenyl)ethyl]amino}(3-pyridyl))carbonylamino]-N-(methylsulfonyl)acetamide |
| 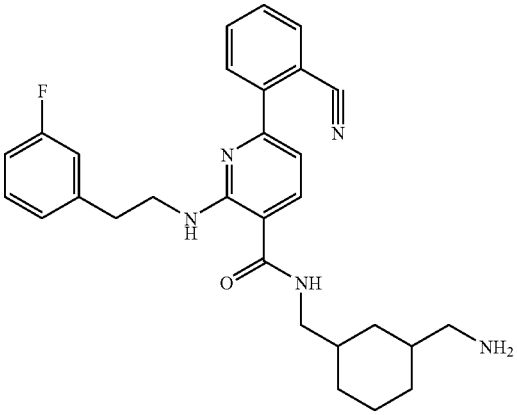<br>Compound 324 | N-{[3-(aminomethyl)cyclohexyl]methyl}(6-(2-cyanophenyl)-2-{[2-(3-fluorophenyl)ethyl]amino}(3-pyridyl))carboxamide |
| 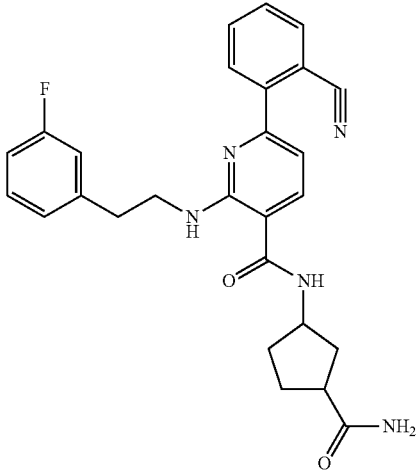<br>Compound 325 | 3-[(6-(2-cyanophenyl)-2-{[2-(3-fluorophenyl)ethyl]amino}-3-pyridyl)carbonylamino]cyclopentanecarboxamide |

| COMPOUND | CHEMICAL NAME |
|---|---|
| 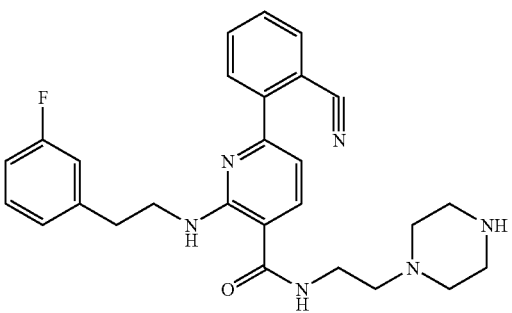<br>Compound 339 | (6-(2-cyanophenyl)-2-{[2-(3-fluorophenyl)ethyl]amino}(3-pyridyl))-N-(2-piperazinylethyl)carboxamide |
| 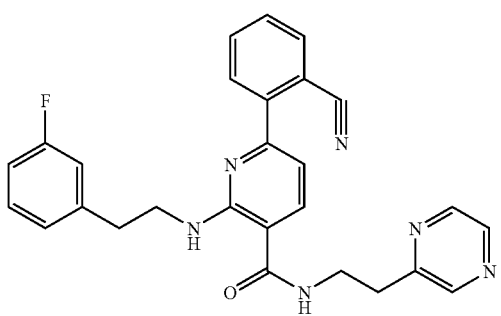<br>Compound 340 | (6-(2-cyanophenyl)-2-{[2-(3-fluorophenyl)ethyl]amino}(3-pyridyl))-N-(2-pyrazin-2-ylethyl)carboxamide |
| 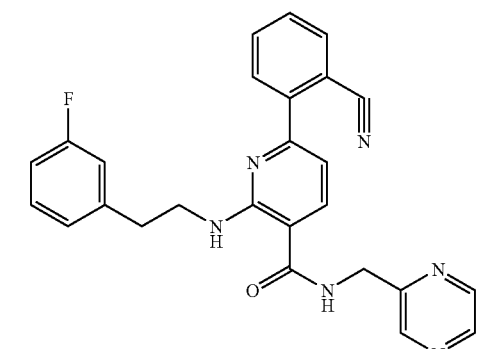<br>Compound 341 | (6-(2-cyanophenyl)-2-{[2-(3-fluorophenyl)ethyl]amino}(3-pyridyl))-N-(pyrazin-2-ylmethyl)carboxamide |
| 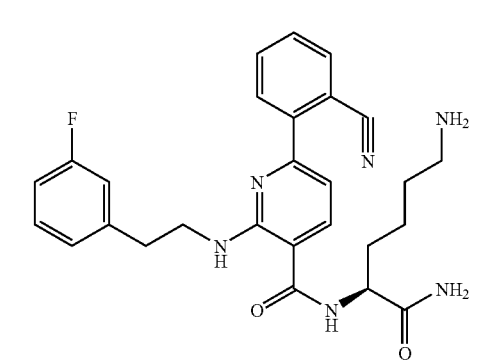<br>Compound 349 | N-((1S)-5-amino-1-carbamoylpentyl)(6-(2-cyanophenyl)-2-{[2-(3-fluorophenyl)ethyl]amino}(3-pyridyl))carboxamide |

-continued

| COMPOUND | CHEMICAL NAME |
|---|---|
| Compound 350 | N-(3-amino-1-carbamoylpropyl)(6-(2-cyanophenyl)-2-{[2-(3-fluorophenyl)ethyl]amino}(3-pyridyl))carboxamide |
| Compound 351 | N-{(1R)-1-carbamoyl-5-[(phenylmethoxy)carbonylamino]pentyl}(6-(2-cyanophenyl)-2-{[2-(3-fluorophenyl)ethyl]amino}(3-pyridyl))carboxamide |
| Compound 352 | N-(4-amino-1-carbamoylbutyl)(6-(2-cyanophenyl)-2-{[2-(3-fluorophenyl)ethyl]amino}(3-pyridyl))carboxamide |
| Compound 353 | N-((1R)-5-amino-1-carbamoylpentyl)(6-(2-cyanophenyl)-2-{[2-(3-fluorophenyl)ethyl]amino}(3-pyridyl))carboxamide |

-continued

| COMPOUND | CHEMICAL NAME |
|---|---|
| 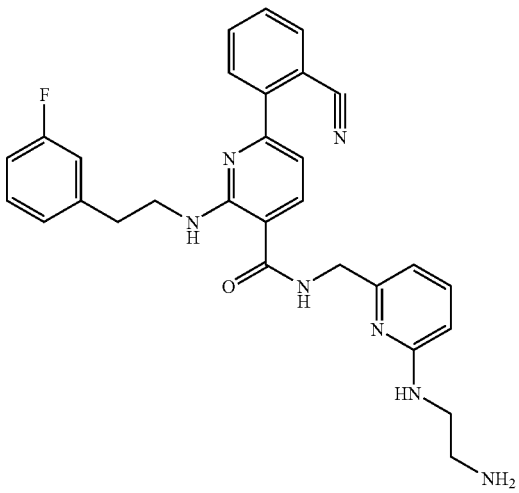<br>Compound 356 | N-({6-[(2-aminoethyl)amino](2-pyridyl)}methyl)(6-(2-cyanophenyl)-2-{[2-(3-fluorophenyl)ethyl]amino}(3-pyridyl))carboxamide |
| 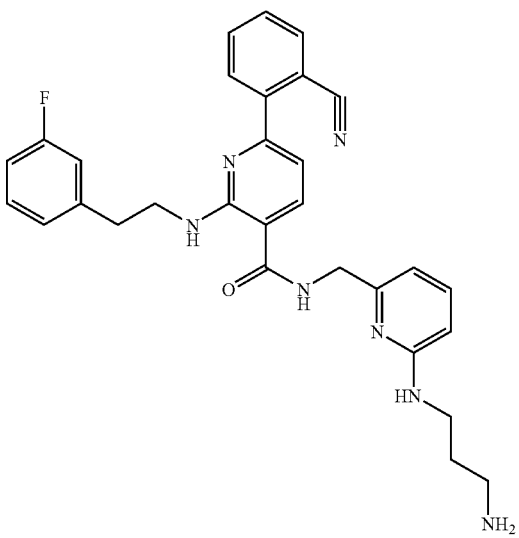<br>Compound 357 | N-({6-[(3-aminopropyl)amino](2-pyridyl)}methyl)(6-(2-cyanophenyl)-2-{[2-(3-fluorophenyl)ethyl]amino}(3-pyridyl))carboxamide |
| 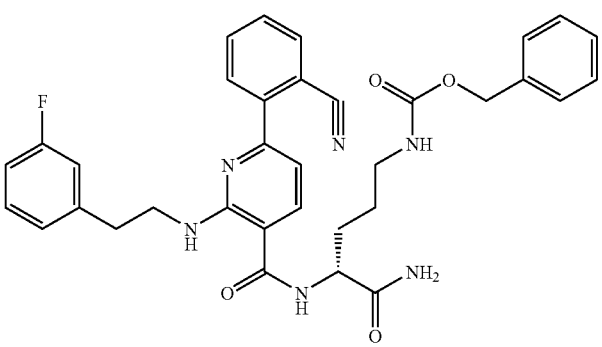<br>Compound 401 | N-{(4R)-4-carbamoyl-4-[(6-(2-cyanophenyl)-2-{[2-(3-fluorophenyl)ethyl]amino}(3-pyridyl))carbonylamino]butyl}(phenylmethoxy)carboxamide |

| COMPOUND | CHEMICAL NAME |
|---|---|
| 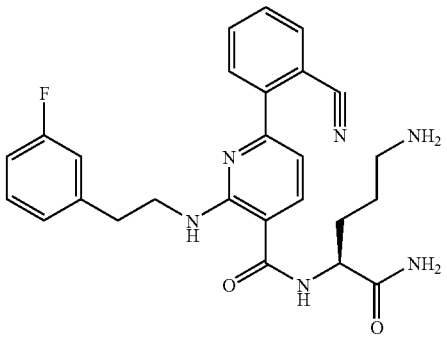
Compound 403 | N-((1S)-4-amino-1-carbamoylbutyl)(6-(2-cyanophenyl)-2-{[2-(3-fluorophenyl)ethyl]amino}(3-pyridyl))carboxamide |
| 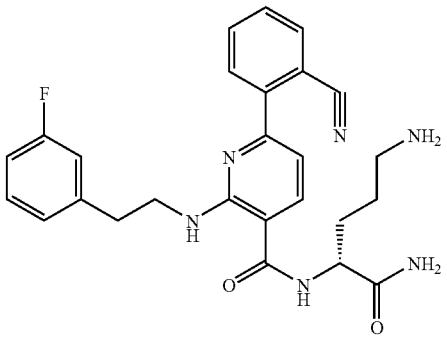
Compound 405 | N-((1R)-4-amino-1-carbamoylbutyl)(6-(2-cyanophenyl)-2-{[2-(3-fluorophenyl)ethyl]amino}(3-pyridyl))carboxamide |
| 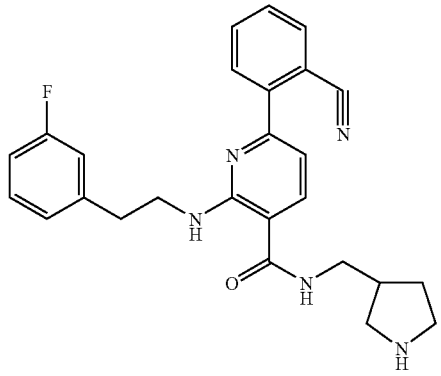
Compound 421 | (6-(2-cyanophenyl)-2-{[2-(3-fluorophenyl)ethyl]amino}(3-pyridyl))-N-(pyrrolidin-3-ylmethyl)carboxamide |

| COMPOUND | CHEMICAL NAME |
|---|---|
| 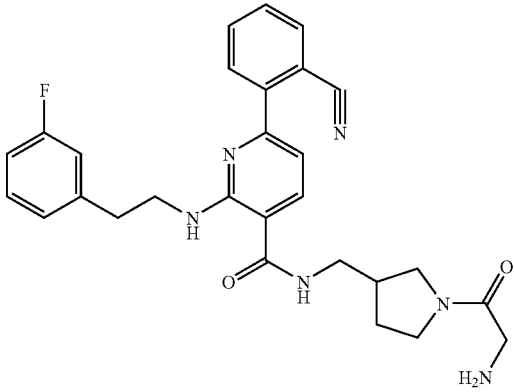
Compound 441 | N-{[1-(2-aminoacetyl)pyrrolidin-3-yl]methyl}(6-(2-cyanophenyl)-2-{[2-(3-fluorophenyl)ethyl]amino}(3-pyridyl))carboxamide |
| 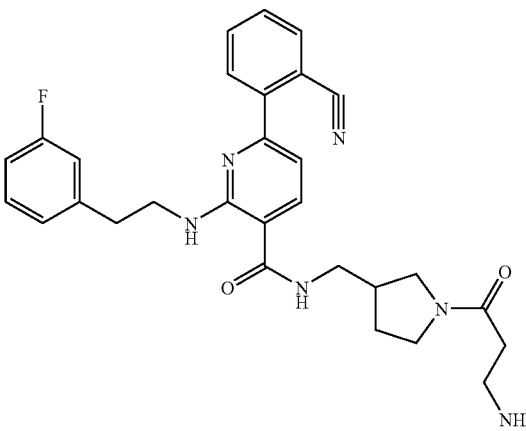
Compound 442 | N-{[1-(3-aminopropanoyl)pyrrolidin-3-yl]methyl}(6-(2-cyanophenyl)-2-{[2-(3-fluorophenyl)ethyl]amino}(3-pyridyl))carboxamide |
| 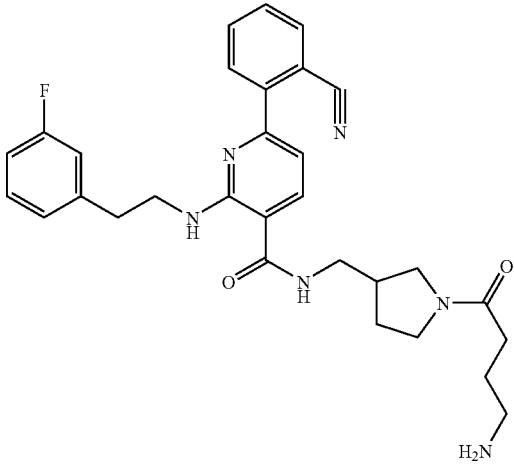
Compound 443 | N-{[1-(4-aminobutanoyl)pyrrolidin-3-yl]methyl}(6-(2-cyanophenyl)-2-{[2-(3-fluorophenyl)ethyl]amino}(3-pyridyl))carboxamide |

-continued
| COMPOUND | CHEMICAL NAME |
|---|---|
| 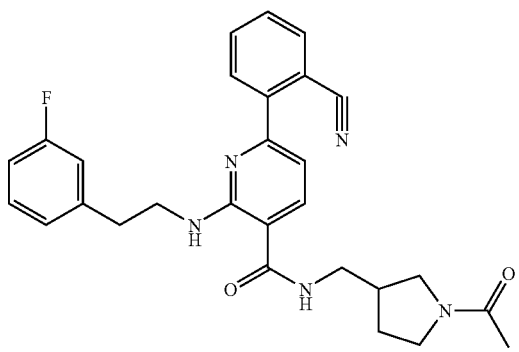
Compound 444 | N-[(1-acetylpyrrolidin-3-yl)methyl](6-(2-cyanophenyl)-2-{[2-(3-fluorophenyl)ethyl]amino}(3-pyridyl))carboxamide |
| 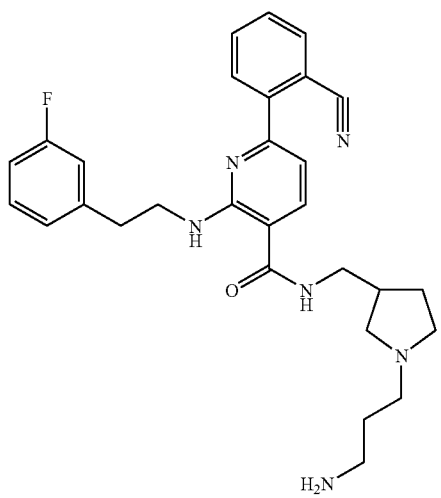
Compound 476 | N-{[1-(3-aminopropyl)pyrrolidin-3-yl]methyl}(6-(2-cyanophenyl)-2-{[2-(3-fluorophenyl)ethyl]amino}(3-pyridyl))carboxamide |
| 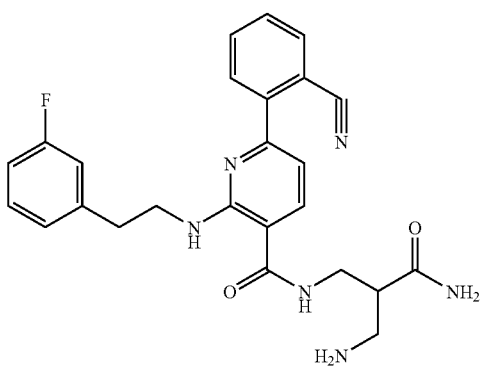
Compound 493 | N-(3-amino-2-carbamoylpropyl)(6-(2-cyanophenyl)-2-{[2-(3-fluorophenyl)ethyl]amino}(3-pyridyl))carboxamide |

| COMPOUND | CHEMICAL NAME |
|---|---|
| 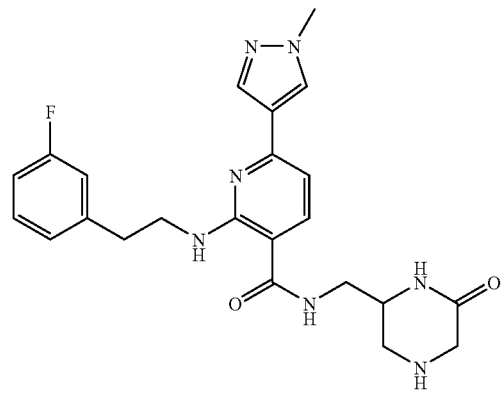<br>Compound 499 | (2-{[2-(3-fluorophenyl)ethyl]amino}-6-(1-methylpyrazol-4-yl)(3-pyridyl))-N-[(6-oxopiperazin-2-yl)methyl]carboxamide |
| 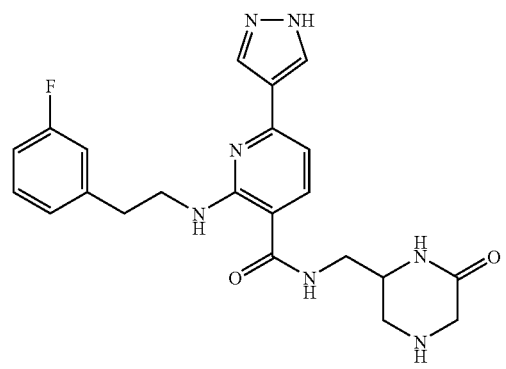<br>Compound 500 | (2-{[2-(3-fluorophenyl)ethyl]amino}-6-pyrazol-4-yl(3-pyridyl))-N-[(6-oxopiperazin-2-yl)methyl]carboxamide |
| 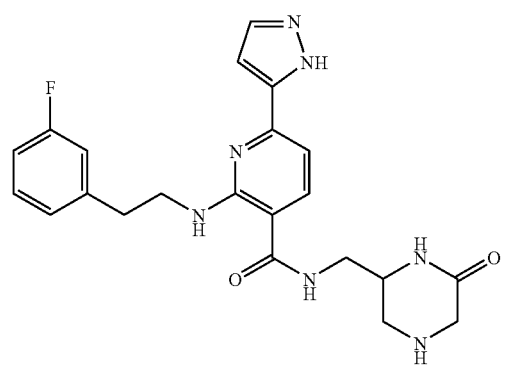<br>Compound 501 | (2-{[2-(3-fluorophenyl)ethyl]amino}-6-pyrazol-5-yl(3-pyridyl))-N-[(6-oxopiperazin-2-yl)methyl]carboxamide |

-continued

| COMPOUND | CHEMICAL NAME |
|---|---|
| 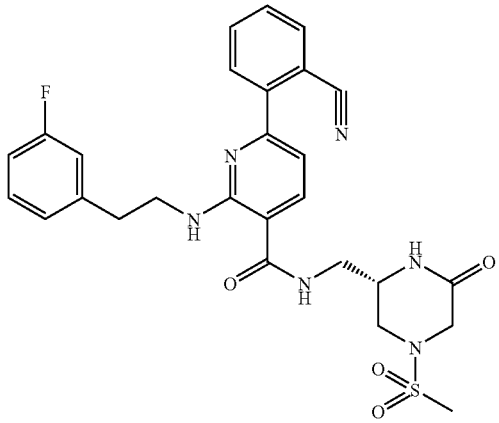<br>Compound 514 | (6-(2-cyanophenyl)-2-{[2-(3-fluorophenyl)ethyl]amino}(3-pyridyl))-N-{[4-(methylsulfonyl)-6-oxopiperazin-2-yl]methyl}carboxamide |
| 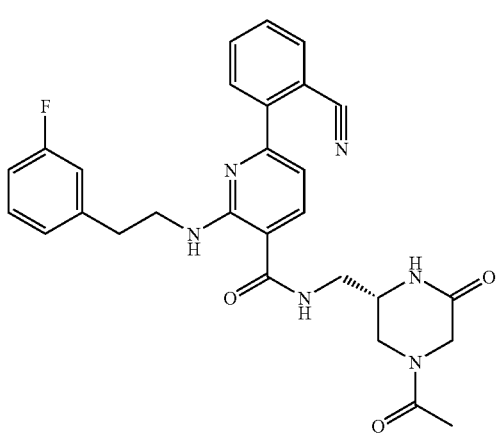<br>Compound 515 | N-[(4-acetyl-6-oxopiperazin-2-yl)methyl](6-(2-cyanophenyl)-2-{[2-(3-fluorophenyl)ethyl]amino}(3-pyridyl))carboxamide |
| 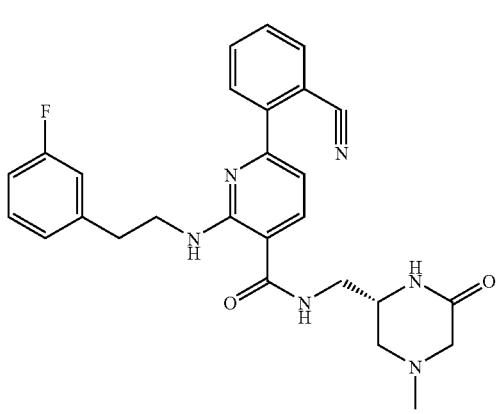<br>Compound 517 | (6-(2-cyanophenyl)-2-{[2-(3-fluorophenyl)ethyl]amino}(3-pyridyl))-N-[(4-methyl-6-oxopiperazin-2-yl)methyl]carboxamide |

| COMPOUND | CHEMICAL NAME |
|---|---|
| Compound 581 | (6-(2-cyanophenyl)-2-{[2-(3-fluorophenyl)ethyl]amino}(3-pyridyl))-N-{2-[(methylamino)carbonylamino]ethyl}carboxamide |
| Compound 582 | N-(2{[(2-aminoethyl)sulfonyl]amino}ethyl)(6-(2-cyanophenyl)-2-{[2-(3-fluorophenyl)ethyl]amino}(3-pyridyl))carboxamide |
| Compound 583 | N-[((2S)pyrrolidin-2-yl)methyl](6-(2-cyanophenyl)-2-{[2-(3-fluorophenyl)ethyl]amino}(3-pyridyl))carboxamide |
| Compound 584 | 2-amino-N-{2-[(6-(2-cyanophenyl)-2-{[2-(3-fluorophenyl)ethyl]amino}(3-pyridyl))carbonylamino]ethyl}acetamide |

-continued

| COMPOUND | CHEMICAL NAME |
|---|---|
| Compound 585 | 3-amino-N-{2-[(6-(2-cyanophenyl)-2-{[2-(3-fluorophenyl)ethyl]amino}(3-pyridyl))carbonylamino]ethyl}propanamide |
| Compound 586 | 4-amino-N-{2-[(6-(2-cyanophenyl)-2-{[2-(3-fluorophenyl)ethyl]amino}(3-pyridyl))carbonylamino]ethyl}butanamide |
| Compound 587 | 2-[(tert-butoxy)carbonylamino]-N-{2-[(6-(2-cyanophenyl)-2-{[2-(3-fluorophenyl)ethyl]amino}(3-pyridyl))carbonylamino]ethyl}-N-methylacetamide |
| Compound 588 | 4-[(tert-butoxy)carbonylamino]-N-{2-[(6-(2-cyanophenyl)-2-{[2-(3-fluorophenyl)ethyl]amino}(3-pyridyl))carbonylamino]ethyl}-N-methylbutanamide |

| COMPOUND | CHEMICAL NAME |
|---|---|
| 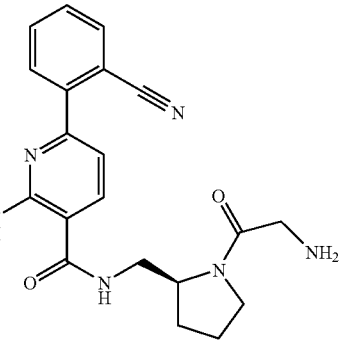
Compound 589 | N-{[(2S)-1-(2-aminoacetyl)pyrrolidin-2-yl]methyl}(6-(2-cyanophenyl)-2-{[2-(3-fluorophenyl)ethyl]amino}(3-pyridyl))carboxamide |
| 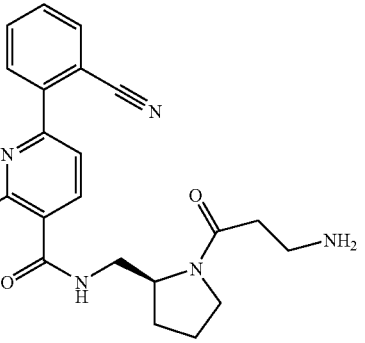
Compound 590 | N-{[(2S)-1-(3-aminopropanoyl)pyrrolidin-2-yl]methyl}(6-(2-cyanophenyl)-2-{[2-(3-fluorophenyl)ethyl]amino}(3-pyridyl))carboxamide |
| 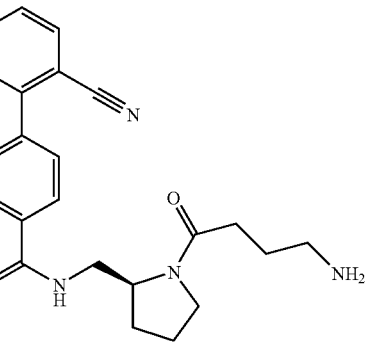
Compound 591 | N-{[(2S)-1-(4-aminobutanoyl)pyrrolidin-2-yl]methyl}(6-(2-cyanophenyl)-2-{[2-(3-fluorophenyl)ethyl]amino}(3-pyridyl))carboxamide |
| 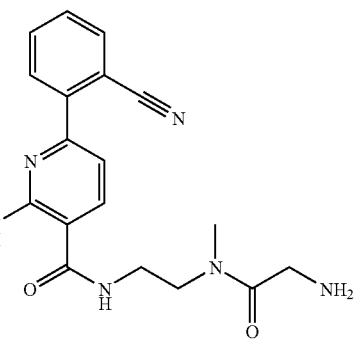
Compound 592 | 2-amino-N-{2-[(6-(2-cyanophenyl)-2-{[2-(3-fluorophenyl)ethyl]amino}(3-pyridyl))carbonylamino]ethyl}-N-methylacetamide |

| COMPOUND | CHEMICAL NAME |
|---|---|
| Compound 593 | 3-amino-N-{2-[(6-(2-cyanophenyl)-2-{[2-(3-fluorophenyl)ethyl]amino}(3-pyridyl))carbonylamino]ethyl}-N-methylpropanamide |
| Compound 594 | 4-amino-N-{2-[(6-(2-cyanophenyl)-2-{[2-(3-fluorophenyl)ethyl]amino}(3-pyridyl))carbonylamino]ethyl}-N-methylbutanamide |
| Compound 595 | (6-(2-cyanophenyl)-2-{[2-(3-fluorophenyl)ethyl]amino}(3-pyridyl))-N-{2-[methyl(methylsulfonyl)amino]ethyl}carboxamide |
| Compound 632 | 3-amino-N-(2-aminoethyl)-2-{[(6-(2-cyanophenyl)-2-{[2-(3-fluorophenyl)ethyl]amino}(3-pyridyl))carbonylamino]methyl}propanamide |

| COMPOUND | CHEMICAL NAME |
|---|---|
| 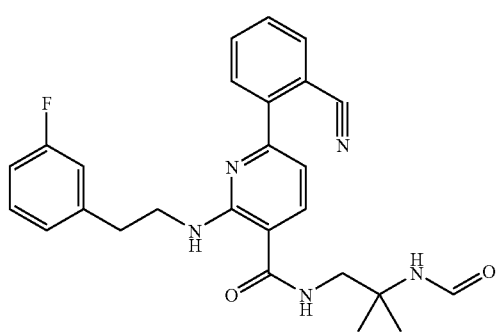
Compound 633 | N-(2-carbonylamino-2-methylpropyl)(6-(2-cyanophenyl)-2-{[2-(3-fluorophenyl)ethyl]amino}(3-pyridyl))carboxamide |
| 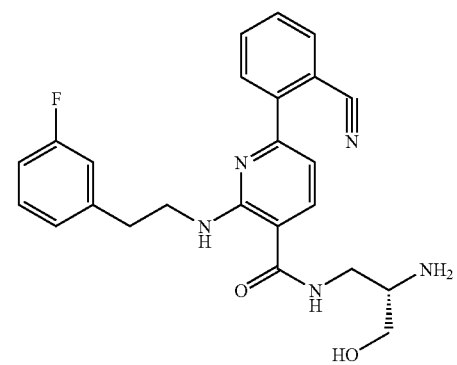
Compound 634 | N-((2S)-2-amino-3-hydroxypropyl)(6-(2-cyanophenyl)-2-{[2-(3-fluorophenyl)ethyl]amino}(3-pyridyl))carboxamide |
| 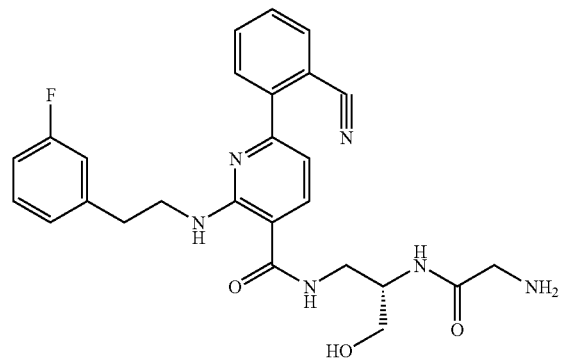
Compound 635 | N-((1S)-1-{[(6-(2-cyanophenyl)-2-{[2-(3-fluorophenyl)ethyl]amino}(3-pyridyl))carbonylamino]methyl}-2-hydroxyethyl)-2-aminoacetamide |

-continued

| COMPOUND | CHEMICAL NAME |
|---|---|
| 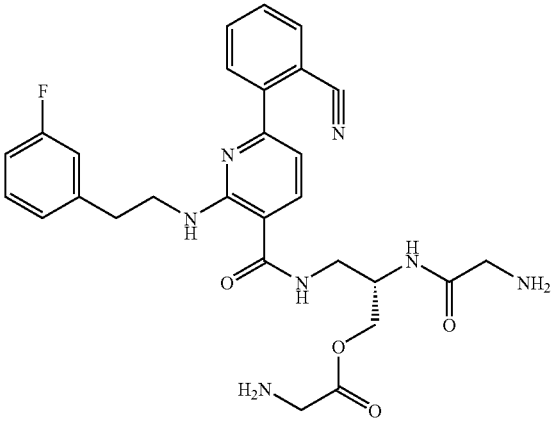<br>Compound 636 | (2S)-2-(2-aminoacetylamino)-3-[(6-(2-cyanophenyl)-2-{[2-(3-fluorophenyl)ethyl]amino}(3-pyridyl))carbonylamino]propyl 2-aminoacetate |
| 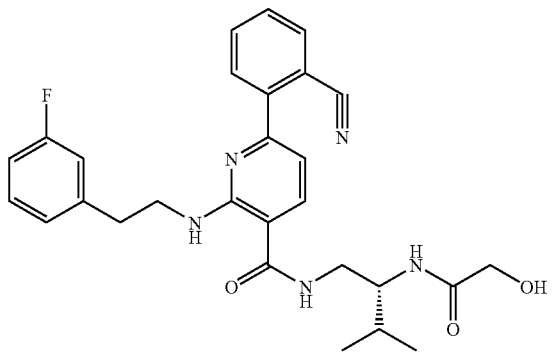<br>Compound 643 | N-((1R)-1-{[(6-(2-cyanophenyl)-2-{[2-(3-fluorophenyl)ethyl]amino}(3-pyridyl))carbonylamino]methyl}-2-methylpropyl)-2-hydroxyacetamide |
| 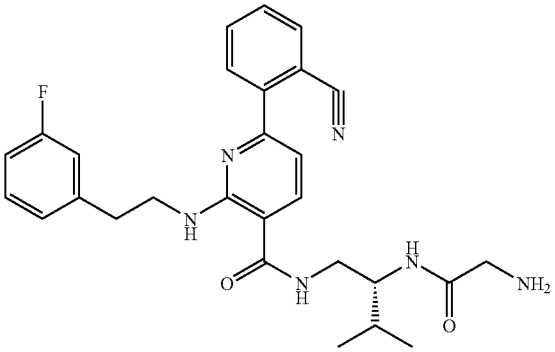<br>Compound 644 | N-((1R)-1-{[(6-(2-cyanophenyl)-2-{[2-(3-fluorophenyl)ethyl]amino}(3-pyridyl))carbonylamino]methyl}-2-methylpropyl)-2-aminoacetamide |

| COMPOUND | CHEMICAL NAME |
|---|---|
| 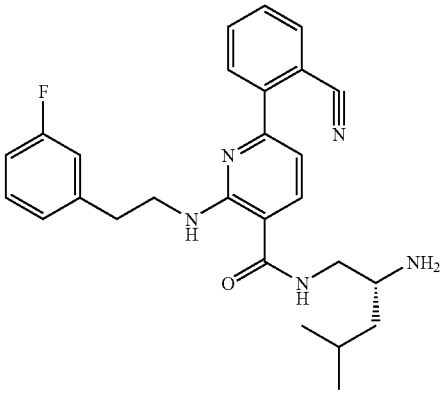<br>Compound 645 | N-((2R)-2-amino-4-methylpentyl)(6-(2-cyanophenyl)-2-{[2-(3-fluorophenyl)ethyl]amino}(3-pyridyl))carboxamide |
| 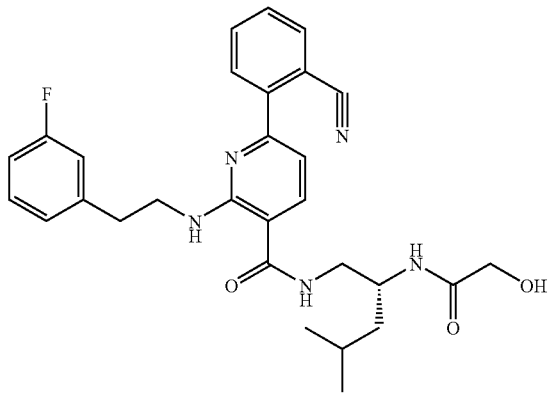<br>Compound 665 | N-((1R)-1-{[(6-(2-cyanophenyl)-2-{[2-(3-fluorophenyl)ethyl]amino}(3-pyridyl))carbonylamino]methyl}-3-methylbutyl)-2-hydroxyacetamide |
| 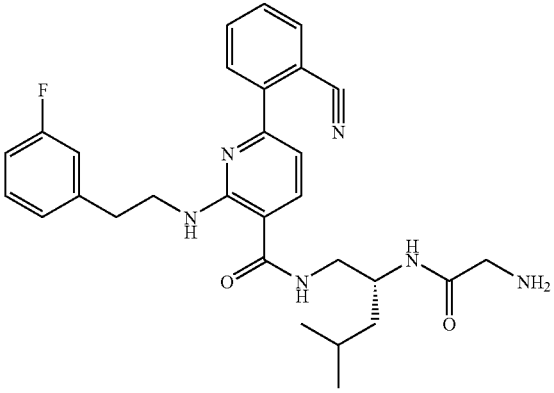<br>Compound 666 | N-((1R)-1-{[(6-(2-cyanophenyl)-2-{[2-(3-fluorophenyl)ethyl]amino}(3-pyridyl))carbonylamino]methyl}-3-methylbutyl)-2-aminoacetamide |

-continued

| COMPOUND | CHEMICAL NAME |
|---|---|
| 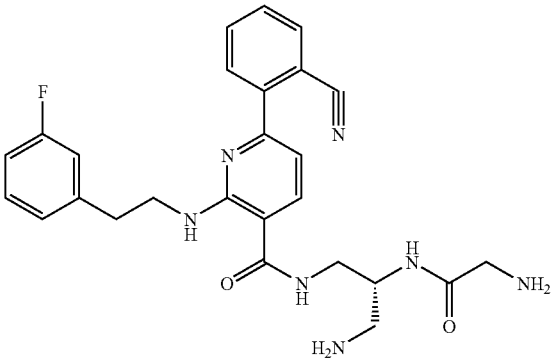<br>Compound 692 | N-((1R)-2-amino-1-{[(6-(2-cyanophenyl)-2-{[2-(3-fluorophenyl)ethyl]amino}(3-pyridyl))carbonylamino]methyl}ethyl)-2-aminoacetamide |
| 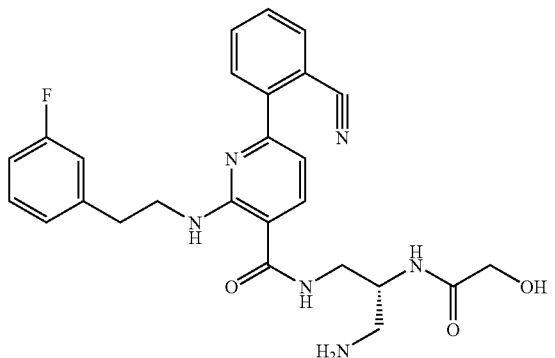<br>Compound 693 | N-((1R)-2-amino-1-{[(6-(2-cyanophenyl)-2-{[2-(3-fluorophenyl)ethyl]amino}(3-pyridyl))carbonylamino]methyl}ethyl)-2-hydroxyacetamide |
| 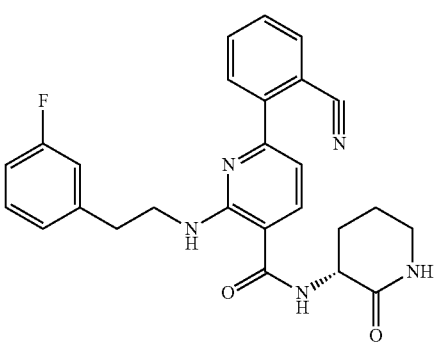<br>Compound 406 | N-((3R)-2-oxo(3-piperidyl))(6-(2-cyanophenyl)-2-{[2-(3-fluorophenyl)ethyl]amino}(3-pyridyl))carboxamide |
| 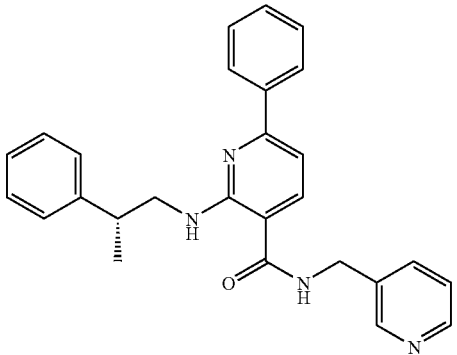<br>Compound 103 | {2-[((2R)-2-phenylpropyl)amino]-6-phenyl(3-pyridyl)}-N-(3-pyridylmethyl)carboxamide |

-continued

| COMPOUND | CHEMICAL NAME |
|---|---|
| 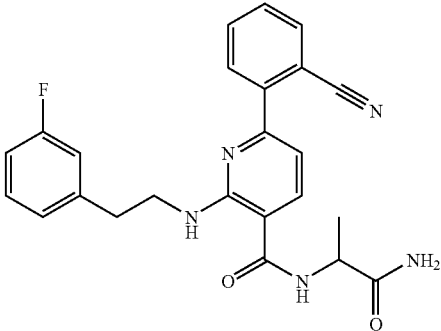<br>Compound 129 | N-(carbamoylethyl)(6-(2-cyanophenyl)-2-{[2-(3-fluorophenyl)ethyl]amino}(3-pyridyl))carboxamide |
| 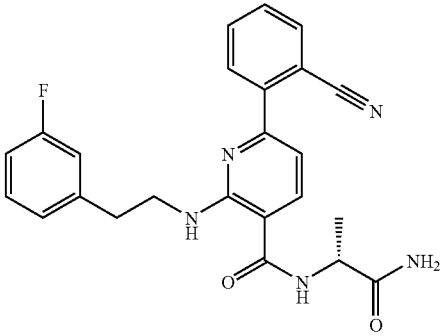<br>Compound 130 | N-((1R)-1-carbamoylethyl)(6-(2-cyanophenyl)-2-{[2-(3-fluorophenyl)ethyl]amino}(3-pyridyl))carboxamide |
| 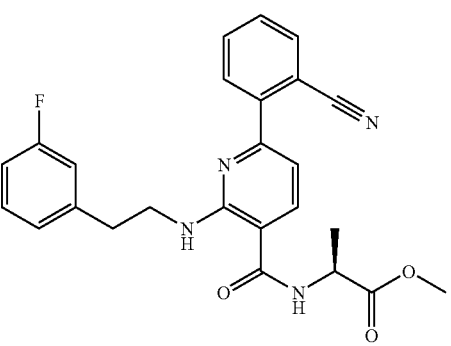<br>Compound 131 | methyl (2S)-2-[(6-(2-cyanophenyl)-2-{[2-(3-fluorophenyl)ethyl]amino}(3-pyridyl))carbonylamino]propanoate |
| 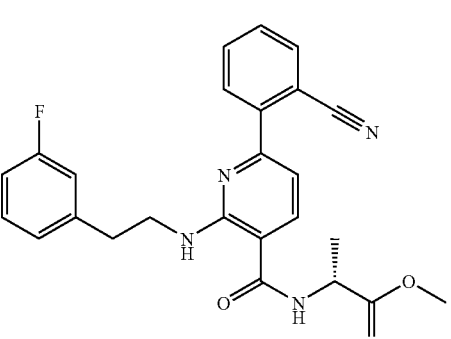<br>Compound 132 | methyl (2R)-2-[(6-(2-cyanophenyl)-2-{[2-(3-fluorophenyl)ethyl]amino}(3-pyridyl))carbonylamino]propanoate |

-continued

| COMPOUND | CHEMICAL NAME |
| --- | --- |
| Compound 133 | methyl 2-[(6-(2-cyanophenyl)-2-{[2-(3-fluorophenyl)ethyl]amino}-3-pyridyl)carbonylamino]acetate |
| Compound 134 | (6-(2-cyanophenyl)-2-{[2-(3-fluorophenyl)ethyl]amino}(3-pyridyl))-N-(2-hydroxyethyl)carboxamide |
| Compound 135 | (6-(2-cyanophenyl)-2-{[2-(3-fluorophenyl)ethyl]amino}(3-pyridyl))-N-(2-methoxyethyl)carboxamide |
| Compound 136 | N-[2-(dimethylamino)ethyl](6-(2-cyanophenyl)-2-{[2-(3-fluorophenyl)ethyl]amino}(3-pyridyl))carboxamide |

| COMPOUND | CHEMICAL NAME |
|---|---|
| 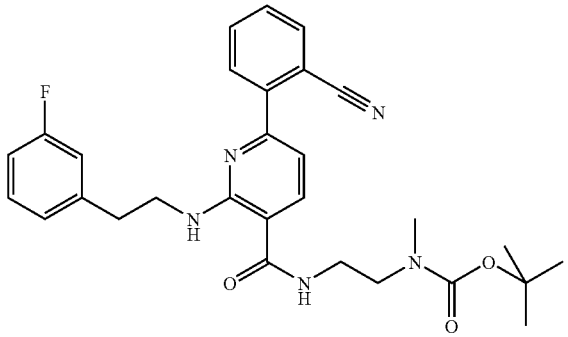<br>Compound 137 | N-{2-[(tert-butoxy)-N-methylcarbonylamino]ethyl}(6-(2-cyanophenyl)-2-{[2-(3-fluorophenyl)ethyl]amino}(3-pyridyl))carboxamide |
| 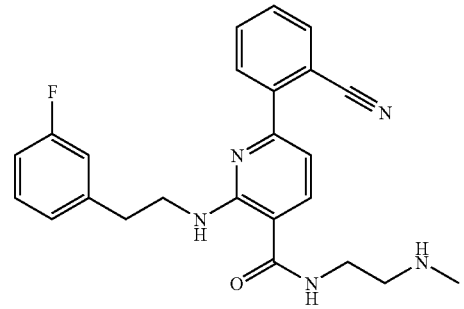<br>Compound 138 | (6-(2-cyanophenyl)-2-{[2-(3-fluorophenyl)ethyl]amino}(3-pyridyl))-N-[2-(methylamino)ethyl]carboxamide |
| 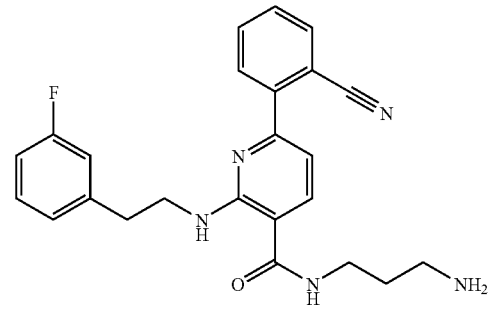<br>Compound 139 | N-(3-aminopropyl)(6-(2-cyanophenyl)-2-{[2-(3-fluorophenyl)ethyl]amino}(3-pyridyl))carboxamide |
| 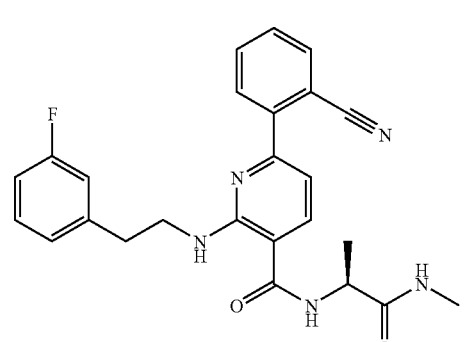<br>Compound 140 | (2S)-2-[(6-(2-cyanophenyl)-2-{[2-(3-fluorophenyl)ethyl]amino}(3-pyridyl))carbonylamino]-N-methylpropanamide |

| COMPOUND | CHEMICAL NAME |
|---|---|
| Compound 292 | (2R)-2-[(6-(2-cyanophenyl)-2-{[2-(3-fluorophenyl)ethyl]amino}(3-pyridyl))carbonylamino]-N-methylpropanamide |
| Compound 291 | N-{2-[(6-(2-cyanophenyl)-2-{[2-(3-fluorophenyl)ethyl]amino}-3-pyridyl)carbonylamino]ethyl}acetamide |
| Compound 143 | (6-(2-cyanophenyl)-2-{[2-(3-fluorophenyl)ethyl]amino}(3-pyridyl))-N-[2-(methoxycarbonylamino)ethyl]carboxamide |
| Compound 144 | (6-(2-cyanophenyl)-2-{[2-(3-fluorophenyl)ethyl]amino}(3-pyridyl))-N-{2-[(methylsulfonyl)amino]ethyl}carboxamide |

-continued

| COMPOUND | CHEMICAL NAME |
|---|---|
| 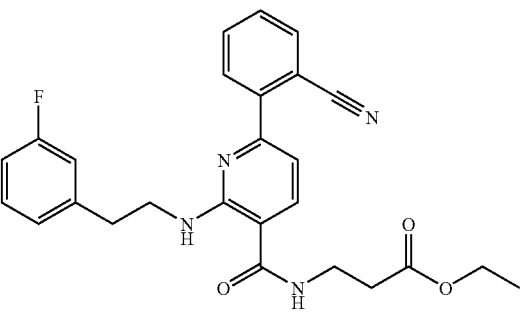<br>Compound 145 | ethyl 3-[(6-(2-cyanophenyl)-2-{[2-(3-fluorophenyl)ethyl]amino}-3-pyridyl)carbonylamino]propanoate |
| 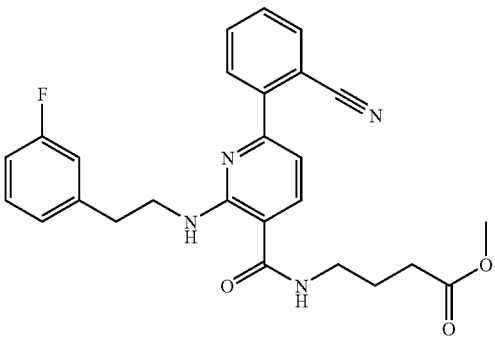<br>Compound 287 | methyl 4-[(6-(2-cyanophenyl)-2-{[2-(3-fluorophenyl)ethyl]amino}-3-pyridyl)carbonylamino]butanoate |
| 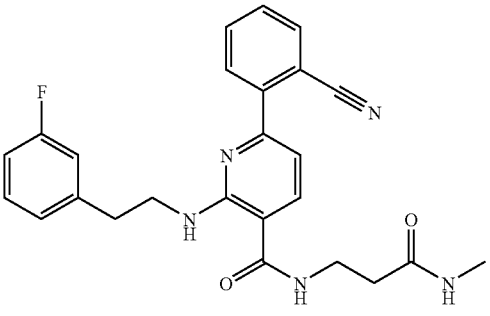<br>Compound 286 | 3-[(6-(2-cyanophenyl)-2-{[2-(3-fluorophenyl)ethyl]amino}(3-pyridyl))carbonylamino]-N-methylpropanamide |
| 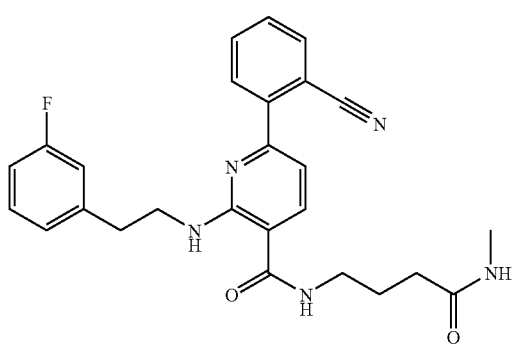<br>Compound 148 | 4-[(6-(2-cyanophenyl)-2-{[2-(3-fluorophenyl)ethyl]amino}(3-pyridyl))carbonylamino]-N-methylbutanamide |

| COMPOUND | CHEMICAL NAME |
|---|---|
| Compound 149 | N-(3-carbamoylpropyl)(6-(2-cyanophenyl)-2-{[2-(3-fluorophenyl)ethyl]amino}(3-pyridyl))carboxamide |
| Compound 283 | 4-[(6-(2-cyanophenyl)-2-{[2-(3-fluorophenyl)ethyl]amino}-3-pyridyl)carbonylamino]butanoic acid |
| Compound 151 | N-(2-aminoethyl)(6-(2-cyanophenyl)-2-{[2-(3-fluorophenyl)ethyl]amino}(3-pyridyl))carboxamide |
| Compound 152 | (6-(2-cyanophenyl)-2-{[2-(3-fluorophenyl)ethyl]amino}(3-pyridyl))-N-[(4-fluorophenyl)methyl]carboxamide |

| COMPOUND | CHEMICAL NAME |
|---|---|
| Compound 153 | (6-(2-cyanophenyl)-2-{[2-(3-fluorophenyl)ethyl]amino}(3-pyridyl))-N-[(4-cyanophenyl)methyl]carboxamide |
| Compound 279 | N-[(3,4-difluorophenyl)methyl](6-(2-cyanophenyl)-2-{[2-(3-fluorophenyl)ethyl]amino}(3-pyridyl))carboxamide |
| Compound 155 | N-((1S)-1-carbamoyl-2-hydroxyethyl)(6-(2-cyanophenyl)-2-{[2-(3-fluorophenyl)ethyl]amino}(3-pyridyl))carboxamide |
| Compound 167 | (6-(2-cyanophenyl)-2-{[2-(3-fluorophenyl)ethyl]amino}(3-pyridyl))-N-(3-hydroxypropyl)carboxamide |

| COMPOUND | CHEMICAL NAME |
|---|---|
| Compound 168 | (6-(2-cyanophenyl)-2-{[2-(3-fluorophenyl)ethyl]amino}(3-pyridyl))-N-(3-methyoxypropyl)carboxamide |
| Compound 169 | methyl (2S)-2-[(6-(2-cyanophenyl)-2-{[2-(3-fluorophenyl)ethyl]amino}(3-pyridyl))carbonylamino]-3-hydroxypropanoate |
| Compound 170 | methyl (2R)-2-[(6-(2-cyanophenyl)-2-{[2-(3-fluorophenyl)ethyl]amino}(3-pyridyl))carbonylamino]-3-hydroxypropanoate |
| Compound 262 | (2S)-2-[(6-(2-cyanophenyl)-2-{[2-(3-fluorophenyl)ethyl]amino}(3-pyridyl))carbonylamino]-3-hydroxy-N-methylpropanamide |

-continued

| COMPOUND | CHEMICAL NAME |
|---|---|
| Compound 716 | (2R)-2-[(6-(2-cyanophenyl)-2-{[2-(3-fluorophenyl)ethyl]amino}(3-pyridyl))carbonylamino]-3-hydroxy-N-methylpropanamide |
| Compound 173 | (6-(2-cyanophenyl)-2-{[2-(3-fluorophenyl)ethyl]amino}(3-pyridyl))-N-(2-pyridylmethyl)carboxamide |
| Compound 174 | (6-(2-cyanophenyl)-2-{[2-(3-fluorophenyl)ethyl]amino}(3-pyridyl))-N-[(4-methylphenyl)methyl]carboxamide |
| Compound 175 | (6-(2-cyanophenyl)-2-{[2-(3-fluorophenyl)ethyl]amino}(3-pyridyl))-N-[(6-methyl(3-pyridyl))methyl]carboxamide |

-continued

| COMPOUND | CHEMICAL NAME |
|---|---|
| Compound 176 | (6-(2-cyanophenyl)-2-{[2-(3-fluorophenyl)ethyl]amino}(3-pyridyl))-N-[(6-methyl(2-pyridyl))methyl]carboxamide |
| Compound 177 | (6-(2-cyanophenyl)-2-{[2-(3-fluorophenyl)ethyl]amino}(3-pyridyl))-N-(2-(2-pyridyl)ethyl)carboxamide |
| Compound 178 | (6-(2-cyanophenyl)-2-{[2-(3-fluorophenyl)ethyl]amino}(3-pyridyl))-N-(2-(3-pyridyl)ethyl)carboxamide |
| Compound 186 | N-[(6-amino(3-pyridyl))methyl](6-(2-cyanophenyl)-2-{[2-(3-fluorophenyl)ethyl]amino}(3-pyridyl))carboxamide |

| COMPOUND | CHEMICAL NAME |
|---|---|
| 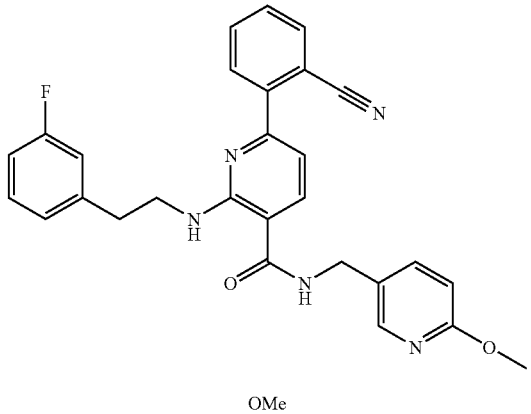 | (6-(2-cyanophenyl)-2-{[2-(3-fluorophenyl)ethyl]amino}(3-pyridyl))-N-[(6-methyoxy(3-pyridyl))methyl]carboxamide |
| 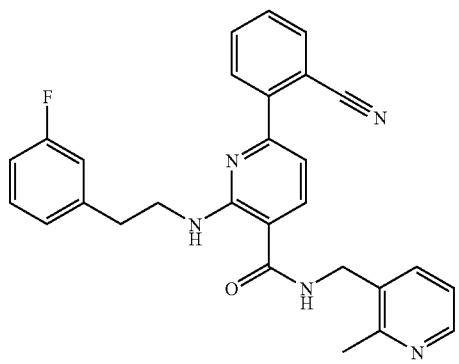<br>Compound 187 | (6-(2-cyanophenyl)-2-{[2-(3-fluorophenyl)ethyl]amino}(3-pyridyl))-N-[(2-methyl(3-pyridyl))methyl]carboxamide |
| 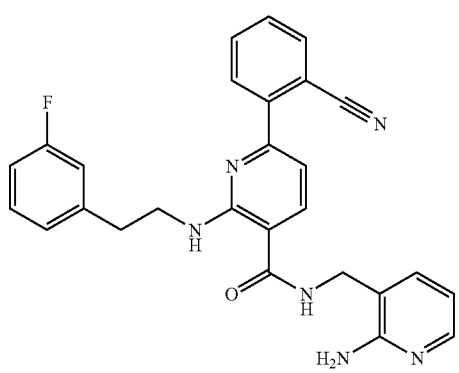<br>Compound 188 | N-[(2-amino(3-pyridyl))methyl](6-(2-cyanophenyl)-2-{[2-(3-fluorophenyl)ethyl]amino}(3-pyridyl))carboxamide |

| COMPOUND | CHEMICAL NAME |
|---|---|
| 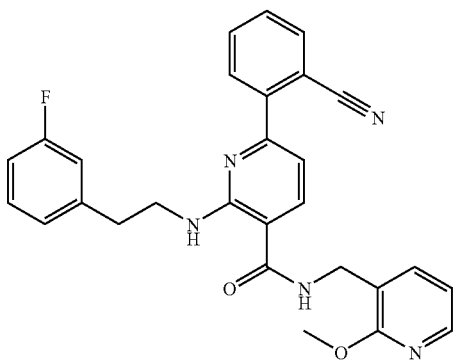
Compound 189 | (6-(2-cyanophenyl)-2-{[2-(3-fluorophenyl)ethyl]amino}(3-pyridyl))-N-[(2-methoxy(3-pyridyl))methyl]carboxamide |
| 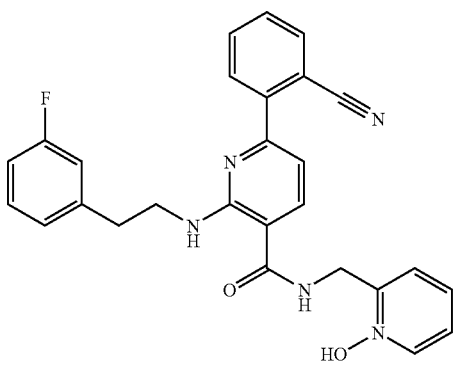
Compound 200 | (6-(2-cyanophenyl)-2-{[2-(3-fluorophenyl)ethyl]amino}(3-pyridyl))-N-[(1-hydroxy(2-pyridyl))methyl]carboxamide |
| 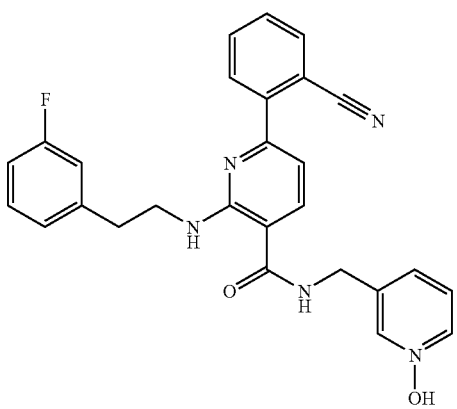
Compound 201 | (6-(2-cyanophenyl)-2-{[2-(3-fluorophenyl)ethyl]amino}(3-pyridyl))-N-[(1-hydroxy(3-pyridyl))methyl]carboxamide |

| COMPOUND | CHEMICAL NAME |
|---|---|
| 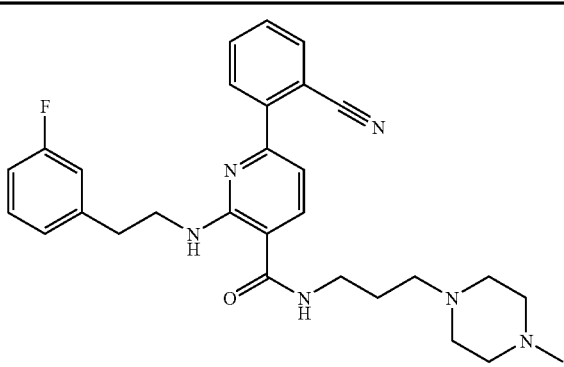
Compound 202 | (6-(2-cyanophenyl)-2-{[2-(3-fluorophenyl)ethyl]amino}(3-pyridyl))-N-[3-(4-methylpiperazinyl)propyl]carboxamide |
| 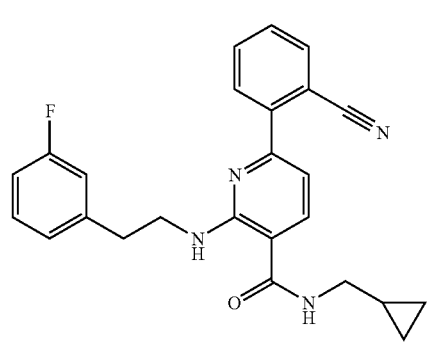
Compound 203 | (6-(2-cyanophenyl)-2-{[2-(3-fluorophenyl)ethyl]amino}(3-pyridyl))-N-(cyclopropylmethyl)carboxamide |
| 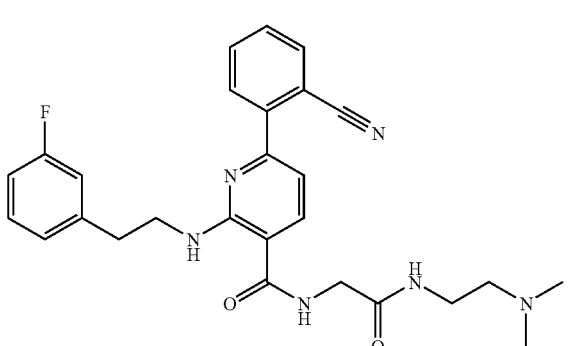
Compound 219 | N-[2-(dimethylamino)ethyl]-2-[(6-(2-cyanophenyl)-2-{[2-(3-fluorophenyl)ethyl]amino}(3-pyridyl))carbonylamino]acetamide |
| 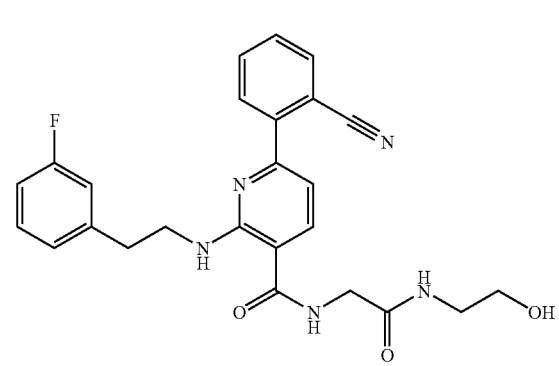
Compound 220 | 2-[(6-(2-cyanophenyl)-2-{[2-(3-fluorophenyl)ethyl]amino}(3-pyridyl))carbonylamino]-N-(2-hydroxyethyl)acetamide |

| COMPOUND | CHEMICAL NAME |
|---|---|
| Compound 221 | N-(2-carbamoylethyl)-2-[(6-(2-cyanophenyl)-2-{[2-(3-fluorophenyl)ethyl]amino}(3-pyridyl))carbonylamino]acetamide |
| Compound 222 | 3-{2-[(6-(2-cyanophenyl)-2-{[2-(3-fluorophenyl)ethyl]amino}-3-pyridyl)carbonylamino]acetylamino}propanoic acid |
| Compound 223 | N-{3-[(tert-butoxy)carbonylamino]propyl}-2-[(6-(2-cyanophenyl)-2-{[2-(3-fluorophenyl)ethyl]amino}(3-pyridyl))carbonylamino]acetamide |
| Compound 224 | N-[3-(dimethylamino)propyl]-2-[(6-(2-cyanophenyl)-2-{[2-(3-fluorophenyl)ethyl]amino}(3-pyridyl))carbonylamino]acetamide |

| COMPOUND | CHEMICAL NAME |
|---|---|
| Compound 225 | 2-[(6-(2-cyanophenyl)-2-{[2-(3-fluorophenyl)ethyl]amino}(3-pyridyl))carbonylamino]-N-(3-hydroxypropyl)acetamide |
| Compound 232 | N-{2-[(tert-butoxy)-N-methylcarbonylamino]ethyl}-2-[(6-(2-cyanophenyl)-2-{[2-(3-fluorophenyl)ethyl]amino}(3-pyridyl))carbonylamino]acetamide |
| Compound 233 | 2-[(6-(2-cyanophenyl)-2-{[2-(3-fluorophenyl)ethyl]amino}(3-pyridyl))carbonylamino]-N-[2-(methylamino)ethyl]acetamide |
| Compound 234 | methyl (2S)-3-amino-2-[(6-(2-cyanophenyl)-2-{[2-(3-fluorophenyl)ethyl]amino}(3-pyridyl))carbonylamino]propanoate |

| COMPOUND | CHEMICAL NAME |
|---|---|
| Compound 235 | N-((1S)-2-amino-1-carbamoylethyl)(6-(2-cyanophenyl)-2-{[2-(3-fluorophenyl)ethyl]amino}(3-pyridyl))carboxamide |
| Compound 236 | (2S)-3-[(tert-butoxy)carbonylamino]-2-[(6-(2-cyanophenyl)-2-{[2-(3-fluorophenyl)ethyl]amino}(3-pyridyl))carbonylamino]propanoic acid |
| Compound 237 | (2S)-3-[(tert-butoxy)carbonylamino]-2-[(6-(2-cyanophenyl)-2-{[2-(3-fluorophenyl)ethyl]amino}(3-pyridyl))carbonylamino]-N-methylpropanamide |
| Compound 238 | (2S)-3-amino-2-[(6-(2-cyanophenyl)-2-{[2-(3-fluorophenyl)ethyl]amino}(3-pyridyl))carbonylamino]-N-methylpropanamide |

| COMPOUND | CHEMICAL NAME |
|---|---|
| Compound 239 | (2S)-3-amino-2-[(6-(2-cyanophenyl)-2-{[2-(3-fluorophenyl)ethyl]amino}(3-pyridyl))carbonylamino]-N,N-dimethylpropanamide |
| Compound 244 | (2S)-3-amino-2-[(6-(2-cyanophenyl)-2-{[2-(3-fluorophenyl)ethyl]amino}(3-pyridyl))carbonylamino]propanoic acid |
| Compound 245 | methyl (2S)-2-amino-3-[(6-(2-cyanophenyl)-2-{[2-(3-fluorophenyl)ethyl]amino}(3-pyridyl))carbonylamino]propanoate |
| Compound 246 | methyl (2S)-2-(acetylamino)-3-[(6-(2-cyanophenyl)-2-{[2-(3-fluorophenyl)ethyl]amino}(3-pyridyl))carbonylamino]propanoate |

| COMPOUND | CHEMICAL NAME |
|---|---|
| 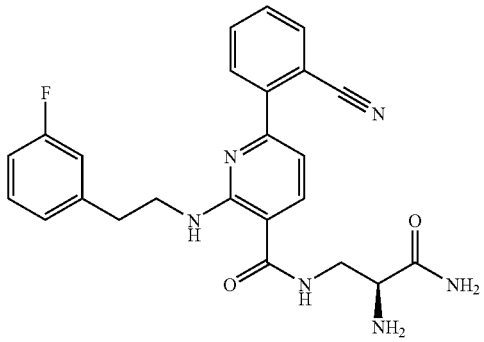
Compound 247 | N-((2S)-2-amino-2-carbamoylethyl)(6-(2-cyanophenyl)-2-{[2-(3-fluorophenyl)ethyl]amino}(3-pyridyl))carboxamide |
| 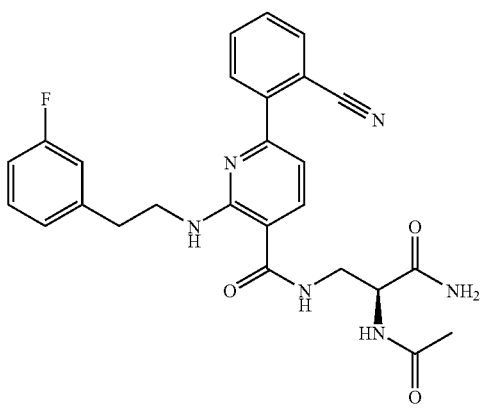
Compound 248 | N-{(1S)-1-carbamoyl-2-[(6-(2-cyanophenyl)-2-{[2-(3-fluorophenyl)ethyl]amino}(3-pyridyl))carbonylamino]ethyl}acetamide |
| 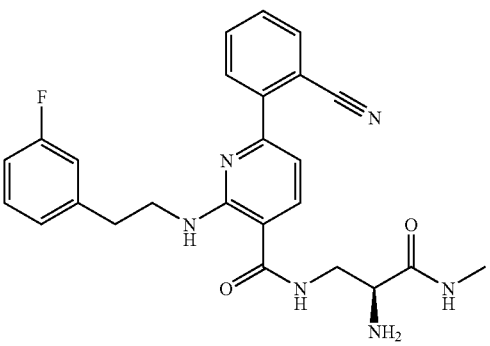
Compound 249 | (2S)-2-amino-3-[(6-(2-cyanophenyl)-2-{[2-(3-fluorophenyl)ethyl]amino}(3-pyridyl))carbonylamino]-N-methylpropanamide |

-continued

| COMPOUND | CHEMICAL NAME |
|---|---|
| Compound 250 | (2S)-2-amino-3-[(6-(2-cyanophenyl)-2-{[2-(3-fluorophenyl)ethyl]amino}(3-pyridyl))carbonylamino]-N,N-dimethylpropanamide |
| Compound 251 | (2S)-2-amino-3-[(6-(2-cyanophenyl)-2-{[2-(3-fluorophenyl)ethyl]amino}(3-pyridyl))carbonylamino]propanoic acid |
| Compound 252 | (2S)-2-(acetylamino)-3-[(6-(2-cyanophenyl)-2-{[2-(3-fluorophenyl)ethyl]amino}(3-pyridyl))carbonylamino]-N-methylpropanamide |
| Compound 255 | methyl (2R)-3-amino-2-[(6-(2-cyanophenyl)-2-{[2-(3-fluorophenyl)ethyl]amino}(3-pyridyl))carbonylamino]propanoate |

-continued

| COMPOUND | CHEMICAL NAME |
|---|---|
| Compound 256 | N-((1R)-2-amino-1-carbamoylethyl)(6-(2-cyanophenyl)-2-{[2-(3-fluorophenyl)ethyl]amino}(3-pyridyl))carboxamide |
| Compound 257 | (2R)-3-amino-2-[(6-(2-cyanophenyl)-2-{[2-(3-fluorophenyl)ethyl]amino}(3-pyridyl))carbonylamino]-N-methylpropanamide |
| Compound 258 | methyl (2R)-2-amino-3-[(6-(2-cyanophenyl)-2-{[2-(3-fluorophenyl)ethyl]amino}(3-pyridyl))carbonylamino]propanoate |
| Compound 259 | N-((2R)-2-amino-2-carbamoylethyl)(6-(2-cyanophenyl)-2-{[2-(3-fluorophenyl)ethyl]amino}(3-pyridyl))carboxamide |

-continued

| COMPOUND | CHEMICAL NAME |
|---|---|
| 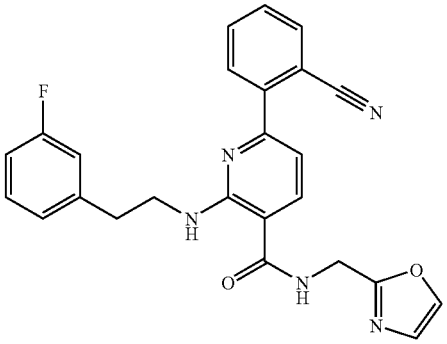<br>Compound 260 | (6-(2-cyanophenyl)-2-{[2-(3-fluorophenyl)ethyl]amino}(3-pyridyl))-N-(1,3-oxazol-2-ylmethyl)carboxamide |
| 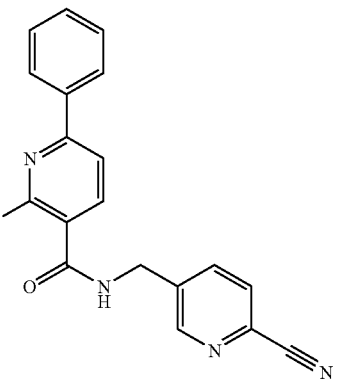<br>Compound 277 | N-[(6-cyano(3-pyridyl))methyl](2-{[2-(3-fluorophenyl)ethyl]amino}-6-phenyl(3-pyridyl))carboxamide |
| 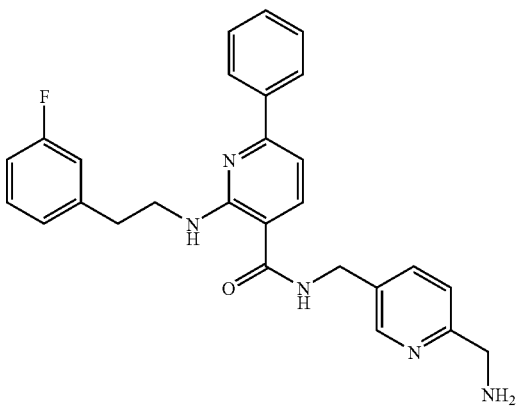<br>Compound 278 | N-{[6-(aminomethyl)(3-pyridyl)]methyl}(2-{[2-(3-fluorophenyl)ethyl]amino}-6-phenyl(3-pyridyl))carboxamide |
| 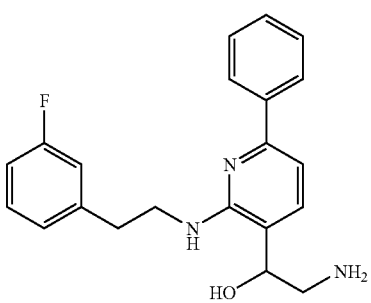<br>Compound 288 | 2-amino-1-(2-{[2-(3-fluorophenyl)ethyl]amino}-6-phenyl(3-pyridyl))ethan-1-ol |

| COMPOUND | CHEMICAL NAME |
|---|---|
| 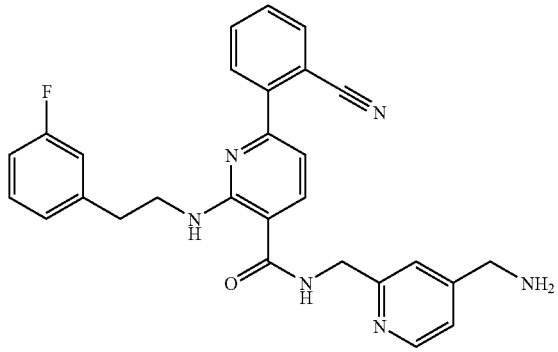
Compound 293 | N-{[4-(aminomethyl)(2-pyridyl)]methyl}(6-(2-cyanophenyl)-2-{[2-(3-fluorophenyl)ethyl]amino}(3-pyridyl))carboxamide |
| 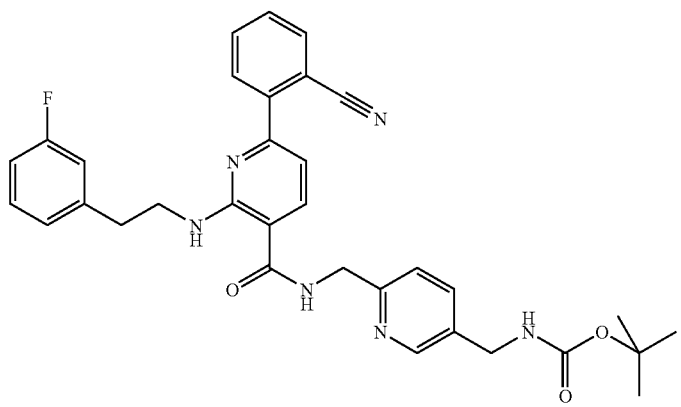
Compound 297 | N-[(5-{[(tert-butoxy)carbonylamino]methyl}(2-pyridyl))methyl](6-(2-cyanophenyl)-2-{[2-(3-fluorophenyl)ethyl]amino}(3-pyridyl))carboxamide |
| 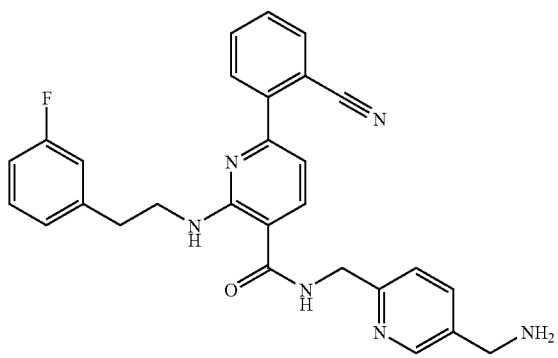
Compound 298 | N-{[5-(aminomethyl)(2-pyridyl)]methyl}(6-(2-cyanophenyl)-2-{[2-(3-fluorophenyl)ethyl]amino}(3-pyridyl))carboxamide |

| COMPOUND | CHEMICAL NAME |
| --- | --- |
| Compound 299 | N-{[4-(aminomethyl)(2-pyridyl)]methyl}(2-{[2-(3-fluorophenyl)ethyl]amino}-6-phenyl(3-pyridyl))carboxamide |
| Compound 300 | N-{[5-(aminomethyl)(2-pyridyl)]methyl}(2-{[2-(3-fluorophenyl)ethyl]amino}-6-phenyl(3-pyridyl))carboxamide |
| Compound 301 | (6-(2-cyanophenyl)-2-{[2-(3-fluorophenyl)ethyl]amino}(3-pyridyl))-N-(isoxazol-5-ylmethyl)carboxamide |
| Compound 302 | 2-{[2-(2-{[2-(3-fluorophenyl)ethyl]amino}-6-phenyl(3-pyridyl))-2-hydroxyethyl]amino}acetamide |

| COMPOUND | CHEMICAL NAME |
|---|---|
| 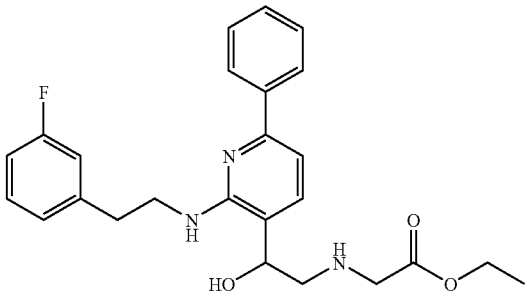<br>Compound 305 | ethyl 2-{[2-(2-{[2-(3-fluorophenyl)ethyl]amino}-6-phenyl(3-pyridyl))-2-hydroxyethyl]amino}acetate |
| 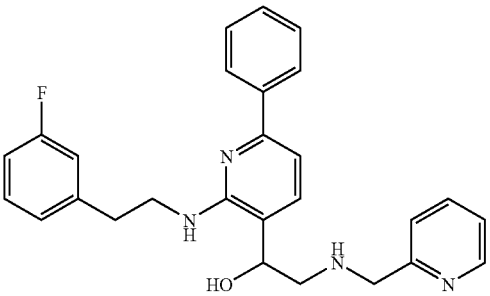<br>Compound 313 | 1-(2-{[2-(3-fluorophenyl)ethyl]amino}-6-phenyl(3-pyridyl))-2-[(2-pyridylmethyl)amino]ethan-1-ol |
| 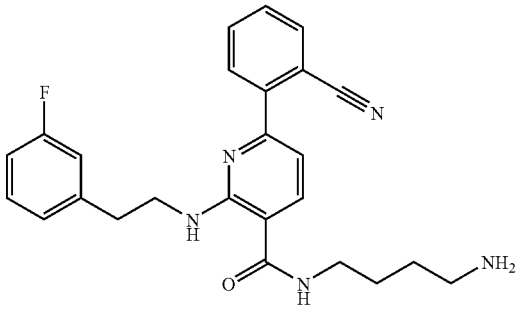<br>Compound 317 | N-(4-aminobutyl)(6-(2-cyanophenyl)-2-{[2-(3-fluorophenyl)ethyl]amino}(3-pyridyl))carboxamide |
| 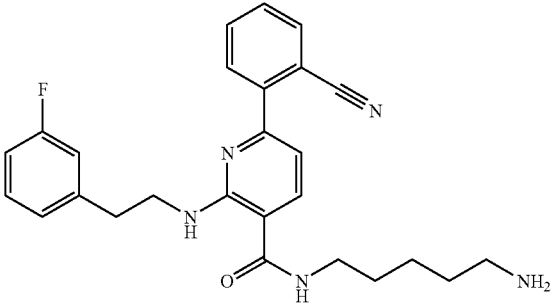<br>Compound 318 | N-(5-aminopentyl)(6-(2-cyanophenyl)-2-{[2-(3-fluorophenyl)ethyl]amino}(3-pyridyl))carboxamide |

-continued

| COMPOUND | CHEMICAL NAME |
|---|---|
| 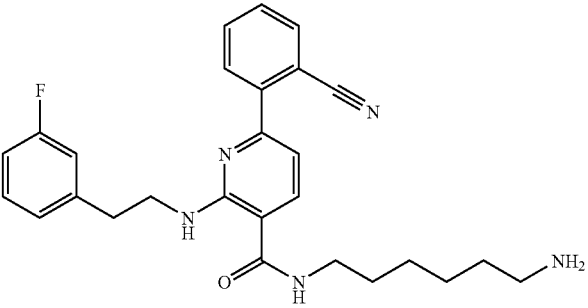<br>Compound 319 | N-(6-aminohexyl)(6-(2-cyanophenyl)-2-{[2-(3-fluorophenyl)ethyl]amino}(3-pyridyl))carboxamide |
| 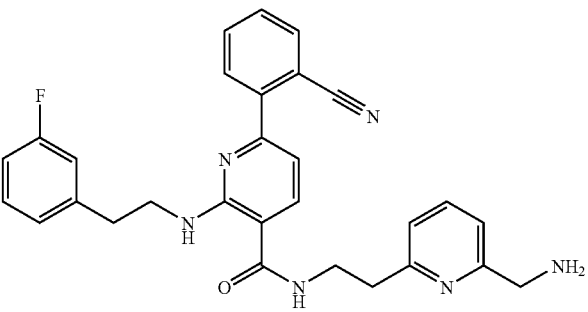<br>Compound 320 | N-{2-[6-(aminomethyl)(2-pyridyl)]ethyl}(6-(2-cyanophenyl)-2-{[2-(3-fluorophenyl)ethyl]amino}(3-pyridyl))carboxamide |
| 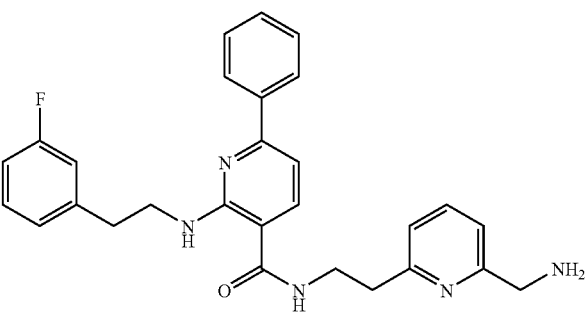<br>Compound 321 | N-{2-[6-(aminomethyl)(2-pyridyl)]ethyl}(2-{[2-(3-fluorophenyl)ethyl]amino}-6-phenyl(3-pyridyl))carboxamide |
| 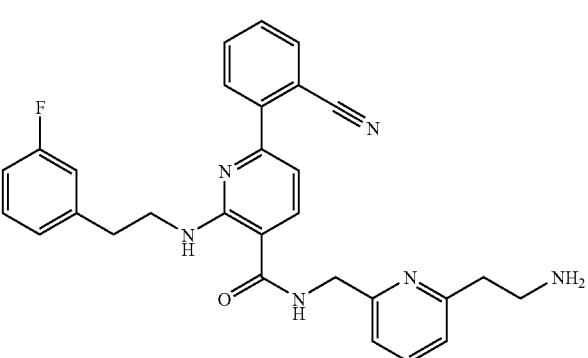<br>Compound 322 | N-{[6-(2-aminomethyl)(2-pyridyl)]methyl}(6-(2-cyanophenyl)-2-{[2-(3-fluorophenyl)ethyl]amino}(3-pyridyl))carboxamide |

| COMPOUND | CHEMICAL NAME |
|---|---|
| 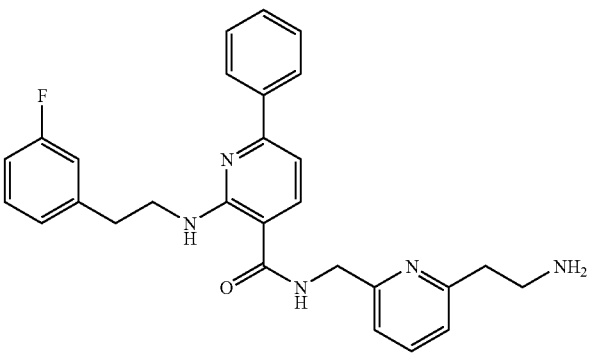<br>Compound 323 | N-{[6-(2-aminomethyl)(2-pyridyl)]methyl}(2-{[2-(3-fluorophenyl)ethyl]amino}-6-phenyl(3-pyridyl))carboxamide |
| 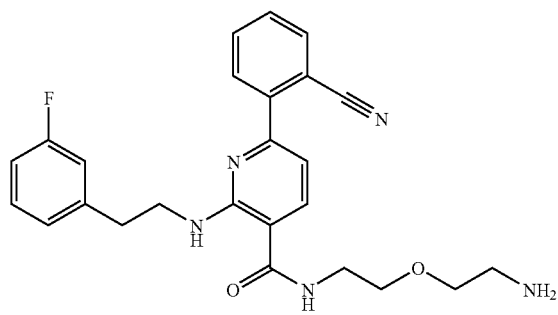<br>Compound 327 | N-[2-(2-aminoethoxy)ethyl](6-(2-cyanophenyl)-2-{[2-(3-fluorophenyl)ethyl]amino}(3-pyridyl))carboxamide |
| 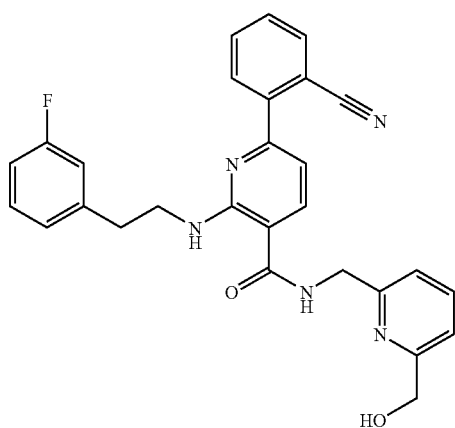<br>Compound 342 | (6-(2-cyanophenyl)-2-{[2-(3-fluorophenyl)ethyl]amino}(3-pyridyl))-N-{[6-(hydroxymethyl)(2-pyridyl)]methyl}carboxamide |

-continued

| COMPOUND | CHEMICAL NAME |
|---|---|
| Compound 343 | N-{[3-(aminomethyl)phenyl]methyl}(6-(2-cyanophenyl)-2-{[2-(3-fluorophenyl)ethyl]amino}(3-pyridyl))carboxamide |
| Compound 347 | 2-[(6-(2-cyanophenyl)-2-{[2-(3-fluorophenyl)ethyl]amino}(3-pyridyl))carbonylamino]-N,N-dimethylacetamide |
| Compound 354 | N-{2-[(2-aminoethyl)amino]ethyl}(6-(2-cyanophenyl)-2-{[2-(3-fluorophenyl)ethyl]amino}(3-pyridyl))carboxamide |
| Compound 355 | (6-(2-cyanophenyl)-2-{[2-(3-fluorophenyl)ethyl]amino}(3-pyridyl))-N-[(2-oxo(3-piperidyl))methyl]carboxamide |

-continued

| COMPOUND | CHEMICAL NAME |
|---|---|
| 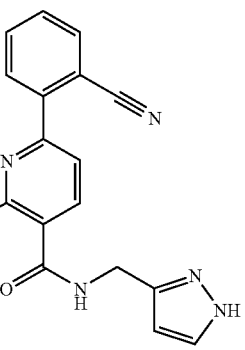<br>Compound 364 | (6-(2-cyanophenyl)-2-{[2-(3-fluorophenyl)ethyl]amino}(3-pyridyl))-N-(pyrazol-3-ylmethyl)carboxamide |
| 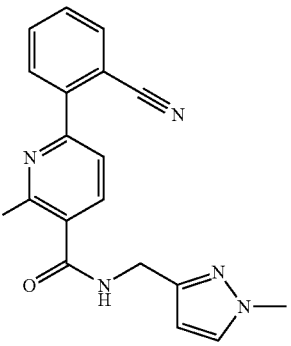<br>Compound 365 | (6-(2-cyanophenyl)-2-{[2-(3-fluorophenyl)ethyl]amino}(3-pyridyl))-N-[(1-methylpyrazol-3-yl)methyl]carboxamide |
| 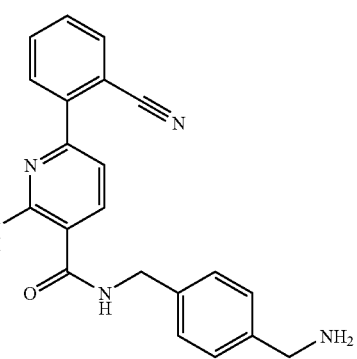<br>Compound 366 | N-{[4-(aminomethyl)phenyl]methyl}(6-(2-cyanophenyl)-2-{[2-(3-fluorophenyl)ethyl]amino}(3-pyridyl))carboxamide |
| 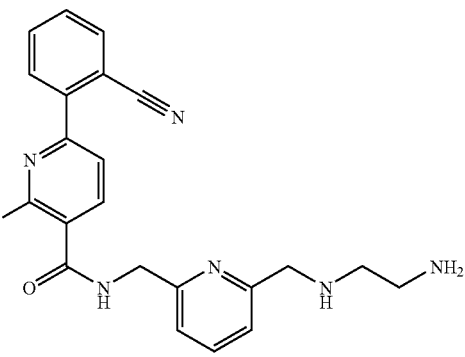<br>Compound 367 | N-[(6-{[(2-aminoethyl)amino]methyl}(2-pyridyl))methyl](6-(2-cyanophenyl)-2-{[2-(3-fluorophenyl)ethyl]amino}(3-pyridyl))carboxamide |

| COMPOUND | CHEMICAL NAME |
|---|---|
| 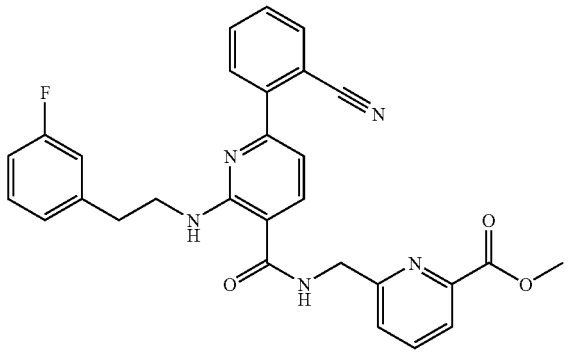
Compound 376 | methyl 6-{[(6-(2-cyanophenyl)-2-{[2-(3-fluorophenyl)ethyl]amino}-3-pyridyl)carbonylamino]methyl}pyridine-2-carboxylate |
| 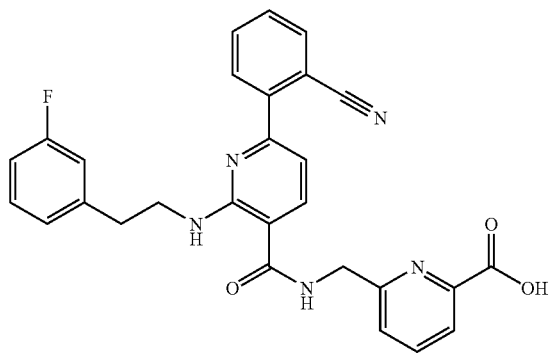
Compound 377 | 6-{[(6-(2-cyanophenyl)-2-{[2-(3-fluorophenyl)ethyl]amino}-3-pyridyl)carbonylamino]methyl}pyridine-2-carboxylic acid |
| 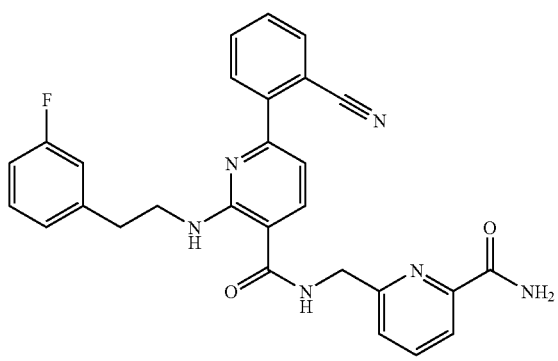
Compound 378 | 6-{[(6-(2-cyanophenyl)-2-{[2-(3-fluorophenyl)ethyl]amino}-3-pyridyl)carbonylamino]methyl}pyridine-2-carboxamide |

-continued

| COMPOUND | CHEMICAL NAME |
|---|---|
| Compound 379 | (6-(2-cyanophenyl)-2-{[2-(3-fluorophenyl)ethyl]amino}(3-pyridyl))-N-[(1-methylpyrazol-5-yl)methyl]carboxamide |
| Compound 380 | N-(1-{2-[(tert-butoxy)carbonylamino]ethyl}-2-oxo(3-piperidyl))(6-(2-cyanophenyl)-2-{[2-(3-fluorophenyl)ethyl]amino}(3-pyridyl))carboxamide |
| Compound 381 | N-[1-(2-aminoethyl)-2-oxo(3-piperidyl)](6-(2-cyanophenyl)-2-{[2-(3-fluorophenyl)ethyl]amino}(3-pyridyl))carboxamide |
| Compound 382 | (6-(2-cyanophenyl)-2-{[2-(3-fluorophenyl)ethyl]amino}(3-pyridyl))-N-(2-{2-oxo-3-[(phenylmethoxy)carbonylamino]piperidyl}ethyl)-carboxamide |

-continued

| COMPOUND | CHEMICAL NAME |
|---|---|
| Compound 383 | N-[2-(3-amino-2-oxopiperidyl)ethyl](6-(2-cyanophenyl)-2-{[2-(3-fluorophenyl)ethyl]amino}(3-pyridyl))carboxamide |
| Compound 384 | N-{[2-(aminomethyl)phenyl]methyl}(6-(2-cyanophenyl)-2-{[2-(3-fluorophenyl)ethyl]amino}(3-pyridyl))carboxamide |
| Compound 397 | (6-(2-cyanophenyl)-2-{[2-(3-fluorophenyl)ethyl]amino}(3-pyridyl))-N-[(2-oxopyrrolidin-3-yl)methyl]carboxamide |
| Compound 415 | N-[(2-{2-[(tert-butoxy)carbonylamino]ethyl}(3-pyridyl))methyl](6-(2-cyanophenyl)-2-{[2-(3-fluorophenyl)ethyl]amino}(3-pyridyl))carboxamide |

-continued

| COMPOUND | CHEMICAL NAME |
|---|---|
| 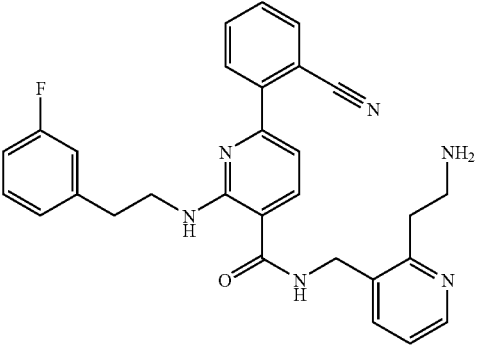<br>Compound 416 | N-{[2-(2-aminoethyl)(3-pyridyl)]methyl}(6-(2-cyanophenyl)-2-{[2-(3-fluorophenyl)ethyl]amino}(3-pyridyl))carboxamide |
| 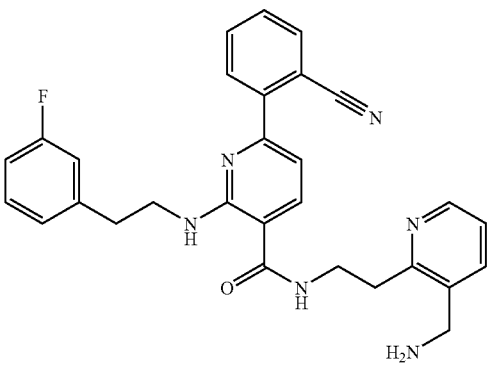<br>Compound 417 | N-{2-[3-(aminomethyl)(2-pyridyl)]ethyl}(6-(2-cyanophenyl)-2-{[2-(3-fluorophenyl)ethyl]amino}(3-pyridyl))carboxamide |
| 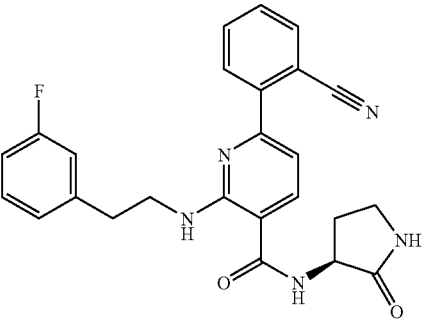<br>Compound 418 | N-((3S)-2-oxopyrrolidin-3-yl)(6-(2-cyanophenyl)-2-{[2-(3-fluorophenyl)ethyl]amino}(3-pyridyl))carboxamide |
| 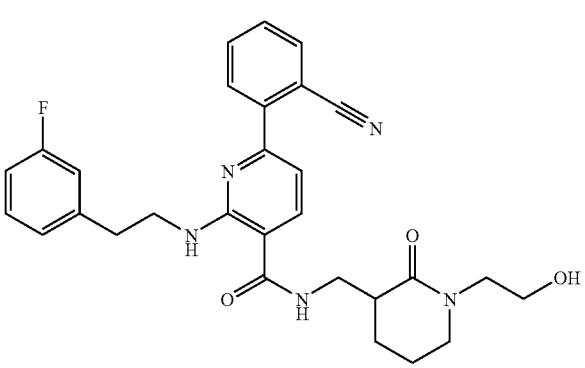<br>Compound 447 | (6-(2-cyanophenyl)-2-{[2-(3-fluorophenyl)ethyl]amino}(3-pyridyl))-N-{[1-(2-hydroxyethyl)-2-oxo(3-piperidyl)]methyl}carboxamide |

| COMPOUND | CHEMICAL NAME |
|---|---|
| 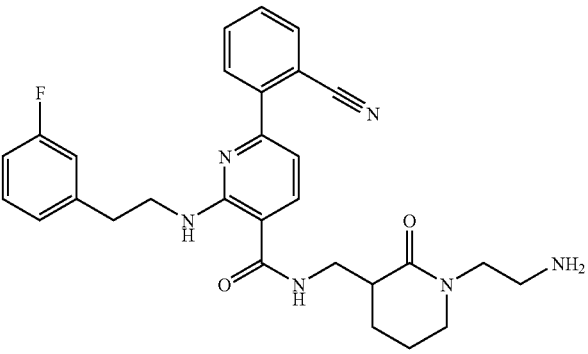
Compound 449 | N-{[1-(2-aminoethyl)-2-oxo(3-piperidyl)]methyl}(6-(2-cyanophenyl)-2-{[2-(3-fluorophenyl)ethyl]amino}(3-pyridyl))carboxamide |
| 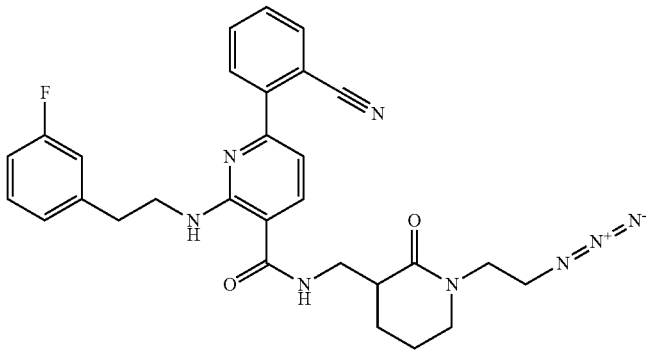
Compound 477 | (6-(2-cyanophenyl)-2-{[2-(3-fluorophenyl)ethyl]amino}(3-pyridyl))-N-{[1-(3-diazo-3-azaprop-3-enyl)-2-oxo(3-piperidyl)]methyl}carboxamide |
| 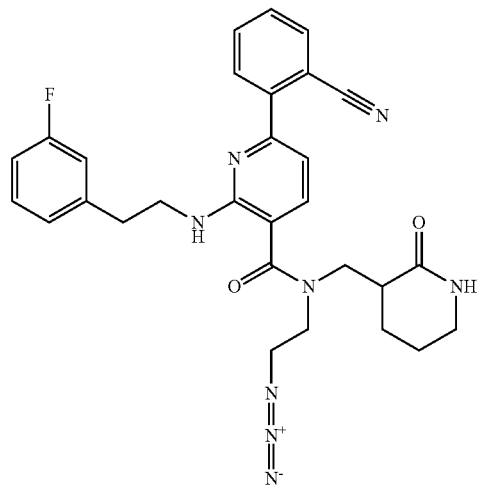
Compound 478 | (6-(2-cyanophenyl)-2-{[2-(3-fluorophenyl)ethyl]amino}(3-pyridyl))-N-{[3-(3-diazo-3-azaprop-3-enyl)-2-oxo(3-piperidyl)]methyl}carboxamide |

| COMPOUND | CHEMICAL NAME |
|---|---|
| 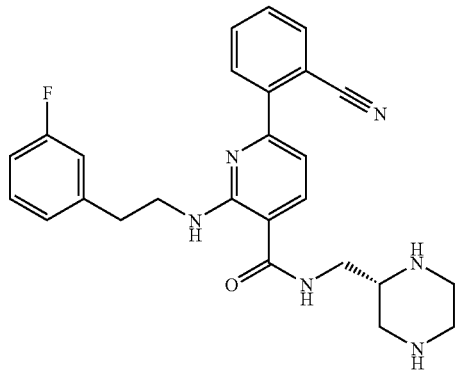
Compound 565 | N-[((2R)piperazin-2-yl)methyl](6-(2-cyanophenyl)-2-{[2-(3-fluorophenyl)ethyl]amino}(3-pyridyl))carboxamide |
| 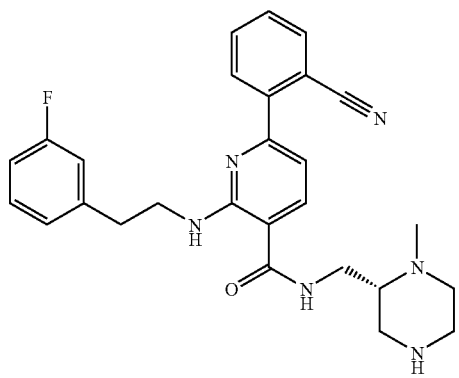
Compound 566 | N-[((2R)-1-methylpiperazin-2-yl)methyl](6-(2-cyanophenyl)-2-{[2-(3-fluorophenyl)ethyl]amino}(3-pyridyl))carboxamide |
| 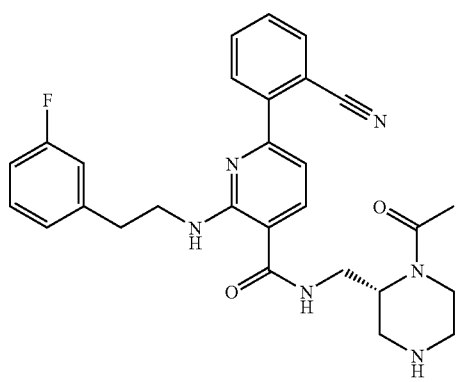
Compound 567 | N-[((2R)-1-acetylpiperazin-2-yl)methyl](6-(2-cyanophenyl)-2-{[2-(3-fluorophenyl)ethyl]amino}(3-pyridyl))carboxamide |

-continued

| COMPOUND | CHEMICAL NAME |
|---|---|
| 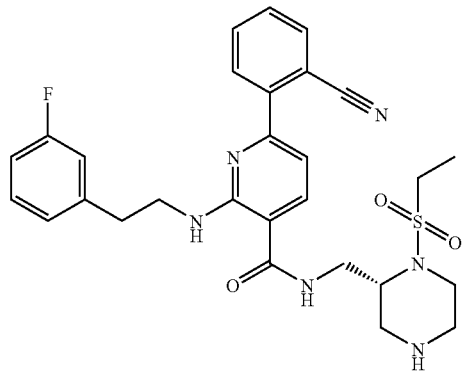<br>Compound 568 | N-{[(2R)-1-(ethylsulfonyl)piperazin-2-yl]methyl}(6-(2-cyanophenyl)-2-{[2-(3-fluorophenyl)ethyl]amino}(3-pyridyl))carboxamide |
| 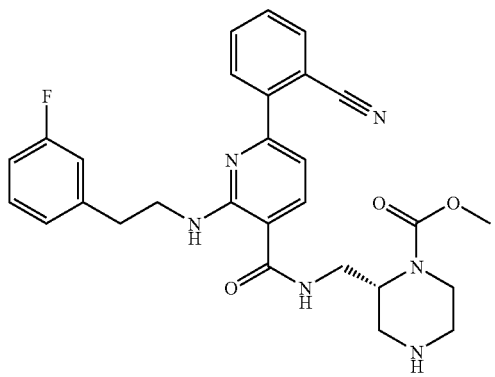<br>Compound 569 | methyl (2R)-2-{[(6-(2-cyanophenyl)-2-{[2-(3-fluorophenyl)ethyl]amino}(3-pyridyl))carbonylamino]methyl}piperazinecarboxylate |
| 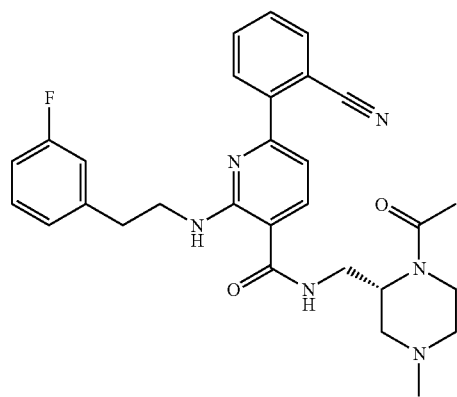<br>Compound 570 | N-[((2S)-1-acetyl-4-methylpiperazin-2-yl)methyl](6-(2-cyanophenyl)-2-{[2-(3-fluorophenyl)ethyl]amino}(3-pyridyl))carboxamide |

-continued

| COMPOUND | CHEMICAL NAME |
|---|---|
| 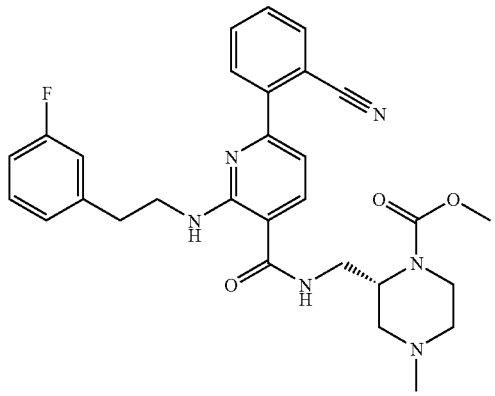  Compound 571 | methyl (2S)-2-{[(6-(2-cyanophenyl)-2-{[2-(3-fluorophenyl)ethyl]amino}(3-pyridyl))carbonylamino]methyl}-4-methylpiperazinecarboxylate |
| 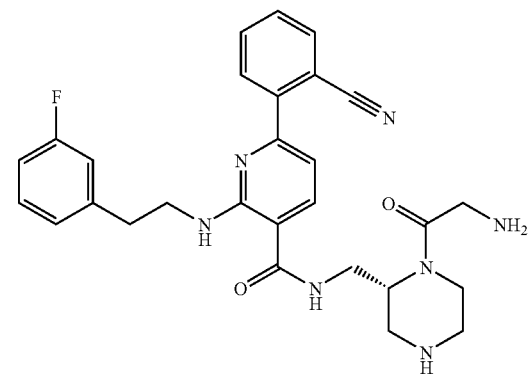  Compound 572 | N-{[(2R)-1-(2-aminoacetyl)piperazin-2-yl]methyl}(6-(2-cyanophenyl)-2-{[2-(3-fluorophenyl)ethyl]amino}(3-pyridyl))carboxamide |
| 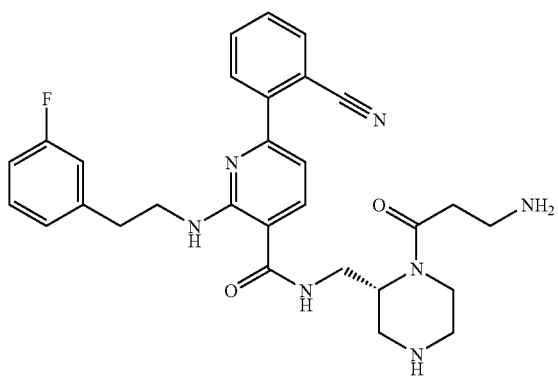  Compound 573 | N-{[(2R)-1-(3-aminopropanoyl)piperazin-2-yl]methyl}(6-(2-cyanophenyl)-2-{[2-(3-fluorophenyl)ethyl]amino}(3-pyridyl))carboxamide |

-continued

| COMPOUND | CHEMICAL NAME |
|---|---|
| 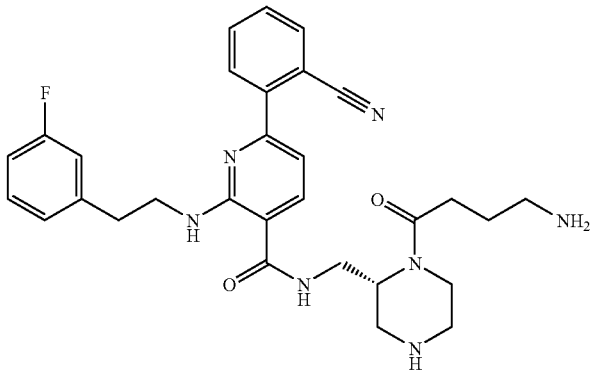<br>Compound 574 | N-{[(2R)-1-(4-aminobutanoyl)piperazin-2-yl]methyl}(6-(2-cyanophenyl)-2-{[2-(3-fluorophenyl)ethyl]amino}(3-pyridyl))carboxamide |
| 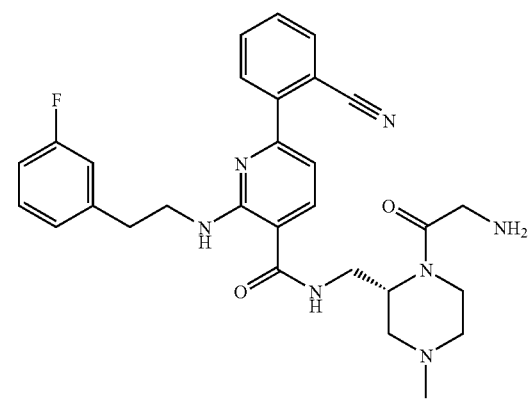<br>Compound 575 | N-{[(2S)-1-(2-aminoacetyl)-4-methylpiperazin-2-yl]methyl}(6-(2-cyanophenyl)-2-{[2-(3-fluorophenyl)ethyl]amino}(3-pyridyl))carboxamide |
| 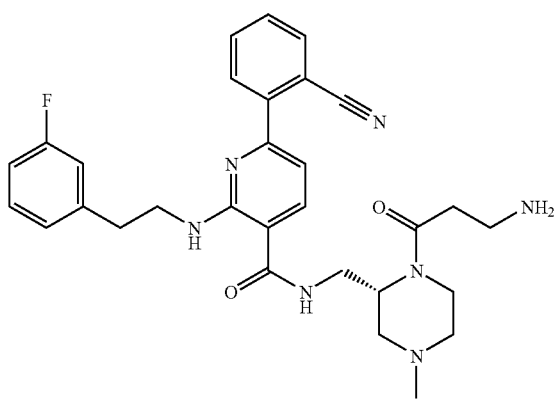<br>Compound 576 | N-{[(2S)-1-(3-aminopropanoyl)-4-methylpiperazin-2-yl]methyl}(6-(2-cyanophenyl)-2-{[2-(3-fluorophenyl)ethyl]amino}(3-pyridyl))carboxamide |

| COMPOUND | CHEMICAL NAME |
|---|---|
| Compound 577 | N-{[(2S)-1-(4-aminobutanoyl)-4-methylpiperazin-2-yl]methyl}(6-(2-cyanophenyl)-2-{[2-(3-fluorophenyl)ethyl]amino}(3-pyridyl))carboxamide |
| Compound 578 | N-{[(2S)-4-(2-aminoacetyl)piperazin-2-yl]methyl}(6-(2-cyanophenyl)-2-{[2-(3-fluorophenyl)ethyl]amino}(3-pyridyl))carboxamide |
| Compound 579 | N-{[(2S)-4-(3-aminopropanoyl)piperazin-2-yl]methyl}(6-(2-cyanophenyl)-2-{[2-(3-fluorophenyl)ethyl]amino}(3-pyridyl))carboxamide |

| COMPOUND | CHEMICAL NAME |
|---|---|
| Compound 580 | N-{[(2S)-4-(4-aminobutanoyl)piperazin-2-yl]methyl}(6-(2-cyanophenyl)-2-{[2-(3-fluorophenyl)ethyl]amino}(3-pyridyl))carboxamide |
| Compound 620 | N-{[(2S)-4-(2-aminoacetyl)-1-methylpiperazin-2-yl]methyl}(6-(2-cyanophenyl)-2-{[2-(3-fluorophenyl)ethyl]amino}(3-pyridyl))carboxamide |
| Compound 621 | N-{[(2S)-4-(3-aminopropanoyl)-1-methylpiperazin-2-yl]methyl}(6-(2-cyanophenyl)-2-{[2-(3-fluorophenyl)ethyl]amino}(3-pyridyl))carboxamide |

-continued
| COMPOUND | CHEMICAL NAME |
|---|---|
| 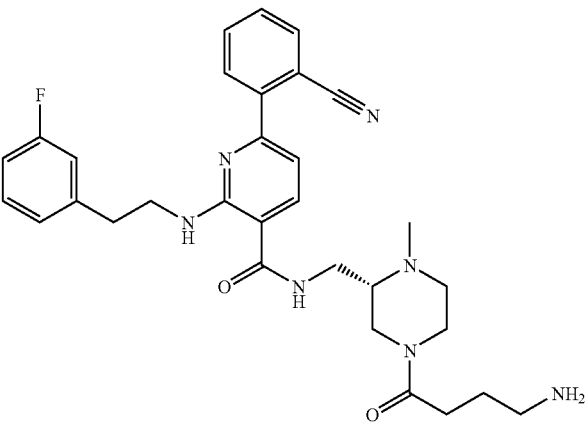  Compound 622 | N-{[(2S)-4-(4-aminobutanoyl)-1-methylpiperazin-2-yl]methyl}(6-(2-cyanophenyl)-2-{[2-(3-fluorophenyl)ethyl]amino}(3-pyridyl))carboxamide |
| 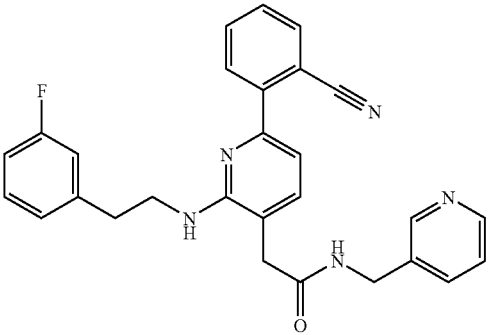  Compound 623 | 2-(6-(2-cyanophenyl)-2-{[2-(3-fluorophenyl)ethyl]amino}(3-pyridyl))-N-(3-pyridylmethyl)acetamide |
| 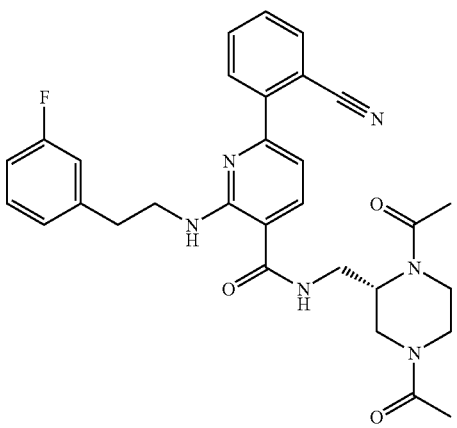  Compound 624 | N-[((2S)-1,4-diacetylpiperazin-2-yl)methyl](6-(2-cyanophenyl)-2-{[2-(3-fluorophenyl)ethyl]amino}(3-pyridyl))carboxamide |

| COMPOUND | CHEMICAL NAME |
|---|---|
| 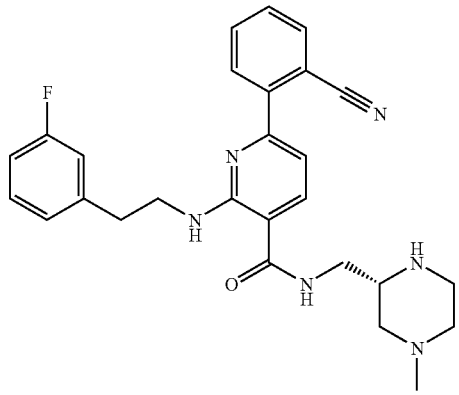<br>Compound 625 | N-[((2S)-4-methylpiperazin-2-yl)methyl](6-(2-cyanophenyl)-2-{[2-(3-fluorophenyl)ethyl]amino}(3-pyridyl))carboxamide |
| 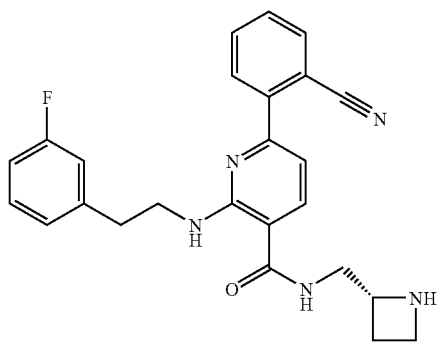<br>Compound 640 | N-[((2R)azetidin-2-yl)methyl](6-(2-cyanophenyl)-2-{[2-(3-fluorophenyl)ethyl]amino}(3-pyridyl))carboxamide |
| 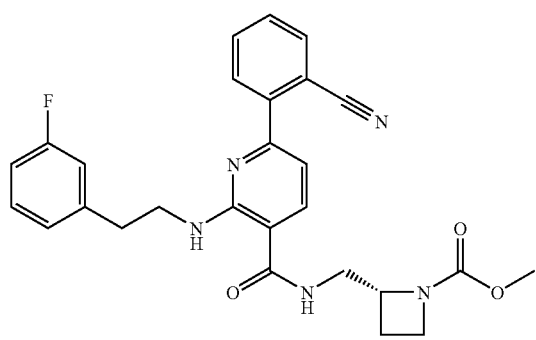<br>Compound 641 | methyl (2R)-2-{[(6-(2-cyanophenyl)-2-{[2-(3-fluorophenyl)ethyl]amino}(3-pyridyl))carbonylamino]methyl}azetidinecarboxylate |

-continued

| COMPOUND | CHEMICAL NAME |
|---|---|
| Compound 642 | (2-{[2-(3-fluorophenyl)ethyl]amino}-6-(1-methylpyrazol-4-yl)(3-pyridyl))-N-[(2-oxopyrrolidin-3-yl)methyl]carboxamide |
| Compound 646 | (2-{[2-(3-fluorophenyl)ethyl]amino}-6-pyrazol-4-yl(3-pyridyl))-N-[(2-oxopyrrolidin-3-yl)methyl]carboxamide |
| Compound 647 | N-{[(2R)-1-(2-hydroxyacetyl)pyrrolidin-2-yl]methyl}(6-(2-cyanophenyl)-2-{[2-(3-fluorophenyl)ethyl]amino}(3-pyridyl))carboxamide |
| Compound 648 | methyl 4-((2R)-2-{[(6-(2-cyanophenyl)-2-{[2-(3-fluorophenyl)ethyl]amino}(3-pyridyl))carbonylamino]methyl}pyrrolidinyl)-4-oxobutanoate |

| COMPOUND | CHEMICAL NAME |
|---|---|
| 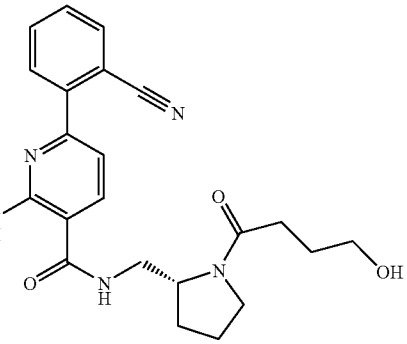<br>Compound 649 | N-{[(2R)-1-(4-hydroxybutanoyl)pyrrolidin-2-yl]methyl}(6-(2-cyanophenyl)-2-{[2-(3-fluorophenyl)ethyl]amino}(3-pyridyl))carboxamide |
| 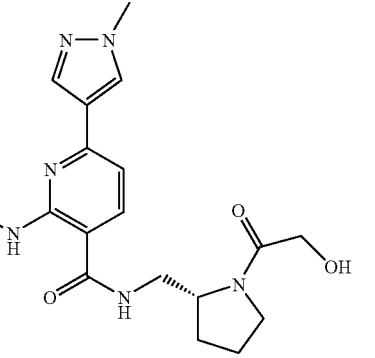<br>Compound 650 | N-{[(2R)-1-(2-hydroxyacetyl)pyrrolidin-2-yl]methyl}(2-{[2-(3-fluorophenyl)ethyl]amino}-6-(1-methylpyrazol-4-yl)(3-pyridyl))carboxamide |
| 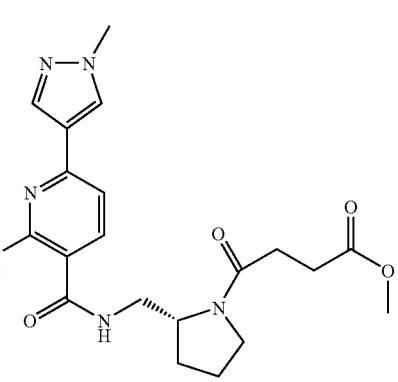<br>Compound 651 | methyl 4-((2R)-2-{[(2-{[2-(3-fluorophenyl)ethyl]amino}-6-(1-methylpyrazol-4-yl)(3-pyridyl))carbonylamino]methyl}pyrrolidinyl)-4-oxobutanoate |
| 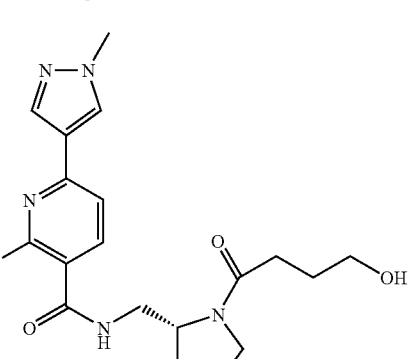<br>Compound 652 | N-{[(2R)-1-(4-hydroxybutanoyl)pyrrolidin-2-yl]methyl}(2-{[2-(3-fluorophenyl)ethyl]amino}-6-(1-methylpyrazol-4-yl)(3-pyridyl))carboxamide |

| COMPOUND | CHEMICAL NAME |
|---|---|
| Compound 653 | N-[((2R)-1-acetylazetidin-2-yl)methyl](6-(2-cyanophenyl)-2-{[2-(3-fluorophenyl)ethyl]amino}(3-pyridyl))carboxamide |
| Compound 654 | N-{[(2R)-1-(methylsulfonyl)azetidin-2-yl]methyl}(6-(2-cyanophenyl)-2-{[2-(3-fluorophenyl)ethyl]amino}(3-pyridyl))carboxamide |
| Compound 655 | N-{[(2R)-1-(2-aminoacetyl)azetidin-2-yl]methyl}(6-(2-cyanophenyl)-2-{[2-(3-fluorophenyl)ethyl]amino}(3-pyridyl))carboxamide |
| Compound 656 | N-{[(2R)-1-(3-aminopropanoyl)azetidin-2-yl]methyl}(6-(2-cyanophenyl)-2-{[2-(3-fluorophenyl)ethyl]amino}(3-pyridyl))carboxamide |

-continued

| COMPOUND | CHEMICAL NAME |
|---|---|
| 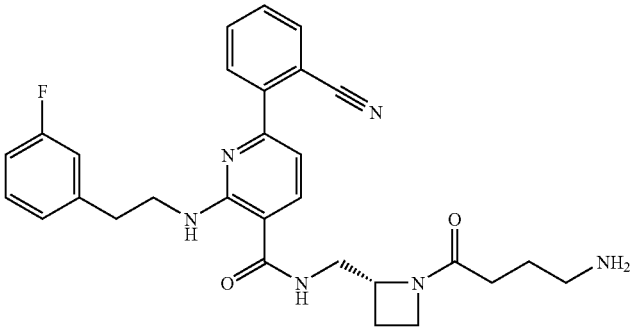

Compound 657 | N-{[(2R)-1-(4-aminobutanoyl)azetidin-2-yl]methyl}(6-(2-cyanophenyl)-2-{[2-(3-fluorophenyl)ethyl]amino}(3-pyridyl))carboxamide |
| 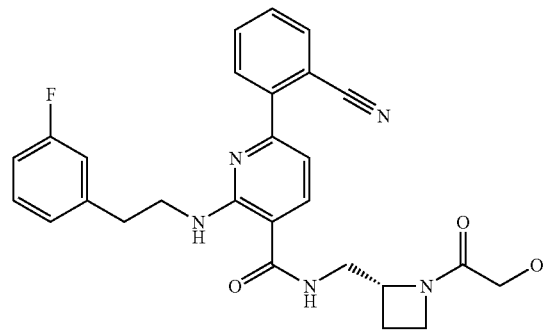

Compound 658 | N-{[(2R)-1-(2-hydroxyacetyl)azetidin-2-yl]methyl}(6-(2-cyanophenyl)-2-{[2-(3-fluorophenyl)ethyl]amino}(3-pyridyl))carboxamide |
| 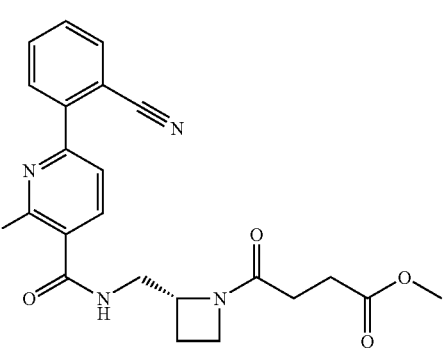

Compound 659 | methyl 4-((2R)-2-{[(6-(2-cyanophenyl)-2-{[2-(3-fluorophenyl)ethyl]amino}(3-pyridyl))carbonylamino]methyl}azetidinyl)-4-oxobutanoate |
| 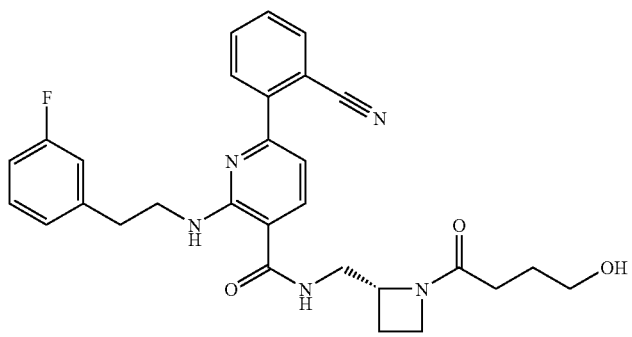

Compound 660 | N-{[(2R)-1-(4-hydroxybutanoyl)azetidin-2-yl]methyl}(6-(2-cyanophenyl)-2-{[2-(3-fluorophenyl)ethyl]amino}(3-pyridyl))carboxamide |

-continued

| COMPOUND | CHEMICAL NAME |
|---|---|
| 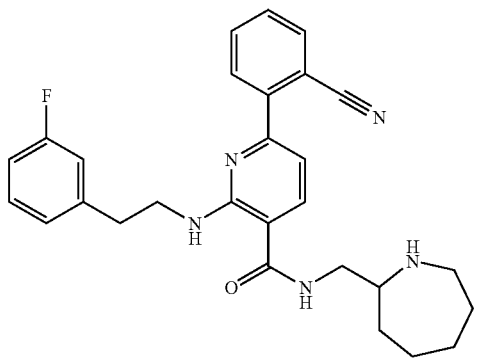<br>Compound 661 | N-(azaperhydroepin-2-ylmethyl)(6-(2-cyanophenyl)-2-{[2-(3-fluorophenyl)ethyl]amino}(3-pyridyl))carboxamide |
| 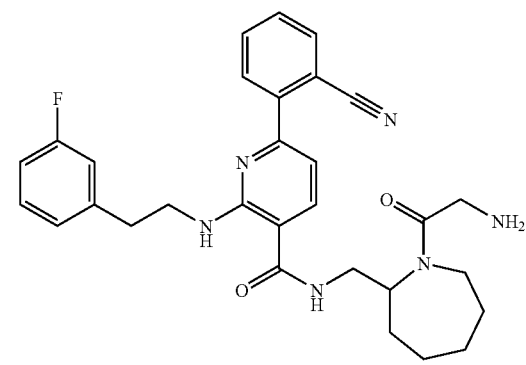<br>Compound 662 | N-{[1-(2-aminoacetyl)azaperhydroepin-2-yl]methyl}(6-(2-cyanophenyl)-2-{[2-(3-fluorophenyl)ethyl]amino}(3-pyridyl))carboxamide |
| 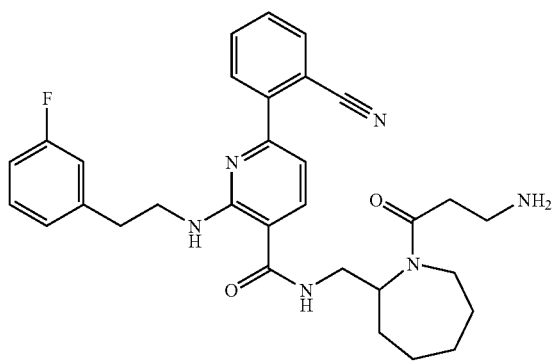<br>Compound 663 | N-{[1-(3-aminopropanoyl)azaperhydroepin-2-yl]methyl}(6-(2-cyanophenyl)-2-{[2-(3-fluorophenyl)ethyl]amino}(3-pyridyl))carboxamide |

| COMPOUND | CHEMICAL NAME |
|---|---|
| 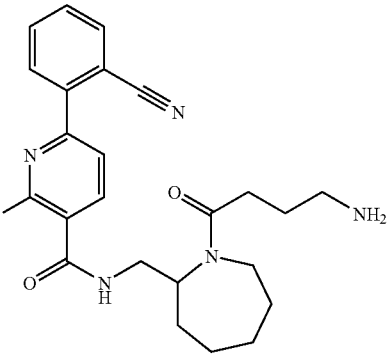<br>Compound 664 | N-{[1-(4-aminobutanoyl)azaperhydroepin-2-yl]methyl}(6-(2-cyanophenyl)-2-{[2-(3-fluorophenyl)ethyl]amino}(3-pyridyl))carboxamide |
| 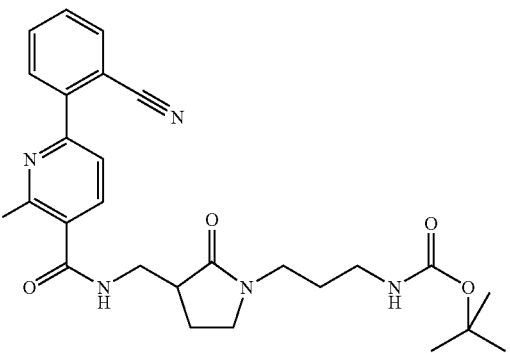<br>Compound 675 | N-[(1-{3-tert-butoxy)carbonylamino]propyl}-2-oxopyrrolidin-3-yl)methyl](6-(2-cyanophenyl)-2-{[2-(3-fluorophenyl)ethyl]amino}(3-pyridyl))carboxamide |
| 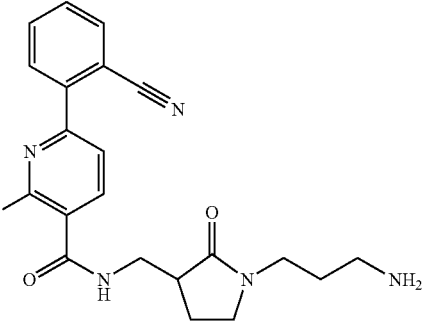<br>Compound 676 | N-{[1-(3-aminopropyl)-2-oxopyrrolidin-3-yl]methyl}(6-(2-cyanophenyl)-2-{[2-(3-fluorophenyl)ethyl]amino}(3-pyridyl))carboxamide |
| 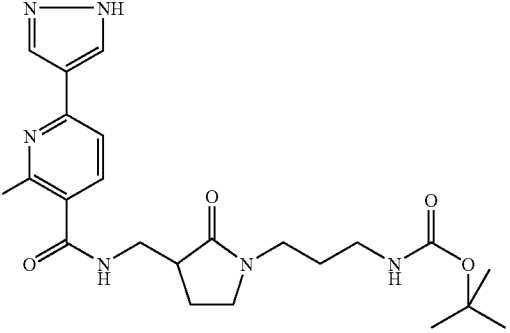<br>Compound 677 | N-[(1-{3-[(tert-butoxy)carbonylamino]propyl}-2-oxopyrrolidin-3-yl)methyl](2-{[2-(3-fluorophenyl)ethyl]amino}-6-pyrazol-4-yl(3-pyridyl))carboxamide |

| COMPOUND | CHEMICAL NAME |
|---|---|
| 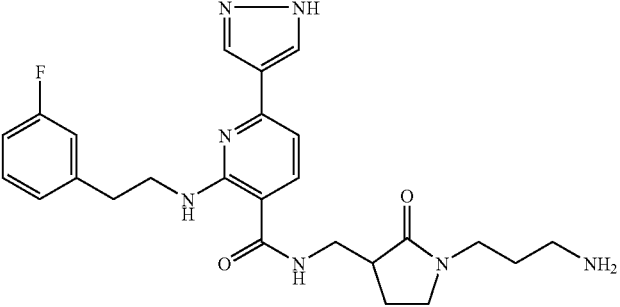
Compound 678 | N-{[1-(3-aminopropyl)-2-oxopyrrolidin-3-yl]methyl}(2-{[2-(3-fluorophenyl)ethyl]amino}-6-pyrazol-4-yl(3-pyridyl))carboxamide |
| 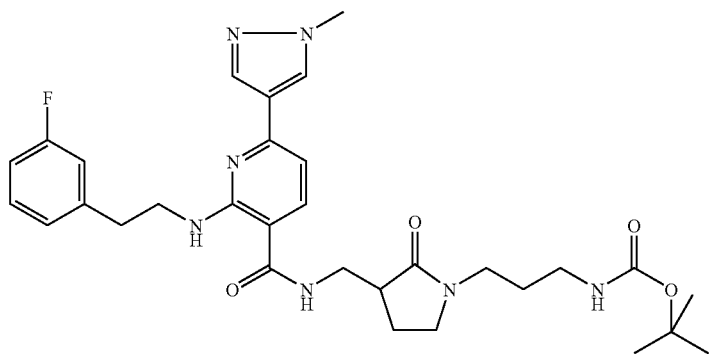
Compound 679 | N-[(1-{3-[(tert-butoxy)carbonylamino]propyl}-2-oxopyrrolidin-3-yl)methyl](2-{[2-(3-fluorophenyl)ethyl]amino}-6-(1-methylpyrazol-4-yl)(3-pyridyl))carboxamide |
| 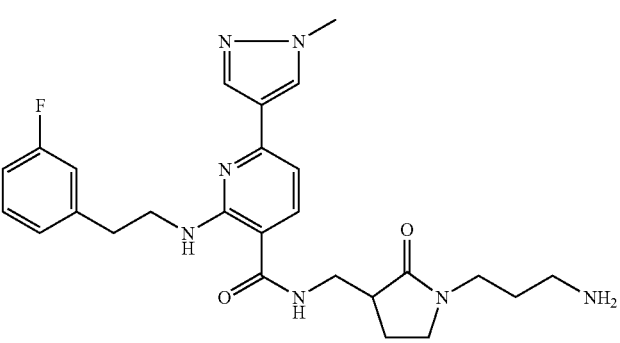
Compound 680 | N-{[1-(3-aminopropyl)-2-oxopyrrolidin-3-yl]methyl}(2-{[2-(3-fluorophenyl)ethyl]amino}-6-(1-methylpyrazol-4-yl)(3-pyridyl))carboxamide |
| 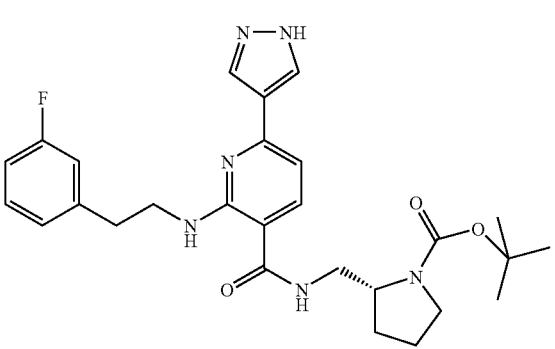
Compound 682 | tert-butyl (2R)-2-{[(2-{[2-(3-fluorophenyl)ethyl]amino}-6-pyrazol-4-yl(3-pyridyl))carbonylamino]methyl}pyrrolidinecarboxylate |

-continued

| COMPOUND | CHEMICAL NAME |
|---|---|
| Compound 683 | N-{[(2R)-1-(2-hydroxyacetyl)pyrrolidin-2-yl]methyl}(2-{[2-(3-fluorophenyl)ethyl]amino}-6-pyrazol-4-yl(3-pyridyl))carboxamide |
| Compound 684 | (6-(2-cyanophenyl)-2-{[2-(3-fluorophenyl)ethyl]amino}(3-pyridyl))-N-[(7-oxoazaperhydroepin-2-yl)methyl]carboxamide |
| Compound 685 | (2-{[2-(3-fluorophenyl)ethyl]amino}-6-pyrazol-4-yl(3-pyridyl))-N-[(7-oxoazaperhydroepin-2-yl)methyl]carboxamide |
| Compound 686 | (2-{[2-(3-fluorophenyl)ethyl]amino}-6-(1-methylpyrazol-4-yl(3-pyridyl))-N-[(7-oxoazaperhydroepin-2-yl)methyl]carboxamide |

-continued

| COMPOUND | CHEMICAL NAME |
|---|---|
| 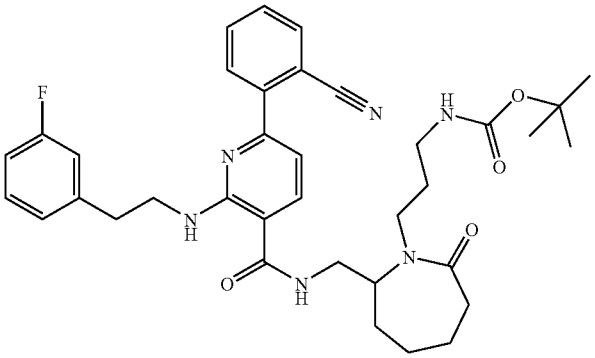<br>Compound 687 | N-[(1-{3-[(tert-butoxy)carbonylamino]propyl}-7-oxoazaperhydroepin-2-yl)methyl](6-(2-cyanophenyl)-2-{[2-(3-fluorophenyl)ethyl]amino}(3-pyridyl))carboxamide |
| 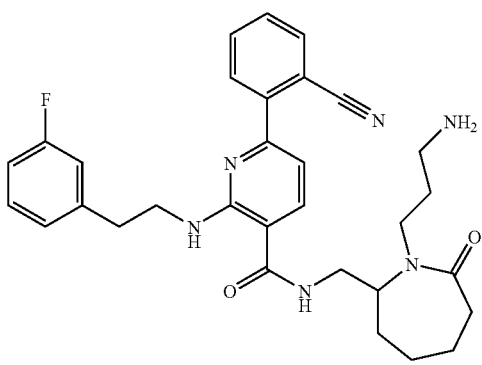<br>Compound 688 | N-{[1-(3-aminopropyl)-7-oxoazaperhydroepin-2-yl]methyl}(6-(2-cyanophenyl)-2-{[2-(3-fluorophenyl)ethyl]amino}(3-pyridyl))carboxamide |
| 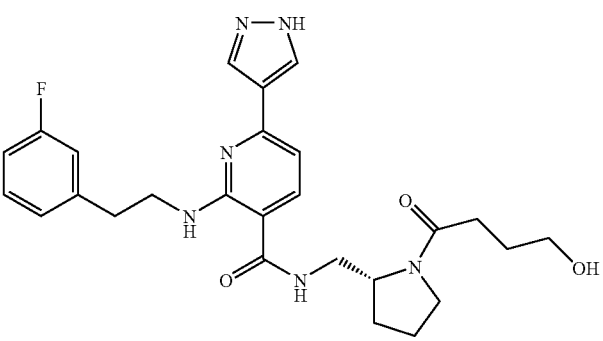<br>Compound 694 | N-{[(2R)-1-(4-hydroxybutanoyl)pyrrolidin-2-yl]methyl}(2-{[2-(3-fluorophenyl)ethyl]amino}-6-pyrazol-4-yl(3-pyridyl))carboxamide |
| 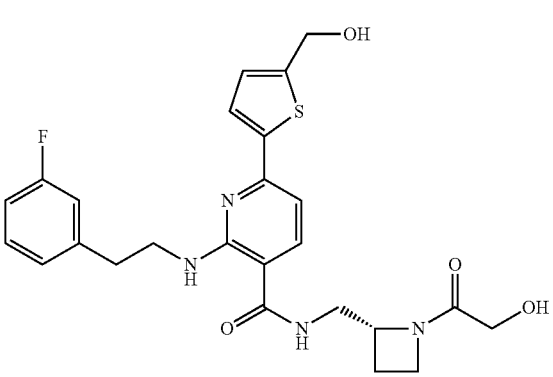<br>Compound 697 | N-{[(2R)-1-(2-hydroxyacetyl)azetidin-2-yl]methyl}(2-{[2-(3-fluorophenyl)ethyl]amino}-6-[5-(hydroxymethyl)(2-thienyl)](3-pyridyl))carboxamide |

| COMPOUND | CHEMICAL NAME |
|---|---|
| 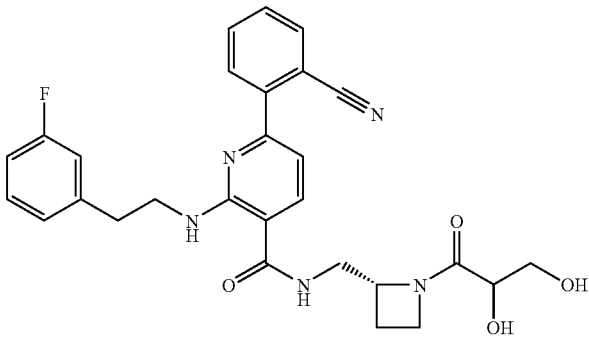<br>Compound 698 | N-{[(2R)-1-(2,3-dihydroxypropanoyl)azetidin-2-yl]methyl}(6-(2-cyanophenyl)-2-{[2-(3-fluorophenyl)ethyl]amino}(3-pyridyl))carboxamide |
| 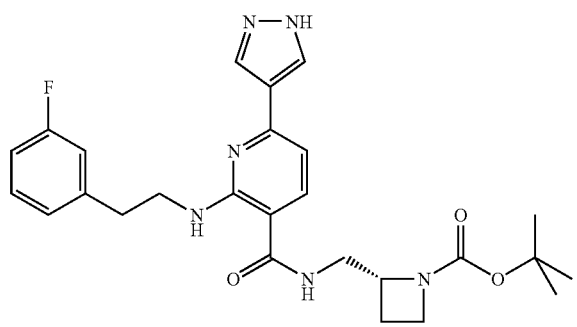<br>Compound 700 | tert-butyl (2R)-2-{[(2-{[2-(3-fluorophenyl)ethyl]amino}-6-pyrazol-4-yl(3-pyridyl))carbonylamino]methyl}azetidinecarboxylate |
| 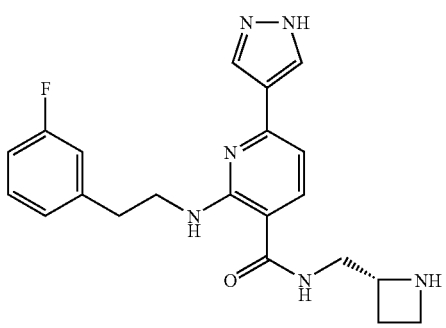<br>Compound 701 | N-[((2R)azetidin-2-yl)methyl](2-{[2-(3-fluorophenyl)ethyl]amino}-6-pyrazol-4-yl(3-pyridyl))carboxamide |

-continued

| COMPOUND | CHEMICAL NAME |
|---|---|
| 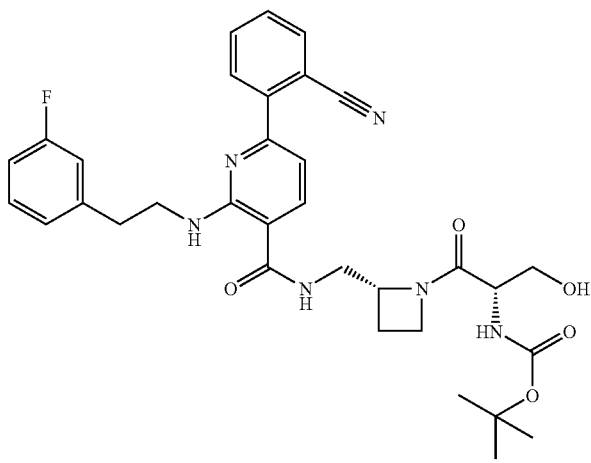<br>Compound 702 | N-[2-((2R)-2-{[(6-(2-cyanophenyl)-2-{[2-(3-fluorophenyl)ethyl]amino}(3-pyridyl))carbonylamino]methyl}azetidinyl)(1S)-1-(hydroxymethyl)-2-oxoethyl](tert-butoxy)carboxamide |
| 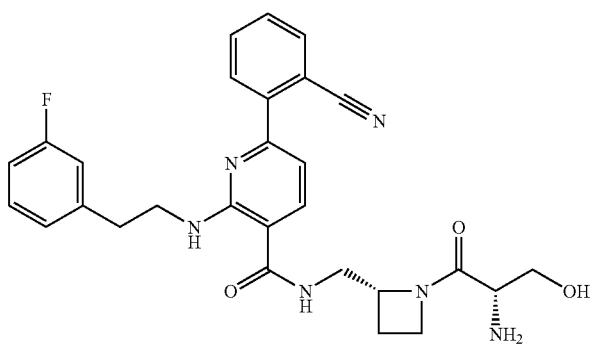<br>Compound 703 | N-{[(2R)-1-((2S)-2-amino-3-hydroxypropanoyl)azetidin-2-yl]methyl}(6-(2-cyanophenyl)-2-{[2-(3-fluorophenyl)ethyl]amino}(3-pyridyl))carboxamide |
| 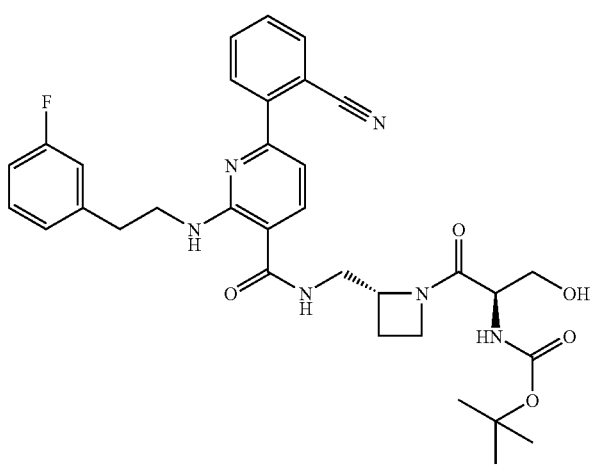<br>Compound 704 | N-[(1R)-2-((2R)-2-{[(6-(2-cyanopheny)-2-{[2-(3-fluorophenyl)ethyl]amino}(3-pyridyl))carbonylamino]methyl}azetidinyl)-1-(hydroxymethyl)-2-oxoethyl](tert-butoxy)carboxamide |

-continued

| COMPOUND | CHEMICAL NAME |
|---|---|
| 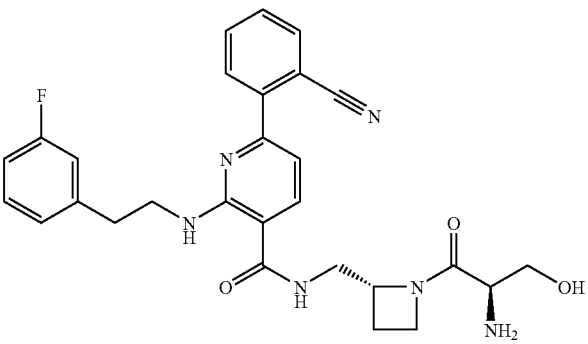<br>Compound 705 | N-{[(2R)-1-((2R)-2-amino-3-hydroxypropanoyl)azetidin-2-yl]methyl}(6-(2-cyanophenyl)-2{[2-(3-fluorophenyl)ethyl]amino}(3-pyridyl))carboxamide |
| 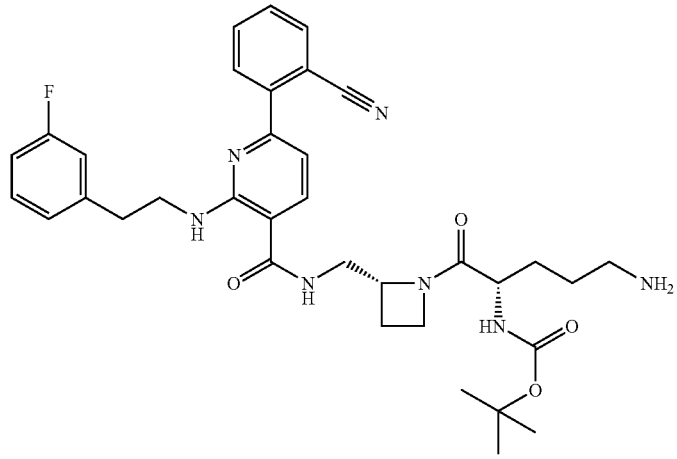<br>Compound 706 | N-[2-((2R)-2-{[(6-(2-cyanophenyl)-2-{[2-(3-fluorophenyl)ethyl]amino}(3-pyridyl))carbonylamino]methyl}azetidinyl)(1S)-1-(3-aminopropyl)-2-oxoethyl](tert-butoxy)carboxamide |
| 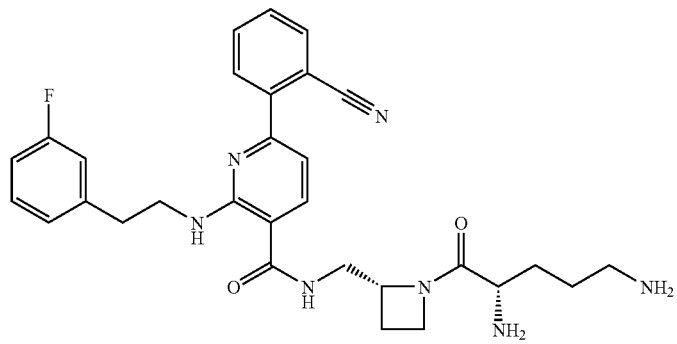<br>Compound 707 | N-{[(2R)-1-((2S)-2,5-diaminopentanoyl)azetidin-2-yl]methyl}(6-(2-cyanophenyl)-2-{[2-(3-fluorophenyl)ethyl]amino}(3-pyridyl))carboxamide |

| COMPOUND | CHEMICAL NAME |
|---|---|
| Compound 708 | N-{[(2R)-1-(2-hydroxyacetyl)azetidin-2-yl]methyl}(2-{[2-(3-fluorophenyl)ethyl]amino}-6-pyrazol-4-yl(3-pyridyl))carboxamide |
| Compound 709 | N-[((2R)-1-{2-[(tert-butoxy)carbonylamino]acetyl}azetidin-2-yl)methyl](2-{[2-(3-fluorophenyl)ethyl]amino}-6-pyrazol-4-yl(3-pyridyl))carboxamide |
| Compound 710 | N-{[(2R)-1-(2-aminoacetyl)azetidin-2-yl]methyl}(2-{[2-(3-fluorophenyl)ethyl]amino}-6-pyrazol-4-yl(3-pyridyl))carboxamide |
| Compound 718 | N-[(6-bromo(2-pyridyl))methyl](2-{[2-(3-fluorophenyl)ethyl]amino}-6-pyrazol-4-yl(3-pyridyl))carboxamide |

| COMPOUND | CHEMICAL NAME |
|---|---|
| 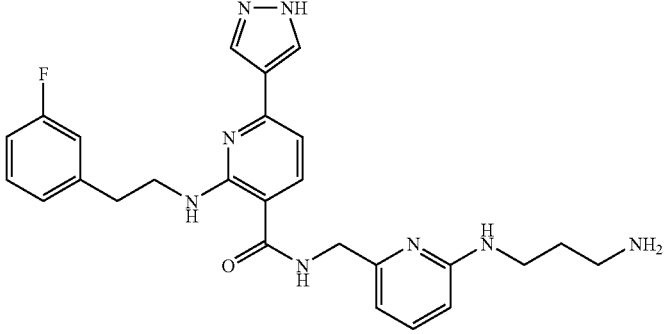<br>Compound 719 | N-({6-[(3-aminopropyl)amino](2-pyridyl)}methyl)(2-{[2-(3-fluorophenyl)ethyl]amino}-6-pyrazol-4-yl(3-pyridyl))carboxamide |
| 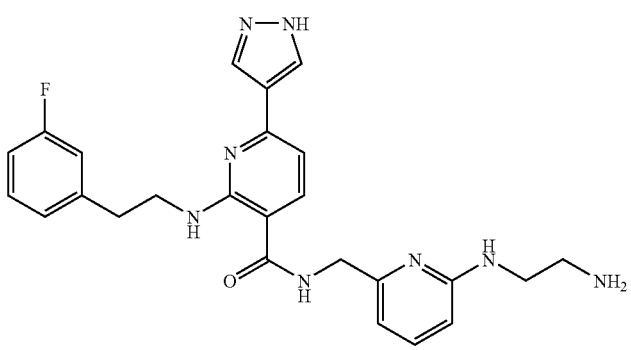<br>Compound 720 | N-({6-[(2-aminoethyl)amino](2-pyridyl)}methyl)(2-{[2-(3-fluorophenyl)ethyl]amino}-6-pyrazol-4-yl(3-pyridyl))carboxamide |
| 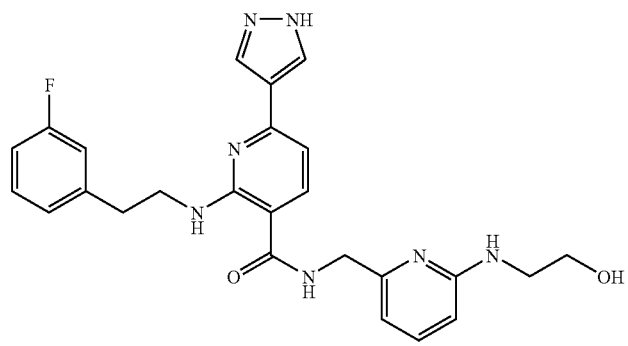<br>Compound 721 | (2-{[2-(3-fluorophenyl)ethyl]amino}-6-pyrzaol-4-yl(3-pyridyl))-N-({6-[(2-hydroxyethyl)amino](2-pyridyl)}methyl)carboxamide |
| 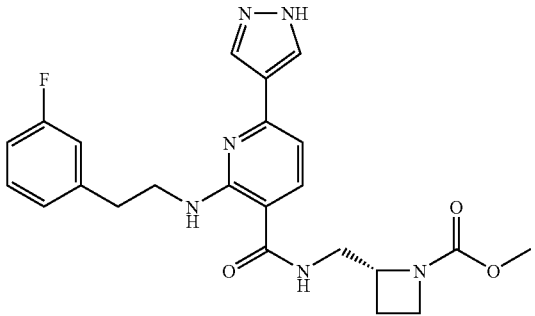<br>Compound 722 | methyl (2R)-2-{[(2-{[2-(3-fluorophenyl)ethyl]amino}-6-pyrazol-4-yl(3-pyridyl))carbonylamino]methyl}azetidinecarboxylate |

| COMPOUND | CHEMICAL NAME |
|---|---|
| 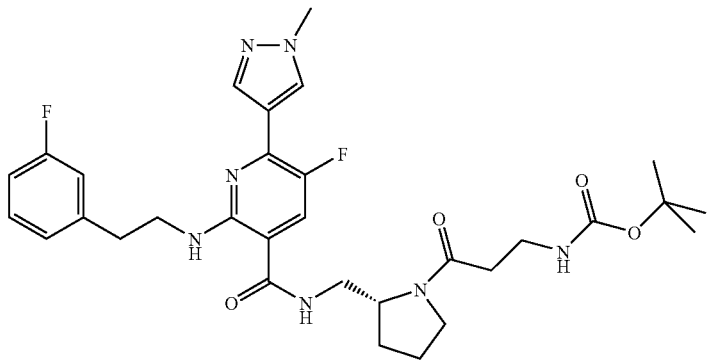<br>Compound 723 | N-[((2R)-1-{3-[(tert-butoxy)carbonylamino]propanoyl}pyrrolidin-2-yl)methyl](5-fluoro-2-{[2-(3-fluorophenyl)ethyl]amino}-6-(1-methylpyrazol-4-yl)(3-pyridyl))carboxamide |
| 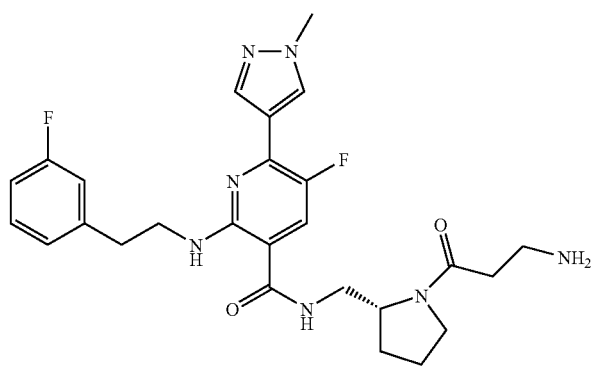<br>Compound 724 | N-{[(2R)-1-(3-aminopropanoyl)pyrrolidin-2-yl]methyl}(5-fluoro-2-{[2-(3-fluorophenyl)ethyl]amino}-6-(1-methylpyrazol-4-yl)(3-pyridyl))carboxamide |
| 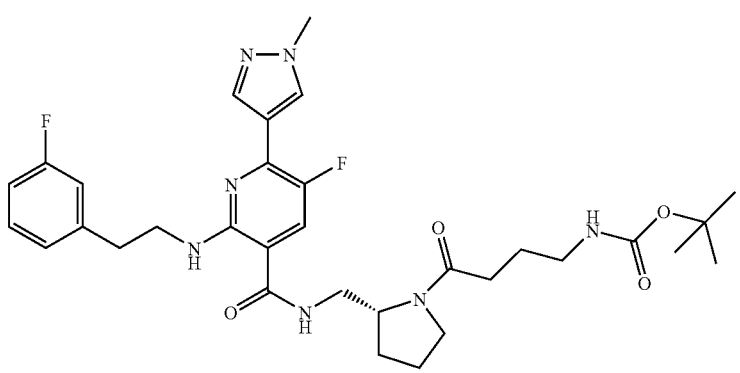<br>Compound 725 | N-[((2R)-1-{4-[(tert-butoxy)carbonylamino]butanoyl}pyrrolidin-2-yl)methyl](5-fluoro-2-{[2-(3-fluorophenyl)ethyl]amino}-6-(1-methylpyrazol-4-yl)(3-pyridyl))carboxamide |

| COMPOUND | CHEMICAL NAME |
|---|---|
| 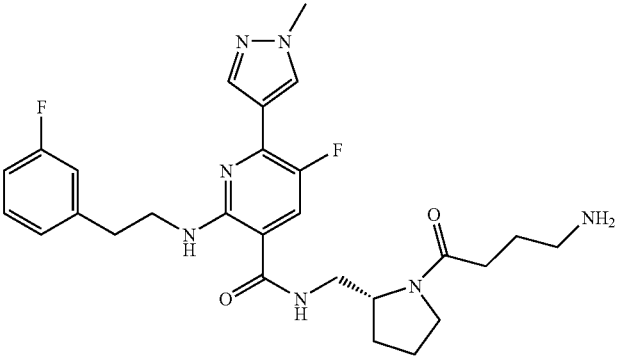

Compound 726 | N-{[(2R)-1-(4-aminobutanoyl)pyrrolidin-2-yl]methyl}(5-fluoro-2-{[2-(3-fluorophenyl)ethyl]amino}-6-(1-methylpyrazol-4-yl)(3-pyridyl))carboxamide |
| 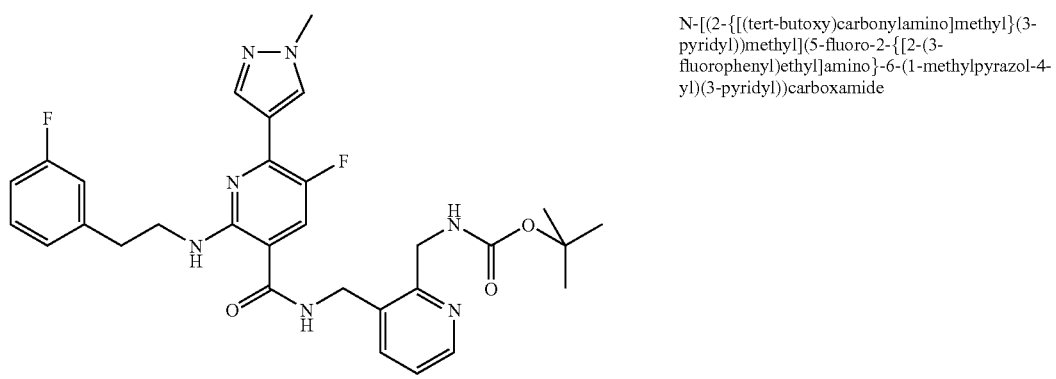

Compound 727 | N-[(2-{[(tert-butoxy)carbonylamino]methyl}(3-pyridyl))methyl](5-fluoro-2-{[2-(3-fluorophenyl)ethyl]amino}-6-(1-methylpyrazol-4-yl)(3-pyridyl))carboxamide |
| 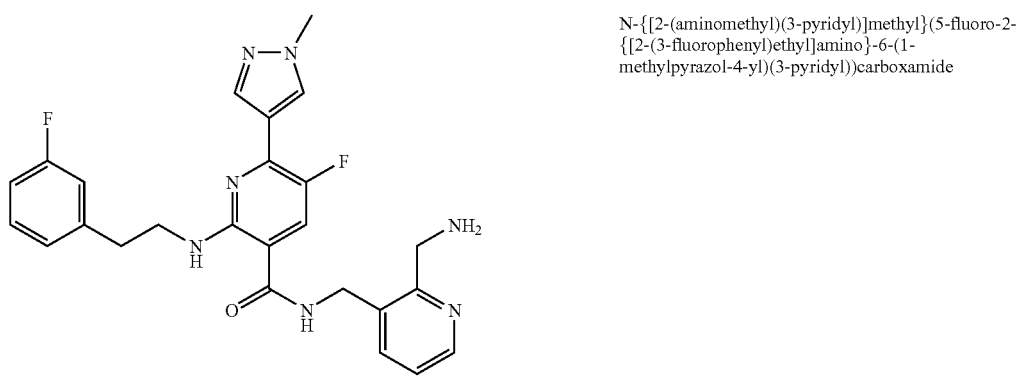

Compound 728 | N-{[2-(aminomethyl)(3-pyridyl)]methyl}(5-fluoro-2-{[2-(3-fluorophenyl)ethyl]amino}-6-(1-methylpyrazol-4-yl)(3-pyridyl))carboxamide |

| COMPOUND | CHEMICAL NAME |
|---|---|
| 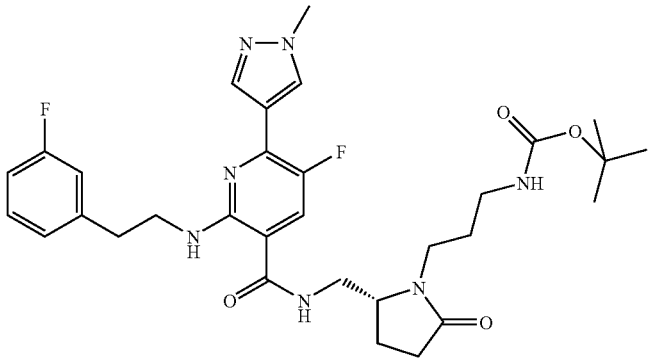<br>Compound 729 | N-[((2R)-1-{3-[(tert-butoxy)carbonylamino]propyl}-5-oxopyrrolidin-2-yl)methyl](5-fluoro-2-{[2-(3-fluorophenyl)ethyl]amino}-6-(1-methylpyrazol-4-yl)(3-pyridyl))carboxamide |
| 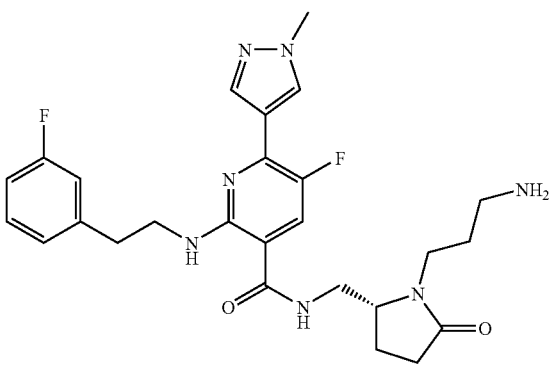<br>Compound 730 | N-{[(2R)-1-(3-aminopropyl)-5-oxopyrrolidin-2-yl]methyl}(5-fluoro-2-{[2-(3-fluorophenyl)ethyl]amino}-6-(1-methylpyrazol-4-yl)(3-pyridyl))carboxamide |
| 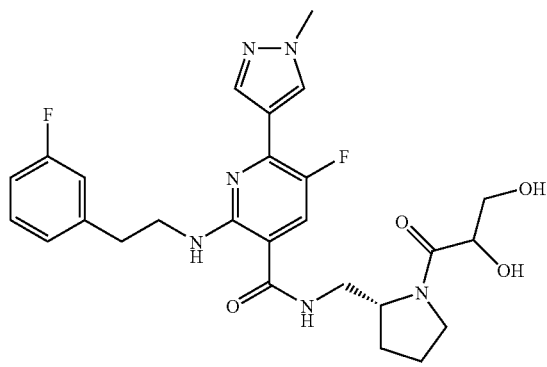<br>Compound 731 | N-{[(2R)-1-(2,3-dihydroxypropanoyl)pyrrolidin-2-yl]methyl}(5-fluoro-2-{[2-(3-fluorophenyl)ethyl]amino}-6-(1-methylpyrazol-4-yl)(3-pyridyl))carboxamide |

-continued

| COMPOUND | CHEMICAL NAME |
|---|---|
| 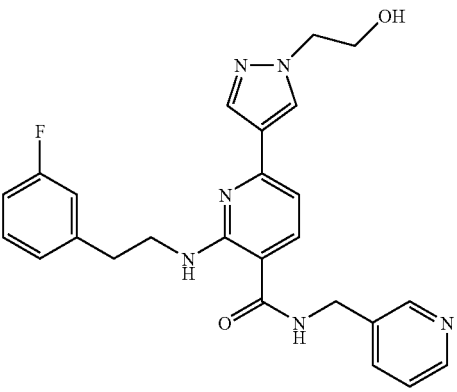<br>Compound 732 | (2-{[2-(3-fluorophenyl)ethyl]amino}-6-[1-(2-hydroxyethyl)pyrazol-4-yl](3-pyridyl))-N-(3-pyridylmethyl)carboxamide |
| 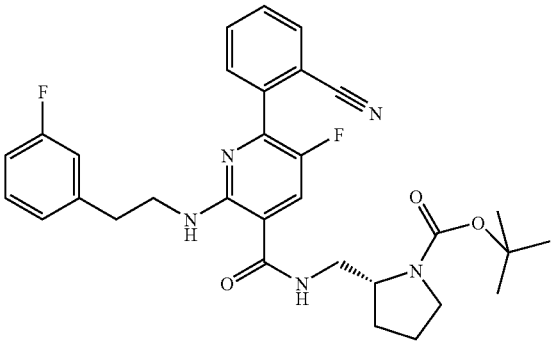<br>Compound 733 | tert-butyl (2R)-2-{[(6-(2-cyanophenyl)-5-fluoro-2-{[2-(3-fluorophenyl)ethyl]amino}(3-pyridyl))carbonylamino]methyl}pyrrolidinecarboxylate |
| 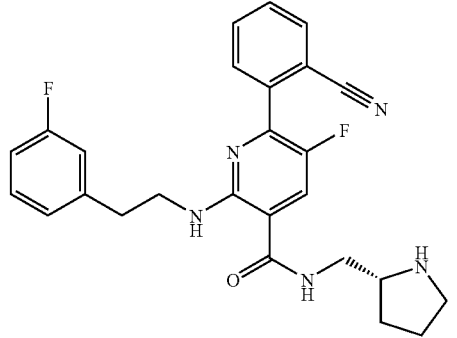<br>Compound 734 | N-[((2R)pyrrolidin-2-yl)methyl](6-(2-cyanophenyl)-5-fluoro-2-{[2-(3-fluorophenyl)ethyl]amino}(3-pyridyl))carboxamide |

| COMPOUND | CHEMICAL NAME |
|---|---|
| 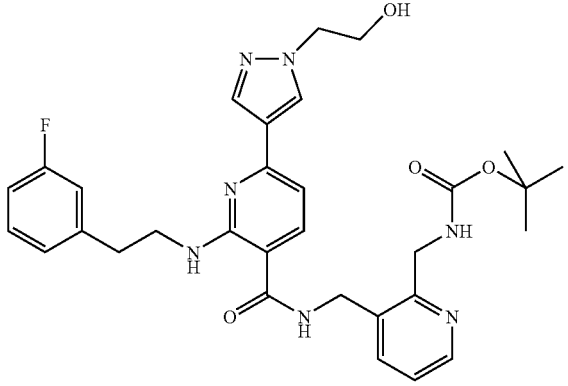<br>Compound 735 | N-[(2-{[(tert-butoxy)carbonylamino]methyl}(3-pyridyl))methyl](2-(3-fluorophenyl)ethyl]amino}-6-[1-(2-hydroxyethyl)pyrazol-4-yl](3-pyridyl))carboxamide |
| 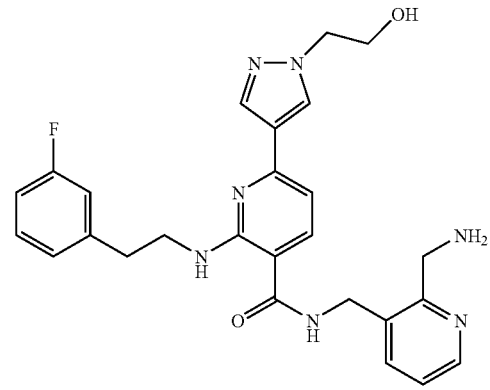<br>Compound 736 | N-{[2-(aminomethyl)(3-pyridyl)]methyl}(2-{[2-(3-fluorophenyl)ethyl]amino}-6-[1-(2-hydroxyethyl)pyrazol-4-yl](3-pyridyl))carboxamide |
| 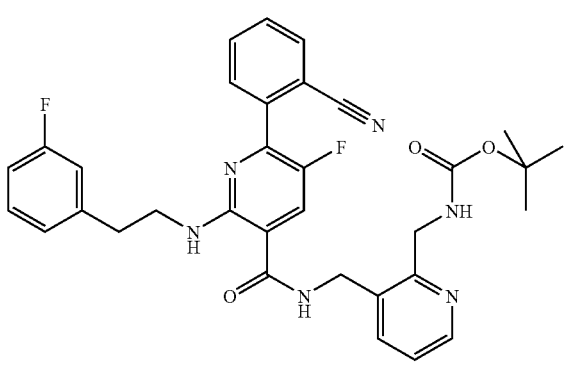<br>Compound 737 | N-[(2-{[(tert-butoxy)carbonylamino]methyl}(3-pyridyl))methyl](6-(2-cyanophenyl)-5-fluoro-2-{[2-(3-fluorophenyl)ethyl]amino}(3-pyridyl))carboxamide |

| COMPOUND | CHEMICAL NAME |
|---|---|
| 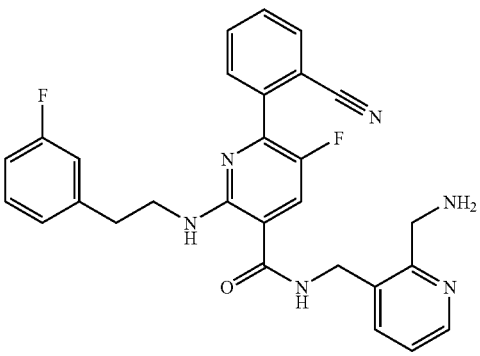<br>Compound 738 | N-{[2-(aminomethyl)(3-pyridyl)]methyl}(6-(2-cyanophenyl)-5-fluoro-2-{[2-(3-fluorophenyl)ethyl]amino}(3-pyridyl))carboxamide |
| 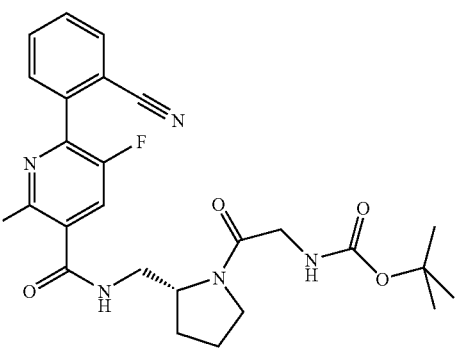<br>Compound 739 | N-[((2R)-1-{2-[(tert-butoxy)carbonylamino]acetyl}pyrrolidin-2-yl)methyl](6-(2-cyanophenyl)-5-fluoro-2-{[2-(3-fluorophenyl)ethyl]amino}(3-pyridyl))carboxamide |
| 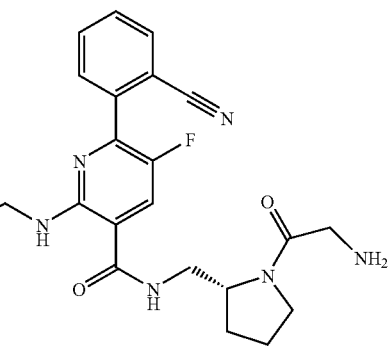<br>Compound 740 | N-{[(2R)-1-(2-aminoacetyl)pyrrolidin-2-yl]methyl}(6-(2-cyanophenyl)-5-fluoro-2-{[2-(3-fluorophenyl)ethyl]amino}(3-pyridyl))carboxamide |
| 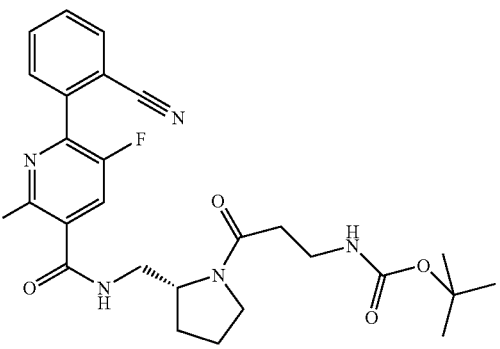<br>Compound 741 | N-[((2R)-1-{3-[(tert-butoxy)carbonylamino]propanoyl}pyrrolidin-2-yl)methyl](6-(2-cyanophenyl)-5-fluoro-2-{[2-(3-fluorophenyl)ethyl]amino}(3-pyridyl))carboxamide |

| COMPOUND | CHEMICAL NAME |
|---|---|
| 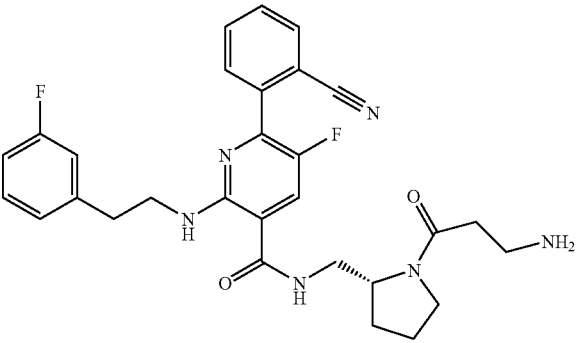

Compound 742 | N-{[(2R)-1-(3-aminopropanoyl)pyrrolidin-2-yl]methyl}(6-(2-cyanophenyl)-5-fluoro-2-{[2-(3-fluorophenyl)ethyl]amino}(3-pyridyl))carboxamide |
| 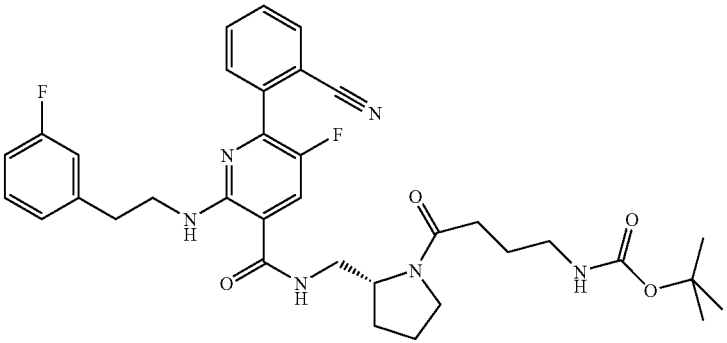

Compound 743 | N-[((2R)-1-{4-[(tert-butoxy)carbonylamino]butanoyl}pyrrolidin-2-yl)methyl](6-(2-cyanophenyl)-5-fluoro-2-{[2-(3-fluorophenyl)ethyl]amino}(3-pyridyl))carboxamide |
| 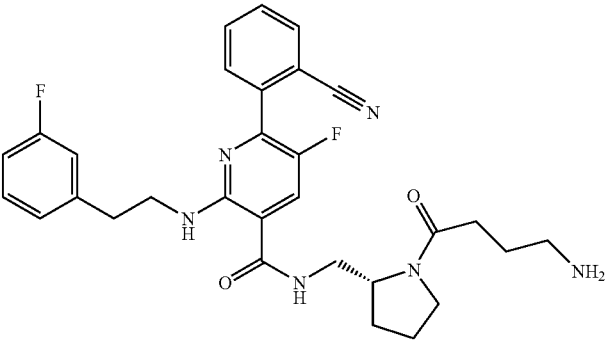

Compound 744 | N-{[(2R)-1-(4-aminobutanoyl)pyrrolidin-2-yl]methyl}(6-(2-cyanophenyl)-5-fluoro-2-{[2-(3-fluorophenyl)ethyl]amino}(3-pyridyl))carboxamide |

| COMPOUND | CHEMICAL NAME |
|---|---|
| 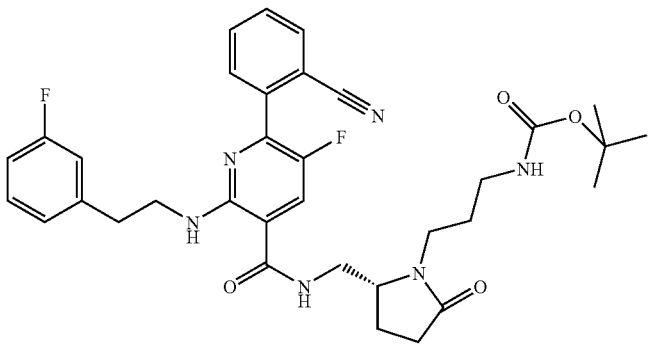

Compound 754 | N-[((2R)-1-{3-[(tert-butoxy)carbonylamino]propyl}-5-oxopyrrolidin-2-yl)methyl](6-(2-cyanophenyl)-5-fluoro-2-{[2-(3-fluorophenyl)ethyl]amino}(3-pyridyl))carboxamide |
| 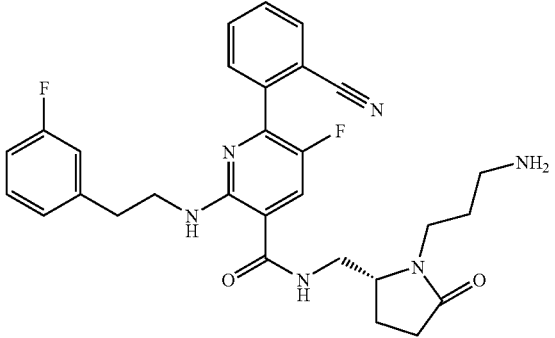

Compound 755 | N-{[(2R)-1-(3-aminopropyl)-5-oxopyrrolidin-2-yl]methyl}(6-(2-cyanophenyl)-5-fluoro-2-{[2-(3-fluorophenyl)ethyl]amino}(3-pyridyl))carboxamide |
| 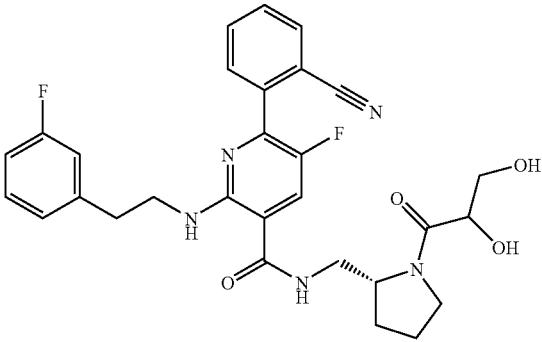

Compound 756 | N-{[(2R)-1-(2,3-dihydroxypropanoyl)pyrrolidin-2-yl]methyl}(6-(2-cyanophenyl)-5-fluoro-2-{[2-(3-fluorophenyl)ethyl]amino}(3-pyridyl))carboxamide |

-continued

| COMPOUND | CHEMICAL NAME |
|---|---|
| 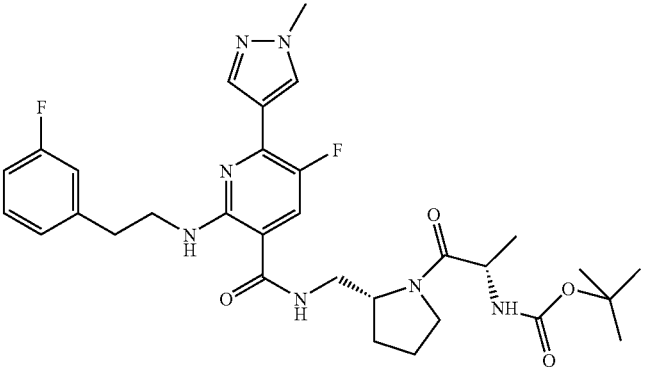<br>Compound 764 | N-[2-((2R)-2-{[(5-fluoro-2-{[2-(3-fluorophenyl)ethyl]amino}-6-(1-methylpyrazol-4-yl)(3-pyridyl))carbonylamino]methyl}pyrrolidinyl)(1S)-1-methyl-2-oxoethyl](tert-butoxy)carboxamide |
| 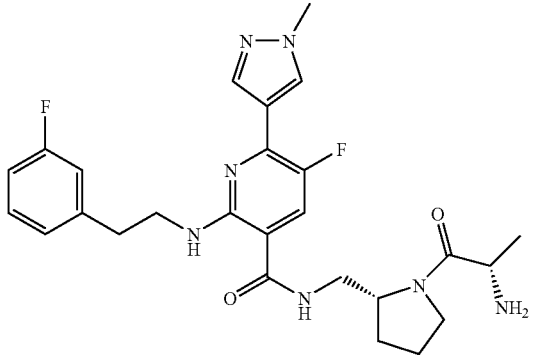<br>Compound 765 | N-{[(2R)-1-((2S)-2-aminopropanoyl)pyrrolidin-2-yl]methyl}(5-fluoro-2-{[2-(3-fluorophenyl)ethyl]amino}-6-(1-methylpyrazol-4-yl)(3-pyridyl))carboxamide |
| 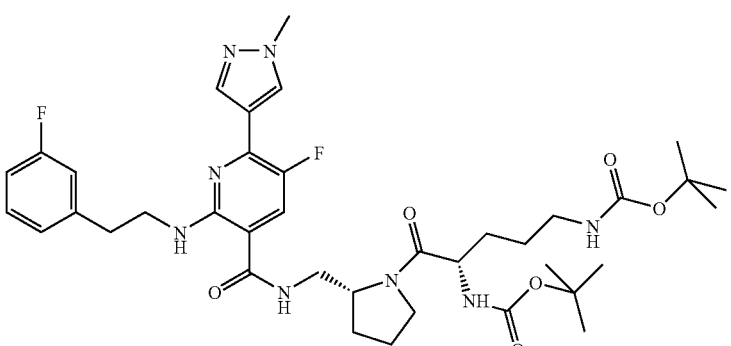<br>Compound 766 | N-[((2R)-1-{(2S)-2,5-bis[(tert-butoxy)carbonylamino]pentanoyl}pyrrolidin-2-yl)methyl](5-fluoro-2-{[2-(3-fluorophenyl)ethyl]amino}-6-(1-methylpyrazol-4-yl)(3-pyridyl))carboxamide |

| COMPOUND | CHEMICAL NAME |
|---|---|
| 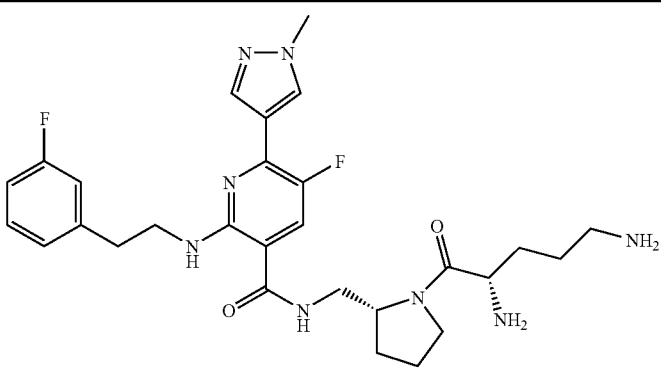<br>Compound 767 | N-{[(2R)-1-((2S)-2,5-diaminopentanoyl)pyrrolidin-2-yl]methyl}(5-fluoro-2-{[2-(3-fluorophenyl)ethyl]amino}-6-(1-methylpyrazol-4-yl)(3-pyridyl))carboxamide |
| 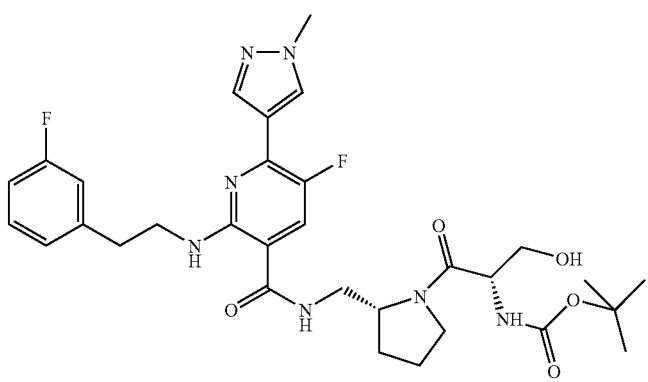<br>Compound 768 | N-[2-((2R)-2-{[(5-fluoro-2-{[2-(3-fluorophenyl)ethyl]amino}-6-(1-methylpyrazol-4-yl)(3-pyridyl))carbonylamino]methyl}pyrrolidinyl)(1S)-1-(hydroxymethyl)-2-oxoethyl](tert-butoxy)carboxamide |
| 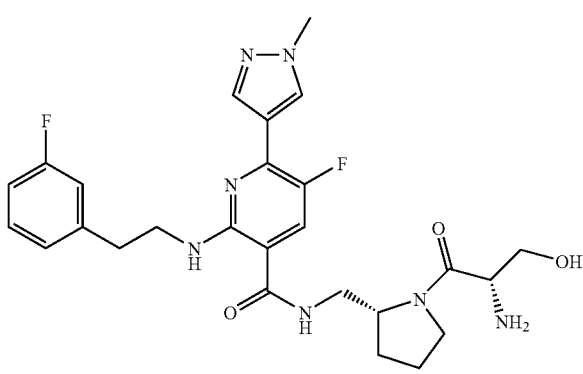<br>Compound 769 | N-{[(2R)-1-((2S)-2-amino-3-hydroxypropanoyl)pyrrolidin-2-yl]methyl}(5-fluoro-2-{[2-(3-fluorophenyl)ethyl]amino}-6-(1-methylpyrazol-4-yl)(3-pyridyl))carboxamide |

| COMPOUND | CHEMICAL NAME |
|---|---|
| 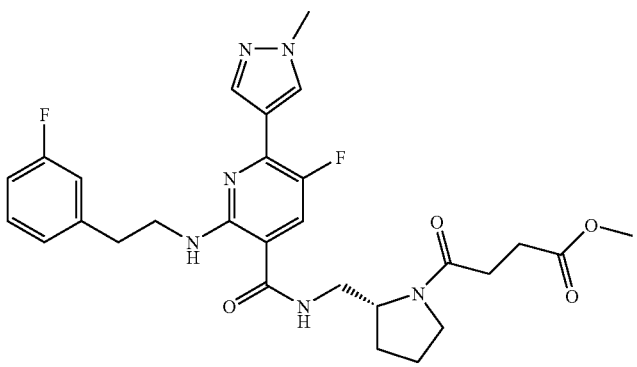<br>Compound 770 | methyl 4-((2R)-2-{[(5-fluoro-2-{[2-(3-fluorophenyl)ethyl]amino}-6-(1-methylpyrazol-4-yl)(3-pyridyl))carbonylamino]methyl}pyrrolidinyl)-4-oxobutanoate |
| 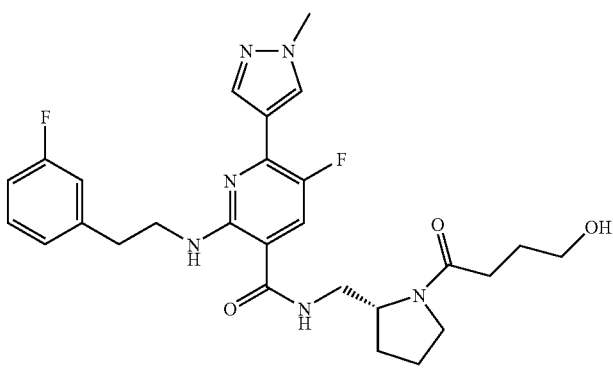<br>Compound 771 | N-{[(2R)-1-(4-hydroxybutanoyl)pyrrolidin-2-yl]methyl}(5-fluoro-2-{[2-(3-fluorophenyl)ethyl]amino}-6-(1-methylpyrazol-4-yl)(3-pyridyl))carboxamide |
| 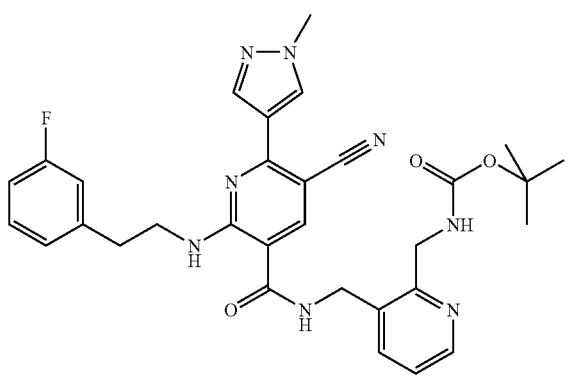<br>Compound 781 | N-[(2-{[(tert-butoxy)carbonylamino]methyl}(3-pyridyl))methyl](5-cyano-2-{[2-(3-fluorophenyl)ethyl]amino}-6-(1-methylpyrazol-4-yl)(3-pyridyl))carboxamide |

| COMPOUND | CHEMICAL NAME |
|---|---|
| 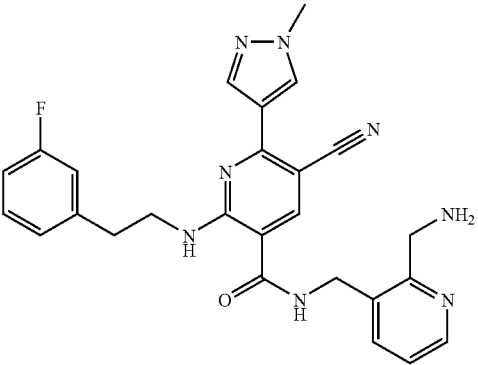

Compound 782 | N-{[2-(aminomethyl)(3-pyridyl)]methyl}(5-cyano-2-{[2-(3-fluorophenyl)ethyl]amino}-6-(1-methylpyrazol-4-yl)(3-pyridyl))carboxamide |
| 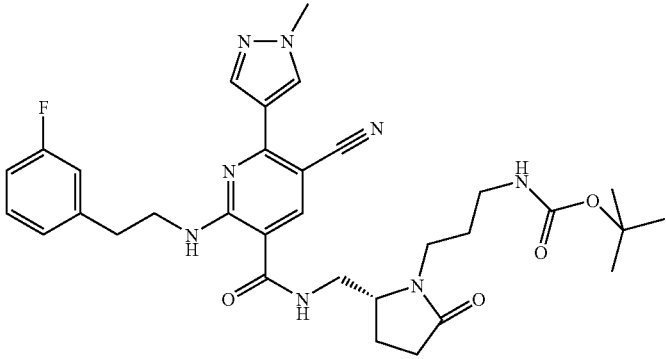

Compound 783 | N-[3-((5R)-5-{[(5-cyano-2-{[2-(3-fluorophenyl)ethyl]amino}-6-(1-methylpyrazol-4-yl)(3-pyridyl))carbonylamino]methyl}-2-oxopyrrolidinyl)propyl](tert-butoxy)carboxamide |
| 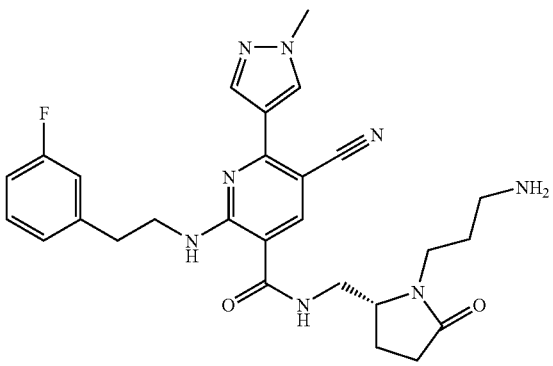

Compound 784 | N-{[(2R)-1-(3-aminopropyl)-5-oxopyrrolidin-2-yl]methyl}(5-cyano-2-{[2-(3-fluorophenyl)ethyl]amino}-6-(1-methylpyrazol-4-yl)(3-pyridyl))carboxamide |

| COMPOUND | CHEMICAL NAME |
|---|---|
| Compound 785 | tert-butyl (2R)-2-{[(5-cyano-2-{[2-(3-fluorophenyl)ethyl]amino}-6-(1-methylpyrazol-4-yl)(3-pyridyl))carbonylamino]methyl}pyrrolidinecarboxylate |
| Compound 786 | N-[((2R)pyrrolidin-2-yl)methyl](5-cyano-2-{[2-(3-fluorophenyl)ethyl]amino}-6-(1-methylpyrazol-4-yl)(3-pyridyl))carboxamide |
| Compound 788 | N-[((2R)-1-{4-[(tert-butoxy)carbonylamino]butanoyl}pyrrolidin-2-yl)methyl](5-cyano-2-{[2-(3-fluorophenyl)ethyl]amino}-6-(1-methylpyrazol-4-yl)(3-pyridyl))carboxamide |

| COMPOUND | CHEMICAL NAME |
|---|---|
| 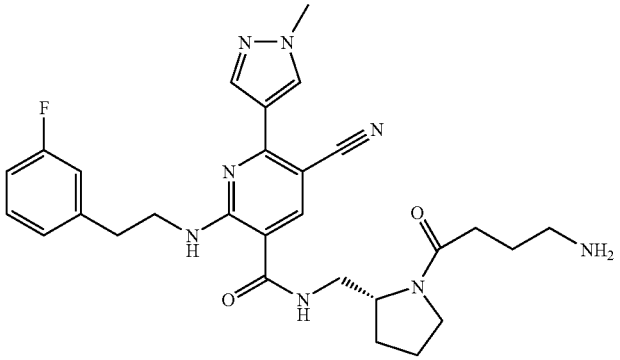<br>Compound 789 | N-{[(2R)-1-(4-aminobutanoyl)pyrrolidin-2-yl]methyl}(5-cyano-2-{[2-(3-fluorophenyl)ethyl]amino}-6-(1-methylpyrazol-4-yl)(3-pyridyl))carboxamide |
| 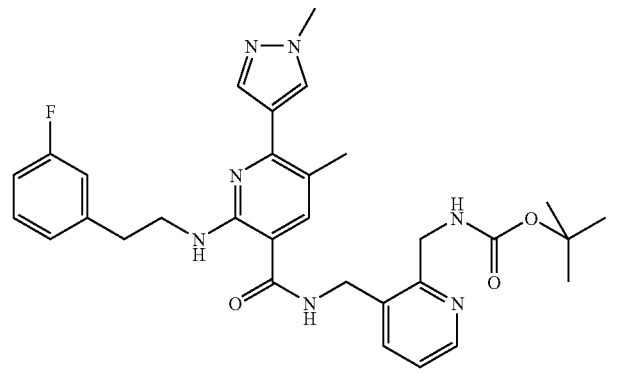<br>Compound 790 | N-[(2-{[(tert-butoxy)carbonylamino]methyl}(3-pyridyl))methyl](2-{[2-(3-fluorophenyl)ethyl]amino}-5-methyl-6-(1-methylpyrazol-4-yl)(3-pyridyl))carboxamide |
| 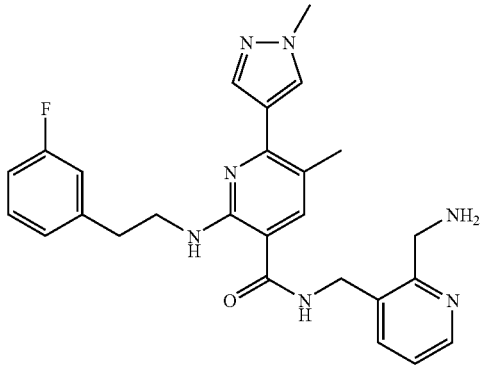<br>Compound 791 | N-{[2-(aminomethyl)(3-pyridyl)]methyl}(2-{[2-(3-fluorophenyl)ethyl]amino}-5-methyl-6-(1-methylpyrazol-4-yl)(3-pyridyl))carboxamide |

-continued

| COMPOUND | CHEMICAL NAME |
|---|---|
| 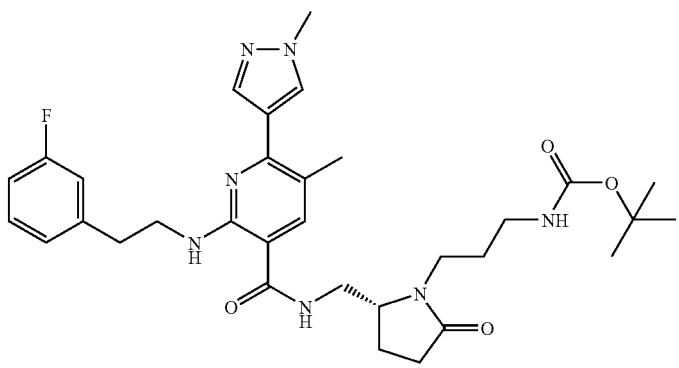  Compound 792 | N-[((2R)-1-{3-[(tert-butoxy)carbonylamino]propyl}-5-oxopyrrolidin-2-yl)methyl](2-{[2-(3-fluorophenyl)ethyl]amino}-5-methyl-6-(1-methylpyrazol-4-yl)(3-pyridyl))carboxamide |
| 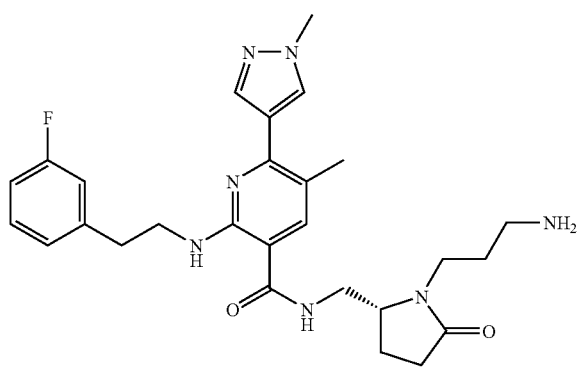  Compound 793 | N-{[(2R)-1-(3-aminopropyl)-5-oxopyrrolidin-2-yl]methyl}(2-{[2-(3-fluorophenyl)ethyl]amino}-5-methyl-6-(1-methylpyrazol-4-yl)(3-pyridyl))carboxamide |
| 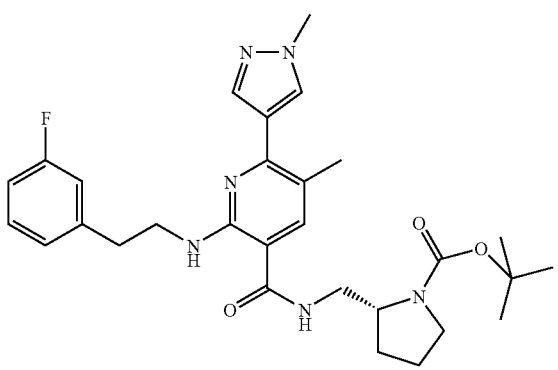  Compound 794 | tert-butyl (2R)-2-{[(2-{[2-(3-fluorophenyl)ethyl]amino}-5-methyl-6-(1-methylpyrazol-4-yl)(3-pyridyl))carbonylamino]methyl}pyrrolidinecarboxylate |

-continued

| COMPOUND | CHEMICAL NAME |
|---|---|
| Compound 795 | N-[((2R)pyrrolidin-2-yl)methyl](2-{[2-(3-fluorophenyl)ethyl]amino}-5-methyl-6-(1-methylpyrazol-4-yl)(3-pyridyl))carboxamide |
| Compound 796 | N-[((2R)-1-{4-[(tert-butoxy)carbonylamino]butanoyl}pyrrolidin-2-yl)methyl](2-{[2-(3-fluorophenyl)ethyl]amino}-5-methyl-6-(1-methylpyrazol-4-yl)(3-pyridyl))carboxamide |
| Compound 797 | N-{[(2R)-1-(4-aminobutanoyl)pyrrolidin-2-yl]methyl}(2-{[2-(3-fluorophenyl)ethyl]amino}-5-methyl-6-(1-methylpyrazol-4-yl)(3-pyridyl))carboxamide |
| Compound 798 | tert-butyl (2R)-2-{[(5-cyano-2-{[2-(3-fluorophenyl)ethyl]amino}-6-pyrazol-4-yl(3-pyridyl))carbonylamino]methyl}pyrrolidinecarboxylate |

| COMPOUND | CHEMICAL NAME |
|---|---|
| 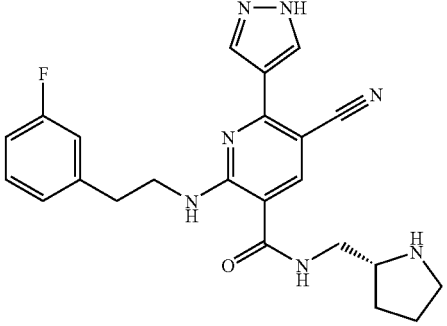
Compound 799 | N-[((2R)pyrrolidin-2-yl)methyl](5-cyano-2-{[2-(3-fluorophenyl)ethyl]amino}-6-pyrazol-4-yl(3-pyridyl))carboxamide |
| 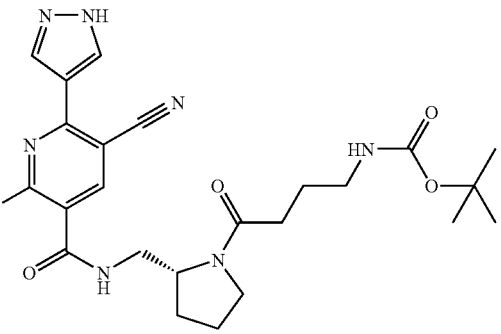
Compound 800 | N-[((2R)-1-{4-[(tert butoxy)carbonylamino]butanoyl}pyrrolidin-2-yl)methyl](5-cyano-2-{[2-(3-fluorophenyl)ethyl]amino}-6-pyrazol-4-yl(3-pyridyl))carboxamide |
| 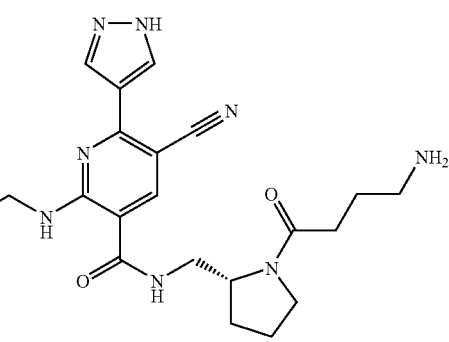
Compound 801 | N-{[(2R)-1-(4-aminobutanoyl)pyrrolidin-2-yl]methyl-}(5-cyano-2-{[2-(3-fluorophenyl)ethyl]amino}-6-pyrazol-4-yl(3-pyridyl))carboxamide |
| 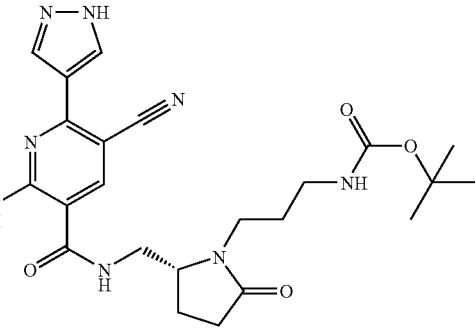
Compound 802 | N-[((2R)-1-{3-[(tert-butoxy)carbonylamino]propyl}-5-oxopyrrolidin-2-yl)methyl](5-cyano-2-{[2-(3-fluorophenyl)ethyl]amino}-6-pyrazol-4-yl(3-pyridyl))carboxamide |

-continued

| COMPOUND | CHEMICAL NAME |
|---|---|
| 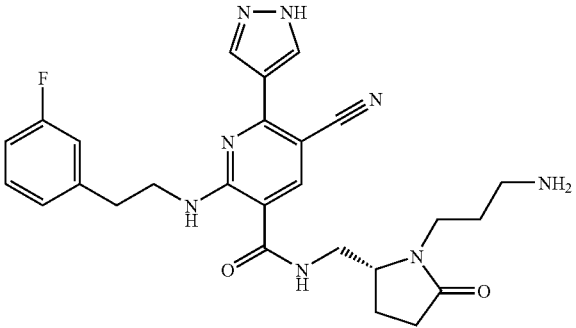<br>Compound 803 | N-{[(2R)-1-(3-aminopropyl)-5-oxopyrrolidin-2-yl]methyl}(5-cyano-2-{[2-(3-fluorophenyl)ethyl]amino}-6-pyrazol-4-yl(3-pyridyl))carboxamide |
| 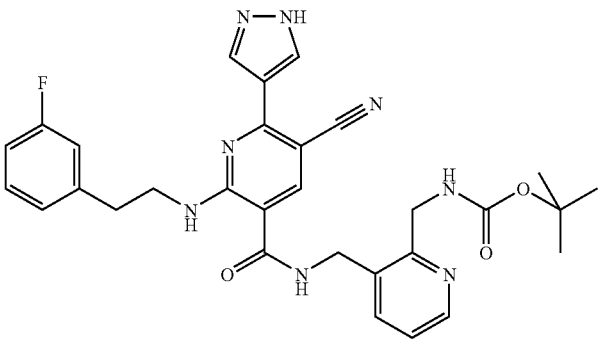<br>Compound 804 | N-[(2-{[(tert-butoxy)carbonylamino]methyl}(3-pyridyl))methyl](5-cyano-2-{[2-(3-fluorophenyl)ethyl]amino}-6-pyrazol-4-yl(3-pyridyl))carboxamide |
| 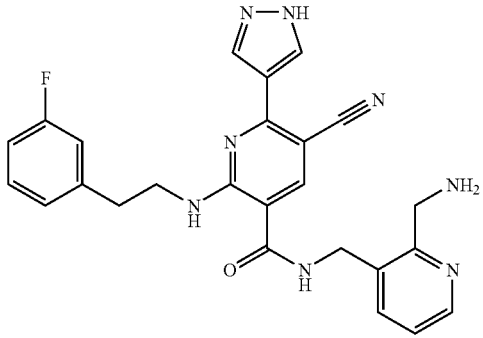<br>Compound 805 | N-{[2-(aminomethyl)(3-pyridyl)]methyl}(5-cyano-2-{[2-(3-fluorophenyl)ethyl]amino}-6-pyrazol-4-yl(3-pyridyl))carboxamide |
| 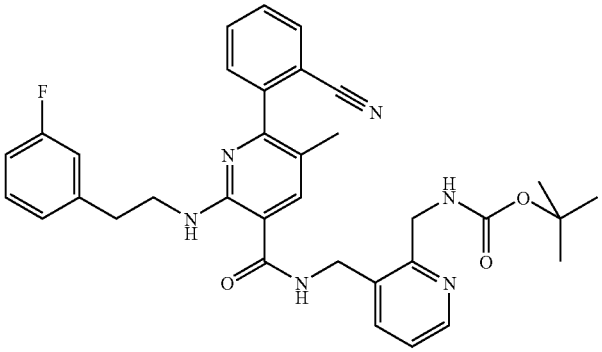<br>Compound 809 | N-[(2-{[(tert-butoxy)carbonylamino]methyl}(3-pyridyl))methyl](6-(2-cyanophenyl)-2-{[2-(3-fluorophenyl)ethyl]amino}-5-methyl(3-pyridyl))carboxamide |

| COMPOUND | CHEMICAL NAME |
|---|---|
| 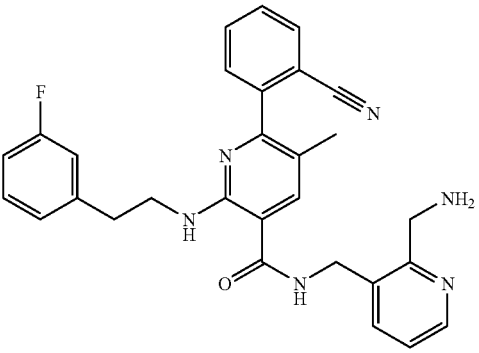<br>Compound 810 | N-{[2-(aminomethyl)(3-pyridyl)]methyl}(6-(2-cyanophenyl)-2-{[2-(3-fluorophenyl)ethyl]amino}-5-methyl(3-pyridyl))carboxamide |
| 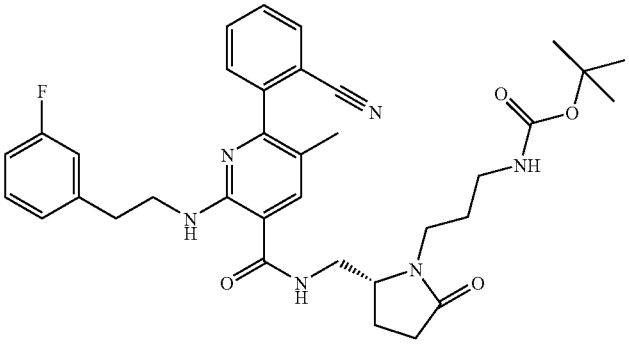<br>Compound 811 | N-[3-((5R)-5-{[(6-(2-cyanophenyl)-2-{[2-(3-fluorophenyl)ethyl]amino}-5-methyl(3-pyridyl))carbonylamino]methyl}-2-oxopyrrolidinyl)propyl](tert-butoxy)carboxamide |
| 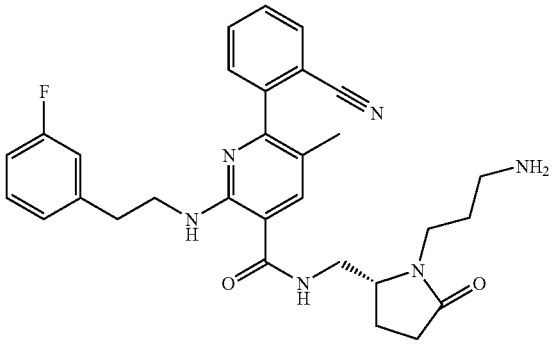<br>Compound 815 | N-{[(2R)-1-(aminopropyl)-5-oxopyrrolidin-2-yl]methyl}(6-(2-cyanophenyl)-2-{[2-(3-fluorophenyl)ethyl]amino}-5-methyl(3-pyridyl))carboxamide |
| 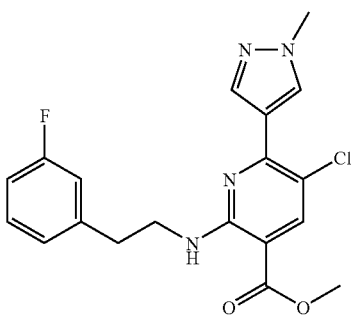<br>Compound 816 | methyl 5-chloro-2-{[2-(3-fluorophenyl)ethyl]amino}-6-(1-methylpyrazol-4-yl)pyridine-3-carboxylate |

-continued

| COMPOUND | CHEMICAL NAME |
|---|---|
| 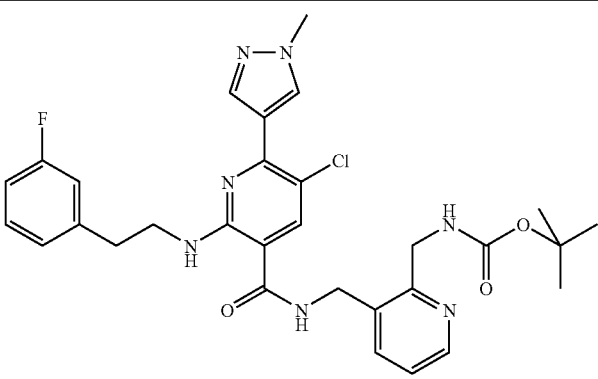

Compound 817 | N-[(2-{[(tert-butoxy)carbonylamino]methyl}(3-pyridyl))methyl](5-chloro-2-{[2-(3-fluorophenyl)ethyl]amino}-6-(1-methylpyrazol-4-yl)(3-pyridyl))carboxamide |
| 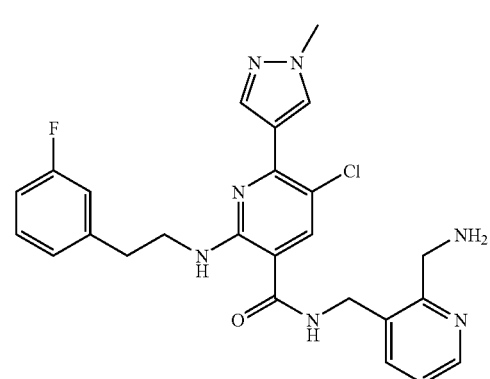

Compound 818 | N-{[2-(aminomethyl)(3-pyridyl)]methyl}(5-chloro-2-{[2-(3-fluorophenyl)ethyl]amino}-6-(1-methylpyrazol-4-yl)(3-pyridyl))carboxamide |
| 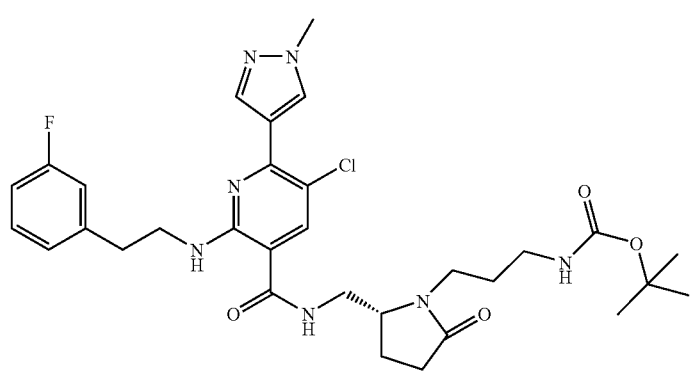

Compound 819 | N-[((2R)-1-{3-[(tert-butoxy)carbonylamino]propyl}-5-oxopyrrolidin-2-yl)methyl](5-chloro-2-{[2-(3-fluorophenyl)ethyl]amino}-6-(1-methylpyrazol-4-yl)(3-pyridyl))carboxamide |

-continued

| COMPOUND | CHEMICAL NAME |
|---|---|
| 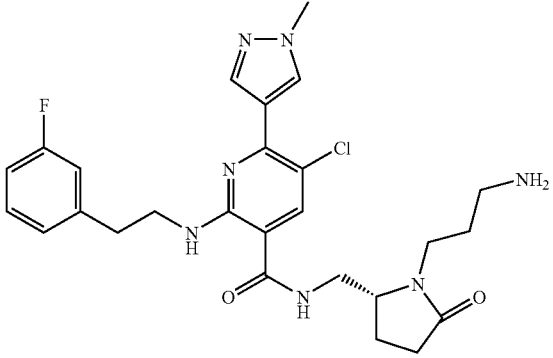  Compound 820 | N-{[(2R)-1-(3-aminopropyl)-5-oxopyrrolidin-2-yl]methyl}(5-chloro-2-{[2-(3-fluorophenyl)ethyl]amino}-6-(1-methylpyrazol-4-yl)(3-pyridyl))carboxamide |
| 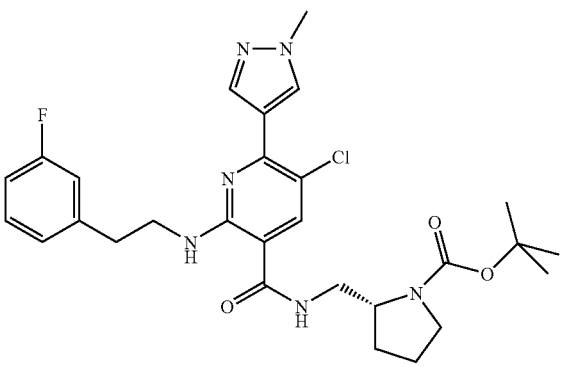  Compound 821 | tert-butyl (2R)-2-{[(5-chloro-2-{[2-(3-fluorophenyl)ethyl]amino}-6-(1-methylpyrazol-4-yl)(3-pyridyl))carbonylamino]methyl}pyrrolidinecarboxylate |
| 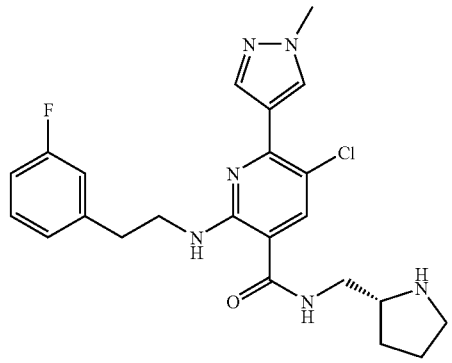  Compound 822 | N-[((2R)pyrrolidin-2-yl)methyl](5-chloro-2-{[2-(3-fluorophenyl)ethyl]amino}-6-(1-methylpyrazol-4-yl)(3-pyridyl))carboxamide |

| COMPOUND | CHEMICAL NAME |
|---|---|
| 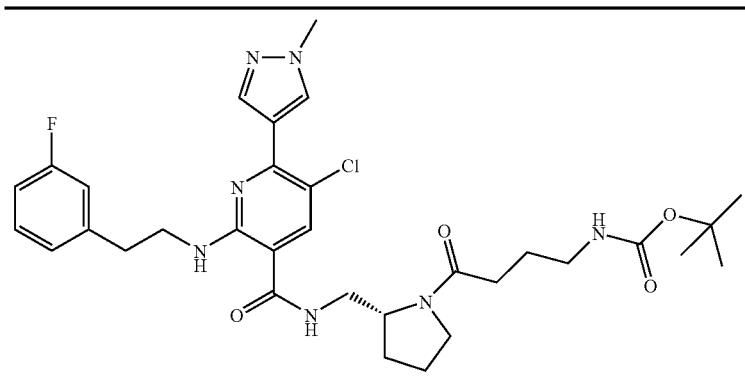<br>Compound 823 | N-[((2R)-1-{4-[((tert-butoxy)carbonylamino]butanoyl}pyrrolidin-2-yl)methyl](5-chloro-2-{[2-(3-fluorophenyl)ethyl]amino}-6-(1-methylpyrazol-4-yl)(3-pyridyl))carboxamide |
| 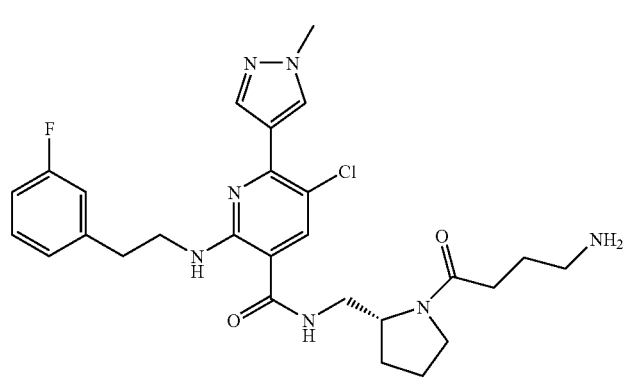<br>Compound 824 | N-{[(2R)-1-(4-aminobutanoyl)pyrrolidin-2-yl]methyl}(5-chloro-2-{[2-(3-fluorophenyl)ethyl]amino}-6-(1-methylpyrazol-4-yl)(3-pyridyl))carboxamide |
| 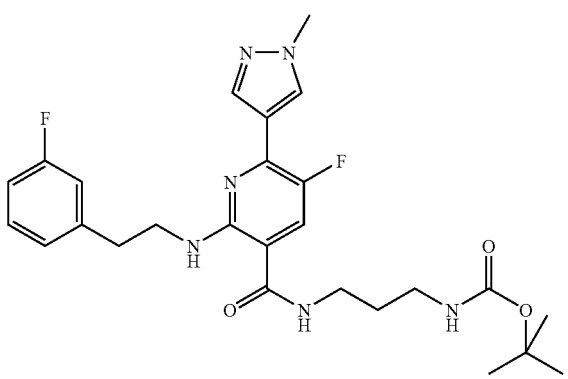<br>Compound 826 | N-{3-[(tert-butoxy)carbonylamino]propyl}(5-fluoro-2-{[2-(3-fluorophenyl)ethyl]amino}-6-(1-methylpyrazol-4-yl)(3-pyridyl))carboxamide |
| 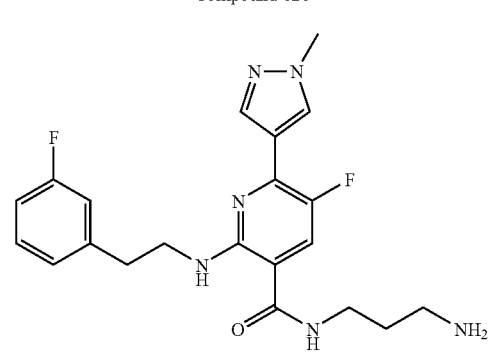<br>Compound 827 | N-(3-aminopropyl)(5-fluoro-2-{[2-(3-fluorophenyl)ethyl]amino}-6-(1-methylpyrazol-4-yl)(3-pyridyl))carboxamide |

| COMPOUND | CHEMICAL NAME |
|---|---|
| Compound 828 | methyl (2R)-3-[(5-fluoro-2-{[2-(3-fluorophenyl)ethyl]amino}-6-(1-methylpyrazol-4-yl)(3-pyridyl))carbonylamino]-2-methylpropanoate |
| Compound 829 | (2R)-3-[(5-fluoro-2-{[2-(3-fluorophenyl)ethyl]amino}-6-(1-methylpyrazol-4-yl)(3-pyridyl))carbonylamino]-2-methylpropanoic acid |
| Compound 838 | 2-[(tert-butoxy)carbonylamino]-N-{3-[(5-fluoro-2-{[2-(3-fluorophenyl)ethyl]amino}-6-(1-methylpyrazol-4-yl)(3-pyridyl))carbonylamino]propyl}acetamide |
| Compound 839 | 2-amino-N-{3-[(5-fluoro-2-{[2-(3-fluorophenyl)ethyl]amino}-6-(1-methylpyrazol-4-yl)(3-pyridyl))carbonylamino]propyl}acetamide |

| COMPOUND | CHEMICAL NAME |
|---|---|
| Compound 840 | N-{3-[(5-fluoro-2-{[2-(3-fluorophenyl)ethyl]amino}-6-(1-methylpyrazol-4-yl)-3-pyridyl)carbonylamino]propyl}acetamide |
| Compound 841 | N-((2R)-3-hydroxy-2-methylpropyl)(5-fluoro-2-{[2-(3-fluorophenyl)ethyl]amino}-6-(1-methylpyrazol-4-yl)(3-pyridyl))carboxamide |
| Compound 842 | N-((2R)-2-carbamoylpropyl)(5-fluoro-2-{[2-(3-fluorophenyl)ethyl]amino}-6-(1-methylpyrazol-4-yl)(3-pyridyl))carboxamide |
| Compound 843 | (2R)-3-[(5-fluoro-2-{[2-(3-fluorophenyl)ethyl]amino}-6-(1-methylpyrazol-4-yl)(3-pyridyl))carbonylamino]-2-methyl-N-methylpropanamide |

-continued

| COMPOUND | CHEMICAL NAME |
|---|---|
| Compound 844 | (5-fluoro-2-{[2-(3-fluorophenyl)ethyl]amino}-6-pyrazol-4-yl(3-pyridyl))-N-(pyrazol-3-ylmethyl)carboxamide |
| Compound 845 | (5-fluoro-2-{[2-(3-fluorophenyl)ethyl]amino}-6-(1-methylpyrazol-4-yl)(3-pyridyl))-N-(pyrazol-3-ylmethyl)carboxamide |
| Compound 853 | N-((2R)-4-diazo-2-methyl-4-azabur-4-enyl)(5-fluoro-2-{[2-(3-fluorophenyl)ethyl]amino}-6-(1-methylpyrazol-4-yl)(3-pyridyl))carboxamide |
| Compound 854 | 5-fluoro-2-{[2-(3-fluorophenyl)ethyl]amino}-6-(1-methylpyrazol-4-yl)(3-pyridyl)3-methylazetidinyl ketone |

| COMPOUND | CHEMICAL NAME |
|---|---|
| Compound 855 | N-((2S)-3-amino-2-methylpropyl)(5-fluoro-2-{[2-(3-fluorophenyl)ethyl]amino}-6-(1-methylpyrazol-4-yl)(3-pyridyl))carboxamide |
| Compound 856 | N-{(2R)-3-[(5-fluoro-2-{[2-(3-fluorophenyl)ethyl]amino}-6-(1-methylpyrazol-4-yl)(3-pyridyl))carbonylamino]-2-methylpropyl}-2-[(tert-butoxy)carbonylamino]acetamide |
| Compound 857 | N-{(2R)-3-[(5-fluoro-2-{[2-(3-fluorophenyl)ethyl]amino}-6-(1-methylpyrazol-4-yl)(3-pyridyl))carbonylamino]-2-methylpropyl}-2-aminoacetamide |
| Compound 858 | N-{(2R)-3-[(5-fluoro-2-{[2-(3-fluorophenyl)ethyl]amino}-6-(1-methylpyrazol-4-yl)(3-pyridyl))carbonylamino]-2-methylpropyl}-2-hydroxyacetamide |

| COMPOUND | CHEMICAL NAME |
|---|---|
| Compound 862 | tert-butyl (2R)-2-{[(5-fluoro-2-{[2-(3-fluorophenyl)ethyl]amino}-6-(1-methylpyrazol-4-yl)(3-pyridyl))carbonylamino]methyl}azetidinecarboxylate |
| Compound 863 | N-[((2R)azetidin-2-yl)methyl](5-fluoro-2-{[2-(3-fluorophenyl)ethyl]amino}-6-(1-methylpyrazol-4-yl)(3-pyridyl))carboxamide |
| Compound 864 | N-[((2R)-1-{2-[(tert-butoxy)carbonylamino]acetyl}azetidin-2-yl)methyl](5-fluoro-2-{[2-(3-fluorophenyl)ethyl]amino}-6-(1-methylpyrazol-4-yl)(3-pyridyl))carboxamide |
| Compound 865 | N-{[(2R)-1-(2-aminoacetyl)azetidin-2-yl]methyl}(5-fluoro-2-{[2-(3-fluorophenyl)ethyl]amino}-6-(1-methylpyrazol-4-yl)(3-pyridyl))carboxamide |

| COMPOUND | CHEMICAL NAME |
|---|---|
| 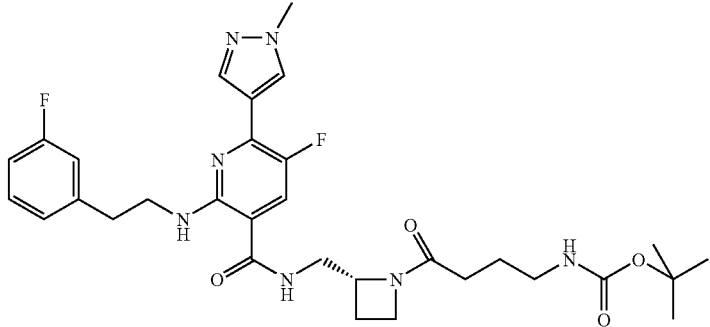
Compound 866 | N-[((2R)-1-{4-[(tert-butoxy)carbonylamino]butanoyl}azetidin-2-yl)methyl](5-fluoro-2-{[2-(3-fluorophenyl)ethyl]amino}-6-(1-methylpyrazol-4-yl)(3-pyridyl))carboxamide |
| 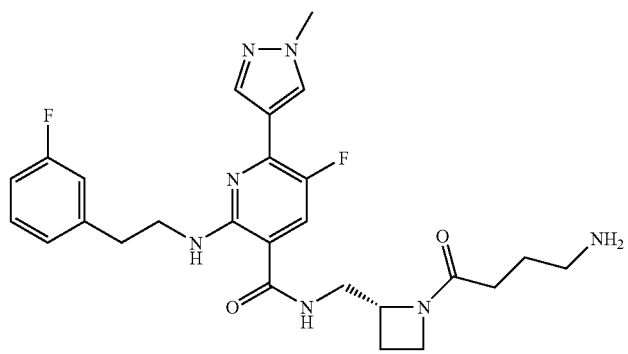
Compound 867 | N-{[(2R)-1-(4-aminobutanoyl)azetidin-2-yl]methyl}(5-fluoro-2-{[2-(3-fluorophenyl)ethyl]amino}-6-(1-methylpyrazol-4-yl)(3-pyridyl))carboxamide |
| 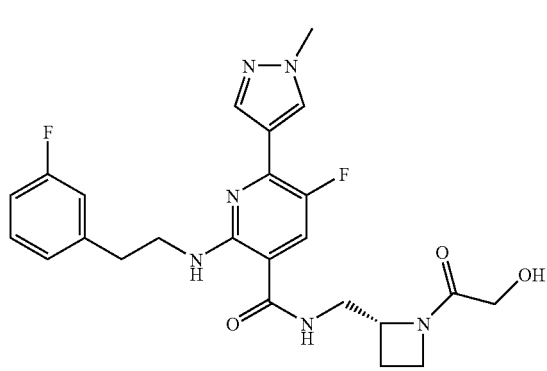
Compound 868 | N-{[(2R)-1-(2-hydroxyacetyl)azetidin-2-yl]methyl}(5-fluoro-2-{[2-(3-fluorophenyl)ethyl]amino}-6-(1-methylpyrazol-4-yl)(3-pyridyl))carboxamide |
| 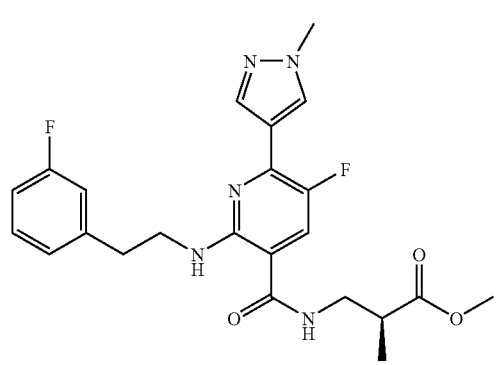
Compound 875 | methyl (2S)-3-[(5-fluoro-2-{[2-(3-fluorophenyl)ethyl]amino}-6-(1-methylpyrazol-4-yl)(3-pyridyl))carbonylamino]-2-methylpropanoate |

| COMPOUND | CHEMICAL NAME |
|---|---|
| 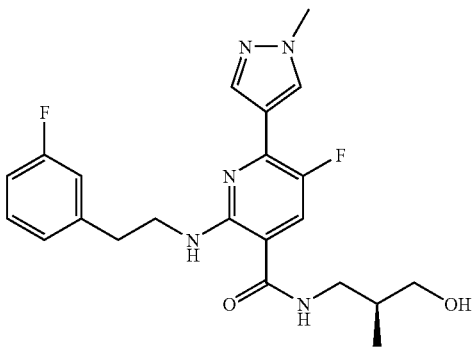

Compound 876 | N-((2S)-3-hydroxy-2-methylpropyl)(5-fluoro-2-{[2-(3-fluorophenyl)ethyl]amino}-6-(1-methylpyrazol-4-yl)(3-pyridyl))carboxamide |
| 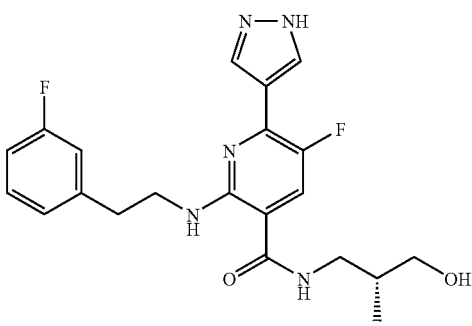

Compound 881 | N-((2R)-3-hydroxy-2-methylpropyl)(5-fluoro-2-{[2-(3-fluorophenyl)ethyl]amino}-6-pyrazol-4-yl(3-pyridyl))carboxamide |
| 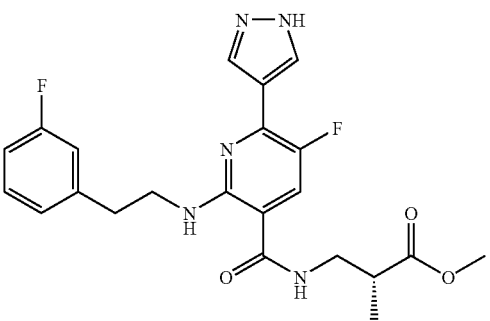

Compound 882 | methyl (2R)-3-[(5-fluoro-2-{[2-(3-fluorophenyl)ethyl]amino}-6-pyrazol-4-yl(3-pyridyl))carbonylamino]-2-methylpropanoate |
| 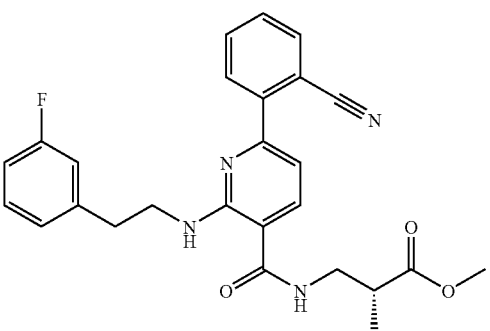

Compound 883 | methyl (2R)-3-[(6-(2-cyanophenyl)-2-{[2-(3-fluorophenyl)ethyl]amino}(3-pyridyl))carbonylamino]-2-methylpropanoate |

| COMPOUND | CHEMICAL NAME |
|---|---|
| 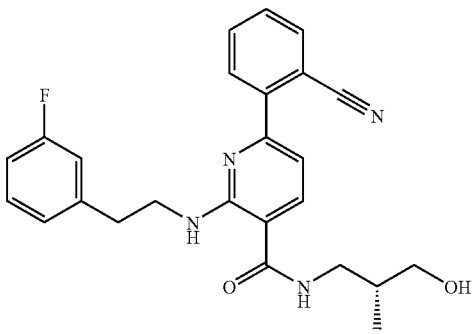<br>Compound 884 | N-((2R)-3-hydroxy-2-methylpropyl)(6-(2-cyanophenyl)-2-{[2-(3-fluorophenyl)ethyl]amino}(3-pyridyl))carboxamide |
| 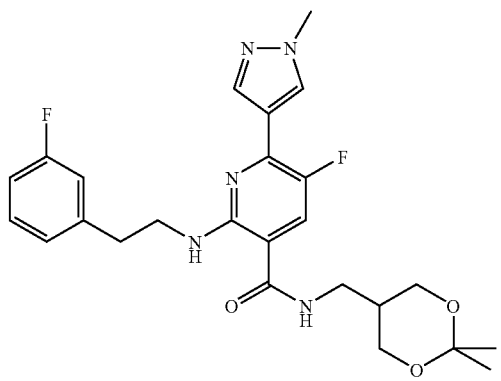<br>Compound 885 | N-[(2,2-dimethyl(1,3-dioxan-5-yl))methyl](5-fluoro-2-{[2-(3-fluorophenyl)ethyl]amino}-6-(1-methylpyrazol-4-yl)(3-pyridyl))carboxamide |
| 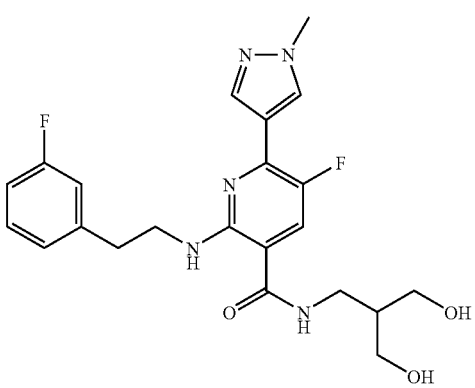<br>Compound 886 | (5-fluoro-2-{[2-(3-fluorophenyl)ethyl]amino}-6-(1-methylpyrazol-4-yl)(3-pyridyl))-N-[3-hydroxy-2-(hydroxymethyl)propyl]carboxamide |

| COMPOUND | CHEMICAL NAME |
|---|---|
| 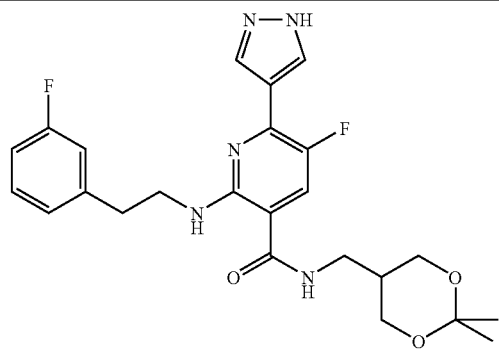<br>Compound 887 | N-[(2,2-dimethyl(1,3-dioxan-5-yl))methyl](5-fluoro-2-{[2-(3-fluorophenyl)ethyl]amino}-6-pyrazol-4-yl(3-pyridyl))carboxamide |
| 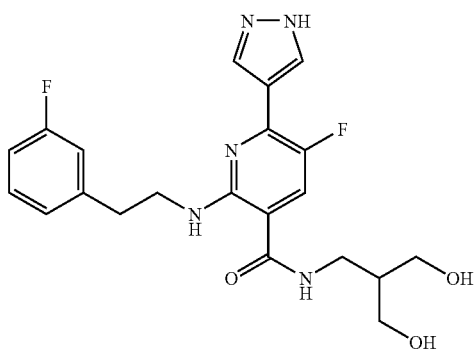<br>Compound 888 | (5-fluoro-2-{[2-(3-fluorophenyl)ethyl]amino}-6-pyrazol-4-yl(3-pyridyl))-N-[3-hydroxy-2-(hydroxymethyl)propyl]carboxamide |
| 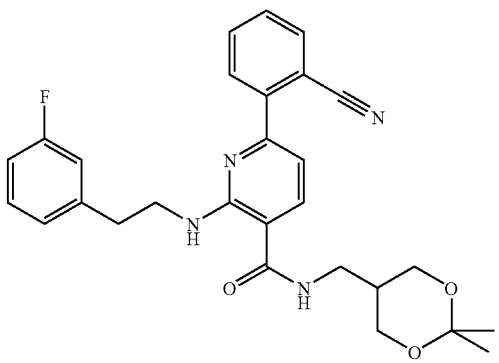<br>Compound 889 | N-[(2,2-dimethyl(1,3-dioxan-5-yl))methyl](6-(2-cyanophenyl)-2-{[2-(3-fluorophenyl)ethyl]amino}(3-pyridyl))carboxamide |
| 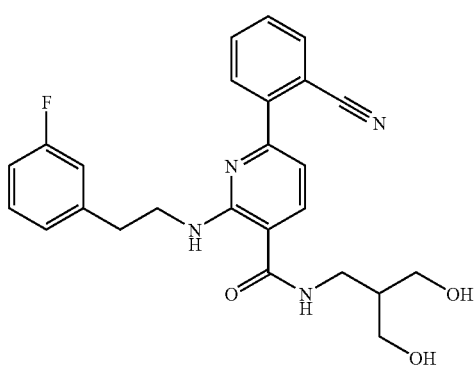<br>Compound 890 | (6-(2-cyanophenyl)-2-{[2-(3-fluorophenyl)ethyl]amino}(3-pyridyl))-N-[3-hydroxy-2-(hydroxymethyl)propyl]carboxamide |

| COMPOUND | CHEMICAL NAME |
|---|---|
| 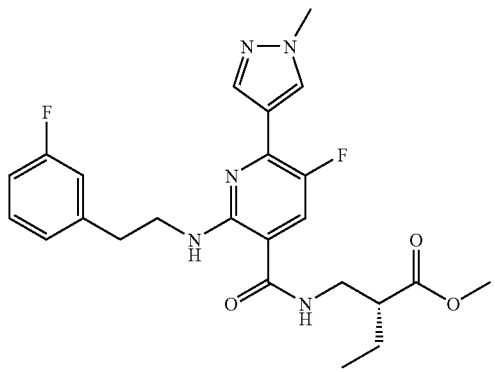<br>Compound 891 | methyl (2R)-2-{[(5-fluoro-2-{[2-(3-fluorophenyl)ethyl]amino}-6-(1-methylpyrazol-4-yl)(3-pyridyl))carbonylamino]methyl}butanoate |
| 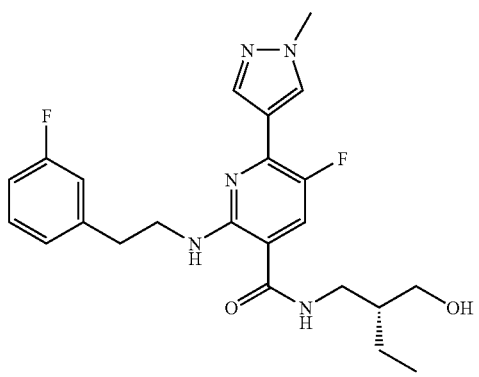<br>Compound 892 | N-((2R)-2-ethyl-3-hydroxypropyl)(5-fluoro-2-{[2-(3-fluorophenyl)ethyl]amino}-6-(1-methylpyrazol-4-yl)(3-pyridyl))carboxamide |
| 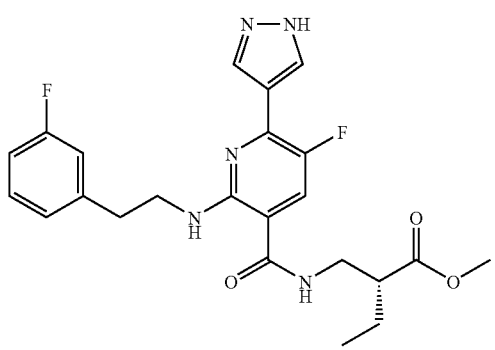<br>Compound 893 | methyl (2R)-2-{[(5-fluoro-2-{[2-(3-fluorophenyl)ethyl]amino}-6-pyrazol-4-yl(3-pyridyl))carbonylamino]methyl}butanoate |

-continued

| COMPOUND | CHEMICAL NAME |
|---|---|
| 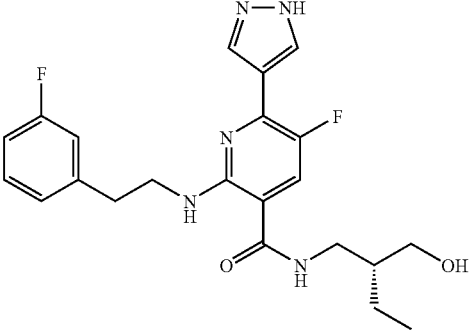

Compound 894 | N-((2R)-2-ethyl-3-hydroxypropyl)(5-fluoro-2-{[2-(3-fluorophenyl)ethyl]amino}-6-pyrazol-4-yl(3-pyridyl))carboxamide |
| 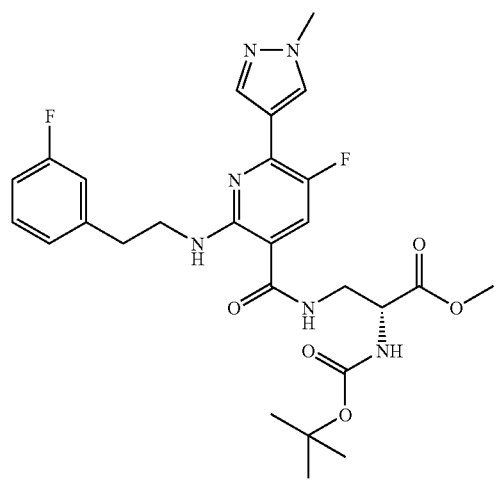

Compound 895 | methyl (2R)-2-[(tert-butoxy)carbonylamino]-3-[(5-fluoro-2-{[2-(3-fluorophenyl)ethyl]amino}-6-(1-methylpyrazol-4-yl)(3-pyridyl))carbonylamino]propanoate |
| 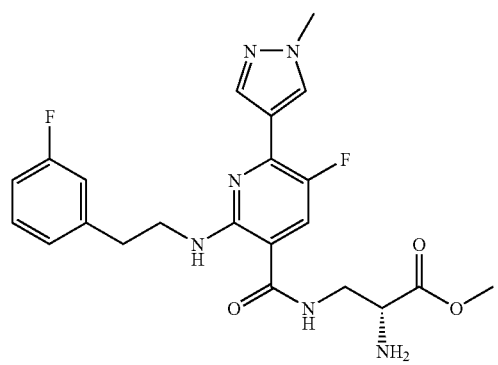

Compound 896 | methyl (2R)-2-amino-3-[(5-fluoro-2-{[2-(3-fluorophenyl)ethyl]amino}-6-(1-methylpyrazol-4-yl)(3-pyridyl))carbonylamino]propanoate |

| COMPOUND | CHEMICAL NAME |
|---|---|
| 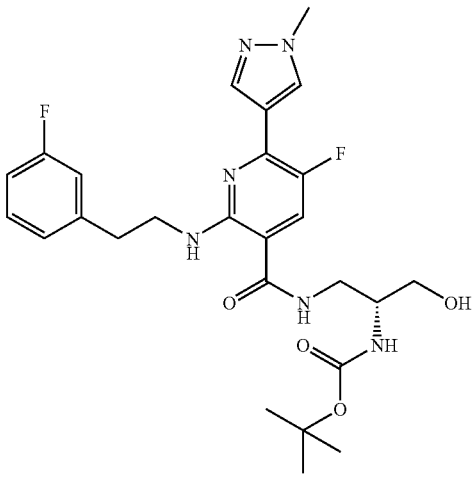<br>Compound 897 | N-((1R)-1-{[(5-fluoro-2-{[2-(3-fluorophenyl)ethyl]amino}-6-(1-methylpyrazol-4-yl)(3-pyridyl))carbonylamino]methyl}-2-hydroxyethyl)tert-butoxy)carboxamide |
| 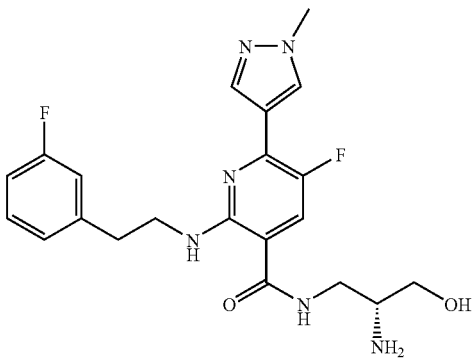<br>Compound 898 | N-((2R)-2-amino-3-hydroxypropyl)(5-fluoro-2-{[2-(3-fluorophenyl)ethyl]amino}-6-(1-methylpyrazol-4-yl)(3-pyridyl))carboxamide |
| 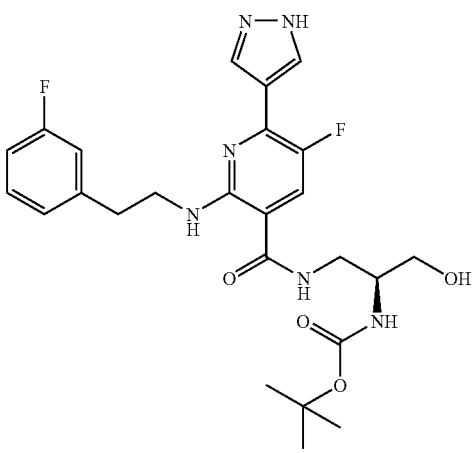<br>Compound 899 | N-((1R)-1-{[(5-fluoro-2-{[2-(3-fluorophenyl)ethyl]amino}-6-pyrazol-4-yl(3-pyridyl))carbonylamino]methyl}-2-hydroxyethyl)(tert-butoxy)carboxamide |

-continued

| COMPOUND | CHEMICAL NAME |
|---|---|
| 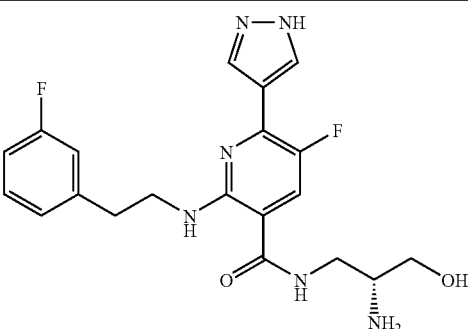
Compound 900 | N-((2R)-2-amino-3-hydroxypropyl)(5-fluoro-2-{[2-(3-fluorophenyl)ethyl]amino}-6-pyrazol-4-yl(3-pyridyl))carboxamide |
| 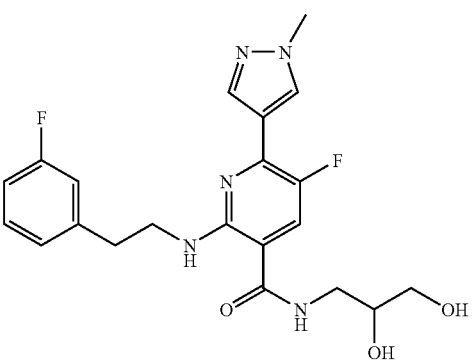
Compound 901 | N-(2,3-dihydroxypropyl)(5-fluoro-2-{[2-(3-fluorophenyl)ethyl]amino}-6-(1-methylpyrazol-4-yl)(3-pyridyl))carboxamide |
| 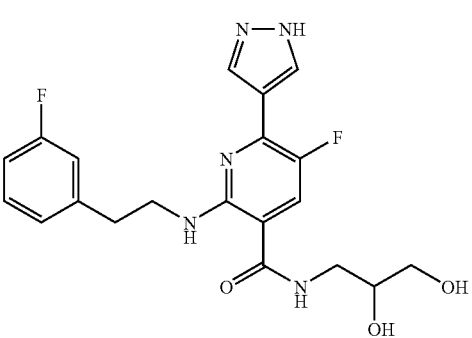
Compound 902 | N-(2,3-dihydroxypropyl)(5-fluoro-2-{[2-(3-fluorophenyl)ethyl]amino}-6-pyrazol-4-yl(3-pyridyl))carboxamide |
| 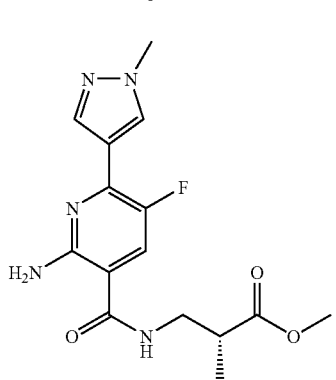
Compound 903 | methyl (2R)-3-{[2-amino-5-fluoro-6-(1-methylpyrazol-4-yl)(3-pyridyl)]carbonylamino}-2-methylpropanoate |

| COMPOUND | CHEMICAL NAME |
|---|---|
| 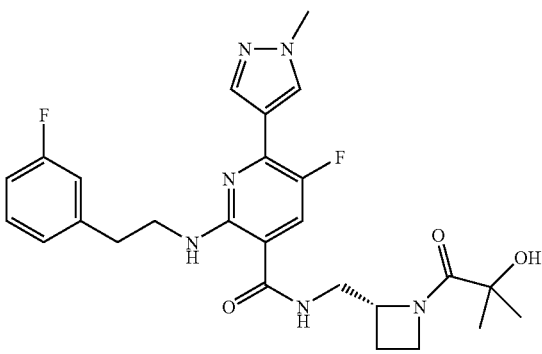<br>Compound 904 | N-{[(2R)-1-(2-hydroxy-2-methylpropanoyl)azetidin-2-yl]methyl}(5-fluoro-2-{[2-(3-fluorophenyl)ethyl]amino}-6-(1-methylpyrazol-4-yl)(3-pyridyl))carboxamide |
| 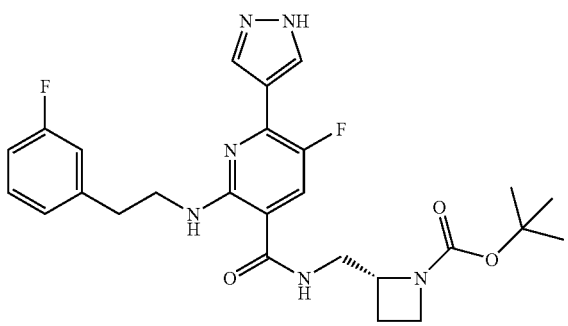<br>Compound 905 | tert-butyl (2R)-2-{[(5-fluoro-2-{[2-(3-fluorophenyl)ethyl]amino}-6-pyrazol-4-yl(3-pyridyl))carbonylamino]methyl}azetidinecarboxylate |
| 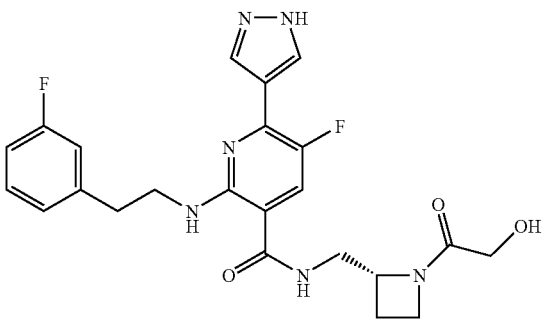<br>Compound 906 | N-{[(2R)-1-(2-hydroxyacetyl)azetidin-2-yl]methyl}(5-fluoro-2-{[2-(3-fluorophenyl)ethyl]amino}-6-pyrazol-4-yl(3-pyridyl))carboxamide |
| 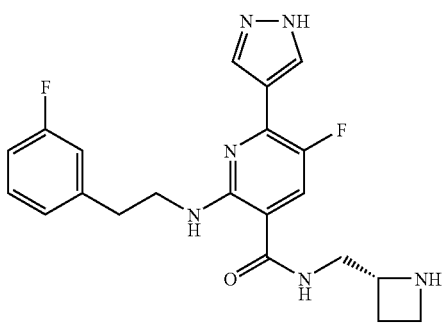<br>Compound 907 | N-[((2R)azetidin-2-yl)methyl](5-fluoro-2-{[2-(3-fluorophenyl)ethyl]amino}-6-pyrazol-4-yl(3-pyridyl))carboxamide |

-continued
| COMPOUND | CHEMICAL NAME |
|---|---|
| 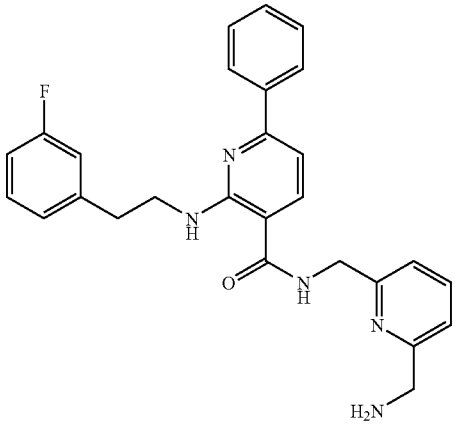
Compound 272 | N-{[6-(aminomethyl)(2-pyridyl)]methyl}(2-{[2-(3-fluorophenyl)ethyl]amino}-6-phenyl(3-pyridyl))carboxamide |
| 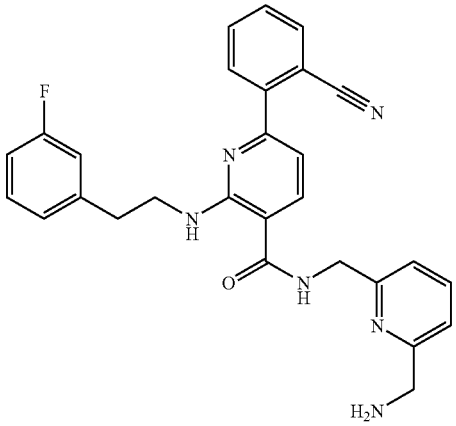
Compound 284 | N-{[6-(aminomethyl)(2-pyridyl)]methyl}(6-(2-cyanophenyl)-2-{[2-(3-fluorophenyl)ethyl]amino}(3-pyridyl))carboxamide |
| 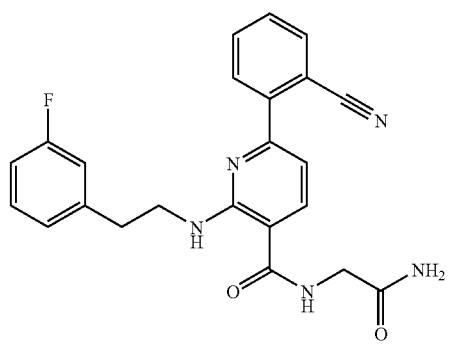
Compound 126 | N-(carbamoylmethyl)(6-(2-cyanophenyl)-2-{[2-(3-fluorophenyl)ethyl]amino}(3-pyridyl))carboxamide |

| COMPOUND | CHEMICAL NAME |
|---|---|
| 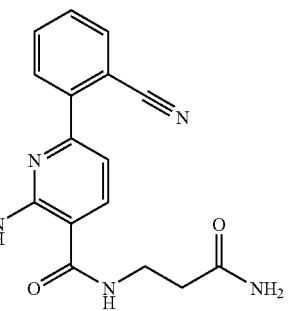

Compound 127 | N-(2-carbamoylethyl)(6-(2-cyanophenyl)-2-{[2-(3-fluorophenyl)ethyl]amino}(3-pyridyl))carboxamide |
| 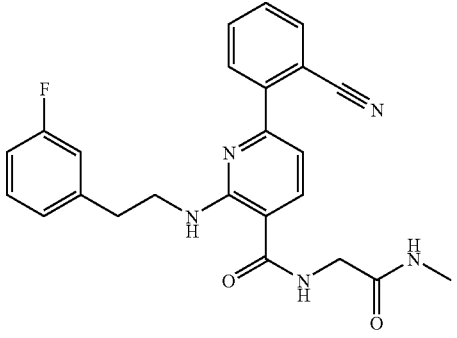

Compound 128 | 2-[(6-(2-cyanophenyl)-2-{[2-(3-fluorophenyl)ethyl]amino}(3-pyridyl))carbonylamino]-N-methylacetatamide |
| 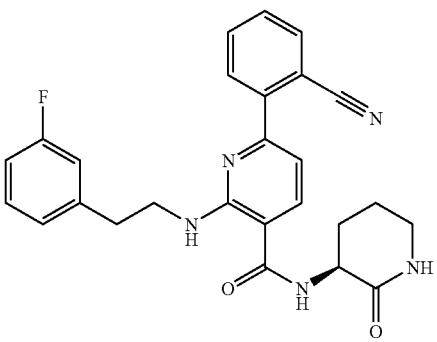

Compound 396 | N-((3S)-2-oxo(3-piperidyl))(6-(2-cyanophenyl)-2-{[2-(3-fluorophenyl)ethyl]amino}(3-pyridyl))carboxamide |

The compounds described herein can be synthesized utilizing techniques well known in the art from commercially available starting materials and reagents. For example, the compounds can be prepared as described below.

Unless specified to the contrary, for each gram of the limiting reagent, one cc (or mL) of solvent constitutes a volume equivalent.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures are provided in the Example. However, other equivalent separation or isolation procedures can, of course, also be used.

When desired, the (R) and (S) isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that when the desired enantiomer is converted into another chemical entity by one of the separation procedures described above, a further step may be required to liberate the desired enantiomeric form. Alternatively, a specific enantiomer may be synthesized by asymmetric synthesis using optically active reagents, substrates, catalysts and/or solvents, or by converting one enantiomer to the other by asymmetric transformation.

The chemical entities described herein may be useful in a variety of applications involving smooth muscle cells and/or non-muscle cells. In certain embodiments, the chemical entities may be used to inhibit smooth muscle myosin. The chemical entities may be useful to bind to, and/or inhibit the activity of, smooth muscle myosin. In certain embodiments, the smooth muscle myosin is human, although the chemical entities may be used to bind to or inhibit the activity of smooth muscle myosin from other organisms, such as other mammals.

In certain embodiments, the chemical entities may be used to inhibit non-muscle myosin. The chemical entities may be useful to bind to, and/or inhibit the activity of, non-muscle myosin. In certain embodiments, the non-muscle myosin is human, although the chemical entities may be used to bind to or inhibit the activity of non-muscle myosin from other organisms, such as other mammals.

The chemical entities described herein may be used to treat disease states associated with smooth muscle and/or non-muscle myosin. Such disease states which can be treated by the chemical entities described herein include, but are not limited to, hypertension, asthma, incontinence, chronic obstructive pulmonary disorder, pre-term labor, and the like. It is appreciated that in some cases the cells may not be in an abnormal state and still require treatment. Thus, in certain embodiments, the chemical entities described herein can be applied to cells or administered to individuals afflicted or subject to impending affliction with any one of these disorders or states.

More specifically, the chemical entities described herein may be useful for the treatment of diseases or symptoms related to abnormal increased muscle tone or excessive contraction, or spasm of vascular smooth muscle in systemic, coronary, pulmonary circulation, and micro-circulatory smooth muscle as well, such as systemic hypertension, malignant hypertension, hypertension crisis, symptomatic hypertension, pulmonary hypertension, pulmonary infarction, angina pectoris, cardiac infarction, micro-circulation malfunction under shock condition, and infarction occurred in other location or organs of the human or animal body. Other diseases or symptoms that can be treated with the chemical entities described herein include: spasm of gastro-intestine smooth muscle, including sphincters, such as gastric spasm, pylorospasm, and spasms of biliary tract, pancreatic tract, urinary tract, caused by inflammation, stimulation of stones or parasites; spasm of other visceral organs such as uterus, Fallopian tube, and so on; spasm of trachea-bronchial tree smooth muscle, diaphragm muscle, such as various asthma, breathlessness, dyspnea, diaphragmatic convulsion, and so on; spasm of alimentary canal smooth muscle, including stomach, intestine and colons, biliary and pancreatic duct etc.; and spasm of urinary tract smooth muscle.

In addition, the chemical entities described herein can be used for control, management and manipulation of labor during pregnancy. The method is particularly useful for inhibition of spontaneous preterm labor which would, if untreated, result in premature delivery or abortion and for inhibition of surgically induced labor during transuterine fetal surgery. The method is also useful for inducing the labor in overterm pregnancies where the labor does not occur on term and when it is necessary to induce labor in order to assure the normal delivery.

Further, the chemical entities described herein can be used for the treatment of "airway wall remodeling", which is a condition associated with diseases or conditions characterized by airway wall thickening and air obstruction, which may, for example occur in the small airways of patients with certain respiratory disease conditions, such as, chronic obstructive pulmonary disease (COPD).

Such disease states which can be treated by the chemical entities, compositions and methods provided herein also include, but are not limited to glaucoma and other ocular indications. More specifically, chemical entities described herein may be useful for the treatment of diseases or symptoms related to glaucoma, including increased intraocular pressure, reduced flow of intraocular aqueous humor, and optical nerve damage. Other diseases or symptoms that can be treated with the chemical entities, compositions, and methods described herein including intraocular hypertension.

ATP hydrolysis is employed by myosin to produce force. An increase in ATP hydrolysis would correspond to an increase in the force or velocity of muscle contraction. In the presence of actin, myosin ATPase activity is stimulated more than 100-fold. Thus, the measurement of ATP hydrolysis not only measures myosin enzymatic activity but also its interaction with the actin filament. Assays for such activity may employ smooth muscle myosin from a human source, although myosin from other organisms can also be used. Systems that model the regulatory role of calcium in myosin binding may also be used.

The in vitro rate of ATP hydrolysis correlates to smooth muscle myosin potentiating activity, which can be determined by monitoring the production of either ADP or phosphate, for example as described in U.S. Pat. No. 6,410,254. ADP production can also be monitored by coupling the ADP production to NADH oxidation (using, for example, the enzymes pyruvate kinase and lactate dehydrogenase) and monitoring the NADH level, by example, either by absorbance or fluorescence (Greengard, P., *Nature* 178 (Part 4534): 632-634 (1956); *Mol Pharmacol* 1970 January; 6(1):31-40). Phosphate production can be monitored using purine nucleoside phosphorylase to couple phosphate production to the cleavage of a purine analog, which results in either a change in absorbance (*Proc Natl Acad Sci USA* 1992 Jun. 1; 89(11): 4884-7) or fluorescence (*Biochem J* 1990 Mar. 1; 266(2):611-4). While a single measurement is employed, multiple measurements of the same sample at different times in order may be used to determine the absolute rate of the protein activity; such measurements have higher specificity particularly in the presence of test compounds that have similar absorbance or fluorescence properties with those of the enzymatic readout.

Test compounds may be assayed in a highly parallel fashion using multiwell plates by placing the compounds either individually in wells or testing them in mixtures. Assay components including the target protein complex, coupling enzymes and substrates, and ATP may then be added to the wells and the absorbance or fluorescence of each well of the plate can be measured with a plate reader.

One method uses a 384 well plate format and a 25 µL reaction volume. A pyruvate kinase/lactate dehydrogenase coupled enzyme system (Huang T G and Hackney D D. (1994) J Biol Chem 269(23):16493-16501) is used to measure the rate of ATP hydrolysis in each well. As will be appreciated by those of skill in the art, the assay components are added in buffers and reagents. Since the methods outlined herein allow kinetic measurements, incubation periods may be optimized to give adequate detection signals over the background. The assay is performed in real time to give the kinetics of ATP hydrolysis to increase the signal-to-noise ratio of the assay.

Selectivity for smooth muscle myosin may be determined by substituting other myosins in one or more of the above-described assays and comparing the results obtained against those obtained using the cardiac equivalents.

Chemical entities identified by the methods described herein as smooth muscle myosin modulators may be further tested in an efficacy screen, such as a screen using strips of permeabilized smooth muscle from, e.g., chicken gizzard. Calcium-sensitive smooth muscle strips are prepared by dissecting chicken gizzard tissue, followed by treatment with 1% Triton X-100 to make the strips permeable to exogenous compounds (Barsotti, R J, et al., Am J Physiol. 1987 May; 252(5 Pt 1):C543-54). These strips can be stored in 50% glycerol for several weeks at −20° C., allowing multiple experiments to be performed with each batch of muscle strips. Experiments are performed using a solution of 20 mM imidazole pH 7.0, 5.5 mM ATP, 7 mM $MgCl_2$, 55 mM KCl, 1 µM Calmodulin, and 10 mM EGTA. Free calcium will be controlled by addition of various amounts of $CaCl_2$, according to the calculations of MAXChelator (Patton, et al. Cell Calcium. 35/5 pp. 427-431, 2004). An isometric muscle fiber apparatus is used to measure isometric tension, for example using an Aurora Scientific 400A transducer with National Instruments PCI-MIO-16E-4, 16 channels, 12 bit A/D board for data acquisition. The chemically skinned gizzard fibers are relaxed when bathed in low calcium solutions (pCa 8), but develop isometric tension when the free calcium of the bathing solution is increased to pCa 5. These fibers can be repeatedly contracted and relaxed by switching between high and low calcium bathing solutions.

Compounds are first tested for their ability to prevent contraction of gizzard strips, by preincubating relaxed fibers with a compound, followed by transfer to high calcium solution containing the compound. Next, compounds are tested for their ability to cause relaxation of contracting fibers by adding the compound to fibers already incubating in high calcium solution. Washout experiments are performed to ensure that the inhibitory effects are reversible, so that the compounds do not cause denaturation or other irreparable damage to the smooth muscle myosin.

The chemical entities are administered at a therapeutically effective dosage, e.g., a dosage sufficient to provide treatment of the disease states previously described. Generally, a daily dose is from about 0.05 to about 100 mg/kg of body weight, such as from about 0.10 to about 10 mg/kg of body weight or from about 0.15 to about 1 mg/kg of body weight. Thus, for administration to a 70 kg person, the dosage range is from about 3.5 to about 7000 mg per day, such as from about 7 to about 700 mg per day or from about 10 to about 100 mg per day. The amount of active chemical entity administered will, of course, be dependent on the subject and disease state being treated, the severity of the affliction, the manner and schedule of administration and the judgment of the prescribing physician; for example, a dose range for oral administration may be from about 70 to about 700 mg per day, whereas for intravenous administration the dose range may be from about 700 to about 7000 mg per day. The active agents may be selected for longer or shorter plasma half-lives, respectively.

Administration of the chemical entities described herein can be via any of the accepted modes of administration for agents that serve similar utilities including, but not limited to, orally, subcutaneously, intravenously, intranasally, topically, transdermally, sublingually, intramucosally, intraperitoneally, intramuscularly, intrapulmonarilly, vaginally, rectally, and intraocularly (including intraocular injection). Oral, topical, parenteral, and intraocular administration are customary in treating many of the indications recited herein.

Pharmaceutically acceptable compositions include solid, semi-solid, liquid and aerosol dosage forms, such as, e.g., tablets, capsules, powders, liquids, suspensions, suppositories, aerosols, and the like. The chemical entities can also be administered in sustained- or controlled-release dosage forms, including depot injections, osmotic pumps, pills, transdermal (including electrotransport) patches, drops and the like, for prolonged and/or timed, pulsed administration at a predetermined rate. The compositions may be provided in unit dosage forms suitable for single administration of a precise dose.

The chemical entities may be administered either alone or in combination with a conventional pharmaceutical carrier or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition may also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate. Generally, depending on the intended mode of administration, the pharmaceutical composition may contain from about 0.005% to about 95%, for example, from about 0.5% to about 50%, by weight of at least one chemical entity. Actual methods of preparing such dosage forms are known or will be apparent, to those skilled in this art; for example, see *Remington's Pharmaceutical Sciences*, Mack Publishing Company, Easton, Pa. Pharmaceutical compositions are also referred to as pharmaceutical formulations.

In addition, the chemical entities may be co-administered with, and the pharmaceutical compositions can include, other medicinal agents, pharmaceutical agents, adjuvants, and the like.

In certain embodiments, the compositions are in the form of a pill or tablet and contain, along with the active ingredient, one or more of a diluent such as lactose, sucrose, dicalcium phosphate, and the like; a lubricant such as magnesium stearate or the like; and a binder such as starch, gum acacia, polyvinylpyrrolidine, gelatin, cellulose, cellulose derivatives and the like. In another solid dosage form, a powder, marume, solution or suspension (e.g., in propylene carbonate, vegetable oils or triglycerides) may be encapsulated in a gelatin capsule.

Liquid pharmaceutical compositions may, for example, be prepared by dissolving, dispersing, etc. at least one chemical entity and one or more optional pharmaceutical adjuvants in a carrier (e.g., water, saline, aqueous dextrose, glycerol, glycols, ethanol and the like) to form a solution or suspension. Injectables may be prepared in conventional forms, either as liquid solutions or suspensions, as emulsions, or in solid forms suitable for dissolution or suspension in liquid prior to injection. The percentage of chemical entities contained in such parenteral compositions is highly dependent on the specific nature thereof, as well as the activity of the chemical entities and the needs of the subject. However, percentages of active ingredient ranging from about 0.01% to about 10% in solution may be used, and may be higher if the composition is a solid which will be subsequently diluted to the above percentages. In certain embodiments, the composition has from about 0.2% to about 2% of the active agent in solution.

Compositions comprising at least one chemical entity may be administered intraocularly (including intraocular, periocular, and retrobulbar injection and perfusion). When administered intraocularly the sterile composition is typically aqueous. An appropriate buffer system may be added to prevent pH drift under storage conditions. When administered during intraocular surgical procedures, such as retrobulbar or periocular injection and intraocular perfusion or injection, the use of balanced salt irrigating solutions may be necessary. When used in a multidose form, preservatives may be required to prevent microbial contamination during use.

Compositions comprising at least one chemical entity may also be administered topically as eye drops, eye wash, creams, ointments, gels, and sprays. When administered as eye drops or eye wash, the active ingredients are typically dissolved or suspended in suitable carrier, typically a sterile aqueous solvent. An appropriate buffer system may be added to prevent pH drift under storage conditions. When used in a multidose form, preservatives may be required to prevent microbial contamination during use.

Compositions comprising at least one chemical entity may also be administered to the respiratory tract as an aerosol or in a solution for a nebulizer, or as a microfine powder for insufflation, alone or in combination with an inert carrier such as lactose. The particles of the composition typically have diameters of less than 50 microns, for example, less than 10 microns.

Generally, to employ the chemical entities described herein in methods of screening for smooth muscle myosin binding, smooth muscle myosin is bound to a support and at least one chemical entity is added to the assay. Alternatively, the chemical entity may be bound to the support and the smooth muscle myosin added. Classes of compounds among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.), and the like. See, e.g., U.S. Pat. No. 6,495,337.

EXAMPLES

The following examples serve to more fully describe the manner of using the invention. These examples are presented for illustrative purposes and should not serve to limit the true scope of the invention.

Example 1

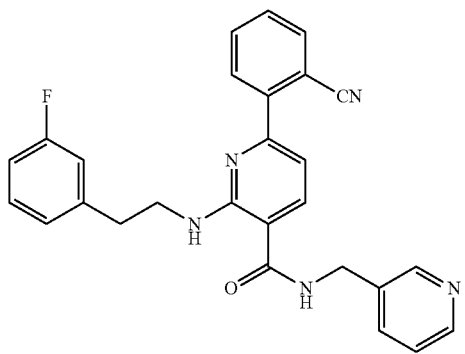

I 6-(2-cyanophenyl)-2-(3-fluorophenethylamino)-N-(pyridin-3-ylmethyl)nicotinamide Method A:

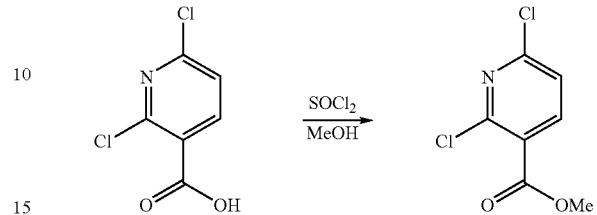

To a solution of 2,6-dichloronicotinic acid (50 g, 0.26 mol) in methanol (250 mL) was added thionyl chloride (22.7 mL, 0.312 mol) slowly. The mixture was refluxed for 4 hours and concentrated to give methyl 2,6-dichloronicotinate as a white solid in quantitative yield.

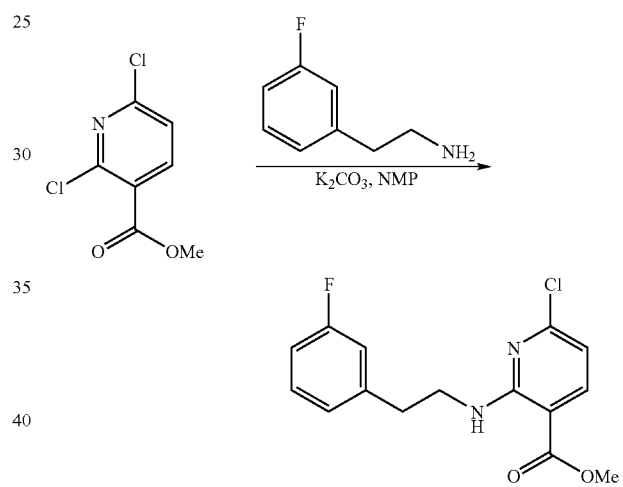

A mixture of methyl 2,6-dichloronicotinate (53.3 g, 0.26 mol), 3-fluorophenethyl amine (37.3 mL, 0.29 mol), $K_2CO_3$ (72 g 0.52 mol) and NMP (150 mL) was stirred at 100° C. for 10 hrs. The mixture was diluted with ethyl acetate (2×300 mL) and washed with brine. The organic layers were combined, dried (MgSO$_4$) and concentrated. The residue was purified by silica gel chromatography using hexane-EtOAc (9:1) as eluant to give methyl 6-chloro-2-(3-fluorophenethylamino)nicotinate as an off-white solid (44 g, 54%). LRMS (M+H$^+$) m/z 309.0.

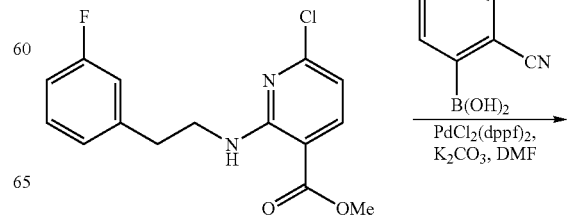

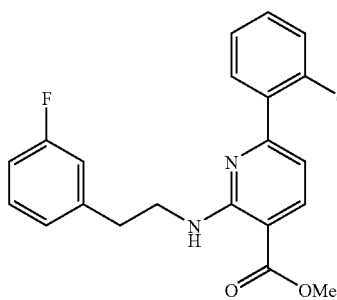

A mixture of chloride methyl 6-chloro-2-(3-fluorophenethylamino)nicotinate (30.8 g, 0.1 mol), 2-cyanophenyl boronic acid (17.6 g, 0.12 mol), PdCl₂(dppf)₂ (3.6 g, 5.0 mmol), K₂CO₃ (41.4 g, 0.3 mol) and anhydrous DMF (100 mL) was degassed with nitrogen for 30 min. The mixture was then stirred at 100° C. for 2 hrs. The mixture was filtered through the Celite and washed with EtOAc. The filtrate was diluted with EtOAc, washed with brine and concentrated to dryness. The residue was purified by silica gel flash chromatography using hexane-EtOAc (4:1) as eluant to give the desired product methyl 6-(2-cyanophenyl)-2-(3-fluorophenethylamino)nicotinate as a yellow solid (31 g, 82%). LRMS (M+H⁺) m/z 376.1.

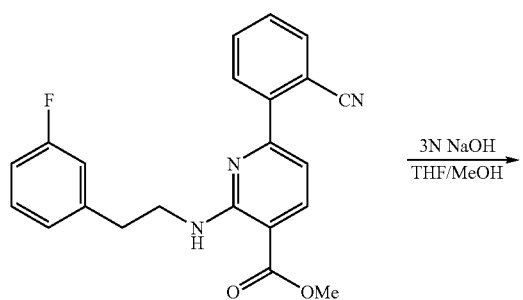

To a mixture of methyl ester methyl 6-(2-cyanophenyl)-2-(3-fluorophenethylamino)nicotinate (15 g, 40 mmol), methanol (80 mL) and THF (80 mL) was added 3N NaOH (40 mL). The mixture was stirred at room temperature for 16 hrs. The mixture was adjusted to pH 7 with 2N HCl. After concentration, the residue in the aqueous solution was acidified to pH 3 with 2N HCl (10 mL) to give the yellow precipitates. The yellow solid was filtered, washed with water and dried to afford 6-(2-cyanophenyl)-2-(3-fluorophenethylamino)nicotinic acid (14.5 g, 100%). LRMS (M+H⁺) m/z 362.1.

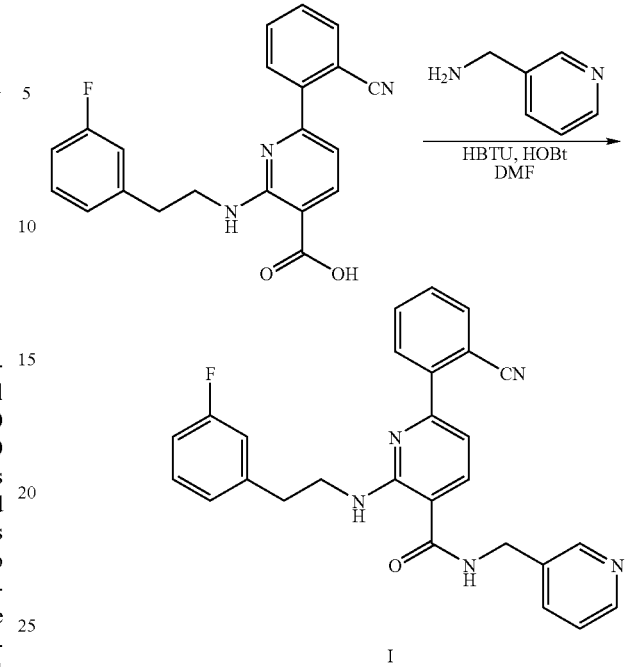

To a mixture of 6-(2-cyanophenyl)-2-(3-fluorophenethylamino)nicotinic acid (2.8 g, 7.76 mmol) in DMF (28 mL) was added HBTU (5.88 g, 15.51 mmol), HOBt (2.1 g, 15.51 mmol), then 3-aminomethylpyridine (1.68 g, 15.51 mmol). The reaction mixture was stirred at room temperature for 1 hr. The crude mixture was purified on RP-HPLC using a mixture of acetonitrile and H₂O to give 6-(2-cyanophenyl)-2-(3-fluorophenethylamino)-N-(pyridin-3-ylmethyl)nicotinamide as a pale yellow solid (3.0 g, 86%). LRMS (M+H⁺) m/z 452.2.
Method B:

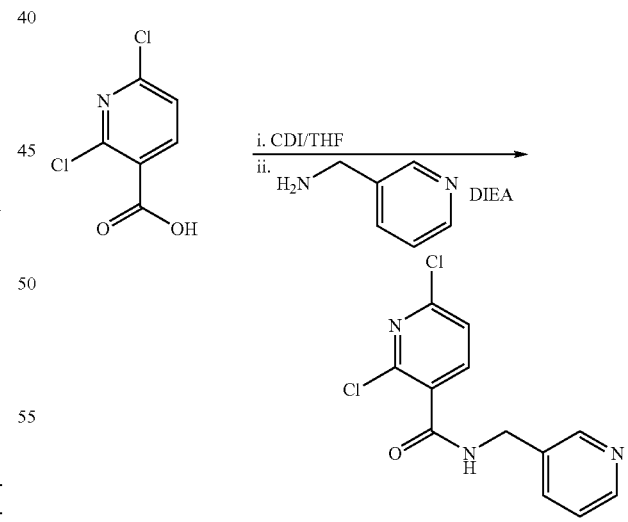

A mixture of acid 2,6-dichloronicotinic acid (19.2 g, 0.1 mol), N,N'-carbonyldiimidazole (CDI, 17.8 g, 0.11 mmol) and THF (1 L) was stirred at 60° C. for 30 min and cooled to room temperature. To the mixture was added 3-aminomethylpyridine (10.2 mL, 0.1 mol) and DIEA (21 mL, 0.12 mol). The reaction mixture was stirred at room temperature for 4 hrs, and diluted with EtOAc. The organic layer was washed with H₂O, brine, dried over Na₂SO₄. Concentration of the organic solution gave 2,6-dichloro-N-(pyridin-3-ylmethyl)nicotinamide (20.5 g, 73%). LRMS (M+H⁺) m/z 282.0; (M+2+H⁺) m/z 283.9.

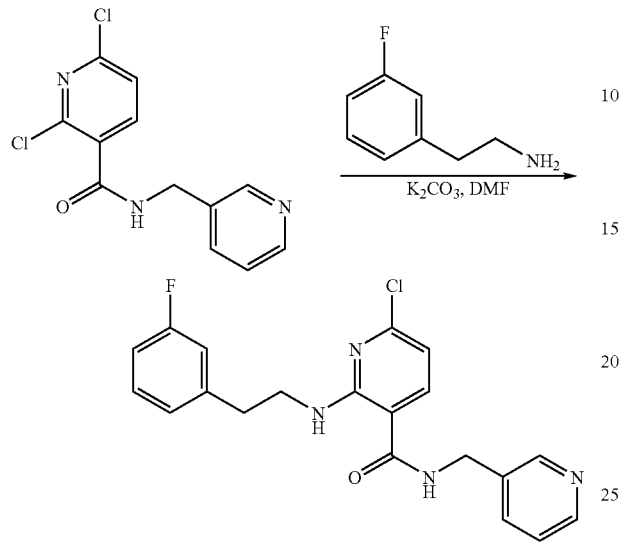

A mixture of 2,6-dichloro-N-(pyridin-3-ylmethyl)nicotinamide (20.4 g, 72.3 mmol), 3-fluorophenethyl amine (11.1 g, 79.5 mmol), K₂CO₃ (20 g 145 mmol) and DMF (200 mL) was stirred at 100° C. for 10 hours. The mixture was diluted with ethyl acetate (2×300 mL) and washed with saturated ammonium chloride, sodium bicarbonate and brine. The organic layers were combined, dried (MgSO₄) and concentrated. The residue was purified by silica gel chromatography to give 6-chloro-2-(3-fluorophenethylamino)-N-(pyridin-3-ylmethyl)nicotinamide (12.6 g, 46%). LRMS (M+H⁺) m/z 385.1.

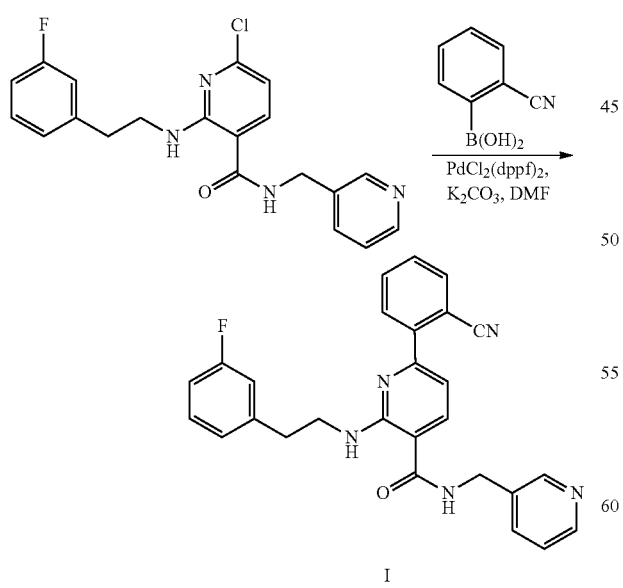

I

A mixture of 6-chloro-2-(3-fluorophenethylamino)-N-(pyridin-3-ylmethyl)nicotinamide (1.0 g, 2.6 mmol), 2-cyanophenyl boronic acid (460 mg, 3.12 mmol), PdCl₂(dppf)₂ (140 mg, 0.26 mmol), K₂CO₃ (1.08 g, 7.8 mmol) and anhydrous DMF (8 mL) was degassed with nitrogen for 10 min. The mixture was then stirred at 125° C. for 1 hr. The mixture was filtered through the silica gel pad and washed with EtOAc. The filtrate was concentrated to dryness and purified by silica gel flash chromatography to give the desired product 6-(2-cyanophenyl)-2-(3-fluorophenethylamino)-N-(pyridin-3-ylmethyl)nicotinamide as a pale yellow solid (740 mg, 63%). LRMS (M+H⁺) m/z 452.1.

Example 2

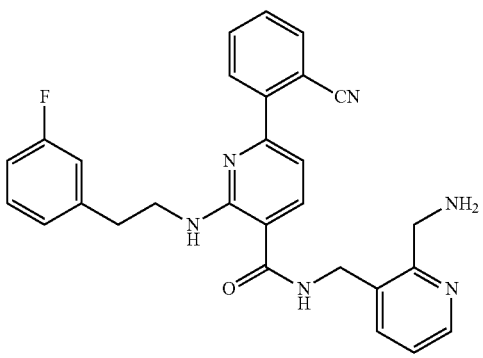

II

N-((2-(aminomethyl)pyridin-3-yl)methyl)-6-(2-cyanophenyl)-2-(3-fluorophenethylamino)nicotinamide

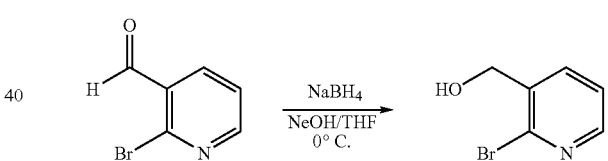

To a mixture of 2-bromonicotinaldehyde (50 g, 0.27 mol), methanol (250 mL) and THF (250 mL) in a 3-necked round bottom flask at 0° C. was added sodium borohydride (10.3 g, 0.27 mol) portion wise. The reaction mixture was stirred at 0° C. for 1 hr and warmed up to room temperature. The reaction mixture was adjusted to pH 7 with 2N HCl (120 mL), and concentrated to remove methanol and THF. The resulting mixture was partitioned between EtOAc and brine three times. The organic layer was combined and washed with brine, dried over Na₂SO₄, and concentrated to give (2-bromopyridin-3-yl)methanol (51 g), which was used without further purification. LRMS (M+H⁺) m/z 187.9.

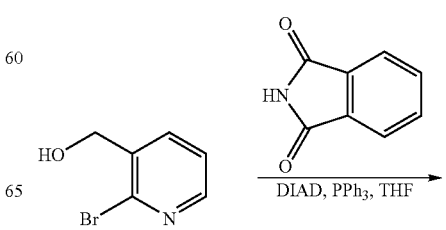

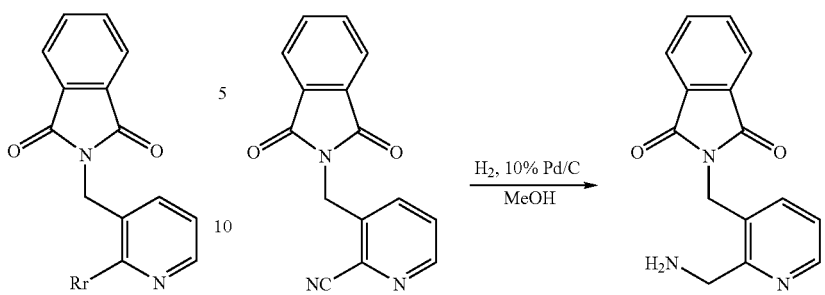

To a mixture of (2-bromopyridin-3-yl)methanol (51 g, 0.27 mol), phthalimide (47.6 g, 0.32 mol), triphenylphosphine (83.8 g, 0.32 mol) and THF (60 mL) at 0° C. was added DIAD (62 mL, 0.32 mol) dropwise. The reaction mixture was allowed to warm to room temperature and stirred for 1 hr. The formed precipitate was filtered and washed with EtOAc (50 mL). The obtained solid 2-((2-bromopyridin-3-yl)methyl)isoindoline-1,3-dione (50.2 g, 59%) was used for next step without further purification. LRMS (M+H$^+$) m/z 317.1.

To a mixture of 3-((1,3-dioxoisoindolin-2-yl)methyl)picolinonitrile (10 g, 38 mmol) and methanol (80 mL) was added conc. HCl (6.5 mL, 76 mmol) and 10% Pd/C (1 g). The mixture was stirred vigorously under 50 Psi H$_2$ for 6 hrs. The mixture was filtered through the Celite pad and washed with methanol. The combined filtrate was concentrated to give the 2-((2-(aminomethyl)pyridin-3-yl)methyl)isoindoline-1,3-dione as a white solid in quantitative yield. LRMS (M+H$^+$) m/z 268.1.

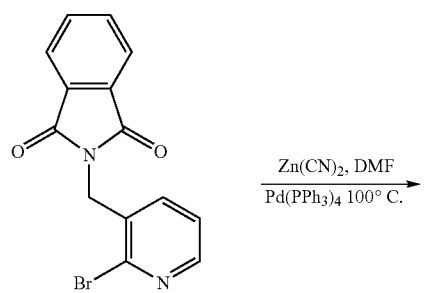

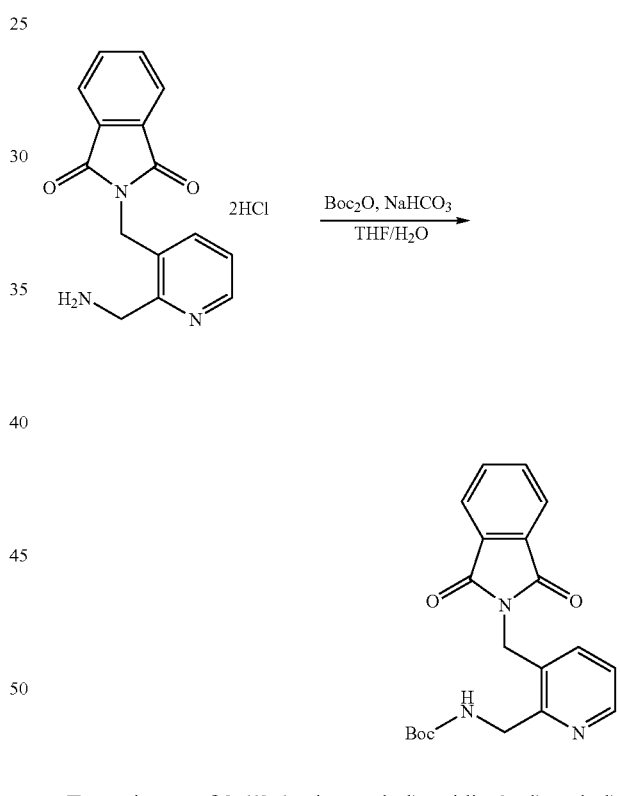

A mixture of bromide 2-((2-bromopyridin-3-yl)methyl)isoindoline-1,3-dione (50 g, 0.16 mol), Zn(CN)$_2$ (37.4 g, 0.32 mol), Pd(PPh$_3$)$_4$ (18.5 g, 16 mmol) and DMF (160 mL) was degassed with nitrogen for 10 min and then stirred at 100° C. for 3 hrs. The mixture was filtered through the Celite and washed with DMF. The combined filtrate was diluted with EtOAc, washed with water, brine, dried (Na$_2$SO$_4$) and concentrated. The residue was triturated with dichloromethane to give the desired product 3-((1,3-dioxoisoindolin-2-yl)methyl)picolinonitrile as an off-white solid (35 g, 83%). LRMS (M+H$^+$) m/z 264.0.

To a mixture of 2-((2-(aminomethyl)pyridin-3-yl)methyl)isoindoline-1,3-dione HCl salt (44.5 g, 0.13 mol), THF (230 mL) and H$_2$O (230 mL) at 0° C. was added NaHCO$_3$ (36 g, 0.43 mol), then Boc$_2$O (31.4 g, 0.144 mol). The mixture was allowed to warm to room temperature and stirred for 2 hrs. The mixture was diluted with ethyl acetate (200 mL), washed with water, brine, dried and concentrated. The residue was triturated with EtOAc (150 mL) to give the desired product as a white solid (30 g, 63%). The EtOAc solution was purified by silica gel flash chromatography using hexane-EtOAc (1:1) as eluant to give the second portion of tert-butyl (3-((1,3-dioxoisoindolin-2-yl)methyl)pyridin-2-yl)methylcarbamate (13.5 g, 28%). LRMS (M+H$^+$) m/z 368.1.

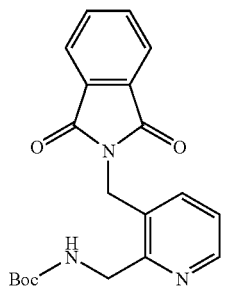 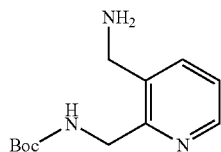 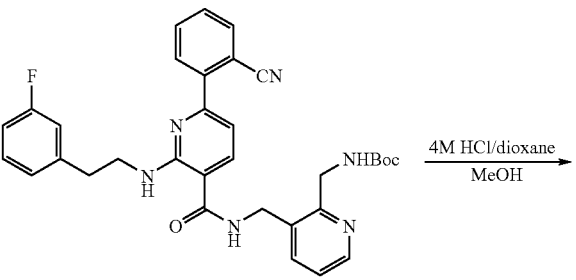

To a solution of tert-butyl (3-((1,3-dioxoisoindolin-2-yl)methyl)pyridin-2-yl)methylcarbamate (30 g, 81 mmol) in MeOH (450 mL) at 0° C. was added hydrazine (25 mL, 810 mmol). The mixture was allowed to warm to room temperature and stirred overnight. The precipitate was filtered off, and the filtrate was concentrated to dryness. The residue was triturated with dichloromethane (500 mL) and filtered. Concentration of the filtrate afforded tert-butyl (3-(aminomethyl)pyridin-2-yl)methylcarbamate in quantitative yield (18.7 g). LRMS (M+H⁺) m/z 238.1.

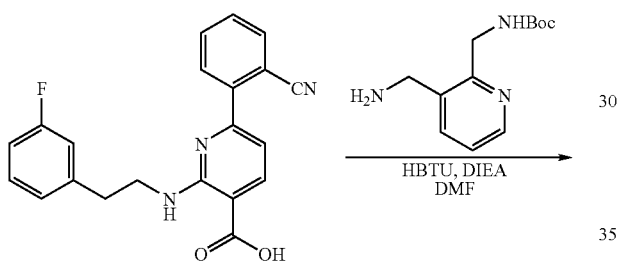

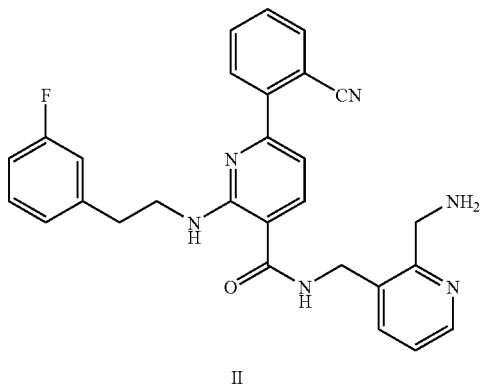

II

To a solution of tert-butyl (3-((6-(2-cyanophenyl)-2-(3-fluorophenethylamino)nicotinamido)methyl)pyridin-2-yl)methylcarbamate (737 mg, 1.27 mmol) in methanol (6 mL) at 0° C. was added a solution of 4M HCl in 1,4-dioxane (3 mL). The mixture was warmed to room temperature and stirred for 2 hrs. Concentration of the mixture followed by the purification on RP-HPLC using a mixture of acetonitrile and H₂O gave N-((2-(aminomethyl)pyridin-3-yl)methyl)-6-(2-cyanophenyl)-2-(3-fluorophenethylamino)nicotinamide as a pale yellow solid (545 mg, 89%). LRMS (M+H⁺) m/z 481.2.

Example 3

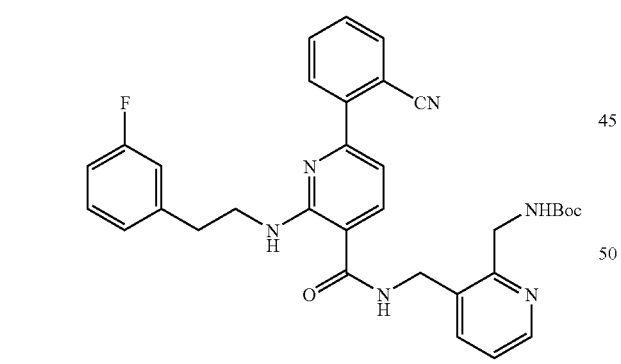

To a mixture of 6-(2-cyanophenyl)-2-(3-fluorophenethylamino)nicotinic acid (0.60 g, 1.66 mmol) in DMF (3 mL) was added DIEA (0.329 mL, 2.53 mmol), HBTU (0.756 g, 2.00 mmol), then tert-butyl (3-(aminomethyl)pyridin-2-yl)methylcarbamate (0.473 g, 2.11 mmol). The reaction mixture was stirred at room temperature for 1 hr. The crude mixture was purified on RP-HPLC using a mixture of acetonitrile and H₂O to give tert-butyl (3-((6-(2-cyanophenyl)-2-(3-fluorophenethylamino)nicotinamido)methyl)pyridin-2-yl)methylcarbamate as a pale yellow solid (545 mg, 57%). LRMS (M+H⁺) m/z 581.3.

III

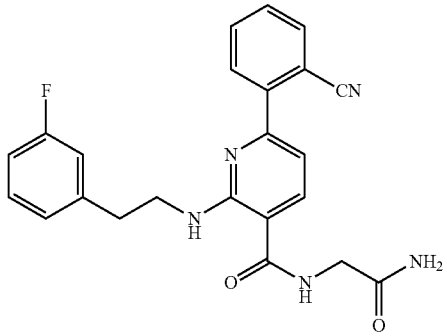

565
N-(2-amino-2-oxoethyl)-6-(2-cyanophenyl)-2-(3-fluorophenethylamino)nicotinamide

566
(R)—N-((1-(4-aminobutanoyl)pyrolidin-2-yl)methyl)-6-(2-cyanophenyl)-2-(3-fluorophenethylamino)nicotinamide

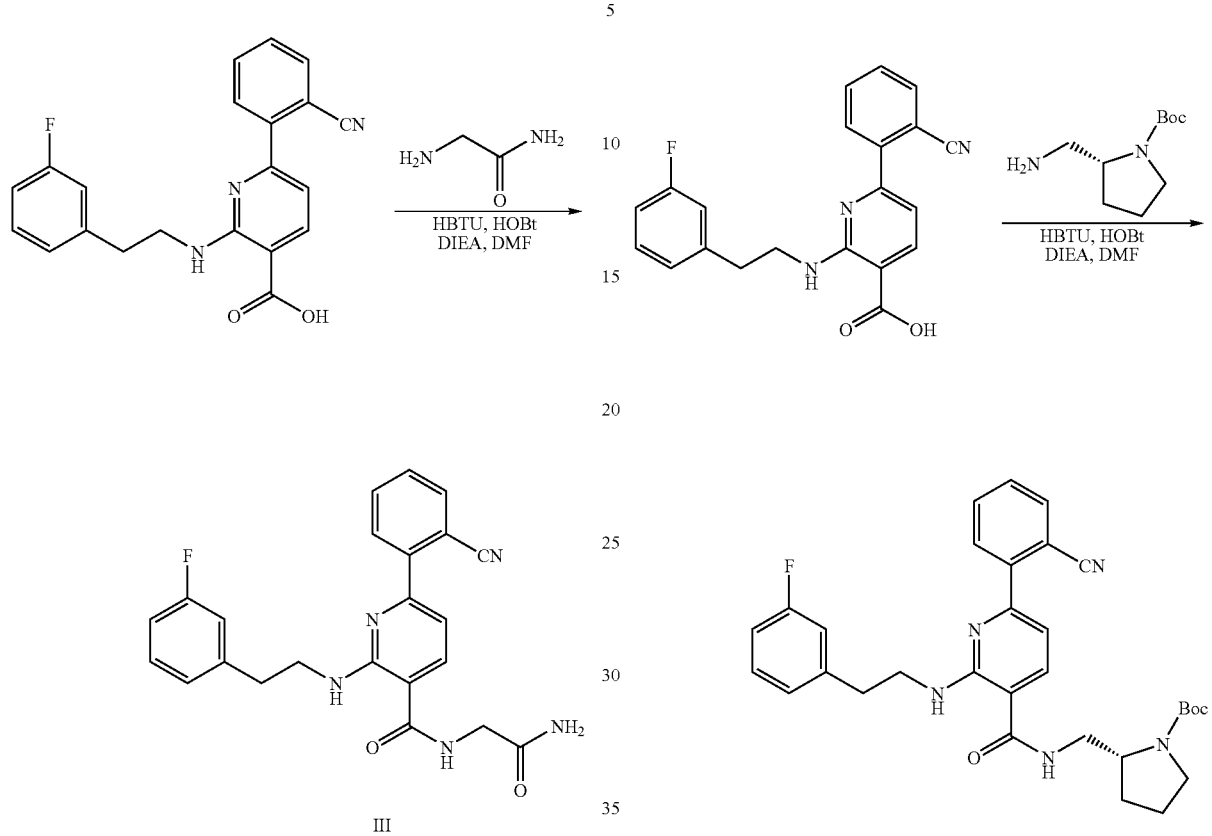

Compound N-(2-amino-2-oxoethyl)-6-(2-cyanophenyl)-2-(3-fluorophenethylamino)nicotinamide was prepared from 6-(2-cyanophenyl)-2-(3-fluorophenethylamino)nicotinic acid and the appropriate amine 2-aminoacetamide according to the procedure (Method A) of preparation of Example 1. LRMS (M+H$^+$) m/z 418.1.

Example 4

To a mixture of 6-(2-cyanophenyl)-2-(3-fluorophenethylamino)nicotinic acid (510 mg, 1.41 mmol), (R)-tert-butyl 2-(aminomethyl)pyrrolidine-1-carboxylate (424 mg, 2.11 mmol), HOBT (285 mg, 2.11 mmol), and HBTU (800 mg, 2.11 mg) in RB flask was added DMF and the mixture was stirred at r.t. for 1 h. LC/MS indicated the reaction was complete and the mixture was filtered and purified on RP-HPLC using a mixture of acetonitrile and water to give (R)-tert-butyl 2-((6-(2-cyanophenyl)-2-(3-fluorophenethylamino)nicotinamido)methyl)pyrrolidine-1-carboxylate (695.1 mg, 91%). LRMS (M+H$^+$) m/z 544.2.

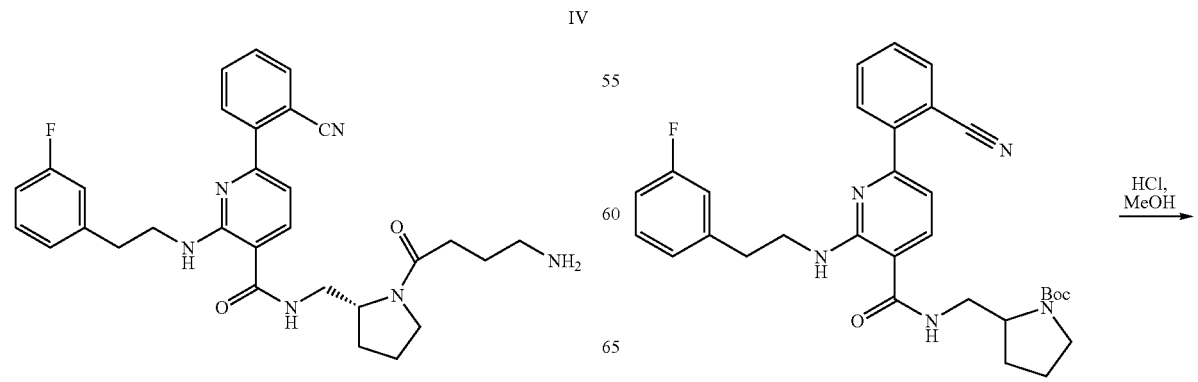

-continued

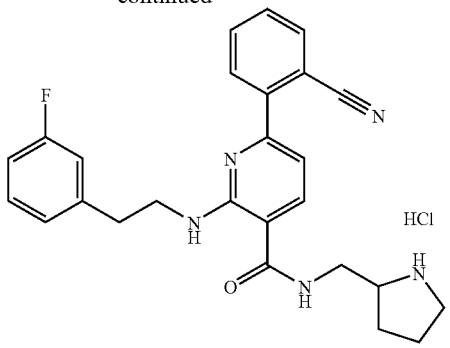

To a solution of (R)-tert-butyl 2-((6-(2-cyanophenyl)-2-(3-fluorophenethylamino)nicotinamido)methyl)pyrrolidine-1-carboxylate (680 mg, 1.25 mmol) in MeOH (20 mL) was added HCl (2.0 mL, 8 mmol, 4 M in dioxane). The reaction was stirred at r.t. for 2 h. LC/MS indicated the reaction was complete. The reaction mixture was concentrated under reduced pressure to give 6-(2-cyanophenyl)-2-(3-fluorophenethylamino)-N-(pyrrolidin-2-ylmethyl)nicotinamide hydrochloride which was used for next step without further purification. LRMS (M+H⁺) m/z 444.2.

To a mixture of 6-(2-cyanophenyl)-2-(3-fluorophenethylamino)-N-(pyrrolidin-2-ylmethyl)nicotinamide hydrochloride (95 mg, 0.2 mmol), 4-(tert-butoxycarbonylamino)butanoic acid (61 mg, 0.3 mmol), HOBT (41 mg, 0.3 mmol), and HBTU (114 mg, 0.3 mmol) were added DMF (1.0 mL) and DIEA (0.1 mL, 0.6 mmol). The reaction mixture was stirred at r.t. for 1 h. LC/MS indicated the reaction was complete. The reaction mixture was then filtered and the filtrate was purified on RP-HPLC using a mixture of acetonitrile and water to give tert-butyl 4-(2-(((6-(2-cyanophenyl)-2-(3-fluorophenethylamino)nicotinamido)methyl)pyrrolidin-1-yl)-4-oxobutylcarbamate (81.2 mg, 65%). LRMS (M+H⁺) m/z 629.2.

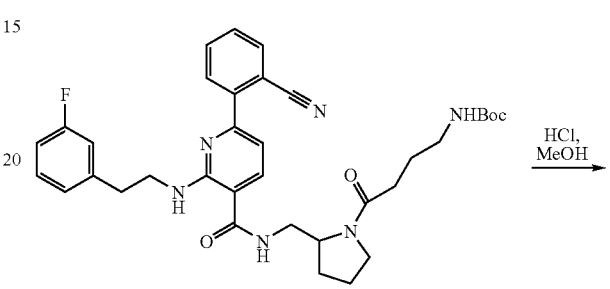

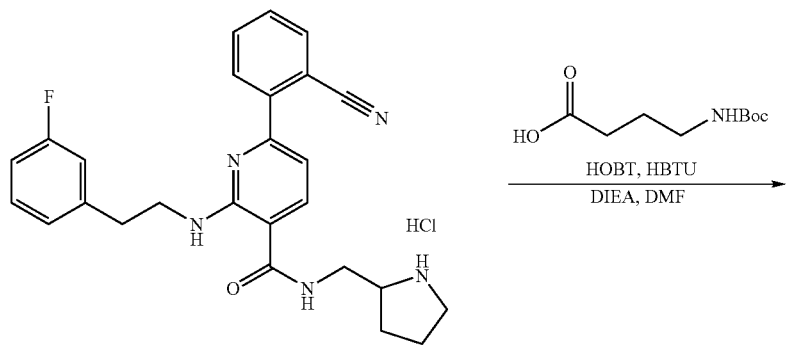

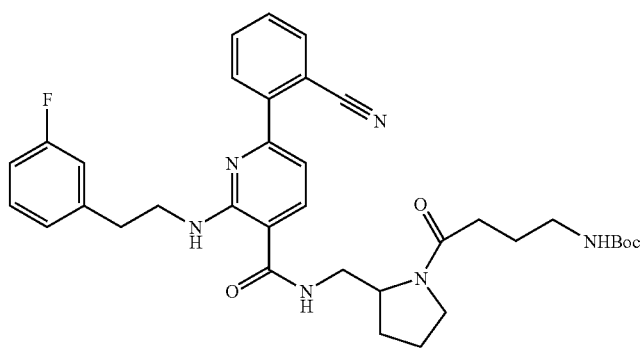

-continued

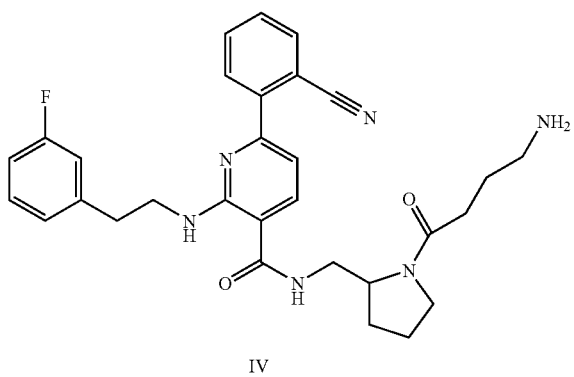

IV

To a solution of tert-butyl 4-(2-((6-(2-cyanophenyl)-2-(3-fluorophenethylamino)nicotinamido)methyl)pyrrolidin-1-yl)-4-oxobutylcarbamate (71 mg, 0.11 mmol) in MeOH (5.0 mL) was added HCl (1.0 mL, 4 mmol, 4 M in dioxane). The reaction mixture was stirred at r.t. for 2 h. LC/MS indicated the reaction was complete. The reaction mixture was concentrated under reduced pressure and the crude was purified on RP-HPLC using a mixture of acetonitrile (0.1% TFA) and water (0.1% TFA) to give N-((1-(4-aminobutanoyl)pyrrolidin-2-yl)methyl)-6-(2-cyanophenyl)-2-(3-fluorophenethylamino)nicotinamide as a pale yellow solid (57.1 mg, 68%). LRMS (M+H$^+$) m/z 529.2.

Example 5

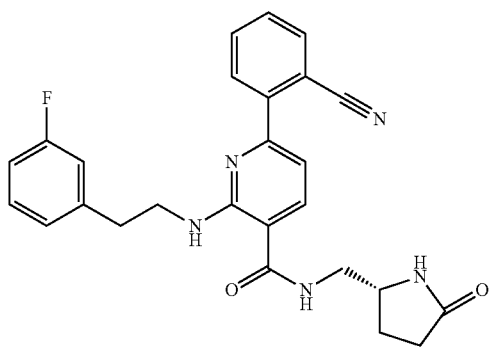

(R)-6-(2-cyanophenyl)-2-(3-fluorophenethylamino)-
N-((5-oxopyrrolidin-2-yl)methyl)nicotinamide

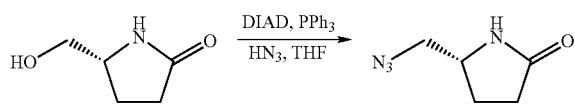

To (R)-5-(hydroxymethyl)pyrrolidin-2-one (660 mg, 5.73 mmol), hydrogen azide (10.8 mL, 8.60 mmol, 0.8 M in toluene), and PPh$_3$ (2.25 g, 8.60 mmol) in THF was added DIAD dropwise. The mixture was stirred at rt for 1 h. LCMS indicated the completion of the reaction. The mixture was partially concentrated, filtered, and purified by RP-HPLC to give (R)-5-(azidomethyl)pyrrolidin-2-one (730 mg, 87%, 90% pure). LRMS (M+H$^+$) m/z 141.1.

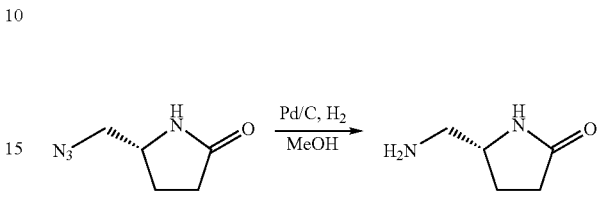

To (R)-5-(azidomethyl)pyrrolidin-2-one (150 mg, 1.07 mmol) in MeOH was added Pd/C. The mixture was the placed into an autoclave, degasses three times, charged with 30 psi of H$_2$ and stirred at rt for 30 min. The mixture was the filtered and the filtrate was concentrated under reduced pressure to give (R)-5-(aminomethyl)pyrrolidin-2-one (92 mg, 75%). LRMS (M+H$^+$) m/z 115.1.

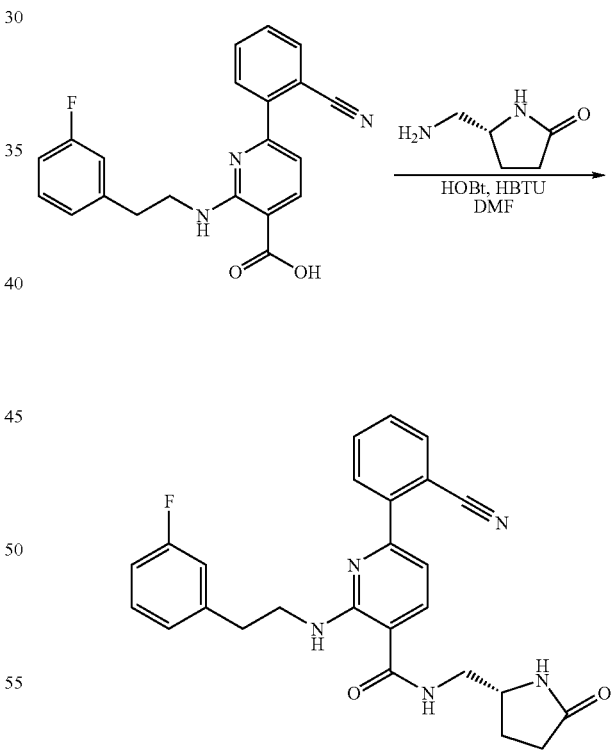

V

To a mixture of 6-(2-cyanophenyl)-2-(3-fluorophenethylamino)nicotinic acid (110 mg, 0.30 mmol), (R)-5-(aminomethyl)pyrrolidin-2-one (52 mg, 0.46 mmol), HOBT (62 mg, 0.46 mmol), and HBTU (174 mg, 0.46 mg) in RB flask was added DMF and the mixture was stirred at r.t. for 1 h. LC/MS indicated the reaction was complete and the mixture was filtered and purified on RP-HPLC using a mixture of acetonitrile and water to give (R)-6-(2-cyanophenyl)-2-(3-fluorophenethylamino)-N-((5-oxopyrrolidin-2-yl)methyl)nicotinamide (91.6 mg, 67%). LRMS (M+H⁺) m/z 458.1.

Example 6

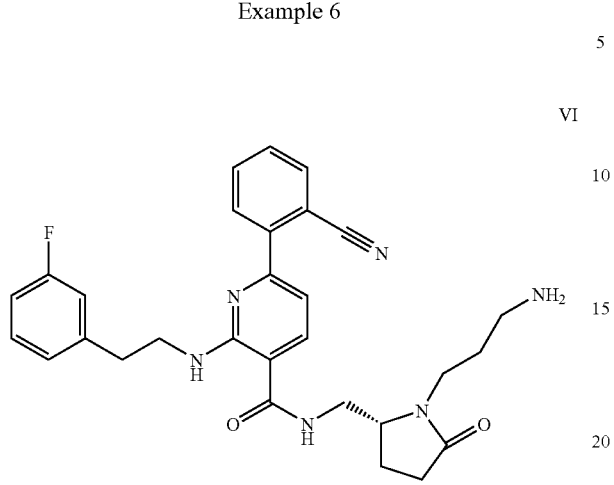

(R)—N-((1-(3-aminopropyl)-5-oxopyrrolidin-2-yl)methyl)-6-(2-cyanophenyl)-2-(3-fluorophenethylamino)nicotinamide To NaH (128 mg, 3.21 mmol) in DMF (5.0 mL) was added (R)-5-(azidomethyl)pyrrolidin-2-one (300 mg, 2.14 mmol) in DMF (5.0 mL) and stirred at rt for 30 min followed by addition of tert-butyl 3-bromopropylcarbamate. The mixture was heated to 60° C. for 2 h and quenched with sat. NH₄Cl solution. The aqueous layer was extracted with EtOAc (50 mL×2) and the combined organic layer was washed with brine, dried over Na2SO4, filtered, and concentrated under reduced pressure to give (R)-tert-butyl 3-(2-(azidomethyl)-5-oxopyrrolidin-1-yl)propylcarbamate (358 mg of crude), which was used for next step without purification. LRMS (M+H⁺-Boc) m/z 198.1.

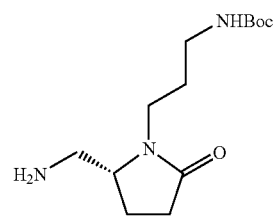

To (R)-tert-butyl 3-(2-(azidomethyl)-5-oxopyrrolidin-1-yl)propylcarbamate (300 mg, 1.01 mmol) in MeOH was added Pd/C. The mixture was the placed into an autoclave, degasses three times, charged with 30 psi of H₂ and stirred at rt for 30 min. The mixture was the filtered and the filtrate was concentrated under reduced pressure to give (R)-tert-butyl 3-(2-(aminomethyl)-5-oxopyrrolidin-1-yl)propylcarbamate (180 mg of crude). LRMS (M+H⁺) m/z 198.1.

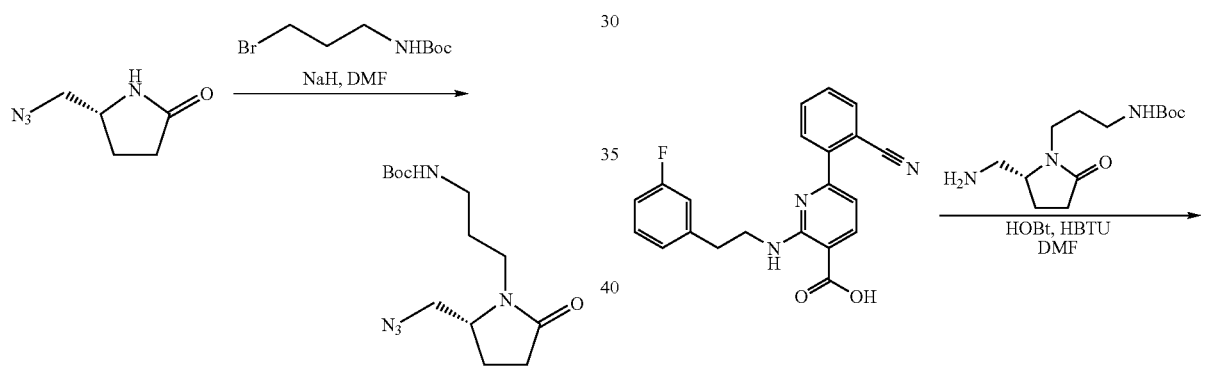

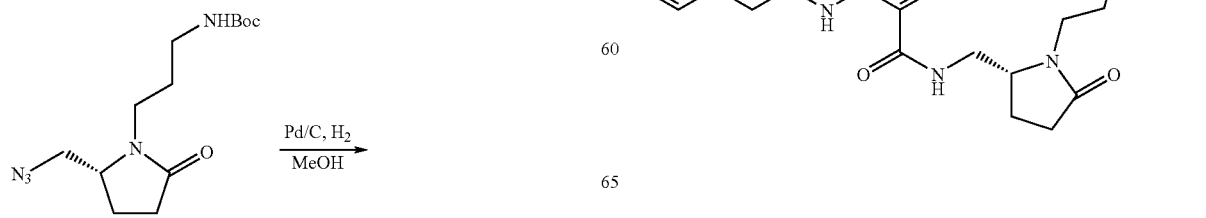

To a mixture of 6-(2-cyanophenyl)-2-(3-fluorophenethylamino)nicotinic acid (110 mg, 0.30 mmol), (R)-tert-butyl 3-(2-(aminomethyl)-5-oxopyrrolidin-1-yl)propylcarbamate (125 mg, 0.46 mmol), HOBT (107 mg, 0.46 mmol), and HBTU (174 mg, 0.46 mg) in RB flask was added DMF and the mixture was stirred at r.t. for 1 h. LC/MS indicated the reaction was complete and the mixture was filtered and purified on RP-HPLC using a mixture of acetonitrile and water to give (R)-tert-butyl 3-(2-((6-(2-cyanophenyl)-2-(3-fluorophenethylamino)nicotinamido)methyl)-5-oxopyrrolidin-1-yl)propylcarbamate (72 mg, 39%). LRMS (M+H⁺) m/z 615.2.

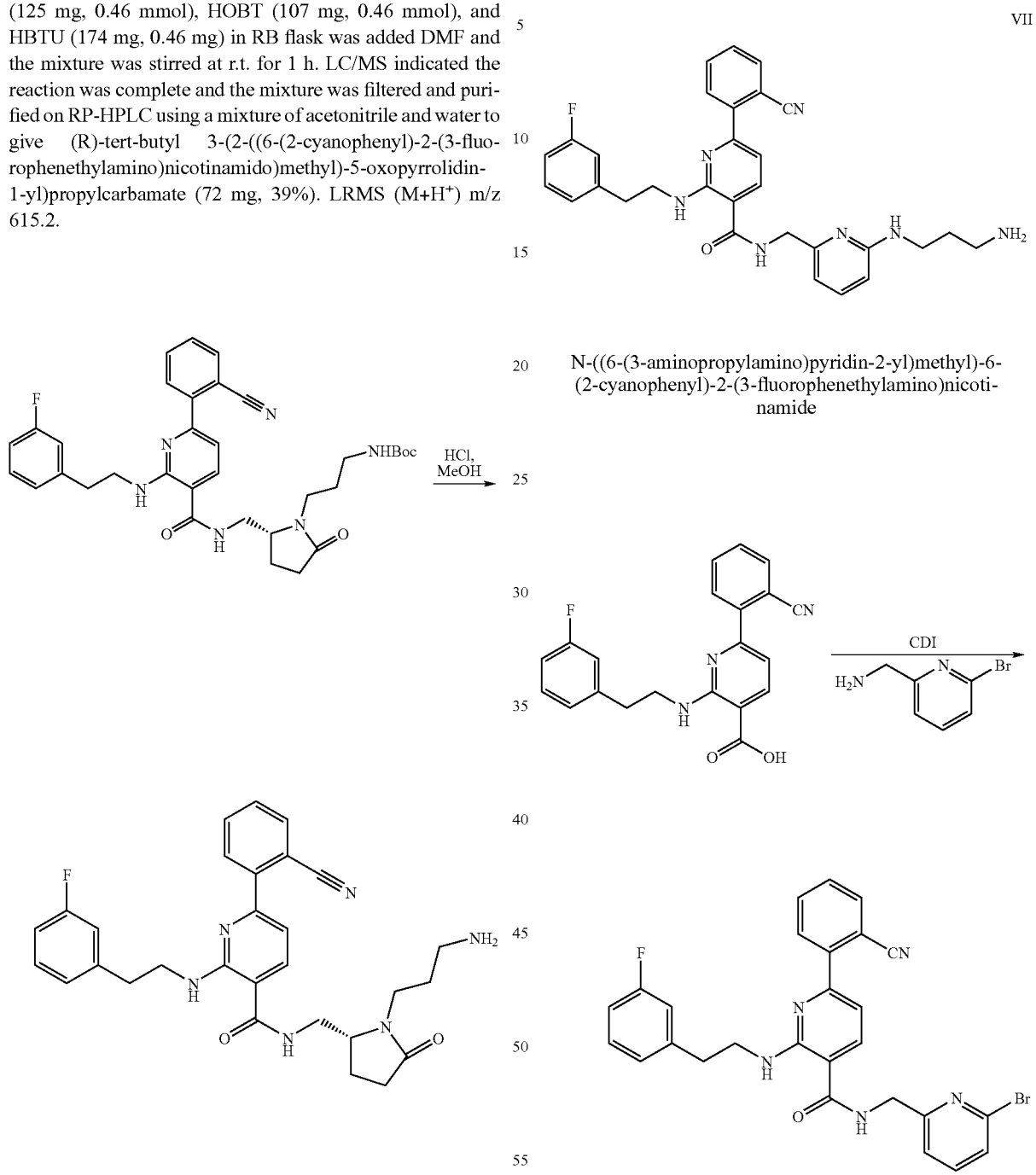

Example 7

N-((6-(3-aminopropylamino)pyridin-2-yl)methyl)-6-(2-cyanophenyl)-2-(3-fluorophenethylamino)nicotinamide To a solution of (R)-tert-butyl 3-(2-((6-(2-cyanophenyl)-2-(3-fluorophenethylamino)nicotinamido)methyl)-5-oxopyrrolidin-1-yl)propylcarbamate (72 mg, 0.12 mmol) in MeOH (5.0 mL) was added HCl (1.0 mL, 4 mmol, 4 M in dioxane). The reaction mixture was stirred at r.t. for 2 h. LC/MS indicated the reaction was complete. The reaction mixture was concentrated under reduced pressure to give (R)—N-((1-(3-aminopropyl)-5-oxopyrrolidin-2-yl)methyl)-6-(2-cyanophenyl)-2-(3-fluorophenethylamino)nicotinamide hydrogen chloride (75 mg, quantitative). LRMS (M+H⁺) m/z 515.1.

To a solution of 6-(2-cyanophenyl)-2-(3-fluorophenethylamino)nicotinic acid (582 mg, 1.61 mmol) and 6-bromopyridin-2-yl-methylamine (300 mg, 1.61 mmol) in DMF was added CDI (261 mg, 1.61 mmol). The reaction mixture was stirred at r.t. for 2 h. The reaction mixture was purified on RP-HPLC to give N-((6-bromopyridin-2-yl)methyl)-6-(2-cyanophenyl)-2-(3-fluorophenethylamino)nicotinamide (700 mg, 82%) LRMS (M+H⁺) m/z 530.1.

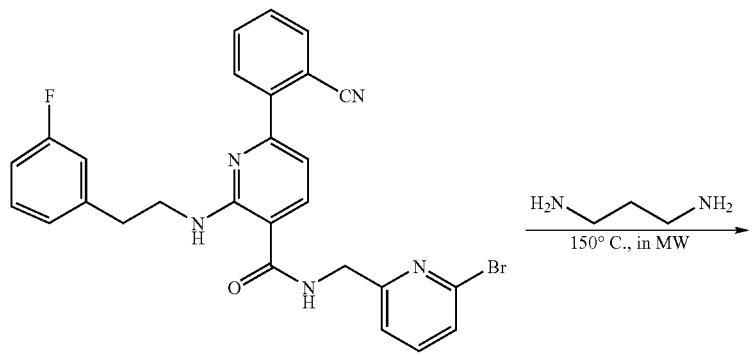

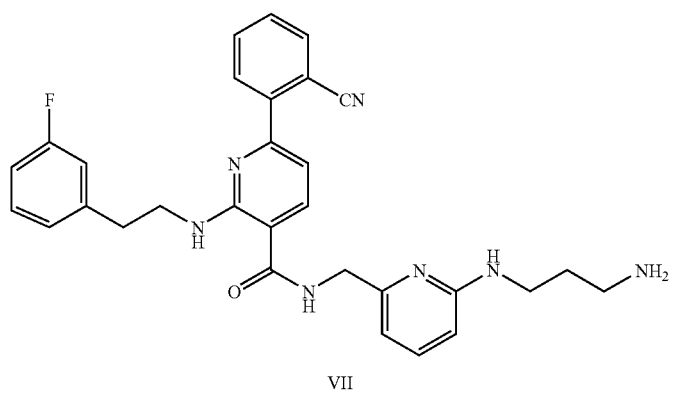

A solution of N-((6-bromopyridin-2-yl)methyl)-6-(2-cyanophenyl)-2-(3-fluorophenethylamino)nicotinamide (50 mg, 0.095 mmol) and propane-1,3-diamine (396 ul, 4.75 mmol) in NMP was stirred in microwave at 15° C. for 15 min. The reaction mixture was purified on RP-HPLC using a mixture of acetonitrile and H$_2$O gave N-((6-(3-aminopropylamino)pyridin-2-yl)methyl)-6-(2-cyanophenyl)-2-(3-fluorophenethylamino)nicotiamide (28 mg, 56%). LRMS (M+H$^+$) m/z 524.1.

Example 8

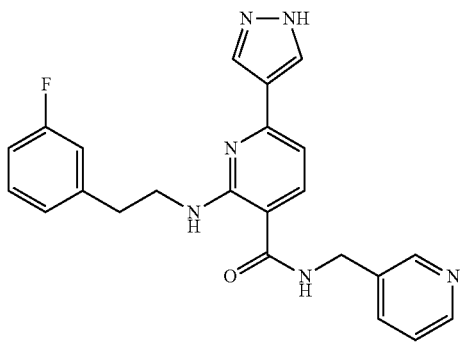

VIII 2-(3-fluorophenethylamino)-6-(1H-pyrazol-4-yl)-N-(pyridin-3-ylmethyl)nicotinamide Method A:

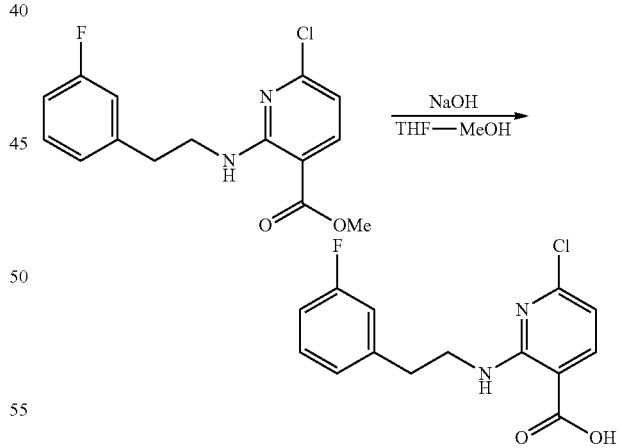

To a mixture of ester methyl 6-chloro-2-(3-fluorophenethylamino)nicotinate (3.08 g, 10 mmol), methanol (20 mL) and THF (20 mL) was added 3N NaOH (10 mL, 30 mmol). The reaction mixture was stirred at room temperature for 2 days. The mixture was concentrated to remove methanol and THF and adjusted pH to 3 with 2N HCl. The precipitate was filtered and washed with water to give the 6-chloro-2-(3-fluorophenethylamino)nicotinic acid in quantitative yield. LRMS (M+H$^+$) m/z 295.1.

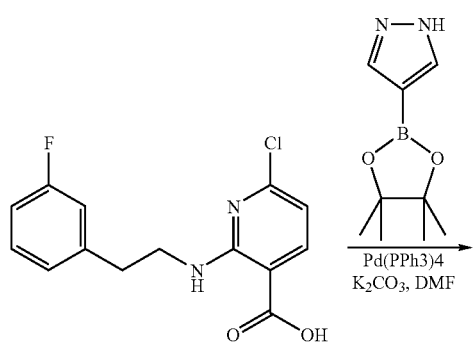

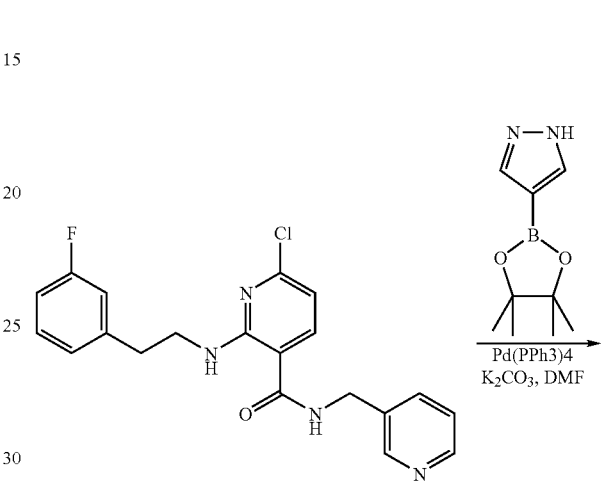

A mixture of 6-chloro-2-(3-fluorophenethylamino)nicotinic acid (10.6 g, 36 mmol), borolane (12.72 g, 43 mmol), Pd(PPh₃)₄ (4.2 g, 3.6 mmol), K₂CO₃ (14.9 g, 108 mmol) and anhydrous DMF (50 mL) was degassed with nitrogen for 10 min. The mixture was then stirred at 120° C. in microwave for 2 hrs. The mixture was filtered through the Celite and washed with DMF. The filtrate was adjusted to pH 4 with 2N HCl (28 mL), and diluted with EtOAc. The organic layer was washed with brine twice and concentrated to dryness. The residue was triturated with dichloromethane (300 mL). Filtration followed by washed with EtOAc (20 mL) gave 2-(3-fluorophenethylamino)-6-(1H-pyrazol-4-yl)nicotinic acid as a yellow solid (7.1 g, 61%). LRMS (M+H⁺) m/z 327.1.

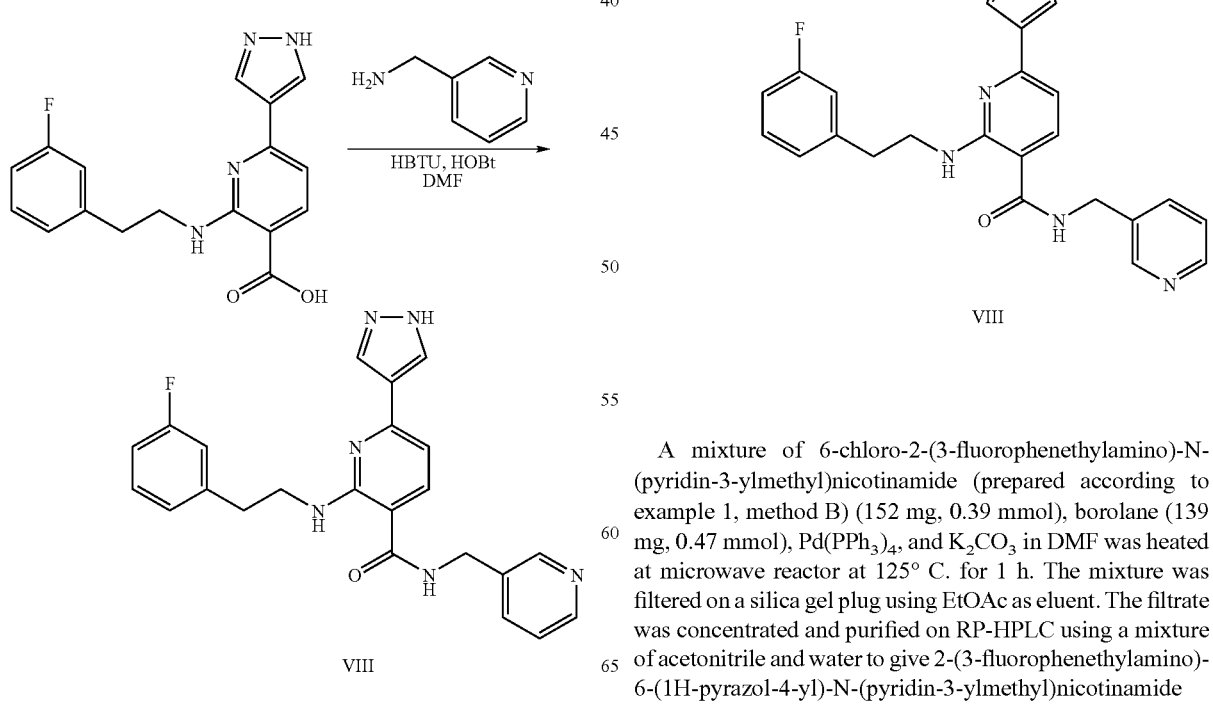

VIII

To a mixture of 2-(3-fluorophenethylamino)-6-(1H-pyrazol-4-yl)nicotinic acid (prepared according to example 1, method A) (1.0 g, 3.07 mmol) in DMF (10 mL) was added HBTU (1.75 g, 4.6 mmol), HOBt (0.62 g, 4.6 mmol), then amine 7 (0.66 g, 6.13 mmol). The reaction mixture was stirred at room temperature for 2 hr. The crude mixture was purified on RP-HPLC using a mixture of acetonitrile and H₂O to give 2-(3-fluorophenethylamino)-6-(1H-pyrazol-4-yl)-N-(pyridin-3-ylmethyl)nicotinamide as a pale yellow solid (0.79 g, 62%). LRMS (M+H⁺) m/z 417.1.

Method B:

A mixture of 6-chloro-2-(3-fluorophenethylamino)-N-(pyridin-3-ylmethyl)nicotinamide (prepared according to example 1, method B) (152 mg, 0.39 mmol), borolane (139 mg, 0.47 mmol), Pd(PPh₃)₄, and K₂CO₃ in DMF was heated at microwave reactor at 125° C. for 1 h. The mixture was filtered on a silica gel plug using EtOAc as eluent. The filtrate was concentrated and purified on RP-HPLC using a mixture of acetonitrile and water to give 2-(3-fluorophenethylamino)-6-(1H-pyrazol-4-yl)-N-(pyridin-3-ylmethyl)nicotinamide (60.5 mg, 37%). LRMS (M+H⁺-Boc) m/z 417.1.

Example 9

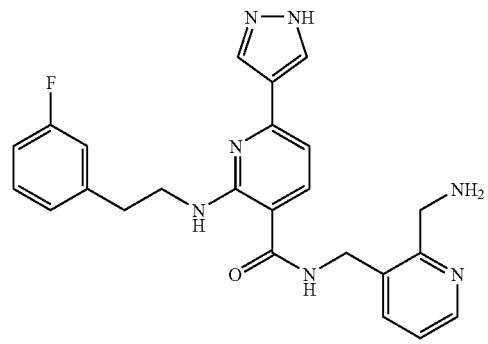

N-((2-(aminomethyl)pyridin-3-yl)methyl)-2-(3-fluorophenethylamino)-6-(1H-pyrazol-4-yl)nicotinamide

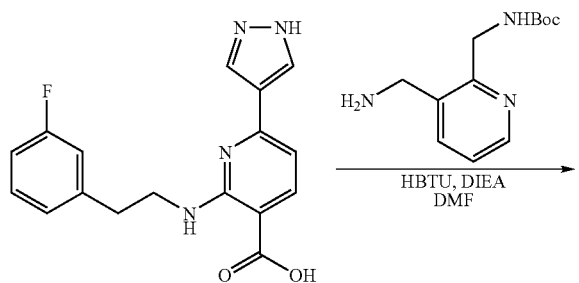

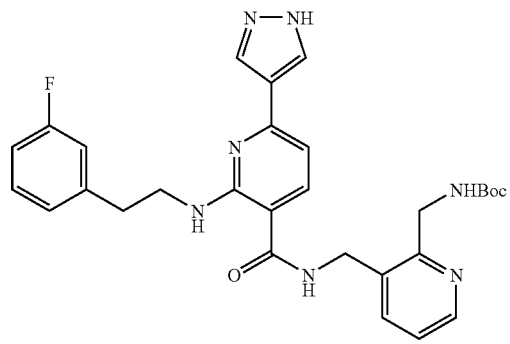

To a mixture of 6-chloro-2-(3-fluorophenethylamino) nicotinic acid (prepared from example 8, method A) (0.72 g, 2.21 mmol) in DMF (5 mL) was added DIEA (0.417 mL, 2.53 mmol), HBTU (0.84 g, 2.21 mmol), HOBt (0.30 g, 2.21 mmol), then amine tert-butyl (3-(aminomethyl)pyridin-2-yl) methylcarbamate (preparations according to example 2) (0.50 g, 2.11 mmol). The reaction mixture was stirred at room temperature for 1 hr. The crude mixture was purified on RP-HPLC using a mixture of acetonitrile and H$_2$O to give tert-butyl (3-((2-(3-fluorophenethylamino)-6-(1H-pyrazol-4-yl)nicotinamido)methyl)pyridin-2-yl)methylcarbamate as a pale yellow solid (737 mg, 60%). LRMS (M+H$^+$) m/z 546.3.

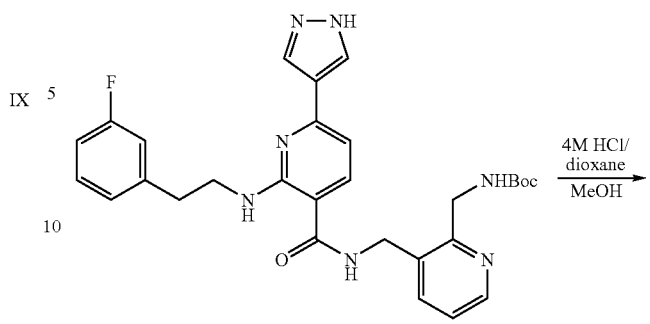

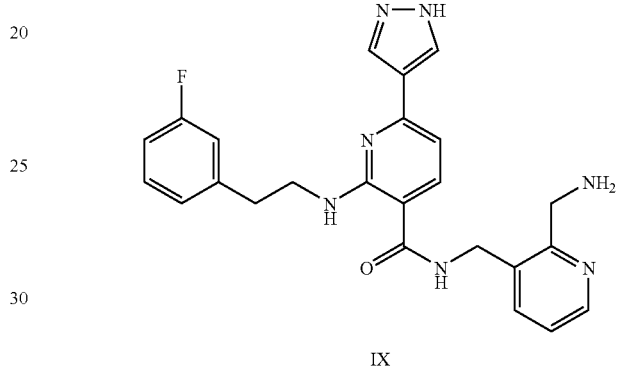

To a solution of tert-butyl (3-((2-(3-fluorophenethylamino)-6-(1H-pyrazol-4-yl)nicotinamido)methyl)pyridin-2-yl)methylcarbamate (737 mg, 1.27 mmol) in methanol (6 mL) at 0° C. was added a solution of 4M HCl in 1,4-dioxane (3 mL). The mixture was warmed to room temperature and stirred for 2 hrs. Concentration of the mixture followed by the purification on RP-HPLC using a mixture of acetonitrile and H$_2$O gave N-((2-(aminomethyl)pyridin-3-yl)methyl)-2-(3-fluorophenethylamino)-6-(1H-pyrazol-4-yl)nicotinamide compound with methanol (1:1) as a pale yellow solid (545 mg, 89%). LRMS (M+H$^+$) m/z 446.2.

Example 10

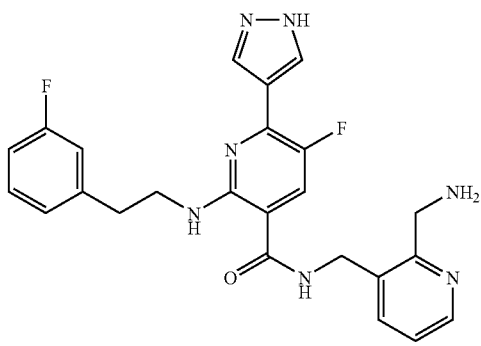

N-((2-(aminomethyl)pyridin-3-yl)methyl)-5-fluoro-
2-(3-fluorophenethylamino)-6-(1H-pyrazol-4-yl)
nicotinamide

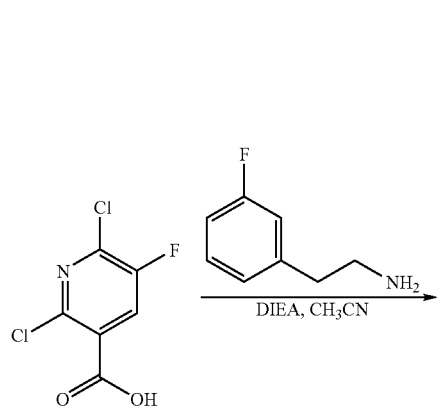

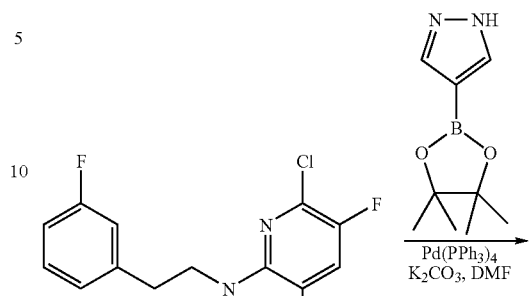

A mixture of 2,6-dichloro-5-fluoronicotinic acid (1.26 g, 6.0 mmol), 3-fluorophenethyl amine (1.25 mL, 9.0 mmol), DIEA (3.14 mL, 18 mmol) and MeCN (6 mL) was refluxed for 48 hrs and concentrated. The residue was dissolved in EtOAc (120 mL) and washed with saturated citric acid, water, brine, dried and concentrated. The organic layers were combined, dried (MgSO$_4$) and concentrated. The residue was purified on RP-HPLC using a mixture of acetonitrile and H$_2$O to give 6-chloro-5-fluoro-2-(3-fluorophenethylamino)nicotinic acid as a solid (920 mg, 49%). LRMS (M+H$^+$) m/z 313.0.

A mixture of 6-chloro-5-fluoro-2-(3-fluorophenethylamino)nicotinic acid (2.2 g, 7.04 mmol), 4,4,5,5-tetramethyl-2-(1H-pyrazol-4-yl)-1,3,2-dioxoborolane (2.04 g, 10.56 mmol), Pd(PPh$_3$)$_4$ (0.81 g, 0.71 mmol), K$_2$CO$_3$ (2.92 g, 21.1 mmol) and anhydrous DMF (10 mL) was degassed with nitrogen for 10 min. The mixture was then stirred at 150° C. in microwave for 3 hrs. The mixture was filtered through the Celite and washed with DMF (50 mL). The filtrate was adjusted to pH 4 with 2N HCl (5 mL), and diluted with EtOAc (150 mL). The organic layer was washed with saturated ammonium chloride, brine and concentrated to dryness. The residue was triturated with dichloromethane (30 mL). Filtration followed by washed with EtOAc (5 mL) gave 5-fluoro-2-(3-fluorophenethylamino)-6-(1H-pyrazol-4-yl)nicotinic acid as a yellow solid (2.1 g, 87%). LRMS (M+H$^+$) m/z 345.3.

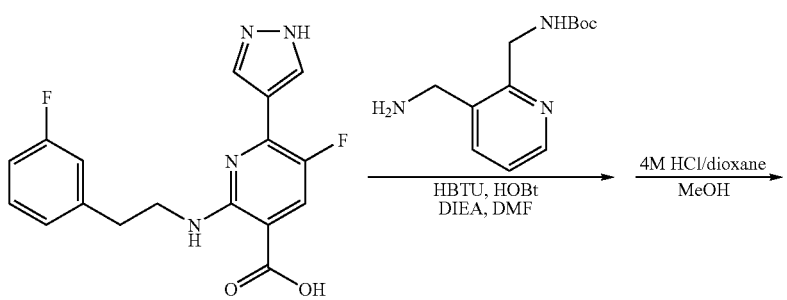

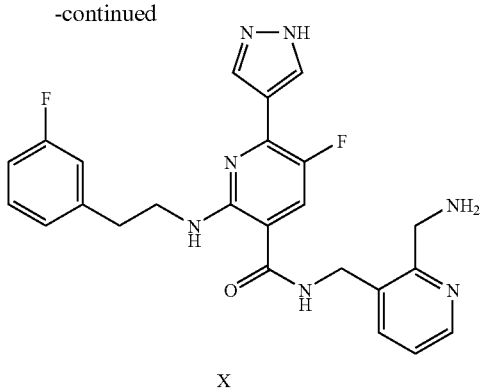

X

Compound X was prepared from 5-fluoro-2-(3-fluorophenethylamino)-6-(1H-pyrazol-4-yl)nicotinic acid and amine tert-butyl (3-(aminomethyl)pyridin-2-yl)methylcarbamate according to the procedure of preparation of Example 9. LRMS (M+H$^+$) m/z 464.1.

Example 11

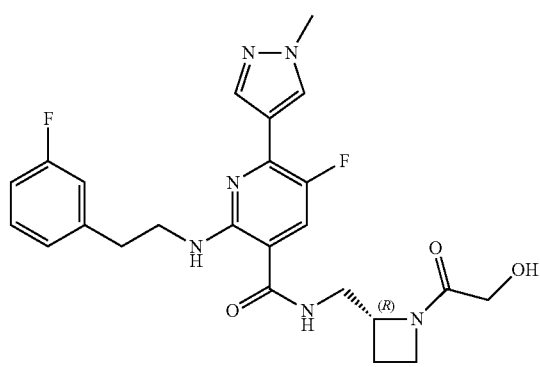

(R)-5-fluoro-2-(3-fluorophenethylamino)-N-((1-(2-hydroxyacetyl)azetidin-2-yl)methyl)-6-(1-methyl-1H-pyrazol-4-yl)nicotinamide

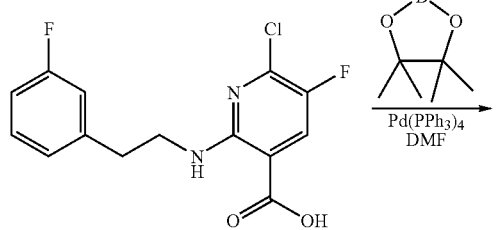

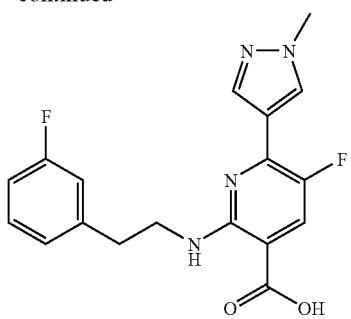

A mixture of 6-chloro-5-fluoro-2-(3-fluorophenethylamino)nicotinic acid (see example 10) (15.6 g, 50 mmol), borolane (12.5 g, 60 mmol), Pd(PPh$_3$)$_4$ (5.8 g, 5 mmol), K$_2$CO$_3$ (20.7 g, 150 mmol) and anhydrous DMF (100 mL) was degassed with nitrogen for 10 min. The mixture was then stirred at 125° C. in microwave for 2 hrs. The mixture was filtered through the Celite and washed with DMF. The filtrate was adjusted to pH 4 with 2N HCl, and diluted with EtOAc. The organic layer was washed with brine twice and concentrated to dryness. The residue was triturated with EtOAc (200 mL). Filtration followed by washed with EtOAc (20 mL) gave 5-fluoro-2-(3-fluorophenethylamino)-6-(1-methyl-1H-pyrazol-4-yl)nicotinic acid as a yellow solid (14.5 g, 85%). LRMS (M+H$^+$) m/z 359.0.

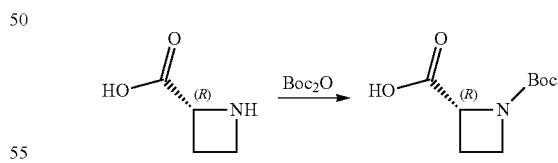

To a mixture of D-azetidine-carboxylic acid (20 g, 200 mmol), H$_2$O (200 mL) and dioxane (200 ml) at 0° C. was added a solution of Boc$_2$O in dioxane (100 mL) with an additional funnel. The mixture was stirred at r.t for 1 hour. After concentration, 200 mL ether and 200 mL H$_2$O were added to the residue. The aqueous layer was acidified with 2N HCl to pH 3-4, and then extracted with 200 mL EtOAc. The organic layer was dried and concentrated to give (R)-1-(tert-butoxycarbonyl)azetidine-2-carboxylic acid in quantitative yield (40 g). LRMS (M−100+H$^+$) m/z 102.1.

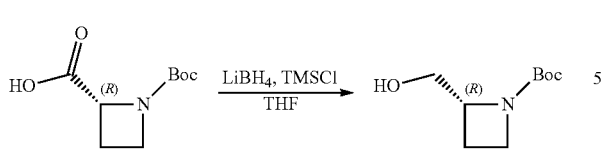

To a solution of 2M LiBH$_4$ (200 ml, 400 mmol) in THF at 0° C. was added TMSCl (101 ml, 800 mmol) slowly. The mixture was warmed up to r.t and stirred at r.t. for 30 min. To the mixture at 0° C. was added a solution of (R)-1-(tert-butoxycarbonyl)azetidine-2-carboxylic acid (40 g, 200 mmol) in 200 ml THF with an additional funnel over 1 hour. The mixture was warmed up to r.t and stirred at r.t. for 2 hours. The mixture was cooled down to 0° C. and then treated with 32 mL MeOH followed by 40 mL H$_2$O. After removal of THF, the residue was extracted with 300 mL EtOAc and washed with 300 mL brine. The organic layer was dried and concentrated to give (R)-tert-butyl 2-(hydroxymethyl)azetidine-1-carboxylate as a colorless oil (32.5 g, 87%). LRMS (M−100+H$^+$) m/z 132.1.

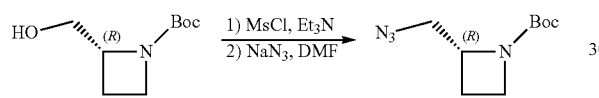

To a mixture of (R)-tert-butyl 2-(hydroxymethyl)azetidine-1-carboxylate (32.5 g, 173 mmol) and Et$_3$N (27 mL, 191 mmol) in THF (650 mL) at 0° C. was added methane sulfonylchloride (14.9 ml, 191 mmol) dropwise. The mixture was stirred for 10 min. The precipitation was filtered off and the filtrate was concentrated. The residue was then dissolved with DMF (200 mL). Sodium azide (34 g, 519 mmol) was then added. The mixture was stirred at 65° C. for 6 hours. 300 mL EtOAc and 300 mL brine were then added to the reaction mixture. The organic layer was dried and concentrated. The residue was purified by Biotage silica gel chromatography (EtOAc:Hexane 1:4) to give (R)-tert-butyl 2-(azidomethyl)azetidine-1-carboxylate as a colorless oil (32 g, 87% yield). LRMS (M−100+H$^+$) m/z 113.1.

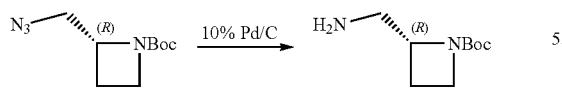

A mixture of (R)-tert-butyl 2-(azidomethyl)azetidine-1-carboxylate (17 g, 80 mmol), 10% Pd/C (2 g) and MeOH (150 mL) was stirred under 45 psi hydrogen for 1 hour. The catalyst was filtered off and the filtrate was concentrated to give (R)-tert-butyl 2-(aminomethyl)azetidine-1-carboxylate (14.9 g, yield 100%). LRMS (M+H$^+$) m/z 187.3.

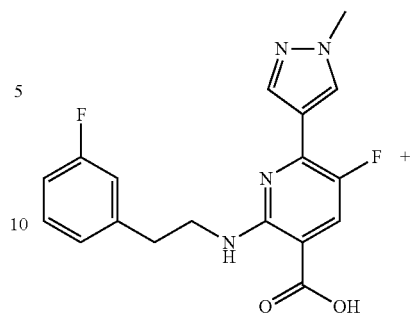

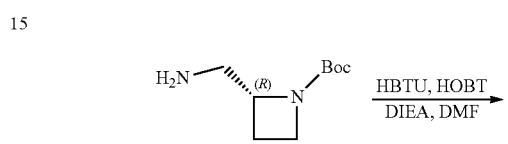

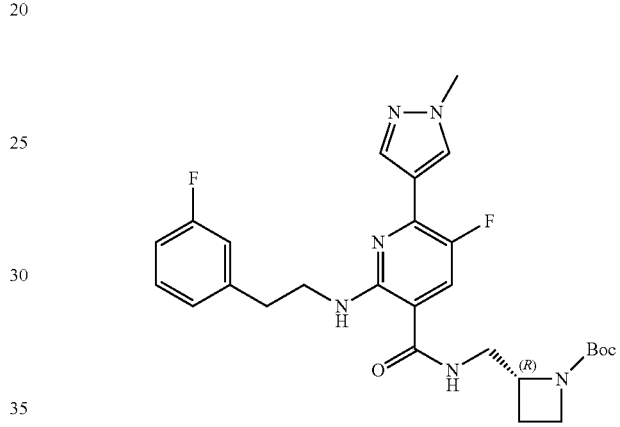

To a mixture of 5-fluoro-2-(3-fluorophenethylamino)-6-(1-methyl-1H-pyrazol-4-yl)nicotinic acid (14.3 g, 40 mmol) and DMF (300 mL) was added of HBTU (18.2 g, 48 mmol) and HOBT (6.49 g, 48 mmol). The mixture was cooled down to 0° C., 8.93 g (48 mmol) of (R)-tert-butyl 2-(aminomethyl)azetidine-1-carboxylate was added, followed by 13.9 ml of DIEA (80 mmol). The mixture was stirred at r.t for 1 hour and extracted with 300 mL EtOAc. The organic layer was washed with 500 mL brine, dried over MgSO$_4$ and then concentrated. The residue was purified by Biotage silica gel chromatography using EtOAc:Hex (1:1) as eluant. (R)-tert-butyl 2-((5-fluoro-2-(3-fluorophenethylamino)-6-(1-methyl-1H-pyrazol-4-yl)nicotinamido)methyl)azetidine-1-carboxylate was obtained as a yellow solid (16.5 g, yield 80%). LRMS (M+H$^+$) m/z 527.1.

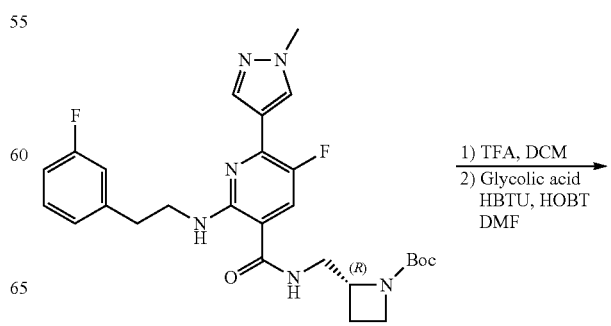

587
-continued

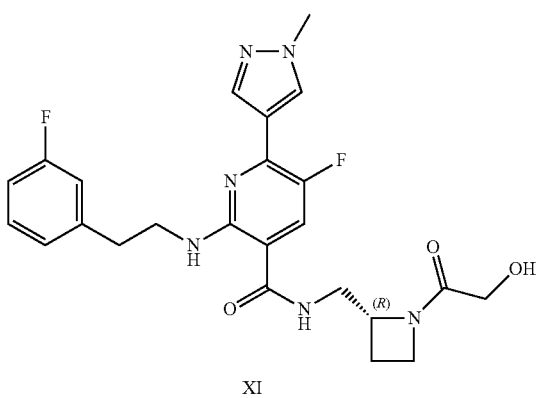

XI

To a mixture of (R)-tert-butyl 2-((5-fluoro-2-(3-fluorophenethylamino)-6-(1-methyl-1H-pyrazol-4-yl)nicotinamido)methyl)azetidine-1-carboxylate (16.5 g, 31.4 mmol) in 100 mL DCM at 0° C. was added trifluoroacetic acid (24 mL, 314 mmol) slowly. The mixture was stirred at r.t for 2 hours until the Boc protection group was completely removed. The mixture was then concentrated. The residue was dissolved in 100 mL DMF and cooled down to 0° C. To the mixture was added a mixture of glycolic acid (2.86 g, 38 mmol), HBTU (14.3 g, 38 mmol), HOBT (5.1 g, 38 mmol) and DIEA (16.4 ml, 94 mmol). The mixture was warmed up to r.t and stirred at r.t. for 2 hours. The mixture was extracted with EtOAc. The organic layer was further washed with 1N NaOH (300 ml) and brine, dried and concentrated. The residue was subjected to a Biotage silica gel chromatography using gradient 0-40% B as eluant (A=dichloromethane, B=10% MeOH in dichloromethane) to give the crude product. The yellow solid was further tritirated with 100 mL EtOAc. (R)-5-fluoro-2-(3-fluorophenethylamino)-N-((1-(2-hydroxyacetyl)azetidin-2-yl)methyl)-6-(1-methyl-1H-pyrazol-4-yl)nicotinamide was obtained as a pale yellow solid (12.7 g, 83% yield). LRMS (M+H⁺) m/z 485.1.

Example 12

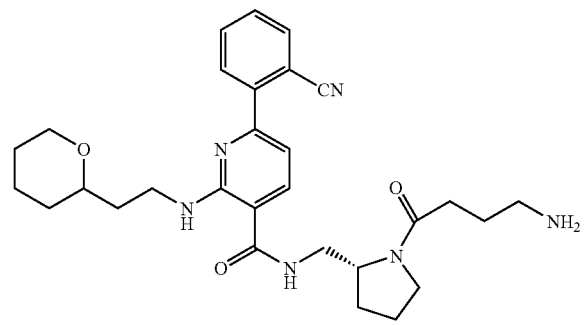

XII

588
N—(((R)-1-(4-aminobutanoyl)pyrrolidin-2-yl)methyl)-6-(2-cyanophenyl)-2-(2-(tetrahydro-2H-pyran-2-yl)ethylamino)nicotinamide

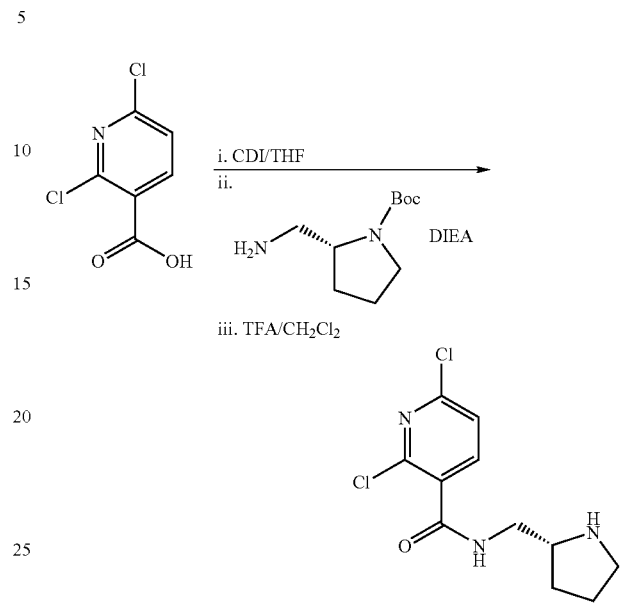

A mixture of 2,6-dichloronicotinic acid (1.0 g, 5.21 mmol), N,N'-carbonyldiimidazole (CDI, 1.01 g, 6.25 mmol) and THF (10 mL) was stirred at 60° C. for 30 min and cooled to room temperature. To the mixture was added (R)-tert-butyl 2-(aminomethyl)pyrrolidine-1-carboxylate (1.04 g, 6.25 mmol) and DIEA (1.03 mL, 5.21 mmol). The reaction mixture was stirred at room temperature for 4 hrs, and diluted with EtOAc. The organic layer was washed with H₂O, brine, dried over Na₂SO₄. Concentration of the organic solution followed by treatment with 30% TFA in dichloromethane (10 mL) gave (R)-2,6-dichloro-N-(pyrrolidin-2-ylmethyl)nicotinamide TFA salt as a white solid (1.7 g, 84%). LRMS (M+H⁺) m/z 274.0.

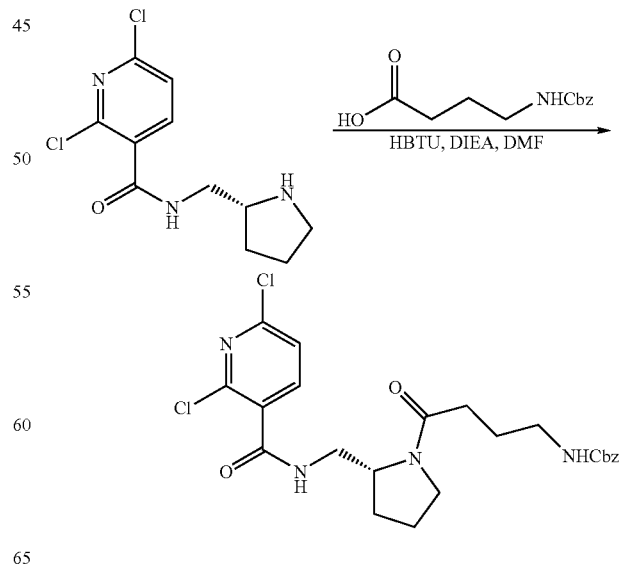

To a mixture of 4-(benzyloxycarbonylamino)butanoic acid (1.29 g, 5.45 mmol) in DMF (4 mL) was added HBTU (2.07 g, 5.45 mmol), DIEA (3.0 mL, 18.17 mmol), then amine (R)-2,6-dichloro-N-(pyrrolidin-2-ylmethyl)nicotinamide (1.7 g, 4.54 mmol). The reaction mixture was stirred at room temperature for 1 hr. The crude mixture was purified by silica gel chromatography using a mixture of EtOAC-MeOH (19:1) to give (R)-benzyl 4-(2-((2,6-dichloronicotinamido)methyl) pyrrolidin-1-yl)-4-oxobutylcarbamate (1.9 g, 85%). LRMS (M+H$^+$) m/z 493.4.

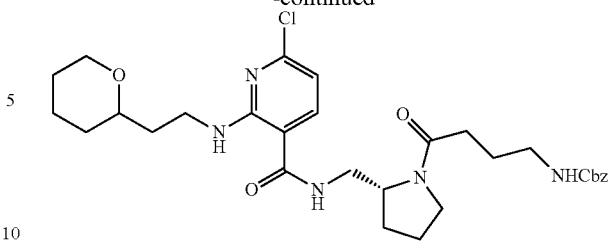

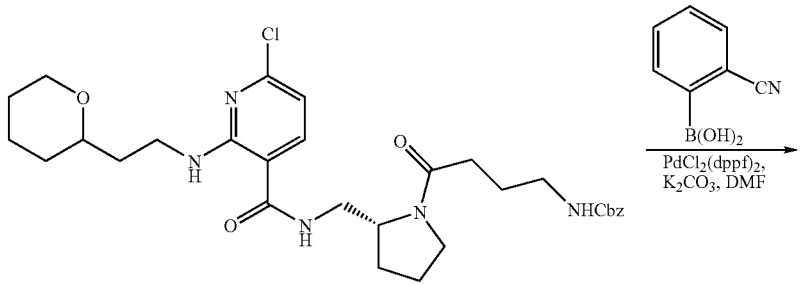

A mixture of chloride (R)-benzyl 4-(2-((2,6-dichloronicotinamido)methyl)pyrrolidin-1-yl)-4-oxobutylcarbamate (150 mg, 0.304 mmol), 2-(tetrahydro-2H-pyran-2-yl)ethanamine HCl salt (76 mg, 0.459 mmol), K$_2$CO$_3$ (125 mg, 0.905 mmol) and DMF (1 mL) was stirred at 100° C. for 10 hrs. The crude mixture was purified on RP-HPLC using a mixture of acetonitrile and H$_2$O to give benzyl 4-((R)-2-((6-chloro-2-(2-(tetrahydro-2H-pyran-2-yl)ethylamino)nicotinamido)methyl)pyrrolidin-1-yl)-4-oxobutylcarbamate (62 mg, 35%). LRMS (M+H$^+$) m/z 586.3.

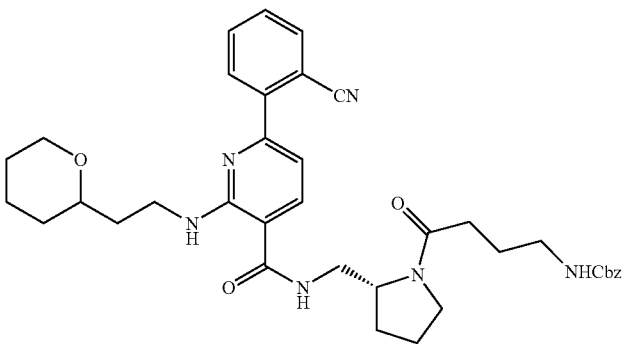

A mixture of benzyl 4-((R)-2-((6-chloro-2-(2-(tetrahydro-2H-pyran-2-yl)ethylamino)nicotinamido)methyl)pyrrolidin-1-yl)-4-oxobutylcarbamate (62 mg, 0.101 mmol), 2-cyanophenyl boronic acid (23 mg, 0.156 mmol), PdCl$_2$(dppf)$_2$ (11 mg, 0.02 mmol), K$_2$CO$_3$(92 g, 0.667 mmol) and anhydrous DMF (1 mL) was stirred at 125° C. for 1 hr. The mixture was filtered through the silica gel pad and washed with EtOAc. The filtrate was concentrated to dryness and purified on RP-HPLC using a mixture of acetonitrile and H$_2$O to give benzyl 4-((R)-2-((6-(2-cyanophenyl)-2-(2-(tetrahydro-2H-pyran-2-yl)ethylamino)nicotinamido)methyl)pyrrolidin-1-yl)-4-oxobutylcarbamate (50 mg, 77%). LRMS (M+H$^+$) m/z 653.3.

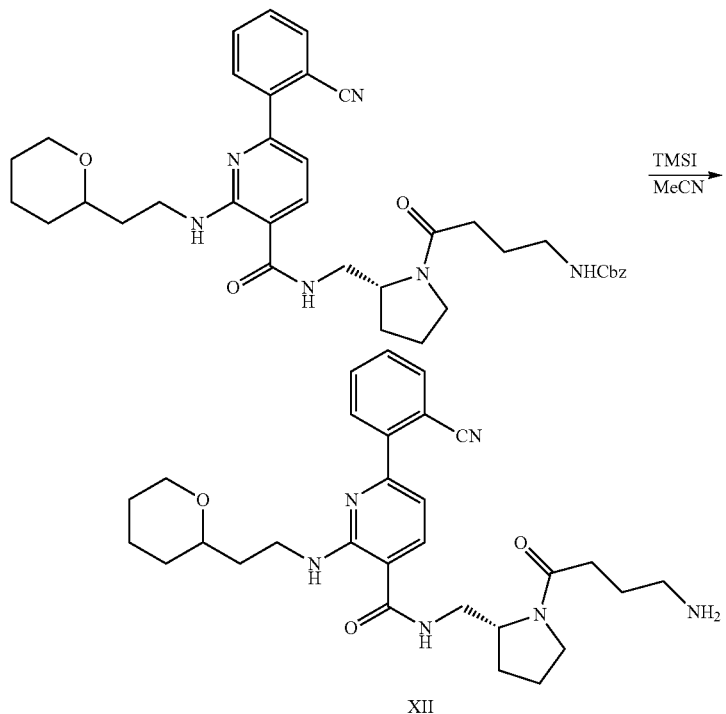

XII

To a solution of benzyl 4-((R)-2-((6-(2-cyanophenyl)-2-(2-(tetrahydro-2H-pyran-2-yl)ethylamino)nicotinamido)methyl)pyrrolidin-1-yl)-4-oxobutylcarbamate (47 mg, 0.072 mmol) in MeCN (1 mL) at 0° C. was added TMSI (72 mg, 0.36 mmol). The mixture was stirred at room temperature for 2 hrs and purified on RP-HPLC using a mixture of acetonitrile and H₂O to give N—(((R)-1-(4-aminobutanoyl)pyrrolidin-2-yl)methyl)-6-(2-cyanophenyl)-2-(2-(tetrahydro-2H-pyran-2-yl)ethylamino)nicotinamide (36 mg, 77%). LRMS (M+H⁺) m/z 519.3.

Example 13

Using procedures similar to those described herein, the compounds in the following table were synthesized and tested.

| IC50 Arithmetic Mean | Ion | m/z | CHEMICAL NAME |
|---|---|---|---|
| 3.123 | M + H | 359.2 | {6-phenyl-2-[(2-(2-pyridyl)ethyl)amino](3-pyridyl)}-N-prop-2-enylcarboxamide |
| 6.747 | M + H | 346.2 | N-methyl(2-{[2-(3-methylphenyl)ethyl]amino}-6-phenyl(3-pyridyl))carboxamide |
| 18.628 | M + H | 332.2 | N-methyl{6-phenyl-2-[(2-phenylethyl)amino](3-pyridyl)}carboxamide |
| 1.062 | M + H | 358.2 | {6-phenyl-2-[(2-phenylethyl)amino](3-pyridyl)}-N-prop-2-enylcarboxamide |
| 3.74 | M + H | 372.3 | (2-{[2-(3-methylphenyl)ethyl]amino}-6-phenyl(3-pyridyl))-N-prop-2-enylcarboxamide |
| 27.729 | M + H | 333.2 | N-methyl{6-phenyl-2-[(2-(2-pyridyl)ethyl)amino](3-pyridyl)}carboxamide |
| 1.564 | M + H | 409.2 | N-benzyl{6-phenyl-2-[(2-(2-pyridyl)ethyl)amino](3-pyridyl)}carboxamide |
| 0.151 | M + H | 409.2 | {6-phenyl-2-[(2-phenylethyl)amino](3-pyridyl)}-N-(3-pyridylmethyl)carboxamide |
| 13.296 | M + H | 361.3 | N-(methylethyl){6-phenyl-2-[(2-(2-pyridyl)ethyl)amino](3-pyridyl)}carboxamide |
| 0.463 | M + H | 410.1 | {6-phenyl-2-[(2-(2-pyridyl)ethyl)amino](3-pyridyl)}-N-(2-pyridylmethyl)carboxamide |
| 1.29 | M + H | 410.2 | {6-phenyl-2-[(2-(2-pyridyl)ethyl)amino](3-pyridyl)}-N-(4-pyridylmethyl)carboxamide |
| 5.373 | M + H | 396.2 | {6-phenyl-2-[(2-(2-pyridyl)ethyl)amino](3-pyridyl)}-N-(3-pyridyl)carboxamide |

-continued

| IC50 Arithmetic Mean | Ion | m/z | CHEMICAL NAME |
|---|---|---|---|
| 7.189 | M + H | 396.2 | {6-phenyl-2-[(2-(2-pyridyl)ethyl)amino](3-pyridyl)}-N-(2-pyridyl)carboxamide |
| 5.209 | M + H | 396.2 | {6-phenyl-2-[(2-(2-pyridyl)ethyl)amino](3-pyridyl)}-N-(4-pyridyl)carboxamide |
| 1.721 | M + H | 415.2 | {6-phenyl-2-[(2-(2-pyridyl)ethyl)amino](3-pyridyl)}-N-(2-thienylmethyl)carboxamide |
| 0.683 | M + H | 415.2 | {6-phenyl-2-[(2-(2-pyridyl)ethyl)amino](3-pyridyl)}-N-(3-thienylmethyl)carboxamide |
| 11.022 | M + H | 403.3 | N-(oxolan-2-ylmethyl){6-phenyl-2-[(2-(2-pyridyl)ethyl)amino](3-pyridyl)}carboxamide |
| 6.821 | M + H | 403.2 | N-[((2S)oxolan-2-yl)methyl]{6-phenyl-2-[(2-(2-pyridyl)ethyl)amino](3-pyridyl)}carboxamide |
| 65.098 | M + H | 518.2 | tert-butyl 2-[({6-phenyl-2-[(2-(2-pyridyl)ethyl)amino]-3-pyridyl}carbonylamino)methyl]morpholine-4-carboxylate |
| 96.68 | M + H | 458.3 | N-[(1-acetyl(4-piperidyl))methyl]{6-phenyl-2-[(2-(2-pyridyl)ethyl)amino](3-pyridyl)}carboxamide |
| 48.434 | M + H | 458.3 | N-[(1-acetyl(3-piperidyl))methyl]{6-phenyl-2-[(2-(2-pyridyl)ethyl)amino](3-pyridyl)}carboxamide |
| 43.709 | M + H | 416.3 | {6-phenyl-2-[(2-(2-pyridyl)ethyl)amino](3-pyridyl)}-N-(4-piperidylmethyl)carboxamide |
| 0.532 | M + H | 413.2 | {2-[(2-cyclohex-1-enylethyl)amino]-6-phenyl(3-pyridyl)}-N-(3-pyridylmethyl)carboxamide |
| 5.689 | M + H | 423.3 | {6-phenyl-2-[(3-phenylpropyl)amino](3-pyridyl)}-N-(3-pyridylmethyl)carboxamide |
| 2.792 | M + H | 395.2 | {6-phenyl-2-[benzylamino](3-pyridyl)}-N-(3-pyridylmethyl)carboxamide |
| 4.897 | M + H | 400.2 | N-(1,3-oxazol-2-ylmethyl){6-phenyl-2-[(2-(2-pyridyl)ethyl)amino](3-pyridyl)}carboxamide |
| 6.148 | M + H | 399.1 | N-(imidazol-2-ylmethyl){6-phenyl-2-[(2-(2-pyridyl)ethyl)amino](3-pyridyl)}carboxamide |
| 15.715 | M + H | 444.3 | N-[((2S)-1-acetylpyrrolidin-2-yl)methyl]{6-phenyl-2-[(2-(2-pyridyl)ethyl)amino](3-pyridyl)}carboxamide |
| 26.904 | M + H | 444.3 | N-[((3R)-1-acetylpyrrolidin-3-yl)methyl]{6-phenyl-2-[(2-(2-pyridyl)ethyl)amino](3-pyridyl)}carboxamide |
| 25.159 | M + H | 444.3 | N-[((3S)-1-acetylpyrrolidin-3-yl)methyl]{6-phenyl-2-[(2-(2-pyridyl)ethyl)amino](3-pyridyl)}carboxamide |
| 1.335 | M + H | 390.2 | methyl 2-({6-phenyl-2-[(2-phenylethyl)amino]-3-pyridyl}carbonylamino)acetate |
| 11.377 | M + H | 347.1 | [6-phenyl-2-(propylamino)(3-pyridyl)]-N-(3-pyridylmethyl)carboxamide |
| 2.484 | M + H | 375.2 | {2-[(3-methylbutyl)amino]-6-phenyl(3-pyridyl)}-N-(3-pyridylmethyl)carboxamide |
| 1.854 | M + H | 415.3 | {2-[(2-cyclohexylethyl)amino]-6-phenyl(3-pyridyl)}-N-(3-pyridylmethyl)carboxamide |
| 20.292 | M + H | 494.3 | N-{[1-(methylsulfonyl)(3-piperidyl)]methyl}{6-phenyl-2-[(2-(2-pyridyl)ethyl)amino](3-pyridyl)}carboxamide |
| 18.23 | M + H | 416.3 | 2-(aminomethyl)piperidyl 6-phenyl-2-[(2-(2-pyridyl)ethyl)amino](3-pyridyl) ketone |
| 21.154 | M + H | 458.3 | N-{[1-({6-phenyl-2-[(2-(2-pyridyl)ethyl)amino]-3-pyridyl}carbonyl)-2-piperidyl]methyl}acetamide |
| 22.226 | M + H | 494.3 | 2-{[(methylsulfonyl)amino]methyl}piperidyl 6-phenyl-2-[(2-(2-pyridyl)ethyl)amino](3-pyridyl) ketone |
| 1.298 | M + H | 413.2 | N-[(1-methylpyrazol-5-yl)methyl]{6-phenyl-2-[(2-(2-pyridyl)ethyl)amino](3-pyridyl)}carboxamide |
| 2.733 | M + H | 413.2 | N-[(1-methylpyrazol-3-yl)methyl]{6-phenyl-2-[(2-(2-pyridyl)ethyl)amino](3-pyridyl)}carboxamide |
| 0.711 | M + H | 399.2 | {6-phenyl-2-[(2-(2-pyridyl)ethyl)amino](3-pyridyl)}-N-(pyrazol-3-ylmethyl)carboxamide |
| 0.836 | M + H | 400.2 | N-(isoxazol-5-ylmethyl){6-phenyl-2-[(2-(2-pyridyl)ethyl)amino](3-pyridyl)}carboxamide |
| 62.553 | M + H | 402.3 | N-[((3S)pyrrolidin-3-yl)methyl]{6-phenyl-2-[(2-(2-pyridyl)ethyl)amino](3-pyridyl)}carboxamide |
| 53.616 | M + H | 402.3 | N-[((3R)pyrrolidin-3-yl)methyl]{6-phenyl-2-[(2-(2-pyridyl)ethyl)amino](3-pyridyl)}carboxamide |
| 5.245 | M + H | 423.3 | {6-phenyl-2-[(2-phenylethyl)amino](3-pyridyl)}-N-(2-(2-pyridyl)ethyl)carboxamide |
| 3.093 | M + H | 423.2 | {6-phenyl-2-[(2-phenylethyl)amino](3-pyridyl)}-N-(2-(3-pyridyl)ethyl)carboxamide |
| 0.486 | M + H | 389.2 | N-methyl-2-({6-phenyl-2-[(2-phenylethyl)amino](3-pyridyl)}carbonylamino)acetamide |
| 30.309 | M + H | 403.3 | N,N-dimethyl-2-({6-phenyl-2-[(2-phenylethyl)amino](3-pyridyl)}carbonylamino)acetamide |
| 0.81 | M + H | 375.2 | N-(carbamoylmethyl){6-phenyl-2-[(2-phenylethyl)amino](3-pyridyl)}carboxamide |

-continued

| IC50 Arithmetic Mean | Ion | m/z | CHEMICAL NAME |
|---|---|---|---|
| 22.145 | M + H | 430.3 | (2-{[2-(2-oxopiperidyl)ethyl]amino}-6-phenyl(3-pyridyl))-N-(3-pyridylmethyl)carboxamide |
| 20.145 | M + H | 430.3 | (2-{[2-(1-methyl(4-piperidyl))ethyl]amino}-6-phenyl(3-pyridyl))-N-(3-pyridylmethyl)carboxamide |
| 0.149 | M + H | 415.2 | {6-phenyl-2-[(2-(2-thienyl)ethyl)amino](3-pyridyl)}-N-(3-pyridylmethyl)carboxamide |
| 32.174 | M + H | 413.2 | (2-{[2-(1-methylimidazol-4-yl)ethyl]amino}-6-phenyl(3-pyridyl))-N-(3-pyridylmethyl)carboxamide |
| 0.294 | M + H | 399.2 | {2-[(2-(2-furyl)ethyl)amino]-6-phenyl(3-pyridyl)}-N-(3-pyridylmethyl)carboxamide |
| 4.835 | M + H | 389.2 | {2-[(oxolan-2-ylmethyl)amino]-6-phenyl(3-pyridyl)}-N-(3-pyridylmethyl)carboxamide |
| 7.122 | M + H | 405.2 | {2-[(2-(1,3-dioxolan-2-yl)ethyl)amino]-6-phenyl(3-pyridyl)}-N-(3-pyridylmethyl)carboxamide |
| 30.307 | M + H | 413.3 | {2-[(3-imidazolylpropyl)amino]-6-phenyl(3-pyridyl)}-N-(3-pyridylmethyl)carboxamide |
| 37.33 | M + H | 418.3 | {2-[(2-morpholin-4-ylethyl)amino]-6-phenyl(3-pyridyl)}-N-(3-pyridylmethyl)carboxamide |
| 20.164 | M + H | 425.2 | {6-phenyl-2-[(2-phenoxyethyl)amino](3-pyridyl)}-N-(3-pyridylmethyl)carboxamide |
| 28.307 | M + H | 453.2 | {2-[(2-(2H-benzo[3,4-d]1,3-dioxolen-5-yl)ethyl)amino]-6-phenyl(3-pyridyl)}-N-(3-pyridylmethyl)carboxamide |
| 70.65 | M + H |  | (2-{[2-(2-oxoimidazolidinyl)ethyl]amino}-6-phenyl(3-pyridyl))-N-(3-pyridylmethyl)carboxamide |
| 10.62 | M + H | 416.2 | (2-{[2-(2-oxopyrrolidinyl)ethyl]amino}-6-phenyl(3-pyridyl))-N-(3-pyridylmethyl)carboxamide |
| 9.766 | M + H | 399.2 | {2-[(2-imidazol-4-ylethyl)amino]-6-phenyl(3-pyridyl)}-N-(3-pyridylmethyl)carboxamide |
| 7.811 | M + H | 417.3 | (2-{[(hydroxycyclohexyl)methyl]amino}-6-phenyl(3-pyridyl))-N-(3-pyridylmethyl)carboxamide |
| 5.941 | M + H | 427.2 | (2-{[2-(3,5-dimethylpyrazol-4-yl)ethyl]amino}-6-phenyl(3-pyridyl))-N-(3-pyridylmethyl)carboxamide |
| 6.833 | M + H | 427.2 | (2-{[2-(3,5-dimethylpyrazolyl)ethyl]amino}-6-phenyl(3-pyridyl))-N-(3-pyridylmethyl)carboxamide |
| 0.028 | M + H | 468.2 | (2-{[2-(2-chlorophenyl)ethyl]amino}-6-(2-cyanophenyl)(3-pyridyl))-N-(3-pyridylmethyl)carboxamide |
| 0.076 | M + H | 448.2 | (6-(2-cyanophenyl)-2-{[2-(2-methylphenyl)ethyl]amino}(3-pyridyl))-N-(3-pyridylmethyl)carboxamide |
| 0.028 | M + H | 452.2 | (6-(2-cyanophenyl)-2-{[2-(2-fluorophenyl)ethyl]amino}(3-pyridyl))-N-(3-pyridylmethyl)carboxamide |
| 0.044 | M + H | 458.2 | (6-(2-cyanophenyl)-2-{[2-(2-cyanophenyl)ethyl]amino}(3-pyridyl))-N-(3-pyridylmethyl)carboxamide |
| 0.029 | M + H | 440.2 | {6-(2-cyanophenyl)-2-[(2-(2-thienyl)ethyl)amino](3-pyridyl)}-N-(3-pyridylmethyl)carboxamide |
| 0.065 | M + H | 424.2 | {6-(2-cyanophenyl)-2-[(2-(2-furyl)ethyl)amino](3-pyridyl)}-N-(3-pyridylmethyl)carboxamide |
| 1.479 | M + H |  | (2-{[2-(3-fluoro(2-pyridyl))ethyl]amino}-6-phenyl(3-pyridyl))-N-(3-pyridylmethyl)carboxamide |
| 0.45 | M + H | 423.3 | (2-{[2-(3-methylphenyl)ethyl]amino}-6-phenyl(3-pyridyl))-N-(3-pyridylmethyl)carboxamide |
| 0.38 | M + H | 450.1 | (6-(2-cyanophenyl)-2-{[2-(2-hydroxyphenyl)ethyl]amino}(3-pyridyl))-N-(3-pyridylmethyl)carboxamide |
| 1.238 | M + H | 429.1 | N-{[2-(aminomethyl)(3-pyridyl)]methyl}{6-pyrazol-4-yl-2-[(2-(2-pyridyl)ethyl)amino](3-pyridyl)}carboxamide |
| 14.214 | M + H | 574.3 | N-{(1R)-2-[(5-fluoro-2-{[2-(3-fluorophenyl)-2-hydroxyethyl]amino}-6-pyrazol-4-yl(3-pyridyl))carbonylamino]-isopropyl}-2-[(tert-butoxy)carbonylamino]acetamide |
| 0.211 | M + H | 407.3 | {5-fluoro-6-pyrazol-4-yl-2-[(2-pyrazolylethyl)amino](3-pyridyl)}-N-(3-pyridylmethyl)carboxamide |
| 4.635 | M + H | 430.3 | N-[(1R)-2-({5-fluoro-6-pyrazol-4-yl-2-[(2-pyrazolylethyl)amino](3-pyridyl)}carbonylamino)-isopropyl]-2-aminoacetamide |
| 0.604 | M + H | 520.1 | (6-(2-cyanophenyl)-2-{[2-(3-fluorophenyl)ethyl]amino}(3-pyridyl))-N-{[6-(trifluoromethyl)(2-pyridyl)]methyl}carboxamide |

-continued

| IC50 Arithmetic Mean | Ion | m/z | CHEMICAL NAME |
|---|---|---|---|
| 1.497 | M + H | 520.1 | (6-(2-cyanophenyl)-2-{[2-(3-fluorophenyl)ethyl]amino}(3-pyridyl))-N-{[5-(trifluoromethyl)(2-pyridyl)]methyl}carboxamide |
| 0.603 | M + H | 520.1 | (6-(2-cyanophenyl)-2-{[2-(3-fluorophenyl)ethyl]amino}(3-pyridyl))-N-{[3-(trifluoromethyl)(2-pyridyl)]methyl}carboxamide |
| 1.789 | M + H | 486.1 | N-[(6-chloro(3-pyridyl))methyl](6-(2-cyanophenyl)-2-{[2-(3-fluorophenyl)ethyl]amino}(3-pyridyl))carboxamide |
| 0.033 | M + H | 458.1 | (6-(2-cyano(3-thienyl))-2-{[2-(3-fluorophenyl)ethyl]amino}(3-pyridyl))-N-(3-pyridylmethyl)carboxamide |
| 57.378 | M + H | 376.1 | (2E)-3-(2-{[2-(3-fluorophenyl)ethyl]amino}-6-phenyl(3-pyridyl))-N-methylprop-2-enamide |
| 0.298 | M + H | 481.2 | (6-(2-cyanophenyl)-2-{[2-(3-fluorophenyl)ethyl]amino}(3-pyridyl))-N-{[6-(methylamino)(3-pyridyl)]methyl}carboxamide |
| 30.234 | M + H | 495.2 | N-{[6-(dimethylamino)(3-pyridyl)]methyl}(6-(2-cyanophenyl)-2-{[2-(3-fluorophenyl)ethyl]amino}(3-pyridyl))carboxamide |
| 59.114 | M + H | 457.2 | (2-{[2-(3-fluorophenyl)ethyl]amino}-4-(hydroxymethyl)-6-phenyl(3-pyridyl))-N-(3-pyridylmethyl)carboxamide |
| 0.021 | M + H | 467.1 | N-[(5-amino(2-pyridyl))methyl](6-(2-cyanophenyl)-2-{[2-(3-fluorophenyl)ethyl]amino}(3-pyridyl))carboxamide |
| 0.625 | M + H | 457.1 | (2-{[2-(3-fluorophenyl)ethyl]amino}-5-(hydroxymethyl)-6-phenyl(3-pyridyl))-N-(3-pyridylmethyl)carboxamide |
| 55.988 | M + H | 561.2 | (2-{[2-(3-fluorophenyl)ethyl]amino}-6-phenyl-5-[N-(3-pyridylmethyl)carbamoyl](3-pyridyl))-N-(3-pyridylmethyl)carboxamide |
| 0.428 | M + H | 482.2 | (5-(2-diazo-2-azavinyl)-2-{[2-(3-fluorophenyl)ethyl]amino}-6-phenyl(3-pyridyl))-N-(3-pyridylmethyl)carboxamide |
| 8.904 | M + H | 456.1 | (5-(aminomethyl)-2-{[2-(3-fluorophenyl)ethyl]amino}-6-phenyl(3-pyridyl))-N-(3-pyridylmethyl)carboxamide |
| 0.04 | M + H | 431.2 | (2-{[2-(3-fluorophenyl)ethyl]amino}-6-(1-methylpyrazol-3-yl)(3-pyridyl))-N-3-pyridylmethyl)carboxamide |
| 0.285 | M + H | 579.2 | N-({6-[3,3-bis(dimethylamino)-2-azaprop-2-enyl](2-pyridyl)}methyl)(6-(2-cyanophenyl)-2-{[2-(3-fluorophenyl)ethyl]amino}(3-pyridyl))carboxamide |
| 1.189 | M + Na | 603.2 | tert-butyl 2-(6-{[(6-(2-cyanophenyl)-2-{[2-(3-fluorophenyl)ethyl]amino}-3-pyridyl)carbonylamino]methyl}-2-pyridyl)acetate |
| 0.401 | M + H | 481.1 | N-{[4-(aminomethyl)(3-pyridyl)]methyl}(6-(2-cyanophenyl)-2-{[2-(3-fluorophenyl)ethyl]amino}(3-pyridyl))carboxamide |
| 0.056 | M + H | 481.1 | N-{[3-(aminomethyl)(4-pyridyl)]methyl}(6-(2-cyanophenyl)-2-{[2-(3-fluorophenyl)ethyl]amino}(3-pyridyl))carboxamide |
| 0.021 | M + H | 497.1 | (5-bromo-2-{[2-(3-fluorophenyl)ethyl]amino}-6-pyrazol-4-yl(3-pyridyl))-N-(3-pyridylmethyl)carboxamide |
| 0.023 | M + H | 509.1 | (5-bromo-2-{[2-(3-fluorophenyl)ethyl]amino}-6-(1-methylpyrazol-4-yl)(3-pyridyl))-N-(3-pyridylmethyl)carboxamide |
| 0.105 | M + H | 442.1 | (6-(5-cyanopyrazol-4-yl)-2-{[2-(3-fluorophenyl)ethyl]amino}(3-pyridyl))-N-(3-pyridylmethyl)carboxamide |
| 0.021 | M + H | 456.1 | (5-cyano-2-{[2-(3-fluorophenyl)ethyl]amino}-6-(1-methylpyrazol-4-yl)(3-pyridyl))-N-(3-pyridylmethyl)carboxamide |
| 0.124 | M + H | 417.1 | (2-{[2-(3-fluorophenyl)ethyl]amino}-6-pyrazol-3-yl(3-pyridyl))-N-(3-pyridylmethyl)carboxamide |
| 0.047 | M + H | 456.1 | (6-(3-cyano-1-methylpyrazol-4-yl)-2-{[2-(3-fluorophenyl)ethyl]amino}(3-pyridyl))-N-(3-pyridylmethyl)carboxamide |
| 0.02 | M + H | 456.1 | (6-(5-cyano-1-methylpyrazol-4-yl)-2-{[2-(3-fluorophenyl)ethyl]amino}(3-pyridyl))-N-(3-pyridylmethyl)carboxamide |
| 0.328 | M + H | 397.0 | 2-[(2-{[2-(3-fluorophenyl)ethyl]amino}-6-pyrazol-4-yl(3-pyridyl))carbonylamino]-N-methylacetamide |

-continued

| IC50 Arithmetic Mean | Ion | m/z | CHEMICAL NAME |
|---|---|---|---|
| 0.35 | M + H | 411.1 | 2-[(2-{[2-(3-fluorophenyl)ethyl]amino}6-(1-methylpyrazol-4-yl)(3-pyridyl))carbonylamino]-N-methylacetamide |
| 0.021 | M + H | 465.1 | (5-chloro-2-{[2-(3-fluorophenyl)ethyl]amino}-6-(1-methylpyrazol-4-yl)(3-pyridyl))-N-(3-pyridylmethyl)carboxamide |
| 0.604 | M + H | 536.1 | N-{[6-(aminomethyl)(2-pyridyl)]methyl}(5-bromo-2-{[2-(3-fluorophenyl)ethyl]amino}-6-phenyl(3-pyridyl))carboxamide |
| 2.725 | M + Na | 606.1 | N-[(1-{2-[(tert-butoxy)carbonylamino]ethyl}pyrazol-3-yl)methyl](6-(2-cyanophenyl)-2-{[2-(3-fluorophenyl)ethyl]amino}(3-pyridyl))carboxamide |
| 2.2 | M + H | 584.2 | N-[(1-{2-[(tert-butoxy)carbonylamino]ethyl}pyrazol-5-yl)methyl](6-(2-cyanophenyl)-2-{[2-(3-fluorophenyl)ethyl]amino}(3-pyridyl))carboxamide |
| 0.296 | M + H | 484.1 | N-{[1-(2-aminoethyl)pyrazol-3-yl]methyl}(6-(2-cyanophenyl)-2-{[2-(3-fluorophenyl)ethyl]amino}(3-pyridyl))carboxamide |
| 0.032 | M + H | 484.1 | N-{[1-(2-aminoethyl)pyrazol-5-yl]methyl}(6-(2-cyanophenyl)-2-{[2-(3-fluorophenyl)ethyl]amino}(3-pyridyl))carboxamide |
| 0.136 | M + H | 460.1 | N-{[6-(aminomethyl)(2-pyridyl)]methyl}(2-{[2-(3-fluorophenyl)ethyl]amino}-6-(1-methylpyrazol-4-yl)(3-pyridyl))carboxamide |
| 0.121 | M + H | 446.1 | N-{[6-(aminomethyl)(2-pyridyl)]methyl}(2-{[2-(3-fluorophenyl)ethyl]amino}-6-pyrazol-4-yl(3-pyridyl))carboxamide |
| 0.027 | M + H | 539.1 | N-{[6-(aminomethyl)(2-pyridyl)]methyl}(5-bromo-2-{[2-(3-fluorophenyl)ethyl]amino}-6-(1-methylpyrazol-4-yl)(3-pyridyl))carboxamide |
| 0.013 | M + H | 458.1 | N-[((2R)-5-oxopyrrolidin-2-yl)methyl](6-(2-cyanophenyl)-2-{[2-(3-fluorophenyl)ethyl]amino}(3-pyridyl))carboxamide |
| 0.133 | M + H | 458.1 | N-[((2S)-5-oxopyrrolidin-2-yl)methyl](6-(2-cyanophenyl)-2-{[2-(3-fluorophenyl)ethyl]amino}(3-pyridyl))carboxamide |
| 16.552 | M + H | 541.1 | N-{3-[(5S)-5-(2-diazo-2-azavinyl)-2-oxopyrrolidinyl]propyl}(6-(2-cyanophenyl)-2-{[2-(3-fluorophenyl)ethyl]amino}(3-pyridyl))carboxamide |
| 4.516 | M + H | 615.2 | N-[((2S)-1-{3-[(tert-butoxy)carbonylamino]propyl}-5-oxopyrrolidin-2-yl)methyl](6-(2-cyanophenyl)-2-{[2-(3-fluorophenyl)ethyl]amino}(3-pyridyl))carboxamide |
| 0.917 | M + H | 501.1 | N-{[(2S)-1-(2-aminoethyl)-5-oxopyrrolidin-2-yl]methyl}(6-(2-cyanophenyl)-2-{[2-(3-fluorophenyl)ethyl]amino}(3-pyridyl))carboxamide |
| 0.431 | M + H | 515.2 | N-{[(2S)-1-(3-aminopropyl)-5-oxopyrrolidin-2-yl]methyl}(6-(2-cyanophenyl)-2-{[2-(3-fluorophenyl)ethyl]amino}(3-pyridyl))carboxamide |
| 11.658 | M + H | 515.1 | N-{3-[(5S)-5-(aminomethyl)-2-oxopyrrolidinyl]propyl}(6-(2-cyanophenyl)-2-{[2-(3-fluorophenyl)ethyl]amino}(3-pyridyl))carboxamide |
| 0.11 | M + H | 501.1 | N-{[(2R)-1-(2-aminoethyl)-5-oxopyrrolidin-2-yl]methyl}(6-(2-cyanophenyl)-2-{[2-(3-fluorophenyl)ethyl]amino}(3-pyridyl))carboxamide |
| 5.621 | M + H | 541.2 | N-{3-[(5R)-5-(2-diazo-2-azavinyl)-2-oxopyrrolidinyl]propyl}(6-(2-cyanophenyl)-2-{[2-(3-fluorophenyl)ethyl]amino}(3-pyridyl))carboxamide |
| 4.951 | M + H | 515.1 | N-{3-[(5R)-5-(aminomethyl)-2-oxopyrrolidinyl]propyl}(6-(2-cyanophenyl)-2-{[2-(3-fluorophenyl)ethyl]amino}(3-pyridyl))carboxamide |
| 17.87 | M + H | 501.1 | N-{2-[(5S)-5-(aminomethyl)-2-oxopyrrolidinyl]ethyl}(6-(2-cyanophenyl)-2-{[2-(3-fluorophenyl)ethyl]amino}(3-pyridyl))carboxamide |
| 19.454 | M + H | 501.1 | N-{2-[(5R)-5-(aminomethyl)-2-oxopyrrolidinyl]ethyl}(6-(2-cyanophenyl)-2-{[2-(3-fluorophenyl)ethyl]amino}(3-pyridyl))carboxamide |
| 0.355 | M + H | 423.1 | N-[((2R)-5-oxopyrrolidin-2-yl)methyl](2-{[2-(3-fluorophenyl)ethyl]amino}-6-pyrazol-3-yl(3-pyridyl))carboxamide |
| 0.156 | M + H | 437.1 | N-[((2R)-5-oxopyrrolidin-2-yl)methyl](2-{[2-(3-fluorophenyl)ethyl]amino}-6-(1-methylpyrazol-4-yl)(3-pyridyl))carboxamide |
| 0.439 | M + H | 444.0 | (6-(2-cyanophenyl)-2-{[2-(3-fluorophenyl)ethyl]amino}(3-pyridyl))-N-(pyrrolidin-2-ylmethyl)carboxamide |

-continued

| IC50 Arithmetic Mean | Ion | m/z | CHEMICAL NAME |
|---|---|---|---|
| 0.119 | M + H | 423.1 | N-[((2R)-5-oxopyrrolidin-2-yl)methyl](2-{[2-(3-fluorophenyl)ethyl]amino}-6-pyrazol-4-yl(3-pyridyl))carboxamide |
| 4.834 | M + H | 587.1 | N-[(1-{2-[(tert-butoxy)carbonylamino]ethyl}pyrrolidin-2-yl)methyl](6-(2-cyanophenyl)-2-{[2-(3-fluorophenyl)ethyl]amino}(3-pyridyl))carboxamide |
| 2.082 | M + H | 601.2 | N-[(1-{3-[(tert-butoxy)carbonylamino]propyl}pyrrolidin-2-yl)methyl](6-(2-cyanophenyl)-2-{[2-(3-fluorophenyl)ethyl]amino}(3-pyridyl))carboxamide |
| 0.758 | M + H | 487.1 | N-{[1-(2-aminoethyl)pyrrolidin-2-yl]methyl}(6-(2-cyanophenyl)-2-{[2-(3-fluorophenyl)ethyl]amino}(3-pyridyl))carboxamide |
| 3.502 | M + H | 501.2 | N-{[1-(4-aminobutyl)pyrrolidin-2-yl]methyl}(6-(2-cyanophenyl)-2-{[2-(3-fluorophenyl)ethyl]amino}(3-pyridyl))carboxamide |
| 0.913 | M + H | 505.1 | methyl 2-({(2S)-2-amino-3-[(6-(2-cyanophenyl)-2-{[2-(3-fluorophenyl)ethyl]amino}(3-pyridyl))carbonylamino]propyl}amino)acetate |
| 10.852 | M + H-OMe | 452.3 | methyl 2-({(2S)-2-amino-3-[(2-{[2-(3-fluorophenyl)ethyl]amino}-6-(1-methylpyrazol-4-yl)(3-pyridyl))carbonylamino]propyl}amino)acetate |
| 16.026 | M + H | 438.2 | N-[((2S)-6-oxopiperazin-2-yl)methyl](2-{[2-(3-fluorophenyl)ethyl]amino}-6-pyrazol-4-yl(3-pyridyl))carboxamide |
| 0.819 | M + H | 473.1 | N-[((2S)-6-oxopiperazin-2-yl)methyl](6-(2-cyanophenyl)-2-{[2-(3-fluorophenyl)ethyl]amino}(3-pyridyl))carboxamide |
| 9.536 | M + H-Boc | 530.2 | N-[((2R)-4-{3-[(tert-butoxy)carbonylamino]propyl}-6-oxopiperazin-2-yl)methyl](6-(2-cyanophenyl)-2-{[2-(3-fluorophenyl)ethyl]amino}(3-pyridyl))carboxamide |
| 13.056 | M + H | 452.1 | N-[((2S)-6-oxopiperazin-2-yl)methyl](2-{[2-(3-fluorophenyl)ethyl]amino}-6-(1-methylpyrazol-4-yl)(3-pyridyl))carboxamide |
| 6.391 | M + H | 438.1 | N-[((2S)-6-oxopiperazin-2-yl)methyl](2-{[2-(3-fluorophenyl)ethyl]amino}-6-pyrazol-3-yl(3-pyridyl))carboxamide |
| 4.522 | M + H | 530.2 | N-{[(2R)-4-(3-aminopropyl)-6-oxopiperazin-2-yl]methyl}(6-(2-cyanophenyl)-2-{[2-(3-fluorophenyl)ethyl]amino}(3-pyridyl))carboxamide |
| 8.4722 | M + H | 516.2 | N-{[(2R)-4-(2-aminoethyl)-6-oxopiperazin-2-yl]methyl}(6-(2-cyanophenyl)-2-{[2-(3-fluorophenyl)ethyl]amino}(3-pyridyl))carboxamide |
| 0.155 | M + H | 473.1 | N-[((2R)-6-oxopiperazin-2-yl)methyl](6-(2-cyanophenyl)-2-{[2-(3-fluorophenyl)ethyl]amino}(3-pyridyl))carboxamide |
| 0.623 | M + H | 515.2 | N-{[(2S)-4-(2-aminoethyl)-6-oxopiperazin-2-yl]methyl}(6-(2-cyanophenyl)-2-{[2-(3-fluorophenyl)ethyl]amino}(3-pyridyl))carboxamide |
| 2.809 | M + H | 530.2 | N-{[(2S)-4-(3-aminopropyl)-6-oxopiperazin-2-yl]methyl}(6-(2-cyanophenyl)-2-{[2-(3-fluorophenyl)ethyl]amino}(3-pyridyl))carboxamide |
| 0.376 | M + H | 659.2 | N-({(2R)-1-[4-(1,3-dioxobenzo[c]azolin-2-yl)butyl]-5-oxopyrrolidin-2-yl}methyl)(6-(2-cyanophenyl)-2-{[2-(3-fluorophenyl)ethyl]amino}(3-pyridyl))carboxamide |
| 0.266 | M + H | 673.2 | N-({(2R)-1-[5-(1,3-dioxobenzo[c]azolin-2-yl)pentyl]-5-oxopyrrolidin-2-yl}methyl)(6-(2-cyanophenyl)-2-{[2-(3-fluorophenyl)ethyl]amino}(3-pyridyl))carboxamide |
| 1.933 | M + H | 544.2 | tert-butyl (2R)-2-{[(6-(2-cyanophenyl)-2-{[2-(3-fluorophenyl)ethyl]amino}(3-pyridyl))carbonylamino]methyl}pyrrolidinecarboxylate |
| 0.0517 | M + H | 529.2 | N-{[(2R)-1-(4-aminobutyl)-5-oxopyrrolidin-2-yl]methyl}(6-(2-cyanophenyl)-2-{[2-(3-fluorophenyl)ethyl]amino}(3-pyridyl))carboxamide |
| 0.039 | M + H | 543.2 | N-{[(2R)-1-(5-aminopentyl)-5-oxopyrrolidin-2-yl]methyl}(6-(2-cyanophenyl)-2-{[2-(3-fluorophenyl)ethyl]amino}(3-pyridyl))carboxamide |
| 0.1738 | M + H | 444.1 | N-[((2R)pyrrolidin-2-yl)methyl](6-(2-cyanophenyl)-2-{[2-(3-fluorophenyl)ethyl]amino}(3-pyridyl))carboxamide |
| 0.034 | M + H | 406.1 | (2-{[2-(3-fluorophenyl)ethyl]amino}-6-pyrazol-4-yl(3-pyridyl))-N-(pyrazol-3-ylmethyl)carboxamide |
| 0.031 | M + H | 420.1 | (2-{[2-(3-fluorophenyl)ethyl]amino}-6-(1-methylpyrazol-4-yl)(3-pyridyl))-N-(pyrazol-3-ylmethyl)carboxamide |

-continued

| IC50 Arithmetic Mean | Ion | m/z | CHEMICAL NAME |
|---|---|---|---|
| 0.092 | M + H | 406.1 | (2-{[2-(3-fluorophenyl)ethyl]amino}-6-pyrazol-3-yl(3-pyridyl))-N-(pyrazol-3-ylmethyl)carboxamide |
| 0.432 | M + H | 629.2 | N-[((2R)-1-{4-[(tert-butoxy)carbonylamino]butanoyl}pyrrolidin-2-yl)methyl](6-(2-cyanophenyl)-2-{[2-(3-fluorophenyl)ethyl]amino}(3-pyridyl))carboxamide |
| 0.047 | M + H | 515.2 | N-{[(2R)-1-(3-aminopropanoyl)pyrrolidin-2-yl]methyl}(6-(2-cyanophenyl)-2-{[2-(3-fluorophenyl)ethyl]amino}(3-pyridyl))carboxamide |
| 0.065 | M + H | 498.2 | N-{[1-(3-aminopropyl)pyrazol-3-yl]methyl}(6-(2-cyanophenyl)-2-{[2-(3-fluorophenyl)ethyl]amino}(3-pyridyl))carboxamide |
| 2.686 | M + H | 477.1 | N-{[1-(3-aminopropyl)pyrazol-3-yl]methyl}(2-{[2-(3-fluorophenyl)ethyl]amino}-6-(1-methylpyrazol-4-yl)(3-pyridyl))carboxamide |
| 3.764 | M + H | 463.2 | N-{[1-(3-aminopropyl)pyrazol-3-yl]methyl}(2-{[2-(3-fluorophenyl)ethyl]amino}-6-pyrazol-3-yl(3-pyridyl))carboxamide |
| 0.228 | M + H | 477.2 | N-{[1-(3-aminopropyl)pyrazol-5-yl]methyl}(2-{[2-(3-fluorophenyl)ethyl]amino}-6-(1-methylpyrazol-4-yl)(3-pyridyl))carboxamide |
| 0.462 | M + H | 463.2 | N-{[1-(3-aminopropyl)pyrazol-5-yl]methyl}(2-{[2-(3-fluorophenyl)ethyl]amino}-6-pyrazol-3-yl(3-pyridyl))carboxamide |
| 3.691 | M + H | 587.2 | N-[((2R)-1-{2-[(tert-butoxy)carbonylamino]ethyl}pyrrolidin-2-yl)methyl](6-(2-cyanophenyl)-2-{[2-(3-fluorophenyl)ethyl]amino}(3-pyridyl))carboxamide |
| 1.341 | M + H | 601.2 | N-[((2R)-1-{3-[(tert-butoxy)carbonylamino]propyl}pyrrolidin-2-yl)methyl](6-(2-cyanophenyl)-2-{[2-(3-fluorophenyl)ethyl]amino}(3-pyridyl))carboxamide |
| 0.705 | M + H | 487.2 | N-{[(2R)-1-(2-aminoethyl)pyrrolidin-2-yl]methyl}(6-(2-cyanophenyl)-2-{[2-(3-fluorophenyl)ethyl]amino}(3-pyridyl))carboxamide |
| 1.389 | M + H | 501.2 | N-{[(2R)-1-(3-aminopropyl)pyrrolidin-2-yl]methyl}(6-(2-cyanophenyl)-2-{[2-(3-fluorophenyl)ethyl]amino}(3-pyridyl))carboxamide |
| 11.966 | M + H | 549.2 | N-[(1-{2-[(tert-butoxy)carbonylamino]ethyl}pyrazol-3-yl)methyl](2-{[2-(3-fluorophenyl)ethyl]amino}-6-pyrazol-3-yl(3-pyridyl))carboxamide |
| 1.488 | M + H | 449.1 | N-{[1-(2-aminoethyl)pyrazol-3-yl]methyl}(2-{[2-(3-fluorophenyl)ethyl]amino}-6-pyrazol-4-yl(3-pyridyl))carboxamide |
| 5.506 | M + H | 449.2 | N-{[1-(2-aminoethyl)pyrazol-3-yl]methyl}(2-{[2-(3-fluorophenyl)ethyl]amino}-6-pyrazol-3-yl(3-pyridyl))carboxamide |
| 0.634 | M + H | 449.2 | N-{[1-(2-aminoethyl)pyrazol-5-yl]methyl}(2-{[2-(3-fluorophenyl)ethyl]amino}-6-pyrazol-3-yl(3-pyridyl))carboxamide |
| 1.862 | M + H | 463.2 | N-{[1-(2-aminoethyl)pyrazol-3-yl]methyl}(2-{[2-(3-fluorophenyl)ethyl]amino}-6-(1-methylpyrazol-4-yl)(3-pyridyl))carboxamide |
| 0.313 | M + H | 463.3 | N-{[1-(2-aminoethyl)pyrazol-5-yl]methyl}(2-{[2-(3-fluorophenyl)ethyl]amino}-6-(1-methylpyrazol-4-yl)(3-pyridyl))carboxamide |
| 0.318 | M + H | 530.3 | N-{[(2R)-1-(3-aminopropyl)-6-oxopiperazin-2-yl]methyl}(6-(2-cyanophenyl)-2-{[2-(3-fluorophenyl)ethyl]amino}(3-pyridyl))carboxamide |
| 3.562 | M + H | 509.3 | N-{[(2R)-1-(3-aminopropyl)-6-oxopiperazin-2-yl]methyl}(2-{[2-(3-fluorophenyl)ethyl]amino}-6-(1-methylpyrazol-4-yl)(3-pyridyl))carboxamide |
| 2.343 | M + H | 495.3 | N-{[(2R)-1-(3-aminopropyl)-6-oxopiperazin-2-yl]methyl}(2-{[2-(3-fluorophenyl)ethyl]amino}-6-pyrazol-4-yl(3-pyridyl))carboxamide |
| 9.627 | M + H | 495.3 | N-{[(2R)-1-(3-aminopropyl)-6-oxopiperazin-2-yl]methyl}(2-{[2-(3-fluorophenyl)ethyl]amino}-6-pyrazol-3-yl(3-pyridyl))carboxamide |
| 0.119 | M + H | 486.2 | N-[((2R)-1-acetylpyrrolidin-2-yl)methyl](6-(2-cyanophenyl)-2-{[2-(3-fluorophenyl)ethyl]amino}(3-pyridyl))carboxamide |
| 1.448 | M + H | 522.2 | N-{[(2R)-1-(methylsulfonyl)pyrrolidin-2-yl]methyl}(6-(2-cyanophenyl)-2-{[2-(3-fluorophenyl)ethyl]amino}(3-pyridyl))carboxamide |

-continued

| IC50 Arithmetic Mean | Ion | m/z | CHEMICAL NAME |
|---|---|---|---|
| 0.214 | M + H | 458.3 | N-[((2R)-1-methylpyrrolidin-2-yl)methyl](6-(2-cyanophenyl)-2-{[2-(3-fluorophenyl)ethyl]amino}(3-pyridyl))carboxamide |
| 2.049 | M | 472.2 | N-[((2R)-1,1-dimethylpyrrolidin-2-yl)methyl](6-(2-cyanophenyl)-2-{[2-(3-fluorophenyl)ethyl]amino}(3-pyridyl))carboxamide |
| 11.341 | M + H | 695.3 | N-[((2R)-1-{[3-(1,3-dioxobenzo[c]azolin-2-yl)propyl]sulfonyl}pyrrolidin-2-yl)methyl](6-(2-cyanophenyl)-2-{[2-(3-fluorophenyl)ethyl]amino}(3-pyridyl))carboxamide |
| 0.071 | M + H | 551.3 | N-({(2R)-1-[(2-aminoethyl)sulfonyl]pyrrolidin-2-yl}methyl)(6-(2-cyanophenyl)-2-{[2-(3-fluorophenyl)ethyl]amino}(3-pyridyl))carboxamide |
| 0.234 | M + H | 565.3 | N-({(2R)-1-[(3-aminopropyl)sulfonyl]pyrrolidin-2-yl}methyl)(6-(2-cyanophenyl)-2-{[2-(3-fluorophenyl)ethyl]amino}(3-pyridyl))carboxamide |
| 1.406 | M + H | 463.1 | N-{[1-(3-aminopropyl)pyrazol-3-yl]methyl}(2-{[2-(3-fluorophenyl)ethyl]amino}-6-pyrazol-4-yl(3-pyridyl))carboxamide |
| 0.095 | M + H | 463.1 | N-{[1-(3-aminopropyl)pyrazol-5-yl]methyl}(2-{[2-(3-fluorophenyl)ethyl]amino}-6-pyrazol-4-yl(3-pyridyl))carboxamide |
| 1.342 | M + H | 594.3 | N-[((2R)-1-{3-[(tert-butoxy)carbonylamino]propyl}-5-oxopyrrolidin-2-yl)methyl](2-{[2-(3-fluorophenyl)ethyl]amino}-6-(1-methylpyrazol-4-yl)(3-pyridyl))carboxamide |
| 2.127 | M + H | 578.4 | N-{[1-(3-aminopropyl)-5-oxopyrrolidin-2-yl]methyl}(6-{1-[(dimethylamino)(dimethylylidene)methyl]pyrazol-4-yl}-2-{[2-(3-fluorophenyl)ethyl]amino}(3-pyridyl))carboxamide |
| 0.29 | M + H | 494.3 | N-{[(2R)-1-(3-aminopropyl)-5-oxopyrrolidin-2-yl]methyl}(2-{[2-(3-fluorophenyl)ethyl]amino}-6-(1-methylpyrazol-4-yl)(3-pyridyl))carboxamide |
| 4.64 | M + H | 523.3 | tert-butyl (2R)-2-{[(2-{[2-(3-fluorophenyl)ethyl]amino}-6-(1-methylpyrazol-4-yl)(3-pyridyl))carbonylamino]methyl}pyrrolidinecarboxylate |
| 0.966 | M + H | 480.2 | N-{[(2R)-1-(3-aminopropyl)-5-oxopyrrolidin-2-yl]methyl}(2-{[2-(3-fluorophenyl)ethyl]amino}-6-pyrazol-4-yl(3-pyridyl))carboxamide |
| 0.518 | M + H | 615.3 | N-[((2R)-1-{3-[(tert-butoxy)carbonylamino]propyl}-5-oxopyrrolidin-2-yl)methyl](6-(2-cyanophenyl)-2-{[2-(3-fluorophenyl)ethyl]amino}(3-pyridyl))carboxamide |
| 0.666 | M + H | 432.2 | N-(2-amino-2-methylpropyl)(6-(2-cyanophenyl)-2-{[2-(3-fluorophenyl)ethyl]amino}(3-pyridyl))carboxamide |
| 4.746 | M + H | 409.2 | N-[((2R)pyrrolidin-2-yl)methyl](2-{[2-(3-fluorophenyl)ethyl]amino}-6-pyrazol-4-yl(3-pyridyl))carboxamide |
| 3.185 | M + H | 423.2 | N-[((2R)pyrrolidin-2-yl)methyl](2-{[2-(3-fluorophenyl)ethyl]amino}-6-(1-methylpyrazol-4-yl)(3-pyridyl))carboxamide |
| 1.473 | M + H | 510.3 | (6-(2-cyanophenyl)-2-{[2-(3-fluorophenyl)ethyl]amino}(3-pyridyl))-N-{2-methyl-2-[(methylsulfonyl)amino]propyl}carboxamide |
| 5.532 | M + H | 580.3 | N-[((2R)-1-{2-[(tert-butoxy)carbonylamino]acetyl}pyrrolidin-2-yl)methyl](2-{[2-(3-fluorophenyl)ethyl]amino}-6-(1-methylpyrazol-4-yl)(3-pyridyl))carboxamide |
| 5.026 | M + H | 594.3 | N-[((2R)-1-{3-[(tert-butoxy)carbonylamino]propanoyl}pyrrolidin-2-yl)methyl](2-{[2-(3-fluorophenyl)ethyl]amino}-6-(1-methylpyrazol-4-yl)(3-pyridyl))carboxamide |
| 3.651 | M + H | 608.3 | N-[((2R)-1-{4-[(tert-butoxy)carbonylamino]butanoyl}pyrrolidin-2-yl)methyl](2-{[2-(3-fluorophenyl)ethyl]amino}-6-(1-methylpyrazol-4-yl)(3-pyridyl))carboxamide |
| 0.581 | M + H | 480.3 | N-{[(2R)-1-(2-aminoacetyl)pyrrolidin-2-yl]methyl}(2-{[2-(3-fluorophenyl)ethyl]amino}-6-(1-methylpyrazol-4-yl)(3-pyridyl))carboxamide |
| 0.587 | M + H | 494.3 | N-{[(2R)-1-(3-aminopropanoyl)pyrrolidin-2-yl]methyl}(2-{[2-(3-fluorophenyl)ethyl]amino}-6-(1-methylpyrazol-4-yl)(3-pyridyl))carboxamide |

-continued

| IC50 Arithmetic Mean | Ion | m/z | CHEMICAL NAME |
| --- | --- | --- | --- |
| 0.351 | M + H | 508.3 | N-{[(2R)-1-(4-aminobutanoyl)pyrrolidin-2-yl]methyl}(2-{[2-(3-fluorophenyl)ethyl]amino}-6-(1-methylpyrazol-4-yl)(3-pyridyl))carboxamide |
| 0.515 | M + H | 418.2 | N-((2S)-2-aminopropyl)(6-(2-cyanophenyl)-2-{[2-(3-fluorophenyl)ethyl]amino}(3-pyridyl))carboxamide |
| 9.572 | M + H | 589.4 | 2-[(tert-butoxy)carbonylamino]-N-{2-[(6-(2-cyanophenyl)-2-{[2-(3-fluorophenyl)ethyl]amino}(3-pyridyl))carbonylamino]-tert-butyl}acetamide |
| 0.194 | M + H | 617.4 | 4-[(tert-butoxy)carbonylamino]-N-{2-[(6-(2-cyanophenyl)-2-{[2-(3-fluorophenyl)ethyl]amino}(3-pyridyl))carbonylamino]-tert-butyl}butanamide |
| 2.019 | M + H | 603.3 | N-{(1S)-2-[(6-(2-cyanophenyl)-2-{[2-(3-fluorophenyl)ethyl]amino}(3-pyridyl))carbonylamino]-isopropyl}-4-[(tert-butoxy)carbonylamino]butanamide |
| 2.94 | M + H | 643.4 | N-[((2R)-1-{5-[(tert-butoxy)carbonylamino]pentanoyl}pyrrolidin-2-yl]methyl](6-(2-cyanophenyl)-2-{[2-(3-fluorophenyl)ethyl]amino}(3-pyridyl))carboxamide |
| 0.32 | M + H | 489.3 | 2-amino-N-{2-[(6-(2-cyanophenyl)-2-{[2-(3-fluorophenyl)ethyl]amino}(3-pyridyl))carbonylamino]-tert-butyl}acetamide |
| 0.277 | M + H | 517.3 | 4-amino-N-{2-[(6-(2-cyanophenyl)-2-{[2-(3-fluorophenyl)ethyl]amino}(3-pyridyl))carbonylamino]-tert-butyl}butanamide |
| 0.307 | M + H | 501.1 | N-{[(2R)-1-(N-methylcarbamoyl)pyrrolidin-2-yl]methyl}(6-(2-cyanophenyl)-2-{[2-(3-fluorophenyl)ethyl]amino}(3-pyridyl))carboxamide |
| 0.101 | M + H | 502.2 | methyl (2R)-2-{[(6-(2-cyanophenyl)-2-{[2-(3-fluorophenyl)ethyl]amino}(3-pyridyl))carbonylamino]methyl}pyrrolidinecarboxylate |
| 1.459 | M + H | 475.2 | N-{(1S)-2-[(6-(2-cyanophenyl)-2-{[2-(3-fluorophenyl)ethyl]amino}(3-pyridyl))carbonylamino]-isopropyl}-2-aminoacetamide |
| 3.56 | M + H | 503.2 | N-{(1S)-2-[(6-(2-cyanophenyl)-2-{[2-(3-fluorophenyl)ethyl]amino}(3-pyridyl))carbonylamino]-isopropyl}-3-aminopropanamide |
| 0.099 | M + H | 543.3 | N-{[(2R)-1-(5-aminopentanoyl)pyrrolidin-2-yl]methyl}(6-(2-cyanophenyl)-2-{[2-(3-fluorophenyl)ethyl]amino}(3-pyridyl))carboxamide |
| 1.215 | M + H | 496.1 | N-{(2S)-2-[(methylsulfonyl)amino]propyl}(6-(2-cyanophenyl)-2-{[2-(3-fluorophenyl)ethyl]amino}(3-pyridyl))carboxamide |
| 0.027 | M + H | 531.2 | 2-aminoethyl (2R)-2-{[(6-(2-cyanophenyl)-2-{[2-(3-fluorophenyl)ethyl]amino}(3-pyridyl))carbonylamino]methyl}pyrrolidinecarboxylate |
| 0.944 | M + H-Me | 432.2 | N-[(2S)-2-(methylamino)propyl](6-(2-cyanophenyl)-2-{[2-(3-fluorophenyl)ethyl]amino}(3-pyridyl))carboxamide |
| 0.399 | M + H | 418.2 | N-((2R)-2-aminopropyl)(6-(2-cyanophenyl)-2-{[2-(3-fluorophenyl)ethyl]amino}(3-pyridyl))carboxamide |
| 1.89 | M + H | 432.2 | N-[(2R)-2-(methylamino)propyl](6-(2-cyanophenyl)-2-{[2-(3-fluorophenyl)ethyl]amino}(3-pyridyl))carboxamide |
| 5.84 | M + H | 510.2 | N-{(2S)-2-[methyl(methylsulfonyl)amino]propyl}(6-(2-cyanophenyl)-2-{[2-(3-fluorophenyl)ethyl]amino}(3-pyridyl))carboxamide |
| 1.333 | M + H | 496.2 | N-{(2R)-2-[(methylsulfonyl)amino]propyl}(6-(2-cyanophenyl)-2-{[2-(3-fluorophenyl)ethyl]amino}(3-pyridyl))carboxamide |
| 7.071 | M + H | 510.2 | N-{(2R)-2-[methyl(methylsulfonyl)amino]propyl}(6-(2-cyanophenyl)-2-{[2-(3-fluorophenyl)ethyl]amino}(3-pyridyl))carboxamide |
| 2.312 | M + H | 575.3 | N-{(1R)-2-[(6-(2-cyanophenyl)-2-{[2-(3-fluorophenyl)ethyl]amino}(3-pyridyl))carbonylamino]-isopropyl}-2-[(tert-butoxy)carbonylamino]acetamide |
| 5.916 | M + H | 589.3 | N-{(1R)-2-[(6-(2-cyanophenyl)-2-{[2-(3-fluorophenyl)ethyl]amino}(3-pyridyl))carbonylamino]-isopropyl}-2-[(tert-butoxy)carbonylamino]-N-methylacetamide |

-continued

| IC50 Arithmetic Mean | Ion | m/z | CHEMICAL NAME |
|---|---|---|---|
| 0.049 | M + H | 603.3 | N-{(1R)-2-[(6-(2-cyanophenyl)-2-{[2-(3-fluorophenyl)ethyl]amino}(3-pyridyl))carbonylamino]-isopropyl}-4-[(tert-butoxy)carbonylamino]butanamide |
| 3.677 | M + H | 617.4 | N-{(1R)-2-[(6-(2-cyanophenyl)-2-{[2-(3-fluorophenyl)ethyl]amino}(3-pyridyl))carbonylamino]-isopropyl}-4-[(tert-butoxy)carbonylamino]-N-methylbutanamide |
| 3.246 | M + H | 489.2 | N-{(1S)-2-[(6-(2-cyanophenyl)-2-{[2-(3-fluorophenyl)ethyl]amino}(3-pyridyl))carbonylamino]-isopropyl}-2-amino-N-methylacetamide |
| 6.826 | M + H | 517.3 | N-{(1S)-2-[(6-(2-cyanophenyl)-2-{[2-(3-fluorophenyl)ethyl]amino}(3-pyridyl))carbonylamino]-isopropyl}-4-amino-N-methylbutanamide |
| 0.041 | M + H | 475.2 | N-{(1R)-2-[(6-(2-cyanophenyl)-2-{[2-(3-fluorophenyl)ethyl]amino}(3-pyridyl))carbonylamino]-isopropyl}-2-aminoacetamide |
| 0.204 | M + H | 503.2 | N-{(1R)-2-[(6-(2-cyanophenyl)-2-{[2-(3-fluorophenyl)ethyl]amino}(3-pyridyl))carbonylamino]-isopropyl}-4-aminobutanamide |
| 0.71 | M + H | 517.2 | N-{(1R)-2-[(6-(2-cyanophenyl)-2-{[2-(3-fluorophenyl)ethyl]amino}(3-pyridyl))carbonylamino]-isopropyl}-4-amino-N-methylbutanamide |
| 0.152 | M + H | 489.2 | N-{(1R)-2-[(6-(2-cyanophenyl)-2-{[2-(3-fluorophenyl)ethyl]amino}(3-pyridyl))carbonylamino]-isopropyl}-2-amino-N-methylacetamide |
| 0.012 | M + H | 449.1 | (5-fluoro-2-{[2-(3-fluorophenyl)ethyl]amino}-6-(1-methylpyrazol-4-yl)(3-pyridyl))-N-(3-pyridylmethyl)carboxamide |
| 0.025 | M + H | 501.2 | N-{[(2R)-1-(2-aminoacetyl)pyrrolidin-2-yl]methyl}(6-(2-cyanophenyl)-2-{[2-(3-fluorophenyl)ethyl]amino}(3-pyridyl))carboxamide |
| 0.029 | M + H | 528.2 | N-{[(2R)-1-(4-aminobutanoyl)pyrrolidin-2-yl]methyl}(6-(2-cyanophenyl)-2-{[2-(3-fluorophenyl)ethyl]amino}(3-pyridyl))carboxamide |
| 0.042 | M + H | 515.2 | N-{[(2R)-1-(3-aminopropyl)-5-oxopyrrolidin-2-yl]methyl}(6-(2-cyanophenyl)-2-{[2-(3-fluorophenyl)ethyl]amino}(3-pyridyl))carboxamide |
| 0.044 | M + H | 417.1 | (2-{[2-(3-fluorophenyl)ethyl]amino}-6-pyrazol-4-yl(3-pyridyl))-N-(3-pyridylmethyl)carboxamide |
| 6.265 | M + H | 424.2 | {6-(3-methylphenyl)-2-[(2-(2-pyridyl)ethyl)amino](3-pyridyl)}-N-(3-pyridylmethyl)carboxamide |
| 0.915 | M + H | 428.2 | {6-(3-fluorophenyl)-2-[(2-(2-pyridyl)ethyl)amino](3-pyridyl)}-N-(3-pyridylmethyl)carboxamide |
| 2.992 | M + H | 435.2 | {6-(3-cyanophenyl)-2-[(2-(2-pyridyl)ethyl)amino](3-pyridyl)}-N-(3-pyridylmethyl)carboxamide |
| 14.933 | M + H | 440.2 | {6-(3-methoxyphenyl)-2-[(2-(2-pyridyl)ethyl)amino](3-pyridyl)}-N-(3-pyridylmethyl)carboxamide |
| 0.79 | M + H | 426.1 | {6-(3-hydroxyphenyl)-2-[(2-(2-pyridyl)ethyl)amino](3-pyridyl)}-N-(3-pyridylmethyl)carboxamide |
| 1.967 | M + H | 444.1 | {6-(3-chlorophenyl)-2-[(2-(2-pyridyl)ethyl)amino](3-pyridyl)}-N-(3-pyridylmethyl)carboxamide |
| 5.927 | M + H | 478.1 | {2-[(2-(2-pyridyl)ethyl)amino]-6-[3-(trifluoromethyl)phenyl](3-pyridyl)}-N-(3-pyridylmethyl)carboxamide |
| 12.404 | M + H | 453.2 | {6-[3-(dimethylamino)phenyl]-2-[(2-(2-pyridyl)ethyl)amino](3-pyridyl)}-N-(3-pyridylmethyl)carboxamide |
| 1.321 | M + H | 428.1 | {6-(2-fluorophenyl)-2-[(2-(2-pyridyl)ethyl)amino](3-pyridyl)}-N-(3-pyridylmethyl)carboxamide |
| 4.438 | M + H | 444.1 | {6-(2-chlorophenyl)-2-[(2-(2-pyridyl)ethyl)amino](3-pyridyl)}-N-(3-pyridylmethyl)carboxamide |
| 11.031 | M + H | 424.2 | {6-(2-methylphenyl)-2-[(2-(2-pyridyl)ethyl)amino](3-pyridyl)}-N-(3-pyridylmethyl)carboxamide |
| 17.936 | M + H | 440.2 | {6-(2-methoxyphenyl)-2-[(2-(2-pyridyl)ethyl)amino](3-pyridyl)}-N-(3-pyridylmethyl)carboxamide |

-continued

| IC50 Arithmetic Mean | Ion | m/z | CHEMICAL NAME |
|---|---|---|---|
| 0.46 | M + H | 435.2 | {6-(2-cyanophenyl)-2-[(2-(2-pyridyl)ethyl)amino](3-pyridyl)}-N-(3-pyridylmethyl)carboxamide |
| 0.797 | M + H | 416.1 | {2-[(2-(2-pyridyl)ethyl)amino]-6-(2-thienyl)(3-pyridyl)}-N-(3-pyridylmethyl)carboxamide |
| 0.414 | M + H | 416.1 | {2-[(2-(2-pyridyl)ethyl)amino]-6-(3-thienyl)(3-pyridyl)}-N-(3-pyridylmethyl)carboxamide |
| 0.586 | M + H | 426.1 | {6-(4-hydroxyphenyl)-2-[(2-(2-pyridyl)ethyl)amino](3-pyridyl)}-N-(3-pyridylmethyl)carboxamide |
| 2.17 | M + H | 426.1 | {6-(2-hydroxyphenyl)-2-[(2-(2-pyridyl)ethyl)amino](3-pyridyl)}-N-(3-pyridylmethyl)carboxamide |
| 2.792 | M + H | 438.2 | {6-(4-ethylphenyl)-2-[(2-(2-pyridyl)ethyl)amino](3-pyridyl)}-N-(3-pyridylmethyl)carboxamide |
| 1.221 | M + H | 467.2 | N-(4-{6-[(2-(2-pyridyl)ethyl)amino]-5-[N-(3-pyridylmethyl)carbamoyl]-2-pyridyl}phenyl)acetamide |
| 0.344 | M + H | 430.1 | {6-(4-methyl(2-thienyl))-2-[(2-(2-pyridyl)ethyl)amino](3-pyridyl)}-N-(3-pyridylmethyl)carboxamide |
| 4.063 | M + H | 430.1 | {6-(4-methyl(3-thienyl))-2-[(2-(2-pyridyl)ethyl)amino](3-pyridyl)}-N-(3-pyridylmethyl)carboxamide |
| 6.945 | M + H | 438.2 | {6-(2,3-dimethylphenyl)-2-[(2-(2-pyridyl)ethyl)amino](3-pyridyl)}-N-(3-pyridylmethyl)carboxamide |
| 13.588 | M + H | 438.2 | {6-(2,5-dimethylphenyl)-2-[(2-(2-pyridyl)ethyl)amino](3-pyridyl)}-N-(3-pyridylmethyl)carboxamide |
| 3.964 | M + H | 438.2 | {6-(2,4-dimethylphenyl)-2-[(2-(2-pyridyl)ethyl)amino](3-pyridyl)}-N-(3-pyridylmethyl)carboxamide |
| 10.138 | M + H | 438.2 | {6-(3,5-dimethylphenyl)-2-[(2-(2-pyridyl)ethyl)amino](3-pyridyl)}-N-(3-pyridylmethyl)carboxamide |
| 3.38 | M + H | 438.2 | {6-(3,4-dimethylphenyl)-2-[(2-(2-pyridyl)ethyl)amino](3-pyridyl)}-N-(3-pyridylmethyl)carboxamide |
| 1.609 | M + H | 427.2 | (2-{[2-(4-fluorophenyl)ethyl]amino}-6-phenyl(3-pyridyl))-N-(3-pyridylmethyl)carboxamide |
| 6.677 | M + H | 443.1 | (2-{[2-(4-chlorophenyl)ethyl]amino}-6-phenyl(3-pyridyl))-N-(3-pyridylmethyl)carboxamide |
| 0.349 | M + H | 443.1 | (2-{[2-(3-chlorophenyl)ethyl]amino}-6-phenyl(3-pyridyl))-N-(3-pyridylmethyl)carboxamide |
| 0.269 | M + H | 439.1 | (2-{[2-(3-methoxyphenyl)ethyl]amino}-6-phenyl(3-pyridyl))-N-(3-pyridylmethyl)carboxamide |
| 0.063 | M + H | 427.1 | (2-{[2-(3-fluorophenyl)ethyl]amino}-6-phenyl(3-pyridyl))-N-(3-pyridylmethyl)carboxamide |
| 0.16 | M + H | 443.1 | (2-{[2-(2-chlorophenyl)ethyl]amino}-6-phenyl(3-pyridyl))-N-(3-pyridylmethyl)carboxamide |
| 0.98 | M + H | 439.1 | (2-{[2-(2-methoxyphenyl)ethyl]amino}-6-phenyl(3-pyridyl))-N-(3-pyridylmethyl)carboxamide |
| 0.326 | M + H | 423.1 | (2-{[2-(2-methylphenyl)ethyl]amino}-6-phenyl(3-pyridyl))-N-(3-pyridylmethyl)carboxamide |
| 0.107 | M + H | 427.1 | (2-{[2-(2-fluorophenyl)ethyl]amino}-6-phenyl(3-pyridyl))-N-(3-pyridylmethyl)carboxamide |
| 0.288 | M + H | 445.1 | (2-{[2-(2,6-difluorophenyl)ethyl]amino}-6-phenyl(3-pyridyl))-N-(3-pyridylmethyl)carboxamide |
| 0.055 | M + H | 445.1 | (2-{[2-(3,5-difluorophenyl)ethyl]amino}-6-phenyl(3-pyridyl))-N-(3-pyridylmethyl)carboxamide |
| 0.521 | M + H | 445.2 | (2-{[2-(3,4-difluorophenyl)ethyl]amino}-6-phenyl(3-pyridyl))-N-(3-pyridylmethyl)carboxamide |
| 0.079 | M + H | 445.2 | (2-{[2-(2,5-difluorophenyl)ethyl]amino}-6-phenyl(3-pyridyl))-N-(3-pyridylmethyl)carboxamide |
| 8.254 | M + H | 477.2 | [6-phenyl-2-({2-[3-(trifluoromethyl)phenyl]ethyl}amino)(3-pyridyl)]-N-(3-pyridylmethyl)carboxamide |
| 0.148 | M + H | 447.2 | (2-{[2-(3-fluorophenyl)ethyl]amino}-6-(4-methyl(2-thienyl))(3-pyridyl))-N-(3-pyridylmethyl)carboxamide |
| 0.048 | M + H | 433.1 | (2-{[2-(3-fluorophenyl)ethyl]amino}-6-(3-thienyl)(3-pyridyl))-N-(3-pyridylmethyl)carboxamide |
| 0.26 | M + H | 443.1 | (2-{[2-(2-cyanophenyl)ethyl]amino}-6-phenyl(3-pyridyl))-N-(3-pyridylmethyl)carboxamide |
| 4.649 | M + H | 434.1 | (2-{[2-(3-cyanophenyl)ethyl]amino}-6-phenyl(3-pyridyl))-N-(3-pyridylmethyl)carboxamide |
| 36.722 | M + H | 425.1 | (2-{[2-(4-hydroxyphenyl)ethyl]amino}-6-phenyl(3-pyridyl))-N-(3-pyridylmethyl)carboxamide |

-continued

| IC50 Arithmetic Mean | Ion | m/z | CHEMICAL NAME |
|---|---|---|---|
| 2.431 | M + H | 425.1 | (2-{[2-(2-hydroxyphenyl)ethyl]amino}-6-phenyl(3-pyridyl))-N-(3-pyridylmethyl)carboxamide |
| 27.106 | M + H | 424.1 | (2-{[2-(4-aminophenyl)ethyl]amino}-6-phenyl(3-pyridyl))-N-(3-pyridylmethyl)carboxamide |
| 11.492 | M + H | 452.1 | 3-[2-({6-phenyl-3-[N-(3-pyridylmethyl)carbamoyl]-2-pyridyl}amino)ethyl]benzamide |
| 0.04 | M + H | 451.1 | (2-{[2-(3,5-difluorophenyl)ethyl]amino}-6-(3-thienyl)(3-pyridyl))-N-(3-pyridylmethyl)carboxamide |
| 0.119 | M + H | 465.1 | (2-{[2-(3,5-difluorophenyl)ethyl]amino}-6-(4-methyl(2-thienyl))(3-pyridyl))-N-(3-pyridylmethyl)carboxamide |
| 0.041 | M + H | 470.1 | (2-{[2-(3,5-difluorophenyl)ethyl]amino}-6-(2-cyanophenyl)(3-pyridyl))-N-(3-pyridylmethyl)carboxamide |
| 0.137 | M + H | 433.1 | (2-{[2-(3-fluorophenyl)ethyl]amino}-6-(2-thienyl)(3-pyridyl))-N-(3-pyridylmethyl)carboxamide |
| 0.097 | M + H | 451.1 | (2-{[2-(3,5-difluorophenyl)ethyl]amino}-6-(2-thienyl)(3-pyridyl))-N-(3-pyridylmethyl)carboxamide |
| 28.097 | M + H | 467.2 | methyl 3-[2-({6-phenyl-3-[N-(3-pyridylmethyl)carbamoyl]-2-pyridyl}amino)ethyl]benzoate |
| 16.384 | M + H | 470.2 | 2-(6-{[2-(3-fluorophenyl)ethyl]amino}-5-[N-(3-pyridylmethyl)carbamoyl]-2-pyridyl)benzamide |
| 0.198 | M + H | 445.2 | (6-(4-fluorophenyl)-2-{[2-(3-fluorophenyl)ethyl]amino}(3-pyridyl))-N-(3-pyridylmethyl)carboxamide |
| 21.862 | M + H | 453.2 | 3-[2-({6-phenyl-3-[N-(3-pyridylmethyl)carbamoyl]-2-pyridyl}amino)ethyl]benzoic acid |
| 1.383 | M + H | 479.1 | (6-(2-chloro-4-fluorophenyl)-2-{[2-(3-fluorophenyl)ethyl]amino}(3-pyridyl))-N-(3-pyridylmethyl)carboxamide |
| 0.138 | M + H | 463.1 | (2-{[2-(3,5-difluorophenyl)ethyl]amino}-6-(4-fluorophenyl)(3-pyridyl))-N-(3-pyridylmethyl)carboxamide |
| 0.038 | M + H | 470.1 | (6-(2-cyano-4-fluorophenyl)-2-{[2-(3-fluorophenyl)ethyl]amino}(3-pyridyl))-N-(3-pyridylmethyl)carboxamide |
| 0.54 | M + H | 479.1 | (6-(2-chloro-6-fluorophenyl)-2-{[2-(3-fluorophenyl)ethyl]amino}(3-pyridyl))-N-(3-pyridylmethyl)carboxamide |
| 2.005 | M + H | 491.1 | (6-(2-chloro-5-methoxyphenyl)-2-{[2-(3-fluorophenyl)ethyl]amino}(3-pyridyl))-N-(3-pyridylmethyl)carboxamide |
| 0.041 | M + H | 482.1 | (6-(2-cyano-5-methoxyphenyl)-2-{[2-(3-fluorophenyl)ethyl]amino}(3-pyridyl))-N-(3-pyridylmethyl)carboxamide |
| 0.086 | M + H | 470.1 | (6-(2-cyano-6-fluorophenyl)-2-{[2-(3-fluorophenyl)ethyl]amino}(3-pyridyl))-N-(3-pyridylmethyl)carboxamide |
| 0.139 | M + H | 445.1 | (6-(2-fluorophenyl)-2-{[2-(3-fluorophenyl)ethyl]amino}(3-pyridyl))-N-(3-pyridylmethyl)carboxamide |
| 0.022 | M + H | 470.1 | (2-{[2-(2,3-difluorophenyl)ethyl]amino}-6-(2-cyanophenyl)(3-pyridyl))-N-(3-pyridylmethyl)carboxamide |
| 1.327 | M + H | 479.1 | (6-(2-chloro-5-fluorophenyl)-2-{[2-(3-fluorophenyl)ethyl]amino}(3-pyridyl))-N-(3-pyridylmethyl)carboxamide |
| 0.053 | M + H | 470.1 | (6-(2-cyano-5-fluorophenyl)-2-{[2-(3-fluorophenyl)ethyl]amino}(3-pyridyl))-N-(3-pyridylmethyl)carboxamide |
| 0.157 | M + H | 445.1 | (6-(3-fluorophenyl)-2-{[2-(3-fluorophenyl)ethyl]amino}(3-pyridyl))-N-(3-pyridylmethyl)carboxamide |
| 16.392 | M + H | 466.2 | (6-[2-(cyanomethyl)phenyl]-2-{[2-(3-fluorophenyl)ethyl]amino}(3-pyridyl))-N-(3-pyridylmethyl)carboxamide |
| 2.245 | M + H | 463.1 | (2-{[2-(3-fluorophenyl)ethyl]amino}-6-[3-(hydroxymethyl)(2-thienyl)](3-pyridyl))-N-(3-pyridylmethyl)carboxamide |
| 0.098 | M + H | 461.1 | (2-{[2-(3-fluorophenyl)ethyl]amino}-6-(5-formyl(3-thienyl))(3-pyridyl))-N-(3-pyridylmethyl)carboxamide |
| 0.073 | M + H | 463.1 | (2-{[2-(3-fluorophenyl)ethyl]amino}-6-[5-(hydroxymethyl)(3-thienyl)](3-pyridyl))-N-(3-pyridylmethyl)carboxamide |

-continued

| IC50 Arithmetic Mean | Ion | m/z | CHEMICAL NAME |
|---|---|---|---|
| 2.078 | M + H | 475.1 | (6-(2-chloro-4-methylphenyl)-2-{[2-(3-fluorophenyl)ethyl]amino}(3-pyridyl))-N-(3-pyridylmethyl)carboxamide |
| 0.996 | M + H | 466.2 | (6-(2-cyano-4-methylphenyl)-2-{[2-(3-fluorophenyl)ethyl]amino}(3-pyridyl))-N-(3-pyridylmethyl)carboxamide |
| 0.281 | M + H | 457.1 | (2-{[2-(3-fluorophenyl)ethyl]amino}-6-[3-(hydroxymethyl)phenyl](3-pyridyl))-N-(3-pyridylmethyl)carboxamide |
| 5.719 | M + H | 471.2 | (2-{[2-(3-fluorophenyl)ethyl]amino}-6-[3-(methoxymethyl)phenyl](3-pyridyl))-N-(3-pyridylmethyl)carboxamide |
| 78.064 | M + H | 419.1 | (6-(1H-1,2,3,4-tetraazol-5-yl)-2-{[2-(3-fluorophenyl)ethyl]amino}(3-pyridyl))-N-(3-pyridylmethyl)carboxamide |
| 1.185 | M + H | 491.1 | (6-[2-chloro-5-(hydroxymethyl)phenyl]-2-{[2-(3-fluorophenyl)ethyl]amino}(3-pyridyl))-N-(3-pyridylmethyl)carboxamide |
| 12.904 | M + H | 475.2 | (2R)-2-amino-4-[(6-(2-cyanophenyl)-2-{[2-(3-fluorophenyl)ethyl]amino}(3-pyridyl))carbonylamino]-N-methylbutanamide |
| 5.022 | M + H | 475.2 | (2S)-2-amino-4-[(6-(2-cyanophenyl)-2-{[2-(3-fluorophenyl)ethyl]amino}(3-pyridyl))carbonylamino]-N-methylbutanamide |
| 4.812 | M + H | 434.1 | N-(3-amino-2-hydroxypropyl)(6-(2-cyanophenyl)-2-{[2-(3-fluorophenyl)ethyl]amino}(3-pyridyl))carboxamide |
| 1.209 | M + H | 581.2 | N-[(2-{[(tert-butoxy)carbonylamino]methyl}(3-pyridyl))methyl](6-(2-cyanophenyl)-2-{[2-(3-fluorophenyl)ethyl]amino}(3-pyridyl))carboxamide |
| 0.008 | M + H | 456.1 | N-{[2-(aminomethyl)(3-pyridyl)]methyl}(2-{[2-(3-fluorophenyl)ethyl]amino}-6-phenyl(3-pyridyl))carboxamide |
| 0.043 | M + H | 446.1 | N-{[2-(aminomethyl)(3-pyridyl)]methyl}(2-{[2-(3-fluorophenyl)ethyl]amino}-6-pyrazol-3-yl(3-pyridyl))carboxamide |
| 0.032 | M + H | 460.1 | N-{[2-(aminomethyl)(3-pyridyl)]methyl}(2-{[2-(3-fluorophenyl)ethyl]amino}-6-(1-methylpyrazol-3-yl)(3-pyridyl))carboxamide |
| 2.148 | M + H | 458.2 | N-[((3R)(3-piperidyl))methyl](6-(2-cyanophenyl)-2-{[2-(3-fluorophenyl)ethyl]amino}(3-pyridyl))carboxamide |
| 0.336 | M + H | 458.2 | (6-(2-cyanophenyl)-2-{[2-(3-fluorophenyl)ethyl]amino}(3-pyridyl))-N-(4-piperidylmethyl)carboxamide |
| 0.572 | M + H | 515.2 | N-{[1-(2-aminoacetyl)(4-piperidyl)]methyl}(6-(2-cyanophenyl)-2-{[2-(3-fluorophenyl)ethyl]amino}(3-pyridyl))carboxamide |
| 3.874 | M + H | 529.2 | N-{[1-(3-aminopropanoyl)(4-piperidyl)]methyl}(6-(2-cyanophenyl)-2-{[2-(3-fluorophenyl)ethyl]amino}(3-pyridyl))carboxamide |
| 0.755 | M + H | 515.2 | N-{[(3S)-1-(2-aminoacetyl)(3-piperidyl)]methyl}(6-(2-cyanophenyl)-2-{[2-(3-fluorophenyl)ethyl]amino}(3-pyridyl))carboxamide |
| 1.261 | M + H | 529.2 | N-{[(3S)-1-(3-aminopropanoyl)(3-piperidyl)]methyl}(6-(2-cyanophenyl)-2-{[2-(3-fluorophenyl)ethyl]amino}(3-pyridyl)carboxamide |
| 1.696 | M + H | 500.3 | N-[(1-acetyl(4-piperidyl))methyl](6-(2-cyanophenyl)-2-{[2-(3-fluorophenyl)ethyl]amino}(3-pyridyl))carboxamide |
| 10.729 | M + H | 500.3 | N-[((3S)-1-acetyl(3-piperidyl))methyl](6-(2-cyanophenyl)-2-{[2-(3-fluorophenyl)ethyl]amino}(3-pyridyl))carboxamide |
| 6.009 | M + H | 543.3 | N-{[1-(4-aminobutanoyl)(4-piperidyl)]methyl}(6-(2-cyanophenyl)-2-{[2-(3-fluorophenyl)ethyl]amino}(3-pyridyl))carboxamide |
| 2.13 | M + H | 516.3 | methyl 4-{[(6-(2-cyanophenyl)-2-{[2-(3-fluorophenyl)ethyl]amino}-3-pyridyl)carbonylamino]methyl}piperidinecarboxylate |
| 1.159 | M + H | 458.3 | N-[((2R)(2-piperidyl))methyl](6-(2-cyanophenyl)-2-{[2-(3-fluorophenyl)ethyl]amino}(3-pyridyl))carboxamide |
| 0.092 | M + H | 515.3 | N-{[(2R)-1-(2-aminoacetyl)(2-piperidyl)]methyl}(6-(2-cyanophenyl)-2-{[2-(3-fluorophenyl)ethyl]amino}(3-pyridyl))carboxamide |

-continued

| IC50 Arithmetic Mean | Ion | m/z | CHEMICAL NAME |
|---|---|---|---|
| 0.155 | M + H | 529.2 | N-{[(2R)-1-(3-aminopropanoyl)(2-piperidyl)]methyl}(6-(2-cyanophenyl)-2-{[2-(3-fluorophenyl)ethyl]amino}(3-pyridyl))carboxamide |
| 0.083 | M + H | 543.2 | N-{[(2R)-1-(4-aminobutanoyl)(2-piperidyl)]methyl}(6-(2-cyanophenyl)-2-{[2-(3-fluorophenyl)ethyl]amino}(3-pyridyl))carboxamide |
| 2.676 | M + H | 500.2 | N-[((2R)-1-acetyl(2-piperidyl))methyl](6-(2-cyanophenyl)-2-{[2-(3-fluorophenyl)ethyl]amino}(3-pyridyl))carboxamide |
| 4.282 | M + H | 516.3 | methyl (2R)-2-{[(6-(2-cyanophenyl)-2-{[2-(3-fluorophenyl)ethyl]amino}(3-pyridyl))carbonylamino]methyl}piperidinecarboxylate |
| 0.37 | M + H | 579.2 | N-({(2R)-1-[(3-aminopropyl)sulfonyl](2-piperidyl)}methyl)(6-(2-cyanophenyl)-2-{[2-(3-fluorophenyl)ethyl]amino}(3-pyridyl))carboxamide |
| 0.488 | M + H | 472.2 | N-[((2R)-1-methyl(2-piperidyl))methyl](6-(2-cyanophenyl)-2-{[2-(3-fluorophenyl)ethyl]amino}(3-pyridyl))carboxamide |
| 0.161 | M + H | 544.3 | N-{[(2R)-1-((2R)-2,3-diaminopropanoyl)(2-piperidyl)]methyl}(6-(2-cyanophenyl)-2-{[2-(3-fluorophenyl)ethyl]amino}(3-pyridyl))carboxamide |
| 0.399 | M + H | 558.3 | N-{[(2R)-1-((2R)-2,4-diaminobutanoyl)(2-piperidyl)]methyl}(6-(2-cyanophenyl)-2-{[2-(3-fluorophenyl)ethyl]amino}(3-pyridyl))carboxamide |
| 0.456 | M + H | 572.2 | N-{[(2R)-1-((2R)-2,5-diaminopentanoyl)(2-piperidyl)]methyl}(6-(2-cyanophenyl)-2-{[2-(3-fluorophenyl)ethyl]amino}(3-pyridyl))carboxamide |
| 0.178 | M + H | 565.2 | N-({(2R)-1-[(2-aminoethyl)sulfonyl](2-piperidyl)}methyl)(6-(2-cyanophenyl)-2-{[2-(3-fluorophenyl)ethyl]amino}(3-pyridyl))carboxamide |
| 0.048 | M + H | 572.3 | N-{[(2R)-1-((2S)-2,5-diaminopentanoyl)(2-piperidyl)]methyl}(6-(2-cyanophenyl)-2-{[2-(3-fluorophenyl)ethyl]amino}(3-pyridyl))carboxamide |
| 0.052 | M + H | 529.3 | N-{[(2R)-1-((2S)-2-aminopropanoyl)(2-piperidyl)]methyl}(6-(2-cyanophenyl)-2-{[2-(3-fluorophenyl)ethyl]amino}(3-pyridyl))carboxamide |
| 0.261 | M + H | 529.2 | N-{[(2R)-1-((2R)-2-aminopropanoyl)(2-piperidyl)]methyl}(6-(2-cyanophenyl)-2-{[2-(3-fluorophenyl)ethyl]amino}(3-pyridyl))carboxamide |
| 2.691 | M + H | 564.1 | 2-chloroethyl (2R)-2-{[(6-(2-cyanophenyl)-2-{[2-(3-fluorophenyl)ethyl]amino}(3-pyridyl))carbonylamino]methyl}piperidinecarboxylate |
| 0.091 | M + H | 545.2 | 2-aminoethyl (2R)-2-{[(6-(2-cyanophenyl)-2-{[2-(3-fluorophenyl)ethyl]amino}(3-pyridyl))carbonylamino]methyl}piperidinecarboxylate |
| 0.023 | M + H | 547.2 | N-{[(2R)-1-(4-aminobutanoyl)pyrrolidin-2-yl]methyl}(2-{[2-(3,5-difluorophenyl)ethyl]amino}-6-(2-cyanophenyl)(3-pyridyl))carboxamide |
| 0.133 | M + H | 515.3 | N-{[(2R)-1-(4-aminobutanoyl)pyrrolidin-2-yl]methyl}{6-(2-cyanophenyl)-2-[(2-cyclohex-1-enylethyl)amino](3-pyridyl)}carboxamide |
| 3.56 | M + H | 506.2 | 3-{[3-(N-{[(2R)-1-(4-aminobutanoyl)pyrrolidin-2-yl]methyl}carbamoyl)-6-(2-cyanophenyl)(2-pyridyl)]amino}-N,N-dimethylpropanamide |
| 0.062 | M + H | 511.2 | N-{[(2R)-1-(4-aminobutanoyl)pyrrolidin-2-yl]methyl}{6-(2-cyanophenyl)-2-[(2-phenylethyl)amino](3-pyridyl)}carboxamide |
| 8.767 | M + H | 519.2 | N-{[(2R)-1-(4-aminobutanoyl)pyrrolidin-2-yl]methyl}{6-(2-cyanophenyl)-2-[(2-(2H-3,4,5,6-tetrahydropyran-4-yl)ethyl)amino](3-pyridyl)}carboxamide |
| 2.038 | M + H | 519.2 | N-{[(2R)-1-(4-aminobutanoyl)pyrrolidin-2-yl]methyl}{6-(2-cyanophenyl)-2-[(2-(2H-3,4,5,6-tetrahydropyran-2-yl)ethyl)amino](3-pyridyl)}carboxamide |
| 0.059 | M + H | 530.2 | N-{[(2R)-1-((2S)-2,3-diaminopropanoyl)pyrrolidin-2-yl]methyl}(6-(2-cyanophenyl)-2-{[2-(3-fluorophenyl)ethyl]amino}(3-pyridyl))carboxamide |
| 0.193 | M + H | 545.2 | N-{[(2R)-1-((2S)-2-amino-3-methoxypropanoyl)pyrrolidin-2-yl]methyl}(6-(2-cyanophenyl)-2-{[2-(3-fluorophenyl)ethyl]amino}(3-pyridyl))carboxamide |
| 0.173 | M + H | 531.2 | N-{[(2R)-1-((2S)-2-amino-3-hydroxypropanoyl)pyrrolidin-2-yl]methyl}(6-(2-cyanophenyl)-2-{[2-(3-fluorophenyl)ethyl]amino}(3-pyridyl))carboxamide |

| IC50 Arithmetic Mean | Ion | m/z | CHEMICAL NAME |
|---|---|---|---|
| 0.014 | M + H | 464.1 | N-{[2-(aminomethyl)(3-pyridyl)]methyl}(5-fluoro-2-{[2-(3-fluorophenyl)ethyl]amino}-6-pyrazol-3-yl(3-pyridyl))carboxamide |
| 0.108 | M + H | 484.1 | N-{[(2R)-1-(2-aminoacetyl)pyrrolidin-2-yl]methyl}(5-fluoro-2-{[2-(3-fluorophenyl)ethyl]amino}-6-pyrazol-3-yl(3-pyridyl))carboxamide |
| 0.269 | M + H | 514.1 | N-{[(2R)-1-((2S)-2-amino-3-hydroxypropanoyl)pyrrolidin-2-yl]methyl}(5-fluoro-2-{[2-(3-fluorophenyl)ethyl]amino}-6-pyrazol-3-yl(3-pyridyl))carboxamide |
| 0.314 | M + H | 498.2 | N-{[(2R)-1-((2S)-2-aminopropanoyl)pyrrolidin-2-yl]methyl}(5-fluoro-2-{[2-(3-fluorophenyl)ethyl]amino}-6-pyrazol-3-yl(3-pyridyl))carboxamide |
| 0.169 | M + H | 512.1 | N-{[(2R)-1-(4-aminobutanoyl)pyrrolidin-2-yl]methyl}(5-fluoro-2-{[2-(3-fluorophenyl)ethyl]amino}-6-pyrazol-3-yl(3-pyridyl))carboxamide |
| 0.92 | M + H | 428.1 | {6-(2-cyanophenyl)-2-[(2-oxolan-2-ylethyl)amino](3-pyridyl)}-N-(3-pyridylmethyl)carboxamide |
| 0.398 | M + H | 415.1 | N-((2R)-2-aminopropyl)(5-fluoro-2-{[2-(3-fluorophenyl)ethyl]amino}-6-(1-methylpyrazol-4-yl)(3-pyridyl))carboxamide |
| 1.754 | M + H | 572.2 | N-{(1R)-2-[(5-fluoro-2-{[2-(3-fluorophenyl)ethyl]amino}-6-(1-methylpyrazol-4-yl)(3-pyridyl))carbonylamino]-isopropyl}-2-[(tert-butoxy)carbonylamino]acetamide |
| 0.076 | M + H | 472.3 | N-{(1R)-2-[(5-fluoro-2-{[2-(3-fluorophenyl)ethyl]amino}-6-(1-methylpyrazol-4-yl)(3-pyridyl))carbonylamino]-isopropyl}-2-aminoacetamide |
| 0.027 | M + H | 455.1 | N-[((2R)-5-oxopyrrolidin-2-yl)methyl](5-fluoro-2-{[2-(3-fluorophenyl)ethyl]amino}-6-(1-methylpyrazol-4-yl)(3-pyridyl))carboxamide |
| 1.804 | M + H | 472.3 | N-{(1S)-2-[(5-fluoro-2-{[2-(3-fluorophenyl)ethyl]amino}-6-(1-methylpyrazol-4-yl)(3-pyridyl))carbonylamino]-isopropyl}-2-aminoacetamide |
| 0.197 | M + H | 473.1 | N-{(1R)-2-[(5-fluoro-2-{[2-(3-fluorophenyl)ethyl]amino}-6-(1-methylpyrazol-4-yl)(3-pyridyl))carbonylamino]-isopropyl}-2-hydroxyacetamide |
| 0.1 | M + H | 600.2 | N-{(1R)-2-[(5-fluoro-2-{[2-(3-fluorophenyl)ethyl]amino}-6-(1-methylpyrazol-4-yl)(3-pyridyl))carbonylamino]-isopropyl}-4-[(tert-butoxy)carbonylamino]butanamide |
| 0.116 | M + H | 500.3 | N-{(1R)-2-[(5-fluoro-2-{[2-(3-fluorophenyl)ethyl]amino}-6-(1-methylpyrazol-4-yl)(3-pyridyl))carbonylamino]-isopropyl}-4-aminobutanamide |
| 2.328 | M + H | 473.1 | N-{(2R)-2-[(2-methoxyethyl)amino]propyl}(5-fluoro-2-{[2-(3-fluorophenyl)ethyl]amino}-6-(1-methylpyrazol-4-yl)(3-pyridyl))carboxamide |
| 8.211 | M + H | 501.1 | N-{(2R)-2-[(tert-butoxy)carbonylamino]propyl}(5-fluoro-2-{[2-(3-fluorophenyl)ethyl]amino}-6-pyrazol-4-yl(3-pyridyl))carboxamide |
| 0.443 | M + H | 401.1 | N-((2R)-2-aminopropyl)(5-fluoro-2-{[2-(3-fluorophenyl)ethyl]amino}-6-pyrazol-4-yl(3-pyridyl))carboxamide |
| 0.251 | M + H | 457.1 | N-{(1R)-2-[(5-fluoro-2-{[2-(3-fluorophenyl)ethyl]amino}-6-(1-methylpyrazol-4-yl)(3-pyridyl))carbonylamino]-isopropyl}acetamide |
| 1.002 | M + H | 493.1 | N-{(2R)-2-[(methylsulfonyl)amino]propyl}(5-fluoro-2-{[2-(3-fluorophenyl)ethyl]amino}-6-(1-methylpyrazol-4-yl)(3-pyridyl))carboxamide |
| 0.122 | M + H | 459.1 | N-{(1R)-2-[(5-fluoro-2-{[2-(3-fluorophenyl)ethyl]amino}-6-pyrazol-4-yl(3-pyridyl))carbonylamino]-isopropyl}-2-aminoacetamide |
| 0.024 | M + H | 435.1 | (5-fluoro-2-{[2-(3-fluorophenyl)ethyl]amino}-6-pyrazol-4-yl(3-pyridyl))-N-(2-pyridylmethyl)carboxamide |
| 0.648 | M + H | 459.2 | N-{(2R)-2-[(2-hydroxyethyl)amino]propyl}(5-fluoro-2-{[2-(3-fluorophenyl)ethyl]amino}-6-(1-methylpyrazol-4-yl)(3-pyridyl))carboxamide |

-continued

| IC50 Arithmetic Mean | Ion | m/z | CHEMICAL NAME |
|---|---|---|---|
| 0.636 | M + H | 472.1 | N-{(2R)-2-[(carbamoylmethyl)amino]propyl}(5-fluoro-2-{[2-(3-fluorophenyl)ethyl]amino}-6-(1-methylpyrazol-4-yl)(3-pyridyl))carboxamide |
| 0.121 | M + H | 500.2 | N-{(1R)-2-[(5-fluoro-2-{[2-(3-fluorophenyl)ethyl]amino}-6-(1-methylpyrazol-4-yl)(3-pyridyl))carbonylamino-isopropyl}-2-(dimethylamino)acetamide |
| 2.264 | M + H | 602.2 | N-{(1R)-2-[(5-fluoro-2-{[2-(3-fluorophenyl)ethyl]amino}-6-(1-methylpyrazol-4-yl)(3-pyridyl))carbonylamino-isopropyl}(2S)-2-[(tert-butoxy)carbonylamino]-3-hydroxypropanamide |
| 0.115 | M + H | 502.2 | N-{(1R)-2-[(5-fluoro-2-{[2-(3-fluorophenyl)ethyl]amino}-6-(1-methylpyrazol-4-yl)(3-pyridyl))carbonylamino-isopropyl}(2S)-2-amino-3-hydroxypropanamide |
| 0.285 | M + H | 500.2 | N-{(1R)-2-[(5-fluoro-2-{[2-(3-fluorophenyl)ethyl]amino}-6-(1-methylpyrazol-4-yl)(3-pyridyl))carbonylamino-isopropyl}-2-amino-2-methylpropanamide |
| 3.04 | M + H | 586.3 | N-((1R)-1-{[(5-fluoro-2-{[2-(3-fluorophenyl)ethyl]amino}-6-(1-methylpyrazol-4-yl)(3-pyridyl))carbonylamino]methyl}propyl)-2-[(tert-butoxy)carbonylamino]acetamide |
| 0.131 | M + H | 486.2 | N-((1R)-1-{[(5-fluoro-2-{[2-(3-fluorophenyl)ethyl]amino}-6-(1-methylpyrazol-4-yl)(3-pyridyl))carbonylamino]methyl}propyl)-2-aminoacetamide |
| 4.323 | M + H | 572.3 | N-((1R)-1-{[(5-fluoro-2-{[2-(3-fluorophenyl)ethyl]amino}-6-pyrazol-4-yl(3-pyridyl))carbonylamino]methyl}propyl)-2-[(tert-butoxy)carbonylamino]acetamide |
| 0.16 | M + H | 472.2 | N-((1R)-1-{[(5-fluoro-2-{[2-(3-fluorophenyl)ethyl]amino}-6-pyrazol-4-yl(3-pyridyl))carbonylamino]methyl}propyl)-2-aminoacetamide |
| 0.131 | M + H | 486.2 | N-{(1R)-2-[(5-fluoro-2-{[2-(3-fluorophenyl)ethyl]amino}-6-(1-methylpyrazol-4-yl)(3-pyridyl))carbonylamino-isopropyl}(2S)-2-aminopropanamide |
| 0.283 | M + H | 444.2 | N-((2R)-3-hydroxy-2-methylbutyl)(5-fluoro-2-{[2-(3-fluorophenyl)ethyl]amino}-6-(1-methylpyrazol-4-yl)(3-pyridyl))carboxamide |
| 0.006 | M + H | 481.1 | N-{[2-(aminomethyl)(3-pyridyl)]methyl}(6-(2-cyanophenyl)-2-{[2-(3-fluorophenyl)ethyl]amino}(3-pyridyl))carboxamide |
| 0.024 | M + H | 446.3 | N-{[2-(aminomethyl)(3-pyridyl)]methyl}(2-{[2-(3-fluorophenyl)ethyl]amino}-6-pyrazol-4-yl(3-pyridyl))carboxamide |
| 0.024 | M + H | 452.1 | (6-(2-cyanophenyl)-2-{[2-(3-fluorophenyl)ethyl]amino}(3-pyridyl))-N-(3-pyridylmethyl)carboxamide |
| 0.512 | M + H | 410.1 | {6-phenyl-2-[(2-(2-pyridyl)ethyl)amino](3-pyridyl)}-N-(3-pyridylmethyl)carboxamide |
| 1.206 | M + H | 446.1 | {6-(3,4-difluorophenyl)-2-[(2-(2-pyridyl)ethyl)amino](3-pyridyl)}-N-(3-pyridylmethyl)carboxamide |
| 1.045 | M + H | 428.2 | {6-(4-fluorophenyl)-2-[(2-(2-pyridyl)ethyl)amino](3-pyridyl)}-N-(3-pyridylmethyl)carboxamide |
| 0.629 | M + H | 444.1 | {6-(4-chlorophenyl)-2-[(2-(2-pyridyl)ethyl)amino](3-pyridyl)}-N-(3-pyridylmethyl)carboxamide |
| 0.677 | M + H | 424.2 | {6-(4-methylphenyl)-2-[(2-(2-pyridyl)ethyl)amino](3-pyridyl)}-N-(3-pyridylmethyl)carboxamide |
| 1.935 | M + H | 435.1 | {6-(4-cyanophenyl)-2-[(2-(2-pyridyl)ethyl)amino](3-pyridyl)}-N-(3-pyridylmethyl)carboxamide |
| 1.063 | M + H | 440.1 | {6-(4-methoxyphenyl)-2-[(2-(2-pyridyl)ethyl)amino](3-pyridyl)}-N-(3-pyridylmethyl)carboxamide |
| 2.43 | M + H | 440.2 | {6-[4-(hydroxymethyl)phenyl]-2-[(2-(2-pyridyl)ethyl)amino](3-pyridyl)}-N-(3-pyridylmethyl)carboxamide |
| 3.375 | M + H | 478.1 | {6-(3,4-dichlorophenyl)-2-[(2-(2-pyridyl)ethyl)amino](3-pyridyl)}-N-(3-pyridylmethyl)carboxamide |
| 2.285 | M + H | 478.1 | {2-[(2-(2-pyridyl)ethyl)amino]-6-[4-(trifluoromethyl)phenyl](3-pyridyl)}-N-(3-pyridylmethyl)carboxamide |

-continued

| IC50 Arithmetic Mean | Ion | m/z | CHEMICAL NAME |
|---|---|---|---|
| 0.989 | M + H | 468.1 | methyl 4-{6-[(2-(2-pyridyl)ethyl)amino]-5-[N-(3-pyridylmethyl)carbamoyl]-2-pyridyl}benzoate |
| 0.809 | M + H | 453.2 | {6-[4-(dimethylamino)phenyl]-2-[(2-(2-pyridyl)ethyl)amino](3-pyridyl)}-N-(3-pyridylmethyl)carboxamide |
| 2.133 | M + H | 452.1 | {6-(4-acetylphenyl)-2-[(2-(2-pyridyl)ethyl)amino](3-pyridyl)}-N-(3-pyridylmethyl)carboxamide |
| 2.187 | M + H | 410.1 | {6-phenyl-2-[(2-(3-pyridyl)ethyl)amino](3-pyridyl)}-N-(3-pyridylmethyl)carboxamide |
| 18.274 | M + H | 454.1 | 4-{6-[(2-(2-pyridyl)ethyl)amino]-5-[N-(3-pyridylmethyl)carbamoyl]-2-pyridyl}benzoic acid |
| 19.129 | M + H | 411.1 | N-(3-pyridylmethyl){6-(3-pyridyl)-2-[(2-(2-pyridyl)ethyl)amino](3-pyridyl)}carboxamide |
| 6.557 | M + H | 411.1 | N-(3-pyridylmethyl){6-(4-pyridyl)-2-[(2-(2-pyridyl)ethyl)amino](3-pyridyl)}carboxamide |
| 5.379 | M + H | 411.2 | N-(3-pyridylmethyl){6-(2-pyridyl)-2-[(2-(2-pyridyl)ethyl)amino](3-pyridyl)}carboxamide |
| 2.538 | M + H | 453.1 | 4-{6-[(2-(2-pyridyl)ethyl)amino]-5-[N-(3-pyridylmethyl)carbamoyl]-2-pyridyl}benzamide |
| 1.942 | M + H | 425.1 | {2-[(2-hydroxy-2-phenylethyl)amino]-6-phenyl(3-pyridyl)}-N-(3-pyridylmethyl)carboxamide |
| 5.342 | M + H | 436.1 | {2-[(2-(2-pyridyl)ethyl)amino]-6-(2-vinylphenyl)(3-pyridyl)}-N-(3-pyridylmethyl)carboxamide |
| 84.495 | M + H | 454.2 | {6-[2-(methoxymethyl)phenyl]-2-[(2-(2-pyridyl)ethyl)amino](3-pyridyl)}-N-(3-pyridylmethyl)carboxamide |
| 8.751 | M + H | 438.2 | {6-(2-formylphenyl)-2-[(2-(2-pyridyl)ethyl)amino](3-pyridyl)}-N-(3-pyridylmethyl)carboxamide |
| 0.559 | M + H | 443.2 | (2-{[2-(3-fluorophenyl)-2-hydroxyethyl]amino}-6-phenyl(3-pyridyl))-N-(3-pyridylmethyl)carboxamide |
| 0.339 | M + H | 468.2 | (6-(2-cyanophenyl)-2-{[2-(3-fluorophenyl)-2-hydroxyethyl]amino}(3-pyridyl))-N-(3-pyridylmethyl)carboxamide |
| 8.662 | M + H | 417.1 | {2-[(2-(2-pyridyl)ethyl)amino]-6-(1,3-thiazol-2-yl)(3-pyridyl)}-N-(3-pyridylmethyl)carboxamide |
| 2.53 | M + H | 414.2 | {6-(1-methylpyrazol-4-yl)-2-[(2-(2-pyridyl)ethyl)amino](3-pyridyl)}-N-(3-pyridylmethyl)carboxamide |
| 39.528 | M + H | 322.1 | [3-(aminomethyl)-6-phenyl(2-pyridyl)][2-(3-fluorophenyl)ethyl]amine |
| 0.534 | M + H | 463.1 | (6-(3,4-difluorophenyl)-2-{[2-(3-fluorophenyl)ethyl]amino}(3-pyridyl))-N-(3-pyridylmethyl)carboxamide |
| 0.28 | M + H | 458.1 | (6-(5-cyano(2-thienyl))-2-{[2-(3-fluorophenyl)ethyl]amino}(3-pyridyl))-N-(3-pyridylmethyl)carboxamide |
| 0.052 | M + H | 461.1 | (2-{[2-(3-fluorophenyl)ethyl]amino}-6-(5-formyl(2-thienyl))(3-pyridyl))-N-(3-pyridylmethyl)carboxamide |
| 0.783 | M + H | 461.1 | (2-{[2-(3-fluorophenyl)ethyl]amino}-6-(3-formyl(2-thienyl))(3-pyridyl))-N-(3-pyridylmethyl)carboxamide |
| 1.482 | M + H | 461.1 | (2-{[2-(3-fluorophenyl)ethyl]amino}-6-(2-formyl(3-thienyl))(3-pyridyl))-N-(3-pyridylmethyl)carboxamide |
| 30.616 | M + H | 699.2 | [2-{[2-(3-fluorophenyl)ethyl]amino}-6-(6-{[2-(3-fluorophenyl)ethyl]amino}-5-[N-(3-pyridylmethyl)carbamoyl](2-pyridyl))(3-pyridyl)]-N-(3-pyridylmethyl)carboxamide |
| 1.567 | M + H | 463.1 | (2-{[2-(3-fluorophenyl)ethyl]amino}-6-[2-(hydroxymethyl)(3-thienyl)](3-pyridyl))-N-(3-pyridylmethyl)carboxamide |
| 49.792 | M + H | 418.1 | (2-{[2-(3-fluorophenyl)ethyl]amino}-6-isoxazol-4-yl(3-pyridyl))-N-(3-pyridylmethyl)carboxamide |
| 0.178 | M + H | 475.1 | (6-(5-acetyl(2-thienyl))-2-{[2-(3-fluorophenyl)ethyl]amino}(3-pyridyl))-N-(3-pyridylmethyl)carboxamide |
| 55.694 | M + H | 462.1 | (6-[3-(aminomethyl)(2-thienyl)]-2-{[2-(3-fluorophenyl)ethyl]amino}(3-pyridyl))-N-(3-pyridylmethyl)carboxamide |
| 0.415 | M + H | 477.1 | (2-{[2-(3-fluorophenyl)ethyl]amino}-6-[5-(hydroxyethyl)(2-thienyl)](3-pyridyl))-N-(3-pyridylmethyl)carboxamide |
| 0.014 | M + H | 458.1 | (6-(4-cyano(3-thienyl))-2-{[2-(3-fluorophenyl)ethyl]amino}(3-pyridyl))-N-(3-pyridylmethyl)carboxamide |
| 2.698 | M + H | 462.1 | (6-[5-(aminomethyl)(2-thienyl)]-2-{[2-(3-fluorophenyl)ethyl]amino}(3-pyridyl))-N-(3-pyridylmethyl)carboxamide |

-continued

| IC50 Arithmetic Mean | Ion | m/z | CHEMICAL NAME |
|---|---|---|---|
| 0.323 | M + H | 481.2 | N-{[5-(aminomethyl)(3-pyridyl)]methyl}(6-(2-cyanophenyl)-2-{[2-(3-fluorophenyl)ethyl]amino}(3-pyridyl))carboxamide |
| 0.081 | M + H | 482.1 | (6-(2-cyanophenyl)-2-{[2-(3-fluorophenyl)ethyl]amino}(3-pyridyl))-N-{[5-(hydroxymethyl)(3-pyridyl)]methyl}carboxamide |
| 2.715 | M + H | 579.2 | N-({5-[3,3-bis(dimethylamino)-2-azaprop-2-enyl](3-pyridyl)}methyl)(6-(2-cyanophenyl)-2-{[2-(3-fluorophenyl)ethyl]amino}(3-pyridyl))carboxamide |
| 0.624 | M + H | 481.1 | N-{[3-(aminomethyl)(2-pyridyl)]methyl}(6-(2-cyanophenyl)-2-{[2-(3-fluorophenyl)ethyl]amino}(3-pyridyl))carboxamide |
| 2.437 | M + H | 824.3 | (6-(2-cyanophenyl)-2-{[2-(3-fluorophenyl)ethyl]amino}(3-pyridyl))-N-[(3-{[(6-(2-cyanophenyl)-2-{[2-(3-fluorophenyl)ethyl]amino}(3-pyridyl))carbonylamino]methyl}(2-pyridyl))methyl]carboxamide |
| 70.994 | M + H | 442.1 | N-[(2-{[2-(3-fluorophenyl)ethyl]amino}-6-phenyl(3-pyridyl))methyl](3-pyridylamino)carboxamide |
| 0.512 | M + H | 486.1 | (5-chloro-6-(2-cyanophenyl)-2-{[2-(3-fluorophenyl)ethyl]amino}(3-pyridyl))-N-(3-pyridylmethyl)carboxamide |
| 2.653 | M + H | 531 | (5-bromo-6-(2-cyanophenyl)-2-{[2-(3-fluorophenyl)ethyl]amino}(3-pyridyl))-N-(3-pyridylmethyl)carboxamide |
| 0.318 | M + H | 477.1 | (5-cyano-6-(2-cyanophenyl)-2-{[2-(3-fluorophenyl)ethyl]amino}(3-pyridyl))-N-(3-pyridylmethyl)carboxamide |
| 0.072 | M + H | 486.1 | N-[(2-chloro(3-pyridyl))methyl](6-(2-cyanophenyl)-2-{[2-(3-fluorophenyl)ethyl]amino}(3-pyridyl))carboxamide |
| 0.013 | M + H | 510.1 | N-({2-[(2-aminoethyl)amino](3-pyridyl)}methyl)(6-(2-cyanophenyl)-2-{[2-(3-fluorophenyl)ethyl]amino}(3-pyridyl))carboxamide |
| 0.088 | M + H | 453.1 | (2-{[2-(3-fluorophenyl)ethyl]amino}-5-oxoindeno[3,2-b]pyridin-3-yl)-N-(3-pyridylmethyl)carboxamide |
| 0.029 | M + H | 472 | (6-(2-cyanophenyl)-2-{[2-(3-fluorophenyl)ethyl]amino}(3-pyridyl))-N-[(6-oxo(2-piperidyl))methyl]carboxamide |
| 0.877 | M + H | 629.2 | N-[(1-{3-[(tert-butoxy)carbonylamino]propyl}-6-oxo(2-piperidyl))methyl](6-(2-cyanophenyl)-2-{[2-(3-fluorophenyl)ethyl]amino}(3-pyridyl))carboxamide |
| 0.025 | M + H | 529.2 | N-{[1-(3-aminopropyl)-6-oxo(2-piperidyl)]methyl}(6-(2-cyanophenyl)-2-{[2-(3-fluorophenyl)ethyl]amino}(3-pyridyl))carboxamide |
| 1.024 | M + H | 458.2 | N-[((2S)(2-piperidyl))methyl](6-(2-cyanophenyl)-2-{[2-(3-fluorophenyl)ethyl]amino}(3-pyridyl))carboxamide |
| 16.979 | M + H | 615.2 | N-[((2S)-1-{2-[(tert-butoxy)carbonylamino]acetyl}(2-piperidyl))methyl](6-(2-cyanophenyl)-2-{[2-(3-fluorophenyl)ethyl]amino}(3-pyridyl))carboxamide |
| 0.074 | M + H | 515.2 | N-{[(2S)-1-(2-aminoacetyl)(2-piperidyl)]methyl}(6-(2-cyanophenyl)-2-{[2-(3-fluorophenyl)ethyl]amino}(3-pyridyl))carboxamide |
| 8.636 | M + H | 629.2 | N-[((2S)-1-{3-[(tert-butoxy)carbonylamino]propanoyl}(2-piperidyl))methyl](6-(2-cyanophenyl)-2-{[2-(3-fluorophenyl)ethyl]amino}(3-pyridyl))carboxamide |
| 0.109 | M + H | 529.2 | N-{[(2S)-1-(3-aminopropanoyl)(2-piperidyl)]methyl}(6-(2-cyanophenyl)-2-{[2-(3-fluorophenyl)ethyl]amino}(3-pyridyl))carboxamide |
| 1.632 | M + H | 536.3 | N-{[(2S)-1-(methylsulfonyl)(2-piperidyl)]methyl}(6-(2-cyanophenyl)-2-{[2-(3-fluorophenyl)ethyl]amino}(3-pyridyl))carboxamide |
| 0.015 | M + H | 472.2 | N-[((2R)-6-oxo(2-piperidyl))methyl](6-(2-cyanophenyl)-2-{[2-(3-fluorophenyl)ethyl]amino}(3-pyridyl))carboxamide |
| 0.392 | M + H | 629.4 | N-[((2R)-1-{3-[(tert-butoxy)carbonylamino]propyl}-6-oxo(2-piperidyl))methyl](6-(2-cyanophenyl)-2-{[2-(3-fluorophenyl)ethyl]amino}(3-pyridyl))carboxamide |
| 0.026 | M + H | 529.2 | N-{[(2R)-1-(3-aminopropyl)-6-oxo(2-piperidyl)]methyl}(6-(2-cyanophenyl)-2-{[2-(3-fluorophenyl)ethyl]amino}(3-pyridyl))carboxamide |
| 1.974 | M + H | 458.1 | N-[((3S)(3-piperidyl))methyl](6-(2-cyanophenyl)-2-{[2-(3-fluorophenyl)ethyl]amino}(3-pyridyl))carboxamide |

-continued

| IC50 Arithmetic Mean | Ion | m/z | CHEMICAL NAME |
|---|---|---|---|
| 0.696 | M + H | 500.3 | N-[((3R)-1-acetyl(3-piperidyl))methyl](6-(2-cyanophenyl)-2-{[2-(3-fluorophenyl)ethyl]amino}(3-pyridyl))carboxamide |
| 0.718 | M + H | 516.3 | methyl (3R)-3-{[(6-(2-cyanophenyl)-2-{[2-(3-fluorophenyl)ethyl]amino}(3-pyridyl))carbonylamino]methyl}piperidinecarboxylate |
| 0.199 | M + H | 615.4 | N-[((3R)-1-{2-[(tert-butoxy)carbonylamino]acetyl}(3-piperidyl))methyl](6-(2-cyanophenyl)-2-{[2-(3-fluorophenyl)ethyl]amino}(3-pyridyl))carboxamide |
| 3.79 | M + H | 629.4 | N-[((3R)-1-{3-[(tert-butoxy)carbonylamino]propanoyl}(3-piperidyl))methyl](6-(2-cyanophenyl)-2-{[2-(3-fluorophenyl)ethyl]amino}(3-pyridyl))carboxamide |
| 6.161 | M + H | 643.4 | N-[((3R)-1-{4-[(tert-butoxy)carbonylamino]butanoyl}(3-piperidyl))methyl](6-(2-cyanophenyl)-2-{[2-(3-fluorophenyl)ethyl]amino}(3-pyridyl))carboxamide |
| 0.246 | M + H | 615.4 | N-{[(3R)-1-(2-aminoacetyl)(3-piperidyl)]methyl}(6-(2-cyanophenyl)-2-{[2-(3-fluorophenyl)ethyl]amino}(3-pyridyl))carboxamide |
| 0.173 | M + H | 629.5 | N-{[(3R)-1-(3-aminopropanoyl)(3-piperidyl)]methyl}(6-(2-cyanophenyl)-2-{[2-(3-fluorophenyl)ethyl]amino}(3-pyridyl))carboxamide |
| 0.512 | M + H | 543.3 | N-{[(3R)-1-(4-aminobutanoyl)(3-piperidyl)]methyl}(6-(2-cyanophenyl)-2-{[2-(3-fluorophenyl)ethyl]amino}(3-pyridyl))carboxamide |
| 0.791 | M + H | 673.3 | N-({(2R)-1-[4-(1,3-dioxobenzo[c]azolin-2-yl)butyl]-6-oxo(2-piperidyl)}methyl)(6-(2-cyanophenyl)-2-{[2-(3-fluorophenyl)ethyl]amino}(3-pyridyl))carboxamide |
| 0.032 | M + H | 543.2 | N-{[(2R)-1-(4-aminobutyl)-6-oxo(2-piperidyl)]methyl}(6-(2-cyanophenyl)-2-{[2-(3-fluorophenyl)ethyl]amino}(3-pyridyl))carboxamide |
| 5.537 | M + H | 523.2 | N-[((3S,4S,2R,5R)-3,4,5,6-tetrahydroxy(2H-3,4,5,6-tetrahydropyran-2-yl))methyl](6-(2-cyanophenyl)-2-{[2-(3-fluorophenyl)ethyl]amino}(3-pyridyl))carboxamide |
| 13.202 | M + H | 533.2 | 2-[5-(N-{[(2R)-1-(3-aminopropyl)-5-oxopyrrolidin-2-yl]methyl}carbamoyl)-6-{[2-(3-fluorophenyl)ethyl]amino}-2-pyridyl]benzamide |
| 3.262 | M + H | 615.2 | N-[2-((2R)-2-{[(6-(2-cyanophenyl)-2-{[2-(3-fluorophenyl)ethyl]amino}(3-pyridyl))carbonylamino]methyl}pyrrolidinyl)(1S)-1-methyl-2-oxoethyl](tert-butoxy)carboxamide |
| 0.053 | M + H | 515.2 | N-{[(2R)-1-((2S)-2-aminopropanoyl)pyrrolidin-2-yl]methyl}(6-(2-cyanophenyl)-2-{[2-(3-fluorophenyl)ethyl]amino}(3-pyridyl))carboxamide |
| 3.94 | M + H | 615.2 | N-[(1R)-2-((2R)-2-{[(6-(2-cyanophenyl)-2-{[2-(3-fluorophenyl)ethyl]amino}(3-pyridyl))carbonylamino]methyl}pyrrolidinyl)-1-methyl-2-oxoethyl](tert-butoxy)carboxamide |
| 0.166 | M + H | 515.2 | N-{[(2R)-1-((2R)-2-aminopropanoyl)pyrrolidin-2-yl]methyl}(6-(2-cyanophenyl)-2-{[2-(3-fluorophenyl)ethyl]amino}(3-pyridyl))carboxamide |
| 0.052 | M + H | 558.2 | N-{[(2R)-1-((2S)-2,5-diaminopentanoyl)pyrrolidin-2-yl]methyl}(6-(2-cyanophenyl)-2-{[2-(3-fluorophenyl)ethyl]amino}(3-pyridyl))carboxamide |
| 0.046 | M + H | 451.1 | N-[(2-chloro(3-pyridyl))methyl](2-{[2-(3-fluorophenyl)ethyl]amino}-6-(1-methylpyrazol-4-yl)(3-pyridyl))carboxamide |
| 0.129 | M + H | 489.2 | N-({2-[(3-aminopropyl)amino](3-pyridyl)}methyl)(2-{[2-(3-fluorophenyl)ethyl]amino}-6-pyrazol-4-yl(3-pyridyl))carboxamide |
| 0.122 | M + H | 475.1 | N-({2-[(2-aminoethyl)amino](3-pyridyl)}methyl)(2-{[2-(3-fluorophenyl)ethyl]amino}-6-pyrazol-4-yl(3-pyridyl))carboxamide |
| 1.459 | M + H | 541.3 | tert-butyl (2R)-2-{[(5-fluoro-2-{[2-(3-fluorophenyl)ethyl]amino}-6-(1-methylpyrazol-4-yl)(3-pyridyl))carbonylamino]methyl}pyrrolidinecarboxylate |
| 0.275 | M + H | 441.1 | N-[((2R)pyrrolidin-2-yl)methyl](5-fluoro-2-{[2-(3-fluorophenyl)ethyl]amino}-6-(1-methylpyrazol-4-yl)(3-pyridyl))carboxamide |

-continued

| IC50 Arithmetic Mean | Ion | m/z | CHEMICAL NAME |
| --- | --- | --- | --- |
| 0.625 | M + H | 598.3 | N-[((2R)-1-{2-[(tert-butoxy)carbonylamino]acetyl}pyrrolidin-2-yl)methyl](5-fluoro-2-{[2-(3-fluorophenyl)ethyl]amino}-6-(1-methylpyrazol-4-yl)(3-pyridyl))carboxamide |
| 0.065 | M + H | 476.1 | (2-{[2-(3-fluorophenyl)ethyl]amino}-6-pyrazol-4-yl(3-pyridyl))-N-({2-[(2-hydroxyethyl)amino](3-pyridyl)}methyl)carboxamide |
| 0.488 | M + H | 564.2 | N-[(2-{[(tert-butoxy)carbonylamino]methyl}(3-pyridyl))methyl](5-fluoro-2-{[2-(3-fluorophenyl)ethyl]amino}-6-pyrazol-4-yl(3-pyridyl))carboxamide |
| 0.012 | M + H | 464.1 | N-{[2-(aminomethyl)(3-pyridyl)]methyl}(5-fluoro-2-{[2-(3-fluorophenyl)ethyl]amino}-6-pyrazol-4-yl(3-pyridyl))carboxamide |
| 1.079 | M + H | 584.2 | N-[((2R)-1-{2-[(tert-butoxy)carbonylamino]acetyl}pyrrolidin-2-yl)methyl](5-fluoro-2-{[2-(3-fluorophenyl)ethyl]amino}-6-pyrazol-4-yl(3-pyridyl))carboxamide |
| 0.061 | M + H | 484.1 | N-{[(2R)-1-(2-aminoacetyl)pyrrolidin-2-yl]methyl}(5-fluoro-2-{[2-(3-fluorophenyl)ethyl]amino}-6-pyrazol-4-yl(3-pyridyl))carboxamide |
| 0.98 | M + H | 598.3 | N-[((2R)-1-{3-[(tert-butoxy)carbonylamino]propanoyl}pyrrolidin-2-yl)methyl](5-fluoro-2-{[2-(3-fluorophenyl)ethyl]amino}-6-pyrazol-4-yl(3-pyridyl))carboxamide |
| 0.09 | M + H | 498.2 | N-{[(2R)-1-(3-aminopropanoyl)pyrrolidin-2-yl]methyl}(5-fluoro-2-{[2-(3-fluorophenyl)ethyl]amino}-6-pyrazol-4-yl(3-pyridyl))carboxamide |
| 0.75 | M + H | 612.2 | N-[((2R)-1-{4-[(tert-butoxy)carbonylamino]butanoyl}pyrrolidin-2-yl)methyl](5-fluoro-2-{[2-(3-fluorophenyl)ethyl]amino}-6-pyrazol-4-yl(3-pyridyl))carboxamide |
| 0.047 | M + H | 512.2 | N-{[(2R)-1-(4-aminobutanoyl)pyrrolidin-2-yl]methyl}(5-fluoro-2-{[2-(3-fluorophenyl)ethyl]amino}-6-pyrazol-4-yl(3-pyridyl))carboxamide |
| 0.394 | M + H | 427.1 | N-[((2R)pyrrolidin-2-yl)methyl](5-fluoro-2-{[2-(3-fluorophenyl)ethyl]amino}-6-pyrazol-4-yl(3-pyridyl))carboxamide |
| 0.354 | M + H | 598.2 | N-[((2R)-1-{3-[(tert-butoxy)carbonylamino]propyl}-5-oxopyrrolidin-2-yl)methyl](5-fluoro-2-{[2-(3-fluorophenyl)ethyl]amino}-6-pyrazol-4-yl(3-pyridyl))carboxamide |
| 0.066 | M + H | 498.1 | N-{[(2R)-1-(3-aminopropyl)-5-oxopyrrolidin-2-yl]methyl}(5-fluoro-2-{[2-(3-fluorophenyl)ethyl]amino}-6-pyrazol-4-yl(3-pyridyl))carboxamide |
| 0.14 | M + H | 401.1 | N-(carbamoylmethyl)(5-fluoro-2-{[2-(3-fluorophenyl)ethyl]amino}-6-pyrazol-4-yl(3-pyridyl))carboxamide |
| 0.065 | M + H | 415 | 2-[(5-fluoro-2-{[2-(3-fluorophenyl)ethyl]amino}-6-pyrazol-4-yl(3-pyridyl))carbonylamino]-N-methylacetamide |
| 1.001 | M + H | 614.3 | N-[((2R)-1-{(2S)-2-[(tert-butoxy)carbonylamino]-3-hydroxypropanoyl}pyrrolidin-2-yl)methyl](5-fluoro-2-{[2-(3-fluorophenyl)ethyl]amino}-6-pyrazol-4-yl(3-pyridyl))carboxamide |
| 0.059 | M + H | 514.1 | N-{[(2R)-1-((2S)-2-amino-3-hydroxypropanoyl)pyrrolidin-2-yl]methyl}(5-fluoro-2-{[2-(3-fluorophenyl)ethyl]amino}-6-pyrazol-4-yl(3-pyridyl))carboxamide |
| 3.665 | M + H | 575.2 | N-[(2-{[(tert-butoxy)carbonylamino]methyl}(3-pyridyl))methyl](5-fluoro-2-{[2-(3-fluorophenyl)ethyl]amino}-6-(2-pyridyl)(3-pyridyl))carboxamide |
| 0.066 | M + H | 475.1 | N-{[2-(aminomethyl)(3-pyridyl)]methyl}(5-fluoro-2-{[2-(3-fluorophenyl)ethyl]amino}-6-(2-pyridyl)(3-pyridyl))carboxamide |
| 0.381 | M + H | 430.1 | (5-fluoro-2-{[2-(3-fluorophenyl)ethyl]amino}-6-(1-methylpyrazol-4-yl)(3-pyridyl))-N-(2-hydroxy-2-methylpropyl)carboxamide |

-continued

| IC50 Arithmetic Mean | Ion | m/z | CHEMICAL NAME |
|---|---|---|---|
| 0.224 | M + H | 444.1 | (5-fluoro-2-{[2-(3-fluorophenyl)ethyl]amino}-6-(1-methylpyrazol-4-yl)(3-pyridyl))-N-(3-hydroxy-2,2-dimethylpropyl)carboxamide |
| 0.109 | M + H | 442.2 | N-((2R)-2-methyl-3-oxobutyl)(5-fluoro-2-{[2-(3-fluorophenyl)ethyl]amino}-6-(1-methylpyrazol-4-yl)(3-pyridyl))carboxamide |
| 1.225 | M + H | 458.1 | N-((2R)-3-hydroxy-2,3-dimethylbutyl)(5-fluoro-2-{[2-(3-fluorophenyl)ethyl]amino}-6-(1-methylpyrazol-4-yl)(3-pyridyl))carboxamide |
| 0.191 | M + H | 642.2 | 2-((2R)-2-{[(5-fluoro-2-{[2-(3-fluorophenyl)ethyl]amino}-6-(1-methylpyrazol-4-yl)(3-pyridyl))carbonylamino]methyl}azetidinyl)-2-oxoethyl 2-[(tert-butoxy)carbonylamino]acetate |
| 0.045 | M + H | 542.2 | 2-((2R)-2-{[(5-fluoro-2-{[2-(3-fluorophenyl)ethyl]amino}-6-(1-methylpyrazol-4-yl)(3-pyridyl))carbonylamino]methyl}azetidinyl)-2-oxoethyl 2-aminoacetate |
| 0.4 | M + H | 593.2 | 2-((2R)-2-{[(5-fluoro-2-{[2-(3-fluorophenyl)ethyl]amino}-6-(1-methylpyrazol-4-yl)(3-pyridyl))carbonylamino]methyl}azetidinyl)-2-oxoethyl dimethyl phosphate |
| 0.041 | M + H | 463.1 | (2-{[2-(3-fluorophenyl)ethyl]amino}-6-[5-(hydroxymethyl)(2-thienyl)](3-pyridyl))-N-(3-pyridylmethyl)carboxamide |
| 0.017 | M + H |  | N-({2-[(3-aminopropyl)amino](3-pyridyl)}methyl)(6-(2-cyanophenyl)-2-{[2-(3-fluorophenyl)ethyl]amino}(3-pyridyl))carboxamide |
| 0.018 | M + H |  | (5-fluoro-2-{[2-(3-fluorophenyl)ethyl]amino}-6-pyrazol-4-yl(3-pyridyl))-N-(3-pyridylmethyl)carboxamide |
| 0.066 | M + H |  | N-{[(2R)-1-(2-aminoacetyl)pyrrolidin-2-yl]methyl}(5-fluoro-2-{[2-(3-fluorophenyl)ethyl]amino}-6-(1-methylpyrazol-4-yl)(3-pyridyl))carboxamide |
| 1.076 | M + H | 466.2 | (6-(2-cyanophenyl)-2-{[2-(3-fluorophenyl)ethyl]amino}-4-methyl(3-pyridyl))-N-(3-pyridylmethyl)carboxamide |
| 16.894 | M + H | 537.2 | (6-(2-cyanophenyl)-2-{[2-(3-fluorophenyl)ethyl]amino}(3-pyridyl))-N-[(6-morpholin-4-yl(3-pyridyl))methyl]carboxamide |
| 66.631 | M + H | 521.2 | (6-(2-cyanophenyl)-2-{[2-(3-fluorophenyl)ethyl]amino}(3-pyridyl))-N-[(6-pyrrolidinyl(3-pyridyl))methyl]carboxamide |
| 1.752 | M + H | 536.2 | (6-(2-cyanophenyl)-2-{[2-(3-fluorophenyl)ethyl]amino}(3-pyridyl))-N-[(6-piperazinyl(3-pyridyl))methyl]carboxamide |
| 7.747 | M + H | 578.2 | N-{[6-(4-acetylpiperazinyl)(3-pyridyl)]methyl}(6-(2-cyanophenyl)-2-{[2-(3-fluorophenyl)ethyl]amino}(3-pyridyl))carboxamide |
| 0.233 | M + H | 530.1 | N-[(6-bromo(2-pyridyl))methyl](6-(2-cyanophenyl)-2-{[2-(3-fluorophenyl)ethyl]amino}(3-pyridyl))carboxamide |
| 0.254 | M + H | 443.1 | 2-[(2-{[2-(3-fluorophenyl)ethyl]amino}-6-[5-(hydroxymethyl)(2-thienyl)](3-pyridyl))carbonylamino]-N-methylacetamide |
| 0.549 | M + H | 443.1 | N-(2-carbamoylethyl)(2-{[2-(3-fluorophenyl)ethyl]amino}-6-[5-(hydroxymethyl)(2-thienyl)](3-pyridyl))carboxamide |
| 0.045 | M + H | 463.1 | (2-{[2-(3-fluorophenyl)ethyl]amino}-6-[5-(hydroxymethyl)(2-thienyl)](3-pyridyl))-N-(2-pyridylmethyl)carboxamide |
| 0.496 | M + H | 429.1 | N-(carbamoylmethyl)(2-{[2-(3-fluorophenyl)ethyl]amino}-6-[5-(hydroxymethyl)(2-thienyl)](3-pyridyl))carboxamide |
| 24.88 | M + H | 496.1 | 2-[(6-(2-cyanophenyl)-2-{[2-(3-fluorophenyl)ethyl]amino}(3-pyridyl))carbonylamino]-N-(methylsulfonyl)acetamide |
| 0.352 | M + H | 486.2 | N-{[3-(aminomethyl)cyclohexyl]methyl}(6-(2-cyanophenyl)-2-{[2-(3-fluorophenyl)ethyl]amino}(3-pyridyl))carboxamide |
| 11.631 | M + H | 472.1 | 3-[(6-(2-cyanophenyl)-2-{[2-(3-fluorophenyl)ethyl]amino}-3-pyridyl)carbonylamino]cyclopentanecarboxamide |
| 16.178 | M + H | 473.2 | (6-(2-cyanophenyl)-2-{[2-(3-fluorophenyl)ethyl]amino}(3-pyridyl))-N-(2-piperazinylethyl)carboxamide |

-continued

| IC50 Arithmetic Mean | Ion | m/z | CHEMICAL NAME |
|---|---|---|---|
| 0.266 | M + H | 467.1 | (6-(2-cyanophenyl)-2-{[2-(3-fluorophenyl)ethyl]amino}(3-pyridyl))-N-(2-pyrazin-2-ylethyl)carboxamide |
| 0.026 | M + H | 453.1 | (6-(2-cyanophenyl)-2-{[2-(3-fluorophenyl)ethyl]amino}(3-pyridyl))-N-(pyrazin-2-ylmethyl)carboxamide |
| 4.421 | M + H | 489.1 | N-((1S)-5-amino-1-carbamoylpentyl)(6-(2-cyanophenyl)-2-{[2-(3-fluorophenyl)ethyl]amino}(3-pyridyl))carboxamide |
| 1.906 | M + H | 461.1 | N-(3-amino-1-carbamoylpropyl)(6-(2-cyanophenyl)-2-{[2-(3-fluorophenyl)ethyl]amino}(3-pyridyl))carboxamide |
| 58.8 | M + H | 623.2 | N-{(1R)-1-carbamoyl-5-[(phenylmethoxy)carbonylamino]pentyl}(6-(2-cyanophenyl)-2-{[2-(3-fluorophenyl)ethyl]amino}(3-pyridyl))carboxamide |
| 0.59 | M + H | 475.1 | N-(4-amino-1-carbamoylbutyl)(6-(2-cyanophenyl)-2-{[2-(3-fluorophenyl)ethyl]amino}(3-pyridyl))carboxamide |
| 1.28 | M + H | 489.1 | N-((1R)-5-amino-1-carbamoylpentyl)(6-(2-cyanophenyl)-2-{[2-(3-fluorophenyl)ethyl]amino}(3-pyridyl))carboxamide |
| 0.007 | M + H | 510.1 | N-({6-[(2-aminoethyl)amino](2-pyridyl)}methyl)(6-(2-cyanophenyl)-2-{[2-(3-fluorophenyl)ethyl]amino}(3-pyridyl))carboxamide |
| 0.005 | M + H | 524.2 | N-({6-[(3-aminopropyl)amino](2-pyridyl)}methyl)(6-(2-cyanophenyl)-2-{[2-(3-fluorophenyl)ethyl]amino}(3-pyridyl))carboxamide |
| 19.6 | M + H | 609.1 | N-{(4R)-4-carbamoyl-4-[(6-(2-cyanophenyl)-2-{[2-(3-fluorophenyl)ethyl]amino}(3-pyridyl))carbonylamino]butyl}(phenylmethoxy)carboxamide |
| 5.404 | M + H | 475.1 | N-((1S)-4-amino-1-carbamoylbutyl)(6-(2-cyanophenyl)-2-{[2-(3-fluorophenyl)ethyl]amino}(3-pyridyl))carboxamide |
| 7.413 | M + H | 475.1 | N-((1R)-4-amino-1-carbamoylbutyl)(6-(2-cyanophenyl)-2-{[2-(3-fluorophenyl)ethyl]amino}(3-pyridyl))carboxamide |
| 0.963 | M + H | 444.1 | (6-(2-cyanophenyl)-2-{[2-(3-fluorophenyl)ethyl]amino}(3-pyridyl))-N-(pyrrolidin-3-ylmethyl)carboxamide |
| 0.203 | M + H | 501.1 | N-{[1-(2-aminoacetyl)pyrrolidin-3-yl]methyl}(6-(2-cyanophenyl)-2-{[2-(3-fluorophenyl)ethyl]amino}(3-pyridyl))carboxamide |
| 0.27 | M + H | 515.1 | N-{[1-(3-aminopropanoyl)pyrrolidin-3-yl]methyl}(6-(2-cyanophenyl)-2-{[2-(3-fluorophenyl)ethyl]amino}(3-pyridyl))carboxamide |
| 0.433 | M + H | 529.1 | N-{[1-(4-aminobutanoyl)pyrrolidin-3-yl]methyl}(6-(2-cyanophenyl)-2-{[2-(3-fluorophenyl)ethyl]amino}(3-pyridyl))carboxamide |
| 0.334 | M + H | 486.1 | N-[(1-acetylpyrrolidin-3-yl)methyl](6-(2-cyanophenyl)-2-{[2-(3-fluorophenyl)ethyl]amino}(3-pyridyl))carboxamide |
| 4.787 | M + H | 501.2 | N-{[1-(3-aminopropyl)pyrrolidin-3-yl]methyl}(6-(2-cyanophenyl)-2-{[2-(3-fluorophenyl)ethyl]amino}(3-pyridyl))carboxamide |
| 6.654 | M + H | 460.5 | N-(3-amino-2-carbamoylpropyl)(6-(2-cyanophenyl)-2-{[2-(3-fluorophenyl)ethyl]amino}(3-pyridyl))carboxamide |
| 1.236 | M + H | 452.3 | (2-{[2-(3-fluorophenyl)ethyl]amino}-6-(1-methylpyrazol-4-yl)(3-pyridyl))-N-[(6-oxopiperazin-2-yl)methyl]carboxamide |
| 0.973 | M + H | 438.3 | (2-{[2-(3-fluorophenyl)ethyl]amino}-6-pyrazol-4-yl(3-pyridyl))-N-[(6-oxopiperazin-2-yl)methyl]carboxamide |
| 6.954 | M + H | 438.3 | (2-{[2-(3-fluorophenyl)ethyl]amino}-6-pyrazol-5-yl(3-pyridyl))-N-[(6-oxopiperazin-2-yl)methyl]carboxamide |
| 2.565 | M + H | 551.1 | (6-(2-cyanophenyl)-2-{[2-(3-fluorophenyl)ethyl]amino}(3-pyridyl))-N-{[4-(methylsulfonyl)-6-oxopiperazin-2-yl]methyl}carboxamide |
| 1.635 | M + H | 515.1 | N-[(4-acetyl-6-oxopiperazin-2-yl)methyl](6-(2-cyanophenyl)-2-{[2-(3-fluorophenyl)ethyl]amino}(3-pyridyl))carboxamide |

| IC50 Arithmetic Mean | Ion | m/z | CHEMICAL NAME |
|---|---|---|---|
| 0.037 | M + H | 487.1 | (6-(2-cyanophenyl)-2-{[2-(3-fluorophenyl)ethyl]amino}(3-pyridyl))-N-[(4-methyl-6-oxopiperazin-2-yl)methyl]carboxamide |
| 0.866 | M + H | 461.2 | (6-(2-cyanophenyl)-2-{[2-(3-fluorophenyl)ethyl]amino}(3-pyridyl))-N-{2-[(methylamino)carbonylamino]ethyl}carboxamide |
| 1.548 | M + H | 511.2 | N-(2-{[(2-aminoethyl)sulfonyl]amino}ethyl)(6-(2-cyanophenyl)-2-{[2-(3-fluorophenyl)ethyl]amino}(3-pyridyl))carboxamide |
| 4.569 | M + H | 444.2 | N-[((2S)pyrrolidin-2-yl)methyl](6-(2-cyanophenyl)-2-{[2-(3-fluorophenyl)ethyl]amino}(3-pyridyl))carboxamide |
| 1.23 | M + H | 461.2 | 2-amino-N-{2-[(6-(2-cyanophenyl)-2-{[2-(3-fluorophenyl)ethyl]amino}(3-pyridyl))carbonylamino]ethyl}acetamide |
| 4.325 | M + H | 475.2 | 3-amino-N-{2-[(6-(2-cyanophenyl)-2-{[2-(3-fluorophenyl)ethyl]amino}(3-pyridyl))carbonylamino]ethyl}propanamide |
| 1.265 | M + H | 489.2 | 4-amino-N-{2-[(6-(2-cyanophenyl)-2-{[2-(3-fluorophenyl)ethyl]amino}(3-pyridyl))carbonylamino]ethyl}butanamide |
| 15.303 | M + H | 575.3 | 2-[(tert-butoxy)carbonylamino]-N-{2-[(6-(2-cyanophenyl)-2-{[2-(3-fluorophenyl)ethyl]amino}(3-pyridyl))carbonylamino]ethyl}-N-methylacetamide |
| 3.883 | M + H | 603.3 | 4-[(tert-butoxy)carbonylamino]-N-{2-[(6-(2-cyanophenyl)-2-{[2-(3-fluorophenyl)ethyl]amino}(3-pyridyl))carbonylamino]ethyl}-N-methylbutanamide |
| 0.995 | M + H | 501.2 | N-{[(2S)-1-(2-aminoacetyl)pyrrolidin-2-yl]methyl}(6-(2-cyanophenyl)-2-{[2-(3-fluorophenyl)ethyl]amino}(3-pyridyl))carboxamide |
| 1.856 | M + H | 515.2 | N-{[(2S)-1-(3-aminopropanoyl)pyrrolidin-2-yl]methyl}(6-(2-cyanophenyl)-2-{[2-(3-fluorophenyl)ethyl]amino}(3-pyridyl))carboxamide |
| 1.27 | M + H | 529.3 | N-{[(2S)-1-(4-aminobutanoyl)pyrrolidin-2-yl]methyl}(6-(2-cyanophenyl)-2-{[2-(3-fluorophenyl)ethyl]amino}(3-pyridyl))carboxamide |
| 1.374 | M + H | 475.2 | 2-amino-N-{2-[(6-(2-cyanophenyl)-2-{[2-(3-fluorophenyl)ethyl]amino}(3-pyridyl))carbonylamino]ethyl}-N-methylacetamide |
| 1.775 | M + H | 489.2 | 3-amino-N-{2-[(6-(2-cyanophenyl)-2-{[2-(3-fluorophenyl)ethyl]amino}(3-pyridyl))carbonylamino]ethyl}-N-methylpropanamide |
| 1.2 | M + H | 503.2 | 4-amino-N-{2-[(6-(2-cyanophenyl)-2-{[2-(3-fluorophenyl)ethyl]amino}(3-pyridyl))carbonylamino]ethyl}-N-methylbutanamide |
| 1.385 | M + H | 496.2 | (6-(2-cyanophenyl)-2-{[2-(3-fluorophenyl)ethyl]amino}(3-pyridyl))-N-{2-[methyl(methylsulfonyl)amino]ethyl}carboxamide |
| 13.725 | M + H | 504.2 | 3-amino-N-(2-aminoethyl)-2-{[(6-(2-cyanophenyl)-2-{[2-(3-fluorophenyl)ethyl]amino}(3-pyridyl))carbonylamino]methyl}propanamide |
| 0.151 | M + H | 460.2 | N-(2-carbonylamino-2-methylpropyl)(6-(2-cyanophenyl)-2-{[2-(3-fluorophenyl)ethyl]amino}(3-pyridyl))carboxamide |
| 1.588 | M + H | 434.3 | N-((2S)-2-amino-3-hydroxypropyl)(6-(2-cyanophenyl)-2-{[2-(3-fluorophenyl)ethyl]amino}(3-pyridyl))carboxamide |
| 0.249 | M + H | 491.1 | N-((1S)-1-{[(6-(2-cyanophenyl)-2-{[2-(3-fluorophenyl)ethyl]amino}(3-pyridyl))carbonylamino]methyl}-2-hydroxyethyl)-2-aminoacetamide |
| 5.705 | M + H | 548.3 | (2S)-2-(2-aminoacetylamino)-3-[(6-(2-cyanophenyl)-2-{[2-(3-fluorophenyl)ethyl]amino}(3-pyridyl))carbonylamino]propyl 2-aminoacetate |
| 0.441 | M + H | 504.2 | N-((1R)-1-{[(6-(2-cyanophenyl)-2-{[2-(3-fluorophenyl)ethyl]amino}(3-pyridyl))carbonylamino]methyl}-2-methylpropyl)-2-hydroxyacetamide |
| 0.939 | M + H | 503.3 | N-((1R)-1-{[(6-(2-cyanophenyl)-2-{[2-(3-fluorophenyl)ethyl]amino}(3-pyridyl))carbonylamino]methyl}-2-methylpropyl)-2-aminoacetamide |
| 1.237 | M + H | 460.3 | N-((2R)-2-amino-4-methylpentyl)(6-(2-cyanophenyl)-2-{[2-(3-fluorophenyl)ethyl]amino}(3-pyridyl))carboxamide |

-continued

| IC50 Arithmetic Mean | Ion | m/z | CHEMICAL NAME |
|---|---|---|---|
| 1.169 | M + H | 518.2 | N-((1R)-1-{[(6-(2-cyanophenyl)-2-{[2-(3-fluorophenyl)ethyl]amino}(3-pyridyl))carbonylamino]methyl}-3-methylbutyl)-2-hydroxyacetamide |
| 0.913 | M + H | 517.2 | N-((1R)-1-{[(6-(2-cyanophenyl)-2-{[2-(3-fluorophenyl)ethyl]amino}(3-pyridyl))carbonylamino]methyl}-3-methylbutyl)-2-aminoacetamide |
| 12.554 | M + H | 490.2 | N-((1R)-2-amino-1-{[(6-(2-cyanophenyl)-2-{[2-(3-fluorophenyl)ethyl]amino}(3-pyridyl))carbonylamino]methyl}ethyl)-2-aminoacetamide |
| 10.561 | M + H | 491.2 | N-((1R)-2-amino-1-{[(6-(2-cyanophenyl)-2-{[2-(3-fluorophenyl)ethyl]amino}(3-pyridyl))carbonylamino]methyl}ethyl)-2-hydroxyacetamide |
| 0.352 | M + H | 458.3 | N-((3R)-2-oxo(3-piperidyl))(6-(2-cyanophenyl)-2-{[2-(3-fluorophenyl)ethyl]amino}(3-pyridyl))carboxamide |
| 17.307 | M + H | 423.1 | {2-[((2R)-2-phenylpropyl)amino]-6-phenyl(3-pyridyl)}-N-(3-pyridylmethyl)carboxamide |
| 0.564 | M + H | 432.1 | N-(carbamoylethyl)(6-(2-cyanophenyl)-2-{[2-(3-fluorophenyl)ethyl]amino}(3-pyridyl))carboxamide |
| 0.532 | M + H | 432.1 | N-((1R)-1-carbamoylethyl)(6-(2-cyanophenyl)-2-{[2-(3-fluorophenyl)ethyl]amino}(3-pyridyl))carboxamide |
| 6.98 | M + H | 447.1 | methyl (2S)-2-[(6-(2-cyanophenyl)-2-{[2-(3-fluorophenyl)ethyl]amino}(3-pyridyl))carbonylamino]propanoate |
| 0.743 | M + H | 447.1 | methyl (2R)-2-[(6-(2-cyanophenyl)-2-{[2-(3-fluorophenyl)ethyl]amino}(3-pyridyl))carbonylamino]propanoate |
| 0.101 | M + H | 433.1 | methyl 2-[(6-(2-cyanophenyl)-2-{[2-(3-fluorophenyl)ethyl]amino}-3-pyridyl)carbonylamino]acetate |
| 1.083 | M + H | 405.1 | (6-(2-cyanophenyl)-2-{[2-(3-fluorophenyl)ethyl]amino}(3-pyridyl))-N-(2-hydroxyethyl)carboxamide |
| 0.238 | M + H | 419.1 | (6-(2-cyanophenyl)-2-{[2-(3-fluorophenyl)ethyl]amino}(3-pyridyl))-N-(2-methoxyethyl)carboxamide |
| 4.222 | M + H | 432.1 | N-[2-(dimethylamino)ethyl](6-(2-cyanophenyl)-2-{[2-(3-fluorophenyl)ethyl]amino}(3-pyridyl))carboxamide |
| 42.246 | M + H | 518.1 | N-{2-[(tert-butoxy)-N-methylcarbonylamino]ethyl}(6-(2-cyanophenyl)-2-{[2-(3-fluorophenyl)ethyl]amino}(3-pyridyl))carboxamide |
| 4.455 | M + H | 418.1 | (6-(2-cyanophenyl)-2-{[2-(3-fluorophenyl)ethyl]amino}(3-pyridyl))-N-[2-(methylamino)ethyl]carboxamide |
| 0.994 | M + H | 418.1 | N-(3-aminopropyl)(6-(2-cyanophenyl)-2-{[2-(3-fluorophenyl)ethyl]amino}(3-pyridyl))carboxamide |
| 0.985 | M + H | 446.1 | (2S)-2-[(6-(2-cyanophenyl)-2-{[2-(3-fluorophenyl)ethyl]amino}(3-pyridyl))carbonylamino]-N-methylpropanamide |
| 1.273 | M + H | 446.1 | (2R)-2-[(6-(2-cyanophenyl)-2-{[2-(3-fluorophenyl)ethyl]amino}(3-pyridyl))carbonylamino]-N-methylpropanamide |
| 0.958 | M + H | 446.1 | N-{2-[(6-(2-cyanophenyl)-2-{[2-(3-fluorophenyl)ethyl]amino}-3-pyridyl)carbonylamino]ethyl}acetamide |
| 1.118 | M + H | 462.1 | (6-(2-cyanophenyl)-2-{[2-(3-fluorophenyl)ethyl]amino}(3-pyridyl))-N-[2-(methoxycarbonylamino)ethyl]carboxamide |
| 0.326 | M + H | 482.1 | (6-(2-cyanophenyl)-2-{[2-(3-fluorophenyl)ethyl]amino}(3-pyridyl))-N-{2-[(methylsulfonyl)amino]ethyl}carboxamide |
| 4.792 | M + H | 461.1 | ethyl 3-[(6-(2-cyanophenyl)-2-{[2-(3-fluorophenyl)ethyl]amino}-3-pyridyl)carbonylamino]propanoate |
| 0.713 | M + H | 461.1 | methyl 4-[(6-(2-cyanophenyl)-2-{[2-(3-fluorophenyl)ethyl]amino}-3-pyridyl)carbonylamino]butanoate |
| 0.34 | M + H | 446.1 | 3-[(6-(2-cyanophenyl)-2-{[2-(3-fluorophenyl)ethyl]amino}-3-pyridyl)carbonylamino]-N-methylpropanamide |
| 2.956 | M + H | 460.1 | 4-[(6-(2-cyanophenyl)-2-{[2-(3-fluorophenyl)ethyl]amino}(3-pyridyl))carbonylamino]-N-methylbutanamide |

-continued

| IC50 Arithmetic Mean | Ion | m/z | CHEMICAL NAME |
|---|---|---|---|
| 0.185 | M + H | 446.1 | N-(3-carbamoylpropyl)(6-(2-cyanophenyl)-2-{[2-(3-fluorophenyl)ethyl]amino}(3-pyridyl))carboxamide |
| 0.627 | M + H | 447.1 | 4-[(6-(2-cyanophenyl)-2-{[2-(3-fluorophenyl)ethyl]amino}-3-pyridyl)carbonylamino]butanoic acid |
| 2.637 | M + H | 404.1 | N-(2-aminoethyl)(6-(2-cyanophenyl)-2-{[2-(3-fluorophenyl)ethyl]amino}(3-pyridyl))carboxamide |
| 2.108 | M + H | 469.1 | (6-(2-cyanophenyl)-2-{[2-(3-fluorophenyl)ethyl]amino}(3-pyridyl))-N-[(4-fluorophenyl)methyl]carboxamide |
| 0.968 | M + H | 476.1 | (6-(2-cyanophenyl)-2-{[2-(3-fluorophenyl)ethyl]amino}(3-pyridyl))-N-[(4-cyanophenyl)methyl]carboxamide |
| 1.981 | M + H | 487.1 | N-[(3,4-difluorophenyl)methyl](6-(2-cyanophenyl)-2-{[2-(3-fluorophenyl)ethyl]amino}(3-pyridyl))carboxamide |
| 1.02 | M + H | 448.1 | N-((1S)-1-carbamoyl-2-hydroxyethyl)(6-(2-cyanophenyl)-2-{[2-(3-fluorophenyl)ethyl]amino}(3-pyridyl))carboxamide |
| 0.318 | M + H | 419.1 | (6-(2-cyanophenyl)-2-{[2-(3-fluorophenyl)ethyl]amino}(3-pyridyl))-N-(3-hydroxypropyl)carboxamide |
| 0.396 | M + H | 433.1 | (6-(2-cyanophenyl)-2-{[2-(3-fluorophenyl)ethyl]amino}(3-pyridyl))-N-(3-methoxypropyl)carboxamide |
| 4.177 | M + H | 463.1 | methyl (2S)-2-[(6-(2-cyanophenyl)-2-{[2-(3-fluorophenyl)ethyl]amino}(3-pyridyl))carbonylamino]-3-hydroxypropanoate |
| 0.513 | M + H | 463.1 | methyl (2R)-2-[(6-(2-cyanophenyl)-2-{[2-(3-fluorophenyl)ethyl]amino}(3-pyridyl))carbonylamino]-3-hydroxypropanoate |
| 1.121 | M + H | 462.1 | (2S)-2-[(6-(2-cyanophenyl)-2-{[2-(3-fluorophenyl)ethyl]amino}(3-pyridyl))carbonylamino]-3-hydroxy-N-methylpropanamide |
| 0.544 | M + H | 462.1 | (2R)-2-[(6-(2-cyanophenyl)-2-{[2-(3-fluorophenyl)ethyl]amino}(3-pyridyl))carbonylamino]-3-hydroxy-N-methylpropanamide |
| 0.029 | M + H | 452.1 | (6-(2-cyanophenyl)-2-{[2-(3-fluorophenyl)ethyl]amino}(3-pyridyl))-N-(2-pyridylmethyl)carboxamide |
| 24.295 | M + H | 465.1 | (6-(2-cyanophenyl)-2-{[2-(3-fluorophenyl)ethyl]amino}(3-pyridyl))-N-[(4-methylphenyl)methyl]carboxamide |
| 0.426 | M + H | 466.1 | (6-(2-cyanophenyl)-2-{[2-(3-fluorophenyl)ethyl]amino}(3-pyridyl))-N-[(6-methyl(3-pyridyl))methyl]carboxamide |
| 0.054 | M + H | 466.1 | (6-(2-cyanophenyl)-2-{[2-(3-fluorophenyl)ethyl]amino}(3-pyridyl))-N-[(6-methyl(2-pyridyl))methyl]carboxamide |
| 0.291 | M + H | 466.1 | (6-(2-cyanophenyl)-2-{[2-(3-fluorophenyl)ethyl]amino}(3-pyridyl))-N-(2-(2-pyridyl)ethyl)carboxamide |
| 0.15 | M + H | 466.1 | (6-(2-cyanophenyl)-2-{[2-(3-fluorophenyl)ethyl]amino}(3-pyridyl))-N-(2-(3-pyridyl)ethyl)carboxamide |
| 0.026 | M + H | 467.1 | N-[(6-amino(3-pyridyl))methyl](6-(2-cyanophenyl)-2-{[2-(3-fluorophenyl)ethyl]amino}(3-pyridyl))carboxamide |
| 8.099 | M + H | 482.1 | (6-(2-cyanophenyl)-2-{[2-(3-fluorophenyl)ethyl]amino}(3-pyridyl))-N-[(6-methoxy(3-pyridyl))methyl]carboxamide |
| 0.022 | M + H | 466.1 | (6-(2-cyanophenyl)-2-{[2-(3-fluorophenyl)ethyl]amino}(3-pyridyl))-N-[(2-methyl(3-pyridyl))methyl]carboxamide |
| 0.022 | M + H | 467.1 | N-[(2-amino(3-pyridyl))methyl](6-(2-cyanophenyl)-2-{[2-(3-fluorophenyl)ethyl]amino}(3-pyridyl))carboxamide |
| 0.087 | M + H | 482.1 | (6-(2-cyanophenyl)-2-{[2-(3-fluorophenyl)ethyl]amino}(3-pyridyl))-N-[(2-methoxy(3-pyridyl))methyl]carboxamide |
| 0.021 | M + H | 470.1 | (6-(2-cyanophenyl)-2-{[2-(3-fluorophenyl)ethyl]amino}(3-pyridyl))-N-[(1-hydroxy(2-pyridyl))methyl]carboxamide |

-continued

| IC50 Arithmetic Mean | Ion | m/z | CHEMICAL NAME |
|---|---|---|---|
| 0.019 | M + H | 470.1 | (6-(2-cyanophenyl)-2-{[2-(3-fluorophenyl)ethyl]amino}(3-pyridyl))-N-[(1-hydroxy(3-pyridyl))methyl]carboxamide |
| 3.064 | M + H | 501.1 | (6-(2-cyanophenyl)-2-{[2-(3-fluorophenyl)ethyl]amino}(3-pyridyl))-N-[3-(4-methylpiperazinyl)propyl]carboxamide |
| 0.136 | M + H | 415.1 | (6-(2-cyanophenyl)-2-{[2-(3-fluorophenyl)ethyl]amino}(3-pyridyl))-N-(cyclopropylmethyl)carboxamide |
| 9.309 | M + H | 489.1 | N-[2-(dimethylamino)ethyl]-2-[(6-(2-cyanophenyl)-2-{[2-(3-fluorophenyl)ethyl]amino}(3-pyridyl))carbonylamino]acetamide |
| 2.07 | M + H | 462.1 | 2-[(6-(2-cyanophenyl)-2-{[2-(3-fluorophenyl)ethyl]amino}(3-pyridyl))carbonylamino]-N-(2-hydroxyethyl)acetamide |
| 12.17 | M + H | 489.1 | N-(2-carbamoylethyl)-2-[(6-(2-cyanophenyl)-2-{[2-(3-fluorophenyl)ethyl]amino}(3-pyridyl))carbonylamino]acetamide |
| 9.666 | M + H | 490.1 | 3-{2-[(6-(2-cyanophenyl)-2-{[2-(3-fluorophenyl)ethyl]amino}-3-pyridyl)carbonylamino]acetylamino}propanoic acid |
| 9.876 | M + H | 575.1 | N-{3-[(tert-butoxy)carbonylamino]propyl}-2-[(6-(2-cyanophenyl)-2-{[2-(3-fluorophenyl)ethyl]amino}(3-pyridyl))carbonylamino]acetamide |
| 12.22 | M + H | 503.1 | N-[3-(dimethylamino)propyl]-2-[(6-(2-cyanophenyl)-2-{[2-(3-fluorophenyl)ethyl]amino}(3-pyridyl))carbonylamino]acetamide |
| 5.836 | M + H | 476.1 | 2-[(6-(2-cyanophenyl)-2-{[2-(3-fluorophenyl)ethyl]amino}(3-pyridyl))carbonylamino]-N-(3-hydroxypropyl)acetamide |
| 65.469 | M + H | 575.1 | N-{2-[(tert-butoxy)-N-methylcarbonylamino]ethyl}-2-[(6-(2-cyanophenyl)-2-{[2-(3-fluorophenyl)ethyl]amino}(3-pyridyl))carbonylamino]acetamide |
| 11.096 | M + H | 475.1 | 2-[(6-(2-cyanophenyl)-2-{[2-(3-fluorophenyl)ethyl]amino}(3-pyridyl))carbonylamino]-N-[2-(methylamino)ethyl]acetamide |
| 2.318 | M + H | 462.1 | methyl (2S)-3-amino-2-[(6-(2-cyanophenyl)-2-{[2-(3-fluorophenyl)ethyl]amino}(3-pyridyl))carbonylamino]propanoate |
| 0.816 | M + H | 447.1 | N-((1S)-2-amino-1-carbamoylethyl)(6-(2-cyanophenyl)-2-{[2-(3-fluorophenyl)ethyl]amino}(3-pyridyl))carboxamide |
| 30.417 | M + H | 548.1 | (2S)-3-[(tert-butoxy)carbonylamino]-2-[(6-(2-cyanophenyl)-2-{[2-(3-fluorophenyl)ethyl]amino}(3-pyridyl))carbonylamino]propanoic acid |
| 43.598 | M + H | 561.1 | (2S)-3-[(tert-butoxy)carbonylamino]-2-[(6-(2-cyanophenyl)-2-{[2-(3-fluorophenyl)ethyl]amino}(3-pyridyl))carbonylamino]-N-methylpropanamide |
| 3.454 | M + H | 461.1 | (2S)-3-amino-2-[(6-(2-cyanophenyl)-2-{[2-(3-fluorophenyl)ethyl]amino}(3-pyridyl))carbonylamino]-N-methylpropanamide |
| 23.721 | M + H | 475.1 | (2S)-3-amino-2-[(6-(2-cyanophenyl)-2-{[2-(3-fluorophenyl)ethyl]amino}(3-pyridyl))carbonylamino]-N,N-dimethylpropanamide |
| 11.072 | M + H | 448.1 | (2S)-3-amino-2-[(6-(2-cyanophenyl)-2-{[2-(3-fluorophenyl)ethyl]amino}(3-pyridyl))carbonylamino]propanoic acid |
| 0.619 | M + H | 462.1 | methyl (2S)-2-amino-3-[(6-(2-cyanophenyl)-2-{[2-(3-fluorophenyl)ethyl]amino}(3-pyridyl))carbonylamino]propanoate |
| 1.639 | M + H | 504.1 | methyl (2S)-2-(acetylamino)-3-[(6-(2-cyanophenyl)-2-{[2-(3-fluorophenyl)ethyl]amino}(3-pyridyl))carbonylamino]propanoate |
| 0.669 | M + H | 447.1 | N-((2S)-2-amino-2-carbamoylethyl)(6-(2-cyanophenyl)-2-{[2-(3-fluorophenyl)ethyl]amino}(3-pyridyl))carboxamide |
| 2.629 | M + H | 489.1 | N-{(1S)-1-carbamoyl-2-[(6-(2-cyanophenyl)-2-{[2-(3-fluorophenyl)ethyl]amino}(3-pyridyl))carbonylamino]ethyl}acetamide |
| 2.318 | M + H | 461.1 | (2S)-2-amino-3-[(6-(2-cyanophenyl)-2-{[2-(3-fluorophenyl)ethyl]amino}(3-pyridyl))carbonylamino]-N-methylpropanamide |

-continued

| IC50 Arithmetic Mean | Ion | m/z | CHEMICAL NAME |
|---|---|---|---|
| 8.179 | M + H | 475.1 | (2S)-2-amino-3-[(6-(2-cyanophenyl)-2-{[2-(3-fluorophenyl)ethyl]amino}(3-pyridyl))carbonylamino]-N,N-dimethylpropanamide |
| 9.758 | M + H | 448.1 | (2S)-2-amino-3-[(6-(2-cyanophenyl)-2-{[2-(3-fluorophenyl)ethyl]amino}(3-pyridyl))carbonylamino]propanoic acid |
| 5.554 | M + H | 503.1 | (2S)-2-(acetylamino)-3-[(6-(2-cyanophenyl)-2-{[2-(3-fluorophenyl)ethyl]amino}(3-pyridyl))carbonylamino]-N-methylpropanamide |
| 2.384 | M + H | 462.1 | methyl (2R)-3-amino-2-[(6-(2-cyanophenyl)-2-{[2-(3-fluorophenyl)ethyl]amino}(3-pyridyl))carbonylamino]propanoate |
| 0.538 | M + H | 447.1 | N-((1R)-2-amino-1-carbamoylethyl)(6-(2-cyanophenyl)-2-{[2-(3-fluorophenyl)ethyl]amino}(3-pyridyl))carboxamide |
| 0.274 | M + H | 461.1 | (2R)-3-amino-2-[(6-(2-cyanophenyl)-2-{[2-(3-fluorophenyl)ethyl]amino}(3-pyridyl))carbonylamino]-N-methylpropanamide |
| 2.29 | M + H | 462.1 | methyl (2R)-2-amino-3-[(6-(2-cyanophenyl)-2-{[2-(3-fluorophenyl)ethyl]amino}(3-pyridyl))carbonylamino]propanoate |
| 0.321 | M + H | 447.1 | N-((2R)-2-amino-2-carbamoylethyl)(6-(2-cyanophenyl)-2-{[2-(3-fluorophenyl)ethyl]amino}(3-pyridyl))carboxamide |
| 0.04 | M + H | 442.1 | (6-(2-cyanophenyl)-2-{[2-(3-fluorophenyl)ethyl]amino}(3-pyridyl))-N-(1,3-oxazol-2-ylmethyl)carboxamide |
| 1.245 | M + H | 452.1 | N-[(6-cyano(3-pyridyl))methyl](2-{[2-(3-fluorophenyl)ethyl]amino}-6-phenyl(3-pyridyl))carboxamide |
| 0.42 | M + H | 456.1 | N-{[6-(aminomethyl)(3-pyridyl)]methyl}(2-{[2-(3-fluorophenyl)ethyl]amino}-6-phenyl(3-pyridyl))carboxamide |
| 52.451 | M + H | 352.1 | 2-amino-1-(2-{[2-(3-fluorophenyl)ethyl]amino}-6-phenyl(3-pyridyl))ethan-1-ol |
| 0.598 | M + H | 481.1 | N-{[4-(aminomethyl)(2-pyridyl)]methyl}(6-(2-cyanophenyl)-2-{[2-(3-fluorophenyl)ethyl]amino}(3-pyridyl))carboxamide |
| 68.638 | M + H | 581.1 | N-[(5-{[(tert-butoxy)carbonylamino]methyl}(2-pyridyl))methyl](6-(2-cyanophenyl)-2-{[2-(3-fluorophenyl)ethyl]amino}(3-pyridyl))carboxamide |
| 0.515 | M + H | 481.1 | N-{[5-(aminomethyl)(2-pyridyl)]methyl}(6-(2-cyanophenyl)-2-{[2-(3-fluorophenyl)ethyl]amino}(3-pyridyl))carboxamide |
| 1.215 | M + H | 456.1 | N-{[4-(aminomethyl)(2-pyridyl)]methyl}(2-{[2-(3-fluorophenyl)ethyl]amino}-6-phenyl(3-pyridyl))carboxamide |
| 1.061 | M + H | 456.1 | N-{[5-(aminomethyl)(2-pyridyl)]methyl}(2-{[2-(3-fluorophenyl)ethyl]amino}-6-phenyl(3-pyridyl))carboxamide |
| 0.021 | M + H | 442.1 | (6-(2-cyanophenyl)-2-{[2-(3-fluorophenyl)ethyl]amino}(3-pyridyl))-N-(isoxazol-5-ylmethyl)carboxamide |
| 51.566 | M + H | 409.1 | 2-{[2-(2-{[2-(3-fluorophenyl)ethyl]amino}-6-phenyl(3-pyridyl))-2-hydroxyethyl]amino}acetamide |
| 15.082 | M + H | 438.1 | ethyl 2-{[2-(2-{[2-(3-fluorophenyl)ethyl]amino}-6-phenyl(3-pyridyl))-2-hydroxyethyl]amino}acetate |
| 19.362 | M + H | 443.1 | 1-(2-{[2-(3-fluorophenyl)ethyl]amino}-6-phenyl(3-pyridyl))-2-[(2-pyridylmethyl)amino]ethan-1-ol |
| 0.416 | M + H | 432.1 | N-(4-aminobutyl)(6-(2-cyanophenyl)-2-{[2-(3-fluorophenyl)ethyl]amino}(3-pyridyl))carboxamide |
| 0.154 | M + H | 446.1 | N-(5-aminopentyl)(6-(2-cyanophenyl)-2-{[2-(3-fluorophenyl)ethyl]amino}(3-pyridyl))carboxamide |
| 1.244 | M + H | 460.1 | N-(6-aminohexyl)(6-(2-cyanophenyl)-2-{[2-(3-fluorophenyl)ethyl]amino}(3-pyridyl))carboxamide |
| 0.032 | M + H | 495.1 | N-{2-[6-(aminomethyl)(2-pyridyl)]ethyl}(6-(2-cyanophenyl)-2-{[2-(3-fluorophenyl)ethyl]amino}(3-pyridyl))carboxamide |
| 0.252 | M + H | 470.1 | N-{2-[6-(aminomethyl)(2-pyridyl)]ethyl}(2-{[2-(3-fluorophenyl)ethyl]amino}-6-phenyl(3-pyridyl))carboxamide |
| 0.011 | M + H | 495.1 | N-{[6-(2-aminoethyl)(2-pyridyl)]methyl}(6-(2-cyanophenyl)-2-{[2-(3-fluorophenyl)ethyl]amino}(3-pyridyl))carboxamide |

| IC50 Arithmetic Mean | Ion | m/z | CHEMICAL NAME |
| --- | --- | --- | --- |
| 0.024 | M + H | 470.1 | N-{[6-(2-aminoethyl)(2-pyridyl)]methyl}(2-{[2-(3-fluorophenyl)ethyl]amino}-6-phenyl(3-pyridyl))carboxamide |
| 1.62 | M + H | 448.1 | N-[2-(2-aminoethoxy)ethyl](6-(2-cyanophenyl)-2-{[2-(3-fluorophenyl)ethyl]amino}(3-pyridyl))carboxamide |
| 0.037 | M + H | 482.1 | (6-(2-cyanophenyl)-2-{[2-(3-fluorophenyl)ethyl]amino}(3-pyridyl))-N-{[6-(hydroxymethyl)(2-pyridyl)]methyl}carboxamide |
| 0.012 | M + H | 480.1 | N-{[3-(aminomethyl)phenyl]methyl}(6-(2-cyanophenyl)-2-{[2-(3-fluorophenyl)ethyl]amino}(3-pyridyl))carboxamide |
| 0.532 | M + H | 446.1 | 2-[(6-(2-cyanophenyl)-2-{[2-(3-fluorophenyl)ethyl]amino}(3-pyridyl))carbonylamino]-N,N-dimethylacetamide |
| 0.444 | M + H | 447.1 | N-{2-[(2-aminoethyl)amino]ethyl}(6-(2-cyanophenyl)-2-{[2-(3-fluorophenyl)ethyl]amino}(3-pyridyl))carboxamide |
| 0.014 | M + H | 472.1 | (6-(2-cyanophenyl)-2-{[2-(3-fluorophenyl)ethyl]amino}(3-pyridyl))-N-[(2-oxo(3-piperidyl))methyl]carboxamide |
| 0.015 | M + H | 441.1 | (6-(2-cyanophenyl)-2-{[2-(3-fluorophenyl)ethyl]amino}(3-pyridyl))-N-(pyrazol-3-ylmethyl)carboxamide |
| 0.032 | M + H | 455.1 | (6-(2-cyanophenyl)-2-{[2-(3-fluorophenyl)ethyl]amino}(3-pyridyl))-N-[(1-methylpyrazol-3-yl)methyl]carboxamide |
| 0.277 | M + H | 480.1 | N-{[4-(aminomethyl)phenyl]methyl}(6-(2-cyanophenyl)-2-{[2-(3-fluorophenyl)ethyl]amino}(3-pyridyl))carboxamide |
| 0.019 | M + H | 524.1 | N-[(6-{[(2-aminoethyl)amino]methyl}(2-pyridyl))methyl](6-(2-cyanophenyl)-2-{[2-(3-fluorophenyl)ethyl]amino}(3-pyridyl))carboxamide |
| 0.064 | M + H | 510.1 | methyl 6-{[(6-(2-cyanophenyl)-2-{[2-(3-fluorophenyl)ethyl]amino}-3-pyridyl)carbonylamino]methyl}pyridine-2-carboxylate |
| 0.047 | M + H | 496.1 | 6-{[(6-(2-cyanophenyl)-2-{[2-(3-fluorophenyl)ethyl]amino}-3-pyridyl)carbonylamino]methyl}pyridine-2-carboxylic acid |
| 0.06 | M + H | 495.1 | 6-{[(6-(2-cyanophenyl)-2-{[2-(3-fluorophenyl)ethyl]amino}-3-pyridyl)carbonylamino]methyl}pyridine-2-carboxamide |
| 0.031 | M + H | 455.1 | (6-(2-cyanophenyl)-2-{[2-(3-fluorophenyl)ethyl]amino}(3-pyridyl))-N-[(1-methylpyrazol-5-yl)methyl]carboxamide |
| 15.254 | M + H | 601.1 | N-(1-{2-[(tert-butoxy)carbonylamino]ethyl}-2-oxo(3-piperidyl))(6-(2-cyanophenyl)-2-{[2-(3-fluorophenyl)ethyl]amino}(3-pyridyl))carboxamide |
| 18.531 | M + H | 501.1 | N-[1-(2-aminoethyl)-2-oxo(3-piperidyl)](6-(2-cyanophenyl)-2-{[2-(3-fluorophenyl)ethyl]amino}(3-pyridyl))carboxamide |
| 11.834 | M + H | 635.1 | (6-(2-cyanophenyl)-2-{[2-(3-fluorophenyl)ethyl]amino}(3-pyridyl))-N-(2-{2-oxo-3-[(phenylmethoxy)carbonylamino]piperidyl}ethyl)carboxamide |
| 2.95 | M + H | 501.1 | N-[2-(3-amino-2-oxopiperidyl)ethyl](6-(2-cyanophenyl)-2-{[2-(3-fluorophenyl)ethyl]amino}(3-pyridyl))carboxamide |
| 0.024 | M + H | 480.1 | N-{[2-(aminomethyl)phenyl]methyl}(6-(2-cyanophenyl)-2-{[2-(3-fluorophenyl)ethyl]amino}(3-pyridyl))carboxamide |
| 0.032 | M + H | 458.1 | (6-(2-cyanophenyl)-2-{[2-(3-fluorophenyl)ethyl]amino}(3-pyridyl))-N-[(2-oxopyrrolidin-3-yl)methyl]carboxamide |
| 0.47 | M + H | 595.1 | N-[(2-{2-[(tert-butoxy)carbonylamino]ethyl}(3-pyridyl))methyl](6-(2-cyanophenyl)-2-{[2-(3-fluorophenyl)ethyl]amino}(3-pyridyl))carboxamide |
| 0.006 | M + H | 495.1 | N-{[2-(2-aminoethyl)(3-pyridyl)]methyl}(6-(2-cyanophenyl)-2-{[2-(3-fluorophenyl)ethyl]amino}(3-pyridyl))carboxamide |
| 0.31 | M + H | 495.1 | N-{2-[3-(aminomethyl)(2-pyridyl)]ethyl}(6-(2-cyanophenyl)-2-{[2-(3-fluorophenyl)ethyl]amino}(3-pyridyl))carboxamide |

-continued

| IC50 Arithmetic Mean | Ion | m/z | CHEMICAL NAME |
|---|---|---|---|
| 3.246 | M + H | 444.1 | N-((3S)-2-oxopyrrolidin-3-yl)(6-(2-cyanophenyl)-2-{[2-(3-fluorophenyl)ethyl]amino}(3-pyridyl))carboxamide |
| 0.059 | M + H | 516.1 | (6-(2-cyanophenyl)-2-{[2-(3-fluorophenyl)ethyl]amino}(3-pyridyl))-N-{[1-(2-hydroxyethyl)-2-oxo(3-piperidyl)]methyl}carboxamide |
| 0.031 | M + H | 515.1 | N-{[1-(2-aminoethyl)-2-oxo(3-piperidyl)]methyl}(6-(2-cyanophenyl)-2-{[2-(3-fluorophenyl)ethyl]amino}(3-pyridyl))carboxamide |
| 0.412 | M + H | 541.1 | (6-(2-cyanophenyl)-2-{[2-(3-fluorophenyl)ethyl]amino}(3-pyridyl))-N-{[1-(3-diazo-3-azaprop-3-enyl)-2-oxo(3-piperidyl)]methyl}carboxamide |
| 15.844 | M + H | 541.1 | (6-(2-cyanophenyl)-2-{[2-(3-fluorophenyl)ethyl]amino}(3-pyridyl))-N-{[3-(3-diazo-3-azaprop-3-enyl)-2-oxo(3-piperidyl)]methyl}carboxamide |
| 12.204 | M + H | 459.1 | N-[((2R)piperazin-2-yl)methyl](6-(2-cyanophenyl)-2-{[2-(3-fluorophenyl)ethyl]amino}(3-pyridyl))carboxamide |
| 15.724 | M + H | 473.1 | N-[((2R)-1-methylpiperazin-2-yl)methyl](6-(2-cyanophenyl)-2-{[2-(3-fluorophenyl)ethyl]amino}(3-pyridyl))carboxamide |
| 7.437 | M + H | 501.1 | N-[((2R)-1-acetylpiperazin-2-yl)methyl](6-(2-cyanophenyl)-2-{[2-(3-fluorophenyl)ethyl]amino}(3-pyridyl))carboxamide |
| 16.793 | M + H | 551.1 | N-{[(2R)-1-(ethylsulfonyl)piperazin-2-yl]methyl}(6-(2-cyanophenyl)-2-{[2-(3-fluorophenyl)ethyl]amino}(3-pyridyl))carboxamide |
| 11.602 | M + H | 517.1 | methyl (2R)-2-{[(6-(2-cyanophenyl)-2-{[2-(3-fluorophenyl)ethyl]amino}(3-pyridyl))carbonylamino]methyl}piperazinecarboxylate |
| 6.789 | M + H | 515.1 | N-[((2S)-1-acetyl-4-methylpiperazin-2-yl)methyl](6-(2-cyanophenyl)-2-{[2-(3-fluorophenyl)ethyl]amino}(3-pyridyl))carboxamide |
| 10.062 | M + H | 531.1 | methyl (2S)-2-{[(6-(2-cyanophenyl)-2-{[2-(3-fluorophenyl)ethyl]amino}(3-pyridyl))carbonylamino]methyl}-4-methylpiperazinecarboxylate |
| 2.775 | M + H | 516.1 | N-{[(2R)-1-(2-aminoacetyl)piperazin-2-yl]methyl}(6-(2-cyanophenyl)-2-{[2-(3-fluorophenyl)ethyl]amino}(3-pyridyl))carboxamide |
| 4.893 | M + H | 530.1 | N-{[(2R)-1-(3-aminopropanoyl)piperazin-2-yl]methyl}(6-(2-cyanophenyl)-2-{[2-(3-fluorophenyl)ethyl]amino}(3-pyridyl))carboxamide |
| 5.475 | M + H | 544.1 | N-{[(2R)-1-(4-aminobutanoyl)piperazin-2-yl]methyl}(6-(2-cyanophenyl)-2-{[2-(3-fluorophenyl)ethyl]amino}(3-pyridyl))carboxamide |
| 1.283 | M + H | 530.1 | N-{[(2S)-1-(2-aminoacetyl)-4-methylpiperazin-2-yl]methyl}(6-(2-cyanophenyl)-2-{[2-(3-fluorophenyl)ethyl]amino}(3-pyridyl))carboxamide |
| 2.393 | M + H | 544.1 | N-{[(2S)-1-(3-aminopropanoyl)-4-methylpiperazin-2-yl]methyl}(6-(2-cyanophenyl)-2-{[2-(3-fluorophenyl)ethyl]amino}(3-pyridyl))carboxamide |
| 2.322 | M + H | 558.1 | N-{[(2S)-1-(4-aminobutanoyl)-4-methylpiperazin-2-yl]methyl}(6-(2-cyanophenyl)-2-{[2-(3-fluorophenyl)ethyl]amino}(3-pyridyl))carboxamide |
| 8.885 | M + H | 516.1 | N-{[(2S)-4-(2-aminoacetyl)piperazin-2-yl]methyl}(6-(2-cyanophenyl)-2-{[2-(3-fluorophenyl)ethyl]amino}(3-pyridyl))carboxamide |
| 11.197 | M + H | 530.1 | N-{[(2S)-4-(3-aminopropanoyl)piperazin-2-yl]methyl}(6-(2-cyanophenyl)-2-{[2-(3-fluorophenyl)ethyl]amino}(3-pyridyl))carboxamide |
| 12.397 | M + H | 544.1 | N-{[(2S)-4-(4-aminobutanoyl)piperazin-2-yl]methyl}(6-(2-cyanophenyl)-2-{[2-(3-fluorophenyl)ethyl]amino}(3-pyridyl))carboxamide |
| 6.97 | M + H | 530.1 | N-{[(2S)-4-(2-aminoacetyl)-1-methylpiperazin-2-yl]methyl}(6-(2-cyanophenyl)-2-{[2-(3-fluorophenyl)ethyl]amino}(3-pyridyl))carboxamide |
| 16.962 | M + H | 544.1 | N-{[(2S)-4-(3-aminopropanoyl)-1-methylpiperazin-2-yl]methyl}(6-(2-cyanophenyl)-2-{[2-(3-fluorophenyl)ethyl]amino}(3-pyridyl))carboxamide |
| 6.717 | M + H | 558.1 | N-{[(2S)-4-(4-aminobutanoyl)-1-methylpiperazin-2-yl]methyl}(6-(2-cyanophenyl)-2-{[2-(3-fluorophenyl)ethyl]amino}(3-pyridyl))carboxamide |

-continued

| IC50 Arithmetic Mean | Ion | m/z | CHEMICAL NAME |
|---|---|---|---|
| 13.156 | M + H | 466.1 | 2-(6-(2-cyanophenyl)-2-{[2-(3-fluorophenyl)ethyl]amino}(3-pyridyl))-N-(3-pyridylmethyl)acetamide |
| 17.175 | M + H | 543.1 | N-[((2S)-1,4-diacetylpiperazin-2-yl)methyl](6-(2-cyanophenyl)-2-{[2-(3-fluorophenyl)ethyl]amino}(3-pyridyl))carboxamide |
| 2.92 | M + H | 473.1 | N-[((2S)-4-methylpiperazin-2-yl)methyl](6-(2-cyanophenyl)-2-{[2-(3-fluorophenyl)ethyl]amino}(3-pyridyl))carboxamide |
| 0.413 | M + H | 430.1 | N-[((2R)azetidin-2-yl)methyl](6-(2-cyanophenyl)-2-{[2-(3-fluorophenyl)ethyl]amino}(3-pyridyl))carboxamide |
| 0.073 | M + H | 488.1 | methyl (2R)-2-{[(6-(2-cyanophenyl)-2-{[2-(3-fluorophenyl)ethyl]amino}(3-pyridyl))carbonylamino]methyl}azetidinecarboxylate |
| 0.248 | M + H | 437.1 | (2-{[2-(3-fluorophenyl)ethyl]amino}-6-(1-methylpyrazol-4-yl)(3-pyridyl))-N-[(2-oxopyrrolidin-3-yl)methyl]carboxamide |
| 0.18 | M + H | 423.1 | (2-{[2-(3-fluorophenyl)ethyl]amino}-6-pyrazol-4-yl(3-pyridyl))-N-[(2-oxopyrrolidin-3-yl)methyl]carboxamide |
| 0.116 | M + H | 502.1 | N-{[(2R)-1-(2-hydroxyacetyl)pyrrolidin-2-yl]methyl}(6-(2-cyanophenyl)-2-{[2-(3-fluorophenyl)ethyl]amino}(3-pyridyl))carboxamide |
| 0.657 | M + H | 558.1 | methyl 4-((2R)-2-{[(6-(2-cyanophenyl)-2-{[2-(3-fluorophenyl)ethyl]amino}(3-pyridyl))carbonylamino]methyl}pyrrolidinyl)-4-oxobutanoate |
| 0.085 | M + H | 530.1 | N-{[(2R)-1-(4-hydroxybutanoyl)pyrrolidin-2-yl]methyl}(6-(2-cyanophenyl)-2-{[2-(3-fluorophenyl)ethyl]amino}(3-pyridyl))carboxamide |
| 1.784 | M + H | 481.1 | N-{[(2R)-1-(2-hydroxyacetyl)pyrrolidin-2-yl]methyl}(2-{[2-(3-fluorophenyl)ethyl]amino}-6-(1-methylpyrazol-4-yl)(3-pyridyl))carboxamide |
| 3.935 | M + H | 537.1 | methyl 4-((2R)-2-{[(2-{[2-(3-fluorophenyl)ethyl]amino}-6-(1-methylpyrazol-4-yl)(3-pyridyl))carbonylamino]methyl}pyrrolidinyl)-4-oxobutanoate |
| 1.456 | M + H | 509.1 | N-{[(2R)-1-(4-hydroxybutanoyl)pyrrolidin-2-yl]methyl}(2-{[2-(3-fluorophenyl)ethyl]amino}-6-(1-methylpyrazol-4-yl)(3-pyridyl))carboxamide |
| 0.043 | M + H | 472.1 | N-[((2R)-1-acetylazetidin-2-yl)methyl](6-(2-cyanophenyl)-2-{[2-(3-fluorophenyl)ethyl]amino}(3-pyridyl))carboxamide |
| 1.524 | M + H | 508.1 | N-{[(2R)-1-(methylsulfonyl)azetidin-2-yl]methyl}(6-(2-cyanophenyl)-2-{[2-(3-fluorophenyl)ethyl]amino}(3-pyridyl))carboxamide |
| 0.044 | M + H | 487.1 | N-{[(2R)-1-(2-aminoacetyl)azetidin-2-yl]methyl}(6-(2-cyanophenyl)-2-{[2-(3-fluorophenyl)ethyl]amino}(3-pyridyl))carboxamide |
| 0.045 | M + H | 501.1 | N-{[(2R)-1-(3-aminopropanoyl)azetidin-2-yl]methyl}(6-(2-cyanophenyl)-2-{[2-(3-fluorophenyl)ethyl]amino}(3-pyridyl))carboxamide |
| 0.025 | M + H | 515.1 | N-{[(2R)-1-(4-aminobutanoyl)azetidin-2-yl]methyl}(6-(2-cyanophenyl)-2-{[2-(3-fluorophenyl)ethyl]amino}(3-pyridyl))carboxamide |
| 0.04 | M + H | 488.1 | N-{[(2R)-1-(2-hydroxyacetyl)azetidin-2-yl]methyl}(6-(2-cyanophenyl)-2-{[2-(3-fluorophenyl)ethyl]amino}(3-pyridyl))carboxamide |
| 0.519 | M + H | 544.1 | methyl 4-((2R)-2-{[(6-(2-cyanophenyl)-2-{[2-(3-fluorophenyl)ethyl]amino}(3-pyridyl))carbonylamino]methyl}azetidinyl)-4-oxobutanoate |
| 0.06 | M + H | 516.1 | N-{[(2R)-1-(4-hydroxybutanoyl)azetidin-2-yl]methyl}(6-(2-cyanophenyl)-2-{[2-(3-fluorophenyl)ethyl]amino}(3-pyridyl))carboxamide |
| 2.501 | M + H | 472.1 | N-(azaperhydroepin-2-ylmethyl)(6-(2-cyanophenyl)-2-{[2-(3-fluorophenyl)ethyl]amino}(3-pyridyl))carboxamide |
| 0.248 | M + H | 529.1 | N-{[1-(2-aminoacetyl)azaperhydroepin-2-yl]methyl}(6-(2-cyanophenyl)-2-{[2-(3-fluorophenyl)ethyl]amino}(3-pyridyl))carboxamide |
| 0.256 | M + H | 543.1 | N-{[1-(3-aminopropanoyl)azaperhydroepin-2-yl]methyl}(6-(2-cyanophenyl)-2-{[2-(3-fluorophenyl)ethyl]amino}(3-pyridyl))carboxamide |

-continued

| IC50 Arithmetic Mean | Ion | m/z | CHEMICAL NAME |
|---|---|---|---|
| 0.383 | M + H | 557.1 | N-{[1-(4-aminobutanoyl)azaperhydroepin-2-yl]methyl}(6-(2-cyanophenyl)-2-{[2-(3-fluorophenyl)ethyl]amino}(3-pyridyl))carboxamide |
| 0.104 | M + H | 615.1 | N-[(1-{3-[(tert-butoxy)carbonylamino]propyl}-2-oxopyrrolidin-3-yl)methyl](6-(2-cyanophenyl)-2-{[2-(3-fluorophenyl)ethyl]amino}(3-pyridyl))carboxamide |
| 0.382 | M + H | 515.1 | N-{[1-(3-aminopropyl)-2-oxopyrrolidin-3-yl]methyl}(6-(2-cyanophenyl)-2-{[2-(3-fluorophenyl)ethyl]amino}(3-pyridyl))carboxamide |
| 0.589 | M + H | 580.1 | N-[(1-{3-[(tert-butoxy)carbonylamino]propyl}-2-oxopyrrolidin-3-yl)methyl](2-{[2-(3-fluorophenyl)ethyl]amino}-6-pyrazol-4-yl(3-pyridyl))carboxamide |
| 3.125 | M + H | 480.1 | N-{[1-(3-aminopropyl)-2-oxopyrrolidin-3-yl]methyl}(2-{[2-(3-fluorophenyl)ethyl]amino}-6-pyrazol-4-yl(3-pyridyl))carboxamide |
| 0.699 | M + H | 594.1 | N-[(1-{3-[(tert-butoxy)carbonylamino]propyl}-2-oxopyrrolidin-3-yl)methyl](2-{[2-(3-fluorophenyl)ethyl]amino}-6-(1-methylpyrazol-4-yl)(3-pyridyl))carboxamide |
| 5.504 | M + H | 494.1 | N-{[1-(3-aminopropyl)-2-oxopyrrolidin-3-yl]methyl}(2-{[2-(3-fluorophenyl)ethyl]amino}-6-(1-methylpyrazol-4-yl)(3-pyridyl))carboxamide |
| 3.167 | M + H | 509.1 | tert-butyl (2R)-2-{[(2-{[2-(3-fluorophenyl)ethyl]amino}-6-pyrazol-4-yl(3-pyridyl))carbonylamino]methyl}pyrrolidinecarboxylate |
| 1.185 | M + H | 467.1 | N-{[(2R)-1-(2-hydroxyacetyl)pyrrolidin-2-yl]methyl}(2-{[2-(3-fluorophenyl)ethyl]amino}-6-pyrazol-4-yl(3-pyridyl))carboxamide |
| 0.095 | M + H | 486.1 | (6-(2-cyanophenyl)-2-{[2-(3-fluorophenyl)ethyl]amino}(3-pyridyl))-N-[(7-oxoazaperhydroepin-2-yl)methyl]carboxamide |
| 0.687 | M + H | 451.1 | (2-{[2-(3-fluorophenyl)ethyl]amino}-6-pyrazol-4-yl(3-pyridyl))-N-[(7-oxoazaperhydroepin-2-yl)methyl]carboxamide |
| 0.603 | M + H | 465.1 | (2-{[2-(3-fluorophenyl)ethyl]amino}-6-(1-methylpyrazol-4-yl)(3-pyridyl))-N-[(7-oxoazaperhydroepin-2-yl)methyl]carboxamide |
| 17.15 | M + H | 643.1 | N-[(1-{3-[(tert-butoxy)carbonylamino]propyl}-7-oxoazaperhydroepin-2-yl)methyl](6-(2-cyanophenyl)-2-{[2-(3-fluorophenyl)ethyl]amino}(3-pyridyl))carboxamide |
| 0.273 | M + H | 543.1 | N-{[1-(3-aminopropyl)-7-oxoazaperhydroepin-2-yl]methyl}(6-(2-cyanophenyl)-2-{[2-(3-fluorophenyl)ethyl]amino}(3-pyridyl))carboxamide |
| 0.963 | M + H | 495.1 | N-{[(2R)-1-(4-hydroxybutanoyl)pyrrolidin-2-yl]methyl}(2-{[2-(3-fluorophenyl)ethyl]amino}-6-pyrazol-4-yl(3-pyridyl))carboxamide |
| 2.541 | M + H | 499.1 | N-{[(2R)-1-(2-hydroxyacetyl)azetidin-2-yl]methyl}(2-{[2-(3-fluorophenyl)ethyl]amino}-6-[5-(hydroxymethyl)(2-thienyl)](3-pyridyl))carboxamide |
| 0.051 | M + H | 518.1 | N-{[(2R)-1-(2,3-dihydroxypropanoyl)azetidin-2-yl]methyl}(6-(2-cyanophenyl)-2-{[2-(3-fluorophenyl)ethyl]amino}(3-pyridyl))carboxamide |
| 0.525 | M + H | 495.1 | tert-butyl (2R)-2-{[(2-{[2-(3-fluorophenyl)ethyl]amino}-6-pyrazol-4-yl(3-pyridyl))carbonylamino]methyl}azetidinecarboxylate |
| 5.442 | M + H | 395.1 | N-[((2R)azetidin-2-yl)methyl](2-{[2-(3-fluorophenyl)ethyl]amino}-6-pyrazol-4-yl(3-pyridyl))carboxamide |
| 2.482 | M + H | 617.1 | N-[2-((2R)-2-{[(6-(2-cyanophenyl)-2-{[2-(3-fluorophenyl)ethyl]amino}(3-pyridyl))carbonylamino]methyl}azetidinyl)(1S)-1-(hydroxymethyl)-2-oxoethyl](tert-butoxy)carboxamide |
| 0.088 | M + H | 517.1 | N-{[(2R)-1-((2S)-2-amino-3-hydroxypropanoyl)azetidin-2-yl]methyl}(6-(2-cyanophenyl)-2-{[2-(3-fluorophenyl)ethyl]amino}(3-pyridyl))carboxamide |
| 0.439 | M + H | 617.1 | N-[(1R)-2-((2R)-2-{[(6-(2-cyanophenyl)-2-{[2-(3-fluorophenyl)ethyl]amino}(3-pyridyl))carbonylamino]methyl}azetidinyl)-1-(hydroxymethyl)-2-oxoethyl](tert-butoxy)carboxamide |

-continued

| IC50 Arithmetic Mean | Ion | m/z | CHEMICAL NAME |
|---|---|---|---|
| 0.083 | M + H | 517.1 | N-{[(2R)-1-((2R)-2-amino-3-hydroxypropanoyl)azetidin-2-yl]methyl}(6-(2-cyanophenyl)-2-{[2-(3-fluorophenyl)ethyl]amino}(3-pyridyl))carboxamide |
| 1.349 | M + H | 644.1 | N-[2-((2R)-2-([(6-(2-cyanophenyl)-2-{[2-(3-fluorophenyl)ethyl]amino}(3-pyridyl))carbonylamino]methyl}azetidinyl)(1S)-1-(3-aminopropyl)-2-oxoethyl](tert-butoxy)carboxamide |
| 0.274 | M + H | 544.1 | N-{[(2R)-1-((2S)-2,5-diaminopentanoyl)azetidin-2-yl]methyl}(6-(2-cyanophenyl)-2-{[2-(3-fluorophenyl)ethyl]amino}(3-pyridyl))carboxamide |
| 0.559 | M + H | 453.1 | N-{[(2R)-1-(2-hydroxyacetyl)azetidin-2-yl]methyl}(2-{[2-(3-fluorophenyl)ethyl]amino}-6-pyrazol-4-yl(3-pyridyl))carboxamide |
| 2.989 | M + H | 552.1 | N-[((2R)-1-{2-[(tert-butoxy)carbonylamino]acetyl}azetidin-2-yl)methyl](2-{[2-(3-fluorophenyl)ethyl]amino}-6-pyrazol-4-yl(3-pyridyl))carboxamide |
| 0.562 | M + H | 452.1 | N-{[(2R)-1-(2-aminoacetyl)azetidin-2-yl]methyl}(2-{[2-(3-fluorophenyl)ethyl]amino}-6-pyrazol-4-yl(3-pyridyl))carboxamide |
| 0.117 | M + H | 494.0 | N-[(6-bromo(2-pyridyl))methyl](2-{[2-(3-fluorophenyl)ethyl]amino}-6-pyrazol-4-yl(3-pyridyl))carboxamide |
| 0.018 | M + H | 489.1 | N-({6-[(3-aminopropyl)amino](2-pyridyl)}methyl)(2-{[2-(3-fluorophenyl)ethyl]amino}-6-pyrazol-4-yl(3-pyridyl))carboxamide |
| 0.02 | M + H | 475.1 | N-({6-[(2-aminoethyl)amino](2-pyridyl)}methyl)(2-{[2-(3-fluorophenyl)ethyl]amino}-6-pyrazol-4-yl(3-pyridyl))carboxamide |
| 0.039 | M + H | 476.1 | (2-{[2-(3-fluorophenyl)ethyl]amino}-6-pyrazol-4-yl(3-pyridyl))-N-({6-[(2-hydroxyethyl)amino](2-pyridyl)}methyl)carboxamide |
| 0.245 | M + H | 453.1 | methyl (2R)-2-{[(2-{[2-(3-fluorophenyl)ethyl]amino}-6-pyrazol-4-yl(3-pyridyl))carbonylamino]methyl}azetidinecarboxylate |
| 0.505 | M + H | 612.1 | N-[((2R)-1-{3-[(tert-butoxy)carbonylamino]propanoyl}pyrrolidin-2-yl)methyl](5-fluoro-2-{[2-(3-fluorophenyl)ethyl]amino}-6-(1-methylpyrazol-4-yl)(3-pyridyl))carboxamide |
| 0.07 | M + H | 512.1 | N-{[(2R)-1-(3-aminopropanoyl)pyrrolidin-2-yl]methyl}(5-fluoro-2-{[2-(3-fluorophenyl)ethyl]amino}-6-(1-methylpyrazol-4-yl)(3-pyridyl))carboxamide |
| 0.483 | M + H | 626.1 | N-[((2R)-1-{4-[(tert-butoxy)carbonylamino]butanoyl}pyrrolidin-2-yl)methyl](5-fluoro-2-{[2-(3-fluorophenyl)ethyl]amino}-6-(1-methylpyrazol-4-yl)(3-pyridyl))carboxamide |
| 0.087 | M + H | 526.1 | N-{[(2R)-1-(4-aminobutanoyl)pyrrolidin-2-yl]methyl}(5-fluoro-2-{[2-(3-fluorophenyl)ethyl]amino}-6-(1-methylpyrazol-4-yl)(3-pyridyl))carboxamide |
| 0.388 | M + H | 578.1 | N-[(2-{[(tert-butoxy)carbonylamino]methyl}(3-pyridyl))methyl](5-fluoro-2-{[2-(3-fluorophenyl)ethyl]amino}-6-(1-methylpyrazol-4-yl)(3-pyridyl))carboxamide |
| 0.012 | M + H | 478.1 | N-{[2-(aminomethyl)(3-pyridyl)]methyl}(5-fluoro-2-{[2-(3-fluorophenyl)ethyl]amino}-6-(1-methylpyrazol-4-yl)(3-pyridyl))carboxamide |
| 0.322 | M + H | 612.1 | N-[((2R)-1-{3-[(tert-butoxy)carbonylamino]propyl}-5-oxopyrrolidin-2-yl)methyl](5-fluoro-2-{[2-(3-fluorophenyl)ethyl]amino}-6-(1-methylpyrazol-4-yl)(3-pyridyl))carboxamide |
| 0.079 | M + H | 512.1 | N-{[(2R)-1-(3-aminopropyl)-5-oxopyrrolidin-2-yl]methyl}(5-fluoro-2-{[2-(3-fluorophenyl)ethyl]amino}-6-(1-methylpyrazol-4-yl)(3-pyridyl))carboxamide |
| 0.143 | M + H | 529.1 | N-{[(2R)-1-(2,3-dihydroxypropanoyl)pyrrolidin-2-yl]methyl}(5-fluoro-2-{[2-(3-fluorophenyl)ethyl]amino}-6-(1-methylpyrazol-4-yl)(3-pyridyl))carboxamide |
| 0.972 | M + H | 461.1 | (2-{[2-(3-fluorophenyl)ethyl]amino}-6-[1-(2-hydroxyethyl)pyrazol-4-yl](3-pyridyl))-N-(3-pyridylmethyl)carboxamide |

-continued

| IC50 Arithmetic Mean | Ion | m/z | CHEMICAL NAME |
|---|---|---|---|
| 9.038 | M + H | 562.1 | tert-butyl (2R)-2-{[(6-(2-cyanophenyl)-5-fluoro-2-{[2-(3-fluorophenyl)ethyl]amino}(3-pyridyl))carbonylamino]methyl}pyrrolidinecarboxylate |
| 0.103 | M + H | 462.1 | N-[((2R)pyrrolidin-2-yl)methyl](6-(2-cyanophenyl)-5-fluoro-2-{[2-(3-fluorophenyl)ethyl]amino}(3-pyridyl))carboxamide |
| 14.993 | M + H | 590.1 | N-[(2-{[(tert-butoxy)carbonylamino]methyl}(3-pyridyl))methyl](2-{[2-(3-fluorophenyl)ethyl]amino}-6-[1-(2-hydroxyethyl)pyrazol-4-yl](3-pyridyl))carboxamide |
| 0.707 | M + H | 490.1 | N-{[2-(aminomethyl)(3-pyridyl)]methyl}(2-{[2-(3-fluorophenyl)ethyl]amino}-6-[1-(2-hydroxyethyl)pyrazol-4-yl](3-pyridyl))carboxamide |
| 5.358 | M + H | 599.1 | N-[(2-{[(tert-butoxy)carbonylamino]methyl}(3-pyridyl))methyl](6-(2-cyanophenyl)-5-fluoro-2-{[2-(3-fluorophenyl)ethyl]amino}(3-pyridyl))carboxamide |
| 0.006 | M + H | 499.1 | N-{[2-(aminomethyl)(3-pyridyl)]methyl}(6-(2-cyanophenyl)-5-fluoro-2-{[2-(3-fluorophenyl)ethyl]amino}(3-pyridyl))carboxamide |
| 2.786 | M + H | 619.1 | N-[((2R)-1-{2-[(tert-butoxy)carbonylamino]acetyl}pyrrolidin-2-yl)methyl](6-(2-cyanophenyl)-5-fluoro-2-{[2-(3-fluorophenyl)ethyl]amino}(3-pyridyl))carboxamide |
| 0.04 | M + H | 519.1 | N-{[(2R)-1-(2-aminoacetyl)pyrrolidin-2-yl]methyl}(6-(2-cyanophenyl)-5-fluoro-2-{[2-(3-fluorophenyl)ethyl]amino}(3-pyridyl))carboxamide |
| 2.771 | M + H | 633.1 | N-[((2R)-1-{3-[(tert-butoxy)carbonylamino]propanoyl}pyrrolidin-2-yl)methyl](6-(2-cyanophenyl)-5-fluoro-2-{[2-(3-fluorophenyl)ethyl]amino}(3-pyridyl))carboxamide |
| 0.042 | M + H | 533.1 | N-{[(2R)-1-(3-aminopropanoyl)pyrrolidin-2-yl]methyl}(6-(2-cyanophenyl)-5-fluoro-2-{[2-(3-fluorophenyl)ethyl]amino}(3-pyridyl))carboxamide |
| 1.059 | M + H | 647.1 | N-[((2R)-1-{4-[(tert-butoxy)carbonylamino]butanoyl}pyrrolidin-2-yl)methyl](6-(2-cyanophenyl)-5-fluoro-2-{[2-(3-fluorophenyl)ethyl]amino}(3-pyridyl))carboxamide |
| 0.038 | M + H | 547.1 | N-{[(2R)-1-(4-aminobutanoyl)pyrrolidin-2-yl]methyl}(6-(2-cyanophenyl)-5-fluoro-2-{[2-(3-fluorophenyl)ethyl]amino}(3-pyridyl))carboxamide |
| 0.845 | M + H | 633.1 | N-[((2R)-1-{3-[(tert-butoxy)carbonylamino]propyl}-5-oxopyrrolidin-2-yl)methyl](6-(2-cyanophenyl)-5-fluoro-2-{[2-(3-fluorophenyl)ethyl]amino}(3-pyridyl))carboxamide |
| 0.042 | M + H | 533.1 | N-{[(2R)-1-(3-aminopropyl)-5-oxopyrrolidin-2-yl]methyl}(6-(2-cyanophenyl)-5-fluoro-2-{[2-(3-fluorophenyl)ethyl]amino}(3-pyridyl))carboxamide |
| 0.11 | M + H | 550.1 | N-{[(2R)-1-(2,3-dihydroxypropanoyl)pyrrolidin-2-yl]methyl}(6-(2-cyanophenyl)-5-fluoro-2-{[2-(3-fluorophenyl)ethyl]amino}(3-pyridyl))carboxamide |
| 1.953 | M + H | 612.1 | N-[2-((2R)-2-{[(5-fluoro-2-{[2-(3-fluorophenyl)ethyl]amino}-6-(1-methylpyrazol-4-yl)(3-pyridyl))carbonylamino]methyl}pyrrolidinyl)(1S)-1-methyl-2-oxoethyl](tert-butoxy)carboxamide |
| 0.099 | M + H | 512.1 | N-{[(2R)-1-((2S)-2-aminopropanoyl)pyrrolidin-2-yl]methyl}(5-fluoro-2-{[2-(3-fluorophenyl)ethyl]amino}-6-(1-methylpyrazol-4-yl)(3-pyridyl))carboxamide |
| 19.6 | M + H | 755.4 | N-[((2R)-1-{(2S)-2,5-bis[(tert-butoxy)carbonylamino]pentanoyl}pyrrolidin-2-yl)methyl](5-fluoro-2-{[2-(3-fluorophenyl)ethyl]amino}-6-(1-methylpyrazol-4-yl)(3-pyridyl))carboxamide |
| 0.078 | M + H | 555.1 | N-{[(2R)-1-((2S)-2,5-diaminopentanoyl)pyrrolidin-2-yl]methyl}(5-fluoro-2-{[2-(3-fluorophenyl)ethyl]amino}-6-(1-methylpyrazol-4-yl)(3-pyridyl))carboxamide |
| 1.195 | M + H | 628.1 | N-[2-((2R)-2-{[(5-fluoro-2-{[2-(3-fluorophenyl)ethyl]amino}-6-(1-methylpyrazol-4-yl)(3-pyridyl))carbonylamino]methyl}pyrrolidinyl)(1S)-1-(hydroxymethyl)-2-oxoethyl](tert-butoxy)carboxamide |

-continued

| IC50 Arithmetic Mean | Ion | m/z | CHEMICAL NAME |
|---|---|---|---|
| 0.072 | M + H | 528.1 | N-{[(2R)-1-((2S)-2-amino-3-hydroxypropanoyl)pyrrolidin-2-yl]methyl}(5-fluoro-2-{[2-(3-fluorophenyl)ethyl]amino}-6-(1-methylpyrazol-4-yl)(3-pyridyl))carboxamide |
| 0.534 | M + H | 555.1 | methyl 4-((2R)-2-{[(5-fluoro-2-{[2-(3-fluorophenyl)ethyl]amino}-6-(1-methylpyrazol-4-yl)(3-pyridyl))carbonylamino]methyl}pyrrolidinyl)-4-oxobutanoate |
| 0.245 | M + H | 527.1 | N-{[(2R)-1-(4-hydroxybutanoyl)pyrrolidin-2-yl]methyl}(5-fluoro-2-{[2-(3-fluorophenyl)ethyl]amino}-6-(1-methylpyrazol-4-yl)(3-pyridyl))carboxamide |
| 0.75 | M + H | 585.1 | N-[(2-{[(tert-butoxy)carbonylamino]methyl}(3-pyridyl))methyl](5-cyano-2-{[2-(3-fluorophenyl)ethyl]amino}-6-(1-methylpyrazol-4-yl)(3-pyridyl))carboxamide |
| 0.05 | M + H | 485.1 | N-{[2-(aminomethyl)(3-pyridyl)]methyl}(5-cyano-2-{[2-(3-fluorophenyl)ethyl]amino}-6-(1-methylpyrazol-4-yl)(3-pyridyl))carboxamide |
| 1.15 | M + H | 619.1 | N-[3-((5R)-5-{[(5-cyano-2-{[2-(3-fluorophenyl)ethyl]amino}-6-(1-methylpyrazol-4-yl)(3-pyridyl))carbonylamino]methyl}-2-oxopyrrolidinyl)propyl](tert-butoxy)carboxamide |
| 0.31 | M + H | 519.1 | N-{[(2R)-1-(3-aminopropyl)-5-oxopyrrolidin-2-yl]methyl}(5-cyano-2-{[2-(3-fluorophenyl)ethyl]amino}-6-(1-methylpyrazol-4-yl)(3-pyridyl))carboxamide |
| 2.518 | M + H | 548.1 | tert-butyl (2R)-2-{[(5-cyano-2-{[2-(3-fluorophenyl)ethyl]amino}-6-(1-methylpyrazol-4-yl)(3-pyridyl))carbonylamino]methyl}pyrrolidinecarboxylate |
| 0.281 | M + H | 448.1 | N-[((2R)pyrrolidin-2-yl)methyl](5-cyano-2-{[2-(3-fluorophenyl)ethyl]amino}-6-(1-methylpyrazol-4-yl)(3-pyridyl))carboxamide |
| 1.613 | M + H | 633.2 | N-[((2R)-1-{4-[(tert-butoxy)carbonylamino]butanoyl}pyrrolidin-2-yl)methyl](5-cyano-2-{[2-(3-fluorophenyl)ethyl]amino}-6-(1-methylpyrazol-4-yl)(3-pyridyl))carboxamide |
| 0.211 | M + H | 533.2 | N-{[(2R)-1-(4-aminobutanoyl)pyrrolidin-2-yl]methyl}(5-cyano-2-{[2-(3-fluorophenyl)ethyl]amino}-6-(1-methylpyrazol-4-yl)(3-pyridyl))carboxamide |
| 1.122 | M + H | 574.1 | N-[(2-{[(tert-butoxy)carbonylamino]methyl}(3-pyridyl))methyl](2-{[2-(3-fluorophenyl)ethyl]amino}-5-methyl-6-(1-methylpyrazol-4-yl)(3-pyridyl))carboxamide |
| 0.129 | M + H | 474.1 | N-{[2-(aminomethyl)(3-pyridyl)]methyl}(2-{[2-(3-fluorophenyl)ethyl]amino}-5-methyl-6-(1-methylpyrazol-4-yl)(3-pyridyl))carboxamide |
| 1.461 | M + H | 608.2 | N-[((2R)-1-{3-[(tert-butoxy)carbonylamino]propyl}-5-oxopyrrolidin-2-yl)methyl](2-{[2-(3-fluorophenyl)ethyl]amino}-5-methyl-6-(1-methylpyrazol-4-yl)(3-pyridyl))carboxamide |
| 0.577 | M + H | 508.2 | N-{[(2R)-1-(3-aminopropyl)-5-oxopyrrolidin-2-yl]methyl}(2-{[2-(3-fluorophenyl)ethyl]amino}-5-methyl-6-(1-methylpyrazol-4-yl)(3-pyridyl))carboxamide |
| 3.702 | M + H | 537.1 | tert-butyl (2R)-2-{[(2-{[2-(3-fluorophenyl)ethyl]amino}-5-methyl-6-(1-methylpyrazol-4-yl)(3-pyridyl))carbonylamino]methyl}pyrrolidinecarboxylate |
| 0.901 | M + H | 437.1 | N-[((2R)pyrrolidin-2-yl)methyl](2-{[2-(3-fluorophenyl)ethyl]amino}-5-methyl-6-(1-methylpyrazol-4-yl)(3-pyridyl))carboxamide |
| 2.265 | M + H | 622.3 | N-[((2R)-1-{4-[(tert-butoxy)carbonylamino]butanoyl}pyrrolidin-2-yl)methyl](2-{[2-(3-fluorophenyl)ethyl]amino}-5-methyl-6-(1-methylpyrazol-4-yl)(3-pyridyl))carboxamide |
| 0.381 | M + H | 522.2 | N-{[(2R)-1-(4-aminobutanoyl)pyrrolidin-2-yl]methyl}(2-{[2-(3-fluorophenyl)ethyl]amino}-5-methyl-6-(1-methylpyrazol-4-yl)(3-pyridyl))carboxamide |

-continued

| IC50 Arithmetic Mean | Ion | m/z | CHEMICAL NAME |
|---|---|---|---|
| 6.407 | M + H | 534.1 | tert-butyl (2R)-2-{[(5-cyano-2-{[2-(3-fluorophenyl)ethyl]amino}-6-pyrazol-4-yl(3-pyridyl))carbonylamino]methyl}pyrrolidinecarboxylate |
| 0.624 | M + H | 434.1 | N-[((2R)pyrrolidin-2-yl)methyl](5-cyano-2-{[2-(3-fluorophenyl)ethyl]amino}-6-pyrazol-4-yl(3-pyridyl))carboxamide |
| 3.421 | M + H | 619.2 | N-[((2R)-1-{4-[(tert-butoxy)carbonylamino]butanoyl}pyrrolidin-2-yl)methyl](5-cyano-2-{[2-(3-fluorophenyl)ethyl]amino}-6-pyrazol-4-yl(3-pyridyl))carboxamide |
| 0.359 | M + H | 519.2 | N-{[(2R)-1-(4-aminobutanoyl)pyrrolidin-2-yl]methyl}(5-cyano-2-{[2-(3-fluorophenyl)ethyl]amino}-6-pyrazol-4-yl(3-pyridyl))carboxamide |
| 3.506 | M + H | 605.1 | N-[((2R)-1-{3-[(tert-butoxy)carbonylamino]propyl}-5-oxopyrrolidin-2-yl)methyl](5-cyano-2-{[2-(3-fluorophenyl)ethyl]amino}-6-pyrazol-4-yl(3-pyridyl))carboxamide |
| 0.735 | M + H | 505.1 | N-{[(2R)-1-(3-aminopropyl)-5-oxopyrrolidin-2-yl]methyl}(5-cyano-2-{[2-(3-fluorophenyl)ethyl]amino}-6-pyrazol-4-yl(3-pyridyl))carboxamide |
| 1.003 | M + H | 571.1 | N-[(2-{[(tert-butoxy)carbonylamino]methyl}(3-pyridyl))methyl](5-cyano-2-{[2-(3-fluorophenyl)ethyl]amino}-6-pyrazol-4-yl(3-pyridyl))carboxamide |
| 0.058 | M + H | 471.1 | N-{[2-(aminomethyl)(3-pyridyl)]methyl}(5-cyano-2-{[2-(3-fluorophenyl)ethyl]amino}-6-pyrazol-4-yl(3-pyridyl))carboxamide |
| 4.252 | M + H | 595.2 | N-[(2-{[(tert-butoxy)carbonylamino]methyl}(3-pyridyl))methyl](6-(2-cyanophenyl)-2-{[2-(3-fluorophenyl)ethyl]amino}-5-methyl(3-pyridyl))carboxamide |
| 0.158 | M + H | 495.2 | N-{[2-(aminomethyl)(3-pyridyl)]methyl}(6-(2-cyanophenyl)-2-{[2-(3-fluorophenyl)ethyl]amino}-5-methyl(3-pyridyl))carboxamide |
| 5.372 | M + H | 629.2 | N-[3-((5R)-5-{[(6-(2-cyanophenyl)-2-{[2-(3-fluorophenyl)ethyl]amino}-5-methyl(3-pyridyl))carbonylamino]methyl}-2-oxopyrrolidinyl)propyl](tert-butoxy)carboxamide |
| 1.226 | M + H | 529.1 | N-{[(2R)-1-(3-aminopropyl)-5-oxopyrrolidin-2-yl]methyl}(6-(2-cyanophenyl)-2-{[2-(3-fluorophenyl)ethyl]amino}-5-methyl(3-pyridyl))carboxamide |
| 15.521 | M + H | 389.0 | methyl 5-chloro-2-{[2-(3-fluorophenyl)ethyl]amino}-6-(1-methylpyrazol-4-yl)pyridine-3-carboxylate |
| 0.414 | M + H | 594.1 | N-[(2-{[(tert-butoxy)carbonylamino]methyl}(3-pyridyl))methyl](5-chloro-2-{[2-(3-fluorophenyl)ethyl]amino}-6-(1-methylpyrazol-4-yl)(3-pyridyl))carboxamide |
| 0.03 | M + H | 494.0 | N-{[2-(aminomethyl)(3-pyridyl)]methyl}(5-chloro-2-{[2-(3-fluorophenyl)ethyl]amino}-6-(1-methylpyrazol-4-yl)(3-pyridyl))carboxamide |
| 0.443 | M + H | 628.2 | N-[((2R)-1-{3-[(tert-butoxy)carbonylamino]propyl}-5-oxopyrrolidin-2-yl)methyl](5-chloro-2-{[2-(3-fluorophenyl)ethyl]amino}-6-(1-methylpyrazol-4-yl)(3-pyridyl))carboxamide |
| 0.16 | M + H | 528.1 | N-{[(2R)-1-(3-aminopropyl)-5-oxopyrrolidin-2-yl]methyl}(5-chloro-2-{[2-(3-fluorophenyl)ethyl]amino}-6-(1-methylpyrazol-4-yl)(3-pyridyl))carboxamide |
| 1.601 | M + H | 557.1 | tert-butyl (2R)-2-{[(5-chloro-2-{[2-(3-fluorophenyl)ethyl]amino}-6-(1-methylpyrazol-4-yl)(3-pyridyl))carbonylamino]methyl}pyrrolidinecarboxylate |
| 0.167 | M + H | 457.1 | N-[((2R)pyrrolidin-2-yl)methyl](5-chloro-2-{[2-(3-fluorophenyl)ethyl]amino}-6-(1-methylpyrazol-4-yl)(3-pyridyl))carboxamide |
| 0.683 | M + H | 642.2 | N-[((2R)-1-{4-[(tert-butoxy)carbonylamino]butanoyl}pyrrolidin-2-yl)methyl](5-chloro-2-{[2-(3-fluorophenyl)ethyl]amino}-6-(1-methylpyrazol-4-yl)(3-pyridyl))carboxamide |

-continued

| IC50 Arithmetic Mean | Ion | m/z | CHEMICAL NAME |
|---|---|---|---|
| 0.047 | M + H | 542.1 | N-{[(2R)-1-(4-aminobutanoyl)pyrrolidin-2-yl]methyl}(5-chloro-2-{[2-(3-fluorophenyl)ethyl]amino}-6-(1-methylpyrazol-4-yl)(3-pyridyl))carboxamide |
| 4.501 | M + H | 515.2 | N-{3-[(tert-butoxy)carbonylamino]propyl}(5-fluoro-2-{[2-(3-fluorophenyl)ethyl]amino}-6-(1-methylpyrazol-4-yl)(3-pyridyl))carboxamide |
| 3.957 | M + H | 415.1 | N-(3-aminopropyl)(5-fluoro-2-{[2-(3-fluorophenyl)ethyl]amino}-6-(1-methylpyrazol-4-yl)(3-pyridyl))carboxamide |
| 0.1 | M + H | 458.1 | methyl (2R)-3-[(5-fluoro-2-{[2-(3-fluorophenyl)ethyl]amino}-6-(1-methylpyrazol-4-yl)(3-pyridyl))carbonylamino]-2-methylpropanoate |
| 3.841 | M + H | 444.1 | (2R)-3-[(5-fluoro-2-{[2-(3-fluorophenyl)ethyl]amino}-6-(1-methylpyrazol-4-yl)(3-pyridyl))carbonylamino]-2-methylpropanoic acid |
| 0.768 | M + H | 572.2 | 2-[(tert-butoxy)carbonylamino]-N-{3-[(5-fluoro-2-{[2-(3-fluorophenyl)ethyl]amino}-6-(1-methylpyrazol-4-yl)(3-pyridyl))carbonylamino]propyl}acetamide |
| 2.494 | M + H | 472.1 | 2-amino-N-{3-[(5-fluoro-2-{[2-(3-fluorophenyl)ethyl]amino}-6-(1-methylpyrazol-4-yl)(3-pyridyl))carbonylamino]propyl}acetamide |
| 2.617 | M + H | 457.1 | N-{3-[(5-fluoro-2-{[2-(3-fluorophenyl)ethyl]amino}-6-(1-methylpyrazol-4-yl)-3-pyridyl)carbonylamino]propyl}acetamide |
| 0.05 | M + H | 430.1 | N-((2R)-3-hydroxy-2-methylpropyl)(5-fluoro-2-{[2-(3-fluorophenyl)ethyl]amino}-6-(1-methylpyrazol-4-yl)(3-pyridyl))carboxamide |
| 0.089 | M + H | 443.1 | N-((2R)-2-carbamoylpropyl)(5-fluoro-2-{[2-(3-fluorophenyl)ethyl]amino}-6-(1-methylpyrazol-4-yl)(3-pyridyl))carboxamide |
| 0.13 | M + H | 457.1 | (2R)-3-[(5-fluoro-2-{[2-(3-fluorophenyl)ethyl]amino}-6-(1-methylpyrazol-4-yl)(3-pyridyl))carbonylamino]-2-methyl-N-methylpropanamide |
| 0.024 | M + H | 424.1 | (5-fluoro-2-{[2-(3-fluorophenyl)ethyl]amino}-6-pyrazol-4-yl(3-pyridyl))-N-(pyrazol-3-ylmethyl)carboxamide |
| 0.02 | M + H | 438.1 | (5-fluoro-2-{[2-(3-fluorophenyl)ethyl]amino}-6-(1-methylpyrazol-4-yl)(3-pyridyl))-N-(pyrazol-3-ylmethyl)carboxamide |
| 0.118 | M + H | 455.2 | N-((2R)-4-diazo-2-methyl-4-azabut-4-enyl)(5-fluoro-2-{[2-(3-fluorophenyl)ethyl]amino}-6-(1-methylpyrazol-4-yl)(3-pyridyl))carboxamide |
| 10.538 | M + H | 412.1 | 5-fluoro-2-{[2-(3-fluorophenyl)ethyl]amino}-6-(1-methylpyrazol-4-yl)(3-pyridyl) 3-methylazetidinyl ketone |
| 1.05 | M + H | 429.2 | N-((2S)-3-amino-2-methylpropyl)(5-fluoro-2-{[2-(3-fluorophenyl)ethyl]amino}-6-(1-methylpyrazol-4-yl)(3-pyridyl))carboxamide |
| 0.373 | M + H | 586.5 | N-{(2R)-3-[(5-fluoro-2-{[2-(3-fluorophenyl)ethyl]amino}-6-(1-methylpyrazol-4-yl)(3-pyridyl))carbonylamino]-2-methylpropyl}-2-[(tert-butoxy)carbonylamino]acetamide |
| 0.152 | M + H | 486.2 | N-{(2R)-3-[(5-fluoro-2-{[2-(3-fluorophenyl)ethyl]amino}-6-(1-methylpyrazol-4-yl)(3-pyridyl))carbonylamino]-2-methylpropyl}-2-aminoacetamide |
| 0.105 | M + H | 487.1 | N-{(2R)-3-[(5-fluoro-2-{[2-(3-fluorophenyl)ethyl]amino}-6-(1-methylpyrazol-4-yl)(3-pyridyl))carbonylamino]-2-methylpropyl}-2-hydroxyacetamide |
| 0.525 | M + H | 527.1 | tert-butyl (2R)-2-{[(5-fluoro-2-{[2-(3-fluorophenyl)ethyl]amino}-6-(1-methylpyrazol-4-yl)(3-pyridyl))carbonylamino]methyl}azetidinecarboxylate |
| 1.582 | M + H | 427.1 | N-[((2R)azetidin-2-yl)methyl](5-fluoro-2-{[2-(3-fluorophenyl)ethyl]amino}-6-(1-methylpyrazol-4-yl)(3-pyridyl))carboxamide |
| 0.436 | M + H | 584.3 | N-[((2R)-1-{2-[(tert-butoxy)carbonylamino]acetyl}azetidin-2-yl)methyl](5-fluoro-2-{[2-(3-fluorophenyl)ethyl]amino}-6-(1-methylpyrazol-4-yl)(3-pyridyl))carboxamide |
| 0.05 | M + H | 484.1 | N-{[(2R)-1-(2-aminoacetyl)azetidin-2-yl]methyl}(5-fluoro-2-{[2-(3-fluorophenyl)ethyl]amino}-6-(1-methylpyrazol-4-yl)(3-pyridyl))carboxamide |

-continued

| IC50 Arithmetic Mean | Ion | m/z | CHEMICAL NAME |
|---|---|---|---|
| 0.122 | M + H | 612.3 | N-[((2R)-1-{4-[(tert-butoxy)carbonylamino]butanoyl}azetidin-2-yl)methyl](5-fluoro-2-{[2-(3-fluorophenyl)ethyl]amino}-6-(1-methylpyrazol-4-yl)(3-pyridyl))carboxamide |
| 0.04 | M + H | 512.1 | N-{[(2R)-1-(4-aminobutanoyl)azetidin-2-yl]methyl}(5-fluoro-2-{[2-(3-fluorophenyl)ethyl]amino}-6-(1-methylpyrazol-4-yl)(3-pyridyl))carboxamide |
| 0.047 | M + H | 485.2 | N-{[(2R)-1-(2-hydroxyacetyl)azetidin-2-yl]methyl}(5-fluoro-2-{[2-(3-fluorophenyl)ethyl]amino}-6-(1-methylpyrazol-4-yl)(3-pyridyl))carboxamide |
| 0.141 | M + H | 458.1 | methyl (2S)-3-[(5-fluoro-2-{[2-(3-fluorophenyl)ethyl]amino}-6-(1-methylpyrazol-4-yl)(3-pyridyl))carbonylamino]-2-methylpropanoate |
| 0.09 | M + H | 430.1 | N-((2S)-3-hydroxy-2-methylpropyl)(5-fluoro-2-{[2-(3-fluorophenyl)ethyl]amino}-6-(1-methylpyrazol-4-yl)(3-pyridyl))carboxamide |
| 0.059 | M + H | 416.1 | N-((2R)-3-hydroxy-2-methylpropyl)(5-fluoro-2-{[2-(3-fluorophenyl)ethyl]amino}-6-pyrazol-4-yl(3-pyridyl))carboxamide |
| 0.073 | M + H | 444.1 | methyl (2R)-3-[(5-fluoro-2-{[2-(3-fluorophenyl)ethyl]amino}-6-pyrazol-4-yl(3-pyridyl))carbonylamino]-2-methylpropanoate |
| 0.186 | M + H | 461.1 | methyl (2R)-3-[(6-(2-cyanophenyl)-2-{[2-(3-fluorophenyl)ethyl]amino}(3-pyridyl))carbonylamino]-2-methylpropanoate |
| 0.061 | M + H | 433.2 | N-((2R)-3-hydroxy-2-methylpropyl)(6-(2-cyanophenyl)-2-{[2-(3-fluorophenyl)ethyl]amino}(3-pyridyl))carboxamide |
| 2.226 | M + H | 486.2 | N-[(2,2-dimethyl(1,3-dioxan-5-yl))methyl](5-fluoro-2-{[2-(3-fluorophenyl)ethyl]amino}-6-(1-methylpyrazol-4-yl)(3-pyridyl))carboxamide |
| 0.134 | M + H | 446.2 | (5-fluoro-2-{[2-(3-fluorophenyl)ethyl]amino}-6-(1-methylpyrazol-4-yl)(3-pyridyl))-N-[3-hydroxy-2-(hydroxymethyl)propyl]carboxamide |
| 0.927 | M + H | 472.2 | N-[(2,2-dimethyl(1,3-dioxan-5-yl))methyl](5-fluoro-2-{[2-(3-fluorophenyl)ethyl]amino}-6-pyrazol-4-yl(3-pyridyl))carboxamide |
| 0.215 | M + H | 432.2 | (5-fluoro-2-{[2-(3-fluorophenyl)ethyl]amino}-6-pyrazol-4-yl(3-pyridyl))-N-[3-hydroxy-2-(hydroxymethyl)propyl]carboxamide |
| 1.023 | M + H | 489.2 | N-[(2,2-dimethyl(1,3-dioxan-5-yl))methyl](6-(2-cyanophenyl)-2-{[2-(3-fluorophenyl)ethyl]amino}(3-pyridyl))carboxamide |
| 0.209 | M + H | 449.2 | (6-(2-cyanophenyl)-2-{[2-(3-fluorophenyl)ethyl]amino}(3-pyridyl))-N-[3-hydroxy-2-(hydroxymethyl)propyl]carboxamide |
| 0.117 | M + H | 472.1 | methyl (2R)-2-{[(5-fluoro-2-{[2-(3-fluorophenyl)ethyl]amino}-6-(1-methylpyrazol-4-yl)(3-pyridyl))carbonylamino]methyl}butanoate |
| 0.039 | M + H | 444.1 | N-((2R)-2-ethyl-3-hydroxypropyl)(5-fluoro-2-{[2-(3-fluorophenyl)ethyl]amino}-6-(1-methylpyrazol-4-yl)(3-pyridyl))carboxamide |
| 0.117 | M + H | 458.1 | methyl (2R)-2-{[(5-fluoro-2-{[2-(3-fluorophenyl)ethyl]amino}-6-pyrazol-4-yl(3-pyridyl))carbonylamino]methyl}butanoate |
| 0.052 | M + H | 430.1 | N-((2R)-2-ethyl-3-hydroxypropyl)(5-fluoro-2-{[2-(3-fluorophenyl)ethyl]amino}-6-pyrazol-4-yl(3-pyridyl))carboxamide |
| 90.761 | M + H | 559.2 | methyl (2R)-2-[(tert-butoxy)carbonylamino]-3-[(5-fluoro-2-{[2-(3-fluorophenyl)ethyl]amino}-6-(1-methylpyrazol-4-yl)(3-pyridyl))carbonylamino]propanoate |
| 0.568 | M + H | 459.2 | methyl (2R)-2-amino-3-[(5-fluoro-2-{[2-(3-fluorophenyl)ethyl]amino}-6-(1-methylpyrazol-4-yl)(3-pyridyl))carbonylamino]propanoate |
| 25.925 | M + H | 531.2 | N-((1R)-1-{[(5-fluoro-2-{[2-(3-fluorophenyl)ethyl]amino}-6-(1-methylpyrazol-4-yl)(3-pyridyl))carbonylamino]methyl}-2-hydroxyethyl)(tert-butoxy)carboxamide |
| 1.258 | M + H | 431.2 | N-((2R)-2-amino-3-hydroxypropyl)(5-fluoro-2-{[2-(3-fluorophenyl)ethyl]amino}-6-(1-methylpyrazol-4-yl)(3-pyridyl))carboxamide |

-continued

| IC50 Arithmetic Mean | Ion | m/z | CHEMICAL NAME |
|---|---|---|---|
| 57.166 | M + H | 517.2 | N-((1R)-1-{[(5-fluoro-2-{[2-(3-fluorophenyl)ethyl]amino}-6-pyrazol-4-yl(3-pyridyl))carbonylamino]methyl}-2-hydroxyethyl)(tert-butoxy)carboxamide |
| 1.825 | M + H | 417.2 | N-((2R)-2-amino-3-hydroxypropyl)(5-fluoro-2-{[2-(3-fluorophenyl)ethyl]amino}-6-pyrazol-4-yl(3-pyridyl))carboxamide |
| 0.307 | M + H | 432.1 | N-(2,3-dihydroxypropyl)(5-fluoro-2-{[2-(3-fluorophenyl)ethyl]amino}-6-(1-methylpyrazol-4-yl)(3-pyridyl))carboxamide |
| 0.448 | M + H | 418.1 | N-(2,3-dihydroxypropyl)(5-fluoro-2-{[2-(3-fluorophenyl)ethyl]amino}-6-pyrazol-4-yl(3-pyridyl))carboxamide |
| 86.027 | M + H | 336.1 | methyl (2R)-3-{[2-amino-5-fluoro-6-(1-methylpyrazol-4-yl)(3-pyridyl)]carbonylamino}-2-methylpropanoate |
| 0.141 | M + H | 513.1 | N-{[(2R)-1-(2-hydroxy-2-methylpropanoyl)azetidin-2-yl]methyl}(5-fluoro-2-{[2-(3-fluorophenyl)ethyl]amino}-6-(1-methylpyrazol-4-yl)(3-pyridyl))carboxamide |
| 0.289 | M + H | 513.1 | tert-butyl (2R)-2-{[(5-fluoro-2-{[2-(3-fluorophenyl)ethyl]amino}-6-pyrazol-4-yl(3-pyridyl))carbonylamino]methyl}azetidinecarboxylate |
| 0.046 | M + H | 471.1 | N-{[(2R)-1-(2-hydroxyacetyl)azetidin-2-yl]methyl}(5-fluoro-2-{[2-(3-fluorophenyl)ethyl]amino}-6-pyrazol-4-yl(3-pyridyl))carboxamide |
| 0.466 | M + H | 413.1 | N-[((2R)azetidin-2-yl)methyl](5-fluoro-2-{[2-(3-fluorophenyl)ethyl]amino}-6-pyrazol-4-yl(3-pyridyl))carboxamide |
| 0.019 | M + H | 456.1 | N-{[6-(aminomethyl)(2-pyridyl)]methyl}(2-{[2-(3-fluorophenyl)ethyl]amino}-6-phenyl(3-pyridyl))carboxamide |
| 0.009 | M + H | 481.1 | N-{[6-(aminomethyl)(2-pyridyl)]methy}(6-(2-cyanophenyl)-2-{[2-(3-fluorophenyl)ethyl]amino}(3-pyridyl))carboxamide |
| 0.104 | M + H | 418.1 | N-(carbamoylmethyl)(6-(2-cyanophenyl)-2-{[2-(3-fluorophenyl)ethyl]amino}(3-pyridyl))carboxamide |
| 0.099 | M + H | 432.1 | N-(2-carbamoylethyl)(6-(2-cyanophenyl)-2-{[2-(3-fluorophenyl)ethyl]amino}(3-pyridyl))carboxamide |
| 0.102 | M + H | 432.1 | 2-[(6-(2-cyanophenyl)-2-{[2-(3-fluorophenyl)ethyl]amino}(3-pyridyl))carbonylamino]-N-methylacetamide |
| 5.614 | M + H | 458.1 | N-((3S)-2-oxo(3-piperidyl))(6-(2-cyanophenyl)-2-{[2-(3-fluorophenyl)ethyl]amino}(3-pyridyl))carboxamide |

Example 14

In Vitro Model of Dose Dependent Smooth Muscle Myosin ATPase Modulation

Screening assays were performed using a pyruvate kinase and lactate dehydrogenase-coupled ATPase assay containing the following reagents: Potassium PIPES (50 mM), MgCl$_2$ (3 mM), KCl (100 mM), ATP (0.15 mM), DTT (1 mM), BSA (0.1 mg/ml), NADH (0.5 mM), PEP (1.5 mM), pyruvate kinase (4 U/ml), lactate dehydrogenase (8 U/ml), and antifoam (50 ppm) (concentrations expressed are final assay concentrations). The pH was adjusted to 6.80 at 22° C. by addition of potassium hydroxide. Lead optimization assays were performed with a more sensitive pyruvate kinase/horseradish peroxidase/pyruvate oxidase-coupled ATPase assay containing the following reagents: Potassium PIPES (12 mM), MgCl$_2$ (2 mM), KCl (100 mM), ATP (0.15 mM), BSA (0.05 mg/ml), potassium phosphate (2 mM), amplex red (0.1 mM), PEP (0.1 mM), pyruvate kinase (4 U/ml), horseradish peroxidase (0.5 U/ml), pyruvate oxidase (0.5 U/ml), and antifoam (50 ppm) (concentrations expressed are final assay concentrations). The pH was adjusted to 7.00 at 22° C. by addition of potassium hydroxide.

The protein components specific to this assay are chicken gizzard smooth muscle myosin subfragment-1 that has been chemically crosslinked to either cardiac or skeletal actin using an excess of 1-Ethyl-3-[3-dimethylaminopropyl]carbodiimide hydrochloride and N-hydroxysuccinimide. The exact concentration of the crosslinked smooth muscle myosin in the assay is determined empirically, by titration to achieve a desired rate of ATP hydrolysis. The concentration varies between protein preparations due to variations in the fraction of active molecules in each preparation.

Compound dose response assays are performed by first preparing a dilution series of test compound, each with an assay mixture containing potassium PIPES, MgCl$_2$, KCl, ATP, BSA, potassium phosphate, amplex red, PEP, crosslinked smooth muscle actomyosin (subfragment-1), antifoam, and water. The assay is started by adding an equal volume of solution containing potassium Pipes, MgCl$_2$, KCl, BSA, potassium phosphate, pyruvate kinase, horseradish peroxidase, pyruvate oxidase, antifoam, and water. ATP hydrolysis is monitored by measuring the fluorescence of amplex red (excitation at 480 nm, emission at 615 nm). The resulting dose response curve is fit by the 4 parameter equation $y = \text{Bottom} + ((\text{Top} - \text{Bottom})/(1 + ((IC_{50}/X)^{\text{Hill}})))$. The $IC_{50}$ is defined as the concentration at which ATPase activity is midway between the top and bottom of the dose response curve.

Certain chemical entities described herein have an $IC_{50}$ less than 10 µM; for example, less than 1 µM.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of Formula III

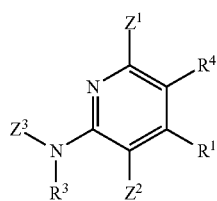

Formula III or a pharmaceutically acceptable salt thereof,
wherein
$R^1$ and $R^4$ are independently chosen from hydrogen, alkyl, cyano, and halo;
$Z^1$ is optionally substituted heteroaryl;
$Z^2$ is —C(O)NR$^2$R$^5$, wherein $R^2$ is optionally substituted alkyl and $R^5$ is chosen from hydrogen and alkyl;
$Z^3$ is chosen from optionally substituted aralkyl and optionally substituted heteroaralkyl; and
$R^3$ is chosen from hydrogen and alkyl.

2. The compound of claim 1 wherein $Z^1$ is chosen from 1H-pyrazol-3-yl; 1H-pyrazol-4-yl; 1H-tetrazol-5-yl; 1-methyl-1H-pyrazol-4-yl; 1-methyl-1H-pyrazol-5-yl; 2-aminomethylthiophen-5-yl; 2-cyanothiophen-3-yl; 2-formylthiophen-3-yl; 2-formylthiophen-4-yl; 2H-pyrrol-1 (5H)-yl; 2-hydroxymethylthiophen-3-yl; 2-hydroxymethylthiophen-4-yl; 2-hydroxymethylthiophen-5-yl; 3-aminomethylthiophen-2 yl; 3-cyano-1-methyl-1H-pyrazol-4-yl; 3-cyanothiophen-4-yl; 3-formylthiophen-2-yl; 3-hydroxymethylthiophen-2-yl; 4-methylthiophen-2-yl; 4-methylthiophen-3-yl; 5-(1-hydroxyeth-1-yl)-thiophen-2-yl; 5-acetylthiophen-5-yl; 5-cyano-1H-pyrazol-4-yl; 5-cyano-1-methyl-1H-pyrazol-4-yl; 5-cyanothiophen-2-yl; 5-formylthiophen-2-yl; 5-hydroxymethylthiophen-2-yl; isoxazol-4-yl; pyridin-2-yl; pyridin-3-yl; pyridin-4-yl; thiazol-2-yl; thiophen-2-yl; and thiophen-3-yl.

3. The compound of claim 1 wherein $Z^1$ is chosen from 1H-pyrazol-3-yl; 1H-pyrazol-4-yl; 1H-tetrazol-5-yl; 1-methyl-1H-pyrazol-4-yl; 1-methyl-1H-pyrazol-5-yl; 2-(hydroxymethyl)thiophen-3-yl; 2,2'-bipyridine; 2,3'-bipyridine; 2,4'-bipyridine; 2-cyanothiophen-3-yl; 2-formylthiophen-3-yl; 3-(hydroxymethyl)thiophen-2-yl; 3-cyano-1-methyl-1H-pyrazol-4-yl; 3-formylthiophen-2-yl; 4-cyanothiophen-3-yl; 4-methylthiophen-2-yl; 4-methylthiophen-3-yl; 5-(1-hydroxyethyl)thiophen-2-yl; 5-(aminomethyl)thiophen-2-yl; 5-(hydroxymethyl)thiophen-2-yl; 5-(hydroxymethyl)thiophen-3-yl; 5-acetylthiophen-2-yl; 5-cyano-1H-pyrazol-4-yl; 5-cyano-1-methyl-1H-pyrazol-4-yl; 5-cyanothiophen-2-yl; 5-formylthiophen-2-yl; 5-formylthiophen-3-yl; 3-(aminomethyl)thiophen-2-yl; isoxazol-4-yl; thiazol-2-yl; thiophen-2-yl; and thiophen-3-yl.

4. The compound of claim 1 wherein $R^3$ is chosen from hydrogen and lower alkyl.

5. The compound of claim 4 wherein $R^3$ is chosen from hydrogen and methyl.

6. The compound of claim 4 wherein $R^3$ is hydrogen.

7. The compound of claim 1 wherein $R^4$ is chosen from hydrogen, cyano, chloro, bromo, fluoro, and methyl.

8. The compound of claim 7 wherein $R^4$ is chosen from hydrogen, cyano, and fluoro.

9. The compound of claim 8 wherein $R^4$ is hydrogen.

10. The compound of claim 1 wherein $R^2$ is chosen from optionally substituted methyl, optionally substituted ethyl, optionally substituted propyl, optionally substituted butyl, optionally substituted pentyl, and optionally substituted hexyl, wherein each optionally substituted group is optionally substituted with one, two or three groups selected from optionally substituted aryl, optionally substituted heteroaryl, optionally substituted heterocycloalkyl, optionally substituted cycloalkyl, optionally substituted aminocarbonyl, optionally substituted amino, hydroxy, carboxyl, optionally substituted alkoxycarbonyl, and optionally substituted alkoxy.

11. The compound of claim 1 wherein $R^2$ is chosen from methyl and ethyl, wherein the methyl and ethyl groups are substituted with one or two groups selected from optionally substituted aryl, optionally substituted heteroaryl, optionally substituted heterocycloalkyl, optionally substituted cycloalkyl, optionally substituted aminocarbonyl, optionally substituted amino, hydroxy, carboxyl, optionally substituted alkoxycarbonyl, and optionally substituted alkoxy.

12. The compound of claim 1 wherein $R^2$ is chosen from (1-(2-aminoethyl)-1H-pyrazol-3-yl)methyl; (1-(methylsulfonyl)piperidin-3-yl)methyl; (1-acetylpiperidin-3-yl)methyl; (1-acetylpyrrolidin-2-yl)methyl; (1H-imidazol-2-yl) methyl;

(1H-pyrazol-3-yl)methyl; (1-methyl-1H-pyrazol-3-yl)methyl; (1-methyl-1H-pyrazol-5-yl)methyl; (2-(aminocarbonyl)ethylamino)carbonylmethyl; (2-(aminomethyl)pyridin-3-yl)methyl; (2-(carboxy)ethylamino) carbonylmethyl; (2-(dimethylamino)ethylamino) carbonylmethyl; (2-(hydroxy)ethylamino) carbonylmethyl; (2-(methylamino)ethylamino) carbonylmethyl; (2-(N-methyl-N-(t-butoxycarbonyl)-amino)ethylamino)carbonylmethyl; (2-oxopiperidin-3-yl)methyl; (3-(dimethylamino)propylamino) carbonylmethyl; (3-(hydroxy)ethylamino) carbonylmethyl; (3-(t-butoxycarbonylamino) propylamino)carbonylmethyl; (4-(aminomethyl) pyridin-2-yl)methyl; (5-(aminomethyl)pyridin-2-yl) methyl; (6-((1,3-dioxoisoindolin-2-yl)methyl)pyridin-2-yl)methyl; (6-(2-aminoethylamino)pyridin-2-yl) methyl; (6-(3-aminopropylamino)pyridin-2-yl)methyl; (6-(aminomethyl)pyridin-2-yl)methyl; (6-(hydroxymethyl)pyridin-2-yl)methyl; (6-bromopyridin-2-yl)methyl; (methylsulfonamido)carbonylmethyl; (pyridin-2-yl)ethylamino; 1-(2-(tert-butoxycarbonylamino)ethyl)-1H-pyrazol-3-ylmethyl; 1-(2-(tert-butoxycarbonylamino)ethyl)-1H-pyrazol-5-ylmethyl; 1-(aminocarbonyl)-2-(amino)-eth-1-yl; 1-(aminocarbonyl)-3-(amino)-propyl; 1-(aminocarbonyl)-4-(amino)-butyl; 1-(aminocarbonyl)-4-(benzyloxycarbonylamino)-pentyl; 1-(aminocarbonyl)-5-(amino)-pentyl; 1-(aminocarbonyl)eth-1-yl; 1-(carboxy)-2-(amino)eth-1-yl; 1-(dimethylaminocarbonyl)-2-(amino)-eth-1-yl; 1-(hydroxy)-2-(aminocarbonylmethylamino)eth-1-yl; 1-(hydroxy)-2-(ethoxycarbonylmethylamino)eth-1-yl; 1-(hydroxy)-2-(pyridin-2-ylmethylamino)eth-1-yl;

1-(methoxycarbonyl)-2-(amino)-eth-1-yl; 1-(methoxycarbonyl)-2-(t-butoxycarbonylamino)-eth-1-yl; 1-(methoxycarbonyl)eth-1-yl; 1-(methylaminocarbonyl)-2-(amino)-eth-1-yl (2 occ); 1-(methylaminocarbonyl)eth-1-yl; 1-aminocarbonyl-2-hydroxy-eth-1-yl; 1-methoxycarbonyl-2-hydroxy-eth-1-yl; 2-(2-aminoethoxy)ethyl; 2-(2-aminoethyl)-pyridin-6-ylmethyl; 2-(2-aminoethylamino)ethyl; 2-(3-fluorophenyl)ethyl; 2-(3-methoxycarbonyl)ethyl; 2-(6-(aminomethyl)pyridin-2-O)ethyl; 2-(acetylamino)ethyl; 2-(amino)ethyl; 2-(aminocarbonyl)-2-(acetylamino)-eth-1-yl; 2-(aminocarbonyl)-2-(amino)-eth-1-yl; 2-(aminocarbonyl)ethyl; 2-(aminomethyl)pyridin-5-ylmethyl; 2-(carboxy)-2-(amino)-eth-1-yl; 2-(dimethylamino)ethyl; 2-(dimethylaminocarbonyl)-2-(amino)-eth-1-yl; 2-(ethoxycarbonyl)ethyl; 2-(methoxycarbonyl)-2-(acetylamino)-eth-1-yl; 2-(methoxycarbonyl)-2-(amino)eth-1-yl; 2-(methoxycarbonylamino)ethyl; 2-(methylamino)ethyl; 2-(methylaminocarbonyl)-2-(acetylamino)-eth-1-yl; 2-(methylaminocarbonyl)-2-(amino)eth-1-yl; 2-(methylsulfonamido)ethyl; 2-(methyoxycarbonyl)-2-(amino)eth-1-yl; 2-(N-(t-butoxycarbonyl)-N-(methyl)-amino)ethyl; 2-(piperazin-1-yl)ethyl; 2-(pyrazin-2-yl)ethyl; 2-(pyridin-2-yl)ethyl; 2-(pyridin-3-yl)ethyl; 2-(t-butoxycarbonylaminomethyl)pyridin-3-ylmethyl; 2-(t-butoxycarbonylaminomethyl)pyridin-6-ylmethyl; 2-(trifluoromethyl)-pyridin-6-ylmethyl; 2-aminopyridin-3-ylmethyl; 2-aminopyridin-5-ylmethyl; 2-chloropyridin-5-ylmethyl; 2-cyanopyridin-5-ylmethyl; 2-hydroxy-3-amino-prop-1-yl; 2-hydroxyethyl; 2-methoxyeth-1-yl; 2-methoxypyridin-3-ylmethyl; 2-methoxypyridin-5-ylmethyl; 2-methylpyridin-3-ylmethyl; 2-methylpyridin-5-ylmethyl; 2-methylpyridin-6-ylmethyl; 3-(2-aminoethyl)cyclohexyl)methyl; 3-(4-methylpiperazin-1-yl)propyl; 3-(amino)-3-(methylaminocarbonyl)prop-1-yl; 3-(aminocarbonyl)propyl; 3-(aminomethyl)benzyl; 3-(aminomethyl)pyridin-2-ylmethyl; 3-(methoxycarbonyl)propyl; 3-(methylaminocarbonyl)propyl; 3-(trifluoromethyl)-pyridin-2-ylmethyl; 3,4-difluorobenzyl; 3-aminomethylpyridin-4-ylmethyl; 3-aminopropyl; 3-carbamoylcyclopentyl; 3-carboxypropyl; 3-hydroxypropyl; 3-methoxypropyl; 4-(aminomethyl)-pyridin-2-ylmethyl; 4-(N,N-dimethylamino)pyridin-3-ylmethyl; 4-(t-butoxycarbonylamino)-morpholinomethyl; 4-aminobutyl; 4-aminomethylpyridin-3-ylmethyl; 4-cyanobenzyl; 4-fluorobenzyl; 4-methylaminopyridin-3-ylmethyl; 4-methylbenzyl; 4-morpholinopyridin-3-ylmethyl; 4-piperazinylpyridin-3-ylmethyl; 5-((bis(dimethylamino)methylamino)methyl)pyridin-3-ylmethyl; 5-(aminomethyl)pyridin-2-ylmethyl; 5-(aminomethyl)pyridin-3-ylmethyl; 5-(hydroxymethyl)pyridin-3-ylmethyl; 5-(t-butoxycarbonylaminomethyl)-pyridin-2-ylmethyl; 5-(trifluoromethyl)-pyridin-2-ylmethyl; 5-aminopentyl; 5-aminopyridin-2-ylmethyl; 6-((bis(dimethylamino)methyleneamino)methyl)pyridin-2-yl)methyl; 6-(4-acetylpiperazin-1-yl)pyridin-3-ylmethyl); 6-(aminomethyl)pyridin-2-yl)methyl; 6-aminohexyl; aminocarbonylmethyl; benzyl; cyclopropylmethyl; dimethylaminocarbonylmethyl; isopropyl; isoxazol-5-ylmethyl; methoxycarbonylmethyl; methyl; methylaminocarbonylmethyl; oxazol-2-ylmethyl; piperidin-4-ylmethyl; pyrazin-2-ylmethyl; pyridin-2-ylmethyl; pyridin-2-ylmethyl-N-oxide; pyridin-3-ylmethyl; pyridin-3-ylmethyl-N-oxide; pyridin-4-ylmethyl; thiophen-2-ylmethyl; and thiophen-3-ylmethyl.

13. The compound of claim 1 wherein $Z^3$ is —$(CH_2)_rR^{20}$ wherein r is chosen from 1, 2, and 3 and $R^{20}$ is chosen from optionally substituted aryl and optionally substituted heteroaryl.

14. The compound of claim 13 wherein $Z^3$ is chosen from 2-(3-methylphenyl)ethyl, 2-(1H-imidazol-4-yl)ethyl, 2-(1-methyl-1H-imidazol-4-yl)ethyl, 2-(2,3-difluorophenyl)ethyl, 2-(2,5-difluorophenyl)ethyl, 2-(2,6-difluorophenyl)ethyl, 2-(2-chlorophenyl)ethyl, 2-(2-cyanophenyl)ethyl, 2-(2-fluorophenyl)ethyl, 2-(2-hydroxyphenyl)ethyl, 2-(2-methoxyphenyl)ethyl, 2-(2-methylphenyl)ethyl, 2-(3-(trifluoromethyl)phenyl)ethyl, 2-(3,4-difluorophenyl)ethyl, 2-(3,5-difluorophenyl)ethyl, 2-(3,5-dimethyl-1H-pyrazol-1-yl)ethyl, 2-(3,5-dimethyl-1H-pyrazol-4-yl)ethyl, 2-(3-carbamoylphenyl)ethyl, 2-(3-carboxyphenyl)ethyl, 2-(3-cyanophenyl)ethyl, 2-(3-fluorophenyl)-2-(hydroxy)-ethyl, 2-(3-fluorophenyl)ethyl, 2-(3-fluoropyridin-2-yl)ethyl, 2-(3-methoxycarbonylphenyl)ethyl, 2-(3-methoxyphenyl)ethyl, 2-(3-methylphenyl)ethyl, 2-(4-aminophenyl)ethyl, 2-(4-chlorophenyl)ethyl, 2-(4-fluorophenyl)ethyl, 2-(4-hydroxyphenyl)ethyl, 2-(benzo[d][1,3]dioxol-5-yl)ethyl, 2-(furan-2-yl)ethyl, 2-(hydroxy)-2-(phenyl)ethyl, 2-(phenyl)ethyl, 2-(pyridin-2-yl)ethyl, 2-(pyridin-3-yl)ethyl, 2-(thiophen-2-yl)ethyl, 2-phenylprop-1-yl, 3-(1H-imidazol-1-yl)prop-1-yl, 3-phenylpropyl, benzyl, pyridin-2-ylmethyl, pyridin-3-ylmethyl, and thiophen-3-ylmethyl.

15. The compound of claim 14 wherein $Z^3$ is chosen from 3-fluorophenethyl, 3,5-difluorophenethyl, and 2-(pyridin-2-yl)ethyl.

16. The compound of claim 1 wherein $R^1$ is chosen from hydrogen and lower alkyl.

17. The compound of claim 16 wherein $R^1$ is chosen from hydrogen and methyl.

18. The compound of claim 17 wherein $R^1$ is hydrogen.

19. The compound of claim 1 wherein $R^2$ is pyridin-3-ylmethyl.

20. The compound of claim 1 wherein $Z^1$ is
heteroaryl optionally substituted by one or two groups selected from cyano, halo, hydroxy, formyl, optionally substituted alkyl, optionally substituted alkenyl, optionally substituted alkoxy, carboxyl, optionally substituted alkoxycarbonyl, optionally substituted acyl, optionally substituted aminocarbonyl, optionally substituted heterocycloalkyl, optionally substituted heteroaryl, optionally substituted carbamimidoyl, and optionally substituted sulfonyl.

21. The compound of claim 1 wherein $Z^1$ is chosen from
pyrazolyl, thiphenyl, pyridinyl, tetrazolyl, thiazolyl and isoxazolyl, wherein each group is optionally substituted by one or two groups selected from cyano, halo, hydroxy, formyl, optionally substituted lower alkyl, optionally substituted lower alkenyl, optionally substituted lower alkoxy, carboxyl, optionally substituted lower alkoxycarbonyl, optionally substituted lower acyl, optionally substituted aminocarbonyl, optionally substituted heterocycloalkyl, optionally substituted heteroaryl, and amino optionally substituted with alkyl.

22. A compound chosen from
N-{[2-(aminomethyl)(3-pyridyl)]methyl}{6-pyrazol-4-yl-2-[(2-(2-pyridyl)ethyl)amino](3-pyridyl)}carboxamide,
N-{(1R)-2-[(5-fluoro-2-{[2-(3-fluorophenyl)-2-hydroxyethyl]amino}-6-pyrazol-4-yl(3-pyridyl))carbonylamino]-isopropyl}-2-[(tert-butoxy)carbonylamino]acetamide,
{5-fluoro-6-pyrazol-4-yl-2-[(2-pyrazolylethyl)amino](3-pyridyl)}-N-(3-pyridylmethyl)carboxamide, N-[(1R)-2-({5-fluoro-6-pyrazol-4-yl-2-[(2-pyrazolyl-ethyl)amino](3-pyridyl)}carbonylamino)-isopropyl]-2-aminoacetamide,
(2-{[2-(3-fluorophenyl)ethyl]amino}-6-(1-methylpyrazol-4-yl)(3-pyridyl))-N-(3-pyridylmethyl)carboxamide,
(5-bromo-2-{[2-(3-fluorophenyl)ethyl]amino}-6-pyrazol-4-yl(3-pyridyl))-N-(3-pyridylmethyl)carboxamide,
(5-bromo-2-{[2-(3-fluorophenyl)ethyl]amino}-6-(1-methylpyrazol-4-yl)(3-pyridyl))-N-(3-pyridylmethyl)carboxamide,
(6-(5-cyanopyrazol-4-yl)-2-{[2-(3-fluorophenyl)ethyl]amino}(3-pyridyl))-N-(3-pyridylmethyl)carboxamide,
(5-cyano-2-{[2-(3-fluorophenyl)ethyl]amino}-6-(1-methylpyrazol-4-yl)(3-pyridyl))-N-(3-pyridylmethyl)carboxamide,
(2-{[2-(3-fluorophenyl)ethyl]amino}-6-pyrazol-3-yl(3-pyridyl))-N-(3-pyridylmethyl)carboxamide,
(6-(3-cyano-1-methylpyrazol-4-yl)-2-{[2-(3-fluorophenyl)ethyl]amino}(3-pyridyl))-N-(3-pyridylmethyl)carboxamide,
(6-(5-cyano-1-methylpyrazol-4-yl)-2-{[2-(3-fluorophenyl)ethyl]amino}(3-pyridyl))-N-(3-pyridylmethyl)carboxamide,
2-(2-{[2-(3-fluorophenyl)ethyl]amino}-6-pyrazol-4-yl(3-pyridyl)carbonylamino, -N-methylacetamide,
2-[(2-{[2-(3-fluorophenyl)ethyl]amino}-6-(1-methylpyrazol-4-yl)(3-pyridyl)carbonylamino]-N-methylacetamide,
(5-chloro-2-{[2-(3-fluorophenyl)ethyl]amino}-6-(1-methylpyrazol-4-yl)3-pyridyl))-N-(3-pyridylmethyl)carboxamide,
N-{[6-(aminomethyl)(2-pyridyl)]methyl}(2-{[2-(3-fluorophenyl)ethyl]amino}-6-(1-methylpyrazol-4-yl)(3-pyridyl))carboxamide,
N-([6-(aminomethyl)(2-pyridyl)]methyl}(2-{[2-(3-fluorophenyl)ethyl]amino}-6-pyrazol-4-yl(3-pyridyl))carboxamide,
N-([6-(aminomethyl)(2-pyridyl)]methyl}(5-bromo-2-[(2-(3-fluorophenyl)ethyl]amino}-6-(1-methylpyrazol-4-yl)(3-pyridyl))carboxamide,
N-[((2R)-5-oxopyrrolidin-2-yl)methyl](2-{[2-(3-fluorophenyl)ethyl]amino}-6-pyrazol-3-yl(3-pyridyl))carboxamide,
N-[((2R)-5-oxopyrrolidin-2-yl)methyl](2-{[2-(3-fluorophenyl)ethyl]amino}-6-(1-methylpyrazol-4-yl)(3-pyridyl))carboxamide,
N-[((2R)-5-oxopyrrolidin-2-yl)methyl](2-{[2-(3-fluorophenyl)ethyl]amino}-6-pyrazol-4-yl(3-pyridyl))carboxamide,
methyl 2-({(2S)-2-amino-3-[(2-{[2-(3-fluorophenyl)ethyl]amino}-6-(1-methylpyrazol-4-yl)(3-pyridyl)carbonylamino]propyl}amino)acetate,
N-[((2S)-6-oxopiperazin-2-yl)methyl](2-{[2-(3-fluorophenyl)ethyl]amino}-6-pyrazol-4-yl(3-pyridyl))carboxamide, pyridyl))carboxamido
N-[((2S)-6-oxopiperazin-2-yl)methyl](2-{[2-(3-fluorophenyl)ethyl]amino}-6-(1-methylpyrazol-4-yl)(3-pyridyl))carboxamide,
N-[((2S)-6-oxopiperazin-2-yl)methyl](2-{[2-(3-fluorophenyl)ethyl]amino}-6-pyrazol-3-yl(3-pyridyl))carboxamide,
N-{[(2R)-4-(3-aminopropyl)-6-oxopiperazin-2-yl]methyl}(2-{[2-(3-fluorophenyl)ethyl]amino}-6-(1-methylpyrazol-4-yl)(3-pyridyl))carboxamide,
(2-{[2-(3-fluorophenyl)ethyl]amino}-6-pyrazol-4-yl(3-pyridyl))-N-(pyrazol-3-ylmethyl)carboxamide,
(2-{[2-(3-fluorophenyl)ethyl]amino}-6-(1-methylpyrazol-4-yl)(3-pyridyl))-N-(pyrazol-3-ylmethyl)carboxamide,
(2-{[2-(3-fluorophenyl)ethyl]amino}-6-pyrazol-3-yl(3-pyridyl))-N-(pyrazol-3-ylmethyl)carboxamide,
N-{[1-(3-aminopropyl)pyrazol-3-yl]methyl}(2-{[2-(3-fluorophenyl)ethyl]amino}-6-(1-methylpyrazol-4-yl)(3-pyridyl))carboxamide,
N-{[1-(3-aminopropyl)pyrazol-3-yl]methyl}(2-{[2-(3-fluorophenyl)ethyl]amino}-6-pyrazol-3-yl(3-pyridyl))carboxamide,
N-{[1-(3-aminopropyl)pyrazol-5-yl]methyl}(2-{[2-(3-fluorophenyl)ethyl]amino}-6-(1-methylpyrazol-4-yl)(3-pyridyl))carboxamide,
N-{[1-(3-aminopropyl)pyrazol-5-yl]methyl}(2-{[2-(3-fluorophenyl)ethyl]amino}-6-pyrazol-3-yl(3-pyridyl))carboxamide,
N-[(1-{2-[(tert-butoxy)carbonylamino]ethyl}pyrazol-3-yl)methyl](2-{[2-(3-fluorophenyl)ethyl]amino}-6-pyrazol-3-yl(3-pyridyl))carboxamide,
N-{[1-(2-aminoethyl)pyrazol-3-yl]methyl}(2-{[2-(3-fluorophenyl)ethyl]amino}-6-pyrazol-4-yl(3-pyridyl))carboxamide,
N-{[1-(2-aminoethyl)pyrazol-3-yl]methyl}(2-{[2-(3-fluorophenyl)ethyl]amino}-6-pyrazol-3-yl(3-pyridyl))carboxamide,
N-{[1-(2-aminoethyl)pyrazol-5-yl]methyl}(2-{[2-(3-fluorophenyl)ethyl]amino}-6-pyrazol-3-yl(3-pyridyl))carboxamide,
N-{[1-(2-aminoethyl)pyrazol-3-yl]methyl}(2-{[2-(3-fluorophenyl)ethyl]amino}-6-(1-methylpyrazol-4-yl)(3-pyridyl))carboxamide,
N-{[1-(2-aminoethyl)pyrazol-5-yl]methyl}(2-{[2-(3-fluorophenyl)ethyl]amino}-6-(1-methylpyrazol-4-yl)(3-pyridyl))carboxamide,
N-{[(2R)-1-(3-aminopropyl)-6-oxopiperazin-2-yl]methyl}(2-{[2-(3-fluorophenyl)ethyl]amino}-6-(1-methylpyrazol-4-yl)(3-pyridyl))carboxamide,
N-{[(2R)-1-(3-aminopropyl)-6-oxopiperazin-2-yl]methyl}(2-{[2-(3-fluorophenyl)ethyl]amino}-6-pyrazol-4-yl(3-pyridyl))carboxamide,
N-{[(2R)-1-(3-aminopropyl)-6-oxopiperazin-2-yl]methyl}(2-{[2-(3-fluorophenyl)ethyl]amino}-6-pyrazol-3-yl(3-pyridyl))carboxamide,
N-{[1-(3-aminopropyl)pyrazol-3-yl]methyl}(2-{[2-(3-fluorophenyl)ethyl]amino}-6-pyrazol-4-yl(3-pyridyl))carboxamide,
N-{[1-(3-aminopropyl)pyrazol-5-yl]methyl}(2-{[2-(3-fluorophenyl)ethyl]amino}-6-pyrazol-4-yl(3-pyridyl))carboxamide,
N-[((2R)-1-{3-[tert-butoxy)carbonylamino]propyl}-5-oxopyrrolidin-2-yl)methyl](2-{[2-(3-fluorophenyl)ethyl]amino}-6-(1-methylpyrazol-4-yl)(3-pyridyl))carboxamide,
N-{[(2R)-1-(3-aminopropyl)-5-oxopyrrolidin-2-yl]methyl}(6-{1-[(dimethylamino)(dimethylylidene)methyl]pyrazol-4-yl}-2-{[2-(3-fluorophenyl)ethyl]amino}(3-pyridyl))carboxamide,
N-{[(2R)-1-(3-aminopropyl)-5-oxopyrrolidin-2-yl]methyl}(2-{[2-(3-fluorophenyl)ethyl]amino}-6-(1-methylpyrazol-4-yl)(3-pyridyl))carboxamide,
tert-butyl (2R)-2-{[(2-{[2-(3-fluorophenyl)ethyl]amino}-6-(1-methylpyrazol-4-yl)(3-pyridyl))carbonylamino]methyl}pyrrolidinecarboxylate,
N-{[(2R)-1-(3-aminopropyl)-5-oxopyrrolidin-2-yl]methyl}(2-{[2-(3-fluorophenyl)ethyl]amino}-6-pyrazol-4-yl(3-pyridyl))carboxamide, N-[((2R)pyrrolidin-2-yl)methyl](2-{[2-(3-fluorophenyl)ethyl]amino}-6-pyrazol-4-yl(3-pyridyl))carboxamide, N-[((2R)pyrrolidin-2-yl)methyl](2-{[2-(3-fluorophenyl)ethyl]amino}-6-(1-methylpyrazol-4-yl)(3-pyridyl))carboxamide, N-[((2R)-1-{2-[(tert-butoxy)carbonylamino]acetyl}pyrrolidin-2-yl)methyl](2-{[2-(3-fluorophenyl)ethyl]amino}-6-(1-methylpyrazol-4-yl)(3-pyridyl))carboxamide, N-[((2R)-1-{3-[(tert-butoxy)carbonylamino]propanoyl}pyrrolidin-2-yl)methyl](2-{[2-(3-fluorophenyl)ethyl]amino}-6-(1-methylpyrazol-4-yl)(3-pyridyl))carboxamide, N-[((2R)-1-{4-[(tert-butoxy)carbonylamino]butanoyl}pyrrolidin-2-yl)methyl](2-{[2-(3-fluorophenyl)ethyl]amino}-6-(1-methylpyrazol-4-yl)(3-pyridyl))carboxamide, N-{[(2R)-1-(2-aminoacetyl)pyrrolidin-2-yl]methyl}(2-{[2-(3-fluorophenyl)ethyl]amino}-6-(1-methylpyrazol-4-yl)(3-pyridyl))carboxamide, N-{[(2R)-1-(3-aminopropanoyl)pyrrolidin-2-yl]methyl}(2-{[2-(3-fluorophenyl)ethyl]amino}-6-(1-methylpyrazol-4-yl)(3-pyridyl))carboxamide, N-{[(2R)-1-(4-aminobutanoyl)pyrrolidin-2-yl]methyl}(2-{[2-(3-fluorophenyl)ethyl]amino}-6-(1-methylpyrazol-4-yl)(3-pyridyl))carboxamide, (5-fluoro-2-{[2-(3-fluorophenyl)ethyl]amino}-6-(1-methylpyrazol-4-yl)(3-pyridyl))-N-(3-pyridylmethyl)carboxamide, (2-{[2-(3-fluorophenyl)ethyl]amino}-6-pyrazol-4-yl(3-pyridyl))-N-(3-pyridylmethyl)carboxamide, N-{[2-aminopropanoyl)(3-pyridyl)]methyl}(2-{[2-(3-fluorophenyl)ethyl]amino}-6-pyrazol-3-yl(3-pyridyl))carboxamide, N-{[2-aminopropanoyl)(3-pyridyl)]methyl}(2-{[2-(3-fluorophenyl)ethyl]amino}-6-(1-methylpyrazol-4-yl(3-pyridyl))carboxamide, N-{[2-(aminomethyl)(3-pyridyl)]methyl}(5-fluoro-2-{[2-(3-fluorophenyl)ethyl]amino}-6-pyrazol-3-yl(3-pyridyl))carboxamide, N-{[(2R)-1-(2-aminoacetyl)pyrrolidin-2-yl]methyl}(5-fluoro-2-{[2-(3-fluorophenyl)ethyl]amino}-6-pyrazol-3-yl(3-pyridyl))carboxamide, N-{[(2R)-1-((2S)-2-amino-3-hydroxypropanoyl)pyrrolidin-2-yl]methyl}(5-fluoro-2-{[2-(3-fluorophenyl)ethyl]amino}-6-pyrazol-3-yl(3-pyridyl))carboxamide, N-{[(2R)-1-((2S)-2-aminopropanoyl)pyrrolidin-2-yl]methyl}(5-fluoro-2-{[2-(3-fluorophenyl)ethyl]amino}-6-pyrazol-3-yl(3-pyridyl))carboxamide, N-{[(2R)-1-(4-aminobutanoyl)pyrrolidin-2-yl]methyl}(5-fluoro-2-{[2-(3-fluorophenyl)ethyl]amino}-6-pyrazol-3-yl(3-pyridyl))carboxamide, N-((2R)-2-aminopropyl)(5-fluoro-2-{[2-(3-fluorophenyl)ethyl]amino}-6-(1-methylpyrazol-4-yl)(3-pyridyl))carboxamide, N-{(1R)-2-[(5-fluoro-2-{[2-(3-fluorophenyl)ethyl]amino}-6-(1-methylpyrazol-4-yl)(3-pyridyl)carbonylamino]-isopropyl}-2-[(tert-butoxy)carbonylamino]acetamide, N-{(1R)-2-[(5-fluoro-2-{[2-(3-fluorophenyl)ethyl]amino}-6-(1-methylpyrazol-4-yl)(3-pyridyl)carbonylamino]-isopropyl}-2-aminoacetamide, N-[((2R)-5-oxopyrrolidin-2-yl)methyl](5-fluoro-2-{[2-(3-fluorophenyl)ethyl]amino}-6-(1-methylpyrazol-4-yl)(3-pyridyl))carboxamide, N-{(1S)-2-[(5-fluoro-2-{[2-(3-fluorophenyl)ethyl]amino}-6-(1-methylpyrazol-4-yl)(3-pyridyl)carbonylamino]-isopropyl}-2-aminoacetamide, N-{(1R)-2-[(5-fluoro-2-{[2-(3-fluorophenyl)ethyl]amino}-6-(1-methylpyrazol-4-yl)(3-pyridyl)carbonylamino]-isopropyl}-2-hydroxyacetamide, N-{(1R)-2-[(5-fluoro-2-{[2-(3-fluorophenyl)ethyl]amino}-6-(1-methylpyrazol-4-yl)(3-pyridyl)carbonylamino]-isopropyl}-4-[(tert-butoxy)carbonylamino]butanamide, N-{(1R)-2-[(5-fluoro-2-{[2-(3-fluorophenyl)ethyl]amino}-6-(1-methylpyrazol-4-yl)(3-pyridyl)carbonylamino]-isopropyl}-4-aminobutanamide, N-{(2R)-2-[(2-methoxyethyl)amino]propyl}(5-fluoro-2-{[2-(3-fluorophenyl)ethyl]amino}-6-(1-methylpyrazol-4-yl)(3-pyridyl))carboxamide, N-{(2R)-2-[(tert-butoxy)carbonylamino]propyl}(5-fluoro-2-{[2-(3-fluorophenyl)ethyl]amino}-6-pyrazol-4-yl(3-pyridyl))carboxamide, N-((2R)-2-aminopropyl)(5-fluoro-2-{[2-(3-fluorophenyl)ethyl]amino}-6-pyrazol-4-yl(3-pyridyl))carboxamide, N-{(1R)-2-[(5-fluoro-2-{[2-(3-fluorophenyl)ethyl]amino}-6-(1-methylpyrazol-4-yl)(3-pyridyl)carbonylamino]-isopropyl}acetamide, N-{(2R)-2-[(methylsulfonyl)amino]propyl}(5-fluoro-2-{[2-(3-fluorophenyl)ethyl]amino}-6-(1-methylpyrazol-4-yl)(3-pyridyl))carboxamide, N-{(1R)-2-[(5-fluoro-2-{[2-(3-fluorophenyl)ethyl]amino}-6-pyrazol-4-yl(3-pyridyl)carbonylamino]-isopropyl}-2-aminoacetamide, (5-fluoro-2-{[2-(3-fluorophenyl)ethyl]amino}-6-pyrazol-4-yl(3-pyridyl))-N-(2-pyridylmethyl)carboxamide, N-{(2R)-2-[(2-hydroxyethyl)amino]propyl}(5-fluoro-2-{[2-(3-fluorophenyl)ethyl]amino}-6-(1-methylpyrazol-4-yl)(3-pyridyl))carboxamide, N-{(2R)-2-[(carbamoylmethyl)amino]propyl}(5-fluoro-2-{[2-(3-fluorophenyl)ethyl]amino}-6-(1-methylpyrazol-4-yl)(3-pyridyl))carboxamide, N-{(1R)-2-[(5-fluoro-2-{[2-(3-fluorophenyl)ethyl]amino}-6-(1-methylpyrazol-4-yl)(3-pyridyl)carbonylamino]-isopropyl}-2-(dimethylamino)acetamide, N-{(1R)-2-[(5-fluoro-2-{[2-(3-fluorophenyl)ethyl]amino}-6-(1-methylpyrazol-4-yl)(3-pyridyl)carbonylamino]-isopropyl}(2S)-2-[(tert-butoxy)carbonylamino]-3-hydroxypropanamide, N-{(1R)-2-[(5-fluoro-2-{[2-(3-fluorophenyl)ethyl]amino}-6-(1-methylpyrazol-4-yl)(3-pyridyl)carbonylamino]-isopropyl}(2S)-2-amino-3-hydroxypropanamide, N-{(1R)-2-[(5-fluoro-2-{[2-(3-fluorophenyl)ethyl]amino}-6-(1-methylpyrazol-4-yl)(3-pyridyl)carbonylamino]-isopropyl}-2-amino-2-methylpropanamide, N-((1R)-1-{[(5-fluoro-2-{[2-(3-fluorophenyl)ethyl]amino}-6-(1-methylpyrazol-4-yl)(3-pyridyl)carbonylamino]methyl}propyl)-2-[(tert-butoxy)carbonylamino]acetamide, N-((1R)-1-{[(5-fluoro-2-{[2-(3-fluorophenyl)ethyl]amino}-6-(1-methylpyrazol-4-yl)(3-pyridyl)carbonylamino]methyl}propyl)-2-aminoacetamide, N-((1R)-1-{[(5-fluoro-2-{[2-(3-fluorophenyl)ethyl]amino}-6-pyrazol-4-yl(3-pyridyl)carbonylamino]methyl}propyl)-2-[(tert-butoxy)carbonylamino]acetamide, N-((1R)-1-{[(5-fluoro-2-{[2-(3-fluorophenyl)ethyl]amino}-6-pyrazol-4-yl(3-pyridyl)carbonylamino]methyl}propyl)-2-aminoacetamide, N-{(1R)-2-[(5-fluoro-2-{[2-(3-fluorophenyl)ethyl]amino}-6-(1-methylpyrazol-4-yl)(3-pyridyl)carbonylamino]-isopropyl}(2S)-2-aminopropanamide, N-((2R)-3-hydroxy-2-methylbutyl)(5-fluoro-2-{[2-(3-fluorophenyl)ethyl]amino}-6-(1-methylpyrazol-4-yl)(3-pyridyl))carboxamide, N-{[2-(aminomethyl)(3-pyridyl)]methyl}(2-{[2-(3-fluorophenyl)ethyl]amino}-6-pyrazol-4-yl(3-pyridyl))carboxamide, {6-(1-methylpyrazol-4-yl)-2-[(2-(2-pyridyl)ethyl)amino](3-pyridyl)}-N-(3-pyridylmethyl)carboxamide, N-[(2-chloro(3-pyridyl))methyl](2-{[2-(3-fluorophenyl)ethyl]amino}-6-pyrazol-4-yl(3-pyridyl))carboxamide, N-({2-[(3-aminopropyl)amino](3-pyridyl)}methyl)(2-{[2-(3-fluorophenyl)ethyl]amino}-6-pyrazol-4-yl(3-pyridyl))carboxamide, N-({2-[(2-aminoethyl)amino](3-pyridyl)}methyl)(2-{[2-(3-fluorophenyl)ethyl]amino}-6-pyrazol-4-yl(3-pyridyl))carboxamide, tert-butyl (2R)-2-{[(5-fluoro-2-{[2-(3-fluorophenyl)ethyl]amino}-6-(1-methylpyrazol-4-yl)(3-pyridyl)carbonylamino]methyl}pyrrolidinecarboxylate, N-[((2R)pyrrolidin-2-yl)methyl](5-fluoro-2-{[2-(3-fluorophenyl)ethyl]amino}-6-(1-methylpyrazol-4-yl)(3-pyridyl))carboxamide, N-((2R)-1-{2-[(tert-butoxy)carbonylamino]acetyl}pyrrolidin-2-yl)methyl)-5-fluoro-2-{[2-(3-fluorophenyl)ethyl]amino}-6-(1-methylpyrazol-4-yl)(3-pyridyl))carboxamide, (2-{[2-(3-fluorophenyl)ethyl]amino}-6-pyrazol-4-yl(3-pyridyl))-N-({2-[(2-hydroxyethyl)amino](3-pyridyl)}methyl)carboxamide, N-[(2-{[(tert-butoxy)carbonylamino]methyl}(3-pyridyl)methyl](5-fluoro-2-{[2-(3-fluorophenyl)ethyl]amino}-6-pyrazol-4-yl(3-pyridyl))carboxamide, N-{[2-(aminomethyl)(3-pyridyl)]methyl}(5-fluoro-2-{[2-(3-fluorophenyl)ethyl]amino}-6-pyrazol-4-yl(3-pyridyl))carboxamide, N-((2R)-1-{2-[(tert-butoxy)carbonylamino]acetyl}pyrrolidin-2-yl)methyl)-5-fluoro-2-{[2-(3-fluorophenyl)ethyl]amino}-6-pyrazol-4-yl(3-pyridyl))carboxamide, N-[((2R)-1-(2-aminoacetyl)pyrrolidin-2-yl)methyl](5-fluoro-2-{[2-(3-fluorophenyl)ethyl]amino}-6-pyrazol-4-yl(3-pyridyl))carboxamide, N-((2R)-1-{3-[(tert-butoxy)carbonylamino]propanoyl}pyrrolidin-2-yl)methyl)-5-fluoro-2-{[2-(3-fluorophenyl)ethyl]amino}-6-pyrazol-4-yl(3-pyridyl))carboxamide, N-{[(2R)-1-(3-aminopropanoyl)pyrrolidin-2-yl]methyl}(5-fluoro-2-{[2-(3-fluorophenyl)ethyl]amino}-6-pyrazol-4-yl(3-pyridyl))carboxamide, N-((2R)-1-{4-[(tert-butoxy)carbonylamino]butanoyl}pyrrolidin-2-yl)methyl)-5-fluoro-2-{[2-(3-fluorophenyl)ethyl]amino}-6-pyrazol-4-yl(3-pyridyl))carboxamide, N-{[(2R)-1-(4-aminobutanoyl)pyrrolidin-2-yl]methyl}(5-fluoro-2-{[2-(3-fluorophenyl)ethyl]amino}-6-pyrazol-4-yl(3-pyridyl))carboxamide, N-[((2R)pyrrolidin-2-yl)methyl](5-fluoro-2-{[2-(3-fluorophenyl)ethyl]amino}-6-pyrazol-4-yl(3-pyridyl))carboxamide, N-[((2R)-1-{3-[(tert-butoxy)carbonylamino]propyl}-5-oxopyrrolidin-2-yl)methyl](5-fluoro-2-[((2-(3-fluorophenyl)ethyl]amino}-6-pyrazol-4-yl(3-pyridyl))carboxamide, N-{[(2R)-1-(3-aminopropyl)-5-oxopyrrolidin-2-yl]methyl}(5-fluoro-2-[((2-(3-fluorophenyl)ethyl]amino}-6-pyrazol-4-yl(3-pyridyl))carboxamide, N-(carbamoylmethyl)(5-fluoro-2-{[((2-(3-fluorophenyl)ethyl]amino}-6-pyrazol-4-yl(3-pyridyl))carboxamide, 2-[(5-fluoro-2-{[2-(3-fluorophenyl)ethyl]amino}-6-pyrazol-4-yl(3-pyridyl)carbonylamino]-N-methylacetamide, N-[((2R)-1-{(2S)-2-[(tert-butoxy)carbonylamino]-3-hydroxypropanoyl}pyrrolidin-2-yl)methyl](5-fluoro-2-[((2-(3-fluorophenyl)ethyl]amino}-6-pyrazol-4-yl(3-pyridyl))carboxamide, N-{[(2R)-1-((2S)-2-amino-3-hydroxypropanoyl)pyrrolidin-2-yl]methyl}(5-fluoro-2-{[2-(3-fluorophenyl)ethyl]amino}-6-pyrazol-4-yl(3-pyridyl))carboxamide, (5-fluoro-2-[((2-(3-fluorophenyl)ethyl]amino}-6-(1-methylpyrazol-4-yl)(3-pyridyl))-N-(2-hydroxy-2-methylpropyl)carboxamide, (5-fluoro-2-[((2-(3-fluorophenyl)ethyl]amino}-6-(1-methylpyrazol-4-yl)(3-pyridyl))-N-(3-hydroxy-2,2-dimethylpropyl)carboxamide, N-((2R)-2-methyl-3-oxobutyl)(5-fluoro-2-{[2-(3-fluorophenyl)ethyl]amino}-6-(1-methylpyrazol-4-yl)(3-pyridyl))carboxamide, N-((2R)-3-hydroxy-2,3-dimethylbutyl)(5-fluoro-2-[((2-(3-fluorophenyl)ethyl]amino}-6-(1-methylpyrazol-4-yl)(3-pyridyl))carboxamide, 2-[((2R)-2-{[(5-fluoro-2-{[2-(3-fluorophenyl)ethyl]amino}-6-(1-methylpyrazol-4-yl)(3-pyridyl)carbonylamino]methyl}azetidinyl)-2-oxoethyl 2-[(tert-butoxy)carbonylamino]acetate, 2-[((2R)-2-{[(5-fluoro-2-{[2-(3-fluorophenyl)ethyl]amino}-6-(1-methylpyrazol-4-yl)(3-pyridyl)carbonylamino]methyl}azetidinyl)-2-oxoethyl 2-aminoacetate, 2-[((2R)-2-{[(5-fluoro-2-{[2-(3-fluorophenyl)ethyl]amino}-6-(1-methylpyrazol-4-yl)(3-pyridyl)carbonylamino]methyl}azetidinyl)-2-oxoethyl dimethyl phosphate, (5-fluoro-2-{[2-(3-fluorophenyl)ethyl]amino}-6-pyrazol-4-yl(3-pyridyl))-N-(3-pyridylmethyl)carboxamide, N-{[(2R)-1-(2-aminoacetyl)pyrrolidin-2-yl]methyl}(5-fluoro-2-{[2-(3-fluorophenyl)ethyl]amino}-6-(1-methylpyrazol-4-yl)(3-pyridyl))carboxamide, (2-[((2-(3-fluorophenyl)ethyl]amino}-6-(1-methylpyrazol-4-yl)(3-pyridyl))-N-[(6-oxopiperazin-2-yl)methyl]carboxamide, (2-[((2-(3-fluorophenyl)ethyl]amino}-6-pyrazol-4-yl(3-pyridyl))-N-[(6-oxopiperazin-2-yl)methyl]carboxamide, (2-[((2-(3-fluorophenyl)ethyl]amino}-6-pyrazol-5-yl(3-pyridyl))-N-[(6-oxopiperazin-2-yl)methyl]carboxamide, (2-{[2-(3-fluorophenyl)ethyl]amino}-6-(1-methylpyrazol-4-yl)(3-pyridyl))-N-[(2-oxopyrrolidin-3-yl)methyl]carboxamide, (2-{[2-(3-fluorophenyl)ethyl]amino}-6-pyrazol-4-yl(3-pyridyl))-N-[(2-oxopyrrolidin-3-yl)methyl]carboxamide, N-{[(2R)-1-(2-hydroxyacetyl)pyrrolidin-2-yl]methyl}(2-{[2-(3-fluorophenyl)ethyl]amino}-6-(1-methylpyrazol-4-yl)(3-pyridyl))carboxamide, methyl 4-[((2R)-2-{[(2-{[2-(3-fluorophenyl)ethyl]amino}-6-(1-methylpyrazol-4-yl)(3-pyridyl)carbonylamino]methyl}pyrrolidinyl)-4-oxobutanoate, N-{[(2R)-1-(4-hydroxybutanoyl)pyrrolidin-2-yl]methyl}(2-{[2-(3-fluorophenyl)ethyl]amino}-6-(1-methylpyrazol-4-yl)(3-pyridyl))carboxamide, N-[(1-{3-[(tert-butoxy)carbonylamino]propyl}-2-oxopyrrolidin-3-yl)methyl](2-{[2-(3-fluorophenyl)ethyl]amino}-6-pyrazol-4-yl(3-pyridyl))carboxamide,
N-{[1-(3-aminopropyl)-2-oxopyrrolidin-3-yl]methyl}(2-{[2-(3-fluorophenyl)ethyl]amino}-6-pyrazol-4-yl(3-pyridyl))carboxamide,
N-[(1-{3-[(tert-butoxy)carbonylamino]propyl}-2-oxopyrrolidin-3-yl)methyl](2-{[2-(3-fluorophenyl)ethyl]amino}-6-(1-methylpyrazol-4-yl)(3-pyridyl))carboxamide,
N-{[1-(3-aminopropyl)-2-oxopyrrolidin-3-yl]methyl}(2-{[2-(3-fluorophenyl)ethyl]amino}-6-(1-methylpyrazol-4-yl)(3-pyridyl))carboxamide,
tert-butyl (2R)-2-{[(2-{[2-(3-fluorophenyl)ethyl]amino}-6-pyrazol-4-yl(3-pyridyl)carbonylamino]methyl}pyrrolidinecarboxylate,
N-{[(2R)-1-(2-hydroxyacetyl)pyrrolidin-2-yl]methyl}(2-{[2-(3-fluorophenyl)ethyl]amino}-6-pyrazol-4-yl(3-pyridyl))carboxamide,
(2-{[2-(3-fluorophenyl)ethyl]amino}-6-pyrazol-4-yl(3-pyridyl))-N-[(7-oxoazaperhydroepin-2-yl)methyl]carboxamide,
(2-{[2-(3-fluorophenyl)ethyl]amino}-6-(1-methylpyrazol-4-yl)(3-pyridyl))-N-[(7-oxoazaperhydroepin-2-yl)methyl]carboxamide,
N-{[(2R)-1-(4-hydroxybutanoyl)pyrrolidin-2-yl]methyl}(2-{[2-(3-fluorophenyl)ethyl]amino}-6-pyrazol-4-yl(3-pyridyl))carboxamide,
tert-butyl (2R)-2-{[(2-{[2-(3-fluorophenyl)ethyl]amino}-6-pyrazol-4-yl(3-pyridyl)carbonylamino]methyl}azetidinecarboxylate,
N-[((2R)azetidin-2-yl)methyl](2-{[2-(3-fluorophenyl)ethyl]amino}-6-pyrazol-4-yl(3-pyridyl))carboxamide,
N-{[(2R)-1-(2-hydroxyacetyl)azetidin-2-yl]methyl}(2-{[2-(3-fluorophenyl)ethyl]amino}-6-pyrazol-4-yl(3-pyridyl))carboxamide,
N-[((2R)-1-{2-[(tert-butoxy)carbonylamino]acetyl}azetidin-2-yl)methyl](2-{[2-(3-fluorophenyl)ethyl]amino}-6-pyrazol-4-yl(3-pyridyl))carboxamide,
N-{[(2R)-1-(2-aminoacetyl)azetidin-2-yl]methyl}(2-{[2-(3-fluorophenyl)ethyl]amino}-6-pyrazol-4-yl(3-pyridyl))carboxamide,
N-[(6-bromo(2-pyridyl))methyl]2-{[2-(3-fluorophenyl)ethyl]amino}-6-pyrazol-4-yl(3-pyridyl))arboxamide,
N-({6-[(3-aminopropyl)amino](2-pyridyl)}methyl)(2-{[2-(3-fluorophenyl)ethyl]amino}-6-pyrazol-4-yl(3-pyridyl))carboxamide,
N({6-[(2-aminoethyl)amino](2-pyridyl)}methyl)(2-{[2-(3-fluorophenyl)ethyl]amino}-6-pyrazol-4-yl(3-pyridyl))carboxamide,
(2-{[2-(3-fluorophenyl)ethyl]amino}-6-pyrazol-4-yl(3-pyridyl))-N-({6-[(2-hydroxyethyl)amino](2-pyridyl)}methyl)carboxamide, methyl (2R)-2-{[(2-{[2-(3-fluorophenyl)ethyl]amino}-6-pyrazol-4-yl(3-pyridyl))carbonylamino]methyl}azetidinecarboxylate,
N-[((2R)-1-{3-[(tert-butoxy)carbonylamino]propanoyl}pyrrolidin-2-yl)methyl](5-fluoro-2-{[2-(3-fluorophenyl)ethyl]amino}-6-(1-methylpyrazol-4-yl)(3-pyridyl))carboxamide,
N-{[(2R)-1-(3-aminopropanoyl)pyrrolidin-2-yl]methyl}(5-fluoro-2-{[2-(3-fluorophenyl)ethyl]amino}-6-(1-methylpyrazol-4-yl)(3-pyridyl))carboxamide,
N-[((2R)-1-{4-[(tert-butoxy)carbonylamino]butanoyl}pyrrolidin-2-yl)methyl](5-fluoro-2-{[2-(3-fluorophenyl)ethyl]amino}-6-(1-methylpyrazol-4-yl)(3-pyridyl))carboxamide,
N-{[(2R)-1-(4-aminobutanoyl)pyrrolidin-2-yl]methyl}(5-fluoro-2-{[2-(3-fluorophenyl)ethyl]amino}-6-(1-methylpyrazol-4-yl)(3-pyridyl))carboxamide,
N-[(2-{[(tert-butoxy)carbonylamino]methyl}(3-pyridyl))methyl](5-fluoro-2-{[2-(3-fluorophenyl)ethyl]amino}-6-(1-methylpyrazol-4-yl)(3-pyridyl))carboxamide,
N-{[2-(aminomethyl)(3-pyridyl)]methyl}(5-fluoro-2-{[2-(3-fluorophenyl)ethyl]amino}-6-(1-methylpyrazol-4-yl)(3-pyridyl))carboxamide,
N-[((2R)-1-{3-[(tert-butoxy)carbonylamino]propyl}-5-oxopyrrolidin-2-yl)methyl](5-fluoro-2-{[2-(3-fluorophenyl)ethyl]amino}-6-(1-methylpyrazol-4-yl)(3-pyridyl))carboxamide,
N-{[(2R)-1-(3-aminopropyl)-5-oxopyrrolidin-2-yl]methyl}(5-fluoro-2-{[2-(3-fluorophenyl)ethyl]amino}-6-(1-methylpyrazol-4-yl)(3-pyridyl))carboxamide,
N-{[(2R)-1-(2,3-dihydroxypropanoyl)pyrrolidin-2-yl]methyl}(5-fluoro-2-{[2-(3-fluorophenyl)ethyl]amino}-6-(1-methylpyrazol-4-yl)(3-pyridyl))carboxamide,
(2-{[2-(3-fluorophenyl)ethyl]amino}-6-[1-(2-hydroxyethyl)pyrazol-4-yl](3-pyridyl))-N-(3-pyridylmethyl)carboxamide,
N-[2-((2R)-2-{[(5-fluoro-2-{[2-(3-fluorophenyl)ethyl]amino}-6-(1-methylpyrazol-4-yl)(3-pyridyl))carbonylamino]methyl}pyrrolidinyl)(1S)-1-methyl-2-oxoethyl](tert-butoxy)carboxamide,
N-{[(2R)-1-((2S)-2-aminopropanoyl)pyrrolidin-2-yl]methyl}(5-fluoro-2-{[2-(3-fluorophenyl)ethyl]amino}-6-(1-methylpyrazol-4-yl)(3-pyridyl))carboxamide,
N-[((2R)-1-{(2S)-2,5-bis[(tert-butoxy)carbonylamino]pentanoyl}pyrrolidin-2-yl)methyl](5-fluoro-2-{[2-(3-fluorophenyl)ethyl]amino}-6-(1-methylpyrazol-4-yl)(3-pyridyl))carboxamide,
N-{[(2R)-1-[((2S)-2,5-diaminopentanoyl)pyrrolidin-2-yl]methyl}(5-fluoro-2-{[2-(3-fluorophenyl)ethyl]amino}-6-(1-methylpyrazol-4-yl)(3-pyridyl))carboxamide,
N-[2-[((2R)-2-{[(5-fluoro-2-{[2-(3-fluorophenyl)ethyl]amino}-6-(1-methylpyrazol-4-yl)(3-pyridyl)carbonylamino]methyl}pyrrolidinyl)(1S)-1-(hydroxymethyl)-2-oxoethyl](tert-butoxy)carboxamide,
N-{[(2R)-1-((2S)-2-amino-3-hydroxypropanoyl)pyrrolidin-2-yl]methyl}(5-fluoro-2-{[2-(3-fluorophenyl)ethyl]amino}-6-(1-methylpyrazol-4-yl)(3-pyridyl))carboxamide,
methyl 4-((2R)-2-{[(5-fluoro-2-{[2-(3-fluorophenyl)ethyl]amino}-6-(1-methylpyrazol-4-yl)(3-pyridyl)carbonylamino]methyl}pyrrolidinyl)-4-oxobutanoate,
N-{[(2R)-1-(4-hydroxybutanoyl)pyrrolidin-2-yl]methyl}(5-fluoro-2-{[2-(3-fluorophenyl)ethyl]amino}-6-(1-methylpyrazol-4-yl)(3-pyridyl))carboxamide,
N-[(2-{[(tert-butoxy)carbonylamino]methyl}(3-pyridyl))methyl](5-cyano-2-{[2-(3-fluorophenyl)ethyl]amino}-6-(1-methylpyrazol-4-yl)(3-pyridyl))carboxamide,
N-{[2-(aminomethyl)(3-pyridyl)]methyl}(5-cyano-2-{[2-(3-fluorophenyl)ethyl]amino}-6-(1-methylpyrazol-4-yl)(3-pyridyl))carboxamide,
N-[3-((5R)-5-{[(5-cyano-2-{[2-(3-fluorophenyl)ethyl]amino}-6-(1-methylpyrazol-4-yl)(3-pyridyl)carbonylamino]methyl}-2-oxopyrrolidinyl)propyl](tert-butoxy)carboxamide,
N-{[(2R)-1-(3-aminopropyl)-5-oxopyrrolidin-2-yl]methyl}(5-cyano-2-{[2-(3-fluorophenyl)ethyl]amino}-6-(1-methylpyrazol-4-yl)(3-pyridyl))carboxamide,
tert-butyl (2R)-2-{[(5-cyano-2-{[2-(3-fluorophenyl)ethyl]amino}-6-(1-methylpyrazol-4-yl)(3-pyridyl)carbonylamino]methyl}pyrrolidinecarboxylate, N-[((2R)pyrrolidin-2-yl)methyl](5-cyano-2-{[2-(3-fluorophenyl)ethyl]amino}-6-(1-methylpyrazol-4-yl)(3-pyridyl))carboxamide, N-[((2R)-1-{-4-[(tert-butoxy)carbonylamino]butanoyl}pyrrolidin-2-yl)methyl](5-cyano-2-{[2-(3-fluorophenyl)ethyl]amino}-6-(1-methylpyrazol-4-yl)(3-pyridyl))carboxamide,
N-{[(2R)-1-(4-aminobutanoyl)pyrrolidin-2-yl]methyl}(5-cyano-2-{[2-(3-fluorophenyl)ethyl]amino}-6-(1-methylpyrazol-4-yl)(3-pyridyl)carboxamide,
N-[(2-{[(tert-butoxy)carbonylamino]methyl}(3-pyridyl)methyl](2-{[2-(3-fluorophenyl)ethyl]amino}-5-methyl-6-(1-methylpyrazol-4-yl)(3-pyridyl))carboxamide,
N-{[2-(aminomethyl)(3-pyridyl)]methyl}(2-{[2-(3-fluorophenyl)ethyl]amino}-5-methyl-6-(1-methylpyrazol-4-yl)(3-pyridyl))carboxamide,
N-[((2R)-1-{3-[(tert-butoxy)carbonylamino]propyl}-5-oxopyrrolidin-2-yl)methyl](2-{[2-(3-fluorophenyl)ethyl]amino}-5-methyl-6-(1-methylpyrazol-4-yl)(3-pyridyl))carboxamide,
N-{[(2R)-1-(3-aminopropyl)-5-oxopyrrolidin-2-yl]methyl}(2-{[2-(3-fluorophenyl)ethyl]amino}-5-methyl-6-(1-methylpyrazol-4-yl)(3-pyridyl))carboxamide,
tert-butyl (2R)-2-{[(2-{[2-(3-fluorophenyl)ethyl]amino}-5-methyl-6-(1 methylpyrazol-4-yl)(3-pyridyl)carbonylamino]methyl}pyrrolidinecarboxylate,
N-[((2R)pyrrolidin-2-yl)methyl](2-{[2-(3-fluorophenyl)ethyl]amino}-5-methyl-6-(1-methylpyrazol-4-yl)(3-pyridyl))carboxamide,
N-[((2R)-1-{4-[(tert-butoxy)carbonylamino]butanoyl}pyrrolidin-2-yl)methyl](2-{[2-(3-fluorophenyl)ethyl]amino}-5-methyl-6-(1-methylpyrazol-4-yl)(3-pyridyl))carboxamide,
N-{[(2R)-1-(4-aminobutanoyl)pyrrolidin-2-yl]methyl}(2-{[2-(3-fluorophenyl)ethyl]amino}-5-methyl-6-(1-methylpyrazol-4-yl)(3-pyridyl))carboxamide,
tert-butyl (2R)-2-{[(5-cyano-2-{[2-(3-fluorophenyl)ethyl]amino}-6-pyrazol-4-yl(3-pyridyl)carbonylamino]methyl}pyrrolidinecarboxylate,
N-[((2R)pyrrolidin-2-yl)methyl](5-cyano-2-{[2-(3-fluorophenyl)ethyl]amino}-6-pyrazol-4-yl(3-pyridyl))carboxamide,
N-[((2R)-1-{4-[(tert-butoxy)carbonylamino]butanoyl}pyrrolidin-2-yl)methyl](5-cyano-2-{[2-(3-fluorophenyl)ethyl]amino}-6-pyrazol-4-yl(3-pyridyl))carboxamide,
N-{[(2R)-1-(4-aminobutanoyl)pyrrolidin-2-yl]methyl}(5-cyano-2-[((2-(3-fluorophenyl)ethyl]amino}-6-pyrazol-4-yl(3-pyridyl))carboxamide,
N-[((2R)-1-{3-[(tert-butoxy)carbonylamino]propyl]-5-oxopyrrolidin-2-yl)methyl](5-cyano-2-{[2-(3-fluorophenyl)ethyl]amino}-6-pyrazol-4-yl(3-pyridyl))carboxamide,
N-{[(2R)-1-(3-aminopropyl)-5-oxopyrrolidin-2-yl]methyl}(5-cyano-2-{[2-(3-fluorophenyl)ethyl]amino}-6-pyrazol-4-yl(3-pyridyl))carboxamide,
N-[(2-{[(tert-butoxy)carbonylamino]methyl}(3-pyridyl))methyl](5-cyano-2-{[2-(3-fluorophenyl)ethyl]amino}-6-pyrazol-4-yl(3-pyridyl))carboxamide,
N-{[2-(aminomethyl)(3-pyridyl)]methyl}(5-cyano-2-{[2-(3-fluorophenyl)ethyl]amino}-6-pyrazol-4-yl(3-pyridyl))carboxamide,
N-[(2-{[(tert-butoxy)carbonylamino]methyl}(3-pyridyl))methyl](5-chloro-2-{[2-(3-fluorophenyl)ethyl]amino}-6-(1-methylpyrazol-4-yl)(3-pyridyl))carboxamide,
N-{[2-(aminomethyl)(3-pyridyl)]methyl}(5-chloro-2-{[2-(3-fluorophenyl)ethyl]amino}-6-(1-methylpyrazol-4-yl)(3-pyridyl))carboxamide,
N-[((2R)-1-[3-[(tert-butoxy)carbonylamino]propyl}-5-oxopyrrolidin-2-yl)methyl](5-chloro-2-[((2-(3-fluorophenyl)ethyl]amino}-6-(1-methylpyrazol-4-yl)(3-pyridyl))carboxamide,
N-{[(2R)-1-(3-aminopropyl)-5-oxopyrrolidin-2-yl]methyl}(5-chloro-2-{[2-(3-fluorophenyl)ethyl]amino}-6-(1-methylpyrazol-4-yl)(3-pyridyl))carboxamide,
tert-butyl (2R)-2-{[(5-chloro-2-[((2-(3-fluorophenyl)ethyl]amino}-6-(1-methylpyrazol-4-yl)(3-pyridyl)carbonylamino]methyl}pyrrolidinecarboxylate,
N-[((2R)pyrrolidin-2-yl)methyl](5-chloro-2-[((2-(3-fluorophenyl)ethyl]amino}-6-(1-methylpyrazol-4-yl)(3-pyridyl))carboxamide,
N-[((2R)-1-[4-[(tert-butoxy)carbonylamino]butanoyl}pyrrolidin-2-yl)methyl](5-chloro-2-[((2-(3-fluorophenyl)ethyl]amino}-6-(1-methylpyrazol-4-yl)(3-pyridyl))carboxamide,
N-{[(2R)-1-(4-aminobutanoyl)pyrrolidin-2-yl]methyl}(5-chloro-2-[((2-(3-fluorophenyl)ethyl]amino}-6-(1-methylpyrazol-4-yl)(3-pyridyl))carboxamide,
N-{3-[(tert-butoxy)carbonylamino]propyl}(5-fluoro-2-[((2-(3-fluorophenyl)ethyl]amino}-6-(1-methylpyrazol-4-yl)(3-pyridyl))carboxamide,
N-(3-aminopropyl)(5-fluoro-2-{[2-(3-fluorophenyl)ethyl]amino}-6-(1-methylpyrazol-4-yl)(3-pyridyl))carboxamide,
methyl (2R)-3-[(5-fluoro-2-{[2-(3-fluorophenyl)ethyl]amino}-6-(1-methylpyrazol-4-yl)(3-pyridyl)carbonylamino]-2-methylpropanoate,
(2R)-34(5-fluoro-2-{[2-(3-fluorophenyl)ethyl]amino}-6-(1-methylpyrazol-4-yl)(3-pyridyl)carbonylamino]-2-methylpropanoic acid,
2-[(tert-butoxy)carbonylamino]-N-{3-[(5-fluoro-2-{[2-(3-fluorophenyl)ethyl]amino}-6-(1-methylpyrazol-4-yl)(3-pyridyl)carbonylamino]propyl}acetamide,
2-amino-N-{3-[(5-fluoro-2-{[2-(3-fluorophenyl)ethyl]amino}-6-(1-methylpyrazol-4-yl)(3-pyridyl)carbonylamino]propyl}acetamide
N-{3-[(5-fluoro-2-{[2-(3-fluorophenyl)ethyl]amino}-6-(1-methylpyrazol-4-yl)-3-pyridyl)carbonylamino]propyl}acetamide,
N-((2R)-3-hydroxy-2-methylpropyl)(5-fluoro-2-{[2-(3-fluorophenyl)ethyl]amino}-6-(1-methylpyrazol-4-yl)(3-pyridyl))carboxamide,
N-((2R)-2-carbamoylpropyl)(5-fluoro-2-{[2-(3-fluorophenyl)ethyl]amino}-6-(1-methylpyrazol-4-yl)(3-pyridyl))carboxamide,
(2R)-34(5-fluoro-2-{[2-(3-fluorophenyl)ethyl]amino}-6-(1-methylpyrazol-4-yl)(3-pyridyl)carbonylamino]-2-methyl-N-methylpropanamide,
(5-fluoro-2-{[2-(3-fluorophenyl)ethyl]amino}-6-pyrazol-4-yl(3-pyridyl))-N-(pyrazol-3-ylmethyl)carboxamide,
(5-fluoro-2-{[2-(3-fluorophenyl)ethyl]amino}-6-(1-methylpyrazol-4-yl)(3-pyridyl))-N-(pyrazol-3-ylmethyl)carboxamide,
N-((2R)-4-diazo-2-methyl-4-azabut-4-enyl)(5-fluoro-2-{[2-(3-fluorophenyl)ethyl]amino}-6-(1-methylpyrazol-4-yl)(3-pyridyl))carboxamide,
N-((2S)-3-amino-2-methylpropyl)(5-fluoro-2-{[2-(3-fluorophenyl)ethyl]amino}-6-(1-methylpyrazol-4-yl)(3-pyridyl))carboxamide, N-{(2R)-3-[(5-fluoro-2-{[2-(3-fluorophenyl)ethyl]amino}-6-(1-methylpyrazol-4-yl)(3-pyridyl)carbonylamino]-2-methylpropyl}-2-[(tert-butoxy)carbonylamino]acetamide, N-{(2R)-3-[(5-fluoro-2-{[2-(3-fluorophenyl)ethyl]amino}-6-(1-methylpyrazol-4-yl)(3-pyridyl)carbonylamino]-2-methylpropyl}-2-aminoacetamide, N-{(2R)-3-[(5-fluoro-2-{[2-(3-fluorophenyl)ethyl]amino}-6-(1-methylpyrazol-4-yl)(3-pyridyl)carbonylamino]-2-methylpropyl}-2-hydroxyacetamide, tert-butyl (2R)-2-{[(5-fluoro-2-{[2-(3-fluorophenyl)ethyl]amino}-6-(1-methylpyrazol-4-yl)(3-pyridyl)carbonylamino]methyl}azetidinecarboxylate, N-[((2R)azetidin-2-yl)methyl](5-fluoro-2-{[2-(3-fluorophenyl)ethyl]amino}-6-(1-methylpyrazol-4-yl)(3-pyridyl))carboxamide, N-[((2R)-1-{2-[(tert-butoxy)carbonylamino]acetyl}azetidin-2-yl)methyl](5-fluoro-2-{[2-(3-fluorophenyl)ethyl]amino}-6-(1-methylpyrazol-4-yl)(3-pyridyl))carboxamide, N-{[(2R)-1-(2-aminoacetyl)azetidin-2-yl]methyl}(5-fluoro-2-{[2-(3-fluorophenyl)ethyl]amino}-6-(1-methylpyrazol-4-yl)(3-pyridyl))carboxamide, N-[((2R)-1-{4-[(tert-butoxy)carbonylamino]butanoyl}azetidin-2-yl)methyl](5-fluoro-2-{[2-(3-fluorophenyl)ethyl]amino}-6-(1-methylpyrazol-4 yl)(3-pyridyl))carboxamide, N-{[(2R)-1-(4-aminobutanoyl)azetidin-2-yl]methyl}(5-fluoro-2-{[2-(3-fluorophenyl)ethyl]amino}-6-(1-methylpyrazol-4-yl)(3-pyridyl))carboxamide, N-{[(2R)-1-(2-hydroxyacetyl)azetidin-2-yl]methyl}(5-fluoro-2-{[2-(3-fluorophenyl)ethyl]amino}-6-(1-methylpyrazol-4-yl)(3-pyridyl))carboxamide, methyl (2S)-3-[(5-fluoro-2-{[2-(3-fluorophenyl)ethyl]amino}-6-(1-methylpyrazol-4-yl)(3-pyridyl)carbonylamino]-2-methylpropanoate, N-((2S)-3-hydroxy-2-methylpropyl)(5-fluoro-2-{[2-(3-fluorophenyl)ethyl]amino}-6-(1-methylpyrazol-4-yl)(3-pyridyl))carboxamide, N-((2R)-3-hydroxy-2-methylpropyl)(5-fluoro-2-{[2-(3-fluorophenyl)ethyl]amino}-6-pyrazol-4-yl(3-pyridyl))carboxamide, methyl (2R)-3-[(5-fluoro-2-{[2-(3-fluorophenyl)ethyl]amino}-6-pyrazol-4-yl(3-pyridyl)carbonylamino]-2-methylpropanoate, N-[(2,2-dimethyl(1,3-dioxan-5-yl))methyl](5-fluoro-2-{[2-(3-fluorophenyl)ethyl]amino}-6-(1-methylpyrazol-4-yl)(3-pyridyl))carboxamide, (5-fluoro-2-{[2-(3-fluorophenyl)ethyl]amino}-6-(1-methylpyrazol-4-yl)(3-pyridyl))-N-[3-hydroxy-2-(hydroxymethyl)propyl]carboxamide, N-[(2,2-dimethyl(1,3-dioxan-5-yl))methyl](5-fluoro-2-{[2-(3-fluorophenyl)ethyl]amino}-6-pyrazol-4-yl(3-pyridyl))carboxamide, (5-fluoro-2-{[2-(3-fluorophenyl)ethyl]amino}-6-pyrazol-4-yl(3-pyridyl))-N-[3-hydroxy-2-(hydroxymethyl)propyl]carboxamide, methyl (2R)-2-{[(5-fluoro-2-{[2-(3-fluorophenyl)ethyl]amino}-6-(1-methylpyrazol-4-yl)(3-pyridyl)carbonylamino]methyl}butanoate, N-((2R)-2-ethyl-3-hydroxypropyl)(5-fluoro-2-{[2-(3-fluorophenyl)ethyl]amino}-6-(1-methylpyrazol-4-yl)(3-pyridyl))carboxamide, methyl (2R)-2-{[(5-fluoro-2-{[2-(3-fluorophenyl)ethyl]amino}-6-pyrazol-4-yl(3-pyridyl)carbonylamino]methyl}butanoate, N-((2R)-2-ethyl-3-hydroxypropyl)(5-fluoro-2-{[2-(3-fluorophenyl)ethyl]amino}-6-pyrazol-4-yl(3-pyridyl))carboxamide, methyl (2R)-2-[(tert-butoxy)carbonylamino]-3-[(5-fluoro-2-{[2-(3-fluorophenyl)ethyl]amino}-6-(1-methylpyrazol-4-yl)(3-pyridyl)carbonylamino]propanoate, methyl (2R)-2-amino-3-[(5-fluoro-2-{[2-(3-fluorophenyl)ethyl]amino}-6-(1-methylpyrazol-4-yl)(3-pyridyl)carbonylamino]propanoate, N-((1R)-1-{[(5-fluoro-2-{[2-(3-fluorophenyl)ethyl]amino}-6-(1-methylpyrazol-4-yl)(3-pyridyl)carbonylamino]methyl}-2-hydroxyethyl)(tert-butoxy)carboxamide, N-((2R)-2-amino-3-hydroxypropyl)(5-fluoro-2-{[2-(3-fluorophenyl)ethyl]amino}-6-(1-methylpyrazol-4-yl)(3-pyridyl))carboxamide, N-((1R)-1-{[(5-fluoro-2-{[2-(3-fluorophenyl)ethyl]amino}-6-pyrazol-4-yl(3-pyridyl)carbonylamino]methyl}-2-hydroxyethyl)(tert-butoxy)carboxamide, N-((2R)-2-amino-3-hydroxypropyl)(5-fluoro-2-{[2-(3-fluorophenyl)ethyl]amino}-6-pyrazol-4-yl(3-pyridyl))carboxamide, N-(2,3-dihydroxypropyl)(5-fluoro-2-{[2-(3-fluorophenyl)ethyl]amino}-6-(1-methylpyrazol-4-yl)(3-pyridyl))carboxamide, N-(2,3-dihydroxypropyl)(5-fluoro-2-{[2-(3-fluorophenyl)ethyl]amino}-6-pyrazol-4-yl(3-pyridyl))carboxamide, N-{[(2R)-1-(2-hydroxy-2-methylpropanoyl)azetidin-2-yl]ethyl}(5-fluoro-2-{[2-(3-fluorophenyl)ethyl]amino}-6-(1-methylpyrazol-4-yl)(3-pyridyl))carboxamide, tert-butyl (2R)-2-{[(5-fluoro-2-{[2-(3-fluorophenyl)ethyl]amino}-6-pyrazol-4-yl(3-pyridyl)carbonylamino]methyl}azetidinecarboxylate, N-{[(2R)-1-(2-hydroxyacetyl)azetidin-2-yl]methyl}(5-fluoro-2-{[2-(3-fluorophenyl)ethyl]amino}-6-pyrazol-4-yl(3-pyridyl))carboxamide, and N-[((2R)azetidin-2-yl)methyl](5-fluoro-2-{[2-(3-fluorophenyl)ethyl]amino}-6-pyrazol-4-yl(3-pyridyl))carboxamide, or a pharmaceutically acceptable salt thereof.

23. The compound of claim 1, wherein $Z^1$ is optionally substituted pyrazolyl.

24. The compound of claim 23, wherein $Z^1$ is optionally substituted pyrazol-4.

25. The compound of claim 24, wherein $Z^1$ is chosen from pyrazol-4-yl and 1-methylpyrazol-4-yl.

26. The compound of claim 23, wherein $Z^1$ is optionally substituted pyrazol-3-yl.

27. The compound of claim 1, wherein $Z^1$ is optionally substituted thienyl.

28. The compound of claim 27, wherein $Z^1$ is optionally substituted thien-2-yl.

29. The compound of claim 28, wherein $Z^1$ is optionally substituted thien-3-yl.

30. The compound of claim 28, wherein $Z^1$ is chosen from thien-2-yl, 4-methylthien-2-yl, 5-methylthien-2-yl, 5-(hydroxymethyl)thien-2-yl, 5-(aminomethyl)thien-2-yl, 5-formylthien-2-yl, 5-acetylthien-2-yl, 5-cyanothien-2-yl, 3-(hydroxymethyl)thien-2-yl, 3-(aminomethyl)thien-2-yl, thien-3-yl, 4-methylthien-3-yl, 5-methylthien-3-yl, 5-(hydroxymethyl)thien-3-yl, 5-(aminomethyl)thien-3-yl, 5-formylthien-3-yl, 5-acetylthien-3-yl, 5-cyanothien-3-yl, 4-cyanothien-3-yl, 2-(hydroxymethyl)thien-3-yl, 2-(aminomethyl)thien-3-yl and 2-formylthien-3-yl.

31. The compound of claim 1, wherein $R^4$ is fluoro.

32. The compound of claim 1, wherein $R^2$ is methyl substituted with a group chosen from optionally substituted aryl, optionally substituted heteroaryl and optionally substituted heterocycloalkyl.

33. The compound of claim 32, wherein $R^2$ is methyl substituted with optionally substituted pyridyl.

34. The compound of claim 33, wherein $R^2$ is chosen from 3-pyridylmethyl, 2-(aminomethyl)(3-pyridyl)]methyl, (2-{[(tert-butoxy)carbonylamino]methyl}(3-pyridyl))methyl, 2-chloro(3-pyridyl))methyl, 2-[(3-aminopropyl)amino](3-pyridyl)}methyl, 2-[(2-aminoethyl)amino](3-pyridyl)}methyl, 2-[(2-hydroxyethyl)amino](3-pyridyl)}methyl, 2-pyridylmethyl, 6-(aminomethyl)(2-pyridyl)]methyl, (6-bromo(2-pyridyl))methyl, {6-[(3-aminopropyl)amino](2-pyridyl)}methyl, {6-[(2-aminoethyl)amino](2-pyridyl)}methyl, and {6-[(2-hydroxyethyl)amino](2-pyridyl)}methyl.

35. The compound of claim 33, wherein $R^2$ is chosen from 3-pyridylmethyl and [2-(aminomethyl)(3-pyridyl)]methyl.

36. The compound of claim 32, wherein $R^2$ is methyl substituted with optionally substituted azetidinyl.

37. The compound of claim 36, wherein $R^2$ is methyl substituted with optionally substituted azetidin-2-yl.

38. The compound of claim 37, wherein $R^2$ is chosen from (azetidin-2-yl)methyl, [1-(2-hydroxyacetyl)azetidin-2-yl]methyl, [1-(2-aminoacetyl)azetidin-2-yl]methyl, [1-(2-hydroxy-2-methylpropanoyl)azetidin-2-yl]methyl, methyl 2-methylazetidine-1-carboxylate, tert-butyl 2-methylazetidine-1-carboxylate, [1-(4-aminobutanoyl)azetidin-2-yl]methyl, (1-{4-[(tert-butoxy)carbonylamino]butanoyl}azetidin-2-yl)methyl, and (1-{2-[(tert-butoxy)carbonylamino]acetyl}azetidin-2-yl)methyl.

39. The compound of claim 37, wherein $R^2$ is chosen from (azetidin-2-yl)methyl, [1-(2-hydroxyacetyl)azetidin-2-yl]methyl, and [1-(2-aminoacetyl)azetidin-2-yl]methyl.

40. The compound of claim 32, wherein $R^2$ is methyl substituted with optionally substituted pyrrolidinyl.

41. The compound of claim 40, wherein $R^2$ is methyl substituted with optionally substituted pyrrolidin-2-yl.

42. The compound of claim 41, wherein $R^2$ is chosen from (pyrrolidin-2-yl)methyl, [1-(2-aminoacetyl)pyrrolidin-2-yl]methyl, (1-{2-[(tert-butoxy)carbonylamino]acetyl}pyrrolidin-2-yl)methyl, [1-(3-aminopropanoyl)pyrrolidin-2-yl]methyl, (1-{3-[(tert-butoxy)carbonylamino]propanoyl}pyrrolidin-2-yl)methyl, [1-4-aminobutanoyl)pyrrolidin-2-yl]methyl, (1-{4-[(tert-butoxy)carbonylamino]butanoyl}pyrrolidin-2-yl)methyl, [1-(2-hydroxyacetyl)pyrrolidin-2-yl]methyl, [2-amino-3-hydroxypropanoyl)pyrrolidin-2-yl]methyl, [2-aminopropanoyl)pyrrolidin-2-yl]methyl, tert-butyl-2-methylpyrrolidine-1-carboxylate, [1-(4-hydroxybutanoyl)pyrrolidin-2-yl]methyl, (5-oxopyrrolidin-2-yl)methyl, [1-[3-aminopropyl)-5-oxopyrrolidin-2-yl]methyl, (1-{3-[(tert-butoxy)carbonylamino]propyl}-5-oxopyrrolidin-2-yl)methyl], (2-oxopyrrolidin-3-yl)methyl, and [1-(3-aminopropyl)-2-oxopyrrolidin-3-yl]methyl.

43. The compound of claim 41, wherein $R^2$ is chosen from (pyrrolidin-2-yl)methyl, [1-(2-hydroxyacetyl)pyrrolidin-2-yl]methyl and [1-(2-aminoacetyl)pyrrolidin-2-yl]methyl.

44. The compound of claim 13, wherein r is 2.

45. The compound of claim 44, wherein $R^{20}$ is aryl substituted with 1, 2 or 3 halo groups.

46. The compound of claim 45, wherein $R^{20}$ is aryl substituted with 1, 2 or 3-fluoro groups.

47. The compound of claim 1, wherein
$Z^1$ is optionally substituted pyrazolyl;
$Z^3$ is —$(CH_2)_rR^{20}$ wherein r is 2 and $R^{20}$ is chosen from optionally substituted aryl and optionally substituted heteroaryl; and
$R^1$ is hydrogen.

48. The compound of claim 47, wherein
$R^2$ is methyl substituted with a group chosen from optionally substituted heteroaryl and optionally substituted heterocycloalkyl; and
$R^5$ is hydrogen.

49. The compound of claim 48, wherein $R^4$ is fluoro.

50. The compound of claim 49, wherein $R^3$ is hydrogen.

51. The compound of claim 48, wherein $R^4$ is hydrogen.

52. The compound of claim 51, wherein $R^3$ is hydrogen.

53. The compound of claim 1, wherein
$Z^3$ is —$(CH_2)_rR^{20}$ wherein r is chosen from 1 and 2 and $R^{20}$ is chosen from optionally substituted aryl and optionally substituted heteroaryl;
$R^1$ is hydrogen; and
$R^4$ is chosen from hydrogen and halo.

54. The compound of claim 53, wherein
$R^2$ is methyl substituted with a group chosen from optionally substituted heteroaryl and optionally substituted heterocycloalkyl; and
$R^5$ is hydrogen.

55. The compound of claim 54, wherein $R^2$ is methyl substituted with a group chosen from optionally substituted pyridyl, optionally substituted azetidinyl and optionally substituted pyrrolidinyl.

56. The compound of claim 55, wherein r is 2.

57. The compound of claim 56, wherein $Z^1$ is chosen from optionally substituted pyrazolyl, optionally substituted thiphenyl, optionally substituted pyridinyl, optionally substituted tetrazolyl, optionally substituted thiazolyl and optionally substituted isoxazolyl.

58. The compound of claim 57, wherein $Z^1$ is chosen from optionally substituted pyrazol-3-yl and optionally substituted pyrazol-4-yl.

59. The compound of claim 58, wherein $R^3$ is hydrogen.

60. A compound chosen from
(6-(2-cyano(3-thienyl))-2-{[2-(3-fluorophenyl)ethyl]amino}(3-pyridyl))-N-(3-pyridylmethyl)carboxamide,
{2-[(2-(2-pyridyl)ethyl)amino]-6-(2-thienyl)(3-pyridyl)}-N-(3-pyridylmethyl)carboxamide,
{6-(4-methyl(2-thienyl))-2-[(2-(2-pyridyl)ethyl)amino](3-pyridyl)}-N-(3-pyridylmethyl)carboxamide,
{6-(4-methyl(3-thienyl))-2-[(2-(2-pyridyl)ethyl)amino](3-pyridyl)}-N-(3-pyridylmethyl)carboxamide,
{2-[(2-(2-pyridyl)ethyl)amino]-6-(3-thienyl)(3-pyridyl)}-N-(3-pyridylmethyl)carboxamide,
(2-{[2-(3-fluorophenyl)ethyl]amino}-6-(4-methyl(2-thienyl))(3-pyridyl))-N-(3-pyridylmethyl)carboxamide,
(2-{[2-(3-fluorophenyl)ethyl]amino}-6-(3-thienyl)(3-pyridyl))-N-(3-pyridylmethyl)carboxamide,
(2-{[2-(3,5-difluorophenyl)ethyl]amino}-6-(3-thienyl)(3-pyridyl))-N-(3-pyridylmethyl)carboxamide,
(2-{[2-(3,5-difluorophenyl)ethyl]amino}-6-(4-methyl(2-thienyl))(3-pyridyl))-N-(3-pyridylmethyl)carboxamide,
(2-{[2-(3-fluorophenyl)ethyl]amino}-6-(2-thienyl)(3-pyridyl))-N-(3-pyridylmethyl)carboxamide,
(2-{[2-(3,5-difluorophenyl)ethyl]amino}-6-(2-thienyl)(3-pyridyl))-N-(3-pyridylmethyl)carboxamide
(2-{[2-(3-fluorophenyl)ethyl]amino}-6-[3-(hydroxymethyl)(2-thienyl)](3-pyridyl))-N-(3-pyridylmethyl)carboxamide,
(2-{[2-(3-fluorophenyl)ethyl]amino}-6-(5-formyl(3-thienyl))(3-pyridyl))-N-(3-pyridylmethyl)carboxamide, (2-{[2-(3-fluorophenyl)ethyl]amino}-6-[5-(hydroxymethyl)(3-thienyl)](3-pyridyl))-N-(3-pyridylmethyl)carboxamide,
(2-{[2-(3-fluorophenyl)ethyl]amino}-6-(2-formyl(3-thienyl))(3-pyridyl))-N-(3-pyridylmethyl)carboxamide,
(2-{[2-(3-fluorophenyl)ethyl]amino}-6-[2-(hydroxymethyl)(3-thienyl)](3-pyridyl))-N-(3-pyridylmethyl)carboxamide,
(6-(5-acetyl(2-thienyl))-2-{[2-(3-fluorophenyl)ethyl]amino}(3-pyridyl))-N-(3-pyridylmethyl)carboxamide,
(6-[3-(aminomethyl)(2-thienyl)]-2-{[2-(3-fluorophenyl)ethyl]amino}(3-pyridyl))-N-(3-pyridylmethyl)carboxamide,
(2-{[2-(3-fluorophenyl)ethyl]amino}-6-[5-(hydroxyethyl)(2-thienyl)](3-pyridyl))-N-(3-pyridylmethyl)carboxamide,
(6-(4-cyano(3-thienyl))-2-{[2-(3-fluorophenyl)ethyl]amino}(3-pyridyl))-N-(3-pyridylmethyl)carboxamide,
(6-[5-(aminomethyl)(2-thienyl)]-2-{[2-(3-fluorophenyl)ethyl]amino}(3-pyridyl))-N-(3-pyridylmethyl)carboxamide,
(2-{[2-(3-fluorophenyl)ethyl]amino}-6-(3-formyl(2-thienyl))(3-pyridyl))-N-(3-pyridylmethyl)carboxamide,
(2-{[2-(3-fluorophenyl)ethyl]amino}-6-(5-formyl(2-thienyl))(3-pyridyl))-N-(3-pyridylmethyl)carboxamide,
(6-(5-cyano(2-thienyl))-2-{[2-(3-fluorophenyl)ethyl]amino}(3-pyridyl))-N-(3-pyridylmethyl)carboxamide,
(2-{[2-(3-fluorophenyl)ethyl]amino}-6-[5-(hydroxymethyl)(2-thienyl)](3-pyridyl))-N-(3-pyridylmethyl)carboxamide,
2-[(2-{[2-(3-fluorophenyl)ethyl]amino}-6-[5-(hydroxymethyl)(2-thienyl)](3-pyridyl)carbonylamino]-N-methylacetamide,
N-(2-carbamoylethyl)(2-[2-(3-fluorophenyl)ethyl]amino}-6-[5-(hydroxymethyl)(2-thienyl)](3-pyridyl))carboxamide,
(2-{[2-(3-fluorophenyl)ethyl]amino}-6-[5-(hydroxymethyl)(2-thienyl)](3-pyridyl))-N-(2-pyridylmethyl)carboxamide,
N-(carbamoylmethyl)(2-{[2-(3-fluorophenyl)ethyl]amino}-6-[5-(hydroxymethyl)(2-thienyl)](3-pyridyl))carboxamide, and
N-{[(2R)-1-(2-hydroxyacetyl)azetidin-2-yl]methyl}(2-{[2-(3-fluorophenyl)ethyl]amino}-6-[5-(hydroxymethyl)(2-thienyl)](3-pyridyl))carboxamide,
or a pharmaceutically acceptable salt thereof.

61. A compound chosen from
(6-(1H-1,2,3,4-tetraazol-5-yl)-2-{[2-(3-fluorophenyl)ethyl]amino}(3-pyridyl))-N-(3-pyridylmethyl)carboxamide,
N-(3-pyridylmethyl){6-(4-pyridyl)-2-[(2-(2-pyridyl)ethyl]amino](3-pyridyl)}carboxamide,
N-(3-pyridylmethyl){6-(2-pyridyl)-2-[(2-(2-pyridyl)ethyl)amino](3-pyridyl)}carboxamide,
N-(3-pyridylmethyl){6-(3-pyridyl)-2-[(2-(2-pyridyl)ethyl)amino](3-pyridyl)}carboxamide,
{2-[(2-(2-pyridyl)ethyl)amino]-6-(1,3-thiazol-2-yl)(3-pyridyl)}-N-(3-pyridylmethyl)carboxamide,
[2-{[2-(3-fluorophenyl)ethyl]amino}-6-(6-{[2-(3-fluorophenyl)ethyl]amino}-5-[N-(3-pyridylmethyl)carbamoyl](2-pyridyl))(3-pyridyl)]-N-(3-pyridylmethyl)carboxamide,
(2-{[2-(3-fluorophenyl)ethyl]amino}-6-isoxazol-4-yl(3-pyridyl))-N-(3-pyridylmethyl)carboxamide,
N-[(2-{[(tert-butoxy)carbonylamino]methyl}(3-pyridyl))methyl](5-fluoro-2-{[2-(3-fluorophenyl)ethyl]amino}-6-(2-pyridyl)(3-pyridyl))carboxamide, and
N-{[2-(aminomethyl)(3-pyridyl)]methyl}(5-fluoro-2-{[2-(3-fluorophenyl)ethyl]amino}-6-(2-pyridyl)(3-pyridyl))carboxamide,
or a pharmaceutically acceptable salt thereof.

62. A pharmaceutically acceptable composition comprising a pharmaceutically acceptable carrier and a compound of claim 1 or a pharmaceutically acceptable salt thereof.

63. The pharmaceutical composition of claim 62 wherein the composition is formulated in a form chosen from a tablet, capsule, powder, liquid, suspension, suppository and aerosol.

64. A packaged pharmaceutical composition comprising a pharmaceutical composition of claim 62 and instructions for using the composition to treat a patient suffering from a disease associated with smooth muscle myosin or non-muscle myosin.

65. The packaged pharmaceutical composition of claim 64 wherein the disease associated with smooth muscle myosin is selected from hypertension, asthma, chronic obstructive pulmonary disease (copd) asthma, bronchoconstrictive disease, glaucoma and other ocular indications, incontinence and other bladder dysfunctions, irritable bowel syndrome, pre-term labor, esophageal dysmotility, strokes, subarachnoid hemorrhages, pre-menstrual cramps, erectile dysfunction and other acute and chronic diseases and conditions associated with smooth muscle myosin and/or non-muscle myosin.

66. A method of treating a disease associated with smooth muscle myosin or non-muscle myosin in a mammal which method comprises administering to a mammal in need thereof a therapeutically effective amount of a compound of claim 1 or a pharmaceutically acceptable salt thereof wherein said disease associated with smooth muscle myosin is selected from hypertension, asthma, chronic obstructive pulmonary disease (copd) asthma, bronchoconstrictive disease, glaucoma and other ocular indications, incontinence and other bladder dysfunctions, irritable bowel syndrome, pre-term labor, esophageal dysmotility, strokes, subarachnoid hemorrhages, pre-menstrual cramps, and erectile dysfunction.

* * * * *